(12) United States Patent
Brubaker et al.

(10) Patent No.: US 8,962,608 B2
(45) Date of Patent: Feb. 24, 2015

(54) CYCLOALKYLNITRILE PYRAZOLE CARBOXAMIDES AS JANUS KINASE INHIBITORS

(71) Applicants: Jason Brubaker, Cambridge, MA (US); Christopher Dinsmore, Newton, MA (US); Dawn Marie Hoffman, Brookline, MA (US); Joon Jung, Newton, MA (US); Duan Liu, Arlington, MA (US); Scott Peterson, Salem, MA (US); Tony Siu, Brookline, MA (US); Luis E. Torres, Norwood, MA (US); Hongjun Zhang, Newton, MA (US); Zhongyong Wei, Beijing (CN); Feng Shi, Beijing (CN)

(72) Inventors: Jason Brubaker, Cambridge, MA (US); Christopher Dinsmore, Newton, MA (US); Dawn Marie Hoffman, Brookline, MA (US); Joon Jung, Newton, MA (US); Duan Liu, Arlington, MA (US); Scott Peterson, Salem, MA (US); Tony Siu, Brookline, MA (US); Luis E. Torres, Norwood, MA (US); Hongjun Zhang, Newton, MA (US); Zhongyong Wei, Beijing (CN); Feng Shi, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/345,976

(22) PCT Filed: Sep. 21, 2012

(86) PCT No.: PCT/CN2012/001291
§ 371 (c)(1),
(2) Date: Mar. 20, 2014

(87) PCT Pub. No.: WO2013/040863
PCT Pub. Date: Mar. 28, 2013

(65) Prior Publication Data
US 2014/0243309 A1    Aug. 28, 2014

Related U.S. Application Data

(60) Provisional application No. 61/537,978, filed on Sep. 22, 2011.

(51) Int. Cl.
*A61K 31/397* (2006.01)
*A61K 31/5377* (2006.01)
*A61K 31/501* (2006.01)
*A61K 31/497* (2006.01)
*A61K 31/415* (2006.01)
*C07D 231/38* (2006.01)
*C07D 403/08* (2006.01)
*C07D 403/12* (2006.01)
*C07D 405/08* (2006.01)
*C07D 401/12* (2006.01)
*C07D 401/14* (2006.01)
*C07D 405/12* (2006.01)
*C07D 409/12* (2006.01)
*C07D 413/12* (2006.01)
*C07D 401/04* (2006.01)
*C07D 403/04* (2006.01)
*C07D 405/04* (2006.01)
*C07D 401/06* (2006.01)
*C07D 403/06* (2006.01)
*C07D 405/06* (2006.01)
*C07D 405/14* (2006.01)
*C07D 409/04* (2006.01)
*C07D 413/14* (2006.01)
*C07D 417/14* (2006.01)

(52) U.S. Cl.
CPC ............ *C07D 405/08* (2013.01); *C07D 403/12* (2013.01); *C07D 401/14* (2013.01); *C07D 231/38* (2013.01); *C07D 401/12* (2013.01); *C07D 403/08* (2013.01); *C07D 405/12* (2013.01); *C07D 409/12* (2013.01); *C07D 413/12* (2013.01); *C07D 401/04* (2013.01); *C07D 403/04* (2013.01); *C07D 405/04* (2013.01); *C07D 401/06* (2013.01); *C07D 403/06* (2013.01); *C07D 405/06* (2013.01); *C07D 405/14* (2013.01); *C07D 409/04* (2013.01); *C07D 413/14* (2013.01); *C07D 417/14* (2013.01)
USPC ............... 514/210.18; 514/210.2; 514/236.5; 514/252.05; 514/254.05; 514/278; 514/407; 544/140; 544/238; 544/371; 546/15; 548/357.5; 548/371.7

(58) Field of Classification Search
USPC ............ 514/210.18, 407, 278, 252.05, 236.5, 514/254.05, 210.2; 548/371.7, 357.5; 546/15; 544/238, 140, 371
See application file for complete search history.

(56) References Cited

FOREIGN PATENT DOCUMENTS

WO    2010014453 A1    2/2010
WO    2010099379 A1    9/2010

*Primary Examiner* — Kristin Vajda
(74) *Attorney, Agent, or Firm* — Patricia A. Shatynski; Laura Ginkel

(57) ABSTRACT

The instant invention provides compounds of formula I which are JAK inhibitors, and as such are useful for the treatment of JAK-mediated diseases such as rheumatoid arthritis, asthma, COPD and cancer.

17 Claims, No Drawings

CYCLOALKYLNITRILE PYRAZOLE CARBOXAMIDES AS JANUS KINASE INHIBITORS

CROSS REFERENCE TO RELATED APPLICATIONS

This application is a U.S. National Phase application under 35 U.S.C. §371 of PCT Application No. PCT/CN2012/001291, filed Sep. 21, 2012, which claims priority under 35 U.S.C. §119(e) from U.S. Provisional Application Ser. No. 61/537,978, filed Sep. 21, 2011.

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines. Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This has been demonstrated using genetically engineered mouse models that are deficient in specific JAKs. Jak1$^{-/-}$ mice die perinatally, while Jak2$^{-/-}$ mice have deficiencies in erythropoesis and die around day E12. Jak3$^{-/-}$ mice are viable, but have a SCID phenotype with deficiencies in T cells, B cells and NK cells. TYK2$^{-/-}$ mice exhibit features of hyper IgE syndrome. These phenotypes demonstrate the essential and non-redundant roles of JAK activity in vivo (K. Ghoreschi, A. Laurence, J. J. O'Shea, *Immunol. Rev.* 228, 273 (2009)).

Furthermore, mutations in the JAK enzymes have been associated with diseases in humans. Inactivating mutations in JAK3 (or the cognate common gamma chain cytokine receptor) cause a severe SCID phenotype (J. J. O'Shea, M. Pesu, D. C. Borie, P. S. Changelian, *Nat. Rev. Drug Discov.* 3, 555 (2004)). Deletions of TYK2 result in hyper IgG syndrome and increased infection risk (Y. Minegishi et al., *Immunity.* 25, 745 (2006)). No inactivating mutations have been reported for JAK1 or JAK2, consistent with the data from mice that demonstrates that JAK1 and JAK2 deficient mice are not viable. However, several mutations that result in constitutively active JAK2 have been identified, resulting in myeloproliferative diseases and confirming the central role of JAK2 in hematopoesis (O. bdel-Wahab, *Curr. Opin. Hematol.* 18, 117 (2011)). JAK2 is the sole JAK family member involved in signal transduction of the critical hematopoetic cytokines IL-3, GMCSF, EPO and TPO.

The wealth of mouse and human genetic data demonstrating a central role for JAK kinase activity in autoimmune disease, hematopoesis and oncology has been supported by the use of pan-JAK inhibitors in clinical trials for autoimmune diseases and neoplasms (See K. Ghoreschi, et al, *Immunol. Rev.* 228, 273 (2009), and A. Quintas-Cardama, H. Kantarjian, J. Cortes, S. Verstovsek, *Nat. Rev. Drug Discov.* 10, 127 (2011)). However, several adverse events have been reported that may be associated with inhibition of JAK2 signaling such as anemia, neutropenia and thrombocytopenia. Thus new or improved agents that selectively inhibit JAK1 activity but spare JAK2 activity are required for the treatment of several human diseases with an improved therapeutic index.

A considerable body of literature has accumulated that link the Jak/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts or stereoisomers thereof:

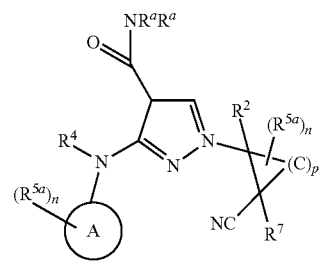

I $R^a$ and $R^4$ are each independently selected from hydrogen and $C_{1-4}$ alkyl;
A is selected from aryl, and heteroaryl;
n is 0, 1, 2, 3, or 4;
p is 2, 3, or 4;
$R^2$ and $R^7$ are each independently selected from:
  hydrogen,
  halogen,
  $C_{1-10}$ alkyl,
  $C_{2-10}$ alkenyl,
  $C_{1-10}$ heteroalkyl,
  aryl $C_{0-10}$ alkyl$C_{0-10}$ alkyl,
  $C_{3-8}$ cycloalkyl$C_{0-10}$ alkyl,
  heteroaryl $C_{0-10}$ alkyl,
  $(C_{3-8})$heterocycloalkyl $C_{0-10}$ alkyl, and wherein each of $R^2$ and $R^7$ are independently substituted with 0, 1, 2, 3, or 4 $R^{5a}$ substituents;
$R^{5a}$ is selected from:
halogen,
$C_{1-10}$ alkyl(oxy)$_{0-1}$(carbonyl)$_{0-1}$C$_{0-10}$ alkyl,
$C_{1-10}$ heteroalkyl(oxy)$_{0-1}$(carbonyl)$_{0-1}$C$_{0-10}$ alkyl,
$C_{2-10}$ alkenyl(oxy)$_{0-1}$(carbonyl)$_{0-1}$C$_{0-10}$ alkyl,
aryl $C_{0-10}$ alkyl(oxy)$_{0-1}$(carbonyl)$_{0-1}$C$_{0-10}$ alkyl,
aryl $C_{2-10}$ alkenyl(oxy)$_{0-1}$(carbonyl)$_{0-1}$C$_{0-10}$ alkyl,
aryl $C_{2-10}$ alkynyl(oxy)$_{0-1}$(carbonyl)$_{0-1}$C$_{0-10}$ alkyl,
$C_{3-8}$ cycloalkyl $C_{0-10}$ alkyl(oxy)$_{0-1}$(carbonyl)$_{0-1}$C$_{0-10}$ alkyl,
heteroaryl $C_{0-10}$ alkyl(oxy)$_{0-1}$(carbonyl)$_{0-1}$C$_{0-10}$ alkyl,
$(C_{3-8})$heterocycloalkyl $C_{0-10}$ alkyl(oxy)$_{0-1}$(carbonyl)$_{0-1}$C$_{0-10}$ alkyl,
$C_{1-10}$ alkyl(carbonyl)$_{0-1}$oxyC$_{0-10}$ alkyl,
$C_{1-10}$ heteroalkyl(carbonyl)$_{0-1}$oxyC$_{0-10}$ alkyl,
$C_{2-10}$ alkenyl(carbonyl)$_{0-1}$oxyC$_{0-10}$ alkyl,
$C_{1-10}$ heteroalkyl(carbonyl)$_{0-1}$oxyC$_{0-10}$ alkyl,
aryl $C_{0-10}$ alkyl (carbonyl)$_{0-1}$oxyC$_{0-10}$ alkyl,
$(C_{3-8})$cycloalkyl $C_{0-10}$ alkyl(carbonyl)$_{0-1}$oxyC$_{0-10}$ alkyl,
heteroaryl$C_{0-10}$ alkyl(carbonyl)$_{0-1}$oxyC$_{0-10}$ alkyl,
$(C_{3-8})$heterocycloalkyl $C_{0-10}$ alkyl(carbonyl)$_{0-1}$oxyC$_{0-10}$ alkyl,
$((C_{0-10})$alkyl)$_{1-2}$aminocarbonyloxy,
$(C_{0-10})$heteroalkylaminocarbonyloxy,
aryl $(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{0-10}$ alkylamino(oxy)$_{0-1}$(carbonyl)$_{0-1}$C$_{2-10}$ alkenyl,
$C_{1-10}$ alkylamino(oxy)$_{0-1}$(carbonyl)$_{0-1}$C$_{0-10}$ alkyl,
$(C_{0-10})$heteroalkylamin(oxy)$_{0-1}$(carbonyl)$_{0-1}$C$_{0-10}$ alkyl,
$C_{3-8}$ cycloalkyl $C_{0-10}$ alkylamino(oxy)$_{0-1}$(carbonyl)$_{0-1}$C$_{0-10}$ alkyl,
aryl $C_{0-1}$ alkylamino(oxy)$_{0-1}$(carbonyl)$_{0-1}$C$_{0-10}$ alkyl,
heteroaryl$C_{0-10}$ alkylamino((oxy)$_{0-1}$(carbonyl)$_{0-1}$C$_{0-10}$ alkyl,
$(C_{3-8})$heterocycloalkyl$C_{0-1}$alkylamino(oxy)$_{0-1}$(carbonyl)$_{0-1}$C$_{0-10}$ alkyl,
$C_{1-10}$ alkyl(oxy)$_{0-1}$(carbonyl)$_{0-1}$aminoC$_{0-10}$ alkyl,
$C_{1-10}$ heteroalkyl (oxy)$_{0-1}$(carbonyl)$_{0-1}$aminoC$_{0-10}$ alkyl,
$C_{3-8}$ cycloalkyl $C_{0-10}$ alkyl (oxy)$_{0-1}$(carbonyl)$_{0-1}$aminoC$_{0-10}$ alkyl,
aryl $C_{0-10}$ alkyl(oxy)$_{0-1}$(carbonyl)$_{0-1}$aminoC$_{0-10}$ alkyl,
heteroaryl $C_{0-10}$ alkyl(oxy)$_{0-1}$(carbonyl)$_{0-1}$aminoC$_{0-10}$ alkyl,
$(C_{3-8})$heterocycloalkyl $C_{0-10}$ alkyl(oxy)$_{0-1}$(carbonyl)$_{0-1}$aminoC$_{0-10}$ alkyl,
—CO$_2$(C$_{0-10}$ alkyl),
—(C$_{0-10}$ alkyl)CO$_2$H,
Oxo (=O),
formyl,
sulfonyl,
$C_{1-10}$ alkylsulfonyl,
$C_{1-10}$ heteroalkylsulfonyl,
$(C_{3-8})$ cycloalkylsulfonyl,
$(C_{3-8})$ cycloheteroalkylsulfonyl,
heteroarylsulfonyl,
arylsulfonyl,
aminosulfonyl,
—SO$_2$N(C$_{0-6}$alkyl)$_{1-2}$,
—SO$_2$C$_{1-6}$alkyl,
—SO$_2$CF$_3$,
—SO$_2$CF$_2$H,
—Si(CH$_3$)$_3$,
$C_{1-10}$ alkylsulfinyl,
amino,
(C$_{0-10}$ alkyl)$_{1-2}$ amino,
$C_{1-4}$acylamino C$_{0-10}$ alkyl,
hydroxyl,
(C$_{1-10}$ alkyl)OH,
$C_{0-10}$ alkylalkoxyl,
imino(C$_{0-10}$alkyl),
(C$_{0-10}$alkyl)imino,
cyano,
$C_{1-6}$alkylcyano, and
$C_{1-6}$haloalkyl;
wherein two $R^{5a}$ and the atom to which they are attached may optionally form a 3-, 4-, 5-, or 6-membered saturated ring system;
wherein $R^{5a}$ is each optionally substituted with 1, 2, 3, or 4 $R^6$ substituents, and $R^6$ independently selected from:
halogen,
$C_{1-10}$ alkyl(oxy)$_{0-1}$(carbonyl)$_{0-1}$C$_{0-10}$ alkyl,
$C_{1-10}$ heteroalkyl(oxy)$_{0-1}$(carbonyl)$_{0-1}$C$_{0-10}$ alkyl,
$C_{2-10}$ alkenyl(oxy)$_{0-1}$(carbonyl)$_{0-1}$C$_{0-10}$ alkyl,
aryl $C_{0-10}$ alkyl(oxy)$_{0-1}$(carbonyl)$_{0-1}$C$_{0-10}$ alkyl,
aryl $C_{2-10}$ alkenyl(oxy)$_{0-1}$(carbonyl)$_{0-1}$C$_{0-10}$ alkyl,
aryl $C_{2-10}$ alkynyl(oxy)$_{0-1}$(carbonyl)$_{0-1}$C$_{0-10}$ alkyl,
$C_{3-8}$ cycloalkyl $C_{0-10}$ alkyl(oxy)$_{0-1}$(carbonyl)$_{0-1}$C$_{0-10}$ alkyl,
heteroaryl $C_{0-10}$ alkyl(oxy)$_{0-1}$(carbonyl)$_{0-1}$C$_{0-10}$ alkyl,
$(C_{3-8})$heterocycloalkyl $C_{0-10}$ alkyl(oxy)$_{0-1}$(carbonyl)$_{0-1}$C$_{0-10}$ alkyl,
$C_{1-10}$ alkyl(carbonyl)$_{0-1}$oxyC$_{0-10}$ alkyl,
$C_{2-10}$ alkenyl(carbonyl)$_{0-1}$oxyC$_{0-10}$ alkyl,
$C_{1-10}$ heteroalkyl(carbonyl)$_{0-1}$oxyC$_{0-10}$ alkyl,
aryl $C_{0-10}$ alkyl (carbonyl)$_{0-1}$oxyC$_{0-10}$ alkyl,
$(C_{3-8})$cycloalkyl $C_{0-10}$ alkyl(carbonyl)$_{0-1}$oxyC$_{0-10}$ alkyl,
heteroaryl$C_{0-10}$ alkyl(carbonyl)$_{0-1}$oxyC$_{0-10}$ alkyl,
$(C_{3-8})$heterocycloalkyl $C_{0-10}$ alkyl(carbonyl)$_{0-1}$oxyC$_{0-10}$ alkyl,
$((C_{0-10})$alkyl)$_{1-2}$aminocarbonyloxy,
aryl $(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{1-10}$ alkylamino(oxy)$_{0-1}$carbonylC$_{0-10}$ alkyl,
$C_{3-8}$ cycloalkyl $C_{0-10}$ alkylamino(oxy)$_{0-1}$carbonylC$_{0-10}$ alkyl,
aryl $C_{0-10}$ alkylamino(oxy)$_{0-1}$carbonylC$_{0-10}$ alkyl,
heteroaryl $C_{0-10}$ alkylamino(oxy)$_{0-1}$carbonylC$_{0-10}$ alkyl,
$(C_{3-8})$heterocycloalkyl $C_{0-10}$ alkylamino(oxy)$_{0-1}$carbonylC$_{0-10}$ alkyl,
$C_{1-10}$ alkyl (oxy)$_{0-1}$(carbonyl)$_{0-1}$aminoC$_{0-10}$ alkyl,
$C_{3-8}$ cycloalkyl $C_{0-10}$ alkyl (oxy)$_{0-1}$(carbonyl)$_{0-1}$aminoC$_{0-10}$ alkyl,
aryl $C_{0-10}$ alkyl(oxy)$_{0-1}$(carbonyl)$_{0-1}$aminoC$_{0-10}$ alkyl,
heteroaryl $C_{0-10}$ alkyl(oxy)$_{0-1}$(carbonyl)$_{0-1}$aminoC$_{0-10}$ alkyl,
$(C_{3-8})$heterocycloalkyl $C_{0-10}$ alkyl(oxy)$_{0-1}$(carbonyl)$_{0-1}$aminoC$_{0-10}$ alkyl,
—CO$_2$(C$_{0-10}$ alkyl),
—(C$_{0-10}$ alkyl)CO$_2$H,
Oxo (=O),
Sulfonyl,
$C_{1-10}$ alkylsulfonyl,
$C_{1-10}$ heteroalkylsulfonyl,
$(C_{3-8})$cycloalkylsulfonyl,
$(C_{3-8})$cycloheteroalkylsulfonyl,
heteroarylsulfonyl,
arylsulfonyl,
aminosulfonyl,
—SO$_2$N(C$_{1-6}$alkyl)$_{1-2}$,
—SO$_2$C$_{1-6}$alkyl,
—SO$_2$CF$_3$, —SO$_2$CF$_2$H,
C$_{1-10}$ alkylsulfinyl,
—OSi(C$_{1-10}$ alkyl)$_3$,
amino,
(C$_{0-10}$ alkyl)$_{1-2}$ amino,
-(oxy)$_{0-1}$(carbonyl)$_{0-1}$N(C$_{0-10}$ alkyl)$_{1-2}$
C$_{1-4}$acylaminoC$_{0-10}$ alkyl,
imino(C$_{0-10}$alkyl),
(C$_{0-10}$alkyl)imino,
hydroxy,
(C$_{1-10}$ alkyl)OH,
C$_{1-10}$ alkoxy,
cyano, and
C$_{1-6}$haloalkyl;
wherein two R$^6$ and the atoms to which they are attached may optionally form a 3-, 4-, 5-, or 6-membered saturated ring system; and
R$^6$ is optionally substituted with 1, 2, or 3 substituents selected from hydrogen, hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C═O)C$_1$-C$_6$ alkyl, NO$_2$, trifluoromethoxy, trifluoroethoxy, trifluoromethyl, trifluoroethyl, —N═C(O)O(C$_{0-6}$) alkyl, C$_{1-10}$ alkylsulfonyl, C$_{1-10}$ heteroalkylsulfonyl, oxo (O═), (C$_{3-8}$) cycloalkylsulfonyl, (C$_{3-8}$) cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —C$_{1-10}$ alkylsulfinyl, —OSi(C$_{1-10}$alkyl)$_3$, —O$_{(0-1)}$(C$_{1-10}$)haloalkyl, amino(C$_{1-6}$alkyl)$_{0-2}$ and NH$_2$;
with the proviso that the compound of formula I is other than:
1-[(1R,2S,6S and 1S,2R,6R)-2-cyano-6-hydroxycyclohexyl]-3-(phenylamino)-1H-pyrazole-4-carboxamide;
1-[(1S,2R and 1R,2S)-2-cyanocyclohexyl]-3-{[2-(trifluoromethyl)pyridin-4-yl]amino}-1H-pyrazole-4-carboxamide; and
3-[(2-chloropyridin-4-yl)amino]-1-[(1S,2R and 1R,2S)-2-cyanocyclohexyl]-1H-pyrazole-4-carboxamide.

Representative compounds of the instant invention include, but are not limited to the following compounds and their pharmaceutically acceptable salts and stereoisomers thereof:

1-[2-cyanocyclopentyl]-3-(phenylamino)-1H-pyrazole-4-carboxamide;
1-{2-cyanocyclopentyl}-3-(phenylamino)-1H-pyrazole-4-carboxamide;
1-[2-cyanocyclohexyl]-3-(phenylamino)-1H-pyrazole-4-carboxamide;
1-{[2-cyanocyclopentyl]}-3-{[4-(methylsulfonyl)phenyl]amino}-1H-pyrazole-4-carboxamide;
1-{2-cyanocyclopentyl]}-3-{[4-(methylsulfonyl)phenyl]amino}-1H-pyrazole-4-carboxamide;
1-((2-cyanocyclohexyl)-3-(phenylamino)-1H-pyrazole-4-carboxamide;
1-[2-cyano-4-hydroxycyclohexyl]-3-(phenylamino)-1H-pyrazole-4-carboxamide;
1-(8-cyano-1,4-dioxaspiro[4.5]dec-7-yl)-3-(phenylamino)-1H-pyrazole-4-carboxamide;
methyl-3-[4-carbamoyl-3-(phenylamino)-1H-pyrazol-1-yl]-4-cyanocyclohexanecarboxylate;
1-[2-cyano-6-hydroxycyclohexyl]-3-(phenylamino)-1H-pyrazole-4-carboxamide;
1-[2-cyano-3-hydroxycyclohexyl]-3-(phenylamino)-1H-pyrazole-4-carboxamide;
1-[2-cyano-5-hydroxycyclohexyl]-3-(phenylamino)-1H-pyrazole-4-carboxamide;
1-[2-cyanocyclohexyl]-3-{[4-(methylsulfonyl)phenyl]amino}-1H-pyrazole-4-carboxamide;
[4-({4-Carbamoyl-1-[2-cyanocyclohexyl]-1H-pyrazol-3-yl}amino)phenyl]acetic acid;
[4-({4-carbamoyl-1-[2-cyanocyclohexyl]-1H-pyrazol-3-yl}amino)phenyl]acetic acid;
1-[2-Cyano-4-hydroxycyclohexyl]-3-[(4-fluorophenyl)amino]-1H-pyrazole-4-carboxamide;
1-[2-Cyano-4-hydroxycyclohexyl]-3-[(4-fluorophenyl)amino]-1H-pyrazole-4-carboxamide;
1-[2-cyano-5-(dimethylamino)cyclohexyl]-3-[(4-fluorophenyl)amino]-1H-pyrazole-4-carboxamide;
1-[2-cyano-5-(dimethylamino)cyclohexyl]-3-[(4-fluorophenyl)amino]-1H-pyrazole-4-carboxamide;
1-{[2-cyano-5-(methylamino)cyclohexyl]-3-[(4-fluorophenyl)amino]-1H-pyrazole-4-carboxamide;
1-{[5-(benzylamino)-2-cyanocyclohexyl}-3-[(4-fluorophenyl)amino]-1H-pyrazole-4-carboxamide;
tert-Butyl-4-{4-carbamoyl-3-[(4-fluorophenyl)amino]-1H-pyrazol-1-yl}-3-cyanocyclohexanecarboxylate;
methyl-4-{4-carbamoyl-3-[(4-fluorophenyl)amino]-1H-pyrazol-1-yl}-3-cyanocyclohexanecarboxylate;
1-2-Cyano-4-(hydroxymethyl)cyclohexyl)-3-((4-fluorophenyl)amino)-1H-pyrazole-4-carboxamide;
1-((4-(Aminomethyl)-2-cyanocyclohexyl)-3-((4-fluorophenyl)amino)-1H-pyrazole-4-carboxamide;
1-((2-Cyano-4-formylcyclohexyl)-3-((4-fluorophenyl)amino)-1H-pyrazole-4-carboxamide;
1-{2-Cyano-5,5-dimethylcyclohexyl}-3-(phenylamino)-1H-pyrazole-4-carboxamide;
tert-butyl[3-{4-carbamoyl-3-[(4-fluorophenyl)amino]-1H-pyrazol-1-yl}-4-cyanocyclohexyl]carbamate;
1-(2-cyano-5-methylcyclohexyl)-3-(phenylamino)-1H-pyrazole-4-carboxamide;
1-(5-cyanospiro[2.5]octan-6-yl)-3-((2-fluoropyridin-4-yl)amino)-1H-pyrazole-4-carboxamide;
tert-butyl {[3-{4-carbamoyl-3-[(4-fluorophenyl)amino]-1H-pyrazol-1-yl}-4-cyanocyclohexyl]methyl}carbamate;
tert-butyl {[3-{4-carbamoyl-3-[(4-fluorophenyl)amino]-1H-pyrazol-1-yl}-4-cyanocyclohexyl]methyl}carbamate;
tert-butyl 3-(4-carbamoyl-3-(phenylamino)-1H-pyrazol-1-yl)-4-cyanocyclohexanecarboxylate;
1-[2-Cyano-4-hydroxycyclohexyl]-3-({4-[(trifluoromethyl)sulfonyl]phenyl}amino)-1H-pyrazole-4-carboxamide;
1-[2-Cyano-4-hydroxycyclohexyl]-3-({4-[(difluoromethyl)sulfonyl]phenyl}amino)-1H-pyrazole-4-carboxamide;
1-[2-Cyano-4-hydroxycyclohexyl]-3-[(2-fluoropyridin-4-yl)amino]-1H-pyrazole-4-carboxamide;
1-[2-cyanocyclohexyl]-3-({4-[(trifluoromethyl)sulfonyl]phenyl}amino)-1H-pyrazole-4-carboxamide;
1-[(2-cyanocyclohexyl]-3-[(2-fluoropyridin-4-yl)amino]-1H-pyrazole-4-carboxamide;
tert-butyl 4-[4-carbamoyl-3-({4-[(trifluoromethyl)sulfonyl]phenyl}amino)-1H-pyrazol-1-yl]-3-cyanocyclohexanecarboxylate;
1-[2-Cyanocyclohexyl]-3-{[2-(trifluoromethyl)pyridin-4-yl]amino}-1H-pyrazole-4-carboxamide;
1-[2-Cyanocyclohexyl]-3-{[2-(trifluoromethyl)pyridin-4-yl]amino}-1H-pyrazole-4-carboxamide;
1-[2-cyanocyclohexyl]-3-{[4-(methylcarbamoyl)phenyl]amino}-1H-pyrazole-4-carboxamide;
1-[2-cyanocyclohexyl]-3-[(4-cyanophenyl)amino]-1H-pyrazole-4-carboxamide;
1-[2-cyanocyclohexyl]-3-{[4-(3-methyl-1,2,4-oxadiazol-5-yl)phenyl]amino}-1H-pyrazole-4-carboxamide;
3-[(2-chloropyridin-4-yl)amino]-1-[2-cyanocyclohexyl]-1H-pyrazole-4-carboxamide;
1-[2-cyanocyclohexyl]-3-{[3-fluoro-4-(methylsulfonyl)phenyl]amino}-1H-pyrazole-4-carboxamide;

1-[2-cyanocyclohexyl]-3-({4-[(difluoromethyl)sulfonyl]phenyl}amino)-1H-pyrazole-4-carboxamide;
1-[(2-cyanocyclohexyl]-3-{[4-(ethylsulfonyl)phenyl]amino}-1H-pyrazole-4-carboxamide;
1-[2-cyanocyclohexyl]-3-[(2-oxo-1,2,3,4-tetrahydroquinolin-6-yl)amino]-1H-pyrazole-4-carboxamide;
1-[2-cyanocyclohexyl]-3-({4-[(2,2,2-trifluoroethyl)sulfonyl]phenyl}amino)-1H-pyrazole-4-carboxamide;
1-[2-cyanocyclohexyl]-3-{[4-(methylcarbamoyl)phenyl]amino}-1H-pyrazole-4-carboxamide;
1-[2-cyanocyclohexyl]-3-[(4-fluorophenyl)amino]-1H-pyrazole-4-carboxamide;
1-[2-cyanocyclohexyl]-3-[(4-cyanophenyl)amino]-1H-pyrazole-4-carboxamide;
1-[2-cyanocyclohexyl]-3-({3-(hydroxymethyl)-4-[(trifluoromethyl)sulfonyl]phenyl}amino)-1H-pyrazole-4-carboxamide;
1-[2-cyanocyclohexyl]-3-[(4-fluorophenyl)amino]-1H-pyrazole-4-carboxamide;
1-[2-cyanocyclohexyl]-3-[(6-fluoropyridin-3-yl)amino]-1H-pyrazole-4-carboxamide;
1-[2-cyanocyclohexyl]-3-{[1-oxo-2-(2,2,2-trifluoroethyl)-2,3-dihydro-1H-isoindol-5-yl]amino}-1H-pyrazole-4-carboxamide;
1-[2-cyanocyclohexyl]-3-{[1-oxo-2-(2,2,2-trifluoroethyl)-2,3-dihydro-1H-isoindol-5-yl]amino}-1H-pyrazole-4-carboxamide;
1-[2-cyanocyclohexyl]-3-{[2-(1-methyl-1H-pyrazol-4-yl)pyridin-4-yl]amino}-1H-pyrazole-4-carboxamide;
1-[2-cyanocyclohexyl]-3-[(6-fluoropyridin-3-yl)amino]-1H-pyrazole-4-carboxamide;
1-[2-cyanocyclohexyl]-3-[(4-formylphenyl)amino]-1H-pyrazole-4-carboxamide;
3-[(4-bromophenyl)amino]-1-[2-cyanocyclohexyl]-1H-pyrazole-4-carboxamide;
3-[(4-acetylphenyl)amino]-1-[2-cyanocyclohexyl]-1H-pyrazole-4-carboxamide;
1-[2-cyanocyclohexyl]-3-({4-[3,3,3-trifluoro-2-hydroxy-1,1-dimethylpropyl]phenyl}amino)-1H-pyrazole-4-carboxamide;
1-[2-cyanocyclohexyl]-3-({4-[3,3,3-trifluoro-2-hydroxy-1,1-dimethylpropyl]phenyl}amino)-1H-pyrazole-4-carboxamide;
1-[2-cyanocyclohexyl]-3-({3-fluoro-4-[3,3,3-trifluoro-2-hydroxy-1,1-dimethylpropyl]phenyl}amino)-1H-pyrazole-4-carboxamide;
1-[2-cyanocyclohexyl]-3-({6-[2,2,2-trifluoro-1-hydroxy-1-methylethyl]pyridin-3-yl}amino)-1H-pyrazole-4-carboxamide;
1-[2-cyanocyclohexyl]-3-({4-[2,2,2-trifluoro-1-hydroxyethyl]phenyl}amino)-1H-pyrazole-4-carboxamide;
1-[2-cyanocyclohexyl]-3-({6-[2,2-difluoro-1-hydroxyethyl]pyridin-3-yl}amino)-1H-pyrazole-4-carboxamide;
1-[2-cyanocyclohexyl]-3-({6-[2,2-difluoro-1-hydroxy-1-methylethyl]pyridin-3-yl}amino)-1H-pyrazole-4-carboxamide;
1-[2-cyanocyclohexyl]-3-[(7-fluoroquinolin-3-yl)amino]-1H-pyrazole-4-carboxamide;
3-[(6-chloropyridin-3-yl)amino]-1-[2-cyanocyclohexyl]-1H-pyrazole-4-carboxamide;
2-[4-({4-carbamoyl-1-[2-cyanocyclohexyl]-1H-pyrazol-3-yl}amino)phenyl]-2-methylpropanoic acid;
3-[(6-chloropyridin-3-yl)amino]-1-[(2-cyanocyclohexyl]-1H-pyrazole-4-carboxamide;
3-[(6-chloropyridin-3-yl)amino]-1-[(1R,2R)-2-cyanocyclohexyl]-1H-pyrazole-4-carboxamide;
3-[(6-chloropyridin-3-yl)amino]-1-[(1S,2S)-2-cyanocyclohexyl]-1H-pyrazole-4-carboxamide;
3-{[4-(aminomethyl)phenyl]amino}-1-[2-cyanocyclohexyl]-1H-pyrazole-4-carboxamide;
1-[2-cyanocyclohexyl]-3-({6-[2,2,2-trifluoro-1-hydroxyethyl]pyridin-3-yl}amino)-1H-pyrazole-4-carboxamide;
3-[(5-chloropyridin-3-yl)amino]-1-[(2-cyanocyclohexyl]-1H-pyrazole-4-carboxamide;
1-[2-cyanocyclohexyl]-3-[(6-fluoroquinolin-3-yl)amino]-1H-pyrazole-4-carboxamide;
1-[(2-cyanocyclohexyl]-3-[(3,4-dichlorophenyl)amino]-1H-pyrazole-4-carboxamide;
1-[2-cyanocyclohexyl]-3-({6-[2,2,2-trifluoro-1-hydroxyethyl]pyridin-3-yl}amino)-1H-pyrazole-4-carboxamide;
3-[(3-chloro-5-fluorophenyl)amino]-1-[2-cyanocyclohexyl]-1H-pyrazole-4-carboxamide;
2-[4-({4-carbamoyl-1-[2-cyanocyclohexyl]-1H-pyrazol-3-yl}amino)phenyl]-2-methylpropanoic acid;
1-[2-cyanocyclohexyl]-3-(pyridazin-4-ylamino)-1H-pyrazole-4-carboxamide;
1-[2-cyanocyclohexyl]-3-[(3,5-dichlorophenyl)amino]-1H-pyrazole-4-carboxamide;
1-[2-cyanocyclohexyl]-3-{[6-(difluoromethyl)pyridin-3-yl]amino}-1H-pyrazole-4-carboxamide;
3-[(4-chloro-3-fluorophenyl)amino]-1-[2-cyanocyclohexyl]-1H-pyrazole-4-carboxamide;
1-[2-cyanocyclohexyl]-3-[(4-{1,1-dimethyl-2-oxo-2-[(2,2,2-trifluoroethyl)amino]ethyl}phenyl)amino]-1H-pyrazole-4-carboxamide;
3-[(3-chloro-4-fluorophenyl)amino]-1-[2-cyanocyclohexyl]-1H-pyrazole-4-carboxamide;
1-[2-cyanocyclohexyl]-3-{[6-(difluoromethyl)pyridin-3-yl]amino}-1H-pyrazole-4-carboxamide;
3-[(6-chloroquinolin-3-yl)amino]-1-[2-cyanocyclohexyl]-1H-pyrazole-4-carboxamide;
3-[(7-chloroquinolin-3-yl)amino]-1-[2-cyanocyclohexyl]-1H-pyrazole-4-carboxamide;
1-[2-cyanocyclohexyl]-3-[(3-hydroxy-1,1-dioxido-2,3-dihydro-1-benzothiophen-5-yl)amino]-1H-pyrazole-4-carboxamide;
1-[2-cyanocyclohexyl]-3-[(1,1-dioxido-1-benzothiophen-5-yl)amino]-1H-pyrazole-4-carboxamide;
1-[(2-cyanocyclohexyl]-3-({4-[(difluoromethyl)sulfonyl]-3-(hydroxymethyl)phenyl}amino)-1H-pyrazole-4-carboxamide;
1-[2-cyanocyclohexyl]-3-({4-[(fluoromethyl)sulfonyl]phenyl}amino)-1H-pyrazole-4-carboxamide;
1-[2-cyanocyclohexyl]-3-({4-[(cyclopropylmethyl)sulfamoyl]phenyl}amino)-1H-pyrazole-4-carboxamide;
1-[2-cyanocyclohexyl]-3-{[4-(pyridin-2-ylsulfamoyl)phenyl]amino}-1H-pyrazole-4-carboxamide;
1-[2-cyanocyclohexyl]-3-({4-[(2-morpholin-4-ylethyl)sulfamoyl]phenyl}amino)-1H-pyrazole-4-carboxamide;
3-({4-[(4-benzylpiperidin-1-yl)sulfonyl]phenyl}amino)-1-[2-cyanocyclohexyl]-1H-pyrazole-4-carboxamide;
methyl 5-({4-carbamoyl-1-[2-cyanocyclohexyl]-1H-pyrazol-3-yl}amino)pyridine-2-carboxylate;
N-tert-butyl-5-({4-carbamoyl-1-[2-cyanocyclohexyl]-1H-pyrazol-3-yl}amino)pyridine-3-carboxamide;
methyl 5-({4-carbamoyl-1-[2-cyanocyclohexyl]-1H-pyrazol-3-yl}amino)pyridine-3-carboxylate;
1-[2-cyanocyclohexyl]-3-[(5-methylpyridin-3-yl)amino]-1H-pyrazole-4-carboxamide;
1-[2-cyanocyclohexyl]-3-[(5-cyanopyridin-3-yl)amino]-1H-pyrazole-4-carboxamide;
1-[2-cyanocyclohexyl]-3-[(6-cyanopyridin-3-yl)amino]-1H-pyrazole-4-carboxamide;

1-[2-cyanocyclohexyl]-3-[(7-oxo-6,7-dihydro-5H-pyrrolo[3,4-b]pyridin-3-yl)amino]-1H-pyrazole-4-carboxamide;
1-[2-cyanocyclohexyl]-3-[(6-cyano-5-methylpyridin-3-yl)amino]-1H-pyrazole-4-carboxamide;
methyl 5-({4-carbamoyl-1-[2-cyanocyclohexyl]-1H-pyrazol-3-yl}amino)-3-methylpyridine-2-carboxylate;
1-[2-cyanocyclohexyl]-3-[(6-cyano-5-fluoropyridin-3-yl)amino]-1H-pyrazole-4-carboxamide;
1-[2-cyanocyclohexyl]-3-[(6-cyclopropylpyridin-3-yl)amino]-1H-pyrazole-4-carboxamide;
1-[2-cyanocyclohexyl]-3-{[4-(pyridin-4-ylsulfamoyl)phenyl]amino}-1H-pyrazole-4-carboxamide;
1-[2-cyanocyclohexyl]-3-{[4-(cyclohexylsulfamoyl)phenyl]amino}-1H-pyrazole-4-carboxamide;
3-{[4-(benzylsulfamoyl)phenyl]amino}-1-[2-cyanocyclohexyl]-1H-pyrazole-4-carboxamide;
1-[2-cyanocyclohexyl]-3-({4-[(pyridin-3-ylmethyl)sulfamoyl]phenyl}amino)-1H-pyrazole-4-carboxamide;
1-[2-cyanocyclohexyl]-3-({4-[(pyridin-2-ylmethyl)sulfamoyl]phenyl}amino)-1H-pyrazole-4-carboxamide;
1-[2-cyanocyclohexyl]-3-({4-[(pyridin-4-ylmethyl)sulfamoyl]phenyl}amino)-1H-pyrazole-4-carboxamide;
1-[2-cyanocyclohexyl]-3-({4-[(2-pyrrolidin-1-ylethyl)sulfamoyl]phenyl}amino)-1H-pyrazole-4-carboxamide;
1-[2-cyanocyclohexyl]-3-({4-[(2,6-dimethylphenyl)sulfamoyl]phenyl}amino)-1H-pyrazole-4-carboxamide;
3-({4-[(4-acetylpiperazin-1-yl)sulfonyl]phenyl}amino)-1-[2-cyanocyclohexyl]-1H-pyrazole-4-carboxamide;
3-({4-[(4-chlorobenzyl)sulfamoyl]phenyl}amino)-1-[2-cyanocyclohexyl]-1H-pyrazole-4-carboxamide;
1-[2-cyanocyclohexyl]-3-{[4-(1,4-dioxa-8-azaspiro[4.5]dec-8-ylsulfonyl)phenyl]amino}-1H-pyrazole-4-carboxamide;
1-[2-cyanocyclohexyl]-3-({4-[(1-methylethyl)sulfamoyl]phenyl}amino)-1H-pyrazole-4-carboxamide;
1-[2-cyanocyclohexyl]-3-{[4-(quinolin-7-ylsulfamoyl)phenyl]amino}-1H-pyrazole-4-carboxamide;
1-[2-cyanocyclohexyl]-3-[(4-{[4-(trifluoromethyl)phenyl]sulfamoyl}phenyl)amino]-1H-pyrazole-4-carboxamide;
1-[2-cyanocyclohexyl]-3-[(4-{[4-(trifluoromethyl)benzyl]sulfamoyl}phenyl)amino]-1H-pyrazole-4-carboxamide;
1-[2-cyanocyclohexyl]-3-[(4-{[4-(3-methoxyphenyl)piperazin-1-yl]sulfonyl}phenyl)amino]-1H-pyrazole-4-carboxamide;
1-[2-cyanocyclohexyl]-3-({4-[(2-methoxyethyl)sulfamoyl]phenyl}amino)-1H-pyrazole-4-carboxamide;
1-[2-cyanocyclohexyl]-3-{[4-(morpholin-4-ylsulfonyl)phenyl]amino}-1H-pyrazole-4-carboxamide;
1-[2-cyanocyclohexyl]-3-[(3,4-difluorophenyl)amino]-1H-pyrazole-4-carboxamide;
1-[2-cyanocyclohexyl]-3-{[6-(trifluoromethyl)pyridin-3-yl]amino}-1H-pyrazole-4-carboxamide;
1-[2-cyanocyclohexyl]-3-{[4-(difluoromethoxy)phenyl]amino}-1H-pyrazole-4-carboxamide;
3-[(4-chlorophenyl)amino]-1-[2-cyanocyclohexyl]-1H-pyrazole-4-carboxamide;
1-[2-cyanocyclohexyl]-3-{[4-(trifluoromethyl)phenyl]amino}-1H-pyrazole-4-carboxamide;
3-[(4-chlorophenyl)amino]-1-[2-cyanocyclohexyl]-1H-pyrazole-4-carboxamide;
1-[2-cyanocyclohexyl]-3-{[6-(trifluoromethyl)pyridin-3-yl]amino}-1H-pyrazole-4-carboxamide;
1-(2-Cyano-5-hydroxy-2-methylcyclohexyl)-3-((4-fluorophenyl)amino)-1H-pyrazole-4-carboxamide;
1-(2-cyano-5-fluoro-2-methylcyclohexyl)-3-((4-fluorophenyl)amino)-1H-pyrazole-4-carboxamide;
1-2-cyano-2-methylcyclohexyl)-3-((4-fluorophenyl)amino)-1H-pyrazole-4-carboxamide;
1-[2-Cyanocyclohexyl]-3-[(1,1-dioxido-2,3-dihydro-1-benzothiophen-5-yl)amino]-1H-pyrazole-4-carboxamide;
1-[(2-Cyanocyclohexyl)-3-{[5-(1-methyl-1H-pyrazol-4-yl)pyridin-3-yl]amino}-1H-pyrazole-4-carboxamide;
1-[(2-cyanocyclohexyl)-3-{[6-(1-methyl-1H-pyrazol-4-yl)pyridin-3-yl]amino}-1H-pyrazole-4-carboxamide;
1-[2-cyanocyclohexyl]-3-{[6-(1H-pyrazol-4-yl)pyridin-3-yl]amino}-1H-pyrazole-4-carboxamide;
1-[2-Cyano-4-fluorocyclohexyl]-3-(phenylamino)-1H-pyrazole-4-carboxamide;
1-[6-cyanocyclohex-3-en-1-yl]-3-(phenylamino)-1H-pyrazole-4-carboxamide;
1-[2-Cyano-6-fluorocyclohexyl]-3-(phenylamino)-1H-pyrazole-4-carboxamide;
1-(2-cyano-4(R)-hydroxycyclohexyl)-3-((4-(trifluoromethoxy)phenyl)amino)-1H-pyrazole-4-carboxamide;
1-[2-cyano-4-hydroxycyclohexyl]-3-{[6-(difluoromethoxy)pyridin-3-yl]amino}-1H-pyrazole-4-carboxamide;
3-[(4-chloro-3-fluorophenyl)amino]-1-[2-cyano-4-hydroxycyclohexyl]-1H-pyrazole-4-carboxamide;
1-[2-cyano-4-hydroxycyclohexyl]-3-[(4-cyanophenyl)amino]-1H-pyrazole-4-carboxamide;
1-[2-cyano-4-hydroxycyclohexyl]-3-{[4-(trifluoromethyl)phenyl]amino}-1H-pyrazole-4-carboxamide;
1-[2-cyano-4-hydroxycyclohexyl]-3-[(3,4-dichlorophenyl)amino]-1H-pyrazole-4-carboxamide;
1-[2-cyano-4-hydroxycyclohexyl]-3-({4-[(1S or 1R)-2,2,2-trifluoro-1-hydroxy-1-methylethyl]phenyl}amino)-1H-pyrazole-4-carboxamide;
1-[2-cyano-4-hydroxycyclohexyl]-3-{[4-(2-fluoro-1,1-dimethylethyl)phenyl]amino}-1H-pyrazole-4-carboxamide;
1-[2-cyano-4-hydroxycyclohexyl]-3-{[6-(trifluoromethyl)pyridin-3-yl]amino}-1H-pyrazole-4-carboxamide;
1-[2-cyano-4-hydroxycyclohexyl]-3-{[4-(1-methoxy-1-methylethyl)phenyl]amino}-1H-pyrazole-4-carboxamide;
3-[(6-chloropyridin-3-yl)amino]-1-[2-cyano-4-hydroxycyclohexyl]-1H-pyrazole-4-carboxamide;
1-[2-cyano-4-hydroxycyclohexyl]-3-({4-[2,2,2-trifluoro-1-hydroxyethyl]phenyl}amino)-1H-pyrazole-4-carboxamide;
1-[2-cyano-4-hydroxycyclohexyl]-3-[(4-cyclopropylphenyl)amino]-1H-pyrazole-4-carboxamide;
1-[2-cyano-4-hydroxycyclohexyl]-3-{[6-(difluoromethyl)pyridin-3-yl]amino}-1H-pyrazole-4-carboxamide;
1-[2-cyano-4-hydroxycyclohexyl]-3-({4-[(1R)-2,2,2-trifluoro-1-hydroxy-1-methylethyl]phenyl}amino)-1H-pyrazole-4-carboxamide;
1-[2-cyano-4-hydroxycyclohexyl]-3-{[4-(3-methyloxetan-3-yl)phenyl]amino}-1H-pyrazole-4-carboxamide;
1-[2-cyano-4-hydroxycyclohexyl]-3-[(2-fluoropyridin-4-yl)amino]-1H-pyrazole-4-carboxamide;
3-[(4-chlorophenyl)amino]-1-[2-cyano-4-hydroxycyclohexyl]-1H-pyrazole-4-carboxamide;
1-[2-cyano-4-hydroxycyclohexyl]-3-{[3-fluoro-4-(trifluoromethyl)phenyl]amino}-1H-pyrazole-4-carboxamide;
1-[2-cyano-4-hydroxycyclohexyl]-3-{[4-(trifluoromethyl)phenyl]amino}-1H-pyrazole-4-carboxamide;
1-[2-cyano-4-hydroxycyclohexyl]-3-[(2-fluoropyridin-4-yl)amino]-1H-pyrazole-4-carboxamide;
1-[2-cyano-4-hydroxycyclohexyl]-3-{[4-(difluoromethoxy)phenyl]amino}-1H-pyrazole-4-carboxamide;
3-[(4-chlorophenyl)amino]-1-[2-cyano-4-hydroxycyclohexyl]-1H-pyrazole-4-carboxamide;
1-[2-cyano-4-hydroxycyclohexyl]-3-{[4-(methylsulfonyl)phenyl]amino}-1H-pyrazole-4-carboxamide;

1-[2-cyano-4-hydroxycyclohexyl]-3-(phenylamino)-1H-pyrazole-4-carboxamide;

1-[2-Cyano-4-(cyclopropylmethoxy)cyclohexyl]-3-[(2-fluoropyridin-4-yl)amino]-1H-pyrazole-4-carboxamide;

1-[2-cyano-4-(cyclopropylmethoxy)cyclohexyl]-3-({4-[(1R or 1S)-2,2,2-trifluoro-1-hydroxyethyl]phenyl}amino)-1H-pyrazole-4-carboxamide;

1-[2-cyano-4-(cyclopropylmethoxy)cyclohexyl]-3-[(4-fluorophenyl)amino]-1H-pyrazole-4-carboxamide;

1-[(4-[4-carbamoyl-3-({4-[(trifluoromethyl)sulfonyl]phenyl}amino)-1H-pyrazol-1-yl]-3-cyano-N,N-dimethylcyclohexanaminium trifluoroacetate;

1-[2-cyano-4-(methylamino)cyclohexyl]-3-[(4-fluorophenyl)amino]-1H-pyrazole-4-carboxamide;

1-[2-cyano-4-(ethylamino)cyclohexyl]-3-({4-[(trifluoromethyl)sulfonyl]phenyl}amino)-1H-pyrazole-4-carboxamide;

1-[2-cyano-4-(methylamino)cyclohexyl]-3-({4-[(trifluoromethyl)sulfonyl]phenyl}amino)-1H-pyrazole-4-carboxamide, 1-[2-cyano-4-(dimethylamino)cyclohexyl]-3-({4-[(trifluoromethyl)sulfonyl]phenyl}amino)-1H-pyrazole-4-carboxamide;

1-[2-cyano-4-(cyclopropylamino)cyclohexyl]-3-({4-[(trifluoromethyl)sulfonyl]phenyl}amino)-1H-pyrazole-4-carboxamide;

1-{2-cyano-4-[(2,2,2-trifluoroethyl)amino]cyclohexyl}-3-(({4-[(trifluoromethyl)sulfonyl]phenyl}amino)-1H-pyrazole-4-carboxamide;

1-{2-cyano-4-[(2,2,2-trifluoroethyl)amino]cyclohexyl}-3-(({4-[(difluoromethyl)sulfonyl]phenyl}amino)-1H-pyrazole-4-carboxamide;

1-[2-cyano-4-(morpholin-4-yl)cyclohexyl]-3-({4-[(trifluoromethyl)sulfonyl]phenyl)amino)-1H-pyrazole-4-carboxamide;

1-{(2-cyano-4-[(2,2-difluoroethyl)amino]cyclohexyl}-3-({4-[(trifluoromethyl)sulfonyl]phenyl)amino)-1H-pyrazole-4-carboxamide;

1-{2-cyano-4-[(2-hydroxyethyl)amino]cyclohexyl}-3-({4-[(trifluoromethyl)sulfonyl]phenyl)amino)-1H-pyrazole-4-carboxamide;

1-{2-cyano-4-[(2-methoxyethyl)amino]cyclohexyl}-3-({4-[(trifluoromethyl)sulfonyl]phenyl)amino)-1H-pyrazole-4-carboxamide;

1-{2-cyano-4-[(2-fluoroethyl)amino]cyclohexyl}-3-({4-[(trifluoromethyl)sulfonyl]phenyl)amino)-1H-pyrazole-4-carboxamide;

1-{2-cyano-4-[(2-fluoroethyl)amino]cyclohexyl}-3-({4-[(trifluoromethyl)sulfonyl]phenyl]amino)-1H-pyrazole-4-carboxamide;

1-[4-(Azetidin-1-yl)-2-cyanocyclohexyl]-3-{[6-(difluoromethoxy)pyridin-3-yl]amino}-1H-pyrazole-4-carboxamide;

1-((4-(Azetidin-1-yl)-2-cyanocyclohexyl)-3-(phenylamino)-1H-pyrazole-4-carboxamide;

1-(4-(tert-butyl(methyl)amino)-2-cyanocyclohexyl)-3-((4-chlorophenyl)amino)-1H-pyrazole-4-carboxamide;

1-{2-cyano-4-[3-(1-hydroxy-1-methylethyl)azetidin-1-yl]cyclohexyl}-3-{[4-(trifluoromethyl)phenyl]amino}-1H-pyrazole-4-carboxamide;

1-[2-cyano-4-{[1-cyclopropylethyl]amino}cyclohexyl]-3-{[6-(trifluoromethyl)pyridin-3-yl]amino}-1H-pyrazole-4-carboxamide;

1-{2-cyano-4-[(2,4-dimethylazetidin-1-yl]cyclohexyl}-3-{[4-(trifluoromethyl)phenyl]amino}-1H-pyrazole-4-carboxamide;

1-{2-cyano-4-[(cyclopropylmethyl)amino]cyclohexyl}-3-{[4-(trifluoromethyl)phenyl]amino}-1H-pyrazole-4-carboxamide;

1-[4-azetidin-1-yl-2-cyanocyclohexyl]-3-{[6-(trifluoromethyl)pyridin-3-yl]amino}-1H-pyrazole-4-carboxamide;

1-[2-cyano-4-(dimethylamino)cyclohexyl]-3-{[6-(difluoromethoxy)pyridin-3-yl]amino}-1H-pyrazole-4-carboxamide;

1-[2-cyano-4-{[(1S)-1-cyclopropylethyl]amino}cyclohexyl]-3-{[6-(difluoromethoxy)pyridin-3-yl]amino}-1H-pyrazole-4-carboxamide;

1-[2-cyano-4-(dimethylamino)cyclohexyl]-3-{[6-(difluoromethoxy)pyridin-3-yl]amino}-1H-pyrazole-4-carboxamide;

1-{2-cyano-4-[6-(hydroxymethyl)-3-azabicyclo[3.1.0]hex-3-yl]cyclohexyl}-3-{[4-(trifluoromethyl)phenyl]amino}-1H-pyrazole-4-carboxamide;

1-[2-cyano-4-{[(3-methyloxetan-3-yl)methyl]amino}cyclohexyl]-3-{[4-(trifluoromethyl)phenyl]amino}-1H-pyrazole-4-carboxamide;

1-[4-(2-azaspiro[3.3]hept-2-yl)-2-cyanocyclohexyl]-3-{[4-(trifluoromethyl)phenyl]amino}-1H-pyrazole-4-carboxamide;

1-[2-cyano-4-(dimethylamino)cyclohexyl]-3-{[6-(trifluoromethyl)pyridin-3-yl]amino}-1H-pyrazole-4-carboxamide;

1-[2-cyano-4-{[(1-hydroxycyclopropyl)methyl]amino}cyclohexyl]-3-{[4-(trifluoromethyl)phenyl]amino}-1H-pyrazole-4-carboxamide;

1-[4-azetidin-1-yl-2-cyanocyclohexyl]-3-[(4-chloro-3-fluorophenyl)amino]-1H-pyrazole-4-carboxamide;

3-[(4-chloro-3-fluorophenyl)amino]-1-2-cyano-4-(dimethylamino)cyclohexyl]-1H-pyrazole-4-carboxamide;

3-[(4-chloro-3-fluorophenyl)amino]-1-[(2-cyano-4-(methylamino)cyclohexyl]-1H-pyrazole-4-carboxamide;

3-[(4-chlorophenyl)amino]-1-[2-cyano-4-(methylamino)cyclohexyl]-1H-pyrazole-4-carboxamide;

1-[2-cyano-4-(3,3-dimethylazetidin-1-yl)cyclohexyl]-3-({4-[2,2,2-trifluoro-1-hydroxyethyl]phenyl}amino)-1H-pyrazole-4-carboxamide;

1-[4-azetidin-1-yl-2-cyanocyclohexyl]-3-({4-[2,2,2-trifluoro-1-hydroxyethyl]phenyl}amino)-1H-pyrazole-4-carboxamide;

3-[(4-chloro-3-fluorophenyl)amino]-1-[2-cyano-4-{[1-cyclopropylethyl]amino}cyclohexyl]-1H-pyrazole-4-carboxamide;

1-[4-azetidin-1-yl-2-cyanocyclohexyl]-3-({4-[(1R)-2,2,2-trifluoro-1-hydroxy-1-methylethyl]phenyl}amino)-1H-pyrazole-4-carboxamide;

1-[4-azetidin-1-yl-2-cyanocyclohexyl]-3-{[6-(difluoromethyl)pyridin-3-yl]amino}-1H-pyrazole-4-carboxamide;

1-[4-(2-azaspiro[3.3]hept-2-yl)-2-cyanocyclohexyl]-3-({4-[2,2,2-trifluoro-1-hydroxyethyl]phenyl}amino)-1H-pyrazole-4-carboxamide;

1-[4-(tert-butylamino)-2-cyanocyclohexyl]-3-({4-[2,2,2-trifluoro-1-hydroxyethyl]phenyl}amino)-1H-pyrazole-4-carboxamide;

1-[4-azetidin-1-yl-2-cyanocyclohexyl]-3-{[4-(2,2,2-trifluoroethyl)phenyl]amino}-1H-pyrazole-4-carboxamide;

1-[2-cyano-4-(dimethylamino)cyclohexyl]-3-{[4-(trifluoromethoxy)phenyl]amino}-1H-pyrazole-4-carboxamide;

1-[2-cyano-4-{[1-cyclopropylethyl]amino}cyclohexyl]-3-{[4-(trifluoromethoxy)phenyl]amino}-1H-pyrazole-4-carboxamide;

1-[4-azetidin-1-yl-2-cyanocyclohexyl]-3-{[4-(trifluoromethoxy)phenyl]amino}-1H-pyrazole-4-carboxamide;

1-[4-(2-azaspiro[3.3]hept-2-yl)-2-cyanocyclohexyl]-3-({4-[2,2,2-trifluoro-1-hydroxyethyl]phenyl}amino)-1H-pyrazole-4-carboxamide;

1-[2-cyano-4-(3,3-dimethylazetidin-1-yl)cyclohexyl]-3-({4-[2,2,2-trifluoro-1-hydroxy-1-methylethyl]phenyl}amino)-1H-pyrazole-4-carboxamide;

3-[(3-chloro-4-fluorophenyl)amino]-1-{2-cyano-4-[(2,2-difluoroethyl)amino]cyclohexyl}-1H-pyrazole-4-carboxamide;

1-[(4-azetidin-1-yl-2-cyanocyclohexyl]-3-[(4-formylphenyl)amino]-1H-pyrazole-4-carboxamide;

3-[(4-chloro-3-fluorophenyl)amino]-1-[2-cyano-4-{[1-cyclopropylethyl]amino}cyclohexyl]-1H-pyrazole-4-carboxamide;

2-[4-({1-[(4-azetidin-1-yl-2-cyanocyclohexyl]-4-carbamoyl-1H-pyrazol-3-yl}amino)phenyl]-2-methylpropanoic acid;

2-[4-({1-[4-(2-azaspiro[3.3]hept-2-yl)-2-cyanocyclohexyl]-4-carbamoyl-1H-pyrazol-3-yl}amino)phenyl]-2-methylpropanoic acid;

1-[2-cyano-4-(oxetan-3-ylamino)cyclohexyl]-3-{[4-(2,2,2-trifluoroethyl)phenyl]amino}-1H-pyrazole-4-carboxamide;

3-[(4-acetylphenyl)amino]-1-[4-azetidin-1-yl-2-cyanocyclohexyl]-1H-pyrazole-4-carboxamide;

1-[2-cyano-4-(3,3-dimethylazetidin-1-yl)cyclohexyl]-3-({4-[2,2,2-trifluoro-1-hydroxy-1-methylethyl]phenyl}amino)-1H-pyrazole-4-carboxamide;

1-[2-cyano-4-(dimethylamino)cyclohexyl]-3-[(4-fluorophenyl)amino]-1H-pyrazole-4-carboxamide;

3-[(4-chlorophenyl)amino]-1-[2-cyano-4-(3-methylazetidin-1-yl)cyclohexyl]-1H-pyrazole-4-carboxamide;

1-[4-(benzylamino)-2-cyanocyclohexyl]-3-[(2-fluoropyridin-4-yl)amino]-1H-pyrazole-4-carboxamide;

3-[(4-chlorophenyl)amino]-1-[2-cyano-4-{[(1S)-1-cyclopropylethyl]amino}cyclohexyl]-1H-pyrazole-4-carboxamide;

1-[2-cyano-4-(3-methoxyazetidin-1-yl)cyclohexyl]-3-{[4-(trifluoromethyl)phenyl]amino}-1H-pyrazole-4-carboxamide;

1-[4-azetidin-1-yl-2-cyanocyclohexyl]-3-[(4-chlorophenyl)amino]-1H-pyrazole-4-carboxamide;

1-[4-azetidin-1-yl-2-cyanocyclohexyl]-3-[(2-fluoropyridin-4-yl)amino]-1H-pyrazole-4-carboxamide;

1-[4-azetidin-1-yl-2-cyanocyclohexyl]-3-{[4-(difluoromethoxy)phenyl]amino}-1H-pyrazole-4-carboxamide;

1-[2-cyano-4-(3-fluoroazetidin-1-yl)cyclohexyl]-3-{[4-(trifluoromethyl)phenyl]amino}-1H-pyrazole-4-carboxamide;

1-{2-cyano-4-[(2,2-difluoroethyl)amino]cyclohexyl}-3-[(2-fluoropyridin-4-yl)amino]-1H-pyrazole-4-carboxamide;

1-{2-cyano-4-[(2,2,2-trifluoroethyl)amino]cyclohexyl}-3-({4-[(trifluoromethyl)sulfonyl]phenyl}amino)-1H-pyrazole-4-carboxamide;

1-[4-azetidin-1-yl-2-cyanocyclohexyl]-3-{[4-(difluoromethoxy)phenyl]amino}-1H-pyrazole-4-carboxamide;

1-[4-azetidin-1-yl-2-cyanocyclohexyl]-3-[(4-chlorophenyl)amino]-1H-pyrazole-4-carboxamide;

1-[4-azetidin-1-yl-2-cyanocyclohexyl]-3-[(2-fluoropyridin-4-yl)amino]-1H-pyrazole-4-carboxamide;

1-{2-cyano-4-[(2,2,2-trifluoroethyl)amino]cyclohexyl}-3-[(2-fluoropyridin-4-yl)amino]-1H-pyrazole-4-carboxamide;

1-[2-cyano-4-(3-fluoroazetidin-1-yl)cyclohexyl]-3-({4-[(trifluoromethyl)sulfonyl]phenyl}amino)-1H-pyrazole-4-carboxamide;

1-{2-cyano-4-[(2,2-difluoroethyl)(methyl)amino]cyclohexyl}-3-({4-[(trifluoromethyl)sulfonyl]phenyl}amino)-1H-pyrazole-4-carboxamide;

1-{2-cyano-4-[(2,2-difluoroethyl)amino]cyclohexyl}-3-[(4-cyanophenyl)amino]-1H-pyrazole-4-carboxamide;

3-[(4-chlorophenyl)amino]-1-[2-cyano-4-(dimethylamino)cyclohexyl]-1H-pyrazole-4-carboxamide;

1-[2-cyano-4-(2-oxa-6-azaspiro[3.3]hept-6-yl)cyclohexyl]-3-{[4-(trifluoromethyl)phenyl]amino}-1H-pyrazole-4-carboxamide;

1-[2-cyano-4-(3-methylazetidin-1-yl)cyclohexyl]-3-{[4-(trifluoromethyl)phenyl]amino}-1H-pyrazole-4-carboxamide;

1-{2-cyano-4-[(2,2-difluoroethyl)amino]cyclohexyl}-3-({4-[(difluoromethyl)sulfonyl]phenyl}amino)-1H-pyrazole-4-carboxamide;

3-[(4-chlorophenyl)amino]-1-[2-cyano-4-(dimethylamino)cyclohexyl]-1H-pyrazole-4-carboxamide;

1-[2-cyano-4-(dimethylamino)cyclohexyl]-3-[(2-fluoropyridin-4-yl)amino]-1H-pyrazole-4-carboxamide;

1-[4-(2-azaspiro[3.3]hept-2-yl)-2-cyanocyclohexyl]-3-{[4-(methylsulfonyl)phenyl]amino}-1H-pyrazole-4-carboxamide;

1-[4-azetidin-1-yl-2-cyanocyclohexyl]-3-{[4-(trifluoromethyl)phenyl]amino}-1H-pyrazole-4-carboxamide;

1-[4-(2-azaspiro[3.3]hept-2-yl)-2-cyanocyclohexyl]-3-[(2-fluoropyridin-4-yl)amino]-1H-pyrazole-4-carboxamide;

1-[2-cyano-4-(3,3-dimethylazetidin-1-yl)cyclohexyl]-3-[(2-fluoropyridin-4-yl)amino]-1H-pyrazole-4-carboxamide;

1-[2-cyano-4-(dimethylamino)cyclohexyl]-3-(phenylamino)-1H-pyrazole-4-carboxamide;

1-[4-(2-azaspiro[3.3]hept-2-yl)-2-cyanocyclohexyl]-3-(phenylamino)-1H-pyrazole-4-carboxamide;

1-[2-cyano-4-(cyclopropylamino)cyclohexyl]-3-{[4-(trifluoromethyl)phenyl]amino}-1H-pyrazole-4-carboxamide;

1-[2-cyano-4-(3,3-dimethylazetidin-1-yl)cyclohexyl]-3-(phenylamino)-1H-pyrazole-4-carboxamide;

1-[2-cyano-4-(cyclopropylamino)cyclohexyl]-3-{[4-(trifluoromethyl)phenyl]amino}-1H-pyrazole-4-carboxamide;

1-[2-cyano-4-(3-methylazetidin-1-yl)cyclohexyl]-3-(phenylamino)-1H-pyrazole-4-carboxamide;

1-[2-cyano-4-(3,3-dimethylazetidin-1-yl)cyclohexyl]-3-[(2-fluoropyridin-4-yl)amino]-1H-pyrazole-4-carboxamide;

1-[4-(2-azaspiro[3.3]hept-2-yl)-2-cyanocyclohexyl]-3-[(2-fluoropyridin-4-yl)amino]-1H-pyrazole-4-carboxamide, 3-[(4-chlorophenyl)amino]-1-[2-cyano-4-(3,3-dimethylazetidin-1-yl)cyclohexyl]-1H-pyrazole-4-carboxamide;

1-[4-(2-azaspiro[3.3]hept-2-yl)-2-cyanocyclohexyl]-3-{[4-(methylsulfonyl)phenyl]amino}-1H-pyrazole-4-carboxamide;

3-[(4-chlorophenyl)amino]-1-[2-cyano-4-(6-oxa-1-azaspiro[3.3]hept-1-yl)cyclohexyl]-1H-pyrazole-4-carboxamide;

1-[2-cyano-4-(3-methoxyazetidin-1-yl)cyclohexyl]-3-({4-[(trifluoromethyl)sulfonyl]phenyl}amino)-1H-pyrazole-4-carboxamide;

1-[2-cyano-4-{[2-(methylsulfonyl)ethyl]amino}cyclohexyl]-3-({4-[(trifluoromethyl)sulfonyl]phenyl}amino)-1H-pyrazole-4-carboxamide;

1-{2-cyano-4-[(2-methoxyethyl)(methyl)amino]cyclohexyl}-3-({4-[(trifluoromethyl)sulfonyl]phenyl}amino)-1H-pyrazole-4-carboxamide;

1-[2-cyano-4-(3-hydroxyazetidin-1-yl)cyclohexyl]-3-({4-[(trifluoromethyl)sulfonyl]phenyl}amino)-1H-pyrazole-4-carboxamide;

1-[2-cyano-4-{[(1,1-dioxidotetrahydrothiophen-3-yl)methyl]amino}cyclohexyl]-3-({4-[(trifluoromethyl)sulfonyl]phenyl}amino)-1H-pyrazole-4-carboxamide;

1-{2-cyano-4-[(1,1-dioxidotetrahydrothiophen-3-yl)amino]cyclohexyl}-3-({4-[(trifluoromethyl)sulfonyl]phenyl}amino)-1H-pyrazole-4-carboxamide;

1-[2-cyano-4-{[2-(dimethylsulfamoyl)ethyl]amino}cyclohexyl]-3-({4-[(trifluoromethyl)sulfonyl]phenyl}amino)-1H-pyrazole-4-carboxamide;

1-[2-cyano-4-(oxetan-3-ylamino)cyclohexyl]-3-({4-[(trifluoromethyl)sulfonyl]phenyl}amino)-1H-pyrazole-4-carboxamide;

1-{2-cyano-4-[(2R)-2-(fluoromethyl)pyrrolidin-1-yl]cyclohexyl}-3-({4-[(trifluoromethyl)sulfonyl]phenyl}amino)-1H-pyrazole-4-carboxamide;

1-{2-cyano-4-[(3S)-3-fluoropyrrolidin-1-yl]cyclohexyl}-3-({4-[(trifluoromethyl)sulfonyl]phenyl}amino)-1H-pyrazole-4-carboxamide;

N-{4-[4-carbamoyl-3-({4-[(trifluoromethyl)sulfonyl]phenyl}amino)-1H-pyrazol-1-yl]-3-cyanocyclohexyl}glycine;

1-{2-cyano-4-[(dicyclopropylmethyl)amino]cyclohexyl}-3-({4-[(trifluoromethyl)sulfonyl]phenyl}amino)-1H-pyrazole-4-carboxamide;

1-{2-cyano-4-[(2,2-difluoroethyl)amino]cyclohexyl}-3-({4-[(trifluoromethyl)sulfonyl]phenyl}amino)-1H-pyrazole-4-carboxamide;

1-{2-cyano-4-[(3,3,3-trifluoropropyl)amino]cyclohexyl}-3-({4-[(trifluoromethyl)sulfonyl]phenyl}amino)-1H-pyrazole-4-carboxamide;

1-[4-azetidin-1-yl-2-cyanocyclohexyl]-3-({4-[(trifluoromethyl)sulfonyl]phenyl}amino)-1H-pyrazole-4-carboxamide;

1-{2-cyano-4-[methyl(3,3,3-trifluoropropyl)amino]cyclohexyl}-3-({4-[(trifluoromethyl)sulfonyl]phenyl}amino)-1H-pyrazole-4-carboxamide;

1-{2-cyano-4-[(cyclopropylmethyl)amino]cyclohexyl}-3-({4-[(trifluoromethyl)sulfonyl]phenyl}amino)-1H-pyrazole-4-carboxamide;

1-{2-cyano-4-[(1-methylethyl)amino]cyclohexyl}-3-({4-[(trifluoromethyl)sulfonyl]phenyl}amino)-1H-pyrazole-4-carboxamide;

1-[2-cyano-4-{[1-cyclopropylethyl]amino}cyclohexyl]-3-({4-[(trifluoromethyl) sulfonyl]phenyl}amino)-1H-pyrazole-4-carboxamide;

1-{2-cyano-4-[(dicyclopropylmethyl)(methyl)amino]cyclohexyl}-3-({4-[(trifluoromethyl)sulfonyl]phenyl)amino)-1H-pyrazole-4-carboxamide;

1-[2-cyano-4-(dicyclopropylamino)cyclohexyl]-3-({4-[(trifluoromethyl)sulfonyl]phenyl}amino)-1H-pyrazole-4-carboxamide;

1-[2-cyano-4-{[(1R)-1-cyclopropylethyl]amino}cyclohexyl]-3-({4-[(trifluoromethyl)sulfonyl]phenyl}amino)-1H-pyrazole-4-carboxamide;

1-[2-cyano-4-(3-methylazetidin-1-yl)cyclohexyl]-3-({4-[(trifluoromethyl)sulfonyl]phenyl}amino)-1H-pyrazole-4-carboxamide;

1-[2-cyano-4-(dimethylamino)cyclohexyl]-3-{[4-(trifluoromethyl)phenyl]amino}-1H-pyrazole-4-carboxamide;

1-[2-cyano-4-{[1-cyclopropylethyl]amino}cyclohexyl]-3-{[4-(trifluoromethyl)phenyl]amino}-1H-pyrazole-4-carboxamide;

1-[2-cyano-4-{[1-cyclopropyl-2,2,2-trifluoroethyl]amino}cyclohexyl]-3-{[4-(trifluoromethyl)phenyl]amino}-1H-pyrazole-4-carboxamide;

1-[2-cyano-4-(2,2-dimethylazetidin-1-yl)cyclohexyl]-3-{[4-(trifluoromethyl)phenyl]amino}-1H-pyrazole-4-carboxamide;

1-[(2-cyano-4-(3-hydroxy-3-methylazetidin-1-yl)cyclohexyl]-3-{[4-(trifluoromethyl)phenyl]amino}-1H-pyrazole-4-carboxamide;

1-{2-cyano-4-[3-hydroxy-3-(trifluoromethyl)azetidin-1-yl]cyclohexyl}-3-{[4-(trifluoromethyl)phenyl]amino}-1H-pyrazole-4-carboxamide;

1-[4-(tert-butylamino)-2-cyanocyclohexyl]-3-{[4-(trifluoromethyl)phenyl]amino}-1H-pyrazole-4-carboxamide;

3-[(4-chlorophenyl)amino]-1-{2-cyano-4-[(1-methylcyclopropyl)amino]cyclohexyl}-1H-pyrazole-4-carboxamide;

3-[(4-chlorophenyl)amino]-1-{2-cyano-4-[(3-methyloxetan-3-yl)amino]cyclohexyl}-1H-pyrazole-4-carboxamide;

3-[(4-chlorophenyl)amino]-1-{2-cyano-4-[(1-cyclopropyl-1-methylethyl)amino]cyclohexyl}-1H-pyrazole-4-carboxamide;

3-[(4-chlorophenyl)amino]-1-{2-cyano-4-[(2-hydroxy-1,1-dimethylethyl)amino]cyclohexyl}-1H-pyrazole-4-carboxamide;

3-[(4-chlorophenyl)amino]-1-{(2-cyano-4-[3-(1-hydroxy-1-methylethyl)azetidin-1-yl]cyclohexyl}-1H-pyrazole-4-carboxamide;

3-[(4-chlorophenyl)amino]-1-{2-cyano-4-[3-hydroxy-3-(trifluoromethyl)azetidin-1-yl]cyclohexyl}-1H-pyrazole-4-carboxamide;

1-{2-cyano-4-[(1-cyclopropyl-1-methylethyl)amino]cyclohexyl}-3-(phenylamino)-1H-pyrazole-4-carboxamide;

1-[4-(tert-butylamino)-2-cyanocyclohexyl]-3-(phenylamino)-1H-pyrazole-4-carboxamide;

1-{2-cyano-4-[(1-methylcyclopropyl)amino]cyclohexyl}-3-(phenylamino)-1H-pyrazole-4-carboxamide;

3-[(4-chlorophenyl)amino]-1-[(2-cyano-4-{[(3-methyloxetan-3-yl)methyl]amino}cyclohexyl]-1H-pyrazole-4-carboxamide;

3-[(4-chlorophenyl)amino]-1-[2-cyano-4-(tetrahydro-2H-pyran-4-ylamino)cyclohexyl]-1H-pyrazole-4-carboxamide;

3-[(4-chlorophenyl)amino]-1-[2-cyano-4-{methyl[(3-methyloxetan-3-yl)methyl]amino}cyclohexyl]-1H-pyrazole-4-carboxamide;

3-[(4-chlorophenyl)amino]-1-[2-cyano-4-{[(1-hydroxycyclopropyl)methyl]amino}cyclohexyl]-1H-pyrazole-4-carboxamide;

3-[(4-chlorophenyl)amino]-1-{2-cyano-4-[(2-hydroxy-2-methylpropyl)amino]cyclohexyl}-1H-pyrazole-4-carboxamide;

3-[(4-chlorophenyl)amino]-1-[2-cyano-4-{[1-(hydroxymethyl)cyclopropyl]amino}cyclohexyl]-1H-pyrazole-4-carboxamide;

3-[(4-chlorophenyl)amino]-1-2-cyano-4-[(2,2,2-trifluoroethyl)amino]cyclohexyl]-1H-pyrazole-4-carboxamide;

3-[(4-chlorophenyl)amino]-1-[(2-cyano-4-{[1-(trifluoromethyl)cyclopropyl]amino}cyclohexyl]-1H-pyrazole-4-carboxamide;

3-[(4-chlorophenyl)amino]-1-{2-cyano-4-[(2-methoxy-2-methylpropyl)amino]cyclohexyl}-1H-pyrazole-4-carboxamide;

3-[(4-chlorophenyl)amino]-1-{2-cyano-4-[(1-cyclopropyl-1-methylethyl)(methyl)amino]cyclohexyl}-1H-pyrazole-4-carboxamide;

1-{2-cyano-4-[(3-methyloxetan-3-yl)amino]cyclohexyl}-3-(phenylamino)-1H-pyrazole-4-carboxamide;

1-{(2-cyano-4-[(2-methoxy-1,1-dimethylethyl)amino]cyclohexyl}-3-(phenylamino)-1H-pyrazole-4-carboxamide;

3-[(4-chlorophenyl)amino]-1-{(2-cyano-4-[methyl(3-methyloxetan-3-yl)amino]cyclohexyl}-1H-pyrazole-4-carboxamide;

1-{2-cyano-4-[methyl(2,2,2-trifluoroethyl)amino]cyclohexyl}-3-[(2-fluoropyridin-4-yl)amino]-1H-pyrazole-4-carboxamide;

1-{2-cyano-4-[methyl(2,2,2-trifluoroethyl)amino]cyclohexyl}-3-[(2-fluoropyridin-4-yl)amino]-1H-pyrazole-4-carboxamide;

3-[(4-chlorophenyl)amino]-1-{2-cyano-4-[(2-methoxy-1,1-dimethylethyl)(methyl)amino]cyclohexyl}-1H-pyrazole-4-carboxamide;

3-[(4-chlorophenyl)amino]-1-{2-cyano-4-[(4-methyltetrahydro-2H-pyran-4-yl)amino]cyclohexyl}-1H-pyrazole-4-carboxamide;

3-[(4-chlorophenyl)amino]-1-{2-cyano-4-[(2-methoxyethyl)amino]cyclohexyl}-1H-pyrazole-4-carboxamide;

3-[(4-chlorophenyl)amino]-1-[(2-cyano-4-{[(1S)-2-methoxy-1-methylethyl]amino}cyclohexyl]-1H-pyrazole-4-carboxamide;

3-[(4-chlorophenyl)amino]-1-{2-cyano-4-[(2-methoxyethyl)(methyl)amino]cyclohexyl}-1H-pyrazole-4-carboxamide;

3-[(4-chlorophenyl)amino]-1-[2-cyano-4-{[2-methoxy-1-methylethyl](methyl)amino}cyclohexyl]-1H-pyrazole-4-carboxamide;

3-[(4-chlorophenyl)amino]-1-[2-cyano-4-{[(1S or 1R)-2-methoxy-1-methylethyl](methyl)amino}cyclohexyl]-1H-pyrazole-4-carboxamide;

4-{4-Carbamoyl-3-[(4-fluorophenyl)amino]-1H-pyrazol-1-yl}-3-cyanocyclohexanaminium trifluoroacetate;

1-{2-Cyano-4-[methyl(oxetan-3-yl)amino]cyclohexyl}-3-{[4-(trifluoromethyl)phenyl]amino}-1H-pyrazole-4-carboxamide;

1-{2-cyano-4-[(cyclopropylmethyl)(methyl)amino]cyclohexyl}-3-{[4-(trifluoromethyl)phenyl]amino}-1H-pyrazole-4-carboxamide;

1-[2-cyano-4-({[3-(1-hydroxy-1-methylethyl)cyclobutyl]methyl}amino)cyclohexyl]-3-{[4-(trifluoromethyl)phenyl]amino}-1H-pyrazole-4-carboxamide;

1-[(2-cyano-4-(spiro[3.4]oct-2-ylamino)cyclohexyl]-3-{[4-(trifluoromethyl)phenyl]amino}-1H-pyrazole-4-carboxamide;

1-{2-cyano-4-[cyclobutyl(cyclopropylmethyl)amino]cyclohexyl}-3-{[4-(trifluoromethyl)phenyl]amino}-1H-pyrazole-4-carboxamide;

1-{2-cyano-4-[(2-methylpropyl)amino]cyclohexyl}-3-{[4-(trifluoromethyl)phenyl]amino}-1H-pyrazole-4-carboxamide;

1-{2-cyano-4-[cyclobutyl(methyl)amino]cyclohexyl}-3-{[4-(trifluoromethyl)phenyl]amino}-1H-pyrazole-4-carboxamide;

1-{2-cyano-4-[(cyclopropylmethyl)(2-methylpropyl)amino]cyclohexyl}-3-{[4-(trifluoromethyl)phenyl]amino}-1H-pyrazole-4-carboxamide;

1-{2-cyano-4-[(cyclopropylmethyl)(oxetan-3-yl)amino]cyclohexyl}-3-{[4-(trifluoromethyl)phenyl]amino}-1H-pyrazole-4-carboxamide;

1-{(2-cyano-4-[(2,6-difluorobenzyl)amino]cyclohexyl}-3-{[4-(trifluoromethyl)phenyl]amino}-1H-pyrazole-4-carboxamide;

1-[(2-cyano-4-cyclobutylamino)cyclohexyl]-3-{[4-(trifluoromethyl)phenyl]amino}-1H-pyrazole-4-carboxamide;

1-{4-[bis(cyclopropylmethyl)amino]-2-cyanocyclohexyl}-3-{[4-(trifluoromethyl)phenyl]amino}-1H-pyrazole-4-carboxamide;

1-{2-cyano-4-[(cyclobutylmethyl)amino]cyclohexyl}-3-{[4-(trifluoromethyl)phenyl]amino}-1H-pyrazole-4-carboxamide;

1-[2-cyano-4-(oxetan-3-ylamino)cyclohexyl]-3-{[4-(trifluoromethyl)phenyl]amino}-1H-pyrazole-4-carboxamide;

1-(4-(4-carbamoyl-3-((4-(trifluoromethyl)phenyl)amino)-1H-pyrazol-1-yl)-3-cyanocyclohexyl)-1-methylazetidin-1-ium 2,2,2-trifluoroacetate;

1-[4-{4-carbamoyl-3-[(4-chlorophenyl)amino]-1H-pyrazol-1-yl}-3-cyanocyclohexyl]-1-methylazetidinium;

1-[4-{4-carbamoyl-3-[(4-chlorophenyl)amino]-1H-pyrazol-1-yl}-3-cyanocyclohexyl]-1-ethylazetidinium;

1-[4-{4-carbamoyl-3-[(4-chlorophenyl)amino]-1H-pyrazol-1-yl}-3-cyanocyclohexyl]-1,3,3-trimethylazetidinium;

1-[4-{4-carbamoyl-3-[(4-chlorophenyl)amino]-1H-pyrazol-1-yl}-3-cyanocyclohexyl]-1-(cyclopropylmethyl)azetidinium;

3-[(4-Chloro-3-fluorophenyl)amino]-1-[2-cyano-4-cyclopropyl-4-hydroxycyclohexyl]-1H-pyrazole-4-carboxamide;

1-[2-cyano-4-hydroxy-4-methylcyclohexyl]-3-{[4-(3,3,3-trifluoro-hydroxy-1,1-dimethylpropyl)phenyl]amino}-1H-pyrazole-4-carboxamide;

1-[2-cyano-4-hydroxy-4-methylcyclohexyl]-3-{[4-(3,3,3-trifluoro-hydroxy-1,1-dimethylpropyl)phenyl]amino}-1H-pyrazole-4-carboxamide;

3-[(4-chlorophenyl)amino]-1-[2-cyano-4-ethenyl-4-hydroxycyclohexyl]-1H-pyrazole-4-carboxamide;

3-[(4-chloro-3-fluorophenyl)amino]-1-[2-cyano-4-hydroxy-4-methylcyclohexyl]-1H-pyrazole-4-carboxamide;

1-[2-cyano-4-hydroxy-4-methylcyclohexyl]-3-({4-[2,2,2-trifluoro-1-hydroxy-1-methylethyl]phenyl}amino)-1H-pyrazole-4-carboxamide;

3-[(4-chlorophenyl)amino]-1-[2-cyano-4-hydroxy-4-methylcyclohexyl]-1H-pyrazole-4-carboxamide;

3-[(4-chlorophenyl)amino]-1-[2-cyano-4-cyclopropyl-4-hydroxycyclohexyl]-1H-pyrazole-4-carboxamide;

1-(2-Cyano-4-hydroxycyclohexyl)-3-((4-(trifluoromethoxy)phenyl)amino)-1H-pyrazole-4-carboxamide;

3-[(4-chlorophenyl)amino]-1-[2-cyano-4-hydroxycyclohexyl]-1H-pyrazole-4-carboxamide;

3-[(4-chloro-3-fluorophenyl)amino]-1-[2-cyano-4-hydroxycyclohexyl]-1H-pyrazole-4-carboxamide;

1-[2-cyano-4-hydroxycyclohexyl]-3-{[4-(trifluoromethyl)phenyl]amino}-1H-pyrazole-4-carboxamide;

1-[2-cyano-4-hydroxycyclohexyl]-3-({4-[(trifluoromethyl)sulfonyl]phenyl}amino)-1H-pyrazole-4-carboxamide;

1-[2-cyano-4-hydroxycyclohexyl]-3-[(4-cyanophenyl)amino]-1H-pyrazole-4-carboxamide;

1-[2-cyano-4-hydroxycyclohexyl]-3-{[6-(difluoromethyl)pyridin-3-yl]amino}-1H-pyrazole-4-carboxamide;

1-[2-cyano-4-hydroxycyclohexyl]-3-{[6-(trifluoromethyl)pyridin-3-yl]amino}-1H-pyrazole-4-carboxamide;

1-[2-cyano-4-hydroxycyclohexyl]-3-({4-[2,2,2-trifluoro-1-hydroxyethyl]phenyl}amino)-1H-pyrazole-4-carboxamide;

1-[2-cyano-4-hydroxycyclohexyl]-3-({4-[2,2,2-trifluoro-1-hydroxy-1-methylethyl]phenyl}amino)-1H-pyrazole-4-carboxamide;

1-[(2-cyano-4-hydroxycyclohexyl]-3-{[4-(3,3,3-trifluoro-hydroxy-1,1-dimethylpropyl)phenyl]amino}-1H-pyrazole-4-carboxamide;

1-[2-cyano-4-hydroxycyclohexyl]-3-[(4-cyclopropylphenyl)amino]-1H-pyrazole-4-carboxamide;

1-[2-cyano-4-hydroxycyclohexyl]-3-{[4-(3-methyloxetan-3-yl)phenyl]amino}-1H-pyrazole-4-carboxamide;

1-[2-cyano-4-hydroxycyclohexyl]-3-[(3,4-dichlorophenyl) amino]-1H-pyrazole-4-carboxamide;

1-[2-cyano-4-hydroxycyclohexyl]-3-{[4-(2-fluoro-1,1-dimethylethyl)phenyl]amino}-1H-pyrazole-4-carboxamide;

1-[2-cyano-4-hydroxycyclohexyl]-3-{[6-(difluoromethoxy) pyridin-3-yl]amino}-1H-pyrazole-4-carboxamide;

4-{4-Carbamoyl-3-[(4-fluorophenyl)amino]-1H-pyrazol-1-yl}-3-cyanocyclohexyl phenylcarbamate;

4-{4-carbamoyl-3-[(4-fluorophenyl)amino]-1H-pyrazol-1-yl}-3-cyanocyclohexyl cyclohexylcarbamate;

4-{4-carbamoyl-3-[(4-fluorophenyl)amino]-1H-pyrazol-1-yl}-3-cyanocyclohexyl phenylcarbamate;

4-{4-carbamoyl-3-[(4-fluorophenyl)amino]-1H-pyrazol-1-yl}-3-cyanocyclohexyl propan-2-ylcarbamate;

4-{4-carbamoyl-3-[(4-fluorophenyl)amino]-1H-pyrazol-1-yl}-3-cyanocyclohexyl methylcarbamate;

4-{4-carbamoyl-3-[(4-fluorophenyl)amino]-1H-pyrazol-1-yl}-3-cyanocyclohexyl ethylcarbamate;

3-((4-chlorophenyl)amino)-1-(2-cyano-4-(3,3-dimethylazetidine-1-carbonyl)cyclohexyl)-1H-pyrazole-4-carboxamide;

3-[(4-chlorophenyl)amino]-1-[2-cyano-4-{[3-(1-hydroxy-1-methylethyl)azetidin-1-yl]carbonyl}cyclohexyl]-1H-pyrazole-4-carboxamide;

1-[4-(2-azaspiro[3.3]hept-2-ylcarbonyl)-2-cyanocyclohexyl]-3-[(4-chlorophenyl)amino]-1H-pyrazole-4-carboxamide;

3-[(4-chlorophenyl)amino]-1-{2-cyano-4-[(dicyclopropylmethyl)carbamoyl]cyclohexyl}-1H-pyrazole-4-carboxamide;

3-[(4-chlorophenyl)amino]-1-{2-cyano-4-[(3,3-difluoroazetidin-1-yl)carbonyl]cyclohexyl}-1H-pyrazole-4-carboxamide;

3-[(4-chlorophenyl)amino]-1-[2-cyano-4-(oxetan-3-ylcarbamoyl)cyclohexyl]-1H-pyrazole-4-carboxamide;

3-[(4-chlorophenyl)amino]-1-[2-cyano-4-{[3-(methylsulfonyl)azetidin-1-yl]carbonyl}cyclohexyl]-1H-pyrazole-4-carboxamide;

3-[(4-chlorophenyl)amino]-1-{2-cyano-4-[(2,2,2-trifluoroethyl)carbamoyl]cyclohexyl}-1H-pyrazole-4-carboxamide;

3-[(4-chlorophenyl)amino]-1-[2-cyano-4-(cyclobutylcarbamoyl)cyclohexyl]-1H-pyrazole-4-carboxamide;

3-[(4-chlorophenyl)amino]-1-[2-cyano-4-{[1-cyclopropyl-2,2,2-trifluoroethyl]carbamoyl}cyclohexyl]-1H-pyrazole-4-carboxamide;

3-[(4-chlorophenyl)amino]-1-{2-cyano-4-[(3,3-difluorocyclobutyl)carbamoyl]cyclohexyl}-1H-pyrazole-4-carboxamide;

3-[(4-chlorophenyl)amino]-1-[2-cyano-4-(cyclopropylcarbamoyl)cyclohexyl]-1H-pyrazole-4-carboxamide;

3-[(4-chlorophenyl)amino]-1-{2-cyano-4-[(3-hydroxy-3-methylazetidin-1-yl)carbonyl]cyclohexyl}-1H-pyrazole-4-carboxamide;

3-[(4-chlorophenyl)amino]-1-{2-cyano-4-[(3,3-difluoropyrrolidin-1-yl)carbonyl]cyclohexyl}-1H-pyrazole-4-carboxamide;

3-[(4-chlorophenyl)amino]-1-[2-cyano-4-{[(3-methyloxetan-3-yl)methyl]carbamoyl}cyclohexyl]-1H-pyrazole-4-carboxamide;

3-[(4-chlorophenyl)amino]-1-{2-cyano-4-[(3-fluoroazetidin-1-yl)carbonyl]cyclohexyl}-1H-pyrazole-4-carboxamide;

1-[4-(tert-butylcarbamoyl)-2-cyanocyclohexyl]-3-[(4-chlorophenyl)amino]-1H-pyrazole-4-carboxamide;

3-[(4-chlorophenyl)amino]-1-[2-cyano-4-(2-oxa-6-azaspiro[3.3]hept-6-ylcarbonyl)cyclohexyl]-1H-pyrazole-4-carboxamide;

3-(4-Chlorophenylamino)-1-(2-cyano-4-(2-hydroxypropan-2-yl)cyclohexyl)-1H-pyrazole-4-carboxamide;

1-[2-Cyano-4-(fluoromethyl)cyclohexyl]-3-[(2-fluoropyridin-4-yl)amino]-1H-pyrazole-4-carboxamide;

1-{2-Cyano-4-[(methylsulfonyl)amino]cyclohexyl}-3-[(4-fluorophenyl)amino]-1H-pyrazole-4-carboxamide;

3-[(4-chlorophenyl)amino]-1-{2-cyano-4-[(methylsulfonyl)amino]cyclohexyl}-1H-pyrazole-4-carboxamide;

3-[(4-chlorophenyl)amino]-1-{2-cyano-4-[methyl(methylsulfonyl)amino]cyclohexyl}-1H-pyrazole-4-carboxamide;

1-[2-Cyanocyclohexyl]-3-({4-[(methoxyimino)methyl]phenyl}amino)-1H-pyrazole-4-carboxamide;

1-[2-Cyanocyclohexyl]-3-{[4-(N-methoxyethanimidoyl)phenyl]amino}-1H-pyrazole-4-carboxamide;

4-(4-Carbamoyl-3-((4-(trifluoromethyl)phenyl)amino)-1H-pyrazol-1-yl)-5-cyano-2-hydroxycyclohexyl acetate;

1-[2-Cyanocyclohexyl]-3-{[4-(methylsulfonyl)phenyl]amino}-1H-pyrazole-4-carboxamide;

1-[2-Cyanocyclohexyl]-3-({4-[(trifluoromethyl)sulfonyl]phenyl}amino)-1H-pyrazole-4-carboxamide;

1-[2-cyanocyclohexyl]-3-[(4-fluorophenyl)amino]-1H-pyrazole-4-carboxamide;

1-[2-cyanocyclohexyl]-3-({4-[(difluoromethyl)sulfonyl]phenyl}amino)-1H-pyrazole-4-carboxamide;

1-[2-cyanocyclohexyl]-3-({4-[(2,2,2-trifluoroethyl)sulfonyl]phenyl}amino)-1H-pyrazole-4-carboxamide;

1-[2-cyano-4-hydroxycyclohexyl]-3-({4-[(trifluoromethyl)sulfonyl]phenyl}amino)-1H-pyrazole-4-carboxamide;

tert-Butyl[3-{4-carbamoyl-3-[(4-fluorophenyl)amino]-1H-pyrazol-1-yl}-4-cyanocyclohexyl]carbamate;

1-[8-Cyano-1,4-dioxaspiro[4.5]dec-7-yl]-3-(phenylamino)-1H-pyrazole-4-carboxamide; and 1-[2-cyanocyclohexyl]-3-[(1,1-dioxido-2,3-dihydro-1-benzothiophen-5-yl)amino]-1H-pyrazole-4-carboxamide.

The invention also encompasses pharmaceutical compositions containing a compound of formula I, and methods for treatment or prevention of JAK mediated diseases using compounds of formula I.

The invention is described using the following definitions unless otherwise indicated.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

"Acyl" means a —C(O)R radical Where R is optionally substituted alkyl, alkenyl, cycloalkyl, heterocycloalkyl, aryl heteroaryl, etc.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

The term "heteroalkyl" refers to an alkyl group where one or more of the carbon atoms is substituted by a heteroatom independently selected from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or C1-6alkyl. Similarly, when an integer defining the presence of a certain number of atoms in a group is equal to zero, it means that the atoms adjacent thereto are connected directly by a bond. For example in the structure

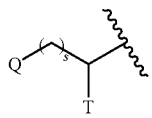

wherein s is an integer equal to zero, 1 or 2, the structure is

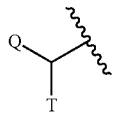

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

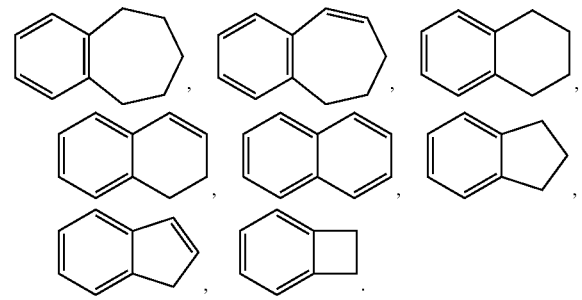

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloalkyl, for example, includes —$CF_3$, —$CF_2CF_3$, $CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and $(C_{3-12})$heterocycloalkyl" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl)

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers to a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsaturated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

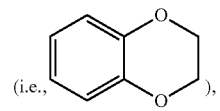

(i.e., ), imidazo(2,1-b)(1,3)thiazole, (i.e.,

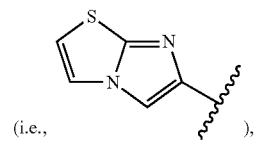 [SMILES: *c1cn2ccsc2n1]

(i.e., ), and benzo-1,3-dioxolyl (i.e.,

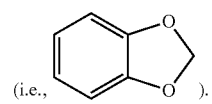

(i.e., ).

In certain contexts herein,

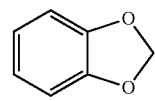

is alternatively referred to as phenyl having as a substituent methylenedioxy attached to two adjacent carbon atoms.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "$CH_3$", e.g. "—$CH_3$" or using a straight line representing the presence of the methyl group, e.g. "—", i.e.,

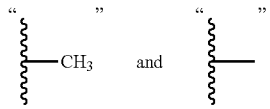

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

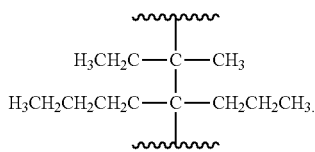

In one embodiment of the invention, $R^a$ is hydrogen or methyl. In a variant of this embodiment, $R^a$ is hydrogen.

In one embodiment of the invention $R^4$ is hydrogen or methyl. In a variant of this embodiment, $R^4$ is hydrogen. In another embodiment $R^4$ is methyl.

In one embodiment, p is 2 or 3.

In one embodiment, $R^2$ and $R^7$ are each independently selected from hydrogen, halogen, $C_{1-10}$ alkyl, and $C_{3-8}$ cycloalkyl$C_{0-10}$ alkyl. In a variant of this embodiment, $R^2$ and $R^7$ are each independently selected from hydrogen, halogen, and $C_{1-10}$ alkyl.

In yet a further embodiment, $R^2$ and $R^7$ are each independently selected from hydrogen, and $C_{1-10}$ alkyl. In one embodiment of the invention, $R^2$ and $R^7$ are each independently selected from hydrogen, ethyl, propyl, butyl, pentyl, or methyl. In a variant of this embodiment, $R^2$ and $R^7$ are each independently selected from hydrogen or methyl. In another variant, $R^2$ is hydrogen.

In one embodiment A is selected from: furanyl, thienyl, pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridinyl, thienopyridinyl, benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 1,2,3,4-tetrahydroquinolinyl, 2,3-dihydro-1H-isoindolyl, quinolinyl, pyridazinyl, 2,3-dihydro-1-benzothiophenyl, 6,7-dihydro-5H-pyrrolo[3,4-b]pyridinyl and 2,3-dihydrobenzo[b]thiophenyl. 2,3-dihydrobenzofuranyl, 2,3-dihydrobenzo-1,4-dioxinyl, imidazo(2,1-b)(1,3)thiazole, and benzo-1,3-dioxolyl, phenyl, indenyl, and naphthyl.

In one embodiment, A is selected from phenyl, pyrindinyl, 1,2,3,4-tetrahydroquinolinyl, isoindolyl, indolyl, 2,3-dihydro-1H-isoindolyl, quinolinyl, pyridazinyl, 2,3-dihydro-1-benzothiophenyl, benzothiophenyl, 6,7-dihydro-5H-pyrrolo[3,4-b]pyridinyl, pyrrolo[3,4-b]pyridinyl, benzo[b]thiophenyl, and 2,3-dihydrobenzo[b]thiophenyl.

In one embodiment, A is selected from phenyl, pyrindinyl, 1,2,3,4-tetrahydroquinolinyl, 2,3-dihydro-1H-isoindolyl, quinolinyl, pyridazinyl, 2,3-dihydro-1-benzothiophenyl, 6,7-dihydro-5H-pyrrolo[3,4-b]pyridinyl and 2,3-dihydrobenzo[b]thiophenyl.

In one embodiment, $R^{5a}$ is selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{2-10}$ alkenyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, aryl $C_{2-10}$ alkenyl(oxy)$_{0-1}$(carbonyl)$_{0-1}C_{0-10}$ alkyl, aryl $C_{2-10}$ alkynyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-8})$heterocycloalkyl $C_{0-10}$ alkyl(oxy)$_{0-1}$(carbonyl)$_{0-1}C_{0-10}$ alkyl, $C_{1-10}$ alkyl(carbonyl)$_{0-1}$oxy$C_{0-10}$ alkyl, $C_{1-10}$ heteroalkyl(carbonyl)$_{0-1}$oxy$C_{0-10}$ alkyl, $C_{2-10}$ alkenyl(carbonyl)$_{0-1}$oxy$C_{0-10}$ alkyl, $C_{1-10}$ heteroalkyl(carbonyl)$_{0-1}$oxy$C_{0-10}$ alkyl, aryl $C_{0-10}$ alkyl (carbonyl)$_{0-1}$oxy$C_{0-10}$ alkyl, $(C_{3-8})$heterocycloalkyl $C_{0-10}$ alkyl(carbonyl)$_{0-1}$oxy$C_{0-10}$ alkyl, $((C_{0-1})$alkyl$)_{1-2}$aminocarbonyloxy, aryl $(C_{0-10})$alkylaminocarbonyloxy, $C_{0-10}$ alkylamino(oxy)$_{0-1}$(carbonyl)$_{0-1}C_{2-10}$ alkenyl, $C_{1-10}$ alkylamino(oxy)$_{0-1}$(carbonyl)$_{0-1}C_{0-10}$ alkyl, heteroaryl$C_{0-10}$alkylamino((oxy)$_{0-1}$(carbonyl)$_{0-1}C_{0-10}$ alkyl, $(C_{3-8})$heterocycloalkyl$C_{0-10}$alkylamino(oxy)$_{0-1}$(carbonyl)$_{0-1}C_{0-10}$ alkyl, $C_{0-10}$ alkyl(oxy)$_{0-1}$(carbonyl)$_{0-1}$amino$C_{0-10}$ alkyl,
$C_{3-8}$ cycloalkyl $C_{0-10}$ alkyl (oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
($C_{3-8}$)heterocycloalkyl $C_{0-10}$ alkyl(oxy)$_{0-1}$(carbonyl)$_{0-1}$amino$C_{0-10}$ alkyl,
—CO$_2$($C_{0-10}$ alkyl),
—($C_{0-10}$ alkyl)CO$_2$H,
Oxo (=O),
formyl,
sulfonyl,
$C_{1-10}$ alkylsulfonyl,
$C_{1-10}$heteroalkylsulfonyl,
($C_{3-8}$) cycloalkylsulfonyl,
($C_{3-8}$) cycloheteroalkylsulfonyl,
heteroarylsulfonyl,
arylsulfonyl,
aminosulfonyl,
—SO$_2$N($C_{0-6}$alkyl)$_{1-2}$,
—SO$_2$C$_{1-6}$alkyl,
—SO$_2$CF$_3$,
—SO$_2$CF$_2$H,
—Si(CH$_3$)$_3$,
$C_{1-10}$ alkylsulfinyl,
amino,
($C_{0-10}$ alkyl)$_{1-2}$ amino,
$C_{1-4}$acylamino $C_{0-10}$ alkyl,
hydroxy,
($C_{1-10}$ alkyl)OH,
$C_{0-10}$ alkylalkoxyl,
imino($C_{0-10}$ alkyl),
($C_{0-10}$alkyl)imino,
cyano,
$C_{1-6}$alkylcyano, and
$C_{1-6}$haloalkyl; wherein two $R^{5a}$ and the atom to which they are attached may optionally form a 3-, 4-, 5-, or 6-membered saturated ring system and wherein $R^{5a}$ is each optionally substituted with 1, 2, 3, or 4 $R^6$ substituents.

In yet another embodiment, $R^{5a}$ is selected from:
halogen,
$C_{1-10}$ alkyl(oxy)$_{0-1}$(carbonyl)$_{0-1}$C$_{0-10}$ alkyl,
$C_{1-10}$ heteroalkyl(oxy)$_{0-1}$(carbonyl)$_{0-1}$C$_{0-10}$ alkyl,
$C_{2-10}$ alkenyl(oxy)$_{0-1}$(carbonyl)$_{0-1}$C$_{0-10}$ alkyl,
aryl $C_{0-10}$ alkyl(oxy)$_{0-1}$(carbonyl)$_{0-1}$C$_{0-10}$ alkyl,
$C_{3-8}$ cycloalkyl $C_{0-10}$ alkyl(oxy)$_{0-1}$(carbonyl)$_{0-1}$C$_{0-10}$ alkyl,
heteroaryl $C_{0-10}$ alkyl(oxy)$_{0-1}$(carbonyl)$_{0-1}$C$_{0-10}$ alkyl,
aryl $C_{0-10}$ alkyl (carbonyl)$_{0-1}$oxyC$_{0-10}$ alkyl,
aryl ($C_{0-10}$)alkylaminocarbonyloxy,
$C_{1-10}$ alkylamino(oxy)$_{0-1}$(carbonyl)$_{0-1}$C$_{0-10}$ alkyl,
heteroaryl$C_{0-10}$alkylamino((oxy)$_{0-1}$(carbonyl)$_{0-1}$C$_{0-10}$ alkyl,
$C_{0-10}$ alkyl(oxy)$_{0-1}$(carbonyl)$_{0-1}$amino$C_{0-10}$ alkyl,
$C_{3-8}$ cycloalkyl $C_{0-10}$ alkyl (oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
($C_{3-8}$)heterocycloalkyl $C_{0-10}$ alkyl(oxy)$_{0-1}$(carbonyl)$_{0-1}$amino$C_{0-10}$ alkyl,
—CO$_2$($C_{0-10}$ alkyl),
—($C_{0-10}$ alkyl)CO$_2$H,
Oxo (=O),
formyl,
sulfonyl,
$C_{1-10}$ alkylsulfonyl,
$C_{1-10}$ heteroalkylsulfonyl,
($C_{3-8}$) cycloalkylsulfonyl,
($C_{3-8}$) cycloheteroalkylsulfonyl,
heteroarylsulfonyl,
arylsulfonyl,
aminosulfonyl,
—SO$_2$N($C_{0-6}$alkyl)$_{1-2}$,
—SO$_2$C$_{1-6}$alkyl,
—SO$_2$CF$_3$,
—SO$_2$CF$_2$H,
—Si(CH$_3$)$_3$,
($C_{0-10}$ alkyl)$_{1-2}$ amino,
hydroxy,
($C_{1-10}$ alkyl)OH,
$C_{0-10}$ alkylalkoxyl,
imino($C_{0-10}$alkyl),
($C_{0-10}$alkyl)imino,
cyano,
$C_{1-6}$alkylcyano, and
$C_{1-6}$haloalkyl;
wherein two $R^{5a}$ and the atom to which they are attached may optionally form a 3-, 4-, 5-, or 6-membered saturated ring system and wherein $R^{5a}$ is each optionally substituted with 1, 2, 3, or 4 $R^6$ substituents.

In another embodiment of the invention, $R^{5a}$ is selected from: methylsulfonyl, hydroxyl, trimethylsilyl, ethoxy, methoxy, methyloxycarbonyl, methylCOOH, hydroxycarbonylmethyl, methyloxycarbonyl, dimethylamino, fluoro, phenylcarbonyloxy, methylamino, oxo, ethylamino, benzylamino, tert-butyloxycarbonyl, methoxycarbonyl, hydroxymethyl, aminomethyl, oxymethyl, methyl, methylaminomethyl, methylaminocarbonyl, oxycarbonylamino, methyloxycarbonyl, ethyloxycarbonylamino, tert-butyloxycarbonylamino, ethyl, methyl, tert-butyloxycarbonylaminomethyl, carbonylamino, trifluoromethylsulfonyl, trifluoromethyl, trifluoroethyl, chloro, pyridinylaminocarbonyl, methylcarbonylamino, cyano, 1,2,4-oxadiazolyl, ethylsulfonyl, oxo, pyrazolyl, formyl (C=O), bromo, carbamoyl, acetyl, 3,3,3-trifluoro-1,1-dimethylpropyl, trifluoropentyl, 2,2,2-trifluoromethylethyl, difluoromethyl, 2,2-difluoromethylethyl, isopropyl, aminomethyl, methylethylcarbonylamino, tert-butylaminocarbonyl, cyclopropyl, sulfamoyl, (methylethyl)sulfamoyl, methylsulfamoyl, ethylsulfamoyl, piperazinylsulfonyl, piperidinylsulfonyl, pyridinylsulfonyl, morpholinylsulfonyl, difluoromethoxy, pyrazolyl, oxetanyl, cyclopropylmethoxy, dimethylamino, cyclopropylamino, morpholinyl, sulfonyl, azetidinyl, tert-butylamino, hydroxymethylethyl, (cyclopropylethyl)amino, (cyclopropylmethyl)amino, trifluoroethylamino, pyrrolidinyl, (oxetanylmethyl)amino, hydroxycarbonylisopropyl, oxetanylamino, hydroxymethyl, methylcarbonyl, (ethyl)(methyl)amino, methoxyethylamino, (tetrahydrothiophenylmethyl)amino, propyl(methyl)amino, cyclopropylamino, (dimethylethyl)amino, methylamino, oxetanylmethylamino, tetrahydro-2H-pyranylamino, tert-butyloxycarbonylamino, cyclobutylamino, butylamino, cyclobutylmethylamino, dimethylpropyl, ethenyl, phenylaminocarbonyloxy, cyclohexylaminocarbonyloxy, propylaminocarbonyloxy, methylaminocarbonyloxy, ethylaminocarbonyloxy, cyclopropylmethlcarbamoyl, tert-butyloxycarbonyl, hydroxycarbonyl, cyclopropylmethylaminocarbonyl, azetidinylcarbonyl, oxetanycarbamoyl, ethylcarbamoyl, cyclobutylcarbamoyl, cyclopropylmethylcarbamoyl, methylcarbamoyl, oxetanylmethycarbamoyl, pyrrolidinylcarbonyl, tert-butylcarbamoyl, hydroxypropanyl, methyloxycarbonyl, iminoC$_{1-10}$ alkyl, and C$_{1-10}$ alkylimino, wherein two $R^{5a}$ and the atom to which they are attached may optionally form a 3-, 4-, 5-, or 6-membered saturated ring system and wherein $R^{5a}$ is each optionally substituted with 1, 2, 3, or 4 substituents, $R^6$.

In one embodiment, $R^6$ is independently selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{2-10}$ alkenyl (oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, aryl $C_{2-10}$ alkenyl(oxy)$_{0-1}$ (carbonyl)$_{0-1}C_{0-10}$ alkyl, aryl $C_{2-10}$ alkynyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$ (carbonyl)$_{0-1}C_{0-10}$ alkyl, $(C_{3-8})$heterocycloalkyl $C_{0-10}$ alkyl (oxy)$_{0-1}$(carbonyl)$_{0-1}C_{0-10}$ alkyl, $C_{1-10}$ alkyl (carbonyl)$_{0-1}$oxy$C_{0-10}$ alkyl, $C_{2-10}$ alkenyl (carbonyl)$_{0-1}$oxy$C_{0-10}$ alkyl, $C_{1-10}$ heteroalkyl (carbonyl)$_{0-1}$oxy$C_{0-10}$ alkyl, $((C_{0-10})$alkyl)$_{1-2}$aminocarbonyloxy, $C_{1-10}$ alkylamino(oxy)$_{0-1}$carbonyl$C_{0-10}$ alkyl, $C_{1-10}$ alkyl (oxy)$_{0-1}$(carbonyl)$_{0-1}$amino$C_{0-10}$ alkyl, $(C_{3-8})$heterocycloalkyl $C_{0-10}$ alkyl(oxy)$_{0-1}$(carbonyl)$_{0-1}$amino$C_{0-10}$ alkyl, —CO$_2$($C_{0-10}$ alkyl), —($C_{0-10}$ alkyl)CO$_2$H, Oxo (=O), Sulfonyl, $C_{1-10}$ alkylsulfonyl, $C_{1-10}$ heteroalkylsulfonyl, $(C_{3-8})$cycloalkylsulfonyl, $(C_{3-8})$cycloheteroalkylsulfonyl, heteroarylsulfonyl, arylsulfonyl, aminosulfonyl, —SO$_2$N($C_{1-6}$alkyl)$_{1-2}$, —SO$_2C_{1-6}$alkyl, —SO$_2$CF$_3$, —SO$_2$CF$_2$H, $C_{1-10}$ alkylsulfinyl, amino, $(C_{0-10}$ alkyl)$_{1-2}$ amino, -(oxy)$_{0-1}$(carbonyl)$_{0-1}$N($C_{0-10}$ alkyl)$_{1-2}$ $C_{1-4}$acylamino$C_{0-10}$ alkyl, imino($C_{0-10}$alkyl), hydroxy, ($C_{1-10}$ alkyl)OH, $C_{1-10}$ alkoxy, cyano, and $C_{1-6}$haloalkyl; wherein two $R^6$ and the atoms to which they are attached may optionally form a 3-, 4-, 5-, or 6-membered saturated ring system and $R^6$ is optionally substituted with 1, 2, or 3 substituents selected from hydrogen, hydroxy, ($C_{1-6}$)alkyl, ($C_{1-6}$)alkoxy, ($C_{1-10}$ alkyl)OH, halogen, CO$_2$H, —($C_{0-6}$)alkylCN, —O(C=O)$C_1$-$C_6$ alkyl, NO$_2$, trifluoromethoxy, trifluoroethoxy, trifluoromethyl, trifluoroethyl, —N—C(O)O($C_{0-6}$)alkyl, $C_{1-10}$ alkylsulfonyl, $C_{1-10}$ heteroalkylsulfonyl, oxo (O=), $(C_{3-8})$ cycloalkylsulfonyl, $(C_{3-8})$ cycloheteroalkylsulfonyl, heteroarylsulfonyl, arylsulfonyl, aminosulfonyl, —SO$_2$N($C_{1-6}$alkyl)$_{1-2}$, —SO$_2C_{1-6}$alkyl, —SO$_2$CF$_3$, —SO$_2$CF$_2$H, —$C_{1-10}$ alkylsulfinyl, —OSi($C_{1-10}$alkyl)$_3$, —O$_{(0-1)}$($C_{1-10}$)haloalkyl, amino($C_{1-6}$alkyl)$_{0-2}$ and NH$_2$.

In another embodiment of the invention $R^6$ is independently selected from: halogen, $C_{1-10}$ alkyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-8})$heterocycloalkyl $C_{0-10}$ alkyl (oxy)$_{0-1}$(carbonyl)$_{0-1}C_{0-10}$ alkyl, $C_{1-10}$ alkyl (carbonyl)$_{0-1}$oxy$C_{0-10}$ alkyl, —CO$_2$($C_{0-10}$ alkyl), Oxo (=O), sulfonyl, $C_{1-10}$ alkylsulfonyl, $(C_{3-8})$cycloalkylsulfonyl, $(C_{3-8})$cycloheteroalkylsulfonyl, heteroarylsulfonyl, —SO$_2$N ($C_{1-6}$alkyl)$_{1-2}$, amino, $(C_{0-10}$ alkyl)$_{1-2}$ amino, hydroxy, ($C_{1-10}$ alkyl)OH, $C_{1-10}$ alkoxy, and $C_{1-6}$haloalkyl; wherein two $R^6$ and the atoms to which they are attached may optionally form a 3-, 4-, 5-, or 6-membered saturated ring system, and $R^6$ is optionally substituted with 1, 2, or 3 substituents selected from hydrogen, hydroxy, ($C_{1-6}$)alkyl, ($C_{1-6}$)alkoxy, ($C_{1-10}$ alkyl)OH, halogen, CO$_2$H, —($C_{0-6}$)alkylCN, —O(C=O)$C_1$-$C_6$ alkyl, NO$_2$, trifluoromethoxy, trifluoroethoxy, trifluoromethyl, trifluoroethyl, —N—C(O)O($C_{0-6}$)alkyl, $C_{1-10}$ alkylsulfonyl, $C_{1-10}$ heteroalkylsulfonyl, oxo (O=), $(C_{3-8})$ cycloalkylsulfonyl, $(C_{3-8})$ cycloheteroalkylsulfonyl, heteroarylsulfonyl, arylsulfonyl, aminosulfonyl, —SO$_2$N($C_{1-6}$alkyl)$_{1-2}$, —SO$_2C_{1-6}$alkyl, —SO$_2$CF$_3$, —SO$_2$CF$_2$H, —$C_{1-10}$ alkylsulfinyl, —OSi($C_{1-10}$alkyl)$_3$, —O$_{(0-1)}$($C_{1-10}$)haloalkyl, amino($C_{1-6}$alkyl)$_{0-2}$ and NH$_2$.

In one particular embodiment, $R^6$ is independently selected from: methyl, sulfonyl, quinolinyl, oxo, ethyl, ethoxy, fluoro, chloro, propyl, ethanol, trifluoromethyl, hydroxy, 1-hydroxy-1-methylethyl, —COOH, trifluoroethyl, hydroxymethyl, methylsulfonyl, difluoromethyl, dimethylsulfamoyl, fluoromethyl, cyclopropyl, cyclobutyl, benzyl, piperidinyl, pyridinyl, morpholinyl, cyclohexyl, phenyl, pyrrolidinyl, piperazinyl, methoxy, tert-butylmethyl, dimethylamino, hydroxyethyl, methylcarbonyl, hydroxymethylethyl, cyclopropylmethyl and methyloxycarbonyl and $R^6$ is optionally substituted with 1, 2, or 3 substituents selected from hydrogen, hydroxy, ($C_{1-6}$)alkyl, ($C_{1-6}$)alkoxy, ($C_{1-10}$ alkyl)OH, halogen, CO$_2$H, —($C_{0-6}$)alkylCN, —O(C=O)$C_1$-$C_6$ alkyl, NO$_2$, trifluoromethoxy, trifluoroethoxy, trifluoromethyl, trifluoroethyl, —N—C(O)O($C_{0-6}$)alkyl, $C_{1-10}$ alkylsulfonyl, $C_{1-10}$ heteroalkylsulfonyl, oxo (O=), $(C_{3-8})$ cycloalkylsulfonyl, $(C_{3-8})$ cycloheteroalkylsulfonyl, heteroarylsulfonyl, arylsulfonyl, aminosulfonyl, —SO$_2$N($C_{1-6}$alkyl)$_{1-2}$, —SO$_2C_{1-6}$alkyl, —SO$_2$CF$_3$, —SO$_2$CF$_2$H, —$C_{1-10}$ alkylsulfinyl, —OSi($C_{1-10}$alkyl)$_3$, —O$_{(0-1)}$($C_{1-10}$)haloalkyl, amino($C_{1-6}$alkyl)$_{0-2}$ and NH$_2$.

In one embodiment, the compounds of the instant invention are selective JAK1 inhibitors relative to JAK2. The determination of relative selectivity for a given compound of JAK1 inhibition is defined as the relative ratio of the (JAK2 IC$_{50}$ value/JAK1 IC$_{50}$ value) is at least 2. In yet another embodiment, for a given compound, the relative ratios of the (JAK2 IC$_{50}$ value/JAK1 IC$_{50}$ value) is at least 5.

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —(CR$^3$R$^3$)$_2$—, each occurrence of the two R$^3$ groups may be the same or different. As used herein, unless explicitly stated to the contrary, each reference to a specific compound of the present invention or a generic formula of compounds of the present invention is intended to include the compound(s) as well as pharmaceutically acceptable salts and stereoisomers thereof.

Optical Isomers-Diastereomers-Geometric Isomers-Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Specific embodiments of the present invention include a compound which is selected from the group consisting of the subject compounds of the Examples herein or a pharmaceutically acceptable salt or stereoisomer thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, 1-(2S,3S and 2R, 3R)-3-cyclobutan-2-yl]-3-(phenylamino)-1H-pyrazole-4-carboxamide, the "and" indicates a racemic mixture of the enantiomers. That is, the individual enantiomers were not individually isolated.

When the stereomeric nomenclature includes "or", for example, 1-(2S,3S or 2R, 3R)-3-cyclobutan-2-yl]-3-(phenylamino)-1H-pyrazole-4-carboxamide, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I and subsets thereof, embodiments thereof, as well as specific compounds are meant to also include the pharmaceutically acceptable salts and the stereoisomers thereof.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts or stereoisomers and pharmaceutical compositions can be used to treat or prevent a variety of conditions or diseases mediated by Janus kinases, in particular diseases or conditions that can be ameliorated by the inhibition of a Janus kinase such as JAK1, JAK2 or JAK3. Such conditions and diseases include, but are not limited to: (1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a JAK-mediated diseases or disorder.

One aspect of the invention is the use of a compound of formula I or a pharmaceutically acceptable salt or a stereoisomer thereof in the manufacture of a medicament for the treatment of a disease or a disorder ameliorated by the selective inhibition of a Janus kinase JAK1 relative to JAK 2.

Another aspect of the invention is the use of a compound of Formula I or a pharmaceutically acceptable salt or a stereoisomer thereof and a second active agent in the manufacture of a medicament for the treatment of a disease or a disorder ameliorated by the selective inhibition of a Janus kinase JAK1 relative to JAK 2.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of formula I may be co-administered with other therapeutic agents. Thus in another aspect the present invention provides pharmaceutical compositions for treating JAK mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

Methods of Synthesis

Schemes and Examples

The abbreviations used herein have the following tabulated meanings. Abbreviations not tabulated below have their meanings as commonly used unless specifically stated otherwise.

| ACN | acetonitrile |
| MeCN | acetonitrile |
| BAST | bis(2-methoxyethyl)aminosulfur trifluoride |
| Chiral SFC | chiral super critical fluid chromatography |
| $CO_2$ | carbon dioxide |
| $Cs_2CO_3$ | cesium carbonate |

-continued

| DBU | 1,8-diazabicyclo[5.4.0]undec-7-ene |
| DCE | 1,2-dichloroethane |
| DCM | dichloromethane |
| DIPEA | N,N-diisopropylethylamine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |
| HATU | O-(7-aza-1H-benzotriazol-1-yl)-N,N,N',N'-tetramethyluronium hexafluorophosphate |
| HCl | hydrogen chloride |
| HOBt | 1-hydroxybenzotriazole |
| HPLC | high pressure liquid chromatography |
| IPA | 2-propanol |
| LDA | lithium diisopropylamide |
| m-CPBA | meta-chloroperoxybenzoic acid |
| LRMS | low resolution mass spectrometry |
| MeI | iodomethane |
| Me—THF | 2-methyltetrahydrofuran |
| MgSO4 | magnesium sulfate |
| MP—(OAc)$_3$BH | solid supported (macro porous) triacetoxyborohydride |
| MPLC | medium pressure liquid chromatography |
| NaH | sodium hydride |
| $Na_2SO_4$ | sodium sulfate |
| NaBH4 | sodium borohydride |
| NaHCO$_3$ | sodium bicarbonate |
| NaOMe | sodium methoxide |
| Pd$_2$(dba)$_3$ | tris(dibenzylideneacetone)dipalladium(0) |
| POCl$_3$ | phosphorus (V) oxychloride |
| PyBOP | (7-azabenzotriazol-1-yloxy)tripyrrolidinophosphonium hexafluorophosphate |
| SEM-Cl | 2-(trimethylsilyl)ethoxymethyl chloride |
| SiliaCat ® DPP-Pd | silica bound diphenylphosphine palladium (II) |
| TBAF | tetra-n-butylammonium fluoride |
| TBS-Cl | tert-butyldimethylsilyl chloride |
| t-BuOH | tert-butanol |
| TEA | triethylamine |
| TFA | trifluoroacetic acid |
| THF | tetrahydrofuran |
| X-Phos | 2-dicyclohexylphosphino-2',4',6'-triisopropylbiphenyl |
| Me$_4$—$^t$Bu—X-Phos | di-tert-butyl[3,4,5,6-tetramethyl-2',4',6'-tri(propan-2-yl)biphenyl-2-yl]phosphane |
| NMO | 4-methylmorpholine N-oxide |
| TPAP | tetra-n-propylammonium perruthenate (VII) |
| HCOOH | formic acid |
| K$^t$OBu | potassium tert-butoxide |
| Na$_2$S$_2$O$_5$ | sodium metabisulfite |
| NMR | nuclear magnetic resonance |
| TLC | thin layer chromatography |
| (EtO)$_2$P(O)CH$_2$CN | diethyl (cyanomethyl)phosphonate |
| MsCl | methanesulfonyl chloride |
| TsOH | p-toluenesulfonic acid |
| KCN | potassium cyanide |
| Si-DMT | silica supported Dimercaptotriazine |
| TMS | trimethylsilane |
| CF$_3$TMS | (trifluoromethyl)trimethylsilane |

| Alkyl Group Abbreviations | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

METHODS OF SYNTHESIS

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:
All reactions were stirred (mechanically, stir bar/stir plate, or shaken) and conducted under an inert atmosphere of nitrogen or argon unless specifically stated otherwise.
All temperatures are degrees Celsius (° C.) unless otherwise noted.
Ambient temperature is 15-25° C.
Most compounds were purified by reverse-phase preparative HPLC, MPLC on silica gel, recrystallization and/or swish (suspension in a solvent followed by filtration of the solid).
The course of the reactions was followed by thin layer chromatography (TLC) and/or LCMS and/or NMR and reaction times are given for illustration only.
All end products were analyzed by NMR and LCMS.
Intermediates were analyzed by NMR and/or TLC and/or LCMS.
Method 1
General procedures to prepare intermediates of the instant invention are described in Scheme 1. Alkyl Grignard reagents are reacted with appropriately substituted (hetero)aryl carboxylates 1A at or around 0° C. in an appropriate solvent, such as THF, to afford intermediates 1B used in the synthesis of examples of the instant invention.

SCHEME 1

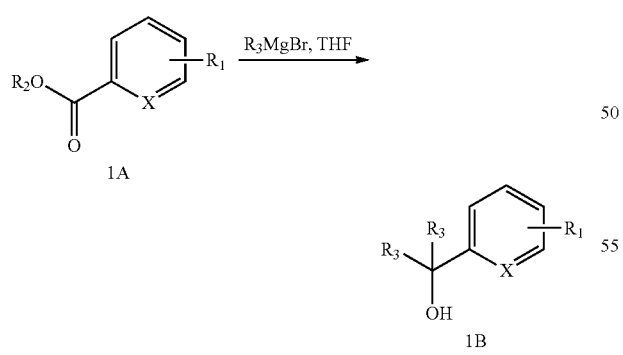

Method 2
General procedures to prepare intermediates of the instant invention are described in Scheme 2. A trifluoromethyl anion equivalent, such as $CF_3TMS$, is reacted with TBAF and an appropriately substituted (hetero)aryl aldehyde 2A in an appropriate solvent, such as THF, to yield intermediates 2B used in the synthesis of examples of the instant invention.

SCHEME 2

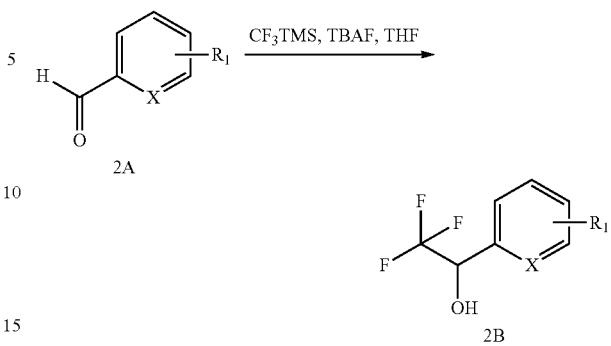

Method 3
General procedures to prepare intermediates of the instant invention are described in Scheme 3. Heteroaryl boronate esters or boronic acids 3B are cross coupled to optionally substituted (hetero)aryl bromides 3A using a suitable palladium complex, such as $Pd(dppf)Cl_2$, and an appropriate base, such as $K_3PO_4$, in a compatible solvent or solvent mixture, such as 10:1 v:v dioxane:water, at or around 90° C. to yield intermediates 3C in the synthesis of examples of the instant invention.

SCHEME 3

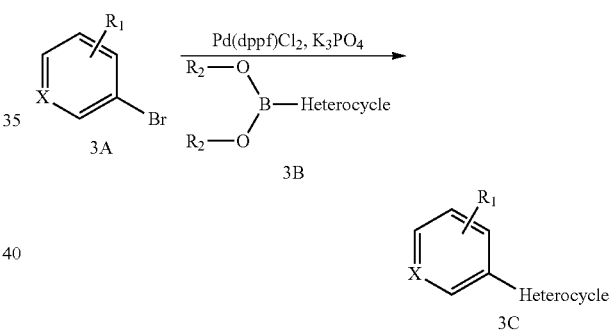

Method 4
General procedures to prepare intermediates of the instant invention are described in Scheme 4. Appropriately substituted benzyl bromides 4A can be reacted with aza heterocycles using a suitable base, such as potassium acetate, or be reacted with sodium azide followed by optionally substituted acetylenes and standard "Click chemistry" reagents to afford intermediates 4B in the synthesis of examples of the instant invention.

SCHEME 4

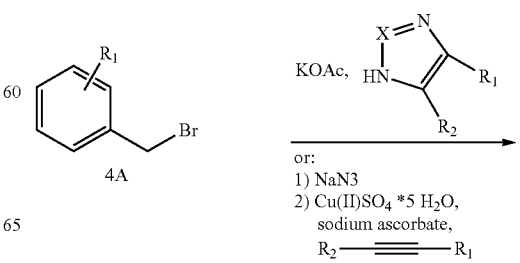

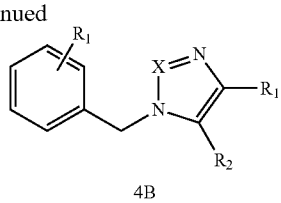

4B

Method 5

General procedures to prepare intermediates of the instant invention are described in Scheme 5. Appropriately substituted benzyl bromides 4A can be reacted with methyl hydroxy acetate in the presence of a suitable base, such as sodium hydride, and then further reacted with alkyl Grignard reagents to afford intermediates 5B used in the synthesis of examples of the instant invention.

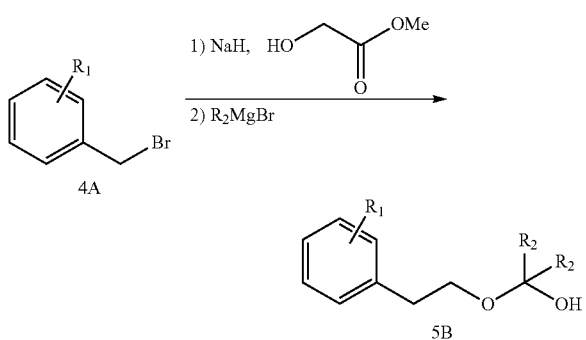

Method 6

General procedures to prepare intermediates of the instant invention are described in Scheme 6. Appropriately substituted thiophenols 6A are reacted with a suitable base, such as sodium hydride, and a trifluoromethylating agent, such as 5-(trifluoromethyl)dibenzo[b,d]thiophenium trifluoromethanesulfonate at ambient temperature in an appropriate solvent, such as DMF. The resulting intermediate is oxidized to the corresponding sulfone 6B with a suitable oxidant, such as m-CPBA, to afford an intermediate used in the synthesis of examples of the instant invention.

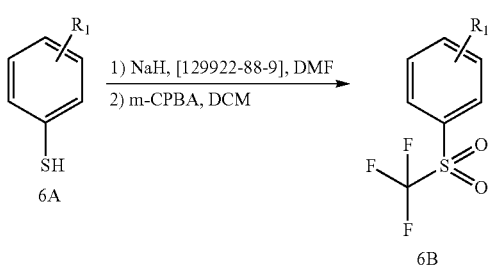

Method 7

General procedures to prepare intermediates of the instant invention are described in Scheme 7. Appropriately substituted phenylacetic esters 7A are reacted with a suitable base, such as sodium hydride, and methylating agent, such as methyliodide at an appropriate temperature, in a suitable solvent, such as THF to provide 7B. The resulting intermediate is reduced to alcohol 7C with a suitable reducing agent, such as LiALH$_4$, which was subsequently oxidized to aldehyde 7D with an oxidant such as PCC. Treatment of 7D with CF$_3$ anion followed by resolution of enantiomers using chiral stationary phase chromatography afford intermediates 7E and 7F used in the synthesis of examples of the instant invention.

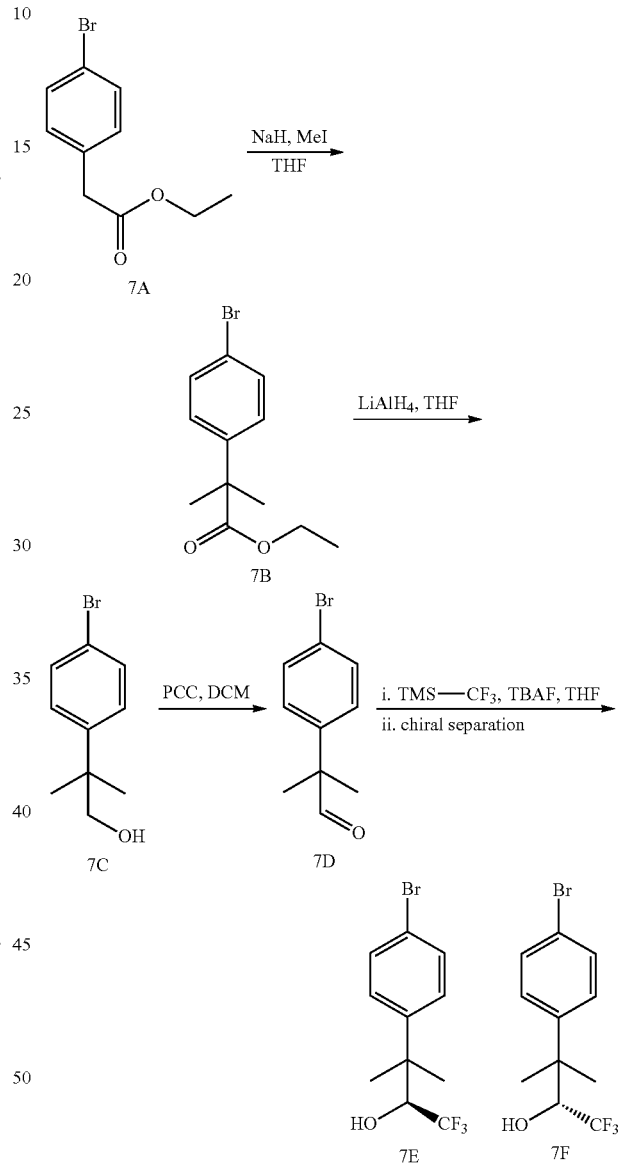

Method 8

General procedures to prepare intermediates of the instant invention are described in Scheme 8. Appropriately substituted benzylbromides 8A are reacted with sodium cyanide in an appropriate solvent, such as aqueous ethanol to provide 8B. The resulting intermediate is reacted with a suitable base, such as sodium hydride, and a methylating agent, such as methyliodide at an appropriate temperature in solvent, such as THF to provide 8C which is subsequently reduced to aldehyde 8D with a suitable reducing agent, such as DIBAL-H, in a suitable solvent such as THF. Treatment of 8D with CF$_3$ anion afford intermediate 8E used in the synthesis of examples of the instant invention.

SCHEME 8

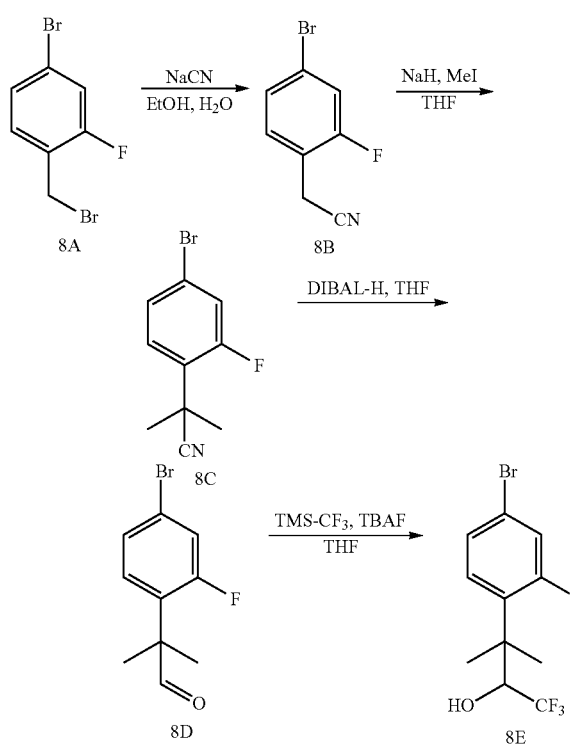

Method 9

General procedures to prepare intermediates of the instant invention are described in Scheme 9. 2-Cyanopropane is reacted with a suitable base, such as NaHMDS, in an appropriate solvent, such as toluene and reacted with 2,5-dibromopyridine 9A to provide 9B which is subsequently reduced to aldehyde 9C with a suitable reducing agent, such as DIBAL-H, in a suitable solvent such as THF. Treatment of 9C with $CF_3$ anion affords intermediate 9D used in the synthesis of examples of the instant invention.

SCHEME 9

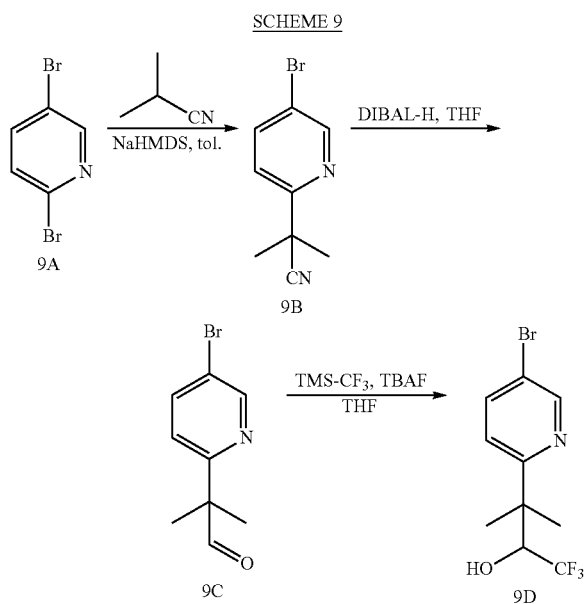

Method 10

General procedures to prepare intermediates of the instant invention are described in Scheme 10. Difluoroacetate is reacted with a suitable base, such as n-BuLi, in an appropriate solvent, such as toluene and reacted with 2,5-dibromopyridine 10A to provide 10B. Ketone 10B is subsequently reduced to alcohol 10C($R_1$ is hydrogen) with a suitable reducing agent, such as $NaBH_4$, in a suitable solvent such as methanol. Alternatively, ketone 10B is reacted with a Grignard reagent to afford alcohol 10C($R_1$ is alkyl) used in the synthesis of examples of the instant invention.

SCHEME 10

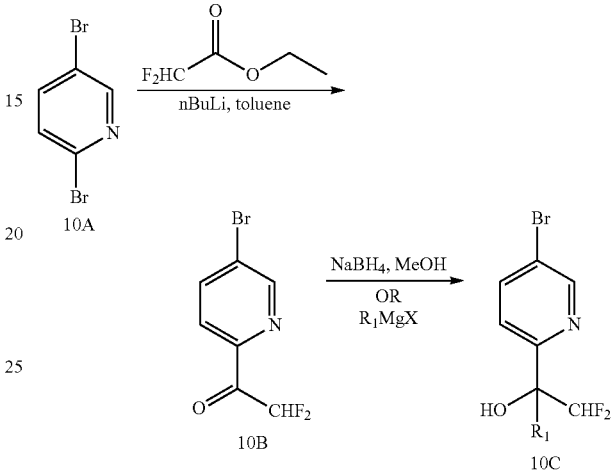

Method 11

General procedures to prepare intermediates of the instant invention are described in Scheme 11. Alcohol 11A is reacted with a nucleophillic fluoride source such as DAST to afford 11B used in the synthesis of examples of the instant invention.

SCHEME 11

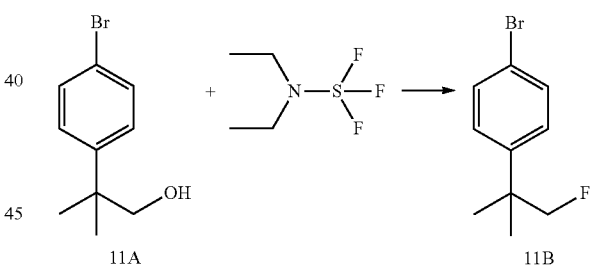

Method 12

General procedures to prepare intermediates of the instant invention are described in Scheme 12. Halo-substituted benzenesulfonyl chloride 12A is reacted with amines in the presence of a base such as TEA to afford sulfonamides 12B used in the synthesis of examples of the instant invention.

SCHEME 12

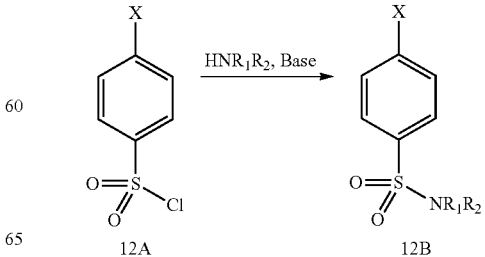

Method 13

General procedures to prepare intermediates of the instant invention are described in Scheme 13. Appropriately substituted thiophenols 13A are reacted with a suitable base, such as potassium hydroxide, and a difluoromethylating agent, such as diethyl [bromo(difluoro)methyl]phosphonate, in an appropriate solvent or solvent mixture, such as 1:1 v:v MeCN:water. The resulting intermediate is oxidized to the corresponding sulfone 13B with a suitable oxidant, such as m-CPBA, to afford an intermediate used in the synthesis of examples of the instant invention.

SCHEME 13

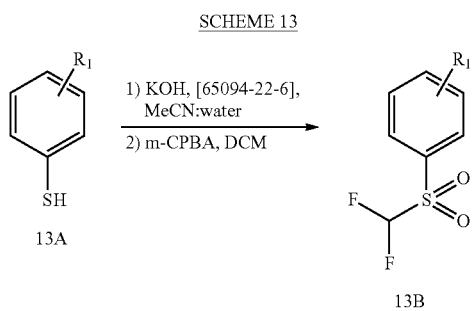

Method 14

General procedures to prepare intermediates of the instant invention are described in Scheme 14. Appropriately substituted aryl sulfoxides 14A are reacted with a lewis acid, such as zinc iodide, and a suitable nucleophilic fluorine source, such as BAST, in a solvent, such as 1,2-DCE, at or around 40° C. The resulting intermediate is oxidized to the corresponding sulfone 14B with a suitable oxidant, such as m-CPBA, to afford an intermediate used in the synthesis of examples of the instant invention.

SCHEME 14

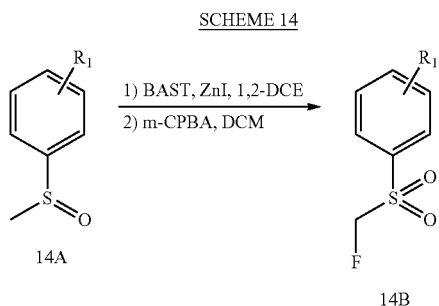

Method 15

General procedures to prepare intermediates of the instant invention are described in Scheme 15. Appropriately substituted benzothiophenes 15A are oxidized to the coorresponding sulfones with a suitable oxidant, such as m-CPBA, and then hydroxylated upon stirring in aqueous sodium hydroxide at or around 100° C. to afford intermediates 15B in the synthesis of examples of the instant invention.

SCHEME 15

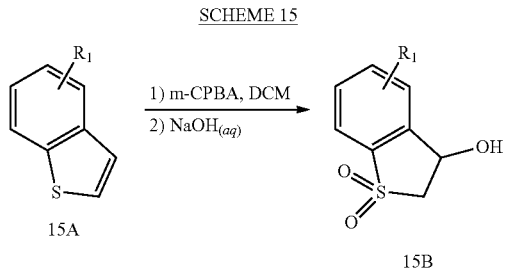

Method 16

General procedures to prepare intermediates of the instant invention are described in Scheme 16. Appropriately substituted 2,3-dihydro-1H-isoindol-ones 16A can be poly-methylated using a suitable base, such as sodium hydride, and methyl iodide to afford intermediates 16B used in the synthesis of examples of the instant invention.

SCHEME 16

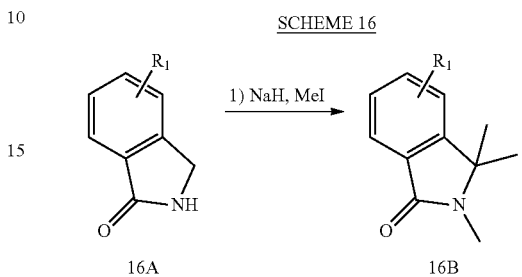

Method 17

General procedures to prepare intermediates of the instant invention are described in Scheme 17. Appropriately substituted 2,3-dihydro-1H-isoindol-ones 16A can be mono-alkylated using a suitable base, such as sodium hydride, and optionally substituted alkylating agents to afford intermediates 17B in the synthesis of examples of the instant invention.

SCHEME 17

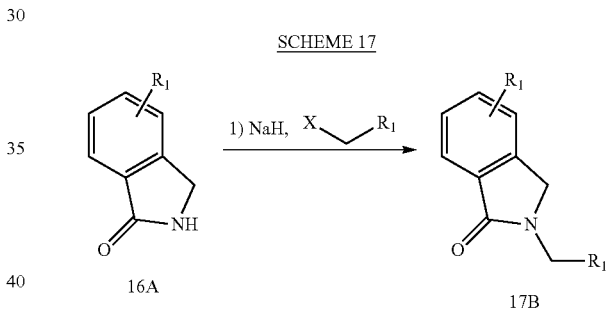

Method 18

General procedures to prepare intermediates of the instant invention are described in Scheme 18. Optionally substituted alkyl aldehydes/ketones 18A are condensed with diethyl(cyanomethyl)phosphonate in the presence of a suitable base, such as potassium tert-butoxide to yield substituted acrylonitriles 18B used as intermediates in the synthesis of examples of the instant invention.

SCHEME 18

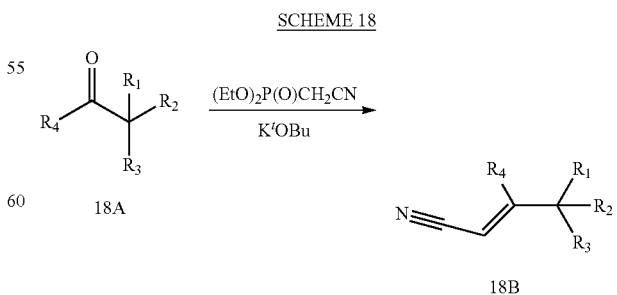

Method 19

General procedures to prepare intermediates of the instant invention are described in Scheme 19. Optionally substituted carbamate protected heterocyclic ketones 19A are condensed with diethyl(cyanomethyl)phosphonate in the presence of a suitable base, such as potassium tert-butoxide, to yield optionally substituted acrylonitriles 19B used as intermediates in the synthesis of examples of the instant invention.

Method 20

General procedures to prepare intermediates of the instant invention are described in Scheme 20. Carbamate protected optionally substituted acrylonitriles 19B are deprotected in the presence of a suitable acid, such as TFA or HCl, to form amino intermediates 20B that are further derivatized to form sulfonamide 20C, urethane 20D, and N-arylated intermediates 20E. Sulfonamide derivatives 20C are formed by reacting deprotected optionally substituted acrylonitriles with optionally substituted sulfoyl chlorides in a suitable solvent, such as DCM, using an appropriate base, such as DIPEA. Urea derivatives 20D are formed by reacting deprotected optionally substituted acrylonitriles with a doubly activated carbonyl equivalent, such as DSC, and optionally substituted alcohols in the presence of a suitable base, such as TEA. N-arylated derivatives 20E are formed by reacting deprotected optionally substituted acrylonitriles with optionally substituted aryl halides using a suitable palladium-ligand system, such as $Pd_2(dba)_3$ and X-Phos, an appropriate base, such as $Cs_2CO_3$, in a solvent, such as t-BuOH, at or around 90° C.

SCHEME 19

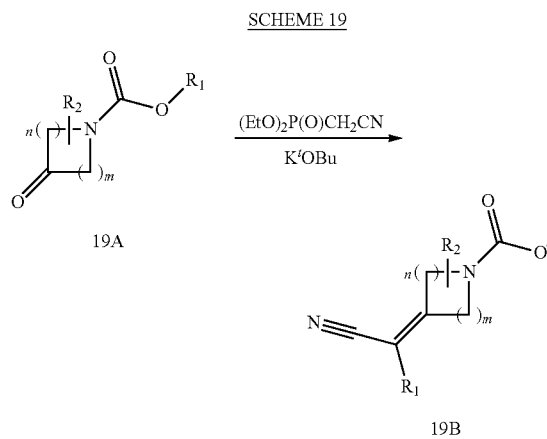

SCHEME 20

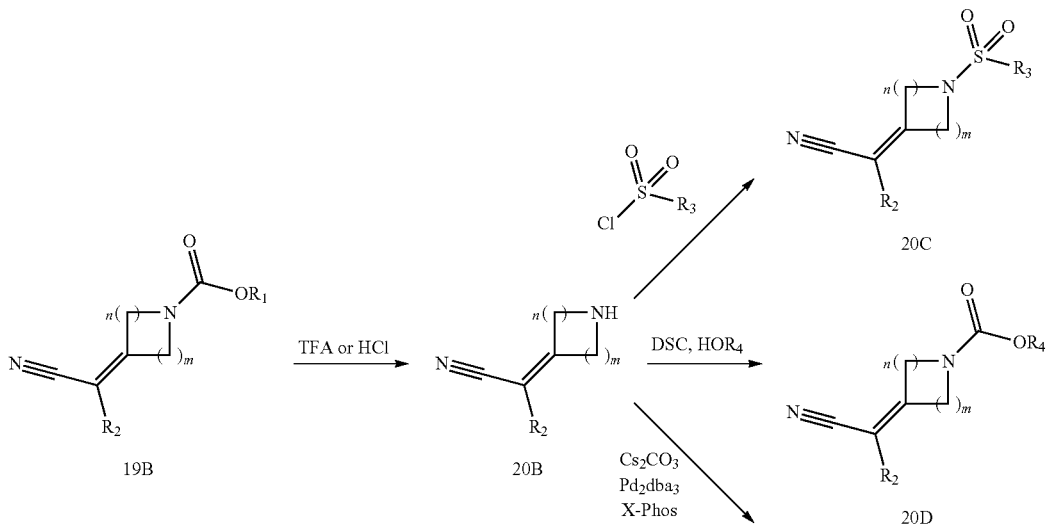

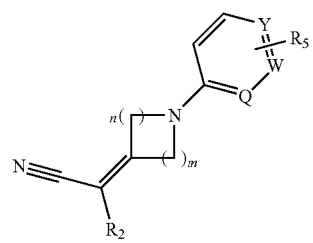

Method 21

General procedures to prepare intermediates of the instant invention are described in Scheme 21. Cyanohydrins 21B of optionally substituted (hetero)cyclic ketones 21A are prepared using aqueous sodium metabisulfite, followed by the addition of a suitable cyanide source, such as potassium cyanide. Hydroxyl group activation with a suitable agent, such as mesyl chloride or POCl₃, followed by elimination under appropriate conditions, such as refluxing pyridine, yields substituted acrylonitriles 21C used as intermediates in the synthesis of examples of the instant invention.

SCHEME 21

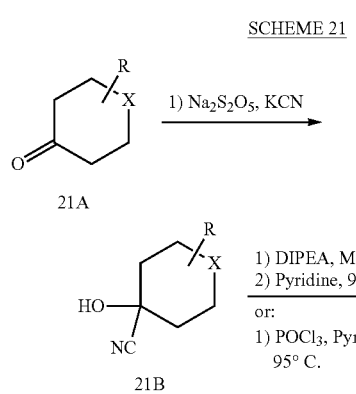

Method 22

General procedures to prepare intermediates of the instant invention are described in Scheme 22. Optionally substituted (hetero)cyclic ketones 22A are enolized with an appropriate base, such as LDA, and reacted with a suitable triflating agent, such as N-(5-chloropyridin-2-yl)-1,1,1-trifluoro-N-(trifluoromethylsulfonyl)methanesulfonamide. The resulting vinyl triflate 22B is reacted with a suitable palladium complex, such as tetrakis(triphenylphosphine) palladium (0), and an appropriate cyanide source, such as zinc cyanide, to afford substituted acrylonitriles 22C used as intermediates in the synthesis of examples of the instant invention.

SCHEME 22

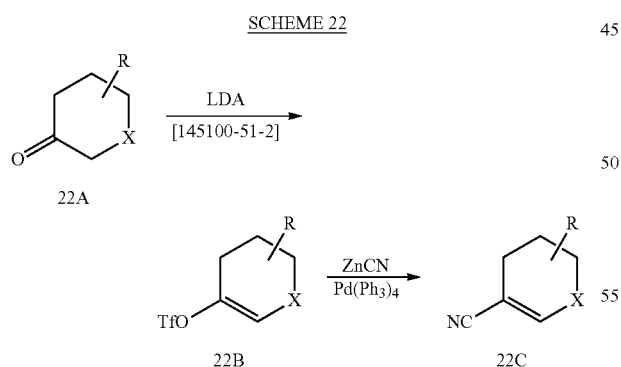

Method 23

General procedures to prepare intermediates of the instant invention are described in Scheme 23. Acrylonitrile is made to under go a Diels-Alder cyclization with an appropriately substituted butadiene using standard conditions, such as refluxing benzene. The cycloaddition product is deprotected with aqueous acid, such as 1N HCl, to provide substituted cyclohexenone 23A, which is then reacted with a suitable reductant, such as cerium (III) chloride and sodium borohydride, to afford intermediates 23B used in the synthesis of examples of the instant invention.

Method 24

SCHEME 23

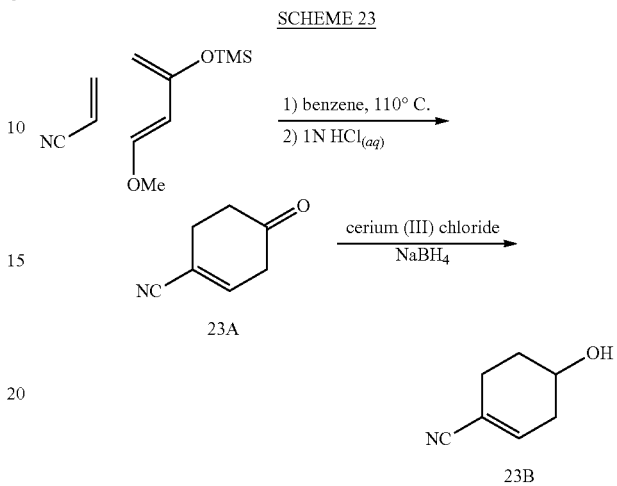

General procedures to prepare intermediates of the instant invention are described in Scheme 24. Racemic alcohol 24A is resolved to enantiomerically enriched (R or S) 24B and 24D. Esterification of alcohol 24A with a suitable ester such as vinylproprionate in the presence of a suitable enzyme such as Amano Lipase PS led to a mixture of enantiomerically enriched 24B and ester 24C which were separated. Saponification of 24C using an appropriate base such as NaOH afforded intermediates 24D used in the synthesis of examples of the instant invention.

SCHEME 24

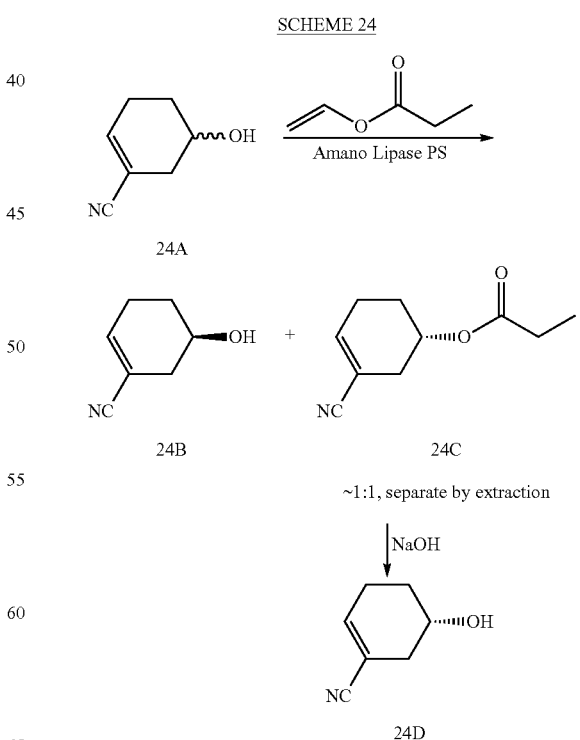

Method 25

General procedures to prepare intermediates of the instant invention are described in Scheme 25. 2-Chloroprop-2-enenitrile is reacted with benzene sulfinic acid sodium salt in aqueous acetic acid. The resulting olefin is regenerated by eliminating the chloro substituent with an appropriate base, such as TEA. The obtained acrylonitrile 25A is made to undergo a Diels-Alder cyclization with an appropriately substituted butadiene using standard conditions, such as refluxing benzene, to yield a cyano benzosulfone substituted cyclohexanone 25B. This substituted cyclohexanone 25B is protected with ethylene glycol under acidic conditions, such as TsOH, in an appropriate solvent, such as benzene, at elevated temperatures, e.g. at or around 110° C. The acetal substituted acrylonitrile 25C is obtained after elimination of the benzosulfone with an appropriate base, such as potassium tert-butoxide. This synthetic sequence affords intermediates 25C used in the synthesis of examples of the instant invention.

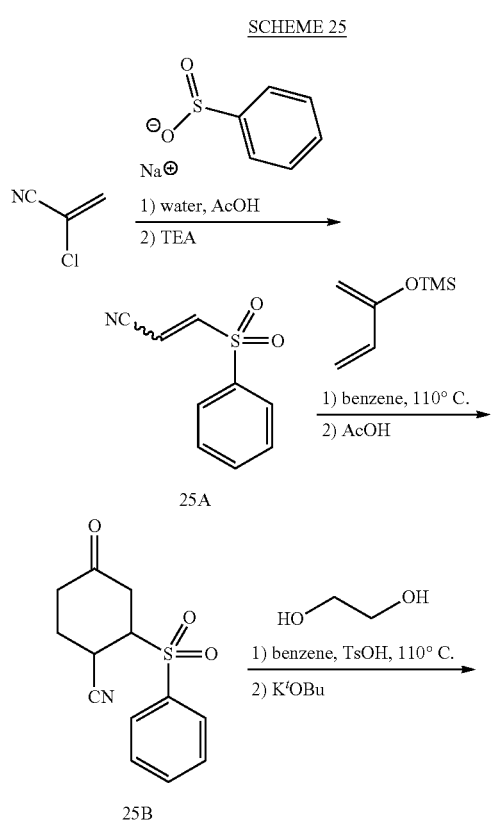

Method 26

General procedures to prepare intermediates of the instant invention are described in Scheme 26. 3-Amino pyrazole carboxamide 26A is cross coupled to (hetero)aryl halides 26B using a catalytic palladium-ligand system, such as $Pd_2(dba)_3$, and $Me_4$-$^tBu$-X-Phos, with a suitable base, such as $K_3PO_4$ or KOAc, in an appropriate solvent, such as 2-propanol, to yield pyrazole intermediates 26C.

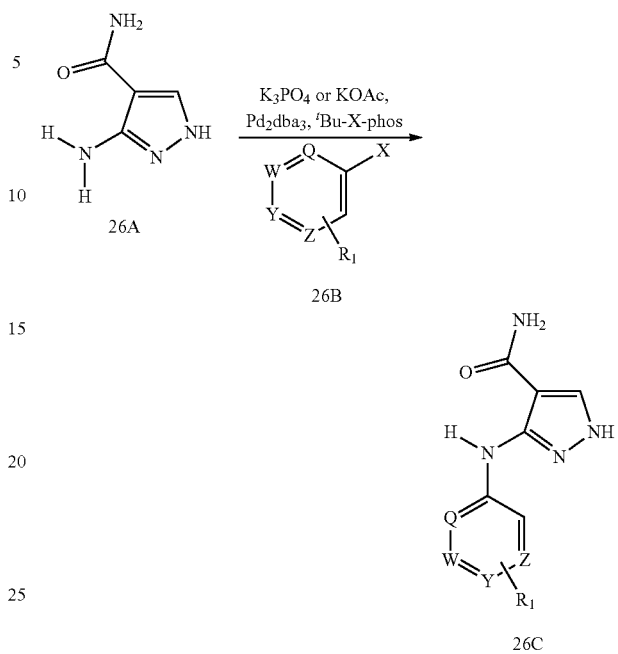

Method 27

General procedures to prepare intermediates of the instant invention are described in Scheme 27. 3-Amino-1H-pyrazole-4-carbonitrile 27A is reacted with a suitable base, such as sodium hydride, and SEM-Cl to yield a mixture of 3-amino pyrazoles 27B and 27C, which are arylated with an appropriately substituted halogenated (hetero)aromatic 26B using a suitable catalytic palladium-ligand system, such as $Pd_2(dba)_3$ and X-Phos, an appropriate base, such as $K_3PO_4$, in a suitable solvent, such as dioxane. The intermediate nitriles 27E and 27F are oxidized to the corresponding amides using an appropriate oxidant, such as hydrogen peroxide mixed with sodium hydroxide, and the SEM group is then removed by acid hydrolysis to yield pyrazole 26C, an intermediate in the synthesis of examples of the instant invention.

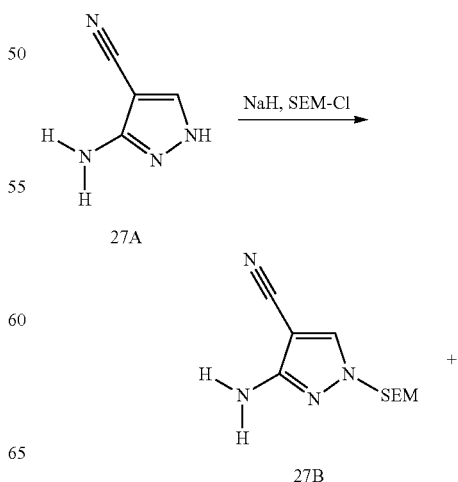

-continued

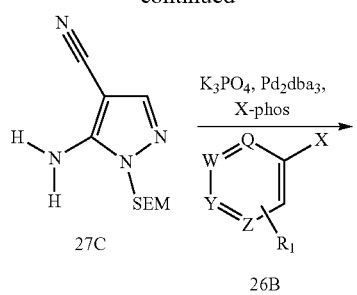

27C

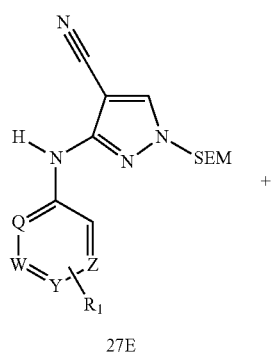

27E

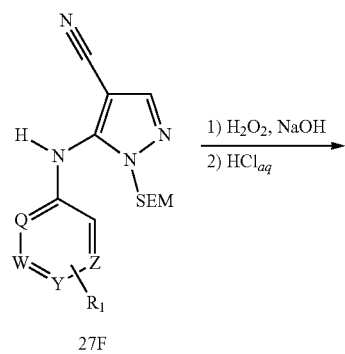

27F

Method 28

General procedures to prepare intermediates of the instant invention are described in Scheme 28. Using an appropriate base, such as DBU, in a suitable solvent, such as MeCN, EtOH, or tert-BuOH, 3-amino pyrazole carboxamide 26A is conjugatively added to optionally substituted acrylonitriles, including but not limited to those illustrated in Schemes #18-25 to yield alkylated pyrazole carboxamide 28B, an intermediate in the synthesis of examples of the instant invention.

SCHEME 28

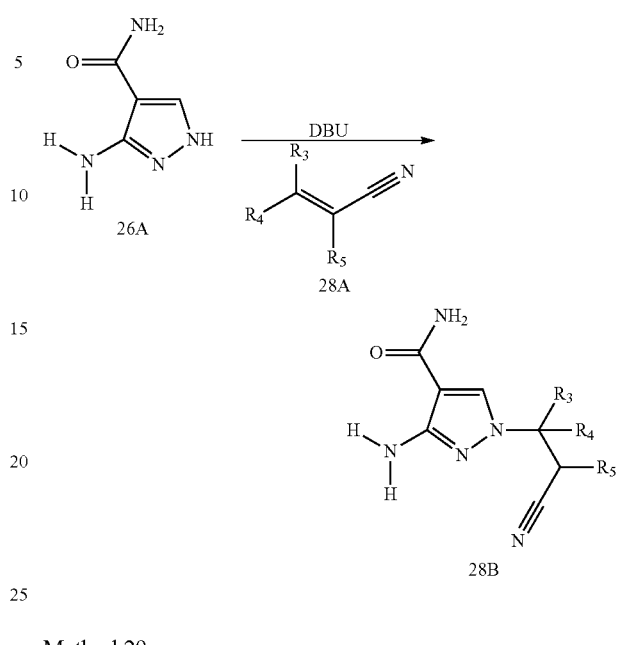

Method 29

General procedures to prepare examples of the instant invention are described in Scheme 29. Methyl 5-amino-1H-pyrazole-4-carboxylate 29A is conjugatively added to substituted acrylonitriles 28A including but not limited to those illustrated in Schemes #18-25 in the presence of a suitable base, such as catalytic sodium methoxide. The resulting intermediates 29B are cross coupled to (hetero)aryl halides 26B using an appropriate catalytic palladium-ligand system, such as $Pd_2(dba)_3$ and X-Phos, and an appropriate base, such as $K_3PO_4$. Saponification of 29D using aqueous hydroxide, such as LiOH, followed by amide formation using standard conditions, such as EDC, HOBT, and optionally substituted primary and secondary amines yields examples 29F of the instant invention.

SCHEME 29

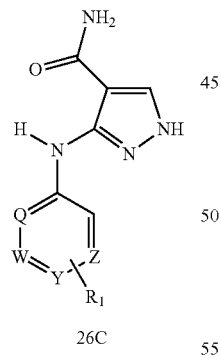

29A

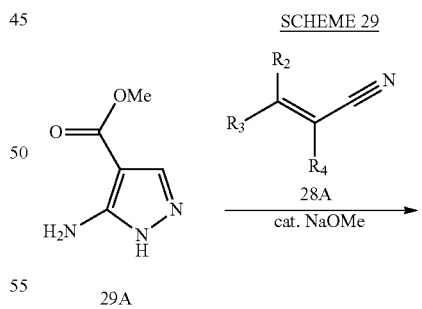

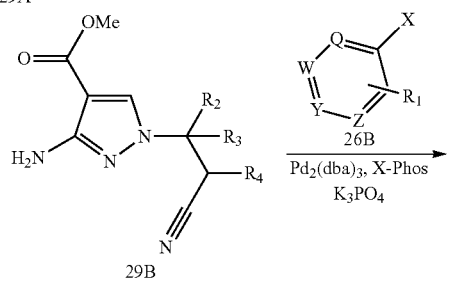

29B

-continued

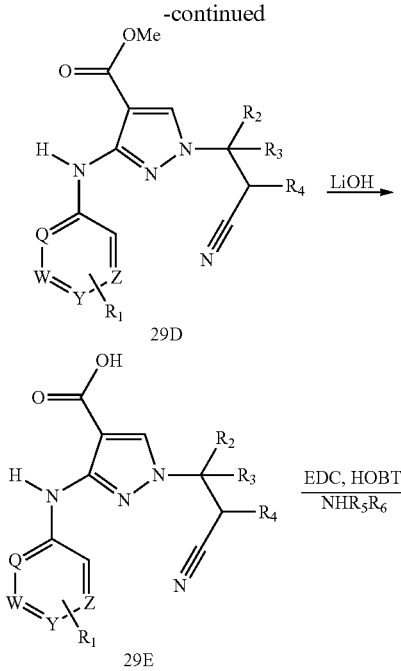

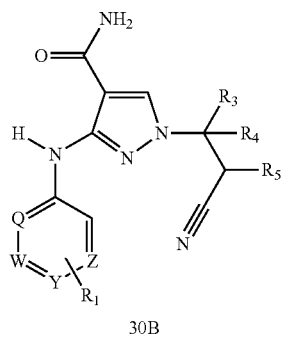

Method 31

General procedures to prepare examples of the instant invention are described in Scheme 31. Alkylated 3-amino pyrazole carboxamides 28B are cross coupled to (hetero)aryl halides 26B using an appropriate catalytic palladium-ligand system, such as $Pd_2(dba)_3$ and X-Phos or $Me_4{}^tBu$-X-Phos, and a suitable base, such as $K_3PO_4$ or KOAc, in solvent, such as dioxane, to yield examples 30B of the instant invention.

SCHEME 31

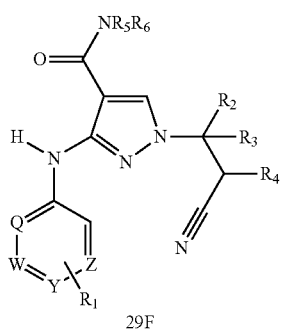

Method 30

General procedures to prepare examples of the instant invention are described in Scheme 30. Using an appropriate base, such as DBU, in a suitable solvent, such as MeCN, EtOH, or tert-BuOH, N-(hetero)arylated pyrazole carboxamides 26C are conjugatively added to optionally substituted acrylonitriles 28A, including but not limited to those illustrated in Schemes #18-25 to yield examples 30B of the instant invention.

SCHEME 30

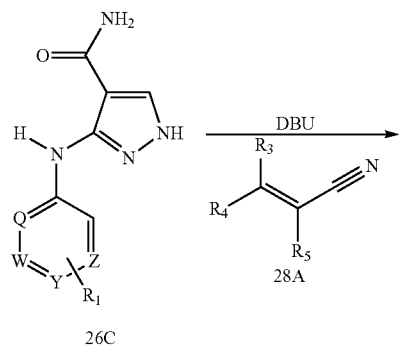

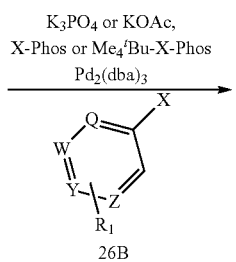

Method 32

General procedures to prepare examples of the instant invention are described in Scheme 32. Using a solid supported palladium system, such as SiliaCat® DPP-Pd and a suitable base, such as, $K_2CO_3$, optionally substituted boronic acids 32B are cross coupled to bromophenyl substituted pyrazoles 32A to yield examples 32C of the instant invention.

SCHEME 32

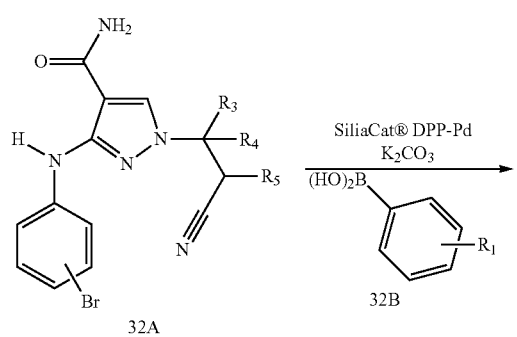

32A

32B

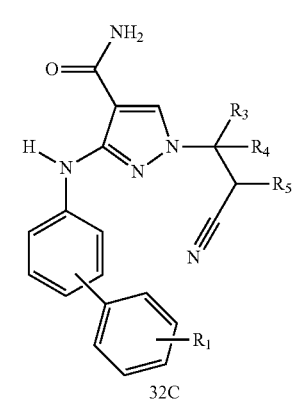

32C

Method 33

General procedures to prepare examples of the instant invention are described in Scheme 33. Hydroxy substituted amino pyrazole carboxamides 33A can be fluorinated using a nucleophilic fluorine source, such as BAST, to afford examples 33B of the instant invention.

SCHEME 33

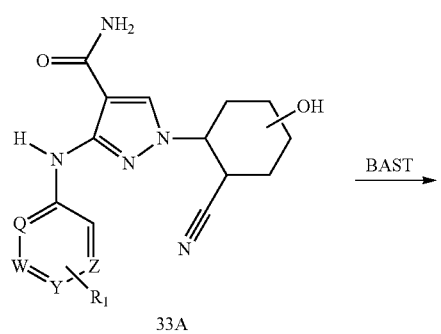

33A

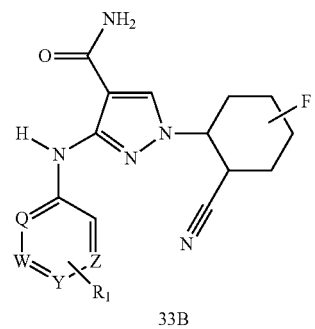

33B

Method 34

General procedures to prepare examples of the instant invention are described in Scheme 34. N-(hetero)arylated pyrazole carboxamides 26C can be alkylated with optionally substituted alkyl halides 34B using heat and an appropriate base, such as $Cs_2CO_3$, to afford examples 34C of the instant invention.

SCHEME 34

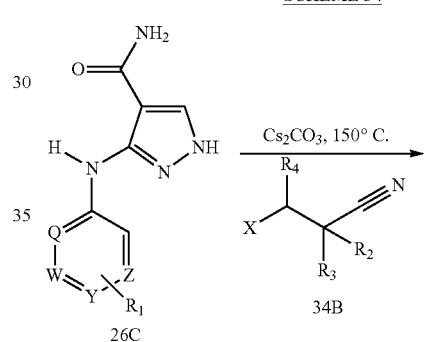

26C

34B

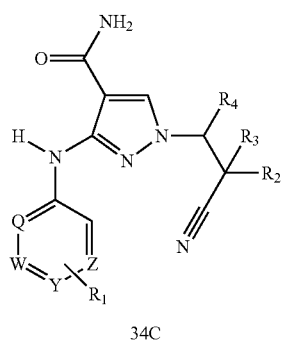

34C

Method 35

General procedures to prepare examples of the instant invention are described in Scheme 35. Carbamate protected substituted amino pyrazole carboxamides 35A are deprotected in the presence of acid, such as TFA or HCl, to provide amino intermediates 35B which are further derivatized using standard conditions known by those skilled in the art to yield examples of the instant invention. Examples include but are not limited to alkylated 35C, reductively aminated 35D, and arylated 35E derivatives, as well as carbamates 35F, ureas 35G, amides 35H, and sulfonamides 35I.

SCHEME 35
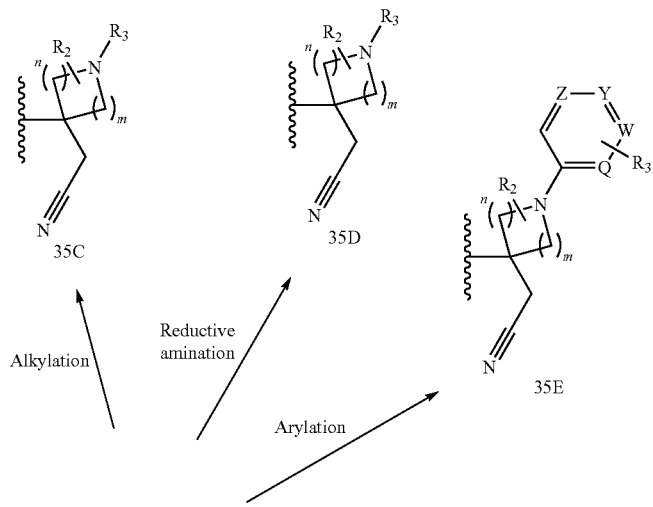
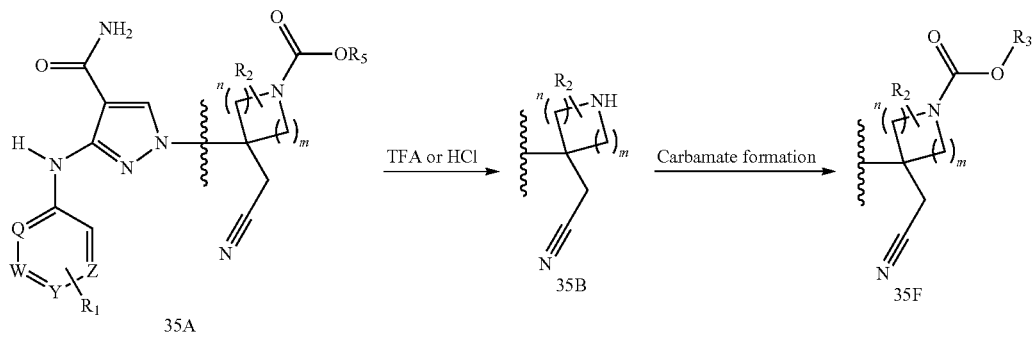
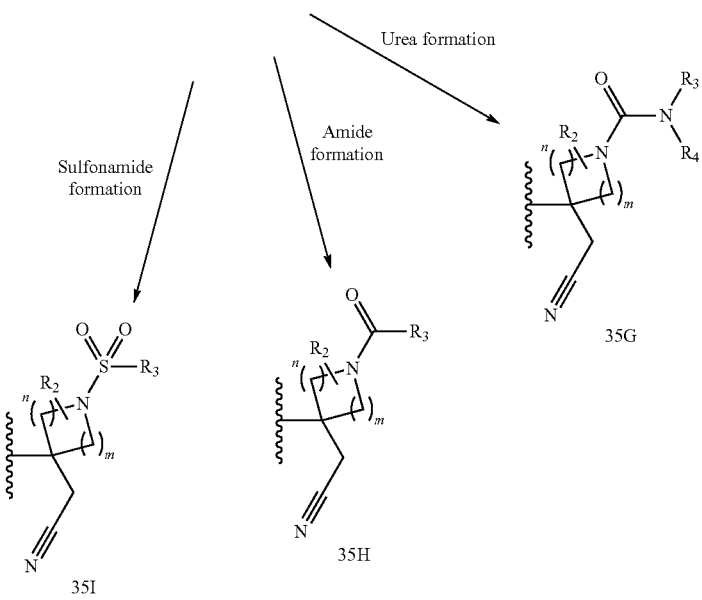

Method 36: Alcohol A

General procedures to prepare examples of the instant invention are described in Scheme 36. Using an appropriate base, such as DBU, in a suitable solvent, such as MeCN, EtOH, or tert-BuOH, N-(hetero)arylated pyrazole carboxamides 26A are conjugatively added to acrylonitrile 24A, 24B, or 24D to afford examples 36B. Alkylated 3-amino pyrazole carboxamides 36B are cross coupled to (hetero)aryl halides 26B using an appropriate catalytic palladium-ligand system, such as Pd$_2$(dba)$_3$ and X-Phos or Me$_4$ $^t$Bu-X-Phos, and a suitable base, such as K$_3$PO$_4$ or KOAc, in solvent, such as dioxane, to yield examples 36D (which are either racemic if alcohol 24A was used or chiral if alcohols 24B or 24D were used) of the instant invention.

SCHEME 36: Alcohol A

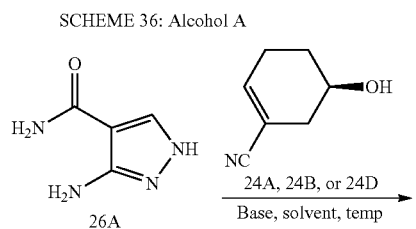

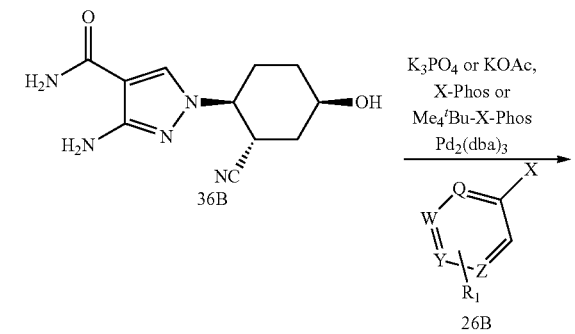

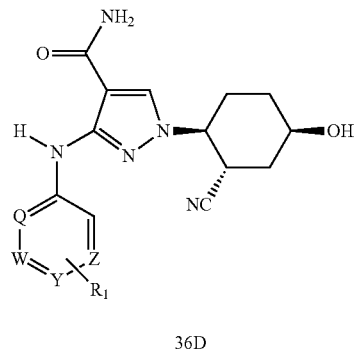

Method 37: Alcohol B

General procedures to prepare examples of the instant invention are described in Scheme 37. Using an appropriate base, such as DBU, in a suitable solvent, such as MeCN, EtOH, or tert-BuOH, N-(hetero)arylated pyrazole carboxamides 26C are conjugatively added to acrylonitrile 24A, 24B, or 24D to afford examples 36D (which are either racemic if alcohol 24A was used or chiral if alcohols 24B or 24D were used) of the instant invention.

SCHEME 37: Alcohol B

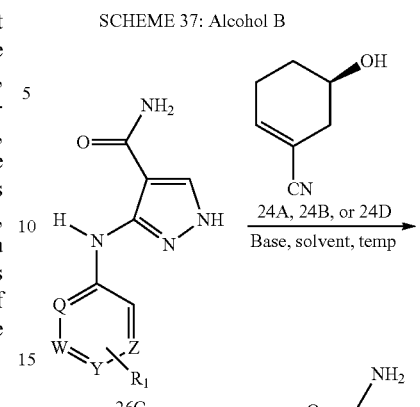

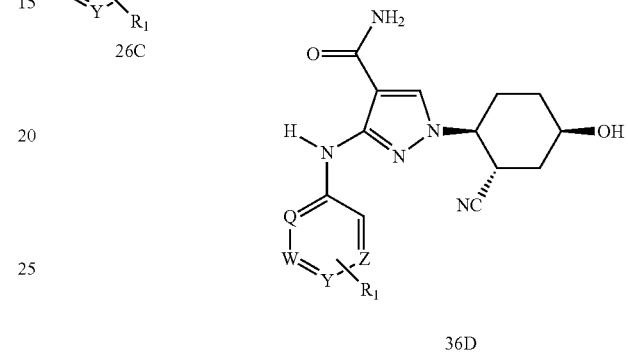

Method 38: Alcohol C

General procedures to prepare examples of the instant invention are described in Scheme 38. Hydroxylated cyclohexyl pyrazole carboxamides 36D can be oxidized with an appropriate oxidant, such as TPAP/NMO or IBX, to afford ketone 38B which is then reacted with alkyl-metal reagents, sucg as Grignard reagents, in an appropriate solvent, such as THF, at an appropriate temperature, for example between −78 and 0° C., to afford examples 38C (which are either racemic if alcohol 24A was used or chiral if alcohols 24B or 24D were used) of the instant invention.

SCHEME 38: Alcohol C

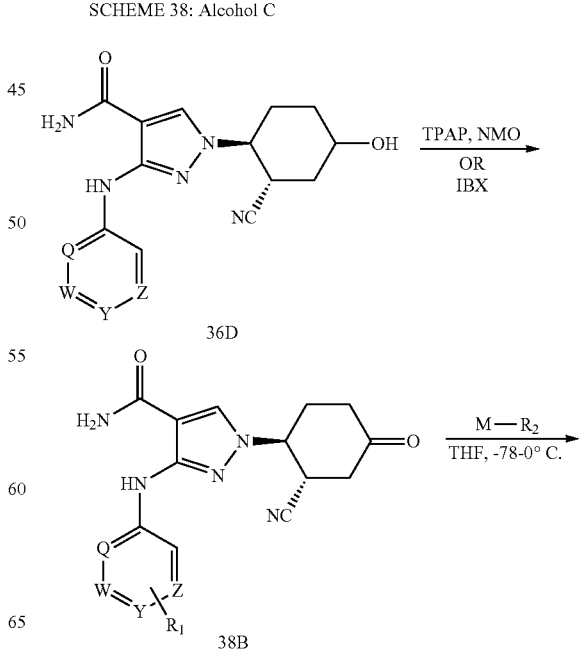

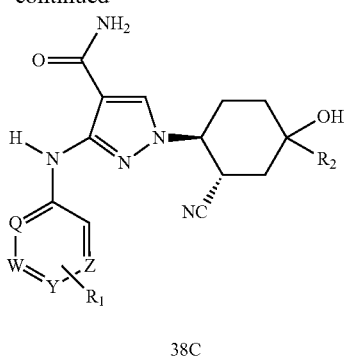

38C

Method 39: Alcohol D

General procedures to prepare examples of the instant invention are described in Scheme 39. Ketone 38B is reduced to alcohol 39A with a suitable reducing agent, such as NaBH$_4$, in a suitable solvent such as methanol to afford examples 39A of the instant invention.

SCHEME 39: Alcohol D

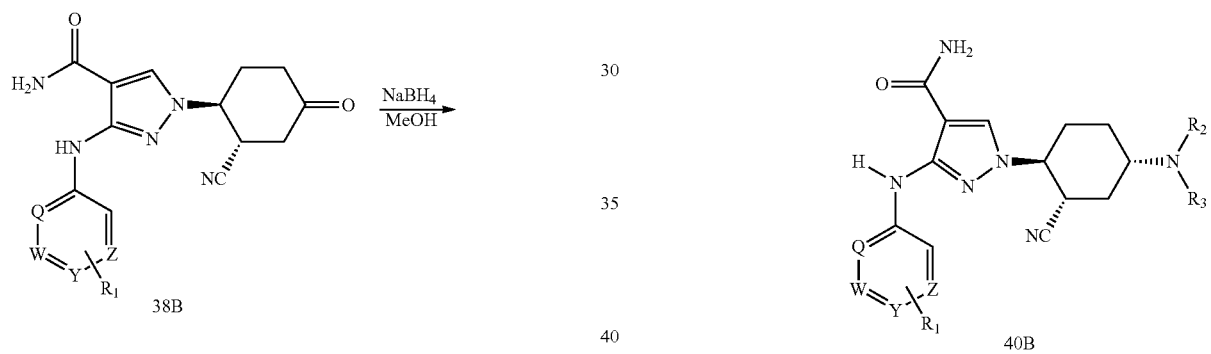

39A

Method 40

General procedures to prepare examples of the instant invention are described in Scheme 40. Hydroxylated cyclohexyl pyrazole carboxamides 36D can be oxidized with an appropriate oxidant, such as TPAP and NMO, and then reductively aminated using standard conditions, such as AcOH, NaCNBH$_3$ and optionally substituted primary and secondary amines, to afford examples 40A and 40B of the instant invention.

SCHEME 40

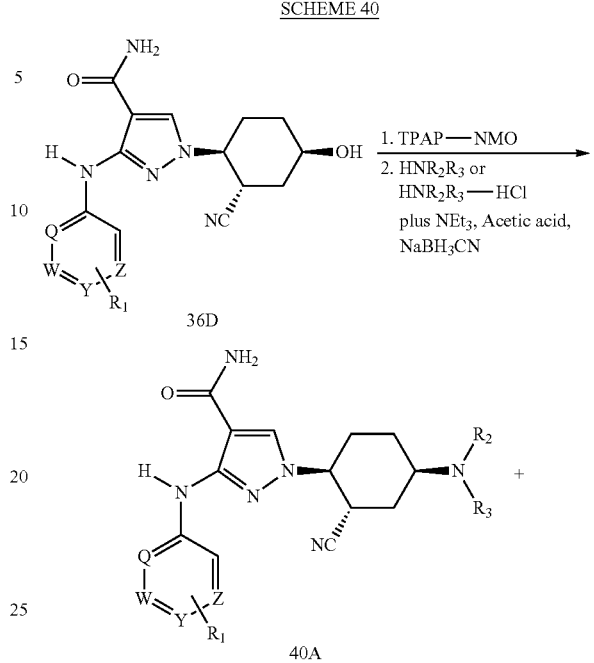

40A

40B

Method 41

General procedures to prepare examples of the instant invention are described in Scheme 41. Hydroxylated cyclohexyl pyrazole carboxamides 36D can be oxidized with an appropriate oxidant, such as IBX, and then reductively aminated using standard conditions, such as AcOH, NaCNBH$_3$, and optionally substituted primary and secondary amines, to afford examples 40A and 40B of the instant invention.

SCHEME 41

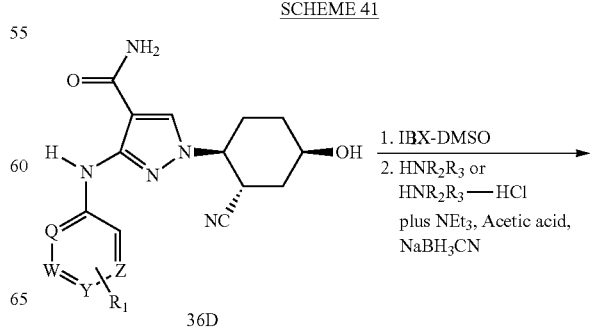

36D

-continued

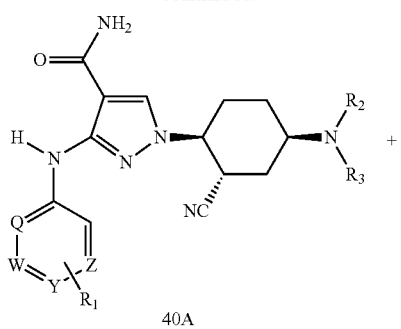

40A

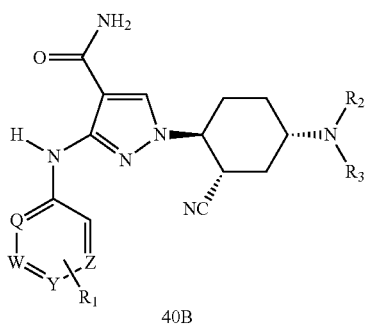

40B

Method 42

General procedures to prepare examples of the instant invention are described in Scheme 42. Hydroxylated cyclohexyl pyrazole carboxamides 36D can be oxidized with an appropriate oxidant, such as IBX, and then reductively aminated using standard conditions, such as AcOH, NaBH(OAc)$_3$, and optionally substituted primary and secondary amines, to afford examples 40A and 40B of the instant invention.

SCHEME 42

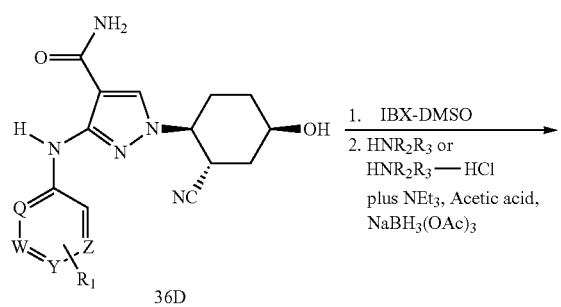

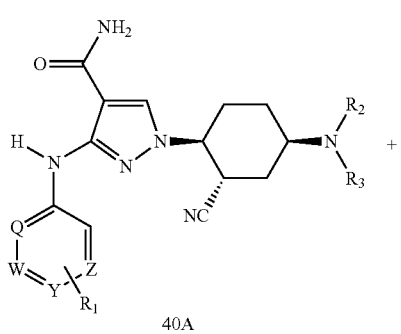

-continued

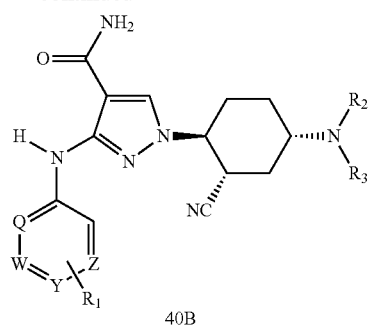

40B

Method 43

General procedures to prepare examples of the instant invention are described in Scheme 43. Hydroxylated cyclohexyl pyrazole carboxamides 36D can be oxidized with an appropriate oxidant, such as IBX, and then reductively aminated using a 2-step protocol. For example, the ketone is treated with a primary amine and a Lewis acid, such as Ti(i-PrO)$_4$ followed by reaction with a metal hydride such as NaBH$_4$ in a solvent such as methanol to afford example 43B of the instant invention.

SCHEME 43

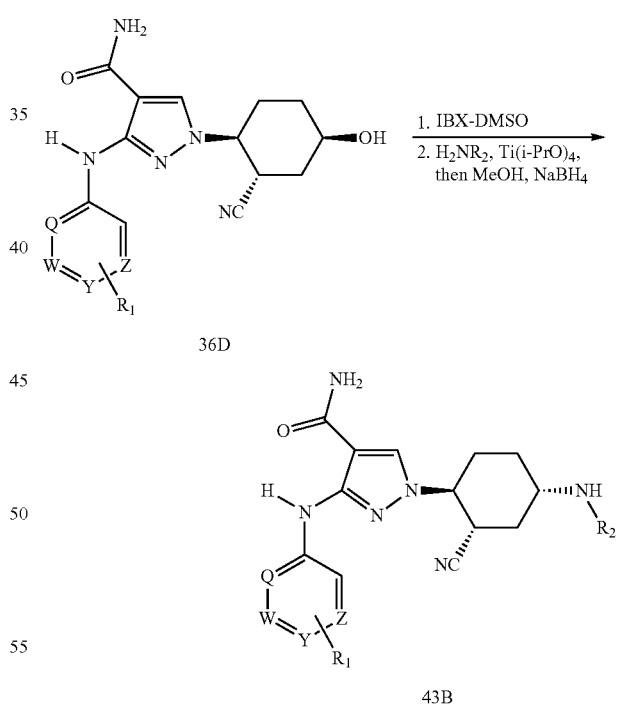

Method 44

General procedures to prepare examples of the instant invention are described in Scheme 44. Secondary amines 43B were subjected to reductive amination conditions such as AcOH, aqueous formaldehyde, a reducing agent such as NaCNBH$_3$, and in a suitable solvent mixture such as THF/methanol to afford examples 44A of the instant invention.

SCHEME 44

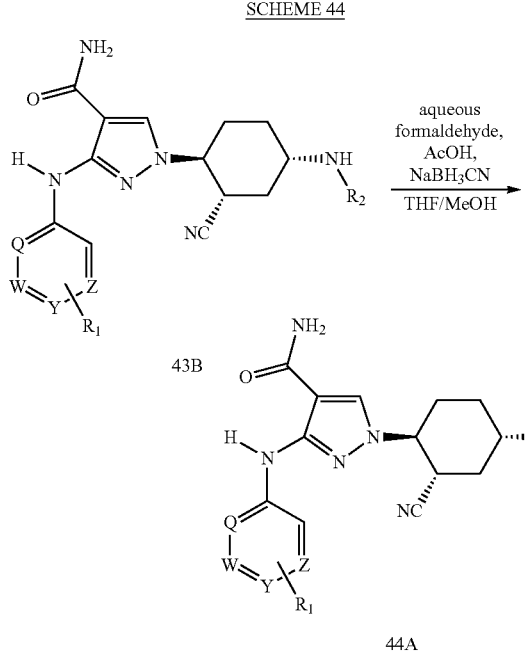

Method 45

General procedures to prepare examples of the instant invention are described in Scheme 45. Tertiaryamino-cyclohexyl pyrazole carboxamides 40B reacted with alkyl halides, such as but not limited to methyl iodide, in a suitable solvent such as acetonitrile, at an appropriate temperature, such as between 23 and 80° C., to afford quaternary amine derivatives 45A of the instant invention.

SCHEME 45

Method 46

General procedures to prepare examples of the instant invention are described in Scheme 46. Hydroxycyclohexyl pyrazole carboxamides 36D reacted with BAST to afford a regioselective dehydration to a cyclohexene derivative which reacted with a peroxide, such as m-CPBA, to afford an epoxide which reacted with acetic acid to afford 46A of the instant invention.

SCHEME 46

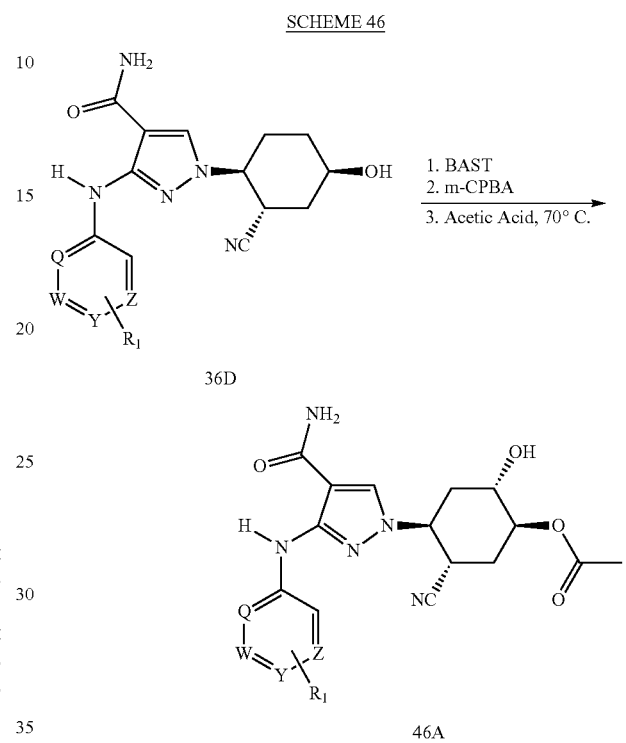

Method 47

General procedures to prepare examples of the instant invention are described in Scheme 47. Ketal-cyclohexyl pyrazole carboxamides 47A reacted under aqueous acid conditions, such as aqueous HCl in THF at a temperature between 23 and 80° C. afforded the ketone derivative, which was reductively aminated using standard conditions, such as AcOH, NaBH(OAc)$_3$, and optionally substituted primary and secondary amines, to afford examples 47B of the instant invention.

SCHEME 47

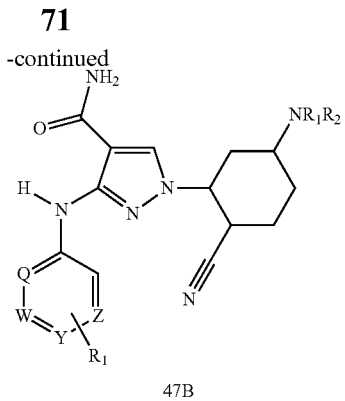

47B

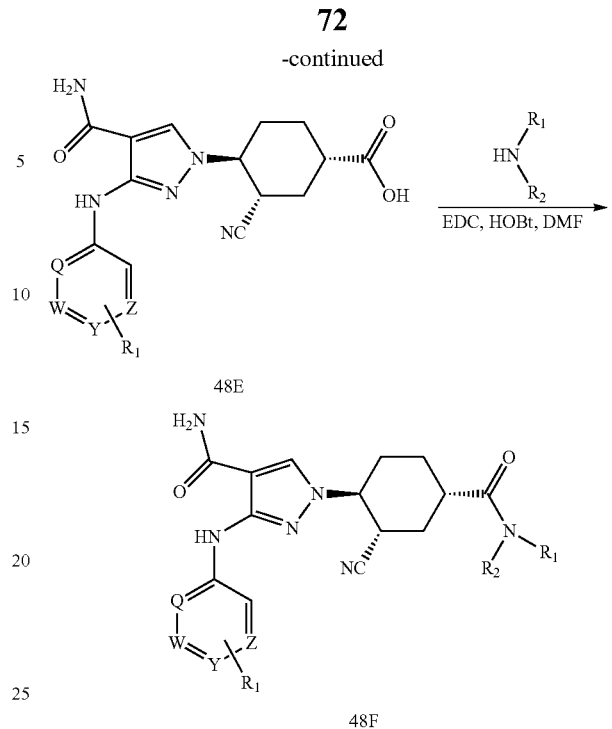

48E

48F

Method 48

General procedures to prepare examples of the instant invention are described in Scheme 48. Using an appropriate base, such as DBU, in a suitable solvent, such as MeCN, pyrazole carboxamide 26A is conjugatively added to acrylonitrile 48A to afford intermediate 48B. Alkylated 3-amino pyrazole carboxamides 48B are cross coupled to (hetero)aryl halides 26B using an appropriate catalytic palladium-ligand system, such as Pd$_2$(dba)$_3$ and X-Phos or Me$_4$ $^t$Bu-X-Phos, and a suitable base, such as KOAc, in solvent, such as 2-propanol, to yield 48D. Carboxylic acid 48E is formed under acidic conditions such as TFA in a suitable solvent such as DCM which is subsequently reacted with suitably substituted primary and secondary amines under standard amide coupling conditions such as EDC/HOBT to afford examples 48F of the instant invention.

Method 49

General procedures to prepare examples of the instant invention are described in Scheme 49. Carboxylic acid derivatives 48E can be reacted under standard coupling conditions such as EDC/HOBT in an alcoholic solvent such as methanol to afford methyl ester 49A which is further reacted with alkyl Grignard reagents in a suitable solvent such as THF to afford alcohol derivatives 49B of the instant invention.

SCHEME 48

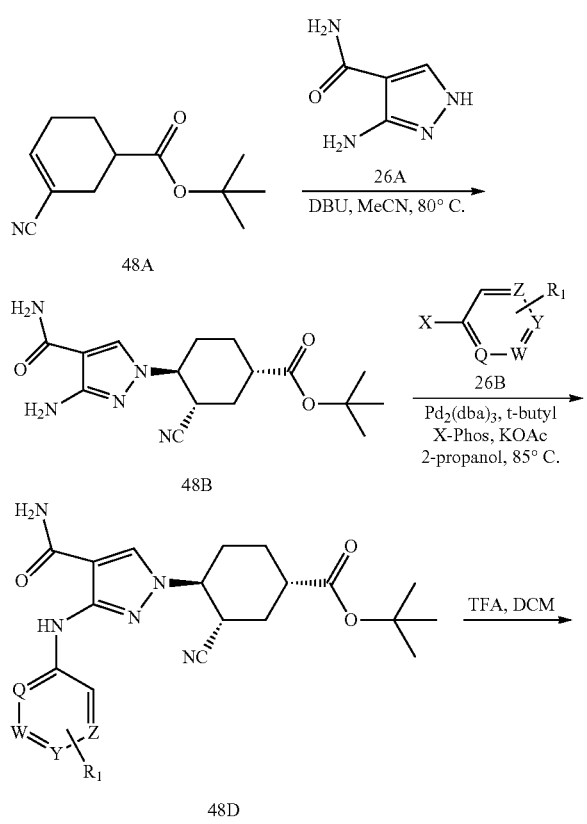

SCHEME 49

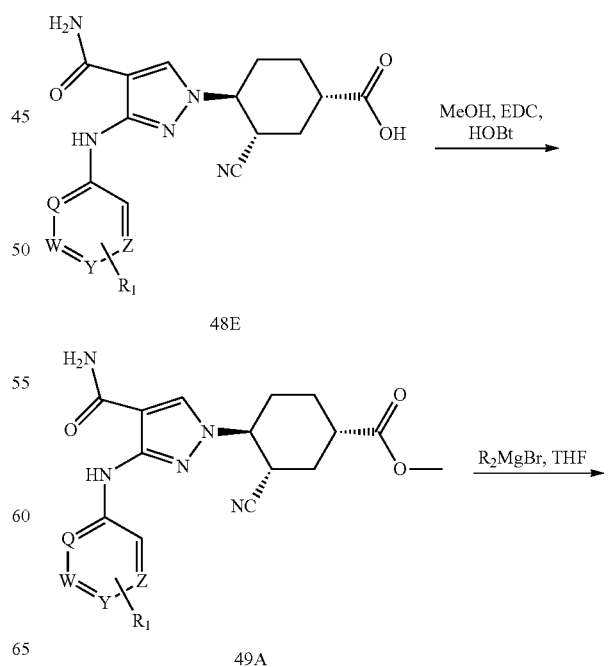

49A

-continued

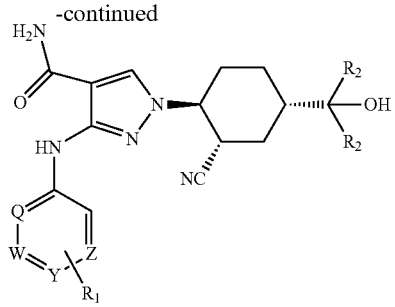

49B

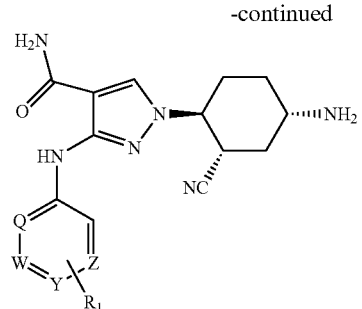

1) R₂CHO
   NaCNBH₃, 0° C.
2) R₃CHO
   NaCNBH₃, 0° C.

50D

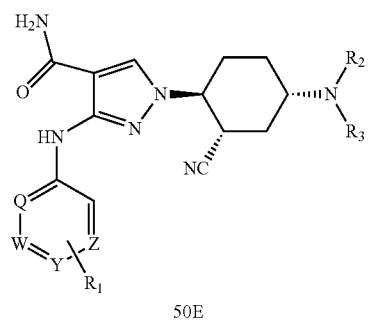

50E

Method 50

General procedures to prepare examples of the instant invention are described in Scheme 50. Using an appropriate base, such as DBU, in a suitable solvent, such as ethanol, pyrazole carboxamide 26A is conjugatively added to acrylonitrile 50A to afford intermediate 50B. Alkylated 3-amino pyrazole carboxamides 50B are cross coupled to (hetero)aryl halides 26B using an appropriate catalytic palladium-ligand system, such as $Pd_2(dba)_3$ and X-Phos or $Me_4$ $^tBu$-X-Phos, and a suitable base, such as KOAc, in solvent, such as 2-propanol, to yield 50C. Under acidic conditions such as TFA in a suitable solvent such as DCM, amine derivatives 50D were formed which were sequentially reductively aminated with optionally substituted aldehydes using standard conditions, such as AcOH, $NaBH(OAc)_3$ which afforded examples 50E of the instant invention.

Method 51

General procedures to prepare examples of the instant invention are described in Scheme 51. Hydroxylated cyclohexene 24A is reacted with an appropriate base such as sodium hydride, in a suitable solvent such as DMF, and treated with optionally substituted alkyl halides to afford ethers 51A. Using an appropriate base, such as DBU, in a suitable solvent, such as ethanol, pyrazole carboxamide 26A is conjugatively added to acrylonitrile 51A to afford intermediate 51B. Alkylated 3-amino pyrazole carboxamides 51B are cross coupled to (hetero)aryl halides 26B using an appropriate catalytic palladium-ligand system, such as $Pd_2(dba)_3$ and X-Phos or $Me_4$ $^tBu$-X-Phos, and a suitable base, such as KOAc, in solvent, such as 2-propanol, to yield examples 51D of the instant invention.

SCHEME 50

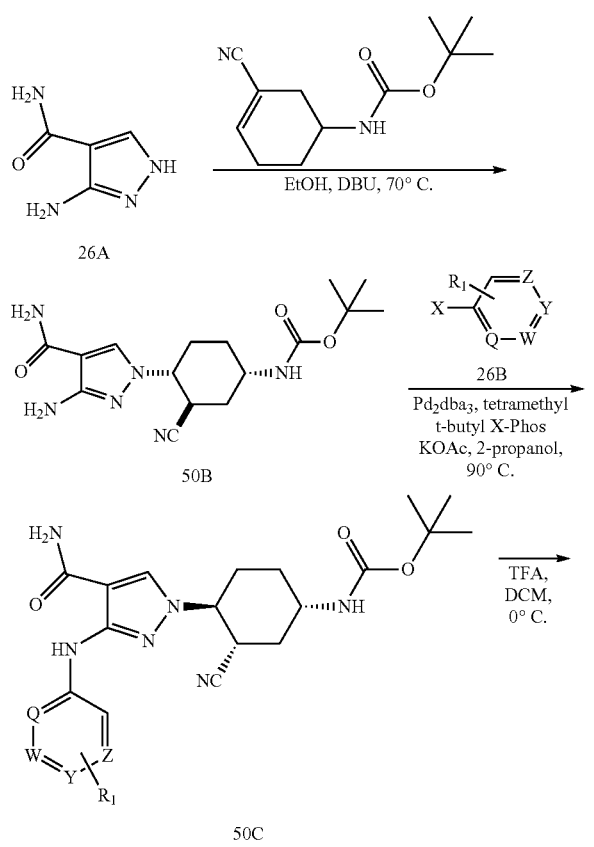

SCHEME 51

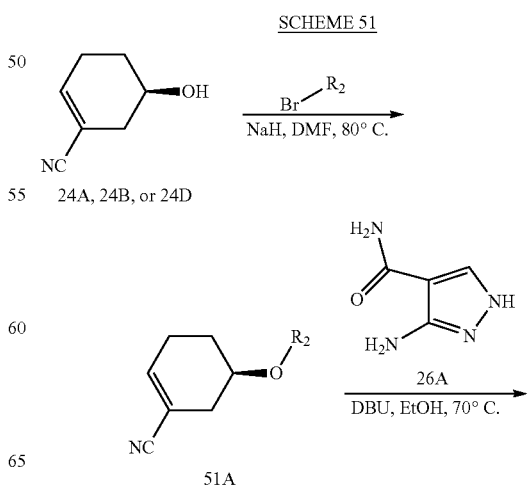

75

-continued

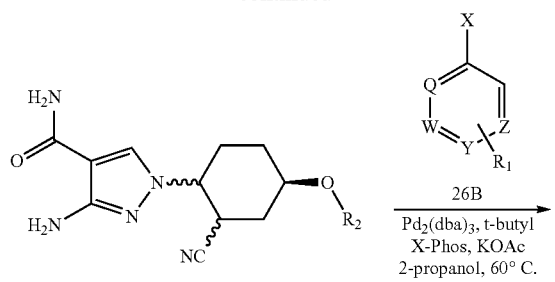

Method 52

General procedures to prepare examples of the instant invention are described in Scheme 52. Hydroxylated cyclohexyl pyrazole carboxamides 33A can be reacted with optionally substituted isocyanates and DMAP to afford carbamate derivatives 52A of the instant invention.

SCHEME 52

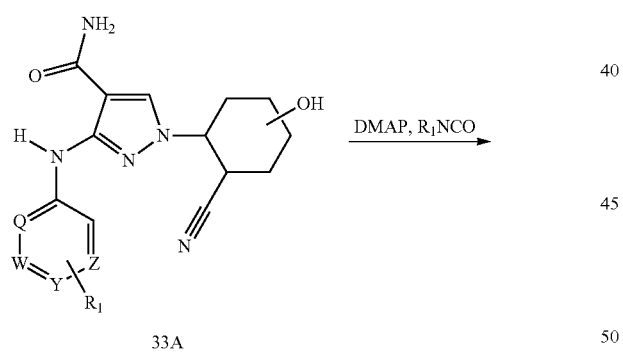

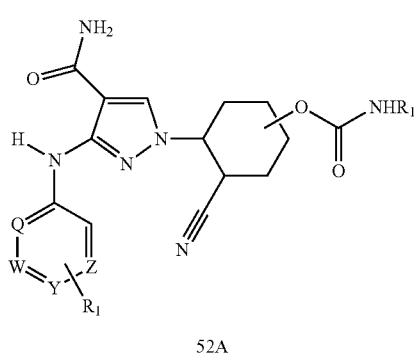

76

Method 53

General procedures to prepare examples of the instant invention are described in Scheme 53. Optionally substituted, carbamate protected pyrazole carboxamides 53A are deprotected in the presence of acid, such as TFA or HCl, and then reacted with optionally substituted alcohols in the presence of a doubly activated carbonyl group, such as DSC or phosgene, to afford carbamate derivatives 53C of the instant invention.

SCHEME 53

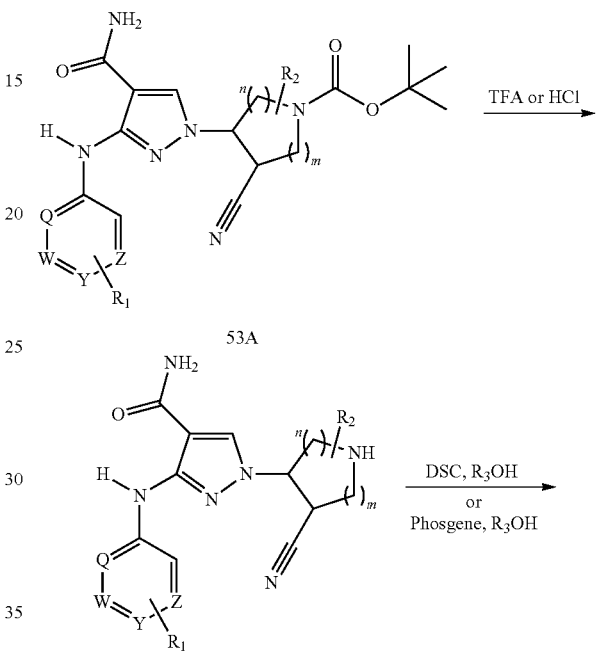

Method 54

General procedures to prepare examples of the instant invention are described in Scheme 54. Alkylated 3-amino pyrazole carboxamides 36B are cross coupled to (hetero)aryl halides 26B using an appropriate catalytic palladium-ligand system, such as $Pd_2(dba)_3$ and X-Phos or $Me_4\ ^tBu$-X-Phos, and a suitable base, such as KOAc, in a solvent such as isopropanol. The racemic derivative is purified on a chiral stationary phase column to yield enantioenriched examples 36D. Hydroxylated cyclohexyl pyrazole carboxamides 36D can be oxidized with an appropriate oxidant, such as a Swern method, and then reductively aminated using standard conditions, such as AcOH, $NaBH(OAc)_3$, and optionally substituted primary and secondary amines, to afford examples 40B of the instant invention.

SCHEME 54

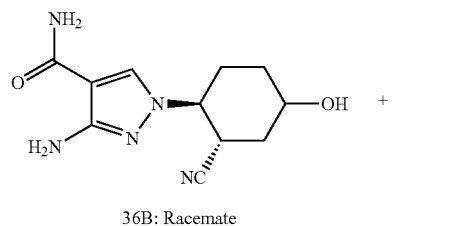

36B: Racemate

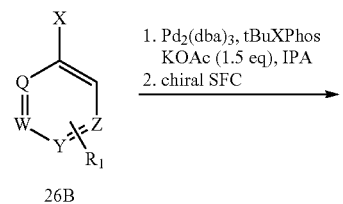

26B

1. Pd₂(dba)₃, tBuXPhos
   KOAc (1.5 eq), IPA
2. chiral SFC

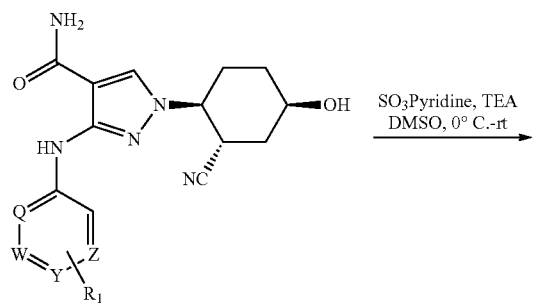

36D: chiral

SO₃Pyridine, TEA
DMSO, 0° C.-rt

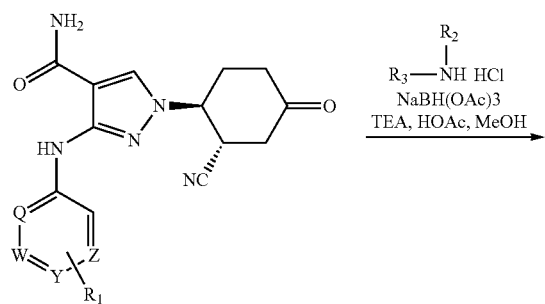

38B $R_3$—NH HCl
$R_2$
NaBH(OAc)₃
TEA, HOAc, MeOH

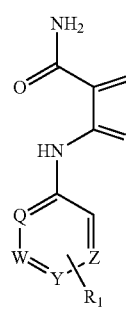

40B

Method 55

General procedures to prepare examples of the instant invention are described in Scheme 55. Substituted amino pyrazole 55A can be aminated with optionally substituted hydroxylamines with heating in a suitable solvent, such as ethanol to afford examples 55B of the instant invention.

SCHEME 55

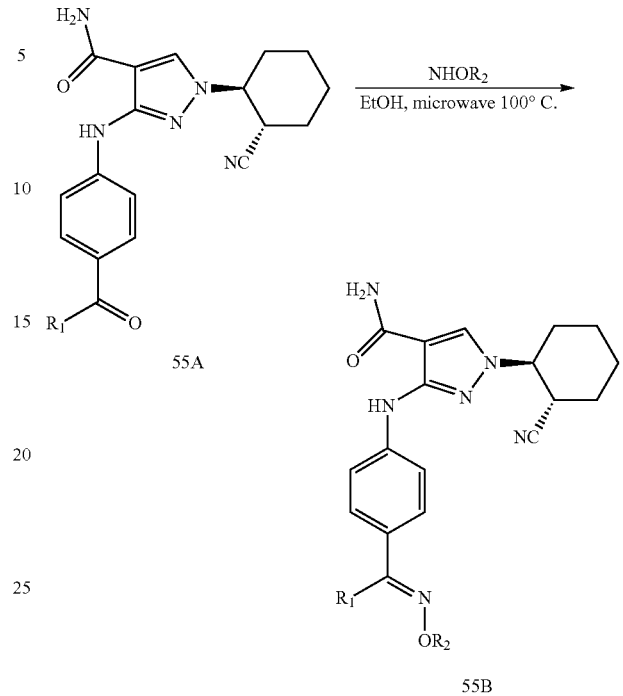

55A

NHOR₂
EtOH, microwave 100° C.

55B

Method 56

General procedures to prepare examples of the instant invention are described in Scheme 56. Hydroxylated cyclohexyl pyrazole carboxamides 36D can be activated with methane sulfonylchloride in the presence of a base such as TEA. The mesylate intermediate can be displaced with a metal-azide, such as sodium azide, which can be subsequently reduced, for example with triphenylphosphine in an appropriate solvent such as aqueous THF, to afford examples 56A of the instant invention.

SCHEME 56

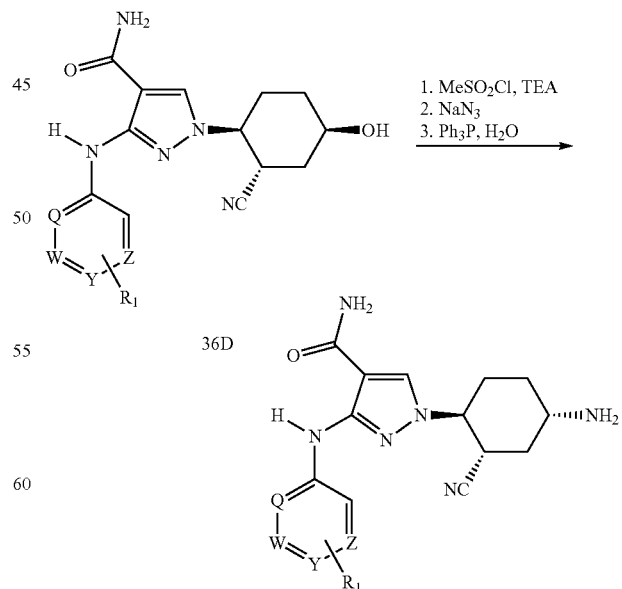

36D

1. MeSO₂Cl, TEA
2. NaN₃
3. Ph₃P, H₂O

56A

Method 57

General procedures to prepare examples of the instant invention are described in Scheme 57. Using an appropriate base, such as DBU, in a suitable solvent, such as ethanol, pyrazole carboxamide 26C is conjugatively added to acrylonitrile 57A to afford example 57C. Ketone 57C is subsequently reduced to alcohol 57D with a suitable reducing agent, such as NaBH$_4$, in a suitable solvent mixture such as THF/methanol. Treatment of 57D with a nucleophilic fluoride source, such as BAST, followed by hydrogenation using a catalyst such as paladium on carbon to reduce an olefin byproduct, afforded 57E and 57F of the instant invention.

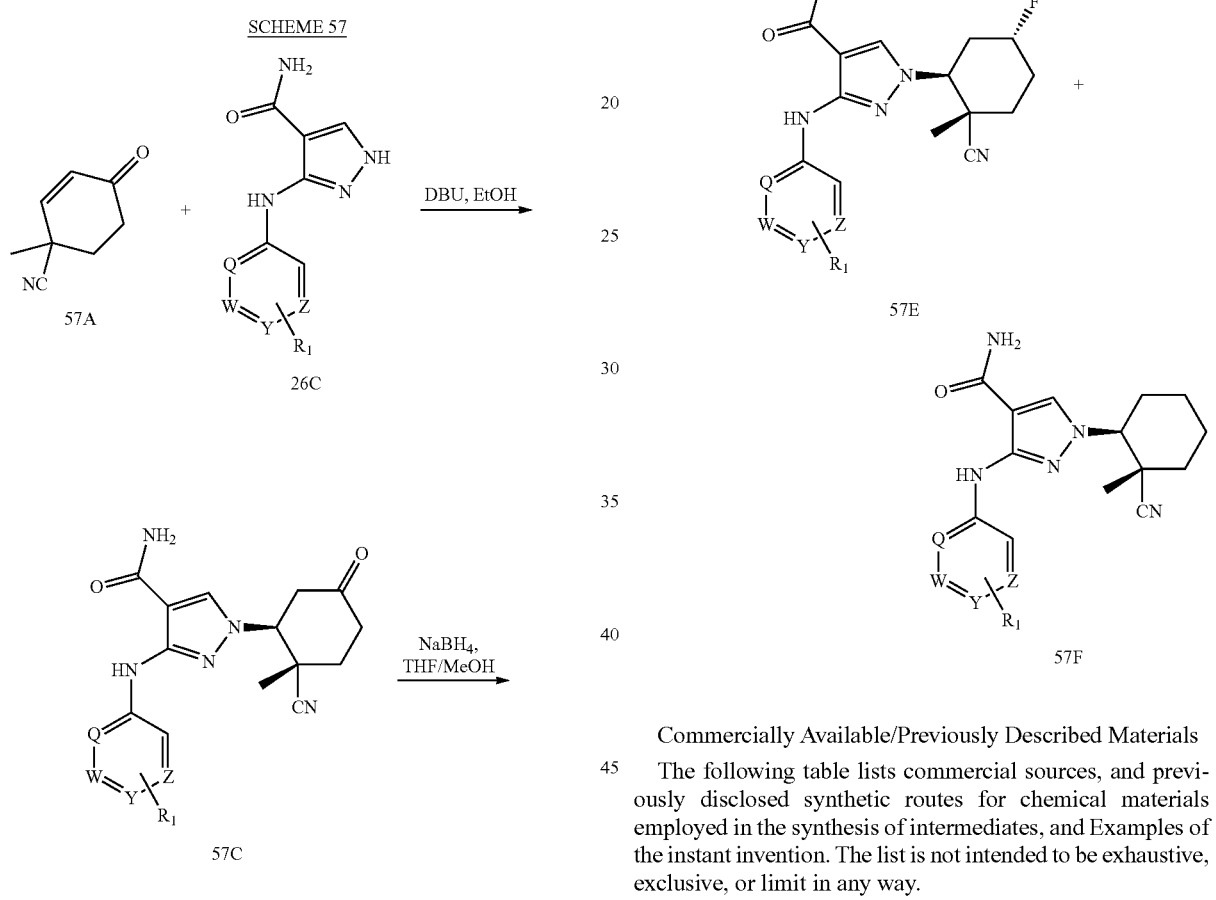

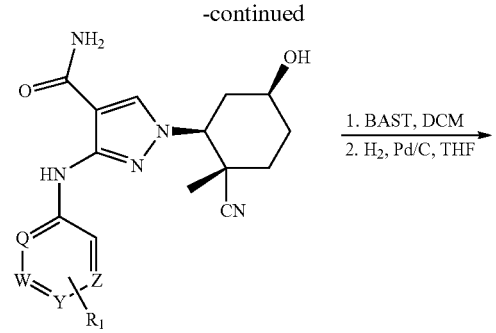

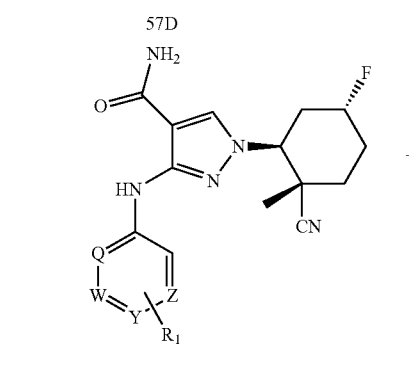

Commercially Available/Previously Described Materials

The following table lists commercial sources, and previously disclosed synthetic routes for chemical materials employed in the synthesis of intermediates, and Examples of the instant invention. The list is not intended to be exhaustive, exclusive, or limit in any way.

| Structure | Compound Name | Vendor |
| --- | --- | --- |
| 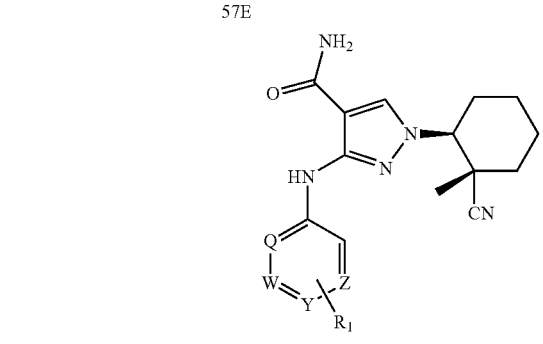 | 4,4,4-trifluorobut-2-enenitrile | Oakwood |
| 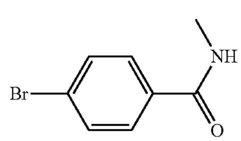 | 4-bromo-N-methylbenzamide | Combi Blocks, Inc. |

-continued

| Structure | Compound Name | Vendor |
|---|---|---|
| 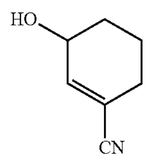 | 3-hydroxycyclohex-1-ene-1-carbonitrile | J. Org. Chem. 2001, 66, 2171-2174. |
| 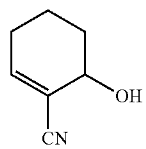 | 6-hydroxycyclohex-1-ene-1-carbonitrile | Tetrahedron Letters 1986, 27, 1577-1578. |
| 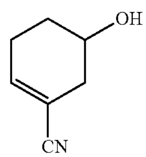 | 5-hydroxycyclohex-1-ene-1-carbonitrile | Canadian Journal of Chemistry 1984, 62, 1093-1098. |
| 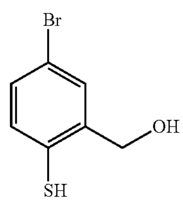 | (5-bromo-2-mercaptophenyl)methanol | Biogene Organics, Inc. |
| 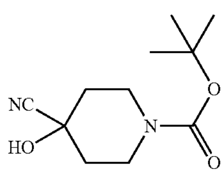 | tert-butyl 4-cyano-4-hydroxypiperidine-1-carboxylate | Sinova, Inc. |
| 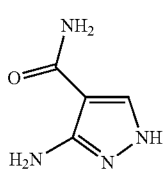 | 3-amino-1H-pyrazole-4-carboxamide | Enamine |
| 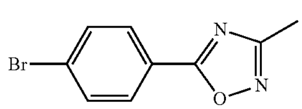 | 5-(4-bromophenyl)-3-methyl-1,2,4-oxadiazole | Maybridge |
| 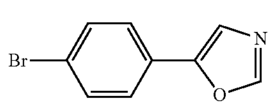 [SMILES: Brc1ccc(-c2cnco2)cc1] | 5-(4-bromophenyl)-1,3-oxazole | Maybridge |
| 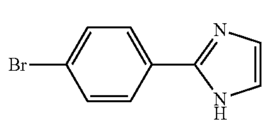 [SMILES: Brc1ccc(-c2ncc[nH]2)cc1] | 2-(4-bromophenyl)-1H-imidazole | J&W Pharmlab LLC |
| 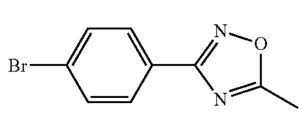 | 3-(4-bromophenyl)-5-methyl-1,2,4-oxadiazole | Maybridge |

-continued

| Structure | Compound Name | Vendor |
|---|---|---|
| 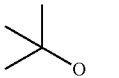 | tert-butyl 5-bromo-1-oxo-1,3-dihydro-2H-isoindole-2-carboxylate | Ontario Chemical, Inc. |
| 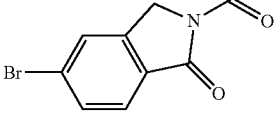 | 5-bromo-2,3-dihydro-1H-isoindol-1-one | Atomole Scientific Co, ltd. |
| 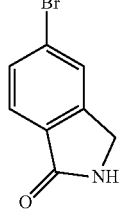 | 5-bromo-2-methyl-2,3-dihydro-1H-isoindol-1-one | J&W Pharmlab LLC |
| 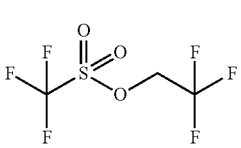 | 2,2,2-trifluoroethyl trifluoromethanesulfonate | Matrix Scientific |
| 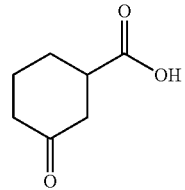 | 3-oxocyclohexanecarboxylic acid | Sigma Aldrich |
| 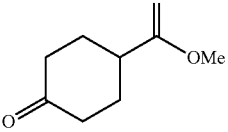 | methyl 4-oxocyclohexanecarboxylate | Astatech Inc |
| 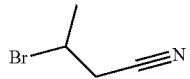 | 3-bromobutyronitrile | TCI America |
| 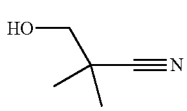 | 3-hydroxy-2,2-dimethylpropanenitrile | Matrix Scientific |
| 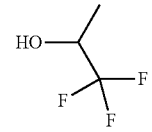 | 1,1,1-trifluoro-2-propanol | Sigma Aldrich |

-continued

| Structure | Compound Name | Vendor |
| --- | --- | --- |
| 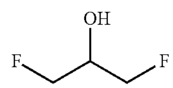 | 1,3-difluoro-2-propanol | Sigma Aldrich |
| 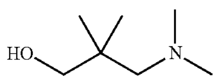 | 3-dimethylamino-2,2-dimethyl-1-propanol | TCI America |
| 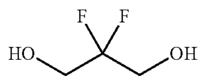 | 2,2-difluoropropane-1,3-diol | Chemstep |
| 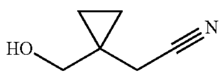 | [1-(hydroxymethyl)cyclopropyl]acetonitrile | Matrix Scientific |
| 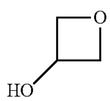 | oxetan-3-ol | Sigma Aldrich |
| 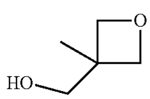 | (3-methyloxetan-3-yl)methanol | Sigma Aldrich |
| 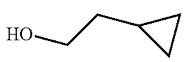 | 2-cyclopropylethanol | Sigma Aldrich |
| 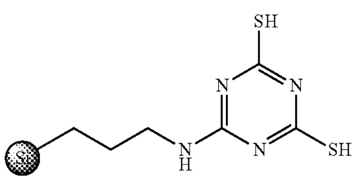 | Silica supported Dimercaptotriazine (Si-DMT) | Silicycle Inc. |
| 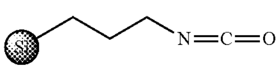 | Silica supported Isocyanate | Silicycle Inc. |
| 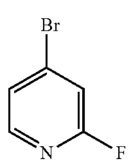 | 4-bromo-2-fluoropyridine | Synthonix |
| 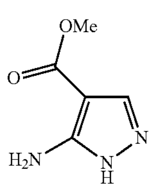 | methyl 5-amino-1H-pyrazole-4-carboxylate | Chembridge Corporation |
| 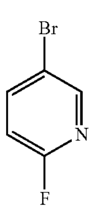 | 5-bromo-2-fluoropyridine | Matrix Scientific |

-continued

| Structure | Compound Name | Vendor |
|---|---|---|
| (4-bromopyridazine structure) | 4-bromopyridazine | Fisher Scientific |
| (4-bromo-N,N-dimethylbenzamide structure) | 4-bromo-N,N-dimethylbenzamide | Chembridge Corporation |
| (4-bromobenzenesulfonamide structure) | 4-bromobenzenesulfonamide | Sigma Aldrich |
| (1-bromo-4-[(trifluoromethyl)sulfonyl]benzene structure) | 1-bromo-4-[(trifluoromethyl)sulfonyl]benzene | Sunshine Chemlab. Inc |
| (1-bromo-4-[(difluoromethyl)sulfonyl]benzene structure) | 1-bromo-4-[(difluoromethyl)sulfonyl]benzene | WXAT |
| (5-bromopyridine-2-carbonitrile structure) | 5-bromopyridine-2-carbonitrile | Sigma Aldrich |
| (methyl (4-bromophenyl)acetate structure) | methyl (4-bromophenyl)acetate | Toyobo Co., Ltd. |
| (methyl 2-hydroxy-2-methylpropanoate structure) | methyl 2-hydroxy-2-methylpropanoate | Sigma Aldrich |
| (tert-butyl 3-methyl-4-oxopiperidine-1-carboxylate structure) | tert-butyl 3-methyl-4-oxopiperidine-1-carboxylate | Small Molecules Inc. |
| (tert-butyl 2-methyl-4-oxopiperidine-1-carboxylate structure) | tert-butyl 2-methyl-4-oxopiperidine-1-carboxylate | Small Molecules Inc. |
| (4-bromo-2-(trifluoromethyl)pyridine structure) | 4-bromo-2-(trifluoromethyl)pyridine | CombiPhos Catalysts, Inc. |
| (3-methylbut-2-enenitrile structure) | 3-methylbut-2-enenitrile | BePharm Ltd. |

| Structure | Compound Name | Vendor |
|---|---|---|
| ![cyclobutanecarbaldehyde] | cyclobutanecarbaldehyde | Beta Pharma Inc |
| ![tetrahydro-2H-pyran-3-carbaldehyde] | tetrahydro-2H-pyran-3-carbaldehyde | J&W Pharmlab LLC |
| ![tetrahydro-2H-pyran-4-ylacetaldehyde] | tetrahydro-2H-pyran-4-ylacetaldehyde | Maybridge |
| ![tert-butyl 4-acetylpiperidine-1-carboxylate] | tert-butyl 4-acetylpiperidine-1-carboxylate | Syntech Development Company |
| ![tert-butyl 4-fluoro-4-formylpiperidine-1-carboxylate] | tert-butyl 4-fluoro-4-formylpiperidine-1-carboxylate | Ark Pharm, Inc. |

INTERMEDIATES

The following experimental procedures detail the preparation of chemical materials used in the synthesis of Examples of the instant invention. The exemplified procedures are for illustrative purposes only, and are not intended to limit the scope f the instant invention in any way.

Intermediate #1

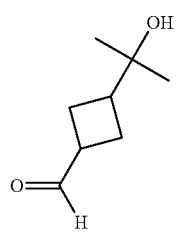

3-(2-Hydroxypropan-2-yl)cyclobutanecarbaldehyde

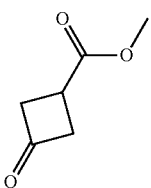

Step A: Methyl 3-oxocyclobutanecarboxylate

3-Oxocyclobutanecarboxylic acid 1 (350 g, 3.06 mol), methanol (190 mL, 4.69 mol), 1-ethyl-3-(3-dimethylaminopropyl) carbodiimide hydrochloride (885 g, 4.69 mol), 4-dimethylaminopyridine (37 g, 0.30 mol) and dichloromethane (6 L) were stirred at ambient temperature for 24 hours. After the completion of the reaction, it was taken in a separating funnel and washed with 1.5 N HCl solution (1 L), water (2 L×2) and brine (1 L×2). The organic layer was dried over anhydrous Na$_2$SO$_4$ and concentrated in vacuo. The residue was taken to the next step without further purification. $^1$H NMR (300 MHz, CDCl$_3$): δ 3.23-3.25 (m, 2H), 3.27-3.32 (m, 2H), 3.33-3.42 (m, 1H), 3.76 (s, 3H). GC-MS: [M]$^+$ m/z=128.

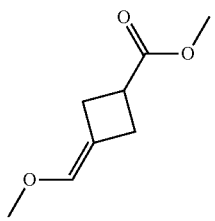

Step B: Methyl 3-(methoxymethylidene)cyclobutanecarboxylate

To a suspension of methoxymethyltriphenylphosphonium chloride (1350 g, 3.90 mol) in anhydrous benzene (12 L), a solution of sodium tert-pentoxide (435 g, 3.90 mol) in anhydrous benzene (4 L) was added slowly under nitrogen atmosphere. The resulting red solution was stirred for 15 minutes at ambient temperature. Then, a solution of methyl 3-oxocyclobutanecarboxylate (250 g, 1.95 mol) in anhydrous benzene (1 L) was added slowly and the reaction mixture was heated at 70° C. for 2 hours. Saturated aqueous ammonium chloride (~4 L) was added to the reaction mixture and extracted with diethyl ether (5 L). The organic layer was washed with water (5 L×2), brine (5 L), dried over anhydrous Na$_2$SO$_4$ and concentrated in vacuo. The crude product was purified by column chromatography over silica gel (mesh 60-120; eluent: 10% diethyl ether in hexane) to afford the title compound as a pale yellow liquid. $^1$H NMR (300 MHz, CDCl$_3$): δ 2.89-2.92 (m, 2H), 2.96-3.0 (m, 2H), 3.14-3.17 (m, 1H), 3.56 (s, 3H), 3.70 (s, 3H), 5.81-5.83 (m, 1H). GC-MS: [M]$^+$ m/z=156.

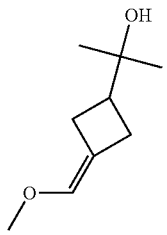

Step C: 2-[3-(Methoxymethylidene)cyclobutyl]propan-2-ol

Methylmagnesium chloride (3 M in THF, 500 mL, 0.736 mol) was slowly added to a solution of methyl 3-(methoxymethylidene)cyclobutanecarboxylate (92 g 0.59 mol) in anhydrous THF (1 L) at 0° C. over a period of 0.5 hours and stirred at ambient temperature for 2 hours. It was cooled to 0° C. and saturated aqueous ammonium chloride (200 mL) was added very slowly. Then the reaction mixture was extracted with EtOAc (250 mL×2) and the combined organic layer was washed with water (250 mL×2), brine (500 mL), dried over anhydrous Na$_2$SO$_4$ and concentrated in vacuo. The crude product was purified by column chromatography over silica gel (mesh 60-120; eluent: 10% EtOAc/hexane) to afford the title compound as pale yellow liquid. $^1$H NMR (400 MHz, CDCl$_3$): δ 1.15 (s, 6H), 2.40-2.44 (m, 1H), 2.54-2.69 (m, 4H), 3.56 (s, 3H), 5.80-5.82 (m, 1H). GC-MS: [M]$^+$ m/z=156.

Step D: 3-(2-Hydroxypropan-2-yl)cyclobutanecarbaldehyde

Oxalic acid dihydrate (68 g, 0.54 mol) was added to a solution of 2-[3-(methoxymethylidene)cyclobutyl]propan-2-ol (70 g, 0.45 mol) in THF:H$_2$O (1:1, 700 mL) at 0° C. and stirred at ambient temperature for 1 hour. Then, 10% aqueous NaHCO$_3$ solution was added to the reaction mixture and extracted with EtOAc (500 mL×4). The combined organic layer was then washed with water (200 mL×2), brine (200 mL) dried over anhydrous Na$_2$SO$_4$ and concentrated in vacuo to afford the title compound as a pale yellow liquid (mixture of cis and trans isomers). $^1$H NMR (400 MHz, CDCl$_3$, mixture of cis and trans): δ 1.09-1.11 (2 s, 6H), 2.07-2.26 (m, 4H), 2.31-2.39 (m, 1H), 2.95-2.99 (m, 1H), 9.75 & 9.84 (2 s, 1H). $^{13}$C NMR (100 MHz, CDCl$_3$, mixture of cis and trans): δ 21.8, 26.1, 39.4, 40.7, 41.8, 70.3, 202.6. $^1$H NMR (400 MHz, DMSO-d$_6$, mixture of cis and trans): δ 0.96 (s, 3H), 0.98 (s, 3H), 1.88-2.29 (m, 5H), 2.87-2.92 (m, 1H), 4.13 & 4.21 (2 s, 1H), 9.56 & 9.74 (2 s, 1H). $^{13}$C NMR (100 MHz, DMSO-d$_6$, mixture of cis and trans): 22.1, 22.7, 26.8, 40.9, 41.9, 42.4, 68.8, 69.1, 203.8, 204.1. $^1$H NMR (400 MHz, DMSO-d$_6$-D$_2$O exchange, mixture of cis and trans): δ 0.94 (s, 3H), 0.96 (s, 3H), 1.85-2.22 (m, 5H), 2.86-2.90 (m, 1H), 9.53 & 9.71 (2 s, 1H).

Intermediate #2

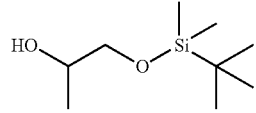

1-{[tert-Butyl(dimethyl)silyl]oxy}propan-2-ol

To a solution of propylene glycol (1.0 g, 13 mmol) in DCM (60.0 mL) was added tert-butyldimethylchlorosilane (2.0 g, 13 mmol) followed by DIPEA (3.2 mL, 18 mmol). The reaction mixture was stirred at ambient temperature for 18 hours. The solution was diluted with ether, washed with saturated aqueous NaHCO$_3$, brine, dried over anhydrous MgSO$_4$, filtered, and concentrated in vacuo to afford the title compound.
LRMS (ESI) calc'd for C$_9$H$_{22}$O$_2$Si [M+H]$^+$: 191. Found: 191.

Intermediate #3

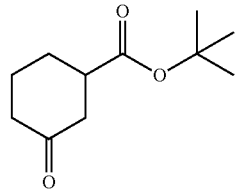

tert-Butyl 3-oxocyclohexanecarboxylate

Anhydrous MgSO$_4$ (3.4 g, 28 mmol) was suspended in DCM (28.1 mL) and to this vigorously stirred mixture was added concentrated sulfuric acid (0.7 g, 7 mmol). The resulting mixture was allowed to stir at ambient temperature for 30 minutes. 3-Oxocyclohexanecarboxylic acid (1.0 g, 7.0 mmol) was added followed by t-BuOH (2.6 g, 35 mmol). The resulting mixture was allowed to stir for 24 hours before it was filtered and flushed with DCM. The filtrate was washed with water, and the organic layer was again washed with water, brine, dried over anhydrous MgSO$_4$, filtered, and concentrated in vacuo to afford the title compound. The residue was used without further purification.

$^1$H NMR (500 MHz, CDCl$_3$): δ 2.72-2.64 (m, 1H), 2.47 (d, J=8.1 Hz, 2H), 2.36-2.24 (m, 2H), 2.08-1.98 (m, 2H), 1.84-1.66 (m, 2H), 1.44 (s, 9H).

Intermediate #4

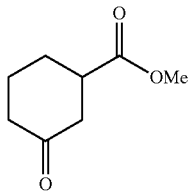 [SMILES: COC(=O)C1CCCC(=O)C1]

Methyl 3-oxocyclohexanecarboxylate

To a solution of 3-oxocyclohexanecarboxylic acid (1.0 g, 7.0 mmol) in diethyl ether (28 mL) was added dropwise TMS-diazomethane (3.5 mL, 7.0 mmol, 2.0 mL in diethyl ether). MeOH (30 mL) was added and the mixture was maintained at ambient temperature for 30 minutes. The mixture was concentrated in vacuo, and the residue was purified by MPLC on silica gel (using a gradient elution of 0-45% EtOAc/hexanes). Desired fractions were identified, combined, and concentrated in vacuo to afford the title compound.

$^1$H NMR (500 MHz, CDCl$_3$): δ 3.66 (s, 3H), 2.82-2.72 (m, 1H), 2.54-2.46 (m, 2H), 2.38-2.24 (m, 2H), 2.12-1.98 (m, 2H), 1.86-1.75 (m, 1H), 1.75-1.64 (m, 1H).

Intermediate #5

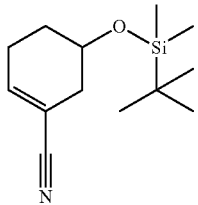 [SMILES: CC(C)(C)[Si](C)(C)OC1CCC=C(C#N)C1]

5-{[tert-Butyl(dimethyl)silyl]oxy}cyclohex-1-ene-1-carbonitrile

5-Hydroxycyclohex-1-ene-1-carbonitrile (500 mg, 4.06 mmol) was dissolved in anhydrous DMF (5.1 mL) and then cooled to 0° C. Imidazole (276 mg, 4.06 mmol) and TBS-Cl (612 mg, 4.06 mmol) were added and the reaction mixture was allowed to stir at 0° C. for 2 hours. The reaction mixture was partitioned between water and DCM. The organic layer was collected and the aqueous layer was again extracted with DCM. The combined organic extracts were washed with brine, dried over anhydrous Na$_2$SO$_4$, filtered, and concentrated in vacuo. The residue was purified by MPLC on silica gel (using a gradient elution of 0-100%, EtOAc/hexanes) to afford the title compound. LRMS (ESI) calc'd for C$_{13}$H$_{23}$NOSi [M+H]$^+$: 238. Found: 238.

Scheme #1

Intermediate #6

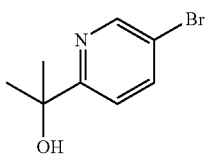

2-(5-Bromopyridin-2-yl)propan-2-ol

Methyl 5-bromopicolinate (500 mg, 2.31 mmol) was dissolved in THF (7.0 mL) and the flask was sealed with a septum and flushed with argon. The mixture was cooled to 0° C. and methylmagnesium bromide (3.1 mL, 9.3 mmol, 3M in THF) was added. The resulting mixture was allowed to stir at 0° C. for 1 hour before the reaction was quenched with saturated aqueous ammonium chloride and extracted with EtOAc. The organic layer was then washed with brine, dried over anhydrous MgSO$_4$, filtered, and concentrated in vacuo to afford the title compound, which was used without further purification. LRMS (ESI) calc'd for C$_8$H$_{10}$BrNO [M+H]$^+$: 216. Found: 216.

Scheme #2

Intermediate #7

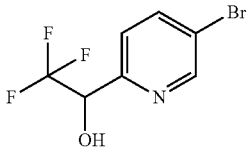 [SMILES: OC(c1ccc(Br)cn1)C(F)(F)F]

1-(5-Bromopyridin-2-yl)-2,2,2-trifluoroethanol

5-Bromopicolinaldehyde (500 mg, 2.70 mmol) was dissolved in THF (9.0 mL) and the flask was then sealed with a septum, flushed with argon, and cooled to 0° C. (Trifluoromethyl)trimethylsilane (0.44 mL, 3.0 mmol) was then added followed by TBAF (2.7 mL, 2.7 mmol, 1M in THF). The resulting mixture was allowed to warm to ambient temperature and was stirred for 2 hours. The reaction was then quenched with water and extracted with DCM (2×). The combined organic extracts were washed with brine, dried over anhydrous MgSO$_4$, and concentrated in vacuo. The residue was purified by MPLC on silica gel (using a gradient elution of 10-20% EtOAc/hexanes) to afford the title compound. LRMS (ESI) calc'd for $C_8H_6BrF_3O$ [M+H]$^+$: 256. Found: 256.

Scheme #3

Intermediate #8-1

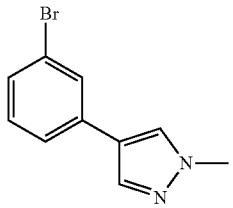

4-(3-Bromophenyl)-1-methyl-1H-pyrazole 1,3-Dibromobenzene (0.38 mL, 3.2 mmol), 1-methyl-4-(4,4,5,5-tetramethyl-1,3,2-dioxaborolan-2-yl)-1H-pyrazole (595 mg, 2.86 mmol), Pd(dppf)Cl$_2$ (260 mg, 0.320 mmol), and potassium phosphate (2.0 g, 9.5 mmol) were combined in a flask and dissolved in dioxane (16.0 mL) and water (1.6 mL). The flask was then sealed and flushed with argon. The reaction mixture was allowed to stir at 90° C. for 90 minutes. The mixture was then cooled to ambient temperature and diluted with EtOAc. The organic layer was washed with water, brine, dried over anhydrous MgSO$_4$, and concentrated in vacuo. The residue was purified by MPLC on silica gel (50% EtOAc/hexanes) to afford the title compound.

LRMS (ESI) calc'd for $C_{10}H_9BrN_2$ [M+H]$^+$: 237. Found: 237.

The following intermediates found in TABLE 1 were prepared according to Scheme #3 following similar procedures described for Intermediate #8-1, which can be achieved by those of ordinary skill in the art of organic synthesis.

TABLE 1

| Intermediate | Structure | COMPOUND Name | Exact Mass [M + H]$^+$ |
|---|---|---|---|
| 8-2 | Br (pyridine-pyrazole structure) | 3-bromo-5-(1-methyl-1H-pyrazol-4-yl)pyridine | Calc'd 238, Found 238 |

Scheme #4

Intermediate #9-1

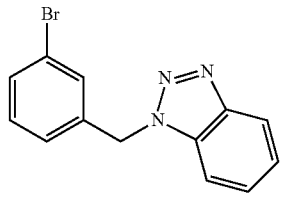 [SMILES: Brc1cccc(Cn2nnc3ccccc32)c1]

1-(3-Bromobenzyl)-1H-benzotriazole

To a solution of 1H-benzotriazole (0.52 g, 4.4 mmol) in THF (25 mL) was added potassium tert-butoxide (4.6 mL, 4.6 mmol, 1M in THF) followed by the addition of 1-bromo-3-(bromomethyl)benzene (1.0 g, 4.0 mmol). The solution was allowed to stir for 4 hours before the reaction was quenched with saturated aqueous NaHCO$_3$ and diluted with EtOAc. The organic layer was separated and washed with brine, dried over anhydrous MgSO$_4$, filtered, and concentrated to dryness in vacuo. The residue was purified by MPLC on silica gel (using a gradient elution of 0-80% EtOAc/hexanes) to afford the title compound as a white solid.

LRMS (ESI) calc'd for $C_{13}H_{11}BrN_3$ [M+H]$^+$: 288. Found 288.

The following intermediates disclosed in TABLE 2 were prepared according to Scheme #4 following similar procedures described for Intermediate #9-1, which can be achieved by those of ordinary skill in the art of organic synthesis.

TABLE 2

| Intermediate | Structure | Compound Name | Exact Mass [M + H]$^+$ |
|---|---|---|---|
| 9-2 | Br (benzyl-imidazole structure) | 1-(3-bromobenzyl)-1H-imidazole | Calc'd 237, Found 237 |

Scheme #6

Intermediate #10

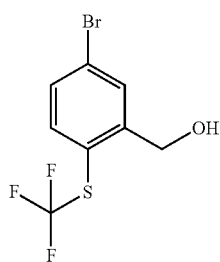 [SMILES: OCc1cc(Br)ccc1SC(F)(F)F]

{5-Bromo-2-[(trifluoromethyl)sulfanyl]phenyl}methanol

NaH (120 mg, 3.01 mmol, 60% dispersion in oil) and 5-(trifluoromethyl)dibenzo[b,d]thiophenium trifluoromethanesulfonate (808 mg, 2.01 mmol) were added sequentially to a solution of (5-bromo-2-sulfanylphenyl)methanol (440 mg, 2.01 mmol) in DMF (10 mL) at 23° C. The reaction mixture was stirred at 23° C. for 45 minutes, and was then partitioned between EtOAc and water. The organic layer was washed with brine, dried over anhydrous Na$_2$SO$_4$, filtered, and concentrated in vacuo. The residue was purified by MPLC on silica gel (using a gradient elution of 0-20%, EtOAc/hexanes) to afford the title compound. $^1$H NMR (500 MHz, CDCl$_3$): δ 7.82 (d, J=1.8 Hz, 1H), 7.53-7.48 (m, 2H), 4.92 (s, 2H), 2.02 (s, 1H).

Scheme #12

Intermediate #11

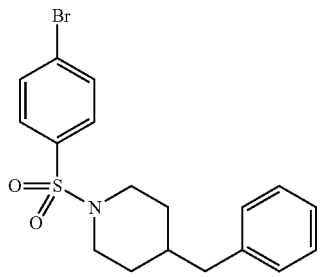 [SMILES: O=S(=O)(c1ccc(Br)cc1)N1CCC(Cc2ccccc2)CC1]

4-Benzyl-1-[(4-bromophenyl)sulfonyl]piperidine

4-Bromobenzene-1-sulfonyl chloride (100 mg, 0.391 mmol) dissolved in DCM (2.0 mL) at ambient temperature. 4-Benzylpiperidine (89 mg, 0.51 mmol) were diluted in DCM (2.0 mL) and treated with DIPEA (0.205 mL, 1.174 mmol) at ambient temperature. To this mixture a solution of 4-bromobenzene-1-sulfonyl chloride (100 mg, 0.391 mmol) dissolved in DCM (2.0 mL) was added and the reaction stirred at ambient temperature for 17 hours. The reaction was then concentrated in vacuo to afford the title compound, which was used without further purification. LRMS (ESI) calc'd for C$_{18}$H$_{20}$BrNO$_2$S [M+H]$^+$: 394. found 394

Scheme #13

Intermediate #12

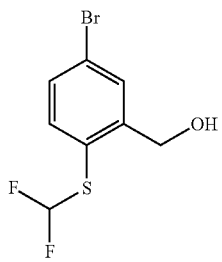 [SMILES: OCc1cc(Br)ccc1SC(F)F]

{5-Bromo-2-[(difluoromethyl)sulfanyl]phenyl}methanol (5-Bromo-2-sulfanylphenyl)methanol (0.50 g, 2.8 mmol) was dissolved in MeCN (11.4 mL) followed by the addition of water (11.4 mL) and solid potassium hydroxide (2.56 g, 45.6 mmol). The mixture was plunged into a −78° C. bath and when the mixture began to freeze diethyl[bromo(difluoro)methyl]phosphonate (1.22 g, 4.56 mmol) was added all at once and the cold bath was removed. The mixture was allowed to warm to ambient temperature and was stirred for 20 minutes. The mixture was then partitioned between EtOAc and water. The organic layer was washed with brine, dried over anhydrous MgSO$_4$ and concentrated in vacuo. The residue was purified by MPLC on silica gel (using a gradient elution of 0-25% EtOAc/hexanes). Desired fractions were identified, combined, and concentrated in vacuo to afford the title compound. $^1$H NMR (500 MHz, CDCl$_3$): δ 7.76 (s, 1H), 7.47 (m, 2H), 6.80 (t, J=56.5 Hz, 1H), 4.87 (s, 2H), 1.96 (br s, 1H).

Intermediate #13

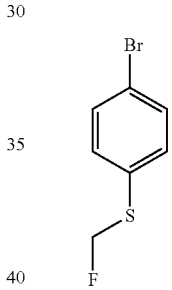

1-Bromo-4-[(fluoromethyl)sulfanyl]benzene

1-Bromo-4-(methylsulfinyl)benzene (1.50 g, 6.85 mmol) was dissolved in 1,2-DCE (14 mL) and stirred at ambient temperature. BAST (3.79 g, 17.1 mmol) was added dropwise followed by zinc iodide (0.07 g, 0.21 mmol). The reaction vessel was sealed and the mixture was heated to 40° C., allowed to stir for 24 hours, and then allowed to cool to ambient temperature. The mixture was partitioned between EtOAc and water, the layers were separated and the organic layer was dried over anhydrous MgSO$_4$, filtered, and concentrated in vacuo. The residue was purified by MPLC on silica gel (using a gradient elution of 0-20% EtOAc/hexanes). Desired fractions were identified, combined, and concentrated in vacuo to afford the title compound. $^1$H NMR (500 MHz, CDCl$_3$): δ 7.49-7.44 (m, 2H), 7.38-7.33 (m, 2H), 5.69 (d, J=52.8 Hz, 2H).

Scheme #6

Intermediate #14-1

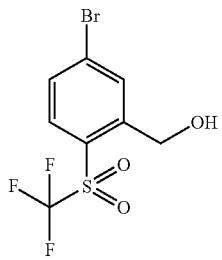 [SMILES: O=S(=O)(c1ccc(Br)cc1CO)C(F)(F)F]

{5-Bromo-2-[(trifluoromethyl)sulfonyl]phenyl}methanol

A mixture of m-CPBA (452 mg, 2.62 mmol) and {5-bromo-2-[(trifluoromethyl)thio]phenyl}methanol (188 mg, 0.655 mmol) in DCM (6.6 mL) was heated to 40° C. and stirred in a microwave reaction vial for 30 hours. After cooling to 23° C., the reaction mixture was partitioned between EtOAc and aqueous potassium bisulfate solution (40% w/w). The organic layer was washed sequentially with saturated aqueous $NaHCO_3$, brine, dried over anhydrous $Na_2SO_4$, filtered, and concentrated in vacuo. The residue was purified by MPLC on silica gel (using a gradient elution of 0-30%, EtOAc/hexanes) to afford the title compound.

$^1$H NMR (500 MHz, $CDCl_3$): δ 8.06 (d, J=1.7 Hz, 1H), 7.91 (d, J=8.6 Hz, 1H), 7.73 (dd, J=8.6, 2.0 Hz, 1H), 5.01 (s, 2H), 2.56 (s, 1H).

TABLE 3 discloses intermediates 14-2 and 14-3 that were prepared according to Schemes #6-8 following similar procedures described for Intermediate #14-1, which can be achieved by those of ordinary skill in the art of organic synthesis.

Scheme #15

Intermediate #15

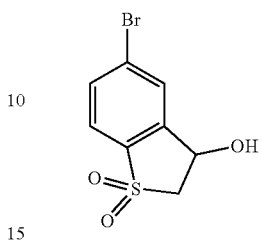

5-Bromo-2,3-dihydro-1-benzothiophene-3-ol 1,1-dioxide

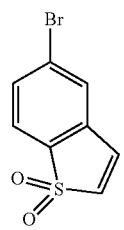 [SMILES: O=S1(=O)C=Cc2cc(Br)ccc21]

Step A: 5-Bromo-1-benzothiophene 1,1-dioxide

5-Bromo-1-benzothiophene (1.50 g, 7.04 mmol) was dissolved in chloroform (47 mL) and allowed to stir vigorously at ambient temperature. m-CPBA (4.34 g, 17.6 mmol) was added in three portions and the resulting mixture was maintained at ambient temperature for 16 hours. The mixture was then diluted with 1M aqueous sodium thiosulfate and extracted with EtOAc. The organic layer was again washed

TABLE 3

| Intermediate | Structure | Compound Name | $^1$H NMR δ (ppm) |
|---|---|---|---|
| 14-2 | ![structure] | {5-bromo-2-[(difluoromethyl)sulfonyl]phenyl}methanol | $^1$H NMR (500 MHz, $CDCl_3$): δ 7.93 (d, J = 1.9 Hz, 1H), 7.89 (d, J = 8.3 Hz, 1H), 7.72 (dd, J = 8.3, 1.9 Hz, 1H), 6.33 (t, J = 53.6 Hz, 1H), 4.98 (d, J = 6.4 Hz, 2H), 2.53 (t, J = 6.4 Hz, 1H). |
| 14-3 | ![structure] | 1-bromo-4-[(fluoromethyl)sulfonyl]benzene | $^1$H NMR (500 MHz, $CDCl_3$): δ 7.86-7.80 (m, 2H), 7.80-7.74 (m, 2H), 5.13 (d, J = 46.9 Hz, 2H). | with 1M aqueous sodium thiosulfate, saturated aqueous NaHCO$_3$, brine, dried over anhydrous MgSO$_4$, filtered, and concentrated in vacuo. The residue was purified by MPLC on silica gel (using a gradient elution of 0-30% EtOAc/hexanes). Desired fractions were identified, combined, and concentrated in vacuo to afford the title compound. $^1$H NMR (600 MHz, CDCl$_3$): δ 7.65 (dd, J=7.9, 1.8 Hz, 1H), 7.55 (d, J=7.9 Hz, 1H), 7.50 (d, J=1.8 Hz, 1H), 7.15 (d, J=6.9 Hz, 1H), 6.74 (d, J=6.9 Hz, 1H).

Step B: 5-Bromo-2,3-dihydro-1-benzothiophene-3-ol 1,1-dioxide

5-Bromo-1-benzothiophene 1,1-dioxide (100 mg, 0.41 mmol) was suspended in 1N aqueous sodium hydroxide (2.0 mL), heated to 100° C. in a microwave, and allowed to stir for 15 minutes. The mixture was then allowed to cool to ambient temperature before the mixture was diluted with saturated aqueous ammonium chloride and extracted with EtOAc. The organic layer was washed with brine, dried over anhydrous MgSO$_4$, filtered, and concentrated in vacuo. The residue was used without further purification. LRMS (ESI) calc'd for C$_8$H$_7$BrO$_3$S [M+Na]$^+$: 285. Found: 285.

Scheme #16

Intermediate #16

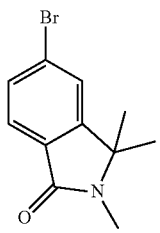

5-Bromo-2,3,3-trimethyl-2,3-dihydro-1H-isoindol-1-one

5-Bromo-2,3-dihydro-1H-isoindol-1-one (150 mg, 0.71 mmol) was dissolved in DMF (3.5 mL) and stirred at ambient temperature. NaH (85 mg, 2.1 mmol, 60% dispersion in oil) was carefully added in two portions, and the resulting mixture was allowed to stir for 15 minutes before MeI (151 mg, 1.06 mmol) was added. The mixture was allowed to stir at ambient temperature for 30 minutes before water (10 mL) was carefully added. The mixture was extracted with EtOAc, and the organic layer was washed with water, brine, dried over anhydrous MgSO$_4$, filtered, and concentrated in vacuo. The residue was purified by MPLC on silica gel (using a gradient elution of 0-20% EtOAc/hexanes). Desired fractions were identified, combined, and concentrated in vacuo to afford the title compound.

LRMS (ESI) calc'd for C$_{11}$H$_{12}$BrNO [M+H]$^+$: 254. Found: 254.

Scheme #17

Intermediate #17

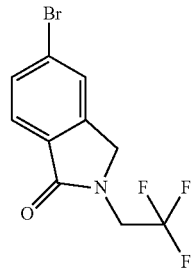 [SMILES: O=C1c2ccc(Br)cc2CN1CC(F)(F)F]

5-Bromo-2-(2,2,2-trifluoroethyl)-2,3-dihydro-1H-isoindol-1-one

5-Bromo-2,3-dihydro-1H-isoindol-1-one (100 mg, 0.47 mmol) was dissolved in DMF (4.7 mL) and stirred at 0° C. NaH (38 mg, 0.94 mmol, 60% dispersion in oil) was carefully added in two portions, and the resulting mixture was allowed to stir at 0° C. for 15 minutes before 2,2,2-trifluoroethyl trifluoromethanesulfonate (110 mg, 0.47 mmol) was added. The mixture was allowed to stir at 0° C. for 30 minutes before saturated aqueous NaHCO$_3$ (10 mL) was carefully added, and the mixture was extracted with EtOAc. The organic layer was washed with water, brine, dried over anhydrous MgSO$_4$, filtered, and concentrated in vacuo. The residue was purified by MPLC on silica gel (using a gradient elution of 0-20% EtOAc/hexanes). Desired fractions were identified, combined, and concentrated in vacuo to afford the title compound. LRMS (ESI) calc'd for C$_{10}$H$_7$BrF$_3$NO [M+H]$^+$: 294. Found: 294.

Scheme #17

Intermediate #18

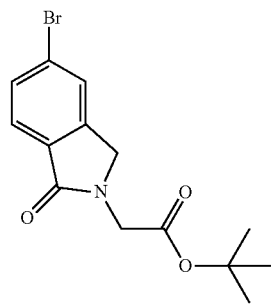 [SMILES: CC(C)(C)OC(=O)CN1Cc2cc(Br)ccc2C1=O]

tert-Butyl (5-bromo-1-oxo-1,3-dihydro-2H-isoindol-2-yl)acetate

5-Bromo-2,3-dihydro-1H-isoindol-1-one (100 mg, 0.47 mmol) was dissolved in DMF (4.7 mL) and stirred at 0° C. NaH (38 mg, 0.94 mmol, 60% dispersion in oil) was carefully added in two portions, and the resulting mixture was allowed to stir at 0° C. for 15 minutes before tert-butyl bromoacetate (92 mg, 0.47 mmol) was added. The mixture was allowed to stir at 0° C. for 30 minutes before saturated aqueous NaHCO₃ (10 mL) was carefully added. The mixture was extracted with EtOAc, and the organic layer was washed with water, brine, dried over anhydrous MgSO₄, filtered, and concentrated in vacuo. The residue was purified by MPLC on silica gel (using a gradient elution of 0-20% EtOAc/hexanes). Desired fractions were identified, combined, and concentrated in vacuo to afford the title compound. LRMS (ESI) calc'd for $C_{14}H_{16}BrNO_3$ [M+Na]⁺: 348. Found: 348.

Scheme #5

Intermediate #19

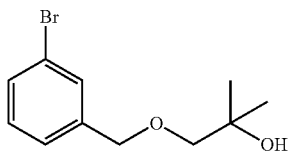

1-[(3-Bromobenzyl)oxy]-2-methylpropan-2-ol

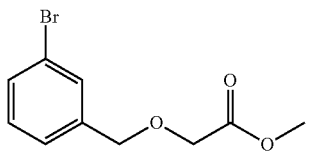

Step A: Methyl [(3-bromobenzyl)oxy]acetate

Methyl hydroxyacetate (0.80 g, 8.8 mmol) was dissolved in THF (10 mL) and allowed to stir at 0° C. under a nitrogen atmosphere. NaH (0.40 g, 9.6 mmol, 60% dispersion in oil) was added portionwise over approximately 5 minutes. The cooling bath was removed and the reaction mixture was allowed to warm to ambient temperature. 1-Bromo-3-(bromomethyl)benzene (2.0 g, 8.0 mmol) was added in a single portion and the resulting mixture was heated to 40° C. After 4 hours, the reaction mixture was allowed to cool to ambient temperature and partitioned between water and EtOAc. The layers were separated, and the organic layer was washed with saturated aqueous NaHCO₃, brine, dried over anhydrous Na₂SO₄, filtered, and concentrated in vacuo to afford the title compound, which was carried forward without further purification. $^1$H NMR (600 MHz, CDCl₃): δ 7.53-7.50 (m, 1H), 7.42-7.38 (m, 1H), 7.30-7.17 (m, 2H), 4.57 (s, 2H), 4.09 (s, 2H), 3.74 (s, 3H).

Step B: 1-[(3-Bromobenzyl)oxy]-2-methylpropan-2-ol

Methyl [(3-bromobenzyl)oxy]acetate (2.0 g, 7.7 mmol) was dissolved in THF (10 mL) and was allowed to stir under a nitrogen atmosphere. Methylmagnesium bromide (7.7 mL, 23 mmol, 3.0 M in THF) was added dropwise. The reaction mixture was allowed to stir at ambient temperature for 4 hours before the reaction was quenched with water and the mixture was extracted with EtOAc. The organic layer was washed with saturated aqueous NaHCO₃, brine, dried over anhydrous Na₂SO₄, filtered, and concentrated in vacuo. The residue was purified by MPLC on silica gel (using a gradient elution of 2-70% EtOAc/hexanes). Desired fractions were identified, combined, and concentrated in vacuo to the title compound.
$^1$H NMR (600 MHz, CDCl₃): δ 7.46 (s, 1H), 7.40 (d, J=7.9 Hz, 1H), 7.25-7.18 (m, 2H), 4.52 (s, 2H), 3.29 (s, 2H), 1.21 (s, 6H).

Scheme #4

Intermediate #20

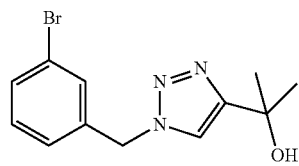 [SMILES: CC(C)(O)c1cn(Cc2cccc(Br)c2)nn1]

Step A-B: 2-[1-(3-Bromobenzyl)-1H-1,2,3-triazol-4-yl]propan-2-ol

To a solution of 1-bromo-3-(bromomethyl)benzene (5.0 g, 20 mmol) in DMSO (40 mL) was added sodium azide (1.3 g, 20 mmol). The resulting mixture was allowed to stir at ambient temperature for 18 hours before it was diluted with water and extracted with diethyl ether (2×). The combined organic extracts were washed with brine, dried over anhydrous Na₂SO₄, filtered, and concentrated in vacuo. The crude residue was dissolved in $^t$BuOH (65 mL and water (39 mL) and to this mixture was added 2-methylbut-3-yn-2-ol (2.3 g, 27 mmol), and then a solution of copper (II) sulfate pentahydrate (0.26 g, 1.0 mmol) in water (10 mL) followed by a solution of sodium ascorbate (0.83 g, 4.2 mmol) in water (8 mL). The resulting mixture was allowed to stir at ambient temperature for 2 hours before it was diluted with water and extracted with EtOAc (2×). The combined organic extracts were washed with brine, dried over anhydrous Na₂SO₄, filtered, and concentrated in vacuo. The residue was used without further purification. LRMS (ESI) calc'd for $C_{12}H_{14}BrN_3O$ [M+H]⁺: 296. Found: 296.

Scheme #7

Intermediate #21-1 and 21-2

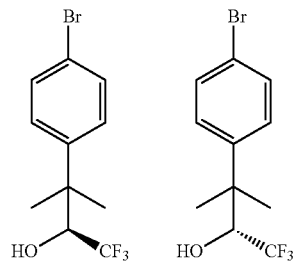 [SMILES: CC(C)(c1ccc(Br)cc1)[C@H](O)C(F)(F)F ; CC(C)(c1ccc(Br)cc1)[C@@H](O)C(F)(F)F]

(S or R)-3-(4-Bromophenyl)-1,1,1-trifluoro-3-methylbutan-2-ol

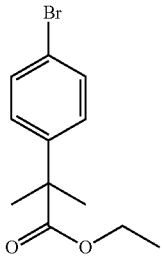

Step A: Ethyl 2-(4-bromophenyl)-2-methylpropanoate

To a stirred solution of ethyl 2-(4-bromophenyl)acetate (10 g, 41 mmol) in THF (80 mL) under nitrogen was added sodium hydride (4.9 g, 60%, 123 mmol) in portions at 0° C. The resulting solution was stirred at 0° C. for 30 minutes before the addition of iodomethane (17 g, 123 mmol) at 0° C. The resulting mixture was stirred at ambient temperature for additional 1 hour before the reaction was quenched with saturated NH$_4$Cl aqueous solution (20 mL) at 0° C. The solution was extracted with EtOAc (3×100 mL). The combined organic layers were dried over sodium sulfate, filtered and concentrated in vacuo. The crude residue was purified by MPLC on silica gel (eluting with 1-2% EtOAc/hexane) to afford the title compound as a light yellow oil. $^1$H NMR (400 MHz, CDCl$_3$) δ 7.46 (d, J=6.8 Hz, 2H), 7.24 (d, J=6.8 Hz, 2H), 4.14 (q, J=7.2 Hz, 2H), 1.58 (s, 6H), 1.20 (t, J=7.2 Hz, 3H). MS ESI: [M+H]$^+$ m/z 271, 273.

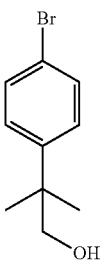

Step B: 2-(4-Bromophenyl)-2-methylpropan-1-ol

To a solution of 2-(4-bromophenyl)-2-methylpropanoate (8.9 g, 33 mmol) in THF (100 mL) under nitrogen was added LiAlH$_4$ (1.6 g, 43 mmol) in portions at 0° C. The resulting solution was stirred at 0° C. for 1 hour before the addition of saturated aqueous NH$_4$Cl (50 mL). The mixture was then extracted with EtOAc (3×80 mL). The combined organic layers were dried over sodium sulfate, filtered and concentrated in vacuo. The crude residue was purified by MPLC on Silica gel with 2-5% EtOAc/hexane to afford 2-(4-bromophenyl)-2-methylpropan-1-ol as a colorless oil. MS ESI: [M+H]$^+$ m/z 229, 231; $^1$H NMR (400 MHz, CDCl$_3$) δ 7.47 (d, J=6.8 Hz, 2H), 7.28 (d, J=6.8 Hz, 2H), 3.61 (s, 2H), 1.58 (s, 6H).

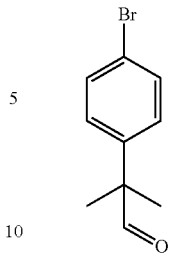

Step C: 2-(4-Bromophenyl)-2-methylpropanal

To a stirred solution of 2-(4-bromophenyl)-2-methylpropan-1-ol (10 g, 44 mmol) in dichloromethane (80 mL) was added PCC (14 g, 65 mmol) in portions at 0° C. The resulting solution was stirred at ambient temperature for 16 hours, and then filtered and concentrated in vacuo. The crude residue was purified by MPLC on silica gel (eluting with 1-2% EtOAc/hexane) to afford the title compound as an off-white solid. $^1$H NMR (300 MHz, CDCl$_3$) δ 9.49 (s, 1H), 7.52 (d, J=6.3 Hz, 2H), 7.17 (d, J=6.3 Hz, 2H), 1.43 (s, 6H).

Step D: (S or R)-3-(4-Bromophenyl)-1,1,1-trifluoro-3-methylbutan-2-ol

To a solution of 2-(4-bromophenyl)-2-methylpropanal (5.7 g, 25 mmol) and trimethyl(trifluoromethyl)silane (7.1 g, 50 mmol) in THF (60 mL) under nitrogen was added a solution of TBAF (0.66 g, 2.5 mmol) in THF (10 mL) dropwise at −30° C. The resulting solution was stirred at −30° C. for 1 hour and at ambient temperature for an additional 1 hour before the addition of 1 N aqueous HCl (20 mL). The mixture was vigorously stirred at ambient temperature for 10 minutes, and then extracted with EtOAc (3×100 mL). The combined organic layers were dried over sodium sulfate, filtered and concentrated in vacuo. The crude residue was purified by MPLC on Silica gel (eluting with 2-4% EtOAc/hexane) to afford (S and R)-3-(4-bromophenyl)-1,1,1-trifluoro-3-methylbutan-2-ol as a light yellow oil. The racemic mixture was resolved by preparative chiral HPLC (Chiralpak IA, 2*25 cm; Mobile phase: 5% ethanol in hexane) to afford the two enantiopure title compounds.

Intermediate #21-1: 1$^{st}$ peak to elute: (S or R)-3-(4-bromophenyl)-1,1,1-trifluoro-3-methylbutan-2-ol. $^1$H NMR (300 MHz, CDCl$_3$) δ 7.46-7.41 (m, 2H), 7.28-7.23 (m, 2H), 4.10-3.97 (m, 1H), 2.08 (br, 1H), 1.44 (s, 6H). MS GC: [M]$^+$ m/z 295, 297.

Intermediate #21-2: 2$^{nd}$ peak to elute: (S or R)-3-(4-bromophenyl)-1,1,1-trifluoro-3-methylbutan-2-ol. $^1$H NMR (300 MHz, CDCl$_3$) δ 7.46-7.41 (m, 2H), 7.28-7.23 (m, 2H), 4.10-3.97 (m, 1H), 2.08 (br, 1H), 1.44 (s, 6H). MS GC: [M]$^+$ m/z 295, 297.

Scheme #8

Intermediate #22

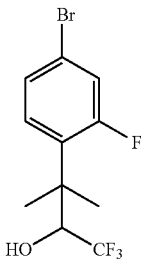

(S and R)-3-(4-Bromo-2-fluorophenyl)-1,1,1-trifluoro-3-methylbutan-2-ol

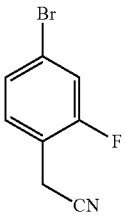

Step A: 2-(4-Bromo-2-fluorophenyl)acetonitrile

A solution of 4-bromo-1-(bromomethyl)-2-fluorobenzene (20 g, 74 mmol) and potassium cyanide (10 g, 150 mmol) in ethanol (150 mL) and water (30 mL) was stirred at 70° C. for 1 hour. The resulting solution was diluted with water (50 mL), and then extracted with EtOAc (3×200 mL). The combined organic layers were dried over anhydrous sodium sulfate, filtered and concentrated in vacuo. The crude residue was purified by MPLC on Silica gel (eluting with 2-5% EtOAc/hexane) to afford the title compound as a light yellow oil. $^1$H NMR (400 MHz, CDCl$_3$) δ 7.38-7.22 (m, 3H), 3.74 (s, 2H). MS ESI: [M+H]+ m/z 214.

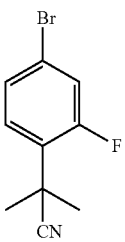

Step B:
2-(4-bromo-2-fluorophenyl)-2-methylpropanenitrile

To the solution of 2-(4-bromo-2-fluorophenyl)acetonitrile (6.0 g, 28 mmol) in THF (80 mL) was added sodium hydride (3.4 g, 60%, 140 mmol) in portions at 0° C. The resulting solution was stirred at 0° C. for 30 minutes before the addition of iodomethane (12 g, 83 mmol) at 0° C. The mixture was stirred at ambient temperature for additional 1 hour before the reaction was quenched with saturated NH$_4$Cl aqueous solution (30 mL) at 0° C. The solution was then extracted with EtOAc (3×50 mL). The combined organic layers were dried over sodium sulfate, filtered and concentrated in vacuo. The crude residue was purified by MPLC on Silica gel with 1-5% EtOAc/hexane to afford 2-(4-bromo-2-fluorophenyl)-2-methylpropanenitrile as a yellow oil. MS ESI: [M+H]$^+$ m/z 242; $^1$H NMR (300 MHz, CDCl$_3$) δ 7.37-7.23 (m, 3H), 1.75 (s, 6H).

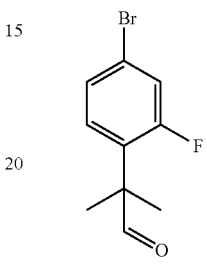

Step C:
2-(4-Bromo-2-fluorophenyl)-2-methylpropanal

To a solution of 2-(4-bromo-2-fluorophenyl)-2-methylpropanenitrile (2.0 g, 8.3 mmol) in THF (20 mL) under nitrogen was added DIBAL-H (19 mL, 19 mmol, 1.0M in THF) dropwise at −30° C. The resulting solution was stirred at ambient temperature for 3 hours before the addition of 2 N aqueous HCl (10 mL) at 0° C. The mixture was stirred at ambient temperature for 10 minutes, then the solution was carefully basified with saturated aqueous NaHCO$_3$ to pH 8-9, and then extracted with EtOAc (3×50 mL). The combined organic layers were dried over sodium sulfate, filtered and concentrated in vacuo. The crude residue was purified by MPLC on Silica gel (eluting with 1-2% EtOAc/hexane) to afford the title compound) as a colorless oil. $^1$H NMR (300 MHz, CDCl$_3$) δ 9.58 (s, 1H), 7.32-7.21 (m, 1H), 7.18-7.03 (m, 2H), 1.41 (s, 6H). MS ESI: [M+H]$^+$ m/z 245.

Step D: (S and R)-3-(4-bromo-2-fluorophenyl)-1,1,1-trifluoro-3-methylbutan-2-ol

To a solution of 2-(4-bromo-2-fluorophenyl)-2-methylpropanal (2.4 g, 9.8 mmol) and trimethyl(trifluoromethyl)silane (2.8 g, 20 mmol) in THF (20 mL) under nitrogen was added a solution of TBAF (1.3 g, 4.8 mmol) in THF (5 mL) dropwise at −30° C. The resulting solution was stirred at −30° C. for 1 hour and at ambient temperature for an additional 1 hour before 1 N aqueous HCl (10 mL) was added. The mixture was vigorously stirred at ambient temperature for 10 minutes, and then extracted with EtOAc (3×30 mL). The combined organic layers were dried over sodium sulfate, filtered and concentrated in vacuo. The crude residue was purified by MPLC on Silica gel (eluting with 1-3% EtOAc/hexane) to the title compound as a yellow oil. $^1$H NMR (300 MHz, CDCl$_3$) δ 7.25-

7.15 (m, 3H), 4.53 (q, J=7.5 Hz, 1H), 2.30 (br, 1H), 1.41 (s, 6H). MS ESI: [M+H]⁺ m/z 315.

Scheme #9

Intermediate #23

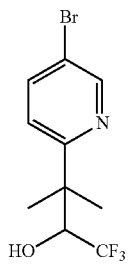

(S and R)-3-(5-Bromopyridin-2-yl)-1,1,1-trifluoro-3-methylbutan-2-ol

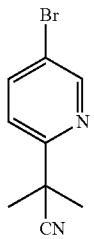

Step A:
2-(5-Bromopyridin-2-yl)-2-methylpropanenitrile

To a solution of 2,5-dibromopyridine (5.0 g, 21 mmol) and 2-methylpropanenitrile (1.6 g, 23 mmol) in toluene (50 mL) under nitrogen was added NaHMDS (12 mL, 23 mmol, 2.0M in THF) dropwise at 0° C. The resulting solution was stirred at ambient temperature overnight before the addition of saturated aqueous NH₄Cl (20 mL). The resulting mixture was extracted with EtOAc (3×30 mL). The combined organic layers were dried over sodium sulfate, filtered and concentrated in vacuo. The crude residue was purified by MPLC on Silica gel (eluting with 1-3% EtOAc/hexane) to afford the title compound as a light yellow solid. ¹H NMR (300 MHz, CDCl₃) δ 8.65 (s, 1H), 7.85 (d, J=8.7 Hz, 1H), 7.51 (d, J=8.7 Hz, 1H), 1.75 (s, 6H). MS ESI [M+H]⁺ m/z 225.227.

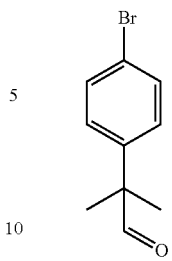

Step B: 2-(5-Bromopyridin-2-yl)-2-methylpropanal

To a solution of 2-(5-bromopyridin-2-yl)-2-methylpropanenitrile (2.0 g, 8.9 mmol) in dichloromethane (20 mL) under nitrogen was added DIBAL-H (12.4 mL, 12.4 mmol, 1.0 M in THF) dropwise at −30° C. The resulting solution was stirred at ambient temperature for 3 hours before the addition of 2 N aqueous HCl (10 mL) at 0° C. The resulting solution was stirred at ambient temperature for 10 minutes, the solution was basified with saturated aqueous NaHCO₃ to pH 8-9, and then extracted with EtOAc (3×20 mL). The combined organic layers were dried over sodium sulfate, filtered and concentrated in vacuo. The crude residue was purified by MPLC on Silica gel (eluting with 2-4% EtOAc/hexane) to afford the title compound as a yellow oil. ¹H NMR (300 MHz, CDCl₃) δ 9.73 (s, 1H), 8.66 (s, 1H), 7.82 (d, J=8.7 Hz, 1H), 7.17 (d, J=8.7 Hz, 1H), 1.47 (s, 6H). MS ESI: [M+H]⁺ m/z 228, 230.

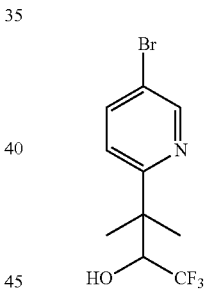

Step C: (S and R)-3-(5-Bromopyridin-2-yl)-1,1,1-trifluoro-3-methylbutan-2-ol

To a solution of 2-(5-bromopyridin-2-yl)-2-methylpropanal (1.0 g, 4.4 mmol) and trimethyl(trifluoromethyl)silane (1.1 g, 7.5 mmol) in THF (10 mL) under nitrogen was added the solution of TBAF (230 mg, 0.88 mmol) in THF (5 mL) dropwise at −30° C. The resulting solution was stirred at −30° C. for 1 hour and at ambient temperature for additional 1 hour before the addition of the second batch of TBAF (1.1 g, 4.4 mmol) at ambient temperature. The resulting mixture was stirred at ambient temperature for 20 minutes, then the reaction solution was diluted with water (10 mL), and extracted with EtOAc (3×15 mL). The combined organic layers were dried over sodium sulfate, filtered and concentrated in vacuo. The crude residue was purified by MPLC on Silica gel (eluting with 2-5% EtOAc/hexane) to afford the title compound as a yellow oil. ¹H NMR (300 MHz, CDCl₃) δ 8.55 (s, 1H), 7.86

(d, J=8.7 Hz, 1H), 7.24 (d, J=8.7 Hz, 1H), 4.01 (q, J=7.8 Hz, 1H), 1.51 (s, 6H). MS ESI: [M+H]+ m/z 298, 300.

Scheme #10

Intermediate #24

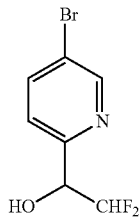

(S and R)-1-(5-Bromopyridin-2-yl)-2,2-difluoroethanol

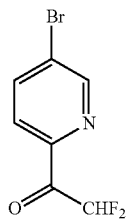

Step A:
1-(5-Bromopyridin-2-yl)-2,2-difluoroethanone

To the solution of 2,5-dibromopyridine (16 g, 67 mmol) in toluene (150 mL) was added n-BuLi (27 mL, 67 mmol) dropwise at −78° C. The resulting solution was stirred at −78° C. for 1 hour before the addition of 2,2-difluoroacetate (10 g, 80 mmol). The mixture was stirred at ambient temperature for 16 hours, then diluted with saturated aqueous NH$_4$Cl (80 mL) at 0° C., and extracted with EtOAc (2×100 mL). The combined organic layers were dried over sodium sulfate, filtered and concentrated in vacuo. The crude residue was purified by MPLC on Silica gel (eluting with 5-10% EtOAc/hexane) to afford the title compound as a white solid. $^1$H NMR (300 MHz, CDCl$_3$) δ 8.82 (s, 1H), 8.08 (d, J=6.0 Hz, 1H), 8.03 (d, J=6.0 Hz, 1H), 7.05 (t, J=54.4 Hz, 1H).

Step B: 1-(5-Bromopyridin-2-yl)-2,2-difluoroethanol

To a solution of 1-(5-bromopyridin-2-yl)-2,2-difluoroethanone (1.0 g, 4.2 mmol) in methanol (10 mL) was added NaBH$_4$ (180 mg, 4.6 mmol) at 0° C. The resulting solution was stirred at ambient temperature for 2 hours before the addition of saturated aqueous NH$_4$Cl (5 mL) at 0° C. Methanol was removed in vacuo, and the resulting aqueous solution was extracted with EtOAc (3×10 mL). The combined organic layers were washed with brine, dried over sodium sulfate, filtered and concentrated in vacuo to afford the title compound as an off-white solid, which was used without further purification. $^1$H NMR (400 MHz, CDCl$_3$) δ 8.70 (s, 1H), 7.91 (d, J=6.0 Hz, 1H), 7.52 (d, J=6.0 Hz, 1H), 5.89 (td, J=54.4, 3.9 Hz, 1H), 4.92-4.84 (m, 1H), 4.52 (br, 1H).

Scheme #10

Intermediate 25

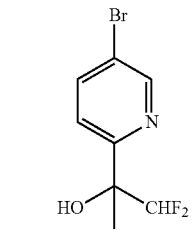

(S and R)-2-(5-Bromopyridin-2-yl)-1,1-difluoropropan-2-ol

To a solution of 1-(5-bromopyridin-2-yl)-2,2-difluoroethanone (1.5 g, 6.4 mmol) in THF (15 mL) under nitrogen was added MeMgBr (3.2 mL, 9.6 mmol, 3.0 M in THF) dropwise at −15° C. The resulting solution was stirred at ambient temperature for 2 hours before the addition of saturated aqueous NH$_4$Cl (10 mL) at 0° C. The resulting mixture was vigorously stirred for 10 minutes, and then extracted with EtOAc (3×20 mL). The combined organic layers were dried over sodium sulfate, filtered and concentrated in vacuo. The crude residue was purified by MPLC on Silica gel (eluting with 1-3% EtOAc/hexane) to afford the title compound as a yellow oil. $^1$H NMR (400 MHz, CDCl$_3$) δ 8.83 (d, J=2.0 Hz, 1H), 7.92 (dd, J=8.4, 2.0 Hz, 1H), 7.43 (d, J=8.4 Hz, 1H), 5.76 (t, J=56.4 Hz, 1H), 5.22 (br, 1H), 1.60 (s, 3H).

Scheme #11

Intermediate #26

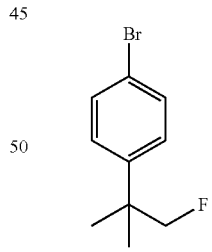

1-Bromo-4-(1-fluoro-2-methylpropan-2-yl)benzene 2-(4-bromophenyl)-2-methylpropan-1-ol (500 mg, 2.182 mmol) was dissolved in Dichloromethane (7.2 mL) in a 20 mL vial. DAST (0.433 mL, 3.27 mmol) was then slowly added to the solution. Stirred at ambient temperature overnight. TLC showed presence of starting material. Another 0.5 eq. of DAST was added and stirred for 4 hours. TLC then showed consumption of starting material. The reaction was loaded directly on a silica column and the column was then dried out. Purified with a Teledyne Isco Combiflash Rf purification system using a gradient of 5% EtOAc/hexanes. Isolated 1-bromo-4-(1-fluoro-2-methylpropan-2-yl)benzene as a clear liquid. $^1$H NMR (500 MHz, CDCl$_3$) δ 7.43-7.42 (d, 2H), 7.10-7.09 (d, 2H), 2.88 (s, 1H), 2.83 (s, 1H), 1.35 (s, 3H), 1.30 (s, 3H).

Scheme #10

Intermediate #27-1 and #27-2

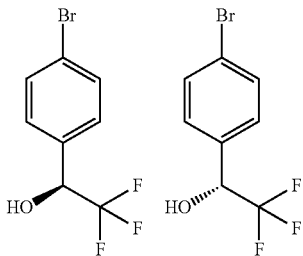

1(S or R)-(4-Bromophenyl)-2,2,2-trifluoroethanol

4'-Bromo-2,2,2-trifluoroacetophenone (3.00 mL, 19.8 mmol) was stirred in MeOH (66 mL) at 0° C. Sodium borohydride (0.748 g, 19.8 mmol) was added and the mixture was allowed to warm to ambient temperature. The mixture was stirred for 3 hours, then quenched with saturated aqueous ammonium chloride and extracted with ethyl acetate. The organic layer was then washed with brine, dried over anhydrous MgSO$_4$, filtered, and concentrated in vacuo. The residue was purified by MPLC (eluting with 5% EtOAc/hexanes). Desired fractions were identified, combined, and concentrated in vacuo to afford a racemic mixture of the title compounds. The racemic residue was resolved by Chiral SFC purification (Chiral Technology OJ-H 2.1×25 cm, 5 uM Column; eluting with 5% isopropyl alcohol/CO2).
Intermediate 27-1:
1$^{st}$ peak to elute; (S or R)-1-(4-bromophenyl)-2,2,2-trifluoroethanol $^1$H NMR (500 MHz, CDCl$_3$) δ 7.56-7.54 (d, 2H), 7.37-7.35 (d, 2H), 5.03-4.98 (m, 1H), 2.79 (bs, 1H).
Intermediate 27-2:
1$^{st}$ peak to elute; (S or R)-1-(4-bromophenyl)-2,2,2-trifluoroethanol. $^1$H NMR (500 MHz, CDCl$_3$) δ 7.56-7.54 (d, 2H), 7.37-7.35 (d, 2H), 5.03-4.98 (m, 1H), 2.79 (bs, 1H).

Scheme #10

Intermediate #28-1 and 28-2

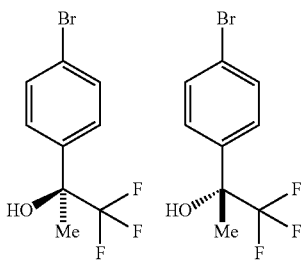

(S or R)-2-(4-Bromophenyl)-1,1,1-trifluoropropan-2-ol

4'-Bromo-2,2,2-trifluoroacetophenone (1.80 mL, 11.9 mmol) was stirred in THF (60 mL) at 0° C. under an argon atmosphere. Methylmagnesium bromide (19.8 mL, 59.3 mmol) was added and the reaction mixture was stirred at 0° C. for 1 hour and then allowed to warm to ambient temperature overnight. The reaction was quenched with saturated aqueous ammonium chloride and extracted with ethyl acetate. The organic layer was washed with brine, dried over anhydrous MgSO$_4$, filtered, and concentrated in vacuo. The residue was purified by MPLC on silica gel (using a gradient elution of 0-25% EtOAc/hexanes). Desired fractions were identified, combined, and concentrated in vacuo to afford a racemic mixture of the title compounds. The racemic residue was resolved by Chiral SFC purification (Chiral Technology AZ-H 2.1×25 cm, 5 uM column, eluted with 5% methanol).
Intermediate 28-1:
1$^{st}$ peak to elute; (S or R)-2-(4-Bromophenyl)-1,1,1-trifluoropropan-2-ol. $^1$H NMR (500 MHz, CDCl$_3$) δ 7.53-7.52 (d, 2H), 7.46-7.45 (d, 2H), 2.64 (bs, 1H), 1.76 (s, 3H).
Intermediate 28-2:
1$^{st}$ peak to elute; (S or R)-2-(4-Bromophenyl)-1,1,1-trifluoropropan-2-ol. $^1$H NMR (500 MHz, CDCl$_3$) δ 7.53-7.52 (d, 2H), 7.46-7.45 (d, 2H), 2.64 (bs, 1H), 1.76 (s, 3H).

Scheme #19

Intermediate #29-1

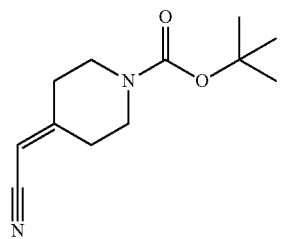 [SMILES: CC(C)(C)OC(=O)N1CCC(=CC#N)CC1]

tert-Butyl 4-(cyanomethylidene)piperidine-1-carboxylate

To a three necked round bottom flask equipped with a mechanical stirring bar was added potassium tert-butoxide (263 mL, 263 mmol, 1.0 M in THF) and THF (200 mL). The mixture was cooled to 0° C., followed by the addition of diethyl(cyanomethyl)phosphonate (43.7 mL, 276 mmol) slowly by syringe. The reaction mixture was maintained at 0° C. for 10 minutes, then warmed to ambient temperature and maintained for 1 hour. The mixture was cooled to 0° C. and treated with the dropwise addition of tert-butyl 4-oxopiperidine-1-carboxylate (50.0 g, 251 mmol) in THF (150 mL) over 30 minutes. After addition, the mixture was maintained at 0° C. for 20 minutes, then warmed to ambient temperature and maintained for 18 hours. The reaction mixture was then diluted with water (800 mL) and extracted with EtOAc (700 mL×2). The combined organic extracts were washed with water, brine, dried over anhydrous Na$_2$SO$_4$, filtered, and concentrated in vacuo to afford the title compound as a light pink solid.
$^1$H-NMR (600 MHz, CDCl$_3$) δ 5.19 (s, 1H), 3.48-3.53 (m, 4H), 2.56 (t, J=5.4 Hz, 2H), 2.33 (t, J=5.4 Hz, 2H), 1.47 (s, 9H).

TABLE 4 discloses Intermediates 29-2 through 29-18 that were prepared according to Scheme #19 following similar procedures described for Intermediate #29-1, which can be achieved by those of ordinary skill in the art of organic synthesis.

TABLE 4

| Intermediate | Structure | Compound Name | Exact Mass [M + H]$^+$ or $^1$H NMR δ (ppm) |
|---|---|---|---|
| 29-2 | 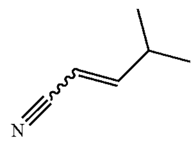 | (2E and Z)-4-methylpent-2-enenitrile | $^1$H NMR (600 MHz, CDCl$_3$): 1:1 E:Z δ 6.68 (dd, J = 16.4, 6.6, 1H), 5.27-5.23 (m, 1H), 1.96-1.82 (m, 1H), 1.04 (d, J = 6.8, 6H); $^1$H NMR (600 MHz, CDCl$_3$): δ 6.31-6.24 (m, 1H), 5.18 (d, J = 10.9, 1H), 1.77-1.64 (m, 1H), 1.06 (d, J = 6.6, 6H). |
| 29-3 | 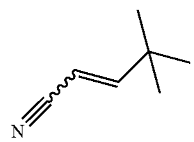 | (2E and Z)-4,4-dimethylpent-2-enenitrile | $^1$H NMR (600 MHz, CDCl$_3$): 1:1 E:Z δ 6.70 (d, J = 16.6, 1H), 5.20 (d, J = 12.3, 5.20, 1H), 1.22 (s, 9H); $^1$H NMR (600 MHz, CDCl$_3$): δ 6.32 (d, J = 12.3, 1H), 5.22 (d, J = 16.6, 1H), 1.05 (s, 9H). |
| 29-4 | 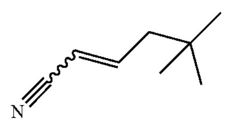 | (2E and Z)-5,5-dimethylhex-2-enenitrile | $^1$H NMR (600 MHz, CDCl$_3$): 1:1 E:Z δ 6.72 (dt, J = 15.9, 7.9, 1H), 5.30 (dt, J = 15.2, 1.49, 1H), 2.08 (dd, J = 7.9, 1.3, 2H), 0.91 (s, 9H). $^1$H NMR (600 MHz, CDCl$_3$) δ 6.53 (dt, J = 11.0, 8.0, 1H), 5.37 (dt, J = 11.0, 1.1, 1H), 2.30 (d, J = 8.0, 2H), 2, 0.95 (s, 9H). |
| 29-5 | 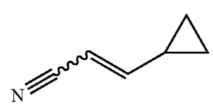 | (2E and 2Z)-3-cyclopropylprop-2-enenitrile | $^1$H NMR (600 MHz, CDCl$_3$): 5:3 E:Z δ 6.10-6.04 (m, 1H), 5.30 (d, J = 16.1 Hz, 1H), 1.58-1.50 (m, 1H), 1.04-0.92 (m, 4H); $^1$H NMR (600 MHz, CDCl$_3$): δ 5.74 (t, J = 10.6, 1H), 5.12 (d, J = 10.6 Hz, 1H), 1.98-1.90 (m, 1H), 0.65-0.58 (m, 4H). |
| 29-6 | 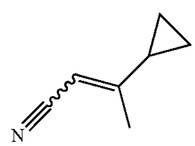 | (2E and Z)-3-cyclopropylbut-2-enenitrile | $^1$H NMR (600 MHz, CDCl$_3$): 3:1 E:Z δ 5.09-5.07 (m, 1H), 1.82-1.81 (m, 3H), 1.53 (t, J = 1.1, 1H), 0.87-0.81 (m, 2H), 0.70-0.65 (m, 2H); $^1$H NMR (600 MHz, CDCl$_3$): δ 5.07-5.06 (m, 1H), 2.17-2.11 (m, 1H), 1.59-1.54 (m, 3H), 0.94-0.88 (m, 2H), 0.78-0.74 (m, 2H). |
| 29-7 | 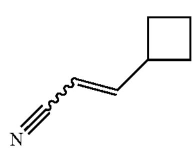 | (2E and Z)-3-cyclobutylprop-2-enenitrile | $^1$H NMR (600 MHz, CDCl$_3$): 1:1 E:Z δ 6.78 (dd, J = 16.3, 6.8, 1H), 5.21 (dd, J = 16.3, 1.5, 1H), 2.30-1.85 (m, 7H); $^1$H NMR (600 MHz, CDCl$_3$): δ 6.53 (dd, J = 10.8, 9.4, 1H), 5.12 (dd, J = 10.9, 0.8, 1H), 2.30-1.85 (m, 7H). |
| 29-8 | 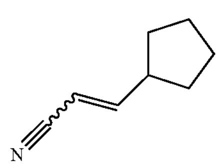 | (2E and 2Z)-3-cyclopentylprop-2-enenitrile | $^1$H NMR (600 MHz, CDCl$_3$): 4:5 E:Z δ 6.68-6.64 (m, 1H), 5.26 (d, J = 17.6 Hz, 1H), 2.60-2.50 (m, 1H), 1.96-1.28 (m, 8H); $^1$H NMR (600 MHz, CDCl$_3$): δ 6.34 (t, J = 10.6, 1H), 5.18 (d, J = 10.9 Hz, 1H), 3.04-2.94 (m, 1H), 1.96-1.28 (m, 8H). |
| 29-9 | 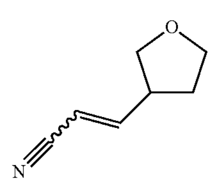 | (2E and 2Z)-3-(tetrahydrofuran-3-yl)prop-2-enenitrile | $^1$H NMR (600 MHz, CDCl$_3$): 1:1 E:Z δ 6.63 (dd, J = 16.3, 8.8, 1H), 6.39 (t, J = 10.5, 1H), 5.40-5.35 (m, 1H), 5.31 (d, J = 10.8, 1H), 3.97-3.87 (m, 4H), 3.82-3.77 (m, 2H), 3.56-3.50 (m, 2H), 3.46-3.39 (m, 1H), 3.02-2.92 (m, 1H), 2.27-2.27 (m, 1H), 2.19-2.13 (m, 1H), 1.79-1.67 (m, 2H). |

TABLE 4-continued

| Intermediate | Structure | Compound Name | Exact Mass [M + H]⁺ or ¹H NMR δ (ppm) |
|---|---|---|---|
| 29-10 | 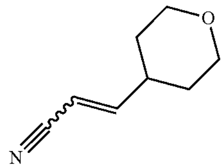 | (2E and 2Z)-3-(tetrahydro-2H-pyran-4-yl)prop-2-enenitrile | ¹H NMR (600 MHz, CDCl₃): 1:1 E:Z δ 6.64 (dd, J = 16.5, 6.6, 1H), 5.29 (dd, J = 16.5, 1.6, 1H), 1.77-1.66 (m, 1H), 1.65-1.59 (m, 4H), 1.56-1.43 (m, 4H); ¹H NMR (600 MHz, CDCl₃): 6.28 (dd, J = 10.8, 9.8, 1H), 5.27-5.25 (m, 1H), 3.99-3.93 (m, 4H), 3.42 (dtd, J = 34.3, 11.8, 2.2, 4H), 2.43-2.33 (m, 1H). |
| 29-11 | 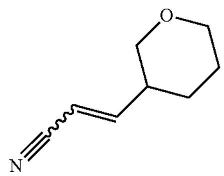 | (2E and 2Z)-3-(tetrahydro-2H-pyran-3-yl)prop-2-enenitrile | ¹H NMR (600 MHz, CDCl₃): 3:5 E:Z δ 6.58 (dd, J = 16.5, 7.3, 1H), 5.36 (dd, J = 16.5, 1.4, 1H), 3.88-1.44 (m, 9H); ¹H NMR (600 MHz, CDCl₃): δ 6.37 (t, J = 10.5 1H), 5.33 (dd, J = 11.0, 0.6, 1H), 3.88-1.44 (m, 9H). |
| 29-12 | 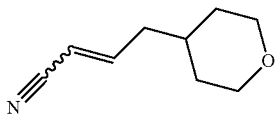 [SMILES: N#CC=CCC1CCOCC1] | (2E and 2Z)-4-(tetrahydro-2H-pyran-4-yl)but-2-enenitrile | ¹H NMR (600 MHz, CDCl₃): 1:1E:Z δ 6.66 (dt, J = 16.2, 7.6, 1H), 5.33 (dt, J = 16.3, 1.5, 1H), 3.97-3.89 (m, 8H), 2.18-2.14 (m, 2H), 1.78-1.54 (m, 1H); ¹H NMR (600 MHz, CDCl₃): 6.48 (dt, J = 10.9, 7.8, 1H), 5.37 (dt, J = 10.9, 1.2, 1H), 3.38-3.31 (m, 8H), 2.37 (t, J = 7.3, 2H), 1.78-1.54 (m, 1H). |
| 29-13 | 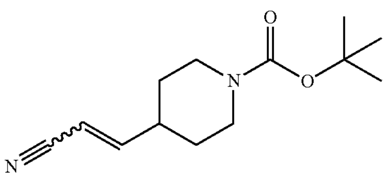 [SMILES: CC(C)(C)OC(=O)N1CCC(C=CC#N)CC1] | tert-butyl 4-[(E and Z)-2-cyanoethenyl]piperidine-1-carboxylate | ¹H NMR (500 MHz, CDCl₃): 18:5 E:Z δ 6.70-6.62 (m, 1H), 5.36-5.28 (m,1H), 4.25-4.05 (m, 2H), 2.85-2.65 (m, 2H), 2.35-2.25 (m, 1H), 1.75-1.68 (m, 2H), 1.46 (s, 9H), 1.38-1.20 (m, 2H); ¹H NMR (500 MHz, CDCl₃): δ 6.28 (t, J = 10.4, 1H), 5.29 (d, J = 10.9 Hz, 1H), 4.25-4.00 (m, 2H), 2.90-2.70 (m, 3H), 1.75-1.65 (m, 2H), 1.46 (s, 9H), 1.43-1.30 (m, 2H). |
| 29-15 | 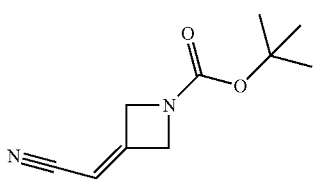 | tert-butyl 3-(cyanomethylidene)azetidine-1-carboxylate | ¹H NMR (600 MHz, CDCl₃): δ 5.38-5.35 (m, 1H), 4.69 (m, 2H), 4.61-4.58 (m, 2H), 1.44 (s, 9H). |
| 29-16 | 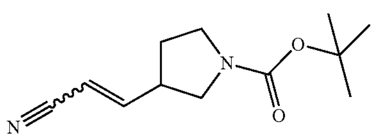 [SMILES: CC(C)(C)OC(=O)N1CCC(C=CC#N)C1] | tert-butyl 3-[(E and Z)-2-cyanoethenyl]pyrrolidine-1-carboxylate | ¹H NMR (600 MHz, CDCl₃): 4:1 E:Z δ 6.37 (t, J = 10.6 Hz, 1H), 5.35 (d, J = 10.6 Hz, 1H), 3.70-2.86 (m, 5H), 2.20-2.00 (m, 1H), 1.84-1.70 (m, 1H), 1.43 (s, 9H); ¹H NMR (600 MHz, CDCl₃): δ 6.68-6.60 (m, 1H), 5.35 (dd, J =16.4, 1.2 Hz, 1H), 3.70-2.86 (m, 5H), 2.20-2.00 (m, 1H), 1.84-1.70 (m, 1H), 1.43 (s, 9H). |
| 29-17 | 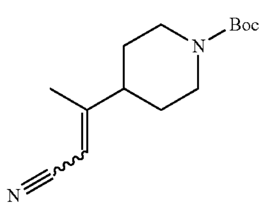 [SMILES: CC(=CC#N)C1CCN(C(=O)OC(C)(C)C)CC1] | tert-butyl 4-[(1E and Z)-1-cyanoprop-1-en-2-yl]piperidine-1-carboxylate | Calc'd 251, Found 195 (M + H − C₄H₈) |
| 29-18 | 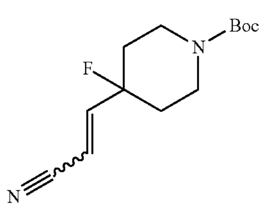 [SMILES: CC(C)(C)OC(=O)N1CCC(F)(C=CC#N)CC1] | tert-butyl 4-[(E and Z)-2-cyanoethenyl]-4-fluoropiperidine-1-carboxylate | Calc'd 255, Found 199 (M + H − C₄H₈) |

Scheme #19

Intermediate #30

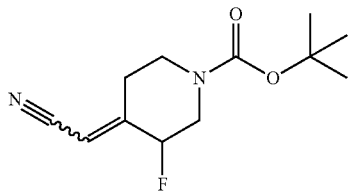 [SMILES: CC(C)(C)OC(=O)N1CCC(=CC#N)C(F)C1]

tert-Butyl (4E and 4Z)-4-(cyanomethylidene)-3-fluoropiperidine-1-carboxylate

To a solution of NaH (0.27 g, 6.6 mmol, 60% in mineral oil) in DMF (10 mL) was added diethyl(cyanomethyl)phosphonate (1.5 g, 6.6 mmol). The mixture was stirred at ambient temperature for 30 minutes before tert-butyl 3-fluoro-4-oxopiperidine-1-carboxylate (0.70 g, 3.3 mmol) was added. The resulting mixture was stirred for 1 hour before the reaction was quenched with water and the mixture was concentrated in vacuo. The crude residue was purified by MPLC on silica gel to afford the title compound. LRMS (ESI) calc'd for $(C_{12}H_{18}FN_2O_2)$ $[M+H]^+$: 241. Found 241.

Scheme #19

Intermediate #31

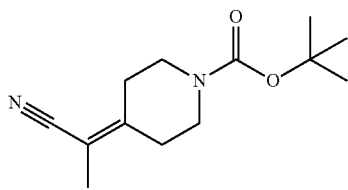 [SMILES: CC(C#N)=C1CCN(C(=O)OC(C)(C)C)CC1]

tert-Butyl 4-(1-cyanoethylidene)piperidine-1-carboxylate

To a solution of MeI (1.42 g, 10 mmol) in DMF was added NaH (0.40 g, 10 mmol, 60% in mineral oil), followed by diethyl(cyanomethyl)phosphonate (2.35 g, 10 mmol). The mixture was stirred at ambient temperature. After 30 minutes another batch of NaH (0.40 g, 10 mmol, 60% in mineral oil) was added, followed by tert-butyl 4-oxopiperidine-1-carboxylate (2.0 g, 10 mmol). The resulting mixture was stirred for 30 minutes before the reaction was quenched with water and the mixture was concentrated in vacuo. The crude residue was purified by MPLC on silica gel to afford the title compound. LRMS (ESI) calc'd for $C_{13}H_{21}N_2O_2$ $[M+H]^+$ 237. Found 237.

Scheme #19

Intermediate #32

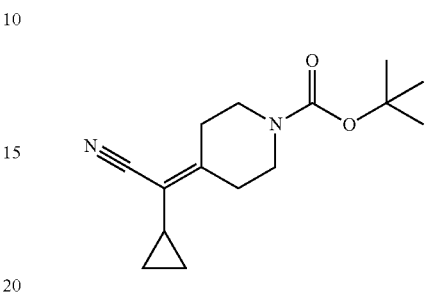

tert-Butyl 4-[cyano(cyclopropyl)methylidene]piperidine-1-carboxylate tert-Butyl 4-oxopiperidine-1-carboxylate (2.0 g, 10 mmol) and cyclopropylacetonitrile (0.97 g, 12 mmol) were dissolved in THF (20 mL), heated to reflux, and allowed to stir for 3 hours. The mixture was then cooled to ambient temperature and concentrated in vacuo. The residue was purified by MPLC on silica gel to afford the title compound as a white solid. LRMS (ESI) calc'd for $C_{15}H_{23}N_2O_2$ $[M+H]^+$ 263. Found 263.

Scheme #20

Intermediate #33

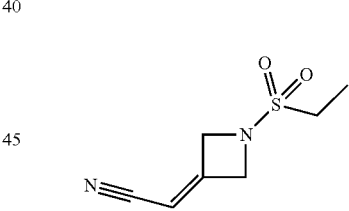

Step A-B.
[1-(Ethylsulfonyl)azetidin-3-ylidene]acetonitrile tert-Butyl 3-(cyanomethylidene)azetidine-1-carboxylate (5.0 g, 26 mmol) was dissolved in 4M HCl in dioxane (25.7 mL) and allowed to stir at ambient temperature for 16 hours. The mixture was concentrated to dryness in vacuo, then dissolved in DCM (30.0 mL) and cooled to −10° C. DIPEA (11.6 g, 90.0 mmol) was added followed by ethanesulfonyl chloride (5.0 g, 39 mmol). The resulting mixture was allowed to stir for 7 hours before the mixture was diluted with water and extracted with DCM. The organic layer was dried over anhydrous $Na_2SO_4$, filtered and concentrated in vacuo. The residue was purified by MPLC on silica gel (using a gradient elution of 5-70% EtOAc/heptane). Desired fractions were identified, combined, and concentrated in vacuo to afford the title compound. LRMS (ESI) calc'd for $C_7H_{10}N_2O_2S$ [M+H]$^+$: 187. Found: 187.

Scheme #20

Intermediate #34

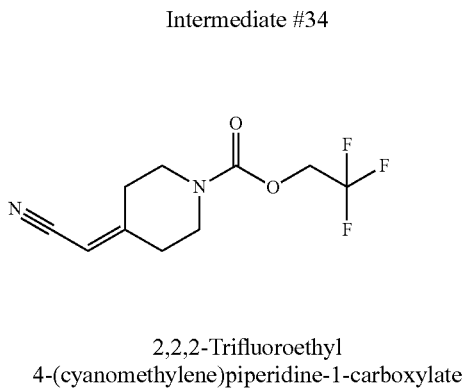

2,2,2-Trifluoroethyl 4-(cyanomethylene)piperidine-1-carboxylate

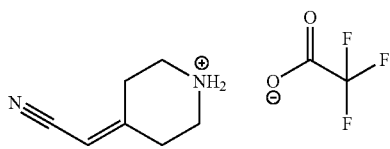 [SMILES: N#CC=C1CC[NH2+]CC1 ; O=C([O-])C(F)(F)F]

Step A. 4-(Cyanomethylidene)piperidinium trifluoroacetate tert-Butyl 4-(cyanomethylene)piperidine-1-carboxylate (5.0 g, 22 mmol) was dissolved in DCM (75.0 mL). TFA (8.70 mL, 112 mmol) was added, and the resulting mixture was allowed to stir at ambient temperature for 2 hours. The mixture was concentrated in vacuo to afford the title compound. LRMS (ESI) calc'd for $C_7H_{10}N_2$ [M+H]$^+$: 123. Found: 123.

Step B. 2,2,2-Trifluoroethyl 4-(cyanomethylene)piperidine-1-carboxylate 2,2,2-Trifluoroethanol (1.6 mL, 22 mmol) and TEA (6.2 mL, 45 mmol) were dissolved in MeCN (200 mL). N,N-disuccinimidyl carbonate (8.6 g, 34 mmol) was added and the resulting mixture was stirred at ambient temperature for 90 minutes. 4-(cyanomethylidene)piperidinium trifluoroacetate (5.3 g, 23 mmol) in DMSO (10 mL) was then added, followed by TEA (6.2 mL, 45 mmol). The resulting mixture was stirred at 50° C. for 16 hours. The reaction mixture was cooled to ambient temperature, diluted with EtOAc and washed sequentially with saturated aqueous NaHCO$_3$ and water. The organic layer was dried over anhydrous MgSO$_4$, filtered, and concentrated in vacuo. The residue was purified by MPLC on silica gel (using a gradient elution of 0-5% MeOH/DCM) to afford the title compound. LRMS (ESI) calc'd for $C_{10}H_{11}F_3N_2O_2$ [M+H]$^+$: 249. Found: 249.

Scheme #20

Intermediate #35-1

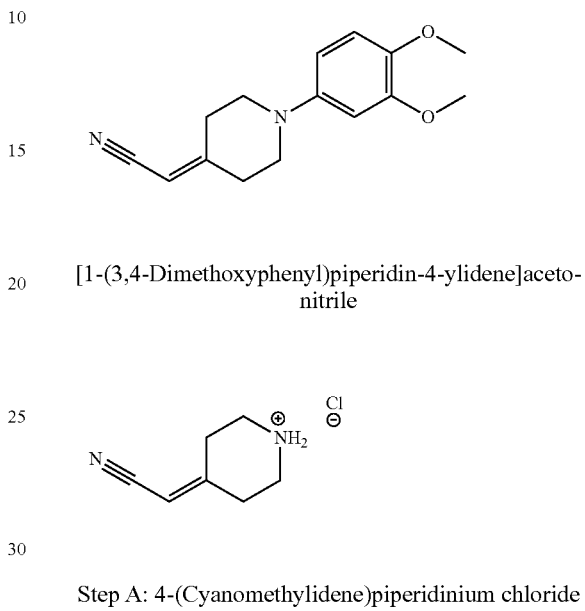

[1-(3,4-Dimethoxyphenyl)piperidin-4-ylidene]acetonitrile

Step A: 4-(Cyanomethylidene)piperidinium chloride tert-Butyl 4-(cyanomethylidene)piperidine-1-carboxylate (20 g, 90 mmol) was dissolved in 4M HCl in dioxane and allowed to stir at ambient temperature for 2 hours. The mixture was then concentrated in vacuo to afford the title compound.
LRMS (ESI) calc'd for $C_7H_{10}N_2$ [M+H]$^+$: 123. Found: 123.

Step B: [1-(3,4-Dimethoxyphenyl)piperidin-4-ylidene]acetonitrile

In a sealed tube, 4-(cyanomethylidene)piperidinium chloride (16 mg, 0.10 mmol), Pd$_2$(dba)$_3$ (14 mg, 0.015 mmol), X-Phos (20 mg, 0.020 mmol), 4-bromo-1,2-dimethoxybenzene (33 mg, 0.15 mmol), and Cs$_2$CO$_3$ (98 mg, 0.30 mmol) were suspended in t-BuOH (0.5 mL). The reaction mixture was purged with argon for 5 minutes, the reaction flask was capped, and heated to 90° C. for 12 hours. The reaction was then cooled to ambient temperature and diluted with DMF/MeCN (1.0 mL, 50:50). To this mixture, Silica Supported-DMT (0.50 mmol, 0.57 mmol/g) followed by Silica Supported-Isocyanate (0.15 mmol, 1.33 mmol/g) was added. The resulting mixture was then shaken at 50° C. for 4 hours. The mixture was then passed through a nylon syringe filter (0.45 μm), and the filtrate was concentrated in vacuo to afford the title compound. The crude residue was used without further purification. LRMS (ESI) calc'd for $C_{15}H_{15}N_2O_2$ [M+H]$^+$: 259. Found: 259.

TABLE 5 depicts intermediates 35-2 through 35-3 that were prepared according to Scheme #20 following similar procedures described for Intermediates #35-1, which can be achieved by those of ordinary skill in the art of organic synthesis.

TABLE 5

| Intermediate | Structure | Compound Name | Exact Mass [M + H]+ |
|---|---|---|---|
| 35-2 | 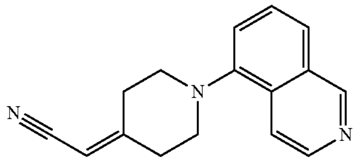 [SMILES: N#CC=C1CCN(c2cccc3cnccc23)CC1] | [1-(isoquinolin-5-yl)piperidin-4-ylidene]acetonitrile | Calc'd 250, Found 250 |
| 35-3 | 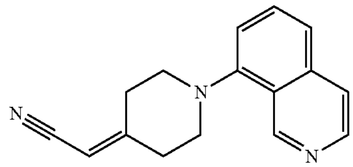 [SMILES: N#CC=C1CCN(c2cccc3ccncc23)CC1] | [1-(isoquinolin-8-yl)piperidin-4-ylidene]acetonitrile | Calc'd 250, Found 250 |

Scheme #21

Intermediate #36-1

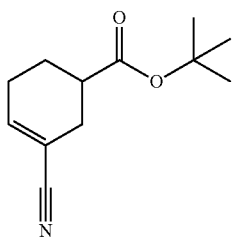

tert-Butyl 3-cyanocyclohex-3-ene-1-carboxylate

Step A-C: tert-Butyl 3-cyanocyclohex-3-ene-1-carboxylate tert-Butyl 3-oxocyclohexanecarboxylate (1.35 g, 6.81 mmol) was taken up in water (11.4 mL) and stirred at ambient temperature. Sodium metabisulfite (0.75 g, 3.9 mmol) was added and the mixture was allowed to stir for 40 minutes. Diethyl ether (11.4 mL) was added, followed by potassium cyanide (0.70 g, 11 mmol). The resulting mixture was allowed to stir vigorously for 1 hour before it was partitioned between diethyl ether and water. The organic layer was washed with water, brine, dried over anhydrous MgSO$_4$, filtered, and concentrated in vacuo. The residue, used without further purification, was dissolved in DCM (22.0 mL). DIPEA (1.07 g, 8.26 mmol) was added and the resulting mixture was cooled to 0° C. Methanesulfonyl chloride (0.69 g, 6.1 mmol) was added dropwise and the resulting mixture was maintained at 0° C. for 20 minutes then allowed to warm to ambient temperature. The mixture was partitioned between DCM and water. The organic layer was dried over anhydrous Na$_2$SO$_4$, filtered, and concentrated in vacuo. The residue, used without further purification, was dissolved in pyridine (13.6 mL) and heated to 95° C. for 20 hours. The mixture was then allowed to cool to ambient temperature and was concentrated in vacuo. The residue was purified by MPLC on silica gel (using a gradient elution of 0-45% EtOAc/hexanes). Desired fractions were identified, combined, and concentrated in vacuo to afford the title compound. $^1$H NMR (500 MHz, CDCl$_3$): δ 6.63-6.58 (m, 1H), 2.54-2.48 (m, 1H), 2.44-2.40 (m, 2H), 2.36-2.16 (m, 2H), 2.02-1.94 (m, 1H), 1.71-1.63 (m, 1H), 1.44 (s, 9H).

TABLE 6 depicts intermediates 36-2 through 36-4 that were prepared according to Scheme #21 following similar procedures described for Intermediate #36-1, which can be achieved by those of ordinary skill in the art of organic synthesis.

TABLE 6

| Intermediate | Structure | Compound Name | $^1$H NMR δ (ppm) |
|---|---|---|---|
| 36-2 | 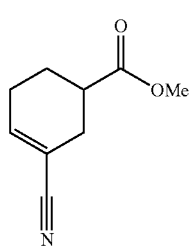 [SMILES: COC(=O)C1CCC=C(C#N)C1] | methyl 3-cyanocyclohex-3-ene-1-carboxylate | $^1$H NMR (500 MHz, CDCl$_3$): δ 6.66-6.60 (m, 1H), 3.70 (s, 3H), 2.68-2.60 (m, 1H), 2.52-2.44 (m, 2H), 2.40-2.18 (m, 2H), 2.10-2.00 (m, 1H), 1.80-1.66 (m, 1H). |

TABLE 6-continued

| Intermediate | Structure | Compound Name | $^1$H NMR δ (ppm) |
|---|---|---|---|
| 36-3 | 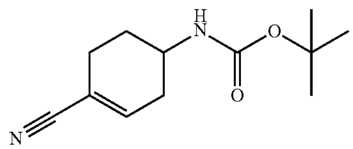 [SMILES: CC(C)(C)OC(=O)NC1CC=C(C#N)CC1] | 4-tert-butyl (4-cyanocyclohex-3-en-1-yl)carbamate | $^1$H NMR (600 MHz, CDCl$_3$): δ 6.53-6.50 (m, 1H), 4.46 (s, 1H), 3.77 (s, 1H), 2.58 (br d, J = 19.9 Hz, 1H), 2.48-2.27 (br d, J = 19.2 Hz, 2H), 2.03 (ddq, J = 19.3, 8.0, 3.6, 1H), 1.96-1.91 (m, 1H), 1.63-1.56 (m, 1H), 1.42 (s, 9H). |
| 36-4 | 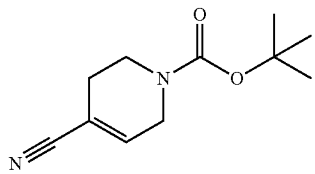 | tert-butyl 4-cyano-3,6-dihydropyridine-1(2H)-carboxylate | $^1$H NMR (500 MHz, CDCl$_3$): δ 6.55 (br s, 1H), 4.05 (m, 2H), 3.55 (t, J = 5.6 Hz, 2H), 2.34 (br s, 2H), 1.46 (s, 9H). |

Scheme #21

Intermediate #37-1

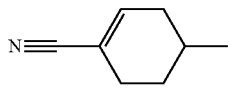

4-Methylcyclohex-1-ene-1-carbonitrile

Step A-B: 4-Methylcyclohex-1-ene-1-carbonitrile

4-Methylcyclohexanone (1.0 g, 8.9 mmol) was added to a stirred solution of water (8.9 mL) containing sodium metabisulfite (0.98 g, 5.2 mmol). The resulting mixture was allowed to stir at ambient temperature for 15-30 minutes before diethyl ether (8.9 mL) was added followed by potassium cyanide (0.91 g, 14 mmol). The biphasic mixture was stirred vigorously for at least 30 minutes before the layers were partitioned and the organic layer was washed with water, followed by brine. The organic layer was dried over anhydrous Na$_2$SO$_4$, filtered, and concentrated in vacuo (23° C. water bath) to afford 4-methyl-1-hydroxycyclohexanecarbonitrile as a crude residue, which was carried forward without further purification. The crude residue (0.50 g, 3.6 mmol) was combined with pyridine (18.3 mL, 226 mmol), and POCl$_3$ (1.34 mL, 14.4 mmol) in a microwave vial and sealed. The reaction mixture was heated to reflux for 16 hours. The reaction mixture was then cooled to ambient temperature, diluted with diethyl ether, and washed with 2N aqueous HCl saturated with sodium chloride (3×). The organic layer was washed with brine, dried over anhydrous MgSO$_4$, filtered, and concentrated in vacuo (23° C. water bath) to afford the title compound as an oil. $^1$H NMR (600 MHz, CDCl$_3$): δ 6.59-6.56 (m, 1H), 2.28-2.20 (m, 3H), 1.80-1.71 (m, 2H), 1.71-1.59 (m, 1H), 1.28-1.21 (m, 1H), 0.96 (d, J=6.6, 3H).

Table 7 depicts intermediates 37-2 and 37-3 were prepared according to Scheme #21 following similar procedures described for Intermediate #37-1, which can be achieved by those of ordinary skill in the art of organic synthesis.

TABLE 7

| Intermediate | Structure | Compound Name | $^1$H NMR δ (ppm) |
|---|---|---|---|
| 37-2 | 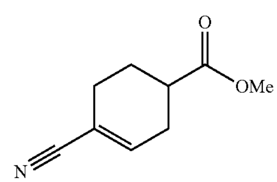 [SMILES: COC(=O)C1CC=C(C#N)CC1] | methyl 4-cyanocyclohex-3-ene-1-carboxylate | $^1$H NMR (600 MHz, CDCl$_3$): δ 6.61-6.57 (m, 1H), 3.68 (s, 3H), 2.62-2.54 (m, 1H), 2.48-2.40 (m 2H), 2.36-2.22 (m, 2H), 2.10-2.02 (m, 1H), 1.80-1.70 (m, 1H). |
| 37-3 | 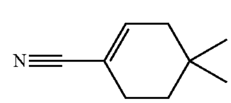 | 4,4-dimethylcyclohex-1-ene-1-carbonitrile | $^1$H NMR (600 MHz, CDCl$_3$): δ 6.55-6.52 (m, 1H), 2.24-2.19 (m, 2H), 1.96-1.91 (m, 2H), 1.41 (t, J = 6.4, 2H), 0.91 (s, 6H). |

127

Scheme #22

Intermediate #38

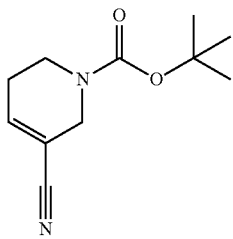

Steps A-B: tert-Butyl
5-cyano-3,6-dihydropyridine-1(2H)-carboxylate

A solution of n-butyllithium (2.8 mL, 7.0 mmol, 2.5 M in hexanes) was added to a solution of diisopropylamine (1.0 mL, 7.0 mmol) in THF (10.0 mL) at −78° C. The cooling bath was removed for 15 minutes, and then the reaction mixture was cooled back to −78° C. A solution of tert-butyl 3-oxopiperidine-1-carboxylate (1.0 g, 5.0 mmol) in THF (6 mL) was added to the cooled solution of LDA dropwise over 5 minutes, maintained for 15 minutes, and then N-(5-chloropyridin-2-yl)-1,1,1-trifluoro-N-[(trifluoromethyl)sulfonyl]methanesulfonamide (2.4 g, 6.0 mmol) was added in one portion. The reaction mixture was stirred at −78° C. for 15 minutes, and then the cooling bath was removed. The reaction mixture was stirred for 45 minutes after removal of the cooling bath, and was then partitioned between EtOAc and water. The organic layer was washed with brine, dried over anhydrous Na$_2$SO$_4$ and filtered. The filtrate was concentrated in vacuo and the residue was purified by MPLC on silica gel (using a gradient elution of 0-20%, diethyl ether/hexanes) to afford tert-butyl 5-{[(trifluoromethyl)sulfonyl]oxy}-3,6-dihydropyridine-1(2H)-carboxylate as the second regioisomer to elute. A portion of the product (123 mg, 0.371 mmol) was combined with zinc cyanide (52 mg, 0.45 mmol), Pd(PPh$_3$)$_4$ (64 mg, 0.056 mmol) and DMF (1.9 mL) in a microwave tube. The reaction mixture was heated in the microwave at 100° C. for 20 minutes. After cooling to 23° C., the reaction mixture was partitioned between EtOAc and water. The organic layer was washed with brine, dried over anhydrous Na$_2$SO$_4$ and filtered. The filtrate was concentrated in vacuo and the residue was purified by MPLC on silica gel (using a gradient elution of 0-100%, EtOAc/hexanes) to afford the title compound. $^1$H NMR (500 MHz, CDCl$_3$): δ 6.73 (br s, 1H), 4.02 (br s, 2H), 3.49 (t, J=5.6 Hz, 2H), 2.29 (br s, 2H), 1.47 (s, 9H).

Scheme #23

Intermediate #39

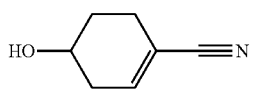

128

4-Hydroxycyclohex-1-ene-1-carbonitrile

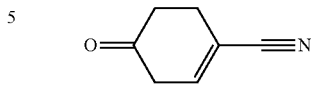

Step A: 4-Oxocyclohex-1-ene-1-carbonitrile

In a sealed tube, {[(3E)-4-methoxybuta-1,3-dien-2-yl]oxy}(trimethyl)silane (5.65 mL, 29.0 mmol) and acrylonitrile (1.91 mL, 29.0 mmol) were combined in benzene (9.67 mL), heated to reflux, and allowed to stir for 16 hours. The reaction mixture was then cooled to ambient temperature and the volatiles were removed in vacuo (23° C. water bath). The residue was stirred into a mixture of 1N aqueous HCl (29.0 mL, 29.0 mmol) and THF (9.7 mL). After being stirred at ambient temperature for 3 hours, the reaction mixture was extracted with diethyl ether. The organic layer was washed with de-ionized water (2×), brine, dried over anhydrous Na$_2$SO$_4$, filtered and concentrated in vacuo (23° C. water bath). The residue was purified by MPLC on silica gel (using a gradient elution of 0-50% hexanes/acetone). Desired fractions were identified, combined and concentrated in vacuo (23° C. water bath) to afford the title compound.

$^1$H NMR (600 MHz, CDCl$_3$): δ 6.68 (tt, J=4.0, 1.5, 1H), 3.05 (dt, J=4.3, 2.2, 2H), 2.71 (tq, J=6.9, 1.9, 2H), 2.61-2.53 (t, J=6.9 2H).

Step B: 4-Hydroxycyclohex-1-ene-1-carbonitrile

To a stirred solution of 4-oxocyclohex-1-ene-1-carbonitrile (170 mg, 1.40 mmol) in MeOH (2.3 mL) at −78° C. was added cerium (III) chloride (484 mg, 1.96 mmol) in MeOH (4.7 mL). The resulting mixture was allowed to stir for 5 minutes at −78° C. before NaBH$_4$ (48 mg, 1.3 mmol) was added in one portion. The mixture was stirred for 20 minutes and then allowed to warm to ambient temperature. After being stirred for 30 minutes, the reaction mixture was diluted with water and extracted with diethyl ether (3×). The combined organic extracts were washed with brine, dried over anhydrous Na$_2$SO$_4$, filtered, and concentrated in vacuo (23° C. water bath) to afford the title compound. $^1$H NMR (600 MHz, CDCl$_3$): δ 6.50 (tt, J=3.9, 1.8, 1H), 4.03-3.98 (m, 1H), 3.50-3.42 (qd, J=11.4, 4.5, 1H), 2.50 (br d, J=19.2, 1H), 2.46-2.38 (m, 1H), 2.33-2.23 (m, 1H), 2.21-2.13 (m, 1H), 1.90-1.84 (m, 1H), 1.76-1.67 (m, 1H).

Scheme #24

Intermediate #40

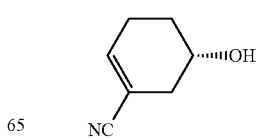

(R or S)-5-Hydroxycyclohex-1-enecarbonitrile

Step A: (R or S)-3-Cyanocyclohex-3-en-1-yl propionate

To a 2 L flask containing racemic 5-hydroxycyclohex-1-ene-1-carbonitrile (151 g, 1.22 mol), vinyl propionate (147 g, 1.47 mol), and MTBE (1.5 L) was added the enzyme AMANO Lipase PS from Burlholderiacepacia (20 g, Sigma-Aldrich). The mixture was stirred at ambient temperature for 48 hours. The mixture was filtered through celite and rinsed with MTBE. The filtrate was concentrated in vacuo to remove both solvent and unreacted vinyl propionate. The residue was diluted with brine (1.5 L) and extracted with hexanes (1000 mL+600 mL×3 respectively). The combined organics was washed with $H_2O$ (400 mL×5), then dried over anhydrous $Na_2SO_4$, and concentrated in vacuo to afford the title compound, which was used without further purification.

Step B: (R or S)-5-Hydroxycyclohex-1-enecarbonitrile

To a solution of (R or S)-3-cyanocyclohex-3-en-1-yl propanoate (210 g, 1.17 mol) in 1:1 THF/EtOH (2 L) at 0° C. was added 3M aqueous NaOH (586 mL, 1.76 mol) dropwise via addition funnel over 30 minutes. After addition, The mixture was stirred at ambient temperature for 2 hours. The mixture was carefully neutralized with 3N aqueous HCl (195 mL), concentrated to remove most of the THF/EtOH. The resulting mixture was diluted with brine (1.5 L) and extracted with EtOAc (1.2 L, then 600 mL×4). The combined organics were washed with brine (200 mL×2). The aqueous layer was back-extracted with EtOAc (200 mL×2), and the combined organic extracts were dried over anhydrous $Na_2SO_4$, and concentrated in vacuo to give the enantioenriched title compound (chiral HPLC: 98.4% ee). $^1H$ NMR data was consistent with that reported in the literature for racemic 5-Hydroxycyclohex-1-enecarbonitrile.

Scheme #25

Intermediate #41

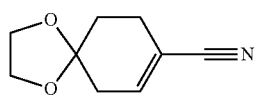

1,4-Dioxaspiro[4.5]dec-7-ene-8-carbonitrile

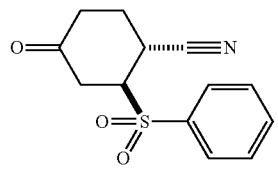

Step A-C: (1R,2S and 1S,2R)-4-Oxo-2-(phenylsulfonyl)cyclohexanecarbonitrile

Benzenesulfinic acid sodium salt (9.4 g, 57 mmol) was dissolved in a mixture of water (18.3 mL) and acetic acid (9.1 mL). 2-Chloroprop-2-enenitrile (4.6 mL, 57 mmol) was added, followed by MeOH (18.3 mL). The resulting mixture was allowed to stir for 10 minutes before the solid product was collected by filtration and rinsed with minimal water. The majority of the solid filtered through with the rinse and so all material was rinsed through the filter. The filtrate was extracted with DCM (2×) and the combined organic layers were washed with saturated aqueous $NaHCO_3$, brine, dried over anhydrous $Na_2SO_4$, filtered, and concentrated in vacuo to afford 2-chloro-3-(phenylsulfonyl)propanenitrile as a crude residue. Crude 2-chloro-3-(phenylsulfonyl)propanenitrile (6.1 g, 27 mmol) was dissolved in chloroform (41 mL) cooled in an ice-salt bath and stirred before adding TEA (3.7 mL, 27 mmol) dropwise. The mixture was allowed to stir at 0° C. for 20 minutes. The reaction mixture was then washed sequentially with dilute 1N aqueous HCl, followed by saturated aqueous $NaHCO_3$. The organic layer was dried over anhydrous $Na_2SO_4$, filtered, and concentrated in vacuo (23° C. water bath) to afford (2E and 2Z)-3-(phenylsulfonyl)prop-2-enenitrile as a crude residue. This crude residue (4.9 g, 25.5 mmol) and (buta-1,3-dien-2-yloxy)(trimethyl)silane (4.2 g, 29.3 mmol) were refluxed together in benzene (63.8 mL) under nitrogen for 16 hours. The reaction mixture was then concentrated in vacuo to afford an oily mixture of intermediate adducts. The residue was dissolved in aqueous acetic acid (80%) and allowed to stir. After 1 hour at ambient temperature, the mixture was diluted with water and extracted with DCM (2×). The combined organic extracts were concentrated in vacuo and the residue was dissolved in DCM. A solid precipitated from the solution and was collected by filtration to afford the title compound.

$^1H$ NMR (600 MHz, $CDCl_3$): δ 7.91 (d, J=7.7, 2H), 7.74 (t, J=7.4, 1H), 7.63 (t, J=7.8, 2H), 3.81 (q, J=4.4, 1H), 3.68 (q, J=4.8, 1H), 2.76 (dd, J=16.5, 6.3, 1H), 2.74-2.66 (m, 1H), 2.62 (dd, J=11.4, 4.5, 1H), 2.61-2.56 (m, 2H), 2.25 (dq, J=14.3, 4.9, 1H).

Step D-E: 1,4-Dioxaspiro[4.5]dec-7-ene-8-carbonitrile

To a pressure vessel was added (1R,2S and 1S,2R)-4-oxo-2-(phenylsulfonyl)cyclohexanecarbonitrile (100 mg, 0.380 mmol), benzene (19.0 mL), ethylene glycol (0.9 mL, 15.6 mmol), and p-toluenesulfonic acid monohydrate (14 mg, 0.076 mmol). The vessel was capped and the reaction mixture was heated to reflux and allowed to stir for 16 hours. The reaction mixture was allowed to cool to ambient temperature before it was diluted with EtOAc. The organic layer was washed with water (3×), brine, dried over anhydrous $Na_2SO_4$, filtered, and concentrated in vacuo (23° C. water bath) to afford (7S,8R and 7R,8S)-7-(phenylsulfonyl)-1,4-dioxaspiro[4.5]decane-8-carbonitrile as a crude residue. To the crude residue (110 mg, 0.358 mmol) was added THF (7.1 mL) and potassium tert-butoxide (137 mg, 1.22 mmol). The reaction mixture was allowed to stir at ambient temperature for 15 minutes before it was diluted with diethyl ether. The organic layer was washed with water, brine, dried over anhydrous $MgSO_4$, filtered, and concentrated in vacuo (23° C. water bath) to afford the title compound.

$^1H$ NMR (600 MHz, $CDCl_3$): δ 6.48 (tt, J=4.0, 1.8, 1H), 3.96 (s, 4H), 2.45 (tq, J=6.6, 2.2, 2H), 2.39 (q, J=3.1, 2H), 1.78 (t, J=6.6, 2H).

Intermediate #42

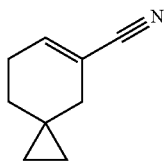

Spiro[2.5]oct-5-ene-5-carbonitrile

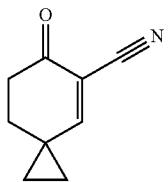 [SMILES: N#CC1=CC2(CCC1=O)CC2]

Step A: 6-Oxospiro[2.5]oct-4-ene-5-carbonitrile

LDA (1.34 mL, 2.69 mmol, 2.0 M in hexanes) was combined with THF (2.4 mL) and cooled to −78° C. To this mixture was added a solution of spiro[2.5]octan-6-one (0.30 g, 2.4 mmol) in THF (2.4 mL). The resulting mixture was stirred at −78° C. for 20 mins then taken up in a syringe and added to a mixture of tosyl cyanide (0.88 g, 4.8 mmol) in THF (2.4 mL) at −78° C. The reaction mixture was allowed to stir at −78° C. for 45 mins then quenched with 0.5 M NaOH and extracted with EtOAc (2×) The combined organic extracts were washed with 1N aqueous HCl, brine, dried over anhydrous Na$_2$SO$_4$, filtered, and concentrated in vacuo. The crude residue was purified by MPLC on silica gel (using a gradient elution of 0-50% EtOAc/hexanes). Desired fractions were identified, combined and concentrated in vacuo to afford the title compound.

$^1$H NMR (500 MHz, CDCl$_3$): δ 7.02 (s, 1H); 2.60-2.61 (m, 2H); 1.96 (t, J=7.0 Hz, 2H); 1.19-1.21 (m, 4H).

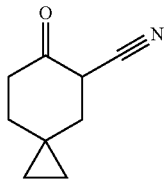 [SMILES: N#CC1CC2(CCC1=O)CC2]

Step B: 6-Oxospiro[2.5]octane-5-carbonitrile

6-Oxospiro[2.5]oct-4-ene-5-carbonitrile (0.16 g, 1.1 mmol) was dissolved in MeOH (11 mL) and combined with 10% palladium on activated carbon (0.12 g, 0.11 mmol). The resulting mixture was subjected to alternating vacuum and H$_2$ gas (4×). The mixture was then stirred under an atmosphere of H$_2$ (50 psi) for 16 hours. The mixture was then subjected to alternating vacuum and N$_2$ gas (4×). The mixture was filtered through celite and rinsed with MeOH. The filtrate was concentrated in vacuo to afford the title compound. The material was used without further purification.

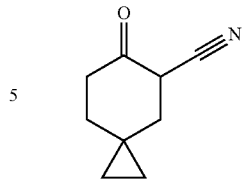

Step C: 6-Hydroxyspiro[2.5]octane-5-carbonitrile

A solution of 6-oxospiro[2.5]octane-5-carbonitrile (130 mg, 0.87 mmol) in THF (4.3 mL) was stirred at ambient temperature and lithium borohydride (76 mg, 3.5 mmol) was added. The resulting mixture was stirred at ambient temperature for 16 hours. The mixture was diluted with water and extracted with EtOAc (2×). The combined organic extracts were washed with water, brine, dried over anhydrous Na$_2$SO$_4$, filtered, and concentrated in vacuo to afford the title compound. The material was used without further purification.

Step D: Spiro[2.5]oct-5-ene-5-carbonitrile

To a solution of 6-hydroxyspiro[2.5]octane-5-carbonitrile (110 mg, 0.73 mmol) in DCM (3.6 mL) was added DIPEA (190 mg, 1.4 mmol) followed by the dropwise addition of methanesulfonyl chloride (92 mg, 0.80 mmol). The resulting mixture was stirred at ambient temperature for 3 hours then DBU was added and stirring continued for 16 hours. The mixture was carefully diluted with water and extracted with EtOAc (2×). The combined organic extracts were washed with 1N aqueous HCl, brine, dried over anhydrous Na$_2$SO$_4$, filtered, and concentrated in vacuo to afford the title compound. The residue was carried forward without further purification.

Intermediate #43

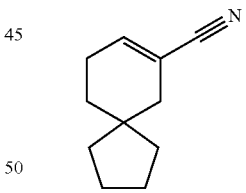

Spiro[4.5]dec-7-ene-7-carbonitrile

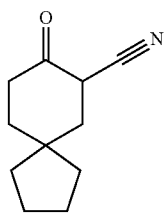 [SMILES: N#CC1CC2(CCCC2)CCC1=O]

Step A: 8-Oxospiro[4.5]decane-7-carbonitrile

LDA (1.83 mL, 3.66 mmol, 2.0 M in hexanes) was combined with THF (3.2 mL) and cooled to −78° C. To this mixture was added a solution of spiro[4.5]decan-8-one (0.50 g, 3.3 mmol) in THF (3.2 mL). The resulting mixture was stirred at −78° C. for 20 mins then taken up in a syringe and added to a mixture of tosyl cyanide (0.59 g, 3.3 mmol) in THF (3.2 mL) at −78° C. The reaction mixture was allowed to stir at −78° C. for 45 mins then quenched with 0.5M NaOH and extracted with EtOAc (2×). The combined organic extracts were washed with 1N aqueous HCl, brine, dried over anhydrous $Na_2SO_4$, filtered, and concentrated in vacuo. The crude residue was purified by MPLC on silica gel (using a gradient elution of 0-50% EtOAc/hexanes). Desired fractions were identified, combined and concentrated in vacuo to afford the title compound. The residue was carried forward without further purification.

Step B: Spiro[4.5]dec-7-ene-7-carbonitrile

The title compound was prepared from 8-oxospiro[4.5] decane-7-carbonitrile according to Steps C and D for Intermediate 42 (Spiro[2.5]oct-5-ene-5-carbonitrile). $^1$H NMR (500 MHz, $CDCl_3$): δ 6.60-6.61 (m, 1H); 2.21-2.22 (m, 2H); 2.07 (d, J=2.7 Hz, 2H); 1.64-1.65 (m, 4H); 1.49 (t, J=6.3 Hz, 2H); 1.38-1.41 (m, 4H).

Scheme #26

Intermediate #44-1

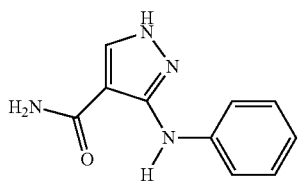 [SMILES: NC(=O)c1c[nH]nc1Nc1ccccc1]

3-(Phenylamino)-1H-pyrazole-4-carboxamide

3-Amino-1H-pyrazole-4-carboxamide (19.8 g, 157 mmol), $K_3PO_4$ (66.7 g, 314 mmol), bromobenzene (23.2 mL, 220 mmol) and 2-propanol (785 mL) were combined in a round bottom flask and purged with a stream of $N_2$ gas for 40 minutes. $Pd_2(dba)_3$ (1.80 g, 1.96 mmol) and 2-di-t-butylphosphino-3,4,5,6-tetramethyl-2',4',6'-tri-1-propylbiphenyl (3.77 g, 7.85 mmol) were added and the reaction was purged for an additional 5 minutes. The reaction mixture was then heated to 80° C. and allowed to stir under a $N_2$ atmosphere for 12 hours. The mixture was then allowed to cool to ambient temperature for an additional 16 hours. The reaction mixture was diluted with EtOAc (300 mL) and filtered through celite (slowly). The celite was washed with EtOAc (300 mL) and the filtrate was concentrated in vacuo to afford an oil which was purified by MPLC on silica gel (using a gradient elution of 0-10% MeOH/DCM). The major, low rf product, was isolated to afford a reddish-brown oily solid. The brown solid was suspended in 40 mL of warm MeOH, cooled to ambient temperature, and water (40 mL) was added. The mixture was stirred for 30 minutes and filtered. The solid was suction dried for 16 hours to afford the title compound as a peach-colored solid.

LRMS (ESI) calc'd for $C_{10}H_{10}N_4O$ [M+H]$^+$: 203. Found: 203.

The following intermediates shown in TABLE 8 were prepared according to Scheme #26 following similar procedures described for Intermediate #44-1, which can be achieved by those of ordinary skill in the art of organic synthesis.

TABLE 8

| Intermediate | Structure | Compound Name | Exact Mass [M + H]$^+$ |
|---|---|---|---|
| 44-2 | (structure shown) | 3-[(4-bromophenyl)amino]-1H-pyrazole-4-carboxamide | Calc'd 280, Found 280 |

TABLE 8-continued

| Intermediate | Structure | Compound Name | Exact Mass [M + H]+ |
|---|---|---|---|
| 44-3 | 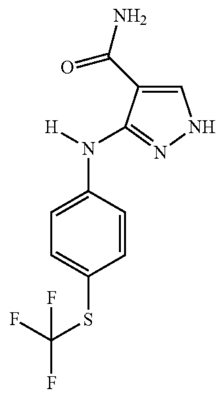 [SMILES: NC(=O)c1c[nH]nc1Nc1ccc(SC(F)(F)F)cc1] | 3-({4-[(trifluoromethyl)sulfanyl]phenyl}amino)-1H-pyrazole-4-carboxamide | Calc'd 303, Found 303 |
| 44-4 | 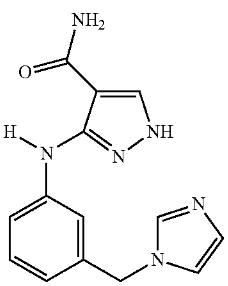 [SMILES: NC(=O)c1c[nH]nc1Nc1cccc(Cn2ccnc2)c1] | 3-{[3-(1H-imidazol-1-ylmethyl)phenyl]amino}-1H-pyrazole-4-carboxamide | Calc'd 283, Found 283 |
| 44-5 | 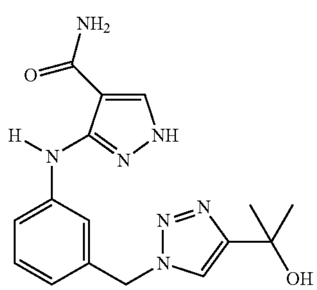 [SMILES: CC(C)(O)c1cn(Cc2cccc(Nc3n[nH]cc3C(N)=O)c2)nn1] | 3-[(3-{[4-(2-hydroxypropan-2-yl)-1H-1,2,3-triazol-1-yl]methyl}phenyl)amino]-1H-pyrazole-4-carboxamide | Calc'd 342, Found 342 |
| 44-6 | 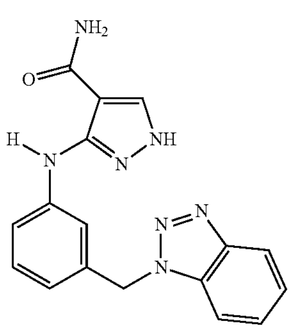 [SMILES: NC(=O)c1c[nH]nc1Nc1cccc(Cn2nnc3ccccc32)c1] | 3-{[3-(1H-benzotriazol-1-ylmethyl)phenyl]amino}-1H-pyrazole-4-carboxamide | Calc'd 334, Found 334 |

TABLE 8-continued

| Intermediate | Structure | Compound Name | Exact Mass [M + H]⁺ |
|---|---|---|---|
| 44-7 | 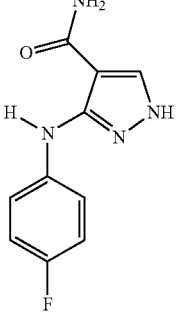 | 3-[(4-fluorophenyl)amino]-1H-pyrazole-4-carboxamide | Calc'd 221, Found 221 |

Intermediate #45

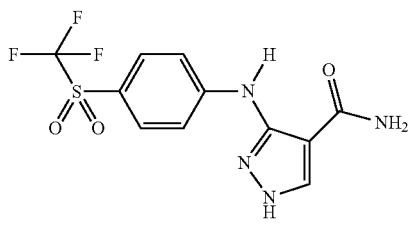 [SMILES: NC(=O)c1c[nH]nc1Nc1ccc(S(=O)(=O)C(F)(F)F)cc1]

3-({4-[(Trifluoromethyl)sulfonyl]phenyl}amino)-1H-pyrazole-4-carboxamide

The title compound, Intermediate #45, can be prepared according to the general procedure described for Intermediate #44-1 using 3-amino-1H-pyrazole-4-carboxamide (0.48 g, 3.8 mmol) and 1-bromo-4-[(trifluoromethyl)sulfonyl]benzene (1.0 g, 3.5 mmol) as starting materials. LRMS (ESI) calc'd for $C_{17}H_{18}FN_5O_2$ [M+H]⁺: 335. Found: 335.

Alternatively, the title compound, Intermediate #45, can also be prepared by dissolving 3-({4-[(trifluoromethyl)sulfanyl]phenyl}amino)-1H-pyrazole-4-carboxamide (0.50 g, 1.6 mmol) in acetic acid (5.0 mL) followed by the addition of hydrogen peroxide (0.87 mL, 9.9 mmol, 35 wt % in water). The resulting mixture was heated to 50° C. for 18 hours before additional hydrogen peroxide (0.87 mL, 9.9 mmol, 35 wt % in water) was added and the mixture was heated to 80° C. for 8 hours. The mixture was cooled to ambient temperature, concentrated in vacuo and diluted with EtOAc. The mixture was washed three times with aqueous sodium thiosulfate adjusted to pH>8 with saturated aqueous NaHCO₃. The organic layer was collected, dried over anhydrous Na₂SO₄, filtered and concentrated in vacuo. The residue was purified by MPLC on silica gel (eluting with 15% MeOH/DCM). Desired fractions were identified, combined, and concentrated in vacuo to afford the title compound. LRMS (ESI) calc'd for $C_{11}H_9F_3N_4O_3S$ [M+H]⁺: 335. Found: 335.

Scheme #26

Intermediate #46

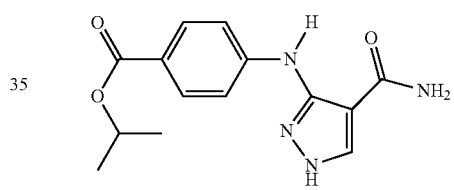

Propan-2-yl 4-[(4-carbamoyl-1H-pyrazol-3-yl)amino]benzoate

A round-bottomed flask was charged with 2-propanol (595 mL), and nitrogen was bubbled through the 2-propanol for 2 hours. Pd₂(dba)₃ (1.63 g, 1.78 mmol) and di-tert-butyl(2',4',6'-triisopropyl-3,4,5,6-tetramethylbiphenyl-2-yl)phosphine (3.43 g, 7.14 mmol) were added, and the mixture was stirred for 20 minutes. Potassium acetate (17.5 g, 178 mmol), 3-amino-1H-pyrazole-4-carboxamide (15.0 g, 119 mmol), and isopropyl 4-bromobenzoate (34.7 g, 143 mmol) were then added, and the reaction mixture was heated to 75° C. for 6.5 hours. The reaction mixture was then cooled to 23° C., diluted with EtOAc (500 mL), and filtered through celite. The filtrate was adsorbed onto silica gel in vacuo, and purified by MPLC on silica gel (using a gradient elution of 30-90%, EtOAc/hexanes) to afford the title compound. LRMS (ESI) calc'd for $C_{14}H_{17}N_4O_3$ [M+H]⁺: 289. Found: 289.

Scheme #27

Intermediate #44-1

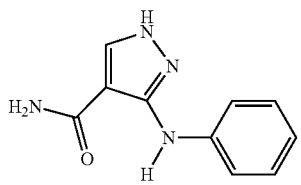 [SMILES: NC(=O)c1c[nH]nc1Nc1ccccc1]

3-(Phenylamino)-1H-pyrazole-4-carboxamide

Intermediate #44-1 can be prepared by general methods described in Scheme #26, vida supra. Alternatively, Intermediate 44-1 can also be prepared using the methods described below.

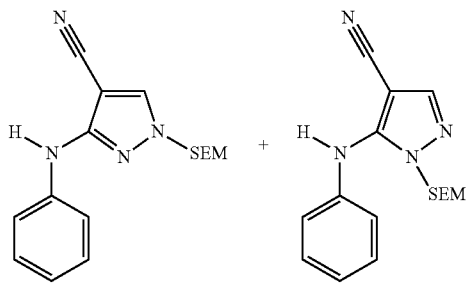 [SMILES: C[Si](C)(C)CCOCn1cc(C#N)c(Nc2ccccc2)n1 ; C[Si](C)(C)CCOCn1ncc(C#N)c1Nc1ccccc1]

Step A: 3-(Phenylamino)-1-{[2-(trimethylsilyl)ethoxy]methyl}-1H-pyrazole-4-carbonitrile and 5-(phenylamino)-1-{[2-(trimethylsilyl)ethoxy]methyl}-1H-pyrazole-4-carbonitrile To a microwave vessel was added a mixture of 3-amino-1-{[2-(trimethylsilyl)ethoxy]methyl}-1H-pyrazole-4-carbonitrile (6.0 g, 25 mmol) 4-iodobenzene (3.38 mL, 30.2 mmol), dioxane (100 mL) and $Cs_2CO_3$ (25 g, 76 mmol). The mixture was degassed by bubbling nitrogen gas for 5 minutes. $Pd_2(dba)_3$ (3.46 g, 3.78 mmol), and X-Phos (0.60 g, 1.3 mmol) were then added, and the mixture was capped and heated to 120° C. After heating for 16 hours, the mixture was allowed to cool to ambient temperature and was filtered through celite. The filtrate was adsorbed on silica gel in vacuo and the mixture was purified by MPLC on silica gel (using a gradient elution of 0-50% EtOAc/hexanes) to afford the title compounds. LRMS (ESI) calc'd for $C_{16}H_{22}N_4OSi$ [M+H]$^+$: 315. Found: 315.

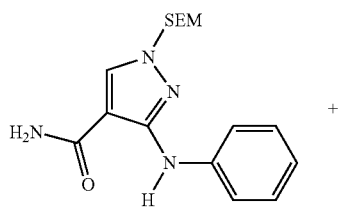

+

Step B: 3-(Phenylamino)-1-{[2-(trimethylsilyl)ethoxy]methyl}-1H-pyrazole-4-carboxamide and 5-(phenylamino)-1-{[2-(trimethylsilyl)ethoxy]methyl}-1H-pyrazole-4-carboxamide To a solution containing a mixture of 3-(phenylamino)-1-{[2-(trimethylsilyl)ethoxy]methyl}-1H-pyrazole-4-carbonitrile and 5-(phenylamino)-1-{[2-(trimethylsilyl)ethoxy]methyl}-1H-pyrazole-4-carbonitrile (2.46 g, 7.82 mmol) in DMSO (26.1 mL) and EtOH (52.2 mL) was added 5M aqueous NaOH (11.0 mL, 54.8 mmol) followed by the dropwise addition of 30% $H_2O_2$ (11.2 mL, 110 mmol). The mixture was maintained for 20 minutes before it was allowed to cool to ambient temperature. EtOAc (200 mL) and water (100 mL) were added and the layers partitioned. The organic layer was washed with brine, dried over anhydrous $Na_2SO_4$, filtered, and concentrated in vacuo to afford a crude mixture of the title compounds, which were used without further purification. LRMS (ESI) calc'd for C16H24N4O2Si [M+H]$^+$: 333. Found: 333. $^1$H NMR (600 MHz, CDCl$_3$) δ 8.65 (s, 4H), 7.80 (s, 1H), 7.69 (s, 1H), 7.57-7.52 (m, 2H), 7.51-7.42 (m, 1H), 7.30-7.21 (m, 2H), 7.15-7.07 (m, 1H), 6.99 (t, J=7.4, 2H), 6.92-6.81 (m, 2H), 5.54 (br s, 2H), 5.31 (s, 2H), 5.17 (s, 2H), 3.70 (dd, J=9.0, 7.7, 2H), 3.50-3.40 (m, 2H), 0.99-0.90 (m, 2H), 0.84-0.78 (m, 2H), −0.01−−0.03 (m, 9H), −0.05−−0.07 (m, 9H).

Step C: 3-(Phenylamino)-1H-pyrazole-4-carboxamide

To a solution containing a mixture of 3-(phenylamino)-1-{[2-(trimethylsilyl)ethoxy]methyl}-1H-pyrazole-4-carbonitrile and 5-(phenylamino)-1-{[2-(trimethylsilyl)ethoxy]me-thyl}-1H-pyrazole-4-carbonitrile (2.6 g, 7.8 mmol) in EtOH (40.3 mL) was added 2N aqueous HCl (40.3 mL). The resulting mixture was heated at 0° C. for 1 hour. The mixture was cooled to ambient temperature and carefully neutralized with 3N aqueous $Na_2CO_3$ until pH ~9. The solution was further diluted with $H_2O$ (400 mL), the layers were partitioned and the aqueous mixture was extracted with EtOAc (2×). The combined organic layers were washed with brine, dried over anhydrous $Na_2SO_4$, filtered, and concentrated in vacuo. The crude residue was adsorbed on silica gel in vacuo and purified by MPLC on silica gel (using a gradient elution of 0-100% EtOAc/DCM) to afford the title compound, which was used without further purification.

LRMS (ESI) calc'd for $C_{10}H_{10}N_4O$ [M+H]$^+$: 202. Found: 203.

The following intermediates shown in TABLE 9 were prepared according to Scheme #27 following similar procedures described for Intermediate #44-1, which can be achieved by those of ordinary skill in the art of organic synthesis.

TABLE 9

| Intermediate | Structure | Compound Name | Exact Mass [M + H]+ |
|---|---|---|---|
| 44-8 | 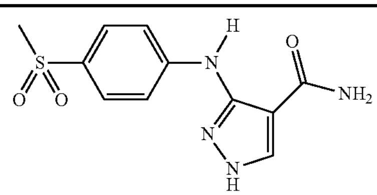 | 3-{[4-(methylsulfonyl)phenyl]amino}-1H-pyrazole-4-carboxamide | Calc'd 281, Found 281 |
| 44-9 | 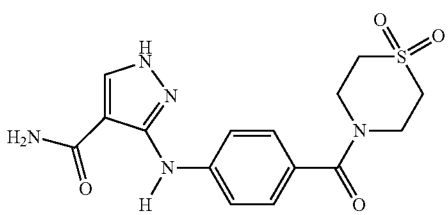 [SMILES: NC(=O)c1c[nH]nc1Nc1ccc(C(=O)N2CCS(=O)(=O)CC2)cc1] | 3-({4-[(1,1-dioxidothiomorpholin-4-yl)carbonyl]phenyl}amino)-1H-pyrazole-4-carboxamide | Calc'd 364, Found 364 |

Scheme #28

Intermediate #47-1

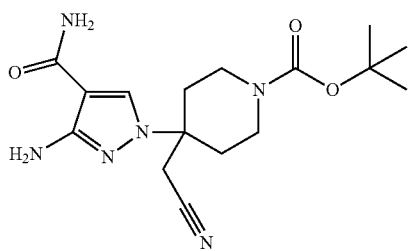 [SMILES: CC(C)(C)OC(=O)N1CCC(CC#N)(n2cc(C(N)=O)c(N)n2)CC1]

tert-Butyl 4-(3-amino-4-carbamoyl-1H-pyrazol-1-yl)-4-(cyanomethyl)piperidine-1-carboxylate 3-Amino-1H-pyrazole-4-carboxamide (0.80 g, 6.3 mmol) and tert-butyl 4-(cyanomethylene)piperidine-1-carboxylate (2.1 g, 9.5 mmol) were combined with MeCN (31 mL) in a pressure vessel. DBU (1.05 mL, 6.98 mmol) was then added at ambient temperature. The reaction vessel was sealed and the mixture was heated to 80° C. for 16 hours. The reaction mixture was then allowed to cool to ambient temperature before water (150 mL) was added. The aqueous mixture was extracted with EtOAc (2×). The organic layers were then combined and washed with brine, dried over anhydrous MgSO$_4$, filtered, and concentrated in vacuo. The crude residue was adsorbed on silica gel in vacuo and purified by MPLC on silica gel (using a gradient elution of 75-100% EtOAc/hexanes) to afford the title compound, Intermediate #47-1.

LRMS (ESI) calc'd for $C_{16}H_{24}N_6O_3$ [M+H]+: 349. Found: 349.

The following intermediates shown in TABLE 10 were prepared according to Scheme #28 following similar procedures described for Intermediate #47-1, which can be achieved by those of ordinary skill in the art of organic synthesis.

TABLE 10

| Intermediate | Structure | Compound Name | Exact Mass [M + H]+ |
|---|---|---|---|
| 47-2 | 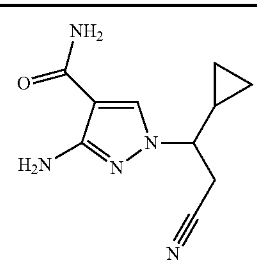 | 3-amino-1-(2-cyano-1-cyclopropylethyl)-1H-pyrazole-4-carboxamide | Calc'd 220, Found 220 |

TABLE 10-continued

| Intermediate | Structure | Compound Name | Exact Mass [M + H]+ |
|---|---|---|---|
| 47-3 | 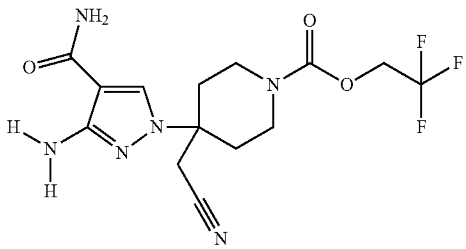 [SMILES: N#CCC1(n2cc(C(N)=O)c(N)n2)CCN(C(=O)OCC(F)(F)F)CC1] | 2,2,2-trifluoroethyl 4-(3-amino-4-carbamoyl-1H-pyrazol-1-yl)-4-(cyanomethyl)piperidine-1-carboxylate | Calc'd 375, Found 375 |
| 47-4 | 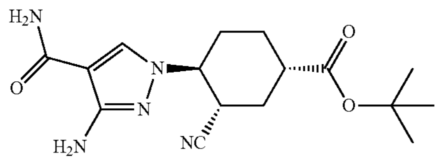 [SMILES: CC(C)(C)OC(=O)[C@H]1CC[C@H](n2cc(C(N)=O)c(N)n2)[C@@H](C#N)C1] | (1S,3S,4S and 1R,3R,4R)-tert-butyl 4-(3-amino-4-carbamoyl-1H-pyrazol-1-yl)-3-cyanocyclohexanecarboxylate | Calc'd 334, Found 334 |

Scheme #28

Intermediate #48-1 and 48-2

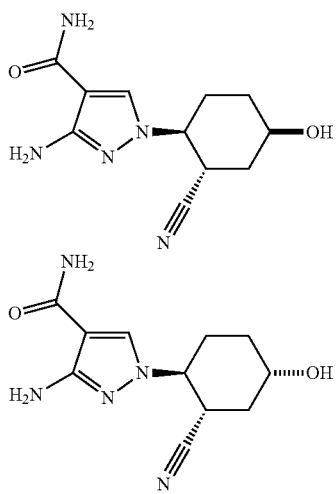

3-Amino-1-[(1S,2S,4R and 1R,2R,4S)-2-cyano-4-hydroxycyclohexyl]-1H-pyrazole-4-carboxamide and 3-amino-1-[(1S,2S,4S and 1R,2R,4R)-2-cyano-4-hydroxycyclohexyl]-1H-pyrazole-4-carboxamide DBU (263 mL, 1.74 mol) was added to a mixture of 3-amino-1H-pyrazole-4-carboxamide (110 g, 872 mmol) and 5-hydroxycyclohex-1-ene-1-carbonitrile (161 g, 1.31 mol) in ethanol (1100 mL) at 23° C. The reaction mixture was then heated to 70° C. for 16 hours. The mixture was then cooled to ambient temperature with stirring. The precipitates were filtered, washed with EtOH (150 mL×2), and dried under a nitrogen flow for 4 hours to afford the title compound. The stereochemistry of the major isomer was 1,2-trans, 1,4-cis, and the minor isomer was 1,2-trans, 1,4-trans, with a ratio of ~6:1.

Intermediate #48-1: Major isomer; 3-Amino-1-[(1S,2S,4R and 1R,2R,4S)-2-cyano-4-hydroxycyclohexyl]-1H-pyrazole-4-carboxamide. LRMS (ESI) calc'd for $C_7H_{16}N_5O_2$ [M+H]+: 250. Found: 250.

Intermediate #48-2: Minor isomer; 3-Amino-1-[(1S,2S,4S and 1R,2R,4R)-2-cyano-4-hydroxycyclohexyl]-1H-pyrazole-4-carboxamide. LRMS (ESI) calc'd for $C_7H_{16}N_5O_2$ [M+H]+: 250. Found: 250.

The following intermediates shown in TABLE 11 were prepared according to Scheme #28 following similar procedures described for Intermediate #48-1 and 48-2, which can be achieved by those of ordinary skill in the art of organic synthesis.

TABLE 11

| Intermediate | Structure | Compound Name | Exact Mass [M + H]+ |
|---|---|---|---|
| 48-3 | 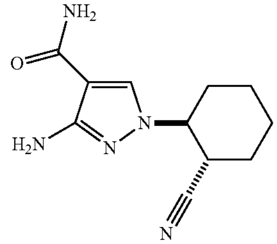 | 3-Amino-1-[(1S,2S and 1R,2R)-2-cyanocyclohexyl]-1H-pyrazole-4-carboxamide | Calc'd 234, Found 234 |

TABLE 11-continued

| Intermediate | Structure | Compound Name | Exact Mass [M + H]+ |
|---|---|---|---|
| 48-4 | 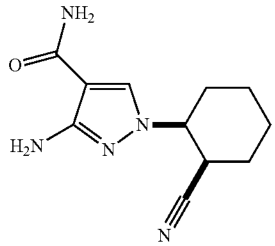 | 3-amino-1-[(1S,2R and 1R,2S)-2-cyanocyclohexyl]-1H-pyrazole-4-carboxamide | Calc'd 234, Found 234 |
| 48-5 | 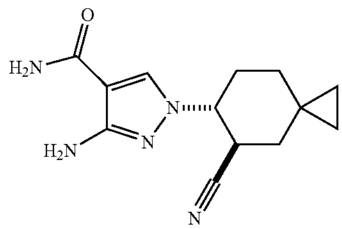 | 3-amino-1-((5R,6R)-5-cyanospiro[2.5]octan-6-yl)-1H-pyrazole-4-carboxamide | Calc'd 260, Found 260 |
| 48-6 | 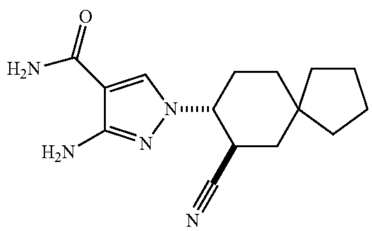 | 3-amino-1-((7R,8R)-7-cyanospiro[4.5]decan-8-yl)-1H-pyrazole-4-carboxamide | Calc'd 287, Found 287 |
| 48-7 | 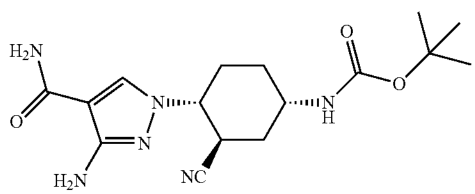 [SMILES: CC(C)(C)OC(=O)N[C@H]1CC[C@@H](n2cc(C(N)=O)c(N)n2)[C@H](C#N)C1] | tert-Butyl [(1R,3S,4S and 1S,3R,4R)-4-(3-amino-4-carbamoyl-1H-pyrazol-1-yl)-3-cyanocyclohexyl]carbamate | Calc'd 349, Found 349 |

Scheme #24, 28 and 36

Intermediate #49

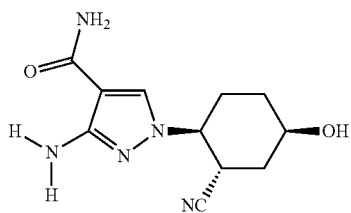 [SMILES: N#C[C@H]1C[C@H](O)CC[C@@H]1n1cc(C(N)=O)c(N)n1]

3-Amino-1-((1S,2S,4R or 1R,2R,4S)-2-cyano-4-hydroxycyclohexyl)-1H-pyrazole-4-carboxamide DBU (56.5 mL, 375 mmol) was added to a mixture of (R or S)-5-hydroxycyclohex-1-enecarbonitrile (Intermediate #40, 46.1 g, 375 mmol) and 3-amino-1H-pyrazole-4-carboxamide (34 g, 270 mmol) in ethanol (346 mL) at 23° C. The reaction vessel capped with a reflux condenser and heated at 75° C. After stirring at 75° C. for 18 hours, the heating source was removed and stirring was continued for 4 hours. The suspended precipitate was filtered, and the solids were washed with two portions of ethanol (50 mL each). The solids were collected and dried under a flow of nitrogen for 16 hours to afford the title compound. $^1$H NMR analysis indicated diastereomeric purity of >95%.

$^1$H NMR (500 MHz, CD$_3$OD) δ 7.98 (s, 1H), 4.15 (td, J=11.5, 4.0 Hz), 4.09-4.06 (m, 1H), 3.59-3.54 (m, 1H), 2.33 (qd, J=13.0, 3.6 Hz, 1H), 2.22 (dq, J=13.7, 3.2 Hz, 1H), 1.98-1.88 (m, 2H), 1.82-1.76 (m, 1H), 1.73-1.66 (m, 1H).

LRMS (ESI) calc'd for C$_{11}$H$_{16}$N$_5$O$_2$ [M+H]$^+$: 250. Found: 250.

Intermediate #50-1 and 50-2

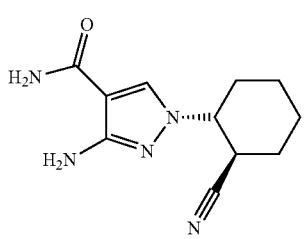

3-Amino-1-((1R,2R or 1S,2S)-2-cyanocyclohexyl)-1H-pyrazole-4-carboxamide

A racemic diastereomeric mixture of 3-amino-1-((1R,2R or 1S,2S)-2-cyanocyclohexyl)-1H-pyrazole-4-carboxamide, Intermediate 48-3, was chirally resolved to the constituent enantiomers by SFC chromatography (Chiral Technology IC-H 2.1×25 cm, 5 uM, 20% MeOH/CO$_2$). Desired fractions were identified, combined, and concentrated in vacuo to afford enantiomerically pure samples of the title compounds:

Example 50-1

1$^{st}$ enantiomer to elute from column; 3-amino-1-((1R,2R or 1S,2S)-2-cyanocyclohexyl)-1H-pyrazole-4-carboxamide. LRMS (ESI) calc'd for C$_{11}$H$_{15}$N$_5$O [M+H]+: 234. Found: 234.

Example 50-2

2$^{nd}$ enantiomer to elute from column; 3-amino-1-((1R,2R or 1S,2S)-2-cyanocyclohexyl)-1H-pyrazole-4-carboxamide. LRMS (ESI) calc'd for C$_{11}$H$_{15}$N$_5$O [M+H]+: 234. Found: 234.

EXAMPLES OF THE INSTANT INVENTION

The following experimental procedures detail the preparation of specific examples of the instant invention. The examples are for illustrative purposes only and are not intended to limit the scope of the instant invention in any way.

Scheme #30

Example #1-1 and 1-2

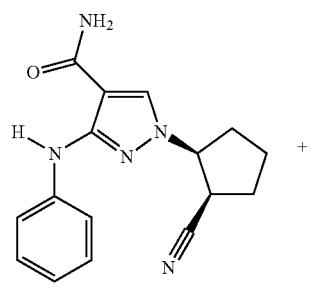

+

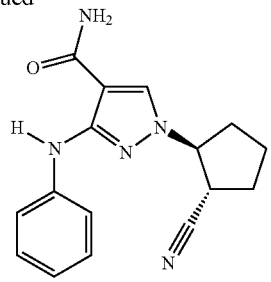

1-{[(1S,2R) and (1R,2S)]-2-cyanocyclopentyl}-3-(phenylamino)-1H-pyrazole-4-carboxamide and 1-{[(1S,2S) and (1R,2R)]-2-cyanocyclopentyl}-3-(phenylamino)-1H-pyrazole-4-carboxamide DBU (0.27 mL, 0.18 mmol) was added to a mixture of 3-(phenylamino)-1H-pyrazole-4-carboxamide (30 mg, 0.15 mmol) and cyclopent-1-ene-carbonitrile (21 mg, 0.22 mmol) in MeCN (0.74 mL). The vial was capped and allowed to stir at ambient temperature for 15 hours. The reaction mixture was taken up in DMSO (2 mL) and purified by reverse-phase preparative HPLC (MeCN/water, with 0.1% v/v TFA modifier). Desired fractions were combined, basified with saturated aqueous NaHCO$_3$, and extracted with EtOAc. The organic layer was dried over anhydrous NaSO$_4$, filtered, and concentrated in vacuo to afford the title compounds in a 1:1 cis/trans ratio.

Example #1-1

$^1$H NMR (600 MHz, cdcl3) δ 8.68 (s, 1H), 7.68 (s, 1H), 7.52 (dd, J=1.0, 8.6, 2H), 7.29-7.25 (m, 2H), 6.88 (t, J=7.3, 1H), 5.56 (s, 2H), 4.68 (q, J=6.8, 1H), 3.26 (dd, J=7.4, 14.2, 1H), 2.45-2.30 (m, 2H), 2.30-2.15 (m, 3H), 1.91-1.78 (m, 1H). LRMS (ESI) calc'd for C$_{16}$H$_{17}$N$_5$O [M+H]$^+$: 296. Found: 296.

Example #1-2

$^1$H NMR (600 MHz, cdcl3) δ 8.74 (s, 1H), 7.64 (s, 1H), 7.51 (d, J=7.7, 2H), 7.27 (dd, J=7.5, 8.4, 2H), 6.89 (t, J=7.3, 1H), 5.67 (s, 2H), 4.59 (q, J=7.7, 1H), 3.36 (q, J=8.5, 1H), 2.43-2.27 (m, 2H), 2.27-2.16 (m, 1H), 2.15-1.97 (m, 2H), 1.97-1.87 (m, 1H).

LRMS (ESI) calc'd for C$_{16}$H$_{17}$N$_5$O [M+H]$^+$: 296. Found: 296.

The following examples shown in TABLE 12 were prepared according to Scheme #23 following similar procedures described for Example #1-1, which can be achieved by those of ordinary skill in the art of organic synthesis.

TABLE 12

| Example | Structure | Compound Name | Exact Mass [M + H]$^+$ |
|---|---|---|---|
| 1-3 | (structure) | 1-[(1S,2R and 1R,2S)-2-cyanocyclohexyl]-3-(phenylamino)-1H-pyrazole-4-carboxamide | Calc'd 310, Found 310 |

TABLE 12-continued

| Example | Structure | Compound Name | Exact Mass [M + H]+ |
|---|---|---|---|
| 1-4 | 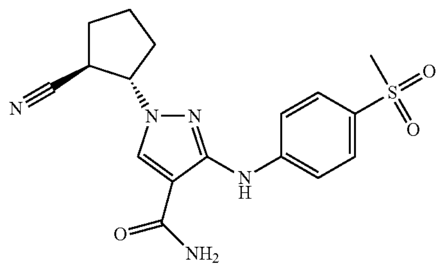 [SMILES: CS(=O)(=O)c1ccc(Nc2nn([C@H]3CCC[C@@H]3C#N)cc2C(N)=O)cc1] | 1-{[(1S,2S) and (1R,2R)-2-cyanocyclopentyl]}-3-{4-(methylsulfonyl)phenyl]amino}-1H-pyrazole-4-carboxamide | Calc'd 374, found 374 |
| 1-5 | 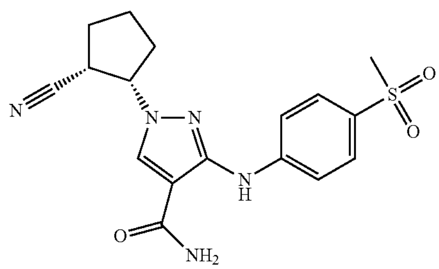 [SMILES: CS(=O)(=O)c1ccc(Nc2nn([C@H]3CCC[C@H]3C#N)cc2C(N)=O)cc1] | 1-{[(1S,2R) and (1R,2S)]-2-cyanocyclopentyl]}-3-{[4-(methylsulfonyl)phenyl]amino}-1H-pyrazole-4-carboxamide | Calc'd 374, found 374 |

Scheme #30

Example #2-1

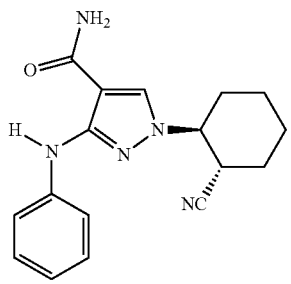 [SMILES: N#C[C@H]1CCCC[C@@H]1n1cc(C(N)=O)c(Nc2ccccc2)n1]

1-((1S,2S and 1R,2R)-2-cyanocyclohexyl)-3-(phenylamino)-1H-pyrazole-4-carboxamide DBU (0.37 mL, 2.4 mmol) was added to a mixture of 3-(phenylamino)-1H-pyrazole-4-carboxamide (Intermediate 44-1, 200 mg, 0.989 mmol) and cyclohex-1-enecarbonitrile (1.12 mL, 9.90 mmol) in DMF (4.9 mL). The reaction vessel was sealed, and the reaction mixture was heated to 120° C. for 4 hours. The reaction mixture was then cooled to ambient temperature and partitioned between EtOAc and water. The organic layer was washed with brine, the washed solution was dried over anhydrous sodium sulfate, and the dried solution was filtered. The filtrate was concentrated in vacuo and purified by MPLC on silica gel (using a gradient elution of 60 to 100% EtOAc/hexanes) to afford the title compound. $^1$H NMR (600 MHz, CDCl$_3$): δ 8.72 (s, 1H), 7.61 (s, 1H), 7.52 (d, J=7.8 Hz, 2H), 7.27 (t, J=7.8 Hz, 2H), 6.88 (t, J=7.2 Hz, 1H), 5.38 (br s, 2H), 3.94 (td, J=11.1, 4.2 Hz, 1H), 3.22-3.17 (m, 1H), 2.31-2.28 (m, 1H), 2.18-2.06 (m, 2H), 1.98-1.94 (m, 1H), 1.88-1.83 (m, 1H), 1.70 (qd, J=13, 3.9 Hz, 1.44-1.38 (m, 2H). LRMS (ESI) calc'd for C$_{17}$H$_{20}$N$_5$O [M]+: 310. Found: 310.

The following examples shown in TABLE 13 were prepared according to Scheme #23 following similar procedures described for Examples #2-1, which can be achieved by those of ordinary skill in the art of organic synthesis.

TABLE 13

| Example | Structure | Compound Name | Exact Mass [M + H]+ |
|---|---|---|---|
| 2-2 | 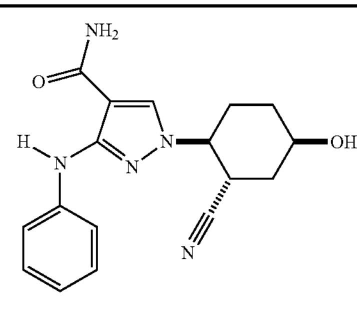 | 1-[(1S,2S,4R and 1R,2R,4S)-2-cyano-4-hydroxycyclohexyl]-3-(phenylamino)-1H-pyrazole-4-carboxamide | Calc'd 326, Found 326 |

TABLE 13-continued

| Example | Structure | Compound Name | Exact Mass [M + H]+ |
|---|---|---|---|
| 2-3 | 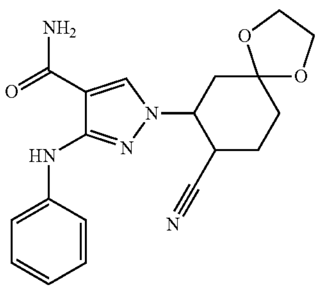 [SMILES: N#CC1CCC2(CC1n1cc(C(N)=O)c(Nc3ccccc3)n1)OCCO2] | 1-(8-cyano-1,4-dioxaspiro[4.5]dec-7-yl)-3-(phenylamino)-1H-pyrazole-4-carboxamide | Calc'd 368, Found 368 |
| 2-4 | 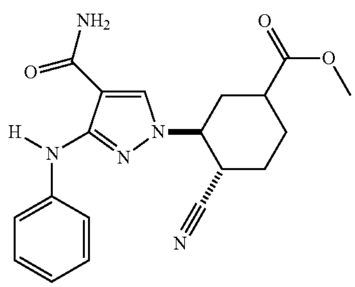 | methyl (3R,4R and 3S,4S)-3-[4-carbamoyl-3-(phenylamino)-1H-pyrazol-1-yl]-4-cyanocyclohexanecarboxylate | Calc'd 368, Found 368 |
| 2-5 | 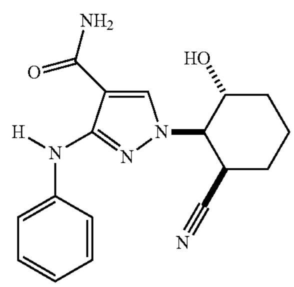 | 1-[(1R,2R,6R and 1S,2S,6S)-2-cyano-6-hydroxycyclohexyl]-3-(phenylamino)-1H-pyrazole-4-carboxamide | Calc'd 326, Found 326 |
| 2-6 | 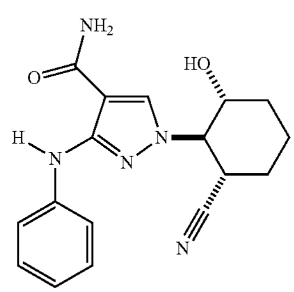 | 1-[(1R,2S,6R and 1S,2R,6S)-2-cyano-6-hydroxycyclohexyl]-3-(phenylamino)-1H-pyrazole-4-carboxamide | Calc'd 326, Found 326 |
| 2-7 | 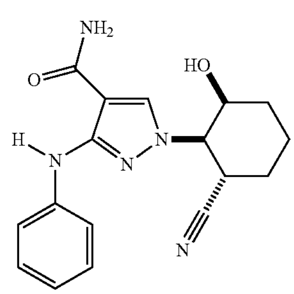 | 1-[(1R,2S,6S and 1S,2R,6R)-2-cyano-6-hydroxycyclohexyl]-3-(phenylamino)-1H-pyrazole-4-carboxamide | Calc'd 326, Found 326 |

TABLE 13-continued

| Example | Structure | Compound Name | Exact Mass [M + H]+ |
|---|---|---|---|
| 2-8 | 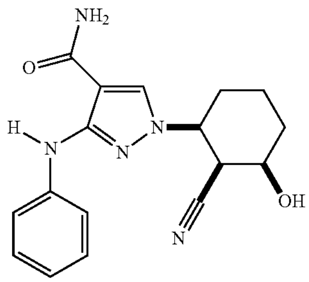 | 1-[(1S,2R,3R and 1R,2S,3S)-2-cyano-3-hydroxycyclohexyl]-3-(phenylamino)-1H-pyrazole-4-carboxamide | Calc'd 326, Found 326 |
| 2-9 | 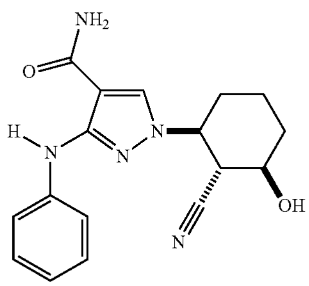 | 1-[(1S,2S,3R and 1R,2R,3S)-2-cyano-3-hydroxycyclohexyl]-3-(phenylamino)-1H-pyrazole-4-carboxamide | Calc'd 326, Found 326 |
| 2-10 | 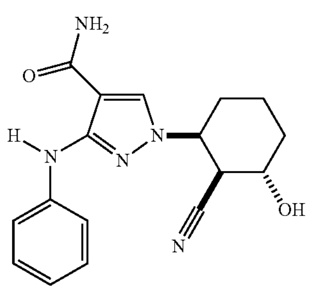 | 1-[(1S,2R,3S and 1R,2S,3R)-2-cyano-3-hydroxycyclohexyl]-3-(phenylamino)-1H-pyrazole-4-carboxamide | Calc'd 326, Found 326 |
| 2-11 | 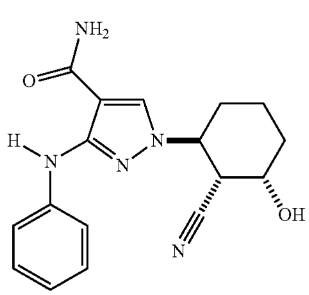 | 1-[(1S,2S,3S and 1R,2R,3R)-2-cyano-3-hydroxycyclohexyl]-3-(phenylamino)-1H-pyrazole-4-carboxamide | Calc'd 326, Found 326 |

TABLE 13-continued

| Example | Compound Name | Exact Mass [M + H]+ |
|---|---|---|
| 2-12 | 1-[(1R,2R,5R and 1S,2S,5S)-2-cyano-5-hydroxycyclohexyl]-3-(phenylamino)-1H-pyrazole-4-carboxamide | Calc'd 326, Found 326 |
| 2-13 | 1-[(1S,2S,5R and 1R,2R,5S)-2-cyano-5-hydroxycyclohexyl]-3-(phenylamino)-1H-pyrazole-4-carboxamide | Calc'd 326, Found 326 |
| 2-14 | 1-[(1S,2R and 1R,2S)-2-cyanocyclohexyl]-3-{[4-(methylsulfonyl)phenyl]amino}-1H-pyrazole-4-carboxamide | Calc'd 388, Found 388 |
| 2-15 | 1-(2-cyanocyclohexyl)-3-{[4-(methylsulfonyl)phenyl]amino}-1H-pyrazole-4-carboxamide | Calc'd 388, Found 388 |

Example #3-1 and 3-2

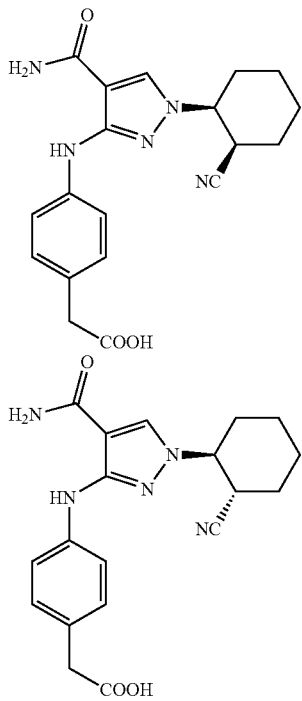

[4-({4-Carbamoyl-1-[(1S,2R and 1R,2S)-2-cyanocyclohexyl]-1H-pyrazol-3-yl}amino)phenyl]acetic acid and [4-({4-carbamoyl-1-[(1S,2S and 1R,2R)-2-cyanocyclohexyl]-1H-pyrazol-3-yl}amino)phenyl]acetic acid

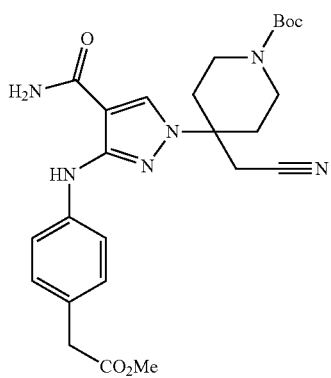 [SMILES: COC(=O)Cc1ccc(Nc2nn(C3(CC#N)CCN(C(=O)OC(C)(C)C)CC3)cc2C(N)=O)cc1]

Step A: tert-Butyl 4-(4-carbamoyl-3-{[4-(2-methoxy-2-oxoethyl)phenyl]amino}-1H-pyrazol-1-yl)-4-(cyanomethyl)piperidine-1-carboxylate To a microwave vessel was added tert-butyl 4-(3-amino-4-carbamoyl-1H-pyrazol-1-yl)-4-(cyanomethyl)piperidine-1-carboxylate (Intermediate 47-1, 0.30 g, 0.86 mmol), KOAc (127 mg, 1.29 mmol), methyl (4-bromophenyl)acetate (237 mg, 1.03 mmol) and 2-propanol (4.3 mL). The mixture was degassed for 5 minutes by bubbling argon gas. $Pd_2(dba)_3$ (39 mg, 0.04 mmol) and 2-di-t-butylphosphino-3,4,5,6-tetramethyl-2',4',6'-tri-1-propylbiphenyl (83 mg, 0.17 mmol) were added, the vial was sealed and heated at 95° C. for 18 hours. The mixture was cooled to ambient temperature, then diluted with EtOAc and washed with $H_2O$. The organic layer was separated, washed with brine, dried over $MgSO_4$, filtered, and concentrated in vacuo. The residue was purified by MPLC on silica gel (using a gradient elution of 50-100% EtOAc/hexanes) to afford the title compound. $^1H$ NMR (600 MHz, Acetone-$d_6$): δ 9.17 (s, 1H), 8.45 (s, 1H), 7.52-7.55 (m, 2H), 7.17 (d, J=8.4 Hz, 2H), 7.14 (brs, 1H), 6.51 (brs, 1H), 3.80-3.90 (m, 2H), 3.60 (s, 3H), 3.53 (s, 2H), 3.15 (s, 2H), 3.00-3.18 (m, 2H), 2.52-2.60 (m, 2H), 2.04-2.12 (m, 2H), 1.42 (s, 9H).

LRMS (ESI) calc'd for $C_{16}H_{25}N_6O_3$ $[M+H]^+$: 497. Found: 497.

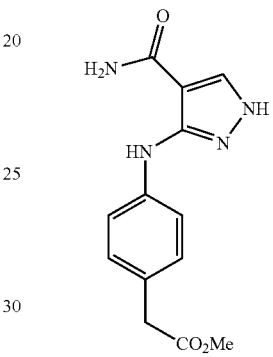

Step B: Methyl {4-[(4-carbamoyl-1H-pyrazol-3-yl)amino]phenyl}acetate

To a solution of tert-Butyl 4-(4-carbamoyl-3-{[4-(2-methoxy-2-oxoethyl)phenyl]amino}-1H-pyrazol-1-yl)-4-(cyanomethyl)piperidine-1-carboxylate (226 mg, 0.46 mmol) in THF (2.3 mL) at 0° C. was added $KO^tBu$ (0.68 mL, 0.68 mmol, 1.0M in THF), and the mixture was stirred at 0° C. for 20 minutes, then ambient temperature for 20 minutes. The mixture was diluted with saturated aqueous $NH_4Cl$, and extracted with EtOAc. The organic layer was washed with brine, dried over anhydrous $MgSO_4$, and concentrated in vacuo. $Et_2O$ (5 mL) was added to the resulting oily residue and a solid precipitated out. This solid was collected by decant, and washed with $Et_2O$ to afford the title compound.

LRMS (ESI) calc'd for $C_{13}H_{15}N_4O_3$ [M+H]+: 275. Found: 275.

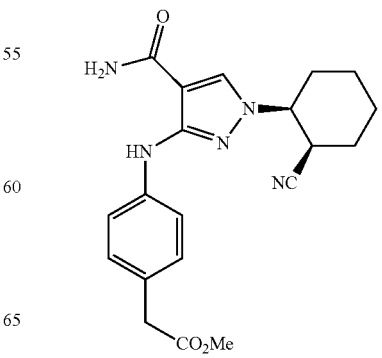

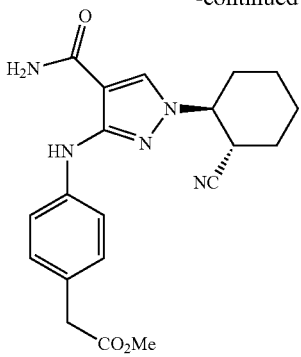

Step C: Methyl [4-({4-carbamoyl-1-[(1S,2R and 1R,2S)-2-cyanocyclohexyl]-1H-pyrazol-3-yl}amino) phenyl]acetate and methyl [4-({4-carbamoyl-1-[(1S,2S and 1R,2R)-2-cyanocyclohexyl]-1H-pyrazol-3-yl}amino)phenyl]acetate To a solution methyl {4-[(4-carbamoyl-1H-pyrazol-3-yl)amino]phenyl}acetate (50 mg, 0.18 mmol) in EtOH (0.7 mL) was added 1-cyanocyclohexene (195 mg, 1.82 mmol) and DBU (0.055 mL, 0.37 mmol). The mixture was heated at 90° C. for 18 hours. The mixture was diluted with saturated aqueous NaHCO$_3$, and extracted with EtOAc. The combined organics were washed with brine, dried over anhydrous MgSO$_4$, filtered, and concentrated in vacuo. The residue was purified by MPLC on silica gel (using a gradient elution of 0-10% MeOH/DCM) to afford the title compounds.

Example #3-1C methyl [4-({4-carbamoyl-1-[(1S,2R and 1R,2S,)-2-cyanocyclohexyl]-1H-pyrazol-3-yl}amino)phenyl]acetate. LRMS (ESI) calc'd for C$_{20}$H$_{24}$N$_5$O$_3$ [M+H]+: 396. Found: 396.

Example #3-2C methyl [4-({4-carbamoyl-1-[(1S,2S and 1R,2R)-2-cyanocyclohexyl]-1H-pyrazol-3-yl}amino)phenyl]acetate. LRMS (ESI) calc'd for C$_{20}$H$_{24}$N$_5$O$_3$ [M+H]+: 396. Found: 396.

Step D: [4-({4-carbamoyl-1-[(1S,2R and 1R,2S)-2-cyanocyclohexyl]-1H-pyrazol-3-yl}amino)phenyl] acetic acid and [4-({4-carbamoyl-1-[(1S,2S and 1R,2R)-2-cyanocyclohexyl]-1H-pyrazol-3-yl}amino) phenyl]acetic acid To a solution of methyl [4-({4-carbamoyl-1-[(1S,2R and 1R,2S)-2-cyanocyclohexyl]-1H-pyrazol-3-yl}amino)phenyl]acetate (Example #3-2C, 5 mg, 0.01 mmol) in 1:1 MeOH/THF (1.0 mL) at ambient temperature was added a solution of LiOH (3.0 mg, 0.13 mmol) in H$_2$O (0.4 mL). The mixture was stirred at ambient temperature for 2 hours, acidified with 1N aqueous HCl to pH 3-4, diluted with H$_2$O, and extracted with EtOAc. The organic layer was washed with brine, dried over anhydrous MgSO$_4$, and concentrated in vacuo to afford [4-({4-carbamoyl-1-[(1S,2R and 1R,2S)-2-cyanocyclohexyl]-1H-pyrazol-3-yl}amino)phenyl]acetic acid, Example #3-1. $^1$H NMR (600 MHz, acetone-d$_6$): δ 10.6 (brs, 1H), 9.18 (s, 1H), 8.21 (s, 1H), 7.54-7.55 (m, 2H), 7.04-7.23 (m, 3H), 6.42 (brs, 1H), 4.36 (dt, J=12.6, 3.6 Hz, 1H), 3.83-3.84 (m, 1H), 2.22-2.25 (m, 1H), 2.09-2.13 (m, 1H), 2.00-2.05 (m, 2H), 1.86-1.94 (m, 2H), 1.74-1.79 (m, 1H), 1.56-1.62 (m, 1H). LRMS (ESI) calc'd for C$_{19}$H$_{22}$N$_5$O$_3$ [M+H]$^+$: 368. Found: 368.

To a solution of methyl [4-({4-carbamoyl-1-[(1S,2S and 1R,2R)-2-cyanocyclohexyl]-1H-pyrazol-3-yl}amino)phenyl]acetate (Example #3-1C, 16 mg, 0.040 mmol) in a mixture of 1:1 MeOH/THF (1.0 mL) was added a solution of LiOH (9.7 mg, 0.41 mmol) in H$_2$O (0.4 mL). The mixture was stirred at ambient temperature for 2 hours. The mixture was acidified with 1N aqueous HCl to pH 3-4, diluted with H$_2$O, and extracted with EtOAc. The organic layer was washed with brine, dried over anhydrous MgSO$_4$, and concentrated in vacuo. The residue was purified by reverse phase preparative HPLC (using a gradient elution of 30-65% MeCN/H$_2$O containing 0.1% TFA). Desired fractions were collected, diluted with saturated aqueous NaHCO$_3$, and extracted with EtOAc. The organic layer was washed with brine, dried over anhydrous MgSO$_4$, filtered, and concentrated in vacuo to afford [4-({4-carbamoyl-1-[(1S,2S and 1R,2R)-2-cyanocyclohexyl]-1H-pyrazol-3-yl}amino)phenyl]acetic acid, Example #3-2. $^1$H NMR (600 MHz, acetone-d$_6$): δ 10.7 (brs, 1H), 9.19 (s, 1H), 8.17 (s, 1H), 7.31-7.54 (m, 2H), 7.02-7.20 (m, 3H), 6.46 (brs, 1H), 4.29 (td, J=10.8 and 4.8 Hz), 3.34 (td, J=10.8 and 4.8 Hz), 2.24-2.28 (m, 1H), 2.02-2.08 (m, 2H), 1.85-1.90 (m, 1H), 1.72-1.82 (m, 2H), 1.38-1.56 (m, 2H). LRMS (ESI) calc'd for C$_{19}$H$_{22}$N$_5$O$_3$ [M+H]+: 368. Found: 368.

Example #4

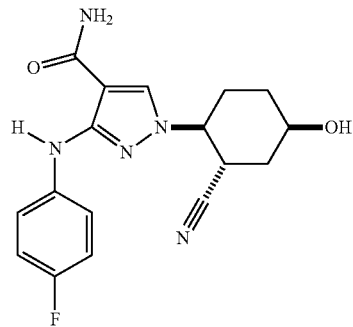

1-[(1S,2S,4R and 1R,2R,4S)-2-Cyano-4-hydroxycyclohexyl]-3-[(4-fluorophenyl)amino]-1H-pyrazole-4-carboxamide The title compound, Example #4, was prepared according to the general procedure describe for Example #2-1 using 3-[(4-fluorophenyl)amino]-1H-pyrazole-4-carboxamide (Intermediate #44-7, 1.0 g, 4.5 mmol) and 5-hydroxycyclohex-1-ene-1-carbonitrile (0.84 g, 6.8 mmol) as starting materials. $^1$H NMR (DMSO-d$_6$): δ 9.11 (s, 1H), 8.25 (s, 1H), 7.63 (br s, 1H), 7.51 (m, 2H), 7.14 (br s, 1H), 7.08 (m, 2H), 4.88 (d, J=2.5 Hz, 1H), 4.40 (ddd, J=11.5, 11.5, 3.5 Hz, 1H), 3.95 (br s, 1H), 3.47 (ddd, J=12.5, 12.5, 4 Hz, 1H), 2.19 (dddd, J=12.5, 12.5, 12.5, 3.5 Hz, 1H), 2.09 (br d, J=12 Hz, 1H), 1.95 (br dd, J=11.5, 11.5 Hz, 1H), 1.74 (m, 2H), 1.62 (br dd, J=13.0, 13.0 Hz, 1H). LRMS (ESI) calc'd for C$_{17}$H$_{18}$FN$_5$O$_2$ [M+H]$^+$: 344. Found: 344.

Example #5

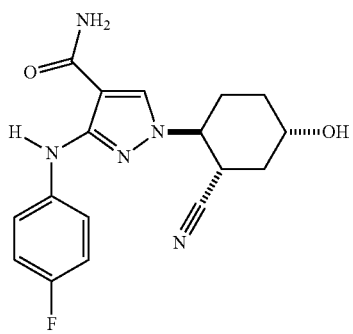

1-[(1S,2S,4S and 1R,2R,4R)-2-Cyano-4-hydroxycyclohexyl]-3-[(4-fluorophenyl)amino]-1H-pyrazole-4-carboxamide

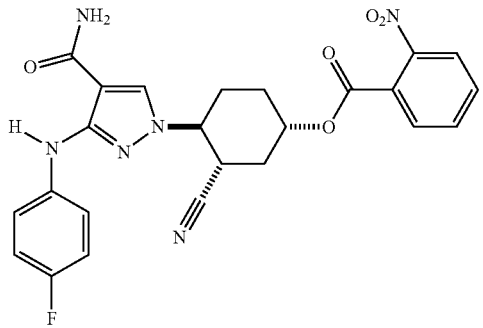

Step A: 1-[(1S,3S,4S and 1R,3R,4R)-4-{4-Carbamoyl-3-(4-fluorophenyl)amino}-1H-pyrazol-1-yl}-3-cyanocyclohexyl 2-nitrobenzoate 1-[(1S,2S,4R and 1R,2R,4S)-2-Cyano-4-hydroxycyclohexyl]-3-[(4-fluorophenyl)amino]-1H-pyrazole-4-carboxamide (Example #4, 500 mg, 1.46 mmol) was dissolved in THF (7.9 mL) and cooled to 0° C. Triphenylphosphine (1.15 g, 4.37 mmol), 2-nitrobenzoic acid (730 mg, 4.37 mmol) and diethyl azodicarboxylate (0.69 mL, 4.37 mmol) were added sequentially, and the reaction mixture was allowed to warm to ambient temperature for 16 hours. The reaction mixture was then partitioned between water and EtOAc. The organic layer was washed with brine, dried over anhydrous $Na_2SO_4$, filtered, and concentrated in vacuo. The residue was purified by MPLC on silica gel (using a gradient elution of 50-100% EtOAc/hexanes) to afford the title compound. LRMS (ESI) calc'd for $C_{24}H_{21}FN_6O_5$ [M+H]$^+$: 493. Found: 493.

Step B: 1-[(1S,2S,4S and 1R,2R,4R)-2-Cyano-4-hydroxycyclohexyl]-3-[(4-fluorophenyl)amino]-1H-pyrazole-4-carboxamide 1-[(1S,3S,4S and 1R,3R,4R)-4-{4-carbamoyl-3-[(4-fluorophenyl)amino-1H-pyrazol-1-yl]-3-cyanocyclohexyl 2-nitrobenzoate (1.15 g, 2.34 mmol) was dissolved in THF (23.4 mL) and cooled to 0° C. NaOMe (1.54 g, 12.5 mmol) was added after 5 minutes. The reaction was allowed to warm to ambient temperature for 45 minutes. The reaction mixture was partitioned between water and EtOAc, the layers were separated and the organic layer was washed with brine, dried over anhydrous $Na_2SO_4$, filtered, and concentrated in vacuo. The residue was purified by MPLC on silica gel (using a gradient elution of 50-100% EtOAc/hexanes followed by a gradient elution of 0-10% MeOH/DCM) to afford the title compound, Example #5. $^1$HNMR (500 MHz, CDCl$_3$): δ 8.72 (s, 1H), 7.63 (s, 1H), 7.48-7.45 (m, 2H), 6.98 (t, J=8.7 Hz, 2H), 5.40 (s, 2H), 4.0 (ddd, J=11.5, 11.5, 4.5 Hz, 1H), 3.90-3.84 (m, 1H), 3.36-3.30 (m, 1H), 2.51 (qd, J=3.5, 12.7 Hz, 1H), 2.29 (dq, J=3.5, 14.0 Hz, 1H), 2.24-2.18 (m, 1H), 2.17-2.08 (m, 1H), 1.83-1.74 (m, 2H) 1.56-1.48 (m, 1H). LRMS (ESI) calc'd for $C_{17}H_{18}FN_5O_2$ [M+H]$^+$: 344. Found: 344.

Scheme #47

Example #6-1 and 6-2

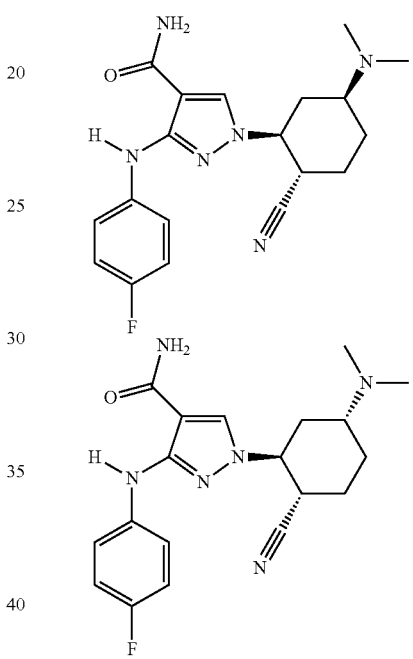

1-[(1S,2S,5S and 1R,2R,5R)-2-cyano-5-(dimethylamino)cyclohexyl]-3-[(4-fluorophenyl)amino]-1H-pyrazole-4-carboxamide and 1-[(1S,2S,5R and 1R,2R,5S)-2-cyano-5-(dimethylamino)cyclohexyl]-3-[(4-fluorophenyl)amino]-1H-pyrazole-4-carboxamide

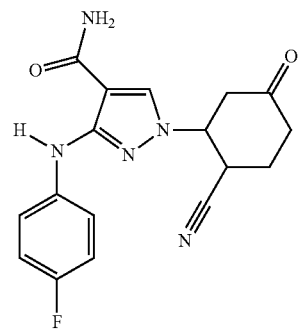 [SMILES: N#CC1CCC(=O)CC1n1cc(C(N)=O)c(Nc2ccc(F)cc2)n1]

Step A: 1-(2-Cyano-5-oxocyclohexyl)-3-(phenylamino)-1H-pyrazole-4-carboxamide To a vial containing 1-(8-cyano-1,4-dioxaspiro[4.5]dec-7-yl)-3-(phenylamino)-1H-pyrazole-4-carboxamide (Example #2-4, 37 mg, 0.10 mmol) was added THF (0.38 mL), and 1N aqueous HCl (0.13 mL). The resulting mixture was heated to 75° C. for 5.5 hours. The reaction mixture was allowed to cool to ambient temperature and was diluted with EtOAc. The layers were separated and the organic layer was washed with water, saturated aqueous NaHCO$_3$, brine, dried over anhydrous Na$_2$SO$_4$, and concentrated in vacuo. The residue was dissolved in DMSO and purified by reverse-phase preparative HPLC (MeCN/water, with 0.1% v/v TFA modifier). Desired fractions were identified, combined, and lyophilized to afford the title compound as a 1:1 mixture of cis and trans isomers.

$^1$H NMR (600 MHz, DMSO-d$_6$) Cis isomer: δ 9.09 (br. S, 1H), 8.26 (s, 1H), 7.65 (br s, 1H), 7.53-7.45 (m, 2H), 7.24-7.12 (m, 3H), 6.83-6.76 (m, 1H), 5.07 (dd, J=8.9, 5.2 Hz, 1H), 3.83 (dt, J=9.9, 3.9 Hz, 1H), 3.08-2.01 (m, 6H). $^1$H NMR (600 MHz, DMSO-d$_6$) Trans isomer: δ 9.17 (br. S, 1H), 8.21 (s, 1H), 7.65 (br s, 1H), 7.42-7.32 (m, 2H), 7.24-7.12 (m, 3H), 6.83-6.76 (m, 1H), 4.92 (td, J=10.9, 4.8 Hz, 1H), 3.74 (td, J=11.4, 3.5 Hz, 1H), 3.08-2.01 (m, 6H). LRMS (ESI) calc'd for C$_{17}$H$_{17}$N$_5$O$_2$ [M+H]$^+$: 324. Found: 324.

Step B. 1-[(1S,2S,5S and 1R,2R,5R)-2-cyano-5-(dimethylamino)cyclohexyl]-3-[(4-fluorophenyl)amino]-1H-pyrazole-4-carboxamide and 1-[(1S,2S,5R and 1R,2R,5S)-2-cyano-5-(dimethylamino)cyclohexyl]-3-[(4-fluorophenyl)amino]-1H-pyrazole-4-carboxamide 1-[(1S,2S and 1R,2R)-2-Cyano-5-oxocyclohexyl]-3-(phenylamino)-1H-pyrazole-4-carboxamide was dissolved in MeOH (0.13 mL) and THF (0.13 mL). In a separate flask, dimethylamine (0.73 mL, 1.5 mmol, 2.0 M in THF) was dissolved in MeOH (0.13 mL) and THF (0.13 mL) before triethylamine (0.20 mL, 1.5 mmol) was added and the mixture was allowed to stir at ambient temperature for 2 minutes before it was added to the reaction vessel containing the dissolved ketone. Acetic acid (0.084 mL, 1.5 mmol) was added and stirring continued for 20 minutes before sodium cyanoborohydride (23 mg, 0.37 mmol) was added. The resulting reaction mixture was allowed to stir at ambient temperature for 18 hours before the reaction mixture was concentrated in vacuo. The residue was purified by reverse-phase preparative HPLC (using a gradient elution of MeCN/water, with 0.1% v/v TFA modifier). Desired fractions were identified, combined, and lyophilized to afford the title compounds:

Example #6-1

1-[(1S,2S,5S and 1R,2R,5R)-2-cyano-5-(dimethylamino)cyclohexyl]-3-[(4-fluorophenyl)amino]-1H-pyrazole-4-carboxamide. $^1$H NMR (600 MHz, acetone-d$_6$) δ 13.39-12.88 (m, 1H), 9.23 (s, 1H), 8.25 (s, 1H), 7.60 (dd, J=8.2, 4.7, 2H), 7.20 (s, 1H), 6.98 (t, J=8.5, 2H), 6.48 (s, 1H), 4.62 (td, J=11.3, 3.4, 1H), 3.57 (t, J=12.2, 1H), 3.49 (td, J=11.8, 3.7, 1H), 3.03 (s, 6H), 2.63 (d, J=10.5, 1H), 2.56-2.46 (m, 1H), 2.43 (dd, J=24.3, 12.2, 1H), 2.34 (d, J=12.4, 1H), 2.03 (s, 1H), 1.99-1.79 (m, 2H), 1.29 (dd, J=14.3, 7.1, 1H). LRMS (ESI) calc'd for C$_{19}$H$_{23}$F$_3$N$_6$O [M+H]$^+$: 371. Found: 371.

Example #6-2

1-[(1S,2S,5R and 1R,2R,5S)-2-cyano-5-(dimethylamino)cyclohexyl]-3-[(4-fluorophenyl)amino]-1H-pyrazole-4-carboxamide. $^1$H NMR (600 MHz, acetone-d$_6$) δ 12.29 (s, 1H), 9.17 (s, 1H), 8.61 (s, 1H), 7.57 (dd, J=8.8, 4.6, 2H), 7.39 (s, 1H), 7.00 (t, J=8.7, 2H), 6.45 (s, 1H), 4.96 (dd, J=9.4, 4.8, 1H), 4.04 (d, J=4.5, 1H), 3.87 (t, J=9.4, 1H), 3.12 (s, 6H), 2.83 (d, J=15.2, 1H), 2.65-2.51 (m, 1H), 2.29-2.14 (m, 2H), 2.11 (dd, J=19.6, 9.7, 1H), 2.06-1.94 (m, 1H).

The following examples shown in TABLE 14 were prepared according to Scheme #47 following similar procedures described for Examples #6-1 and #6-2, which can be achieved by those of ordinary skill in the art of organic synthesis.

TABLE 14

| Example | Structure | Compound Name | Exact Mass [M + H]$^+$ |
|---|---|---|---|
| 6-3 | 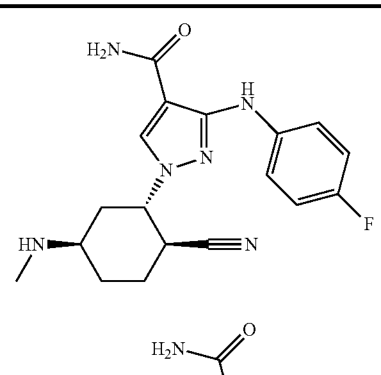 | 1-{[(1S,2S,5R) and (1R,2R,5S)]-2-cyano-5-(methylamino)cyclohexyl}-3-[(4-fluorophenyl)amino]-1H-pyrazole-4-carboxamide | Calc'd 357, found 357 |
| 6-4 | 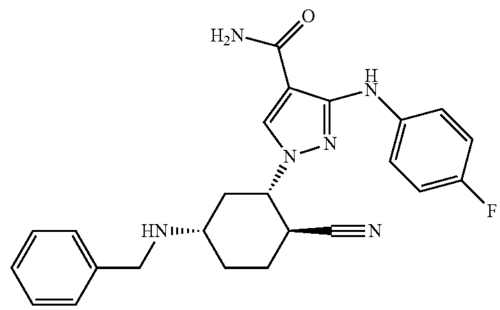 [SMILES: N#C[C@H]1CC[C@H](NCc2ccccc2)C[C@@H]1n1cc(C(N)=O)c(Nc2ccc(F)cc2)n1] | 1-{[(1S,2S,5S) and (1R,2R,5R)]-5-(benzylamino)-2-cyanocyclohexyl}-3-[(4-fluorophenyl)amino]-1H-pyrazole-4-carboxamide | Calc'd 433, found 433 |

TABLE 14-continued

| Example | Structure | Compound Name | Exact Mass [M + H]+ |
|---|---|---|---|
| 6-5 | 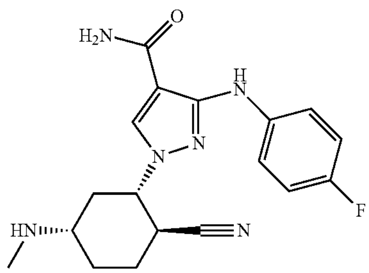 [SMILES: CN[C@H]1CC[C@H](C#N)[C@@H](n2cc(C(N)=O)c(Nc3ccc(F)cc3)n2)C1] | 1-{[(1S,2S,5S) and (1R,2R,5R)-2-cyano-5-(methylamino)cyclohexyl]-3-[(4-fluorophenyl)amino]-1H-pyrazole-4-carboxamide | Calc'd 357, found 357 |
| 6-6 | 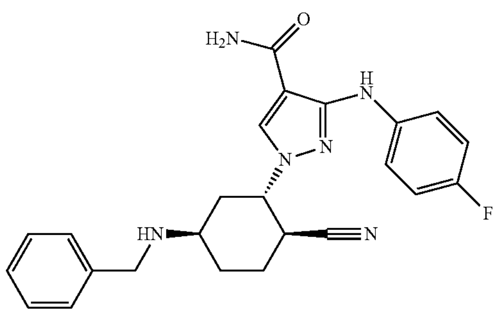 [SMILES: N#C[C@H]1CC[C@@H](NCc2ccccc2)C[C@@H]1n1cc(C(N)=O)c(Nc2ccc(F)cc2)n1] | 1-{[(1S,2S,5R) and (1R,2R,5S)]-5-(benzylamino)-2-cyanocyclohexyl}-3-[(4-fluorophenyl)amino]-1H-pyrazole-4-carboxamide | Calc'd 433, found 433 |

Scheme #30

Example #7-1

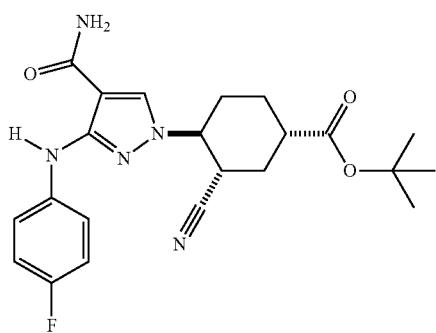

tert-Butyl (1S,3S,4S and 1R,3R,4R)-4-{4-carbamoyl-3-[(4-fluorophenyl)amino]-1H-pyrazol-1-yl}-3-cyanocyclohexanecarboxylate 3-[(4-Fluorophenyl)amino]-1H-pyrazole-4-carboxamide (Example #44-7, 195 mg, 0.941 mmol) was added to a mixture of tert-butyl 3-cyanocyclohex-3-ene-1-carboxylate (249 mg, 1.13 mmol) in MeCN (4.7 mL). DBU (0.43 mL, 2.8 mmol) was added, the reaction vessel was capped and the reaction mixture was heated to 80° C. for 16 hours. The reaction mixture was cooled to ambient temperature, concentrated in vacuo and purified by reverse phase preparative HPLC (using a gradient elution of 45-80% MeCN/water, with 0.1% v/v TFA modifier). Desired fractions were combined, basified with saturated aqueous NaHCO$_3$, and extracted with EtOAc. The organic layer was dried over anhydrous NaSO$_4$, filtered, and concentrated in vacuo to afford the title compound, Example #7-1. $^1$H NMR (500 MHz, 10:1 CDCl$_3$: CD$_3$OD): δ 7.83 (s, 1H), 7.46-7.38 (m, 2H), 6.96-6.89 (m, 2H), 4.02-3.95 (m, 1H), 3.28-3.18 (m, 1H), 2.50-2.42 (m, 1H), 2.42-2.35 (m, 1H), 2.22-2.06 (m, 3H), 1.88-1.78 (m, 1H), 1.60-1.48 (m, 1H), 1.42 (s, 9H).

LRMS (ESI) calc'd for C$_{22}$H$_{26}$FN$_5$O$_3$ [M+H]+: 428. Found: 428.

The following examples shown in TABLE 15 were prepared according to Scheme #30 following similar procedures described for Example #7-1, which can be achieved by those of ordinary skill in the art of organic synthesis.

TABLE 15

| Example | Structure | Compound Name | Exact Mass [M + H]+ |
|---|---|---|---|
| 7-2 | 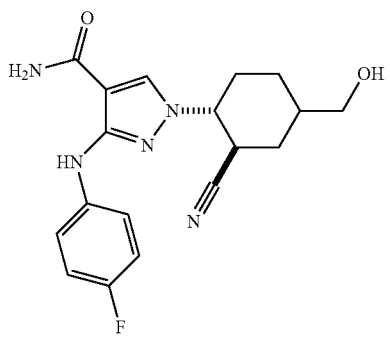 | methyl (1S,3S,4S and 1R,3R,4R)-4-{4-carbamoyl-3-[(4-fluorophenyl)amino]-1H-pyrazol-1-yl}-3-cyanocyclohexanecarboxylate | Calc'd 386, Found 386 |

Example #8

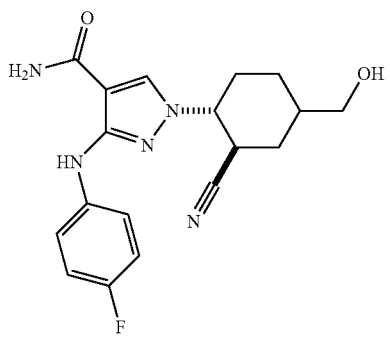

1-((1R,2R and 1S,2S)-2-Cyano-4-(hydroxymethyl)cyclohexyl)-3-((4-fluorophenyl)amino)-1H-pyrazole-4-carboxamide A solution of tert-butyl (1S,3S,4S and 1R,3R,4R)-4-{4-carbamoyl-3-[(4-fluorophenyl)amino]-1H-pyrazol-1-yl}-3-cyanocyclohexanecarboxylate (Example #7-1, 50 mg, 0.12 mmol) in THF (1.1 mL) was stirred at ambient temperature and lithium borohydride (5 mg, 0.2 mmol) was added. The resulting mixture was stirred at 50° C. for 3 hours. The mixture was cooled to ambient temperature, diluted with water and extracted with EtOAc (2×). The combined organic extracts were washed with water, brine, dried over anhydrous $Na_2SO_4$, filtered, and concentrated in vacuo. The crude residue was purified by MPLC on silica gel (using a gradient elution of 0-5% MeOH/DCM). Desired fractions were identified, combined and concentrated in vacuo to afford the title compound. LRMS (ESI) calc'd for $C_{18}H_{20}FN_5O_2$ [M+H]+: 358. Found: 358.

Example #9

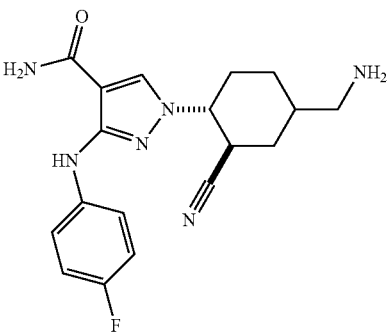

1-((1R,2R and 1S,2S)-4-(Aminomethyl)-2-cyanocyclohexyl)-3-((4-fluorophenyl)amino)-1H-pyrazole-4-carboxamide

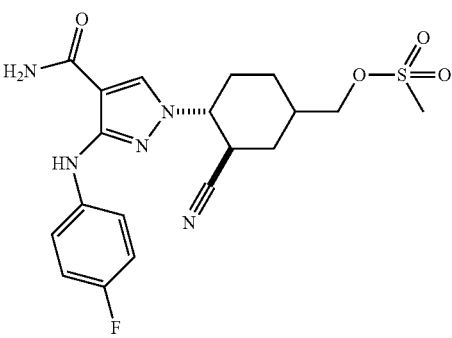

Step A: ((3R,4R and 3S,4S)-4-(4-Carbamoyl-3-((4-fluorophenyl)amino)-1H-pyrazol-1-yl)-3-cyanocyclohexyl)methyl methanesulfonate A solution of 1-((1R,2R and 1S,2S)-2-cyano-4-(hydroxymethyl)cyclohexyl)-3-((4-fluorophenyl)amino)-1H-pyrazole-4-carboxamide (Example #8, 50 mg, 0.14 mmol) in DCM (1.4 mL) was stirred at 0° C. DIPEA (54 mg, 0.42 mmol) was added followed by the dropwise addition of methanesulfonyl chloride (19 mg, 0.17 mmol). The resulting mixture was stirred at 0° C. for 30 minutes then warmed to ambient temperature and stirred for an additional 1 hour. The mixture was carefully diluted with water and extracted with DCM (2×). The combined organic extracts were washed with 1N aqueous HCl, brine, dried over anhydrous $Na_2SO_4$, filtered, and concentrated in vacuo. The crude residue was purified by MPLC on silica gel (using a gradient elution of 0-5% MeOH/DCM). Desired fractions were identified, combined and concentrated in vacuo to afford the title compound. LRMS (ESI) calc'd for $C_{19}H_{22}FN_5O_4$ [M+H]$^+$: 436. Found: 436.

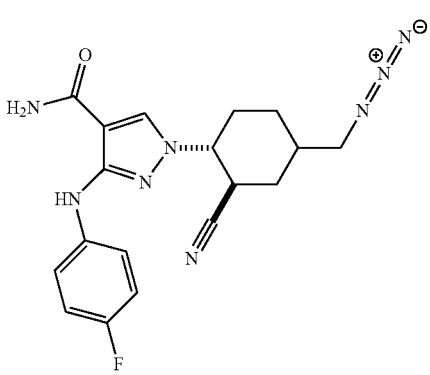

Step B: 1-((1R,2R and 1S,2S)-4-(Azidomethyl)-2-cyanocyclohexyl)-3-((4-fluorophenyl)amino)-1H-pyrazole-4-carboxamide To a solution of ((3R,4R and 3S,4S)-4-(4-carbamoyl-3-((4-fluorophenyl)amino)-1H-pyrazol-1-yl)-3-cyanocyclohexyl)methyl methanesulfonate (57 mg, 0.13 mmol) in DMF (1.3 mL) was added sodium azide (13 mg, 0.20 mmol). The resulting mixture was heated at 80° C. for 3 hours. The mixture was cooled to ambient temperature, diluted with water and extracted with EtOAc (2×). The combined organic extracts were washed with brine, dried over anhydrous $Na_2SO_4$, filtered, and concentrated in vacuo. The crude residue was carried on without further purification. LRMS (ESI) calc'd for $C_{18}H_{19}FN_8O$ [M+H]$^+$: 383. Found: 383.

Step C: 1-((1R,2R and 1S,2S)-4-(aminomethyl)-2-cyanocyclohexyl)-3-((4-fluorophenyl)amino)-1H-pyrazole-4-carboxamide To a solution of 1-((1R,2R and 1S,2S)-4-(azidomethyl)-2-cyanocyclohexyl)-3-((4-fluorophenyl)amino)-1H-pyrazole-4-carboxamide (36 mg, 0.094 mmol) in THF (1 mL) was added resin bound triphenylphosphine (0.11 mmol). The resulting mixture was stirred at 0° C. for 30 mins before water (0.02 mL) was added. The resulting mixture was allowed to warm to ambient temperature and was stirred for 5 hours. The reaction mixture was filtered and the solids were flushed with DCM (2×). The filtrate was washed with brine, dried over anhydrous $Na_2SO_4$, filtered, and concentrated in vacuo. The residue was purified by reverse-phase preparative HPLC (MeCN/water, with 0.1% v/v TFA modifier). Desired fractions were identified, combined, basified with saturated aqueous $NaHCO_3$, and extracted with EtOAc (2×). The combined organic extracts were washed with brine, dried over anhydrous $Na_2SO_4$, filtered, and concentrated in vacuo to afford the title compound. LRMS (ESI) calc'd for $C_{18}H_{21}FN_6O$ [M+H]$^+$: 357. Found: 357.

Example #10

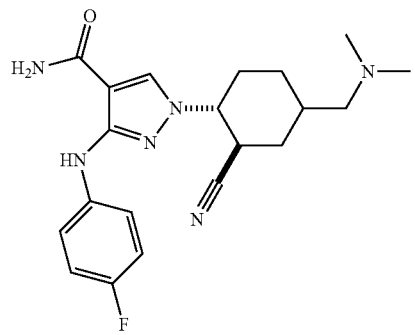

1-((1R,2R and 1S,2S)-2-Cyano-4-((dimethylamino)methyl)cyclohexyl)-3-((4-fluorophenyl)amino)-1H-pyrazole-4-carboxamide

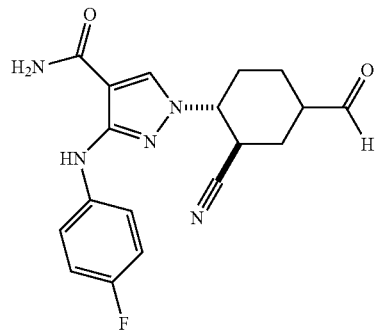 [SMILES: N#C[C@@H]1CC(C=O)CC[C@H]1n1cc(C(N)=O)c(Nc2ccc(F)cc2)n1]

Step A: 1-((1R,2R and 1S,2S)-2-Cyano-4-formylcyclohexyl)-3-((4-fluorophenyl)amino)-1H-pyrazole-4-carboxamide 1-((1R,2R and 1S,2S)-2-Cyano-4-(hydroxymethyl)cyclohexyl)-3-((4-fluorophenyl)amino)-1H-pyrazole-4-carboxamide (Example #8, 50 mg, 0.14 mmol) was dissolved in 1:1 DCM (0.7 mL):MeCN (0.7 mL). NMO (34 mg, 0.29 mmol) and 4 Å molecular sieves (200 mg/mmol) were added and the reaction mixture was maintained at ambient temperature for 15 minutes. TPAP (10 mg, 0.03 mmol) was added to the reaction mixture and it was maintained at ambient temperature for 1 hour. The reaction mixture was then adsorbed on silica gel in vacuo and purified directly by MPLC on silica gel (using a gradient elution of 0-10%, MeOH/DCM). Desired fractions were identified, combined, and concentrated in vacuo to afford the title compound. LRMS (ESI) calc'd for $C_{18}H_{18}FN_5O_2$ [M+H]$^+$: 356. Found: 356.

Step B: 1-((1R,2R and 1S,2S)-2-Cyano-4-((dimethylamino)methyl)cyclohexyl)-3-((4-fluorophenyl)amino)-1H-pyrazole-4-carboxamide To a solution of 1-((1R,2R and 1S,2S)-2-cyano-4-formylcyclohexyl)-3-((4-fluorophenyl)amino)-1H-pyrazole-4-carboxamide (24 mg, 0.068 mmol) in 1:1 MeOH:THF (1.3 mL) was added dimethylamine (0.034 mL, 0.68 mmol, 2M in THF), acetic acid (41 mg, 0.67 mmol) and sodium cyanoborohydride (11 mg, 0.17 mmol). The resulting mixture was maintained at ambient temperature for 1 hour. The crude reaction mixture was concentrated in vacuo and the resulting residue was purified by reverse phase preparative HPLC (using a gradient elution of 5-80% MeCN/water, with 0.1% v/v TFA modifier). Desired fractions were identified, combined, basified with saturated aqueous NaHCO$_3$, and extracted with EtOAc (2×). The combined organic extracts were washed with brine, dried over anhydrous Na$_2$SO$_4$, filtered, and concentrated in vacuo to afford the title compound. LRMS (ESI) calc'd for C$_{20}$H$_{25}$FN$_6$O [M+H]$^+$: 385. Found: 385.

Scheme #30

Example #11-1 and 11-2

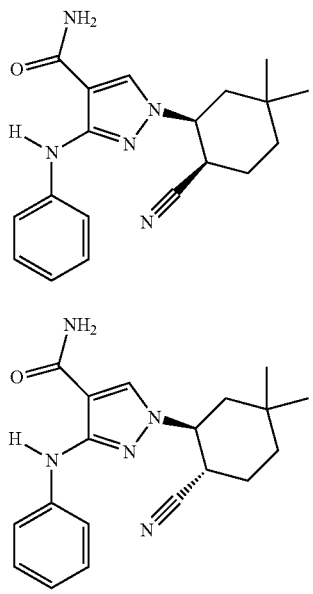

1-{[(1S,2S) and (1R,2R)]-2-Cyano-5,5-dimethylcyclohexyl}-3-(phenylamino)-1H-pyrazole-4-carboxamide and 1-{[(1S,2R) and (1R,2S)]-2-Cyano-5,5-dimethylcyclohexyl}-3-(phenylamino)-1H-pyrazole-4-carboxamide DBU (0.22 mL, 1.5 mmol) was added to a mixture of 3-(phenylamino)-1H-pyrazole-4-carboxamide (150 mg, 0.74 mmol) and 4,4-dimethylcyclohex-1-ene-1-carbonitrile (280 mg, 2.07 mmol) in ethanol (3.8 mL) and the vial capped and allowed to stir at 90° C. for 45 hours. The reaction mixture was concentrated in vacuo and the residue purified by MPLC on silica gel (using a gradient elution of 0-20% MeOH/DCM) to afford a 1:2 cis/trans mixture of the title compounds. This mixture was further purified by reverse-phase preparative HPLC (MeCN/water, with 0.1% v/v TFA modifier) to afford the title compounds.

Example #11-1

$^1$H NMR (600 MHz, DMSO-d$_6$) δ 9.08 (s, 1H), 8.32 (s, 1H), 7.55 (s, 1H), 7.50 (d, 2H), 7.20 (dd, J=8.5, 7.4, 2H), 7.08 (s, 1H), 6.79 (t, J=7.3, 1H), 4.47 (m, 1H), 3.78-3.73 (m, 1H), 2.06-1.95 (m, 1H), 1.85 (dd, J=14.2, 2.5, 2H), 1.76 (t, J=12.8, 1H), 1.44-1.32 (m, J=14.2, 10.5, 2H), 1.02 (d, J=32.8, 6H). LRMS (ESI) calc'd for C$_{19}$H$_{23}$N$_5$O [M+H]$^+$: 338. Found: 338.

Example #11-2

$^1$H NMR (600 MHz, DMSO-d$_6$) δ 9.11 (s, 1H), 8.20 (s, 1H), 7.60 (s, 1H), 7.46 (d, J=7.8, 2H), 7.22 (t, J=7.9, 2H), 7.10 (s, 1H), 6.79 (t, J=7.3, 1H), 4.50 (td, J=11.9, 4.2, 1H), 3.20-3.10 (m, 1H), 2.02 (dd, J=13.4, 3.3, 1H), 1.87 (ddd, J=26.5, 13.2, 3.6, 1H), 1.71 (t, J=12.7, 1H), 1.64 (d, J=10.1, 1H), 1.38 (d, J=13.6, 1H), 1.35-1.23 (m, 1H), 0.96 (d, J=36.2, 6 H). LRMS (ESI) calc'd for C$_{19}$H$_{23}$N$_5$O [M+H]$^+$: 338. Found: 338.

The following examples shown in TABLE 16 were prepared according to Scheme #30 following similar procedures described for Example #11-1, which can be achieved by those of ordinary skill in the art of organic synthesis.

TABLE 16

| Example | Structure | Compound Name | Exact Mass [M + H]$^+$ |
|---|---|---|---|
| 11-3 | 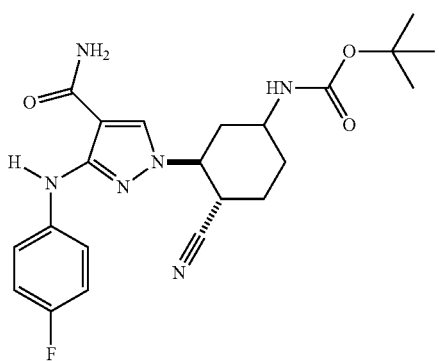 | tert-butyl [(1R,3S,4S and 1S,3R,4R) or (1S,3S,4S and 1R,3R,4R)-3-{4-carbamoyl-3-[(4-fluorophenyl)amino]-1H-pyrazol-1-yl}-4-cyanocyclohexyl]carbamate | Calc'd 443, Found 443 |

TABLE 16-continued

| Example | Structure | Compound Name | Exact Mass [M + H]+ |
|---|---|---|---|
| 11-4 | 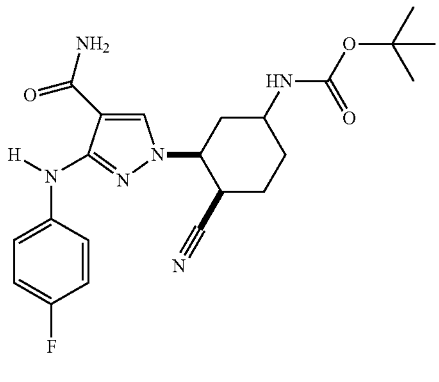 | tert-butyl [(3R,4S and 3S,4R)-3-{4-carbamoyl-3-[(4-fluorophenyl)amino]-1H-pyrazol-1-yl}-4-cyanocyclohexyl]carbamate | Calc'd 443, Found 443 |
| 11-5 | 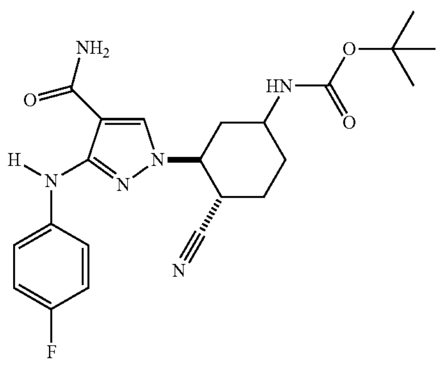 | tert-butyl [(1R,3S,4S and 1S,3R,4R) or (1S,3S,4S and 1R,3R,4R)-3-{4-carbamoyl-3-[(4-fluorophenyl)amino]-1H-pyrazol-1-yl}-4-cyanocyclohexyl]carbamate | Calc'd 443, Found 443 |
| 11-6 | 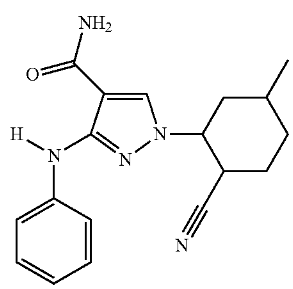 [SMILES: CC1CCC(C#N)C(n2cc(C(N)=O)c(Nc3ccccc3)n2)C1] | 1-(2-cyano-5-methylcyclohexyl)-3-(phenylamino)-1H-pyrazole-4-carboxamide | Calc'd 324, Found 324 |
| 11-7 | 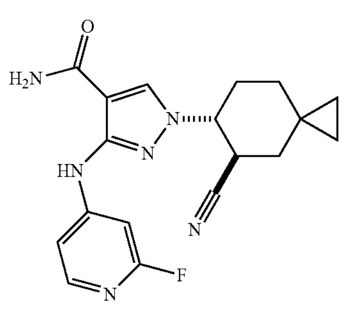 | 1-((5R,6R and 5S,6S)-5-cyanospiro[2.5]octan-6-yl)-3-((2-fluoropyridin-4-yl)amino)-1H-pyrazole-4-carboxamide | Calc'd 355, Found 355 |

TABLE 16-continued

| Example | Structure | Compound Name | Exact Mass [M + H]+ |
|---|---|---|---|
| 11-8 | 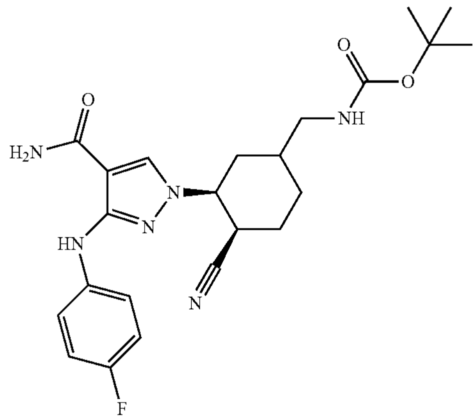 [SMILES: CC(C)(C)OC(=O)NCC1CC[C@@H](C#N)[C@@H](n2cc(C(N)=O)c(Nc3ccc(F)cc3)n2)C1] | tert-butyl {[(3S,4R) and (3R,4S)]-3-{4-carbamoyl-3-[(4-fluorophenyl)amino]-1H-pyrazol-1-yl}-4-cyanocyclohexyl]methyl}carbamate | Calc'd 457, found 457 |
| 11-9 | 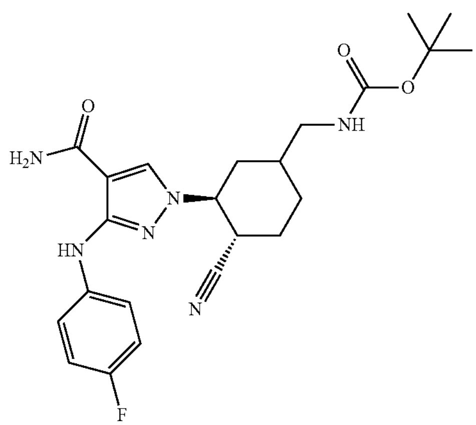 [SMILES: CC(C)(C)OC(=O)NCC1CC[C@H](C#N)[C@@H](n2cc(C(N)=O)c(Nc3ccc(F)cc3)n2)C1] | tert-butyl {[(1R or S 3S,4S) and (1S or R, 3R, 4R)]-3-{4-carbamoyl-3-[(4-fluorophenyl)amino]-1H-pyrazol-1-yl}-4-cyanocyclohexyl]methyl}carbamate | Calc'd 457, found 457 |
| 11-10 | 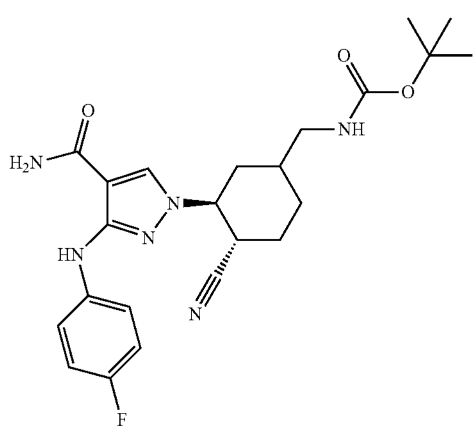 [SMILES: CC(C)(C)OC(=O)NCC1CC[C@H](C#N)[C@@H](n2cc(C(N)=O)c(Nc3ccc(F)cc3)n2)C1] | tert-butyl {[(1S or R,3S,4S) and (1R or S,3R,4R)]-3-{4-carbamoyl-3-[(4-fluorophenyl)amino]-1H-pyrazol-1-yl}-4-cyanocyclohexyl]methyl}carbamate | Calc'd 457, found 457 |

Scheme #30

Examples #12-1 and 12-2

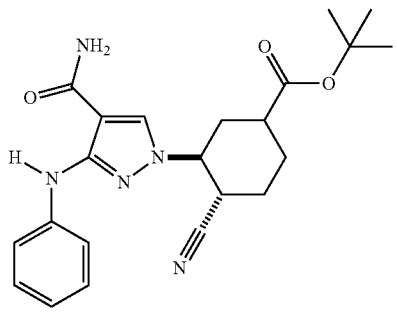

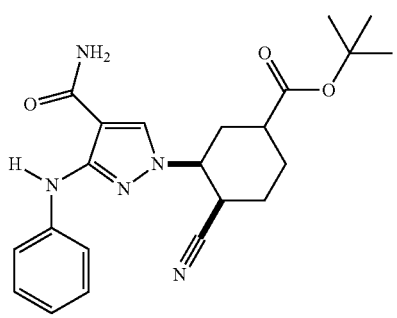

(3S,4S and 3R,4R)-tert-butyl 3-(4-carbamoyl-3-(phenylamino)-1H-pyrazol-1-yl)-4-cyanocyclohexanecarboxylate and (3S,4R and 3R,4S)-tert-butyl 3-(4-carbamoyl-3-(phenylamino)-1H-pyrazol-1-yl)-4-cyanocyclohexanecarboxylate 3-(Phenylamino)-1H-pyrazole-4-carboxamide (Example #44-1, 50 mg, 0.25 mmol) was combined with DBU (75 mg, 0.50 mmol) and tert-butyl 4-cyanocyclohex-3-ene-1-carboxylate (100 mg, 0.50 mmol) in t-BuOH (1.2 mL). The reaction mixture was heated to 90° C. and allowed to stir for 18 hours. The mixture was then cooled to 23° C. and purified directly by reverse-phase preparative HPLC (MeCN/water, with 0.1% v/v TFA modifier). Desired fractions were identified, combined, and concentrated in vacuo to afford the title compounds.

Example #12-1

(3S,4S and 3R,4R)-tert-butyl 3-(4-carbamoyl-3-(phenylamino)-1H-pyrazol-1-yl)-4-cyanocyclohexanecarboxylate: $^1$H NMR (600 MHz, CDCl$_3$): δ 8.67 (s, 1H), 7.61 (s, 1H), 7.51 (d, J=8.0 Hz, 2H), 7.26 (t, J=7.9 Hz, 2H), 6.87 (t, J=7.2 Hz, 1H), 5.56 (br. S, 2H), 4.46 (td, J=11.7, 3.9 Hz, 1H), 3.22 (br. S, 1H), 3.07-2.96 (m, 1H), 2.41 (td, J=13.2, 4.5 Hz, 1H), 2.26 (d, J=14.0 Hz, 1H), 2.22-2.13 (m, 1H), 2.10 (d, J=13.6 Hz, 1H), 1.98-1.89 (m, 1H), 1.79-1.71 (m, 1H), 1.26 (s, 9H). LRMS (ESI) calc'd for $C_{22}H_{27}N_5O_3$ [M+H]$^+$ 410. Found 410.

Example #12-2

(3S,4R and 3R,4S)-tert-butyl 3-(4-carbamoyl-3-(phenylamino)-1H-pyrazol-1-yl)-4-cyanocyclohexanecarboxylate. $^1$H NMR (600 MHz, CDCl$_3$): δ 8.72 (s, 1H), 7.72 (s, 1H), 7.51 (d, J=7.8 Hz, 2H), 7.26 (t, J=7.9 Hz, 2H), 6.88 (t, J=7.3 Hz, 1H), 5.55 (s, 2H), 4.31 (dt, J=12.9, 3.5 Hz, 1H), 3.73-3.68 (m, 1H), 2.49-1.49 (m, 7H), 1.23 (s, 9H). LRMS (ESI) calc'd for $C_{22}H_{27}N_5O_3$ [M+H]$^+$ 410. Found 410.

Scheme #31

Examples #13-1 and 13-2

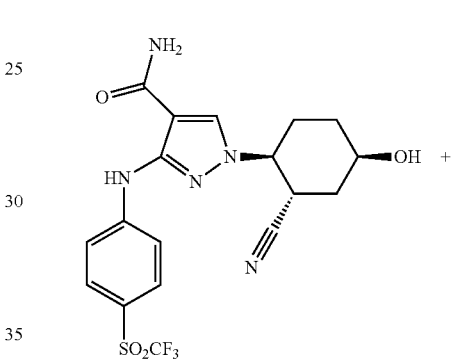

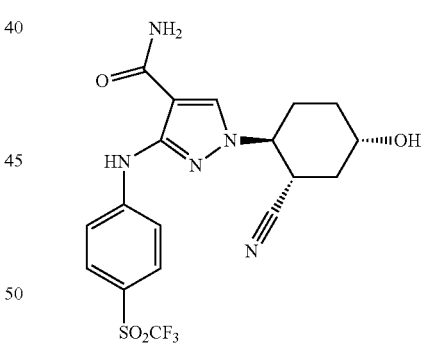

1-[(1S,2S,4R and 1R,2R,4S)-2-Cyano-4-hydroxycyclohexyl]-3-({4-[(trifluoromethyl)sulfonyl]phenyl}amino)-1H-pyrazole-4-carboxamide and 1-[(1S,2S,4S and 1R,2R,4R)-2-cyano-4-hydroxycyclohexyl]-3-({4-[(trifluoromethyl)sulfonyl]phenyl}amino)-1H-pyrazole-4-carboxamide Nitrogen was bubbled through a mixture of 3-amino-1-[(1S,2S and 1R,2R)-2-cyano-4-hydroxycyclohexyl]-1H- pyrazole-4-carboxamide (Intermediates #48-1 and 48-2, 2.00 g, 8.02 mmol), 1-bromo-4-[(trifluoromethyl)sulfonyl]benzene (2.32 g, 8.02 mmol), $K_3PO_4$ (2.38 g, 11.2 mmol), and X-Phos (1.15 g, 2.41 mmol) in dioxane (27 mL) for 5 minutes, and then $Pd_2(dba)_3$ (735 mg, 0.802 mmol) was added. The reaction vessel was sealed, and heated to 105° C. After 40 minutes, the reaction mixture was cooled to ambient temperature and partitioned between EtOAc and water. The organic layer was washed with saturated aqueous sodium chloride solution, and the washed solution was filtered. The filtrate was concentrated in vacuo and the residue was purified by MPLC on silica gel (using a gradient elution of 60-100%, EtOAc/hexanes followed by a gradient elution of 5%-10%, MeOH/DCM) to afford the title compounds.

Example 13-1

1-[(1S,2S,4R and 1R,2R,4S)-2-cyano-4-hydroxycyclohexyl]-3-({4-[(trifluoromethyl)sulfonyl]phenyl}amino)-1H-pyrazole-4-carboxamide. $^1$HNMR (500 MHz, $CD_3OD$): δ 8.22 (s, 1H), 7.92-7.87 (m, 4H), 4.38 (td, J=11.5, 4.0 Hz, 1H), 4.15-4.12 (m, 1H), 3.69 (td, J=11.7, 3.7 Hz, 1H), 2.46 (qd, 13.5, 3.6 Hz, 1H), 2.31-2.26 (m, 1H), 2.05-1.88 (m, 3H), 1.80-1.73 (m, 1H). LRMS (ESI) calc'd for $C_{18}H_{19}F_3N_5O_4S$ [M+H]$^+$: 458. Found: 458.

Example 13-2

1-[(1S,2S,4S and 1R,2R,4R)-2-cyano-4-hydroxycyclohexyl]-3-({4-[(trifluoromethyl)sulfonyl]phenyl}amino)-1H-pyrazole-4-carboxamide. $^1$HNMR (500 MHz, $CD_3OD$): δ 8.19 (s, 1H), 7.92-7.85 (m, 4H), 4.38 (td, 11.0, 4.0 Hz, 1H), 3.81-3.74 (m, 1H), 3.56-3.49 (m, 1H), 2.46-2.40 (m, 1H), 2.23-2.06 (m, 3H), 1.76 (q, J=12.1 Hz, 1H), 1.58-1.49 (m, 1H). LRMS (ESI) calc'd for $C_{18}H_{19}F_3N_5O_4S$ [M+H]$^+$: 458. Found: 458.

Scheme #31

Example #14

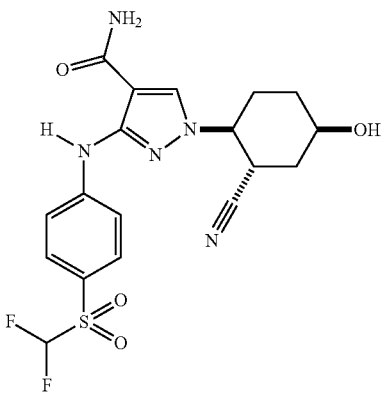

1-[(1S,2S,4R and 1R,2R,4S)-2-Cyano-4-hydroxycyclohexyl]-3-({4-[(difluoromethyl) sulfonyl] phenyl}amino)-1H-pyrazole-4-carboxamide Nitrogen was bubbled through a mixture of 3-amino-1-[(1S,2S,4R and 1R,2R,4S)-2-cyano-4-hydroxycyclohexyl]-1H-pyrazole-4-carboxamide (Intermediate #48-1, 200 mg, 0.802 mmol), 1-bromo-4-[(difluoromethyl)sulfonyl]benzene (217 mg, 0.802 mmol), $K_3PO_4$ (0.238 g, 1.12 mmol), and X-Phos (115 mg, 0.241 mmol) in dioxane (2.7 mL) for 5 minutes, and then $Pd_2(dba)_3$ (73 mg, 0.080 mmol) was added. The reaction vessel was sealed, and heated to 105° C. After 60 minutes, the reaction mixture was cooled to 23° C. and partitioned between EtOAc and water. The organic layer was washed with saturated aqueous sodium chloride solution, and the washed solution was filtered. The filtrate was concentrated in vacuo and the residue was purified by MPLC on silica gel (using a gradient elution of 60-100%, EtOAc/hexanes) to afford the title compound. Example #14. $^1$HNMR (500 MHz, $CD_3OD$): δ 8.20 (s, 1H), 7.85-7.80 (m, 4H), 6.62 (t, JH-$_F$=53.4 Hz, 1H), 4.35 (td, J=11.5, 4.0 Hz, 1H), 4.14-4.10 (m, 1H), 3.72-3.66 (m, 1H), 2.47 (qd, J=13.4, 3.4 Hz, 1H), 2.29-2.24 (m, 1H), 2.04-1.86 (m, 3H), 1.74 (tt, J=13.5, 2.9 Hz, 1H). LRMS (ESI) calc'd for $C_{18}H_{20}F_2N_5O_4S$ [M+H]$^+$: 440. Found: 440.

Scheme #31

Example #15

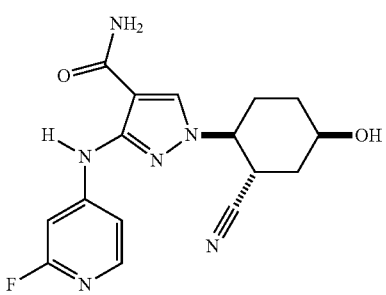

1-[(1S,2S,4R and 1R,2R,4S)-2-Cyano-4-hydroxycyclohexyl]-3-[(2-fluoropyridin-4-yl)amino]-1H-pyrazole-4-carboxamide Nitrogen was bubbled through a mixture of 3-amino-1-[(1S,2S,4R and 1R,2R,4S)-2-cyano-4-hydroxycyclohexyl]-1H-pyrazole-4-carboxamide (Intermediate #48-1, 200 mg, 0.802 mmol), 4-bromo-2-fluoropyridine (141 mg, 0.802 mmol), $K_3PO_4$ (0.238 g, 1.12 mmol), and X-Phos (115 mg, 0.241 mmol) in dioxane (2.7 mL) for 5 minutes, and then $Pd_2(dba)_3$ (73 mg, 0.080 mmol) was added. The reaction vessel was sealed, and heated to 105° C. After 40 minutes, the reaction mixture was cooled to 23° C. and partitioned between EtOAc and water. The organic layer was washed with saturated aqueous sodium chloride solution, and the washed solution was filtered. The filtrate was concentrated in vacuo and the residue was purified by MPLC on silica gel (using a gradient elution of 60-100% EtOAc/hexanes) to afford the title compound, Example #15. ¹HNMR (500 MHz, CD₃OD): δ 8.20 (s, 1H), 7.89 (d, J=5.4 Hz, 1H), 7.43 (s, 1H), 7.23 (d, J=6.0 Hz, 1H), 4.37 (td, J=11.5, 3.8 Hz, 1H), 4.14-4.11 (m, 1H), 3.70-3.54 (m, 1H), 2.47 (qd, J=13.2, 3.7 Hz, 1H), 2.30-2.26 (m, 1H), 2.04-1.87 (m, 3H), 1.79-1.73 (m, 1H). LRMS (ESI) calc'd for $C_{16}H_{18}N_6O_4$ [M+H]⁺: 345. Found: 345.

Scheme #31

Example #16

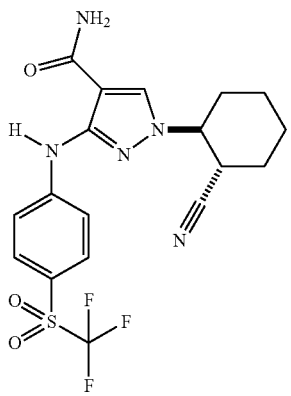

1-[(1S,2S and 1R,2R)-2-cyanocyclohexyl]-3-({4-[(trifluoromethyl)sulfonyl]phenyl}amino)-1H-pyrazole-4-carboxamide Nitrogen was bubbled through a mixture of 3-amino-1-[(1S,2S and 1R,2R)-2-cyanocyclohexyl]-1H-pyrazole-4-carboxamide (Intermediate #48-3, 20.2 g, 87.0 mmol), 1-bromo-4-[(trifluoromethyl)sulfonyl]benzene (27.5 g, 95.0 mmol), K₃PO₄ (27.6 g, 130 mmol), X-Phos (4.54 g, 9.53 mmol), and Pd₂(dba)₃ (3.96 g, 4.33 mmol) in dioxane (202 mL). The reaction mixture was then heated to 80° C. After 3 hours, the reaction mixture was cooled to ambient temperature, diluted with ethyl acetate, and filtered through celite. The crude filtrate was adsorbed onto silica gel, and purified by MPLC on silica gel (eluting with MeOH/DCM). Desired fractions were identified, combined and concentrated in vacuo. The residue was dissolved in ethyl acetate, hexane was then added to the solution, which resulted in recrystallization. The slurry was stirred for 30 minutes, and was then filtered to afford the title compound, Example #16. ¹HNMR (600 MHz, CDCl₃): δ 9.58 (s, 1H), 7.91 (d, J=9.0 Hz, 2H), 7.30 (d, J=9.0 Hz, 2H), 7.73 (s, 1H), 5.59 (s, 2H), 4.06-4.00 (m, 1H), 3.19-3.13 (m, 1H), 2.35 (br d, J=12.0 Hz, 1H), 2.16-2.12 (m, 2H), 2.01 (br d, J=13.2 Hz, 1H), 1.91 (br d, J=11.7 Hz, 1H), 1.78-70 (m, 1H), 1.49-40 (m, 2H). LRMS (ESI) calc'd for $C_{18}H_{19}F_3N_5O_3S$ [M+H]⁺: 442. Found: 442.

Scheme #31

Example #17-1

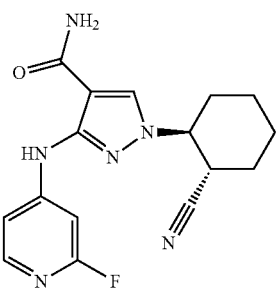 [SMILES: N#C[C@H]1CCCC[C@@H]1n1cc(C(N)=O)c(Nc2ccnc(F)c2)n1]

1-[(1S,2S and 1R,2R)-2-cyanocyclohexyl]-3-[(2-fluoropyridin-4-yl)amino]-1H-pyrazole-4-carboxamide Nitrogen was bubbled through a mixture of 3-amino-1-[(1S,2S and 1R,2R)-2-cyanocyclohexyl]-1H-pyrazole-4-carboxamide (Intermediate #48-3, 4.82 g, 20.7 mmol), 4-bromo-2-fluoropyridine (5.45 g, 31.0 mmol), K₃PO₄ (6.58 g, 31.0 mmol), and X-Phos (2.96 g, 6.20 mmol) in dioxane (67 mL) for 5 minutes, and then Pd₂(dba)₃ (1.89 g, 2.07 mmol) was added. The reaction vessel was sealed, and heated to 100° C. After 4 hours, the reaction mixture was cooled to ambient temperature, and additional portions of X-Phos (500 mg, 1.00 mmol) and Pd₂(dba)₃ (500 mg, 0.540 mmol) were added. The reaction vessel was sealed and heated to 100° C. for an additional 45 minutes, and was then cooled to ambient temperature. The cooled reaction mixture was partitioned between EtOAc and water. The organic layer was washed with saturated aqueous sodium chloride solution, and the washed solution was filtered. The filtrate was concentrated and the residue was purified by MPLC on silica gel (using a gradient elution of 85-100% EtOAc/hexanes) to afford the title compound, Example #17-1.

¹HNMR (500 MHz, CD₃OD): δ 8.18 (s, 1H), 7.90 (d, J=6.0 Hz, 1H), 7.41 (d, J=1.0 Hz, 1H), 7.23 (d, J=5.5 Hz, 1H), 4.31 (td, J=11.5, 3.8 Hz, 1H), 3.32-3.27 (m, 1H), 2.32-2.27 (m, 1H), 2.14-2.08 (m, 1H), 2.02 (qd, J=12.2, 3.7 Hz, 1H), 1.97-1.92 (m, 1H), 1.88-1.74 (m, 2H), 1.59-1.40 (m, 2H). LRMS (ESI) calc'd for $C_{16}H_{18}FN_6O$ [M+H]⁺: 329. Found: 329.

The following examples, disclosed in TABLE 17 were prepared according to Scheme #31 following similar procedures described for Example #17-1, and optionally using the chiral resolution methods described for Examples 42-45 or the chiral Intermediates 50-1 and 50-2 which can be achieved by those of ordinary skill in the art of organic synthesis.

TABLE 17

| Example | Structure | Compound Name | Exact Mass [M + H]+ |
|---|---|---|---|
| 17-2 | 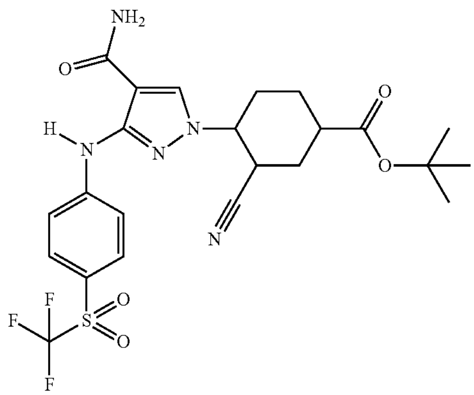 [SMILES: CC(C)(C)OC(=O)C1CCC(n2cc(C(N)=O)c(Nc3ccc(S(=O)(=O)C(F)(F)F)cc3)n2)C(C#N)C1] | tert-butyl 4-[4-carbamoyl-3-({4-[(trifluoromethyl)sulfonyl]phenyl}amino)-1H-pyrazol-1-yl]-3-cyanocyclohexanecarboxylate | Calc'd 542, Found 542 |
| 17-3 | 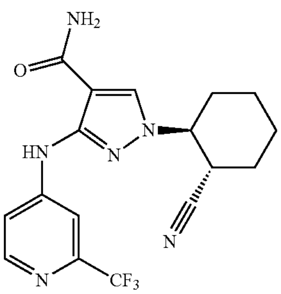 [SMILES: N#C[C@H]1CCCC[C@@H]1n1cc(C(N)=O)c(Nc2ccnc(C(F)(F)F)c2)n1] | 1-[(1S,2S and 1R,2R)-2-Cyanocyclohexyl]-3-{[2-(trifluoromethyl)pyridin-4-yl]amino}-1H-pyrazole-4-carboxamide | Calc'd 379, Found 379 |
| 17-4 | 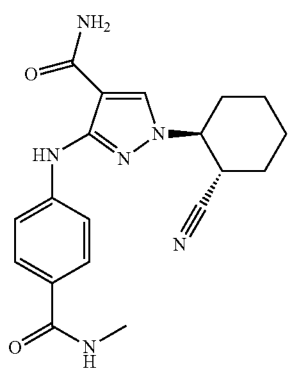 [SMILES: CNC(=O)c1ccc(Nc2nn([C@H]3CCCC[C@@H]3C#N)cc2C(N)=O)cc1] | 1-[(1S,2S and 1R,2R)-2-cyanocyclohexyl]-3-{[4-(methylcarbamoyl)phenyl]amino}-1H-pyrazole-4-carboxamide | Calc'd 367, Found 367 |
| 17-5 | 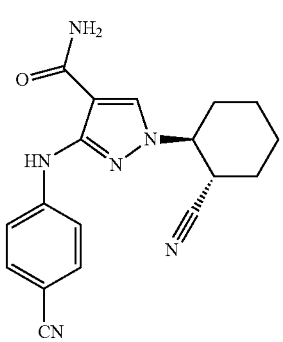 [SMILES: N#Cc1ccc(Nc2nn([C@H]3CCCC[C@@H]3C#N)cc2C(N)=O)cc1] | 1-[(1S,2S and 1R,2R)-2-cyanocyclohexyl]-3-[(4-cyanophenyl)amino]-1H-pyrazole-4-carboxamide | Calc'd 335, Found 335 |

TABLE 17-continued

| Example | Structure | Compound Name | Exact Mass [M + H]+ |
|---|---|---|---|
| 17-6 | 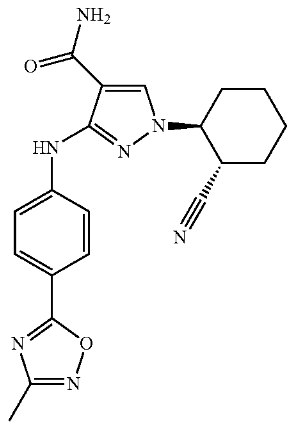 [SMILES: Cc1noc(-c2ccc(Nc3nn([C@H]4CCCC[C@@H]4C#N)cc3C(N)=O)cc2)n1] | 1-[(1S,2S and 1R,2S)-2-cyanocyclohexyl]-3-{[4-(3-methyl-1,2,4-oxadiazol-5-yl)phenyl]amino}-1H-pyrazole-4-carboxamide | Calc'd 392, Found 392 |
| 17-7 | 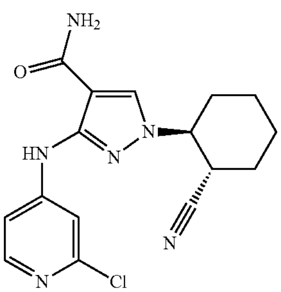 [SMILES: N#C[C@H]1CCCC[C@@H]1n1cc(C(N)=O)c(Nc2ccnc(Cl)c2)n1] | 3-[(2-chloropyridin-4-yl)amino]-1-[(1S,2S and 1R,2R)-2-cyanocyclohexyl]-1H-pyrazole-4-carboxamide | Calc'd 345, Found 345 |
| 17-8 | 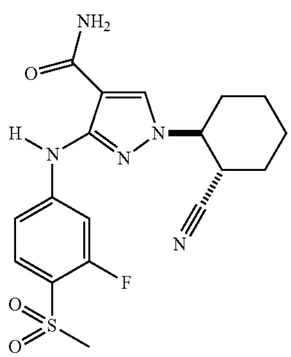 | 1-[(1S,2S and 1R,2R)-2-cyanocyclohexyl]-3-{[3-fluoro-4-(methylsulfonyl)phenyl]amino}-1H-pyrazole-4-carboxamide | Calc'd 406, Found 406 |
| 17-9 | 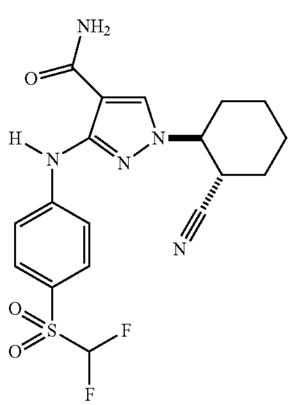 | 1-[(1S,2S and 1R,2R)-2-cyanocyclohexyl]-3-({4-[(difluoromethyl)sulfonyl]phenyl}amino)-1H-pyrazole-4-carboxamide | Calc'd 424, Found 424 |

TABLE 17-continued

| Example | Structure | Compound Name | Exact Mass [M + H]+ |
|---|---|---|---|
| 17-10 | 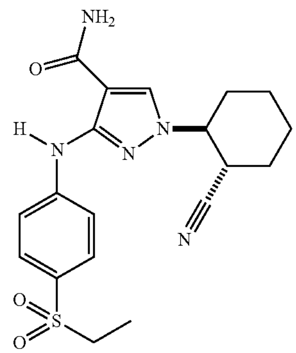 | 1-[(1S,2S and 1R,2R)-2-cyanocyclohexyl]-3-{[4-(ethylsulfonyl)phenyl]amino}-1H-pyrazole-4-carboxamide | Calc'd 402, Found 402 |
| 17-11 | 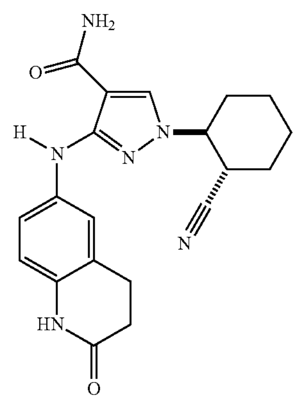 | 1-[(1S,2S and 1R,2R)-2-cyanocyclohexyl]-3-[(2-oxo-1,2,3,4-tetrahydroquinolin-6-yl)amino]-1H-pyrazole-4-carboxamide | Calc'd 379, Found 379 |
| 17-12 | 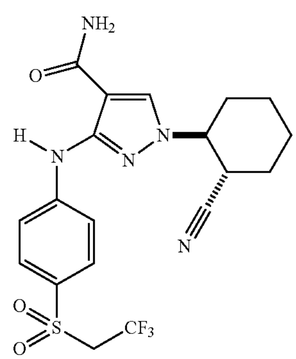 | 1-[(1S,2S and 1R,2R)-2-cyanocyclohexyl]-3-({4-[(2,2,2-trifluoroethyl)sulfonyl]phenyl}amino)-1H-pyrazole-4-carboxamide | Calc'd 456, Found 456 |
| 17-13 | 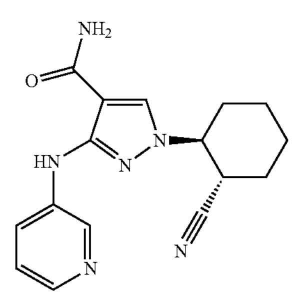 [SMILES: N#C[C@H]1CCCC[C@@H]1n1cc(C(N)=O)c(Nc2cccnc2)n1] | 1-[(1S,2S and 1R,2R)-2-cyanocyclohexyl]-3-(pyridin-3-ylamino)-1H-pyrazole-4-carboxamide | Calc'd 311, Found 311 |

TABLE 17-continued

| Example | Structure | Compound Name | Exact Mass [M + H]+ |
|---|---|---|---|
| 17-14 | 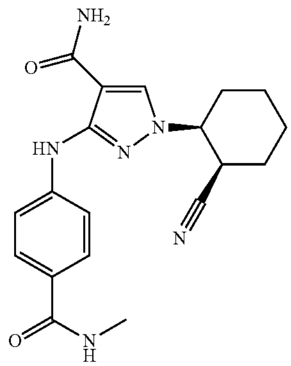 [SMILES: CNC(=O)c1ccc(Nc2nn([C@H]3CCCC[C@H]3C#N)cc2C(N)=O)cc1] | 1-[(1S,2R and 1R,2S)-2-cyanocyclohexyl]-3-{[4-(methylcarbamoyl)phenyl]amino}-1H-pyrazole-4-carboxamide | Calc'd 367, Found 367 |
| 17-15 | 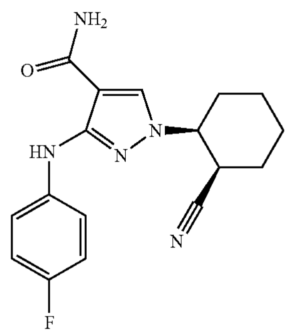 [SMILES: N#C[C@@H]1CCCC[C@@H]1n1cc(C(N)=O)c(Nc2ccc(F)cc2)n1] | 1-[(1S,2R and 1R,2S)-2-cyanocyclohexyl]-3-[(4-fluorophenyl)amino]-1H-pyrazole-4-carboxamide | Calc'd 328, Found 328 |
| 17-16 | 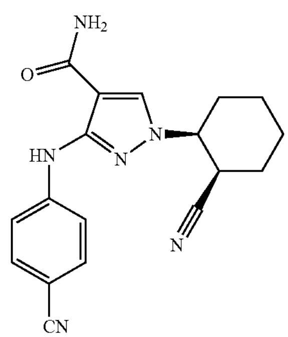 [SMILES: N#Cc1ccc(Nc2nn([C@H]3CCCC[C@H]3C#N)cc2C(N)=O)cc1] | 1-[(1S,2R and 1R,2S)-2-cyanocyclohexyl]-3-[(4-cyanophenyl)amino]-1H-pyrazole-4-carboxamide | Calc'd 335, Found 335 |
| 17-17 | 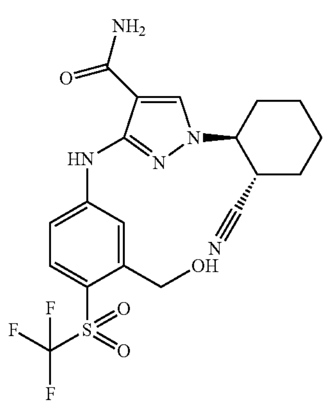 [SMILES: N#C[C@H]1CCCC[C@@H]1n1cc(C(N)=O)c(Nc2ccc(S(=O)(=O)C(F)(F)F)c(CO)c2)n1] | 1-[(1S,2S and 1R,2R)-2-cyanocyclohexyl]-3-({3-(hydroxymethyl)-4-[(trifluoromethyl)sulfonyl]phenyl}amino)-1H-pyrazole-4-carboxamide | Calc'd 472, Found 472 |

TABLE 17-continued

| Example | Compound Name | Exact Mass [M + H]+ |
|---|---|---|
| 17-18 | 1-[(1S,2S and 1R,2R)-2-cyanocyclohexyl]-3-[(4-fluorophenyl)amino]-1H-pyrazole-4-carboxamide | Calc'd 328, Found 328 |
| 17-19 | 1-[(1S,2S or 1R,2R)-2-cyanocyclohexyl]-3-[(6-fluoropyridin-3-yl)amino]-1H-pyrazole-4-carboxamide | Calc'd 329, found 329 |
| 17-20 | 1-[(1S,2S or 1R,2R)-2-cyanocyclohexyl]-3-{[1-oxo-2-(2,2,2-trifluoroethyl)-2,3-dihydro-1H-isoindol-5-yl]amino}-1H-pyrazole-4-carboxamide | Calc'd 447, found 447 |
| 17-21 | 1-[(1R,2R or 1S,2S)-2-cyanocyclohexyl]-3-{[1-oxo-2-(2,2,2-trifluoroethyl)-2,3-dihydro-1H-isoindol-5-yl]amino}-1H-pyrazole-4-carboxamide | Calc'd 447, found 447 |

TABLE 17-continued

| Example | Structure | Compound Name | Exact Mass [M + H]+ |
|---|---|---|---|
| 17-22 | 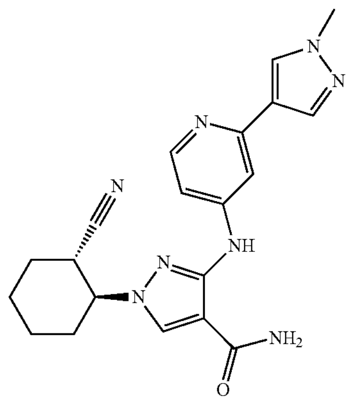 [SMILES: Cn1cc(-c2cc(Nc3nn([C@H]4CCCC[C@@H]4C#N)cc3C(N)=O)ccn2)cn1] | 1-[(1S,2S and 1R,2R)-2-cyanocyclohexyl]-3-{[2-(1-methyl-1H-pyrazol-4-yl)pyridin-4-yl]amino}-1H-pyrazole-4-carboxamide | Calc'd 391, found 391 |
| 17-23 | 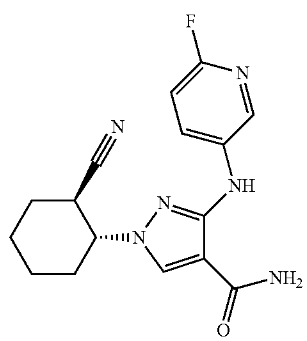 [SMILES: N#C[C@@H]1CCCC[C@H]1n1cc(C(N)=O)c(Nc2ccc(F)nc2)n1] | 1-[(1R,2R or 1S,2S)-2-cyanocyclohexyl]-3-[(6-fluoropyridin-3-yl)amino]-1H-pyrazole-4-carboxamide | Calc'd 329., found 329 |
| 17-24 | 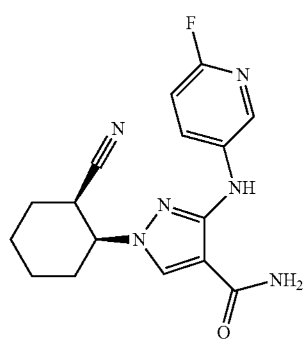 [SMILES: N#C[C@@H]1CCCC[C@@H]1n1cc(C(N)=O)c(Nc2ccc(F)nc2)n1] | 1-[(1S,2R and 1R,2S)-2-cyanocyclohexyl]-3-[(6-fluoropyridin-3-yl)amino]-1H-pyrazole-4-carboxamide | Calc'd 329, found 329 |
| 17-25 | 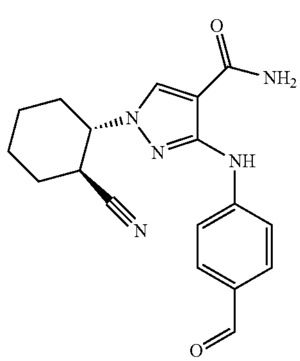 [SMILES: N#C[C@H]1CCCC[C@@H]1n1cc(C(N)=O)c(Nc2ccc(C=O)cc2)n1] | 1-[(1S,2S or 1R,2R)-2-cyanocyclohexyl]-3-[(4-formylphenyl)amino]-1H-pyrazole-4-carboxamide | Calc'd 338, found 338 |

TABLE 17-continued

| Example | Compound Name | Exact Mass [M + H]+ |
|---|---|---|
| 17-26 | 3-[(4-bromophenyl)amino]-1-[(1S,2S or 1R,2R)-2-cyanocyclohexyl]-1H-pyrazole-4-carboxamide | Calc'd 388, found 388 |
| 17-27 | 3-[(4-acetylphenyl)amino]-1-[(1S,2S or 1R,2R)-2-cyanocyclohexyl]-1H-pyrazole-4-carboxamide | Calc'd 352, found 352 |
| 17-28 | 1-[(1R,2R or 1S,2S)-2-cyanocyclohexyl]-3-({4-[(2S or 2R)-3,3,3-trifluoro-2-hydroxy-1,1-dimethylpropyl]phenyl}amino)-1H-pyrazole-4-carboxamide | Calc'd 450, found 450 |
| 17-29 | 1-[(1S,2S or 1R,2R)-2-cyanocyclohexyl]-3-({4-[(2S or 2R)-3,3,3-trifluoro-2-hydroxy-1,1-dimethylpropyl]phenyl}amino)-1H-pyrazole-4-carboxamide | Calc'd 450, found 450 |

TABLE 17-continued

| Example | Structure | Compound Name | Exact Mass [M + H]+ |
|---|---|---|---|
| 17-30 | 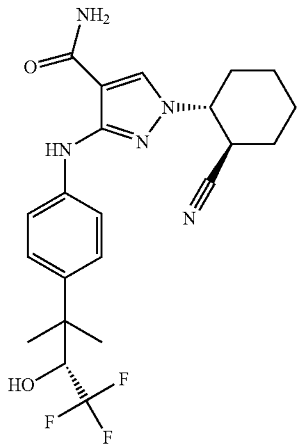 [SMILES: CC(C)(c1ccc(Nc2nn([C@@H]3CCCC[C@H]3C#N)cc2C(N)=O)cc1)[C@@H](O)C(F)(F)F] | 1-[(1R,2R or 1S,2S)-2-cyanocyclohexyl]-3-({4-[(2R or 2S)-3,3,3-trifluoro-2-hydroxy-1,1-dimethylpropyl]phenyl}amino)-1H-pyrazole-4-carboxamide | Calc'd 450, found 450 |
| 17-31 | 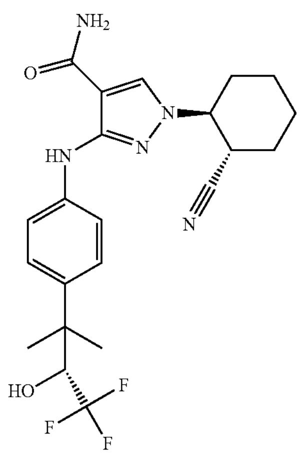 [SMILES: CC(C)(c1ccc(Nc2nn([C@H]3CCCC[C@@H]3C#N)cc2C(N)=O)cc1)[C@@H](O)C(F)(F)F] | 1-[(1S,2S or 1R,2R)-2-cyanocyclohexyl]-3-({4-[(2R or 2S)-3,3,3-trifluoro-2-hydroxy-1,1-dimethylpropyl]phenyl}amino)-1H-pyrazole-4-carboxamide | Calc'd 450, found 450 |
| 17-32 | 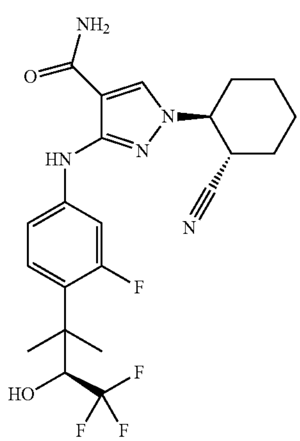 [SMILES: CC(C)(c1ccc(Nc2nn([C@H]3CCCC[C@@H]3C#N)cc2C(N)=O)cc1F)[C@H](O)C(F)(F)F] | 1-[(1S,2S or 1R,2R)-2-cyanocyclohexyl]-3-({3-fluoro-4-[(2S or 2R)-3,3,3-trifluoro-2-hydroxy-1,1-dimethylpropyl]phenyl}amino)-1H-pyrazole-4-carboxamide | Calc'd 468, found 468 |

TABLE 17-continued

| Example | Structure | Compound Name | Exact Mass [M + H]+ |
|---|---|---|---|
| 17-33 | 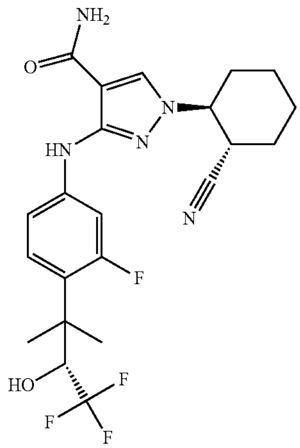 [SMILES: CC(C)(c1ccc(Nc2nn([C@H]3CCCC[C@@H]3C#N)cc2C(N)=O)cc1F)[C@@H](O)C(F)(F)F] | 1-[(1S,2S or 1R,2R)-2-cyanocyclohexyl]-3-({3-fluoro-4-[(2R or 2S)-3,3,3-trifluoro-2-hydroxy-1,1-dimethylpropyl]phenyl}amino)-1H-pyrazole-4-carboxamide | Calc'd 468, found 468 |
| 17-34 | 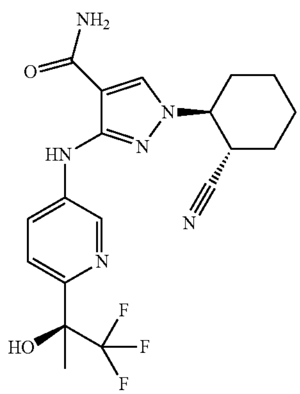 [SMILES: C[C@](O)(c1ccc(Nc2nn([C@H]3CCCC[C@@H]3C#N)cc2C(N)=O)cn1)C(F)(F)F] | 1-[(1S,2S or 1R,2R)-2-cyanocyclohexyl]-3-({6-[(1S or 1R)-2,2,2-trifluoro-1-hydroxy-1-methylethyl]pyridin-3-yl}amino)-1H-pyrazole-4-carboxamide | Calc'd 423, found 423 |
| 17-35 | 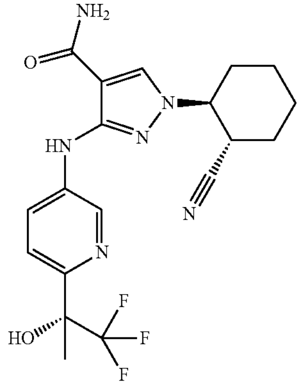 [SMILES: C[C@@](O)(c1ccc(Nc2nn([C@H]3CCCC[C@@H]3C#N)cc2C(N)=O)cn1)C(F)(F)F] | 1-[(1S,2S or 1R,2R)-2-cyanocyclohexyl]-3-({6-[(1R or 1S)-2,2,2-trifluoro-1-hydroxy-1-methylethyl]pyridin-3-yl}amino)-1H-pyrazole-4-carboxamide | Calc'd 423, found 423 |

TABLE 17-continued

| Example | Structure | Compound Name | Exact Mass [M + H]+ |
|---|---|---|---|
| 17-36 | 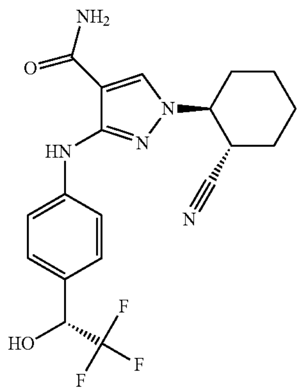 [SMILES: N#C[C@H]1CCCC[C@@H]1n1cc(C(N)=O)c(Nc2ccc([C@@H](O)C(F)(F)F)cc2)n1] | 1-[(1S,2S or 1R,2R)-2-cyanocyclohexyl]-3-({4-[(1R or 1S)-2,2,2-trifluoro-1-hydroxyethyl]phenyl}amino)-1H-pyrazole-4-carboxamide | Calc 408, found 498 |
| 17-37 | 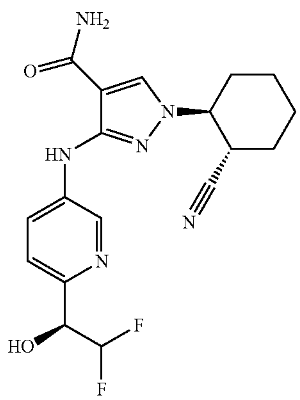 [SMILES: N#C[C@H]1CCCC[C@@H]1n1cc(C(N)=O)c(Nc2ccc([C@H](O)C(F)F)nc2)n1] | 1-[(1S,2S or 1R,2R)-2-cyanocyclohexyl]-3-({6-[(1S or 1R)-2,2-difluoro-1-hydroxyethyl]pyridin-3-yl}amino)-1H-pyrazole-4-carboxamide | Calc'd 391, found 391 |
| 17-38 | 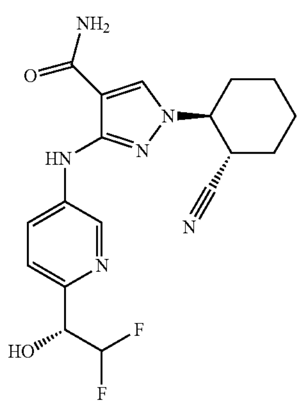 [SMILES: N#C[C@H]1CCCC[C@@H]1n1cc(C(N)=O)c(Nc2ccc([C@@H](O)C(F)F)nc2)n1] | 1-[(1S,2S or 1R,2R)-2-cyanocyclohexyl]-3-({6-[(1R or 1S)-2,2-difluoro-1-hydroxyethyl]pyridin-3-yl}amino)-1H-pyrazole-4-carboxamide | Calc'd 391, found 391 |
| 17-39 | 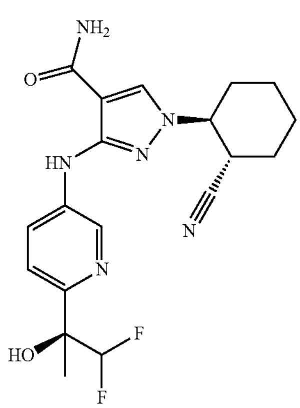 [SMILES: C[C@](O)(c1ccc(Nc2nn([C@H]3CCCC[C@@H]3C#N)cc2C(N)=O)cn1)C(F)F] | 1-[(1S,2S or 1R,2R)-2-cyanocyclohexyl]-3-({6-[(1S or 1R)-2,2-difluoro-1-hydroxy-1-methylethyl]pyridin-3-yl}amino)-1H-pyrazole-4-carboxamide | Calc'd 405, found 405 |

TABLE 17-continued

| Example | Structure | Compound Name | Exact Mass [M + H]+ |
|---|---|---|---|
| 17-40 | 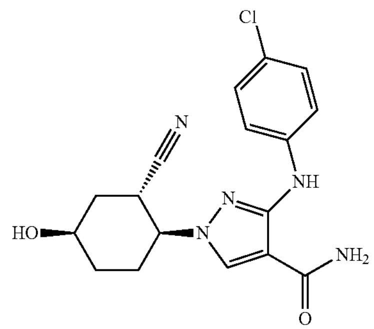 [SMILES: N#C[C@H]1C[C@H](O)CC[C@@H]1n1cc(C(N)=O)c(Nc2ccc(Cl)cc2)n1] | 1-[(1S,2S or 1R,2R)-2-cyanocyclohexyl]-3-({6-[(1R or 1S)-2,2-difluoro-1-hydroxy-1-methylethyl]pyridin-3-yl}amino)-1H-pyrazole-4-carboxamide | Calc'd 405, found 405 |
| 17-41 | 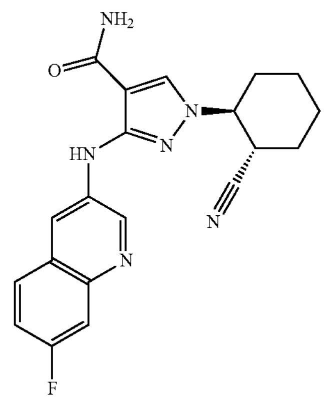 [SMILES: N#C[C@H]1CCCC[C@@H]1n1cc(C(N)=O)c(Nc2cnc3cc(F)ccc3c2)n1] | 1-[(1S,2S or 1R,2R)-2-cyanocyclohexyl]-3-[(7-fluoroquinolin-3-yl)amino]-1H-pyrazole-4-carboxamide | Calc'd 379.0, found 379 |
| 17-42 | 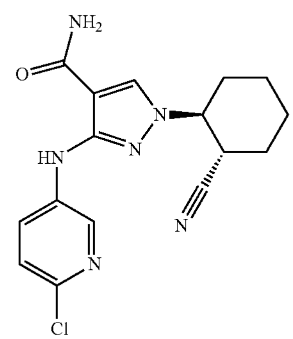 [SMILES: N#C[C@H]1CCCC[C@@H]1n1cc(C(N)=O)c(Nc2ccc(Cl)nc2)n1] | 3-[(6-chloropyridin-3-yl)amino]-1-[(1S,2S or 1R,2R)-2-cyanocyclohexyl]-1H-pyrazole-4-carboxamide | Calc'd 345, found 345 |
| 17-43 | 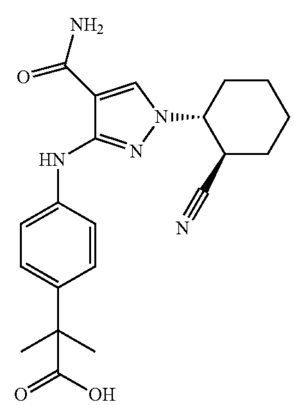 [SMILES: CC(C)(C(=O)O)c1ccc(Nc2nn([C@@H]3CCCC[C@H]3C#N)cc2C(N)=O)cc1] | 2-[4-({4-carbamoyl-1-[(1R,2R or 1S,2S)-2-cyanocyclohexyl]-1H-pyrazol-3-yl}amino)phenyl]-2-methylpropanoic acid | Calc'd 396, found 396 |

TABLE 17-continued

| Example | Structure | Compound Name | Exact Mass [M + H]+ |
|---|---|---|---|
| 17-44 | 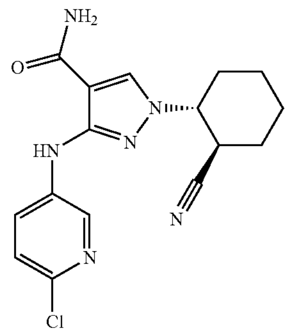 [SMILES: N#C[C@@H]1CCCC[C@H]1n1cc(C(N)=O)c(Nc2ccc(Cl)nc2)n1] | 3-[(6-chloropyridin-3-yl)amino]-1-[(1R,2R or 1S,2S)-2-cyanocyclohexyl]-1H-pyrazole-4-carboxamide | Calc'd 345, found 345 |
| 17-45 | 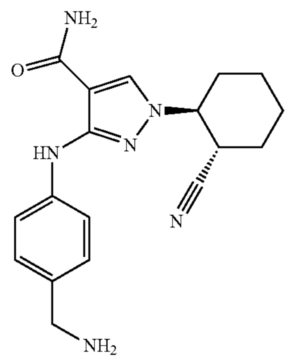 [SMILES: N#C[C@H]1CCCC[C@@H]1n1cc(C(N)=O)c(Nc2ccc(CN)cc2)n1] | 3-{[4-(aminomethyl)phenyl]amino}-1-[(1S,2S and 1R,2R)-2-cyanocyclohexyl]-1H-pyrazole-4-carboxamide | Calc'd 339, found [M − NH₂] 322 |
| 17-46 | 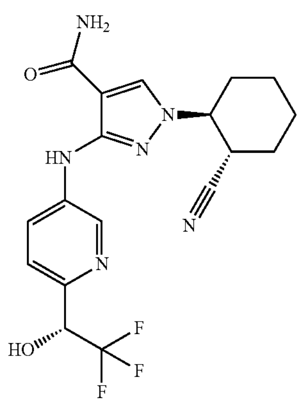 [SMILES: N#C[C@H]1CCCC[C@@H]1n1cc(C(N)=O)c(Nc2ccc([C@@H](O)C(F)(F)F)nc2)n1] | 1-[(1S,2S or 1R,2R)-2-cyanocyclohexyl]-3-({6-[(1R or 1S)-2,2,2-trifluoro-1-hydroxyethyl]pyridin-3-yl}amino)-1H-pyrazole-4-carboxamide | Calc'd 409, found 409 |
| 17-47 | 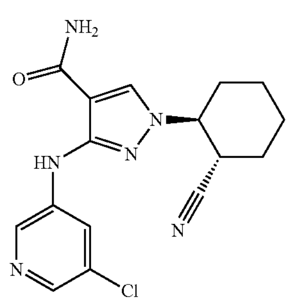 [SMILES: N#C[C@H]1CCCC[C@@H]1n1cc(C(N)=O)c(Nc2cncc(Cl)c2)n1] | 3-[(5-chloropyridin-3-yl)amino]-1-[(1S,2S or 1R,2R)-2-cyanocyclohexyl]-1H-pyrazole-4-carboxamide | Calc'd 345, found 345 |

TABLE 17-continued

| Example | Compound Name | Exact Mass [M + H]+ |
|---|---|---|
| 17-48 | 1-[(1S,2S or 1R,2R)-2-cyanocyclohexyl]-3-[(6-fluoroquinolin-3-yl)amino]-1H-pyrazole-4-carboxamide | Calc'd 379, found 379 |
| 17-49 | 1-[(1S,2S or 1R,2R)-2-cyanocyclohexyl]-3-[(3,4-dichlorophenyl)amino]-1H-pyrazole-4-carboxamide | Calc'd 378, found 378 |
| 17-50 | 1-[(1S,2S or 1R,2R)-2-cyanocyclohexyl]-3-({6-[(1S or 1R)-2,2,2-trifluoro-1-hydroxyethyl]pyridin-3-yl}amino)-1H-pyrazole-4-carboxamide | Calc'd 409, found 409 |
| 17-51 | 3-[(3-chloro-5-fluorophenyl)amino]-1-[(1S,2S or 1R,2R)-2-cyanocyclohexyl]-1H-pyrazole-4-carboxamide | Calc'd 362, found 362 |

TABLE 17-continued

| Example | Structure | Compound Name | Exact Mass [M + H]+ |
|---|---|---|---|
| 17-52 | | 3-[(4-chloro-3-fluorophenyl)amino]-1-[(1S,2S or 1R,2R)-2-cyanocyclohexyl]-1H-pyrazole-4-carboxamide | Calc'd 362, found 362 |
| 17-52 | | 2-[4-({4-carbamoyl-1-[(1S,2S or 1R,2R)-2-cyanocyclohexyl]-1H-pyrazol-3-yl}amino)phenyl]-2-methylpropanoic acid | Calc'd 396, found 396 |
| 17-53 | 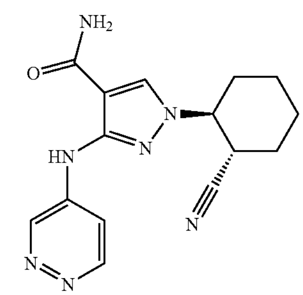 | 1-[(1S,2S or 1R,2R)-2-cyanocyclohexyl]-3-(pyridazin-4-ylamino)-1H-pyrazole-4-carboxamide | Calc'd 312, found 312 |
| 17-54 | 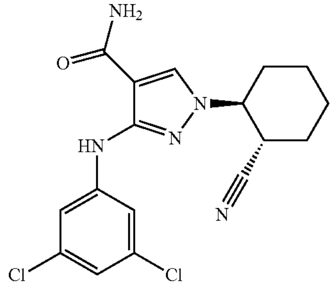 [SMILES: N#C[C@H]1CCCC[C@@H]1n1cc(C(N)=O)c(Nc2cc(F)cc(Cl)c2)n1] | 1-[(1S,2S or 1R, 2R)-2-cyanocyclohexyl]-3-[(3,5-dichlorophenyl)amino]-1H-pyrazole-4-carboxamide | Calc'd 378, found 378 |

TABLE 17-continued

| Example | Structure | Compound Name | Exact Mass [M + H]+ |
|---|---|---|---|
| 17-55 | 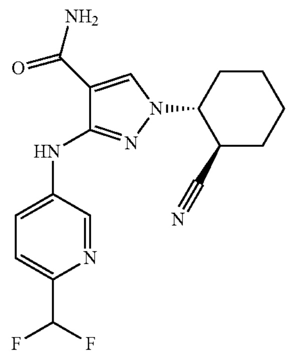 [SMILES: N#C[C@@H]1CCCC[C@H]1n1cc(C(N)=O)c(Nc2ccc(C(F)F)nc2)n1] | 1-[(1R,2R or 1S,2S)-2-cyanocyclohexyl]-3-{[6-(difluoromethyl)pyridin-3-yl]amino}-1H-pyrazole-4-carboxamide | Calc'd 361, found 361 |
| 17-56 | 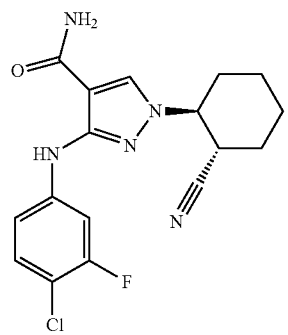 [SMILES: N#C[C@H]1CCCC[C@@H]1n1cc(C(N)=O)c(Nc2ccc(Cl)c(F)c2)n1] | 3-[(4-chloro-3-fluorophenyl)amino]-1-[(1S,2S and 1R,2R)-2-cyanocyclohexyl]-1H-pyrazole-4-carboxamide | Calc'd 362, found 362 |
| 17-57 | 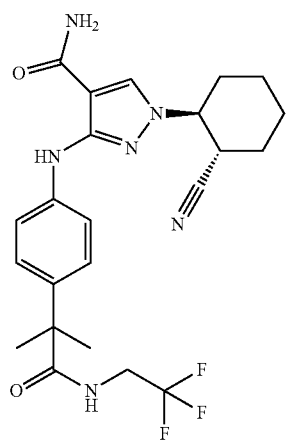 [SMILES: CC(C)(C(=O)NCC(F)(F)F)c1ccc(Nc2nn([C@H]3CCCC[C@@H]3C#N)cc2C(N)=O)cc1] | 1-[(1S,2S or 1R,2R)-2-cyanocyclohexyl]-3-[(4-{1,1-dimethyl-2-oxo-2-[(2,2,2-trifluoroethyl)amino]ethyl}phenyl)amino]-1H-pyrazole-4-carboxamide | Calc'd 477, found 477 |
| 17-58 | 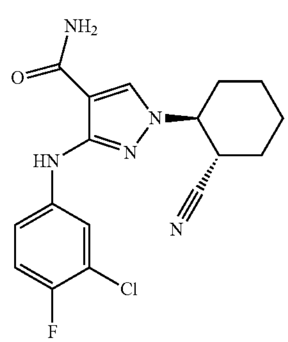 [SMILES: N#C[C@H]1CCCC[C@@H]1n1cc(C(N)=O)c(Nc2ccc(F)c(Cl)c2)n1] | 3-[(3-chloro-4-fluorophenyl)amino]-1-[(1S,2S and 1R,2R)-2-cyanocyclohexyl]-1H-pyrazole-4-carboxamide | Calc'd 362, found 362 |

TABLE 17-continued

| Example | Structure | Compound Name | Exact Mass [M + H]+ |
|---|---|---|---|
| 17-59 | 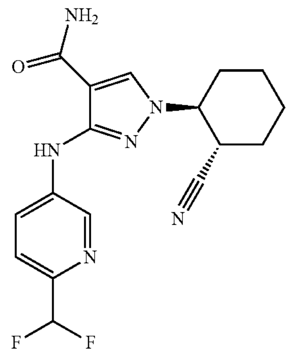 [SMILES: N#C[C@H]1CCCC[C@@H]1n1cc(C(N)=O)c(Nc2ccc(C(F)F)nc2)n1] | 1-[(1S,2S or 1R,2R)-2-cyanocyclohexyl]-3-{[6-(difluoromethyl)pyridin-3-yl]amino}-1H-pyrazole-4-carboxamide | Calc'd 361, found 361 |
| 17-60 | 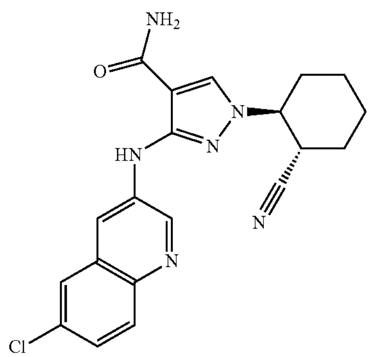 [SMILES: N#C[C@H]1CCCC[C@@H]1n1cc(C(N)=O)c(Nc2cnc3ccc(Cl)cc3c2)n1] | 3-[(6-chloroquinolin-3-yl)amino]-1-[(1S,2S or 1R,2R)-2-cyanocyclohexyl]-1H-pyrazole-4-carboxamide | Calc'd 395, found 395 |
| 17-61 | 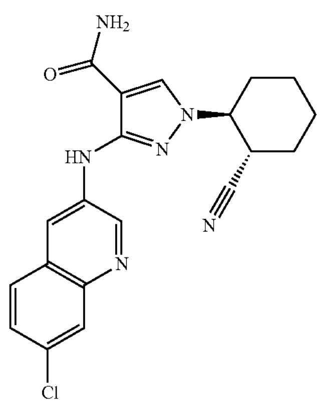 | 3-[(7-chloroquinolin-3-yl)amino]-1-[(1S,2S or 1R,2R)-2-cyanocyclohexyl]-1H-pyrazole-4-carboxamide | Calc'd 395, found 395 |
| 17-62 | 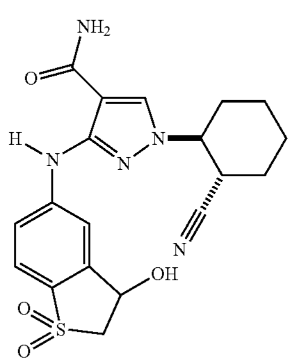 | 1-[(1S,2S and 1R,2R)-2-cyanocyclohexyl]-3-[(3-hydroxy-1,1-dioxido-2,3-dihydro-1-benzothiophen-5-yl)amino]-1H-pyrazole-4-carboxamide | Calc'd 416, Found 416 |

TABLE 17-continued

| Example | Compound Name | Exact Mass [M + H]+ |
|---|---|---|
| 17-63 | 1-[(1S,2S and 1R,2R)-2-cyanocyclohexyl]-3-[(1,1-dioxido-1-benzothiophen-5-yl)amino]-1H-pyrazole-4-carboxamide | Calc'd 398, Found 398 |
| 17-64 | 1-[(1S,2S and 1R,2R )-2-cyanocyclohexyl]-3-({4-[(difluoromethyl)sulfonyl]-3-(hydroxymethyl)phenyl}amino)-1H-pyrazole-4-carboxamide | Calc'd 454, Found 454 |
| 17-65 | 1-[(1S,2S and 1R,2R)-2-cyanocyclohexyl]-3-({4-[(fluoromethyl)sulfonyl]phenyl}amino)-1H-pyrazole-4-carboxamide | Calc'd 406, Found 406 |
| 17-66 | 1-[(1R,2R or 1S,2S)-2-cyanocyclohexyl]-3-({4-[(cyclopropylmethyl)sulfamoyl]phenyl}amino)-1H-pyrazole-4-carboxamide | Calc'd 443, found 443 |

TABLE 17-continued

| Example | Compound Name | Exact Mass [M + H]+ |
|---------|---------------|---------------------|
| 17-67 | 1-[(1R,2R or 1S,2S)-2-cyanocyclohexyl]-3-{[4-(pyridin-2-ylsulfamoyl)phenyl]amino}-1H-pyrazole-4-carboxamide | Calc'd 466.0, found 466 |
| 17-68 | 1-[(1R,2R or 1S,2S)-2-cyanocyclohexyl]-3-({4-[(2-morpholin-4-ylethyl)sulfamoyl]phenyl}amino)-1H-pyrazole-4-carboxamide | Calc'd 502, found 502 |
| 17-69 | 3-({4-[(4-benzylpiperidin-1-yl)sulfonyl]phenyl}amino)-1-[(1R,2R or 1S,2S)-2-cyanocyclohexyl]-1H-pyrazole-4-carboxamide | Calc'd 547, found 547 |

| Example | Structure | Compound Name | Exact Mass [M + H]+ |
|---|---|---|---|
| 17-70 | 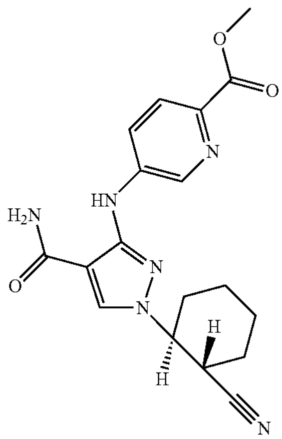 | methyl 5-({4-carbamoyl-1-[(1R,2R or 1S,2S)-2-cyanocyclohexyl]-1H-pyrazol-3-yl}amino)pyridine-2-carboxylate | Calc'd 369, found 369 |
| 17-71 | 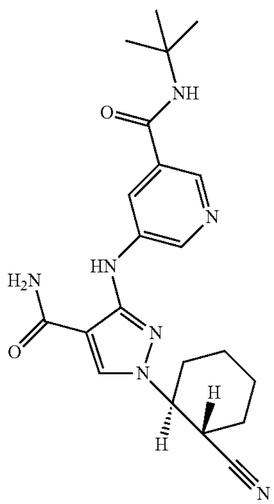 | N-tert-butyl-5-({4-carbamoyl-1-[(1R,2R or 1S,2S)-2-cyanocyclohexyl]-1H-pyrazol-3-yl}amino)pyridine-3-carboxamide | Calc'd 410, found 410 |
| 17-72 | 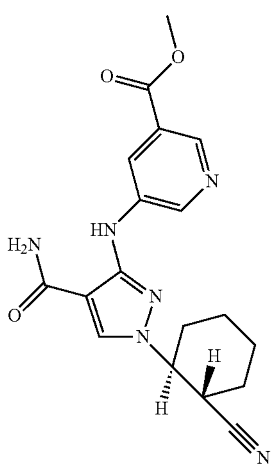 | methyl 5-({4-carbamoyl-1-[(1R,2R or 1S,2S)-2-cyanocyclohexyl]-1H-pyrazol-3-yl}amino)pyridine-3-carboxylate | Calc'd 369, found 369 |

TABLE 17-continued

| Example | Structure | Compound Name | Exact Mass [M + H]+ |
|---|---|---|---|
| 17-73 | 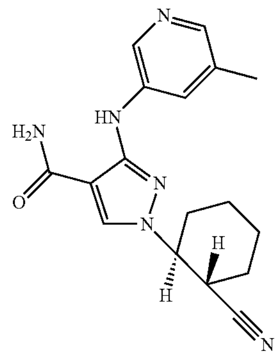 | 1-[(1S,2S)-2-cyanocyclohexyl]-3-[(5-methylpyridin-3-yl)amino]-1H-pyrazole-4-carboxamide | Calc'd 325, found 325 |
| 17-74 | 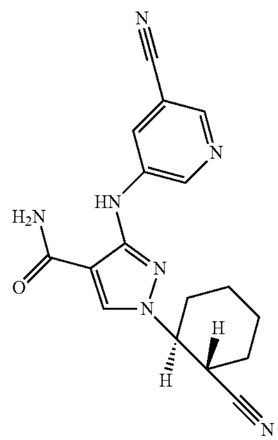 | 1-[(1R,2R or 1S,2S)-2-cyanocyclohexyl]-3-[(5-cyanopyridin-3-yl)amino]-1H-pyrazole-4-carboxamide | Calc'd 336, found 336 |
| 17-75 | 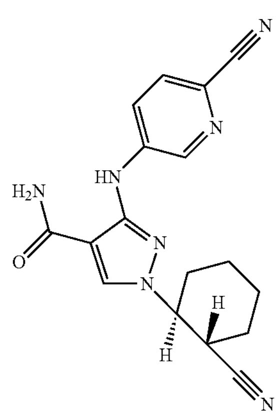 | 1-[(1R,2R or 1S,2S)-2-cyanocyclohexyl]-3-[(6-cyanopyridin-3-yl)amino]-1H-pyrazole-4-carboxamide | Calc'd 336, found 336 |

TABLE 17-continued

| Example | Structure | Compound Name | Exact Mass [M + H]+ |
|---|---|---|---|
| 17-76 | 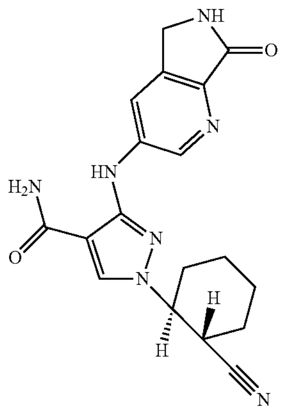 | 1-[(1R,2R or 1S,2S)-2-cyanocyclohexyl]-3-[(7-oxo-6,7-dihydro-5H-pyrrolo[3,4-b]pyridin-3-yl)amino]-1H-pyrazole-4-carboxamide | Calc'd 366, found 366 |
| 17-77 | 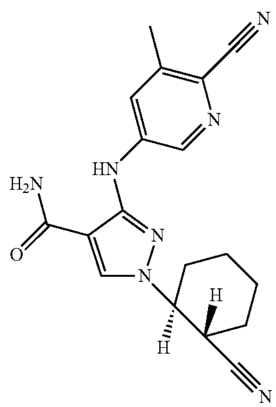 | 1-[(1R,2R or 1S,2S)-2-cyanocyclohexyl]-3-[(6-cyano-5-methylpyridin-3-yl)amino]-1H-pyrazole-4-carboxamide | Calc'd 350, found 350 |
| 17-78 | 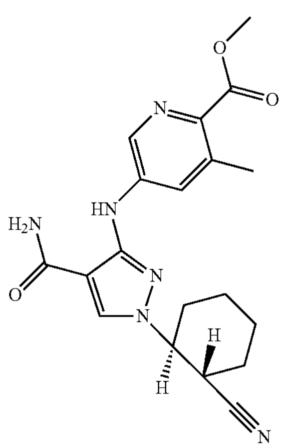 | methyl 5-({4-carbamoyl-1-[(1R,2R or 1S,2S)-2-cyanocyclohexyl]-1H-pyrazol-3-yl}amino)-3-methylpyridine-2-carboxylate | Calc'd 383, found 383 |

TABLE 17-continued

| Example | Structure | Compound Name | Exact Mass [M + H]+ |
|---|---|---|---|
| 17-79 | 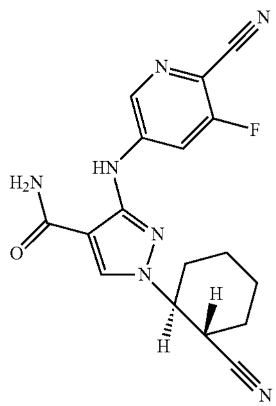 | 1-[(1R,2R or 1S,2S)-2-cyanocyclohexyl]-3-[(6-cyano-5-fluoropyridin-3-yl)amino]-1H-pyrazole-4-carboxamide | Calc'd 354, found 354 |
| 17-80 | 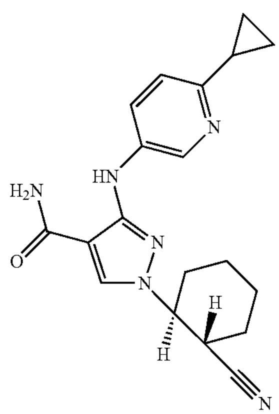 | 1-[(1R,2R or 1S,2S)-2-cyanocyclohexyl]-3-[(6-cyclopropylpyridin-3-yl)amino]-1H-pyrazole-4-carboxamide | Calc'd 351, found 351 |
| 17-81 | 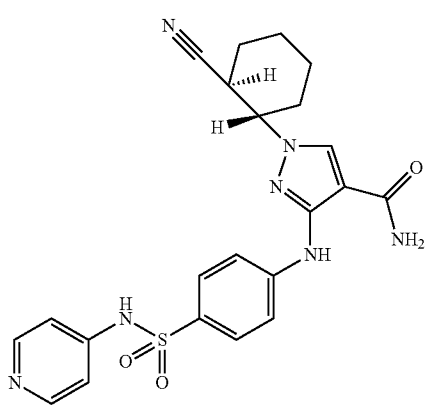 | 1-[(1R,2R or 1S,2S)-2-cyanocyclohexyl]-3-{[4-(pyridin-4-ylsulfamoyl)phenyl]amino}-1H-pyrazole-4-carboxamide | Calc'd 466, found 466 |

TABLE 17-continued

| Example | Structure | Compound Name | Exact Mass [M + H]+ |
|---|---|---|---|
| 17-82 | 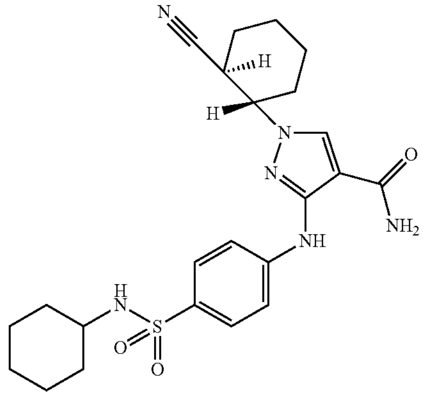 | 1-[(1R,2R or 1S,2S)-2-cyanocyclohexyl]-3-{[4-(cyclohexylsulfamoyl)phenyl]amino}-1H-pyrazole-4-carboxamide | Calc'd 471, found 471 |
| 17-83 | 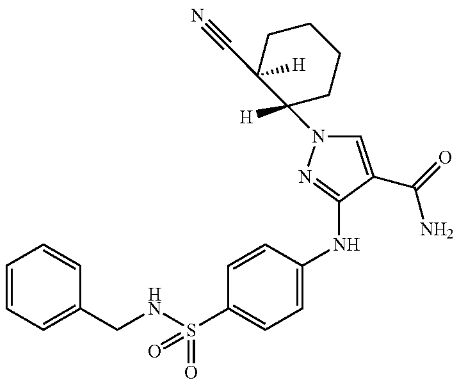 | 3-{[4-(benzylsulfamoyl)phenyl]amino}-1-[(1R,2R or 1S,2S)-2-cyanocyclohexyl]-1H-pyrazole-4-carboxamide | Calc'd 479, found 479 |
| 17-84 | 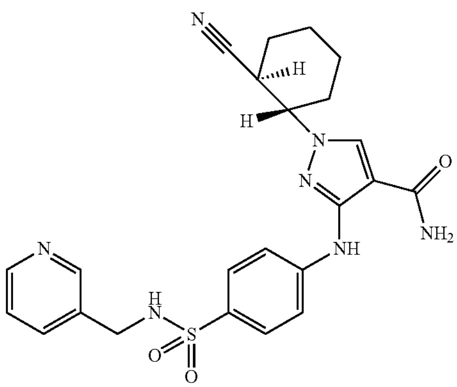 | 1-[(1R,2R or 1S,2S)-2-cyanocyclohexyl]-3-({4-[(pyridin-3-ylmethyl)sulfamoyl]phenyl}amino)-1H-pyrazole-4-carboxamide | Calc'd 480, found 480 |
| 17-85 | 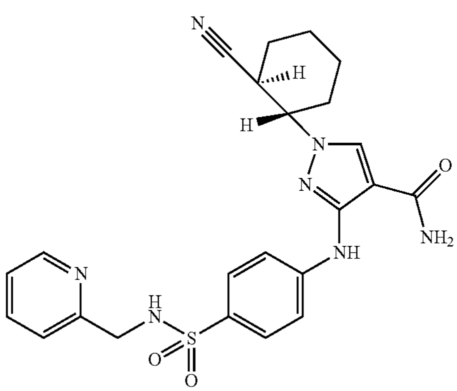 | 1-[(1R,2R or 1S,2S)-2-cyanocyclohexyl]-3-({4-[(pyridin-2-ylmethyl)sulfamoyl]phenyl}amino)-1H-pyrazole-4-carboxamide | Calc'd 480, found 480 |

TABLE 17-continued

| Example | Structure | Compound Name | Exact Mass [M + H]+ |
|---|---|---|---|
| 17-86 | 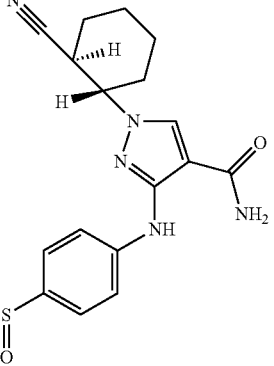 | 1-[(1R,2R or 1S,2S)-2-cyanocyclohexyl]-3-({4-[(pyridin-4-ylmethyl)sulfamoyl]phenyl}amino)-1H-pyrazole-4-carboxamide | Calc'd 480, found 480 |
| 17-87 | 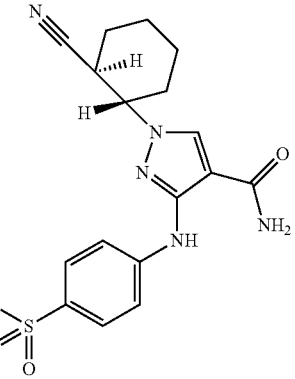 | 1-[(1R,2R or 1S,2S)-2-cyanocyclohexyl]-3-({4-[(2-pyrrolidin-1-ylethyl)sulfamoyl]phenyl}amino)-1H-pyrazole-4-carboxamide | Calc'd 486, found 486 |
| 17-88 | 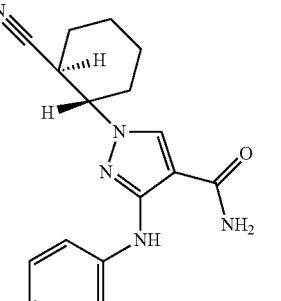 | 1-[(1R,2R or 1S,2S)-2-cyanocyclohexyl]-3-({4-[(2,6-dimethylphenyl)sulfamoyl]phenyl}amino)-1H-pyrazole-4-carboxamide | Calc'd 493, found 493 |
| 17-89 | 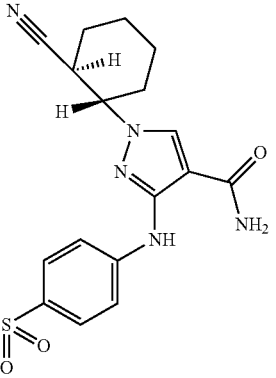 | 3-({4-[(4-acetylpiperazin-1-yl)sulfonyl]phenyl}amino)-1-[(1R,2R or 1S,2S)-2-cyanocyclohexyl]-1H-pyrazole-4-carboxamide | Calc'd 500, found 500 |

TABLE 17-continued

| Example | Compound Name | Exact Mass [M + H]+ |
|---|---|---|
| 17-90 | 3-({4-[(4-chlorobenzyl)sulfamoyl]phenyl}amino)-1-[(1R,2R or 1S,2S)-2-cyanocyclohexyl]-1H-pyrazole-4-carboxamide | Calc'd 513, found 513 |
| 17-91 | 3-({4-[(2-chlorobenzyl)sulfamoyl]phenyl}amino)-1-[(1R,2R or 1S,2S)-2-cyanocyclohexyl]-1H-pyrazole-4-carboxamide | Calc'd 513, found 513 |
| 17-92 | 1-[(1R,2R or 1S,2S)-2-cyanocyclohexyl]-3-{[4-(1,4-dioxa-8-azaspiro[4.5]dec-8-ylsulfonyl)phenyl]amino}-1H-pyrazole-4-carboxamide | Calc'd 515, found 515 |
| 17-93 | 1-[(1R,2R or 1S,2S)-2-cyanocyclohexyl]-3-({4-[(1-methylethyl)sulfamoyl]phenyl}amino)-1H-pyrazole-4-carboxamide | Calc'd 431, found 431 |

TABLE 17-continued

| Example | Structure | Compound Name | Exact Mass [M + H]+ |
|---|---|---|---|
| 17-94 | 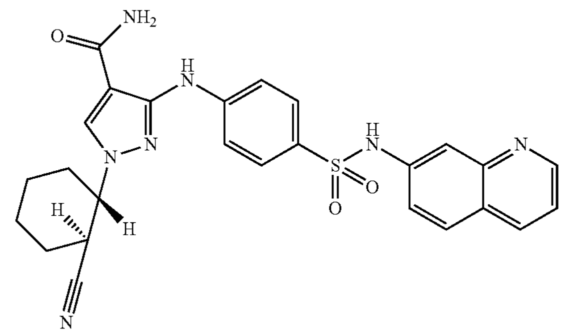 | 1-[(1R,2R or 1S,2S)-2-cyanocyclohexyl]-3-{[4-(quinolin-7-ylsulfamoyl)phenyl]amino}-1H-pyrazole-4-carboxamide | Calc'd 516, found 516 |
| 17-95 | 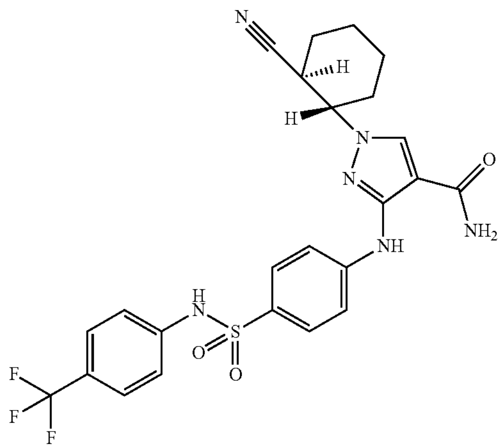 | 1-[(1R,2R or 1S,2S)-2-cyanocyclohexyl]-3-[(4-{[4-(trifluoromethyl)phenyl]sulfamoyl}phenyl)amino]-1H-pyrazole-4-carboxamide | Calc'd 533, found 533 |
| 17-96 | 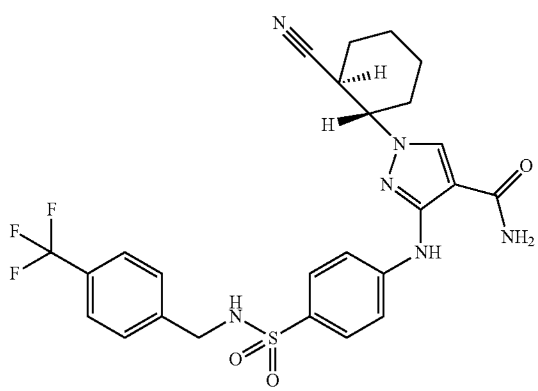 | 1-[(1R,2R or 1S,2S)-2-cyanocyclohexyl]-3-[(4-{[4-(trifluoromethyl)benzyl]sulfamoyl}phenyl)amino]-1H-pyrazole-4-carboxamide | Calc'd 547, found 547 |
| 17-97 | 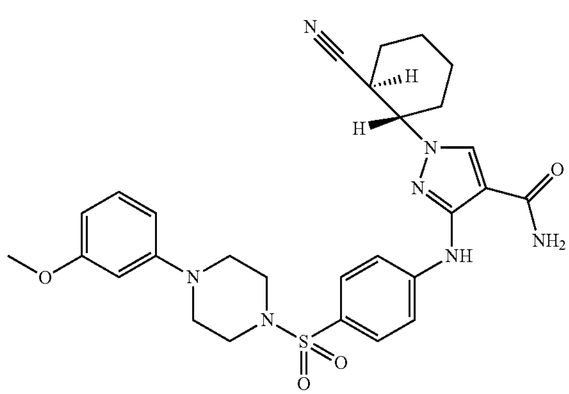 | 1-[(1R,2R or 1S,2S)-2-cyanocyclohexyl]-3-[(4-{[4-(3-methoxyphenyl)piperazin-1-yl]sulfonyl}phenyl)amino]-1H-pyrazole-4-carboxamide | Calc'd 564, found 564 |

TABLE 17-continued

| Example | Structure | Compound Name | Exact Mass [M + H]+ |
|---|---|---|---|
| 17-98 | 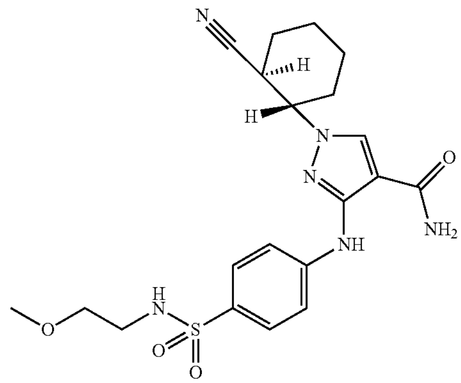 | 1-[(1R,2R or 1S,2S)-2-cyanocyclohexyl]-3-({4-[(2-methoxyethyl)sulfamoyl]phenyl}amino)-1H-pyrazole-4-carboxamide | Calc'd 447, found 447 |
| 17-99 | 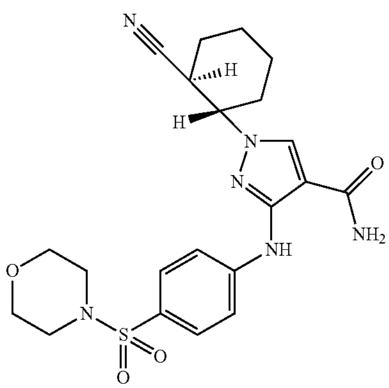 | 1-[(1R,2R or 1S,2S)-2-cyanocyclohexyl]-3-{[4-(morpholin-4-ylsulfonyl)phenyl]amino}-1H-pyrazole-4-carboxamide | Calc'd 459, found 459 |
| 17-100 | 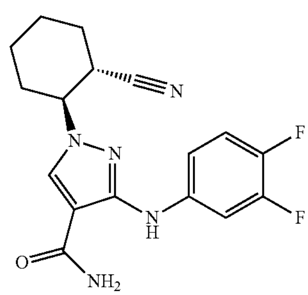 [SMILES: N#C[C@H]1CCCC[C@@H]1n1cc(C(N)=O)c(Nc2ccc(F)c(F)c2)n1] | 1-[(1S,2S and 1R,2R)-2-cyanocyclohexyl]-3-[(3,4-difluorophenyl)amino]-1H-pyrazole-4-carboxamide | Calc'd 346, found 346 |
| 17-101 | 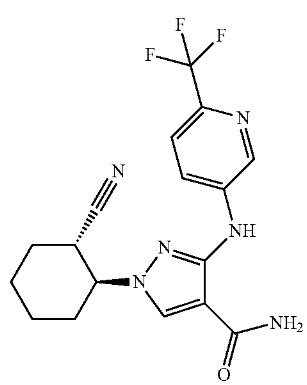 [SMILES: N#C[C@H]1CCCC[C@@H]1n1cc(C(N)=O)c(Nc2ccc(C(F)(F)F)nc2)n1] | 1-[(1S,2S or 1R,2R)-2-cyanocyclohexyl]-3-{[6-(trifluoromethyl)pyridin-3-yl]amino}-1H-pyrazole-4-carboxamide | Calc'd 379, found 379 |

TABLE 17-continued

| Example | Structure | Compound Name | Exact Mass [M + H]+ |
|---|---|---|---|
| 17-102 | 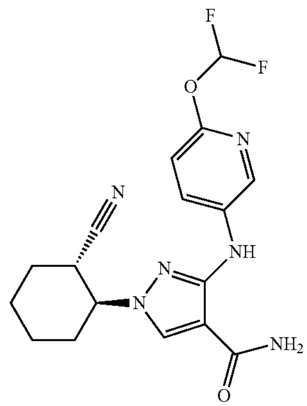 [SMILES: N#C[C@H]1CCCC[C@@H]1n1cc(C(N)=O)c(Nc2ccc(OC(F)F)nc2)n1] | 1-[(1S,2S and 1R,2R)-2-cyanocyclohexyl]-3-{[6-(difluoromethoxy)pyridin-3-yl]amino}-1H-pyrazole-4-carboxamide | Calc'd 377, found 377 |
| 17-103 | 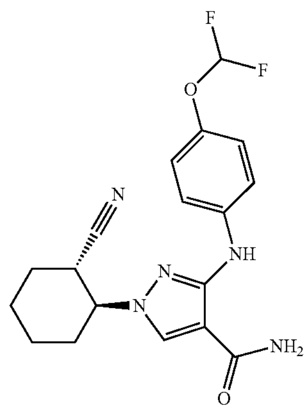 [SMILES: N#C[C@H]1CCCC[C@@H]1n1cc(C(N)=O)c(Nc2ccc(OC(F)F)cc2)n1] | 1-[(1S,2S or 1R,2R)-2-cyanocyclohexyl]-3-{[4-(difluoromethoxy)phenyl]amino}-1H-pyrazole-4-carboxamide | Calc'd 376, found 376 |
| 17-104 | 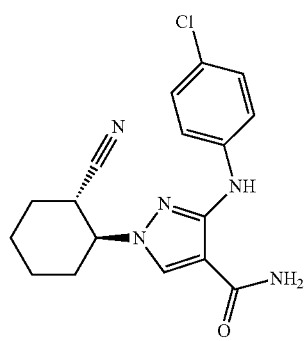 [SMILES: N#C[C@H]1CCCC[C@@H]1n1cc(C(N)=O)c(Nc2ccc(Cl)cc2)n1] | 3-[(4-chlorophenyl)amino]-1-[(1S,2S and 1R,2R)-2-cyanocyclohexyl]-1H-pyrazole-4-carboxamide | Calc'd 344, found 344 |
| 17-105 | 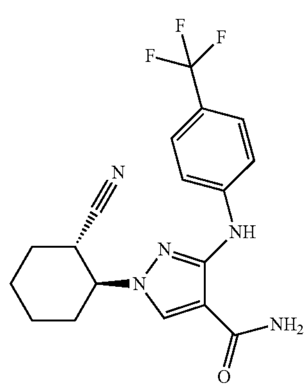 [SMILES: N#C[C@H]1CCCC[C@@H]1n1cc(C(N)=O)c(Nc2ccc(C(F)(F)F)cc2)n1] | 1-[(1S,2S or 1R,2R)-2-cyanocyclohexyl]-3-{[4-(trifluoromethyl)phenyl]amino}-1H-pyrazole-4-carboxamide | Calc'd 378, found 378 |

TABLE 17-continued

| Example | Compound Name | Exact Mass [M + H]+ |
|---|---|---|
| 17-106 | 1-[(1S,2S or 1R,2R)-2-cyanocyclohexyl]-3-{[4-(trifluoromethoxy)phenyl]amino}-1H-pyrazole-4-carboxamide | Calc'd 394, found 394 |
| 17-107 | 3-[(4-chlorophenyl)amino]-1-[(1S,2S or 1R,2R)-2-cyanocyclohexyl]-1H-pyrazole-4-carboxamide | Calc'd 344, found 344 |
| 17-108 | 3-[(4-chlorophenyl)amino]-1-[(1S,2S or 1R,2R)-2-cyanocyclohexyl]-1H-pyrazole-4-carboxamide | Calc'd 344, found 344 |
| 17-109 | 1-[(1S,2S or 1R,2R)-2-cyanocyclohexyl]-3-{[6-(trifluoromethyl)pyridin-3-yl]amino}-1H-pyrazole-4-carboxamide | Calc'd 379, found 379 |

Scheme #56

Example #18

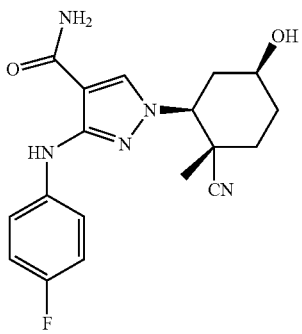 [SMILES: C[C@]1(C#N)CC[C@H](O)C[C@@H]1n1cc(C(N)=O)c(Nc2ccc(F)cc2)n1]

Step A: 1-((1S,2S and 1R,2R)-2-Cyano-2-methyl-5-oxocyclohexyl)-3-((4-fluorophenyl)amino)-1H-pyrazole-4-carboxamide

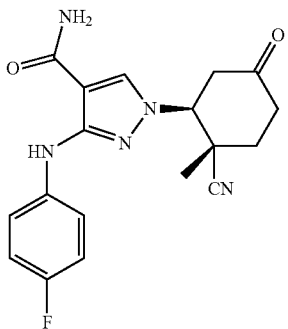 [SMILES: C[C@]1(C#N)CCC(=O)C[C@@H]1n1cc(C(N)=O)c(Nc2ccc(F)cc2)n1]

DBU (1.0 mL, 6.7 mmol) was added to a mixture of 1-methyl-4-oxocyclohex-2-enecarbonitrile (1.00 g, 5.18 mmol) and 3-[(4-fluorophenyl)amino]-1H-pyrazole-4-carboxamide (Intermediate #44-7, 1.14 g, 5.18 mmol) in ethanol (2 mL). The reaction mixture was stirred for 3 hours at 23° C., and was then adsorbed onto silica gel in vacuo and purified by MPLC on silica gel (using a gradient elution of 0 to 10% MeOH/DCM). Desired fractions were identified, combined and concentrated in vacuo (23° C. water bath) to afford the title compound. LRMS (ESI) calc'd for $C_{18}H_{19}FN_5O_2$ [M+H]$^+$: 356. Found: 356.

Step B: 1-((1S,2S,5S and 1R,2R,5R)-2-Cyano-5-hydroxy-2-methylcyclohexyl)-3-((4-fluorophenyl)amino)-1H-pyrazole-4-carboxamide Sodium borohydride (10 mg, 0.27 mmol) was added to a solution of 1-((1S,2S and 1R,2R)-2-cyano-2-methyl-5-oxocyclohexyl)-3-((4-fluorophenyl)amino)-1H-pyrazole-4-carboxamide (48 mg, 0.14 mmol) in THF (0.68 mL) and methanol (0.68 mL) at ambient temperature. The reaction mixture was stirred for 5 minutes at ambient temperature, and then concentrated in vacuo. The residue was partitioned between EtOAc and saturated aqueous sodium bicarbonate solution. The organic layer was washed with brine, and the washed solution was dried over anhydrous sodium sulfate. The dried solution was filtered, and the filtrate was concentrated in vacuo to afford the title compound. $^1$H NMR (500 MHz, CD$_3$OD): δ 8.15 (s, 1H), 7.55-7.52 (m, 2H), 6.96 (t, J=9.0 Hz, 2H), 4.55 (dd, J=10.5, 5.0 Hz, 1H), 3.83-3.77 (m, 1H), 2.24-1.90 (m, 5H), 1.59-1.51 (m, 1H), 1.30 (s, 3H). LRMS (ESI) calc'd for $C_1H_{21}FN_5O_2$ [M+H]$^+$: 358. Found: 358.

Scheme #56

Example #19-1 and 19-2

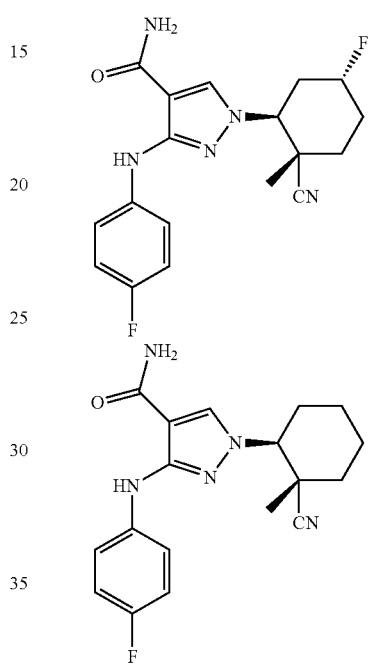

1-((1S,2S,5R and 1R,2R,5S)-2-cyano-5-fluoro-2-methylcyclohexyl)-3-((4-fluorophenyl)amino)-1H-pyrazole-4-carboxamide and 1-((1S,2S and 1R,2R)-2-cyano-2-methylcyclohexyl)-3-((4-fluorophenyl)amino)-1H-pyrazole-4-carboxamide BAST (47 mg, 0.21 mmol) was added to a mixture of 1-((1S,2S,5S and 1R,2R,5R)-2-cyano-5-hydroxy-2-methylcyclohexyl)-3-((4-fluorophenyl)amino)-1H-pyrazole-4-carboxamide (38 mg, 0.11 mmol) in DCM (2.1 mL) at 0° C. The cooling bath was removed and the reaction mixture was allowed to warm to ambient temperature. 20 minutes after the addition of BAST, the reaction mixture was partitioned between EtOAc and saturated aqueous sodium bicarbonate solution. The organic layer was washed with brine, and the washed solution was dried over anhydrous sodium sulfate. The dried solution was filtered, and the filtrate was concentrated in vacuo to afford a mixture of olefin isomers and a fluorinated product. The crude reaction product (36 mg, 0.11 mmol) was dissolved in THF (2.1 mL), and palladium (10% on carbon, 45 mg, 0.040 mmol) was added. The flask was equipped with a three-way adapter with outlets to vacuum and a hydrogen balloon. The reaction mixture was alternately evacuated and filled with hydrogen gas three times, then allowed to stir under hydrogen at ambient temperature for 4 hours. The reaction mixture was filtered through cotton, and the filtrate was concentrated in vacuo. The residue was purified by reverse-phase HPLC (using a gradient elution of MeCN/water, with 0.1% v/v TFA modifier). Desired fractions were identified, combined, neutralized with saturated aqueous NaHCO$_3$ and extracted with EtOAc. The organic layer was dried over anhydrous Na$_2$SO$_4$, filtered, and concentrated in vacuo to afford the title compounds.

Example 19-1

First product to elute from reverse phase HPLC; 1-((1S,2S, 5R and 1R,2R,5S)-2-cyano-5-fluoro-2-methylcyclohexyl)-3-((4-fluorophenyl)amino)-1H-pyrazole-4-carboxamide. $^1$H NMR (500 MHz, CD$_3$OD): δ 8.15 (s, 1H), 7.51 (dd, J=9.0, 4.5 Hz, 2H), 6.97 (t, J=8.7 Hz, 2H), 5.17 (br d, J=48.0 Hz, 1H), 4.73 (dd, J=11.0, 4.5 Hz, 1H), 2.60 (dddd, J=36.0, 14.5, 11.5, 3.0 Hz, 1H), 2.33-2.27 (m, 2H), 2.09-1.93 (m, 3H), 1.39 (s, 3H). LRMS (ESI) calc'd for C$_{18}$H$_{20}$F$_2$N$_5$O [M+H]$^+$: 360. Found: 360.

Example 19-2

Second product to elute from reverse phase HPLC; 1-((1S, 2S and 1R,2R)-2-cyano-2-methylcyclohexyl)-3-((4-fluorophenyl)amino)-1H-pyrazole-4-carboxamide. $^1$H NMR (500 MHz, CDCl$_3$): δ 8.68 (s, 1H), 7.71 (s, 1H), 7.51-7.48 (m, 2H), 6.97 (t, J=8.7 Hz, 2H), 5.56 (br s, 2H), 4.21 (dd, J=11.0, 3.7 Hz, 1H), 2.35-2.27 (m, 1H), 2.15 (dt, J=14.0, 3.2 Hz, 1H), 2.06-1.92 (m, 2H), 1.74-1.47 (m, 4H), 1.36 (s, 3H). LRMS (ESI) calc'd for C$_{18}$H$_{21}$FN$_5$O [M+H]$^+$: 342. Found: 342.

Scheme #30

Example #20

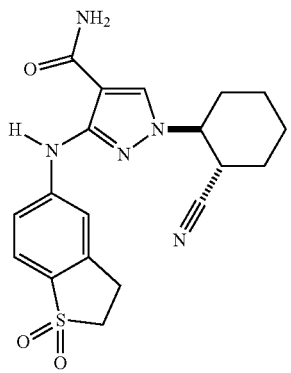

1-[(1S,2S and 1R,2R)-2-Cyanocyclohexyl]-3-[(1,1-dioxido-2,3-dihydro-1-benzothiophen-5-yl)amino]-1H-pyrazole-4-carboxamide

[(1S,2S and 1R,2R)-2-Cyanocyclohexyl]-3-[(1,1-dioxido-1-benzothiophen-5-yl)amino]-1H-pyrazole-4-carboxamide (Example #17-82, 0.11 g, 0.28 mmol) was dissolved in 1:1 EtOAc:EtOH (55 mL) and added to a Parr shaker. 10% Palladium on activated carbon (0.03 g, 0.03 mmol) was added and the resulting mixture was subjected to alternating vacuum and H$_2$ gas (4×). The mixture was then allowed to shake under an atmosphere of H$_2$ (50 psi) for 1.5 hours. The mixture was then subjected to alternating vacuum and N$_2$ gas (4×). The mixture was filtered through celite and rinsed with DCM. The filtrate was concentrated in vacuo, and the residue was purified by MPLC on silica gel (using a gradient elution of 0-60% EtOAc/hexanes followed by a gradient elution of 0-10% MeOH/DCM). Desired fractions were identified, combined, and concentrated in vacuo to afford the title compound, Example #20. $^1$H NMR (500 MHz, CDCl$_3$): δ 9.29 (s, 1H), 7.77 (s, 1H), 7.60 (s, 2H), 7.48 (s, 1H), 5.22 (br s, 2H), 4.05-3.95 (m, 1H), 3.48 (t, J=7.1 Hz, 2H), 3.34 (t, J=7.1 Hz, 2H), 3.20-3.10 (m, 1H), 2.35-2.28 (m, 1H), 2.15-1.90 (m, 3H), 1.90-1.80 (m, 1H), 1.78-1.64 (m, 1H), 1.50-1.30 (m, 2H). LRMS (ESI) calc'd for C$_{19}$H$_{21}$N$_5$O$_3$S [M+H]$^+$: 400. Found: 400.

Scheme #24

Example #21-1

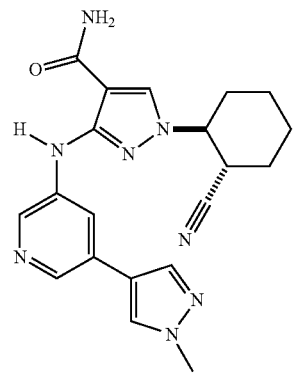

1-[(1S,2S or 1R,2R)-2-Cyanocyclohexyl]-3-{[5-(1-methyl-1H-pyrazol-4-yl)pyridin-3-yl]amino}-1H-pyrazole-4-carboxamide

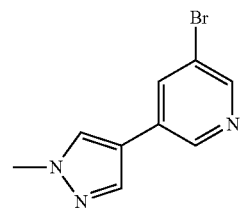

Step A:
3-Bromo-5-(1-methyl-1H-pyrazol-4-yl)pyridine 3,5-Dibromopyridine (500 mg, 2.11 mmol), 1-methyl-4-(4,4,5,5-tetramethyl-1,3,2-dioxaborolan-2-yl)-1H-pyrazole (400 mg, 1.9 mmol), 1,1'bis(diphenylphosphino)ferrocene-palladium(II)dichloride dichloromethane complex (172 mg, 0.211 mmol), and potassium phosphate tribasic (1.34 g, 6.33 mmol) were combined in a 20 mL microwave vial and dissolved in dioxane (9 mL) and water (1 mL). The vial was sealed and flushed with argon. The reaction mixture was stirred at 90° C. for 2 hours. The vial was then cooled to ambient temperature and diluted with ethyl acetate. The organic layer was washed with water, brine, and then dried over anhydrous magnesium sulfate. The solution was then filtered and concentrated in vacuo. The crude material was purified by MPLC on silica gel (using a gradient elution of 0-10% MeOH/DCM) to afford the title compound. $^1$H NMR (500 MHz, CDCl$_3$) δ 8.58 (s, 1H), 8.44 (s, 1H), 7.82 (s, 1H), 7.72 (s, 1H), 7.63 (s, 1H), 3.91 (s, 3H). LRMS (ESI) calc'd for C$_9$H$_8$BrN$_3$ [M+H]$^+$: 238. Found: 238.

Step B: 1-((1S,2S or 1R,2R)-2-Cyanocyclohexyl)-3-((5-(1-methyl-1H-pyrazol-4-yl)pyridin-3-yl)amino)-1H-pyrazole-4-carboxamide 3-Bromo-5-(1-methyl-1H-pyrazol-4-yl)pyridine (51 mg, 0.21 mmol), 3-amino-1-((1S,2S or 1R,2R)-2-cyanocyclohexyl)-1H-pyrazole-4-carboxamide (50 mg, 0.21 mmol), Pd$_2$(dba)$_3$ (20 mg, 0.021 mmol), 2-di-t-butylphosphino-3,4,5,6-teramethyl-2',4',6'-triisopropylbiphenyl (31 mg, 0.064 mmol), and K$_3$PO$_4$ (136 mg, 0.643 mmol) were combined in a 4 mL vial and mixed with 1,4-dioxane (1.0 mL). The vial was capped and flushed with argon. The reaction was stirred at 90° C. for 16 hours and then cooled to ambient temperature and diluted with ethyl acetate. The organic layer was then washed with water and brine, dried over anhydrous magnesium sulfate, filtered, and concentrated in vacuo. The crude residue was purified using mass-triggered reverse phase preparative HPLC (MeCN/water, with 0.1% v/v TFA modifier) to give the title compound as a trifluoroacetate salt. $^1$H NMR (500 MHz, DMSO-d$_6$) δ 9.65 (s, 1H), 9.10 (s, 1H), 8.61 (s, 1H), 8.57 (s, 1H), 8.37 (s, 1H), 8.33 (s, 1H), 8.07 (s, 1H), 7.83 (br, 1H), 7.32 (br, 1H), 4.49-4.44 (m, 1H), 3.89 (s, 3H), 3.36-3.31 (m, 1H), 2.18-2.15 (m, 1H), 2.02-1.99 (m 1H), 1.89-1.70 (m, 4H), 1.50-1.42 (m, 1H), 1.35-1.28 (m, 1H). LRMS (ESI) calc'd for C$_{20}$H$_{22}$N$_8$O [M+H]$^+$: 391. Found: 391.

The following compounds found in TABLE 18 were prepared according to Scheme #26 following similar procedures described for Example #21-1, which can be achieved by those of ordinary skill in the art of organic synthesis.

TABLE 18

| Example | Structure | Compound Name | Exact Mass [M + H]$^+$ |
|---|---|---|---|
| 21-2 | 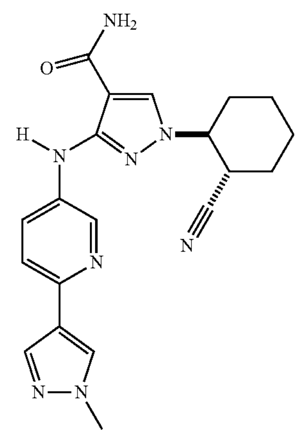 | 1-[(1S,2S and 1R,2R)-2-cyanocyclohexyl]-3-{[6-(1-methyl-1H-pyrazol-4-yl)pyridin-3-yl]amino)-1H-pyrazole-4-carboxamide | Cal'd 391, Found 391 |
| 21-3 | 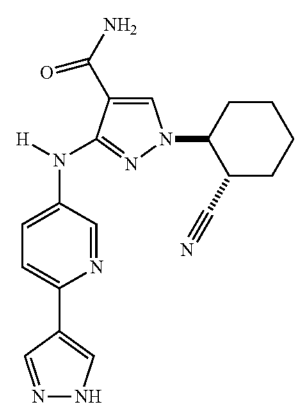 | 1-[(1S,2S and 1R,2R)-2-cyanocyclohexyl]-3-{[6-(1H-pyrazol-4-yl)pyridin-3-yl]amino}-1H-pyrazole-4-carboxamide | Cal'd 377, Found 377 |

Scheme #33

Example #22-1 and 22-2

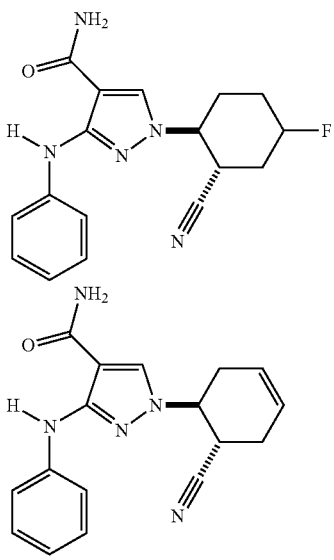

1-[(1S,2S and 1R,2R)-2-Cyano-4-fluorocyclohexyl]-3-(phenylamino)-1H-pyrazole-4-carboxamide and 1-[(1S,6S)-6-cyanocyclohex-3-en-1-yl]-3-(phenylamino)-1H-pyrazole-4-carboxamide 1-[(1S,2S,4R and 1R,2R,4S)-2-Cyano-4-hydroxycyclohexyl]-3-(phenylamino)-1H-pyrazole-4-carboxamide (25 mg, 0.077 mmol) was dissolved in DCM (0.77 mL) and cooled to −78° C. BAST (0.014 mL, 0.077 mmol) was added to the reaction mixture and it was allowed to stir at −78° C. for 1 hour. The reaction mixture was then partitioned between saturated aqueous $NaHCO_3$ and EtOAc. The organic layer was washed with brine, dried over anhydrous $Na_2SO_4$, filtered, and concentrated in vacuo. The residue was dissolved in DMSO (2 mL) and purified by mass-triggered reverse phase preparative HPLC (MeCN/water, with 0.1% v/v TFA modifier). Desired fractions were identified, combined, and lyophilized to afford the title compounds,

Example #22-1

1-[(1S,2S and 1R,2R)-2-Cyano-4-fluorocyclohexyl]-3-(phenylamino)-1H-pyrazole-4-carboxamide: $^1$H NMR (DMSO-$d_6$): δ 9.15 (br s, 1H), 8.21 (s, 1H), 7.69 (br s, 1H), 7.49 (d, J=8.5 Hz, 2H), 7.23 (dd, J=7.5, 7.5 Hz. 2H), 7.16 (br s, 1H), 6.82 (dd, J=7.0, 7.0 Hz, 1H), 4.77 (ddddd, J=48, 10.5, 10.5, 4.5, 4.5 Hz, 1H), 4.51 (ddd, J=10.5, 10.5, 5.5 Hz, 1H), 3.53 (dd, J=11.5, 11.5 Hz, 1H), 2.18-1.90 (m, 5H), 1.70 (m, 1H). LRMS (ESI) calc'd for $C_{17}H_{18}FN_5O$ [M+H]$^+$: 328. Found: 328.

Example #22-2

1-[(1S,6S)-6-cyanocyclohex-3-en-1-yl]-3-(phenylamino)-1H-pyrazole-4-carboxamide: $^1$H NMR (500 MHz, DMSO-$d_6$): δ 9.16 (s, 1H); 8.25 (s, 1H); 7.69 (s, 1H); 7.50 (d, J=8.0 Hz, 2H); 7.24 (t, J=7.7 Hz, 2H); 7.15 (s, 1H); 6.81 (t, J=7.3 Hz, 1H); 5.69-5.73 (m, 2H); 4.66 (td, J=10.3, 5.7 Hz, 1H); 3.52 (td, J=10.5, 5.9 Hz, 1H); 2.40-2.70 (m, 4H). LRMS (ESI) calc'd for $C_{17}H_{18}FN_5O$ [M+H]$^+$: 308. Found: 308.

Scheme #33

Example #23-1

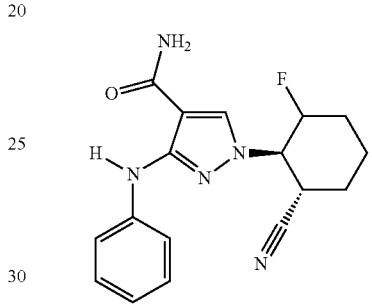

1-[(1R,2S and 1S,2R)-2-Cyano-6-fluorocyclohexyl]-3-(phenylamino)-1H-pyrazole-4-carboxamide A solution of 3-anilino-1-[(1R,2S,6R and 1S,2R,6S)-2-cyano-6-hydroxycyclohexyl]-1H-pyrazole-4-carboxamide (Example #2-6, 43 mg, 0.13 mmol) in DCM was cooled to 0° C. and allowed to stir. BAST (0.12 mL, 0.66 mmol) was added to the mixture, and then the cooling bath was removed. The reaction mixture was allowed to stir at ambient temperature for 3 hours. The reaction mixture was then partitioned between EtOAc and saturated aqueous $NaHCO_3$. The organic layer was washed with brine, dried over anhydrous $Na_2SO_4$, filtered, and concentrated in vacuo. The residue was purified by MPLC on silica gel (using a gradient elution of 60-100%, EtOAc/hexanes) to afford the title compound, Example #23-1. $^1$HNMR (600 MHz, CDCl$_3$): δ 8.66 (s, 1H), 7.69 (d, J=1.8 Hz, 1H), 7.53 (dd, J=8.7, 0.9 Hz, 2H), 7.26 (t, J=8.4 Hz, 2H), 6.88 (t, J=7.5 Hz, 1H), 5.50 (br s, 2H), 5.10-5.01 (m, 1H), 4.40 (ddd, J=28.2, 12.0, 1.8 Hz, 1H), 3.34 (td, J=12.0, 3.6 Hz, 1H), 2.38-2.34 (m, 1H), 2.24-2.19 (m, 1H), 1.82 (qd, J=12.0, 3.9 Hz, 1H), 1.76-1.60 (m, 3H). LRMS (ESI) calc'd for $C_{17}H_{19}FN_5O$ [M+H]$^+$: 328. Found: 328.

The following compounds found in TABLE 19 were prepared according to Scheme #33 following similar procedures described for Example #23-1, which can be achieved by those of ordinary skill in the art of organic synthesis.

TABLE 19

| Example | Structure | Compound Name | Exact Mass [M + H]+ |
|---|---|---|---|
| 23-2 | 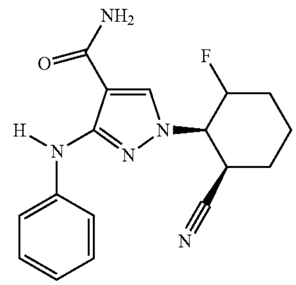 [SMILES: N#C[C@@H]1CCCC(F)[C@@H]1n1cc(C(N)=O)c(Nc2ccccc2)n1] | 1-[(1R,2R and 1S,2S)-2-cyano-6-fluorocyclohexyl]-3-(phenylamino)-1H-pyrazole-4-carboxamide | Cal'd 328, Found 328 |

Scheme #36

Example #24

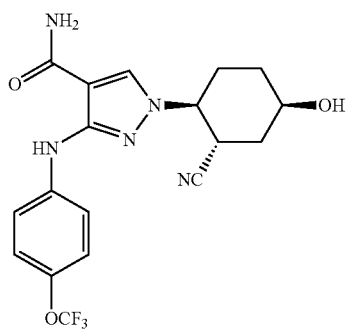 [SMILES: N#C[C@H]1C[C@H](O)CC[C@@H]1n1cc(C(N)=O)c(Nc2ccc(OC(F)(F)F)cc2)n1]

1-((1S,2S or 1R,2R)-2-cyano-4(R)-hydroxycyclohexyl)-3-((4-(trifluoromethoxy)phenyl)amino)-1H-pyrazole-4-carboxamide 3-Amino-1-((1S,2S,4R or 1R,2R,4S)-2-cyano-4-hydroxycyclohexyl)-1H-pyrazole-4-carboxamide (2.5 g, 10.03 mmol), 1-bromo-4-(trifluoromethoxy)benzene (1.79 mL, 12.0 mmol), 2-di-tert-butylphosphino-2',4',6'-triisopropylbiphenyl (1.29 g, 3.01 mmol), and KOAc (2.95 g, 30.1 mmol) were combined in 2-propanol (50.1 mL). Argon was bubbled through the resulting mixture for 10 minutes followed by addition of $Pd_2(dba)_3$ (1.38 g, 1.50 mmol). The flask was then sealed and flushed with more argon. The reaction mixture was stirred at 85° C. for 16 hours. The reaction mixture was cooled to ambient temperature, diluted with EtOAc and scavenged with Quadrapure TU for 2 hours. The mixture was filtered through celite and the filtrate was concentrated in vacuo. The crude residue was purified by MPLC (using a gradient elution of 0-10% MeOH/DCM) to afford the title compound. $^1$H NMR (500 MHz, DMSO-$d_6$) δ 9.28 (s, 1H), 8.27 (s, 1H), 7.67 (br, 1H), 7.61-7.59 (d, 2H), 7.25-7.23 (d, 2H), 7.19 (br, 1H), 4.89 (s, 1H), 4.45-4.39 (m, 1H), 3.96 (m, 1H), 3.52-3.46 (m, 1H), 2.25-2.16 (m, 1H), 2.11-2.07 (m, 1H), 1.98-1.92 (m, 1H), 1.76-1.72 (m, 2H), 1.66-1.60 (m, 1H). LRMS (ESI) calc'd for $C_{18}H_{18}F_3N_5O_3$ [M+H]+: 410. Found: 410.

The following compounds found in TABLE 20 were prepared according to Scheme #36 following similar procedures described for Example #24, which can be achieved by those of ordinary skill in the art of organic synthesis.

TABLE 20

| Example | Structure | Compound Name | Exact Mass [M + H]+ |
|---|---|---|---|
| 25-1 | 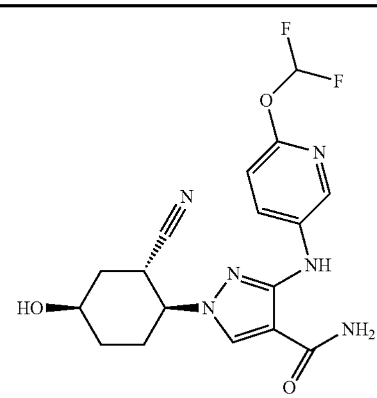 | 1-[(1S,2S,4R or 1R,2R,4S)-2-cyano-4-hydroxycyclohexyl]-3-{[6-(difluoromethoxy)pyridin-3-yl]amino}1H-pyrazole-4-carboxamide | Cal'd 393, found 393 |

TABLE 20-continued

| Example | Compound Name | Exact Mass [M + H]+ |
|---|---|---|
| 25-2 | 1-[(1S,2S,4S or 1R,2R,4R)-2-cyano-4-hydroxycyclohexyl]-3-{[6-(difluoromethoxy)pyridin-3-yl]amino}-1H-pyrazole-4-carboxamide | Cal'd 393, found 393 |
| 25-3 | 3-[(4-chloro-3-fluorophenyl)amino]-1-[(1S,2S,4R or 1R,2R,4S)-2-cyano-4-hydroxycyclohexyl]-1H-pyrazole-4-carboxamide | Cal'd 378, found 378 |
| 25-4 | 1-[(1S,2S,4R or 1R,2R,4S)-2-cyano-4-hydroxycyclohexyl]-3-[(4-cyanophenyl)amino]-1H-pyrazole-4-carboxamide | Cal'd 351, found 351 |
| 25-5 | 1-[(1S,2S,4R or 1R,2R,4S)-2-cyano-4-hydroxycyclohexyl]-3-{[4-(trifluoromethyl)phenyl]amino}-1H-pyrazole-4-carboxamide | Cal'd 394, found 394 |

TABLE 20-continued

| Example | Structure | Compound Name | Exact Mass [M + H]+ |
|---|---|---|---|
| 25-6 | 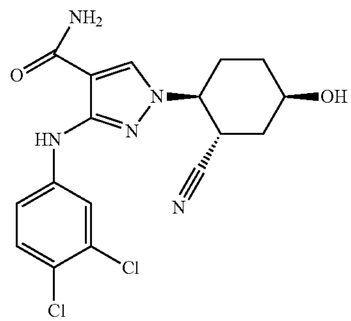 [SMILES: N#C[C@H]1C[C@H](O)CC[C@@H]1n1cc(C(N)=O)c(Nc2ccc(Cl)c(Cl)c2)n1] | 1-[(1S,2S,4R or 1R,2R,4S)-2-cyano-4-hydroxycyclohexyl]-3-[(3,4-dichlorophenyl)amino]-1H-pyrazole-4-carboxamide | Cal'd 394, found 394 |
| 25-8 | 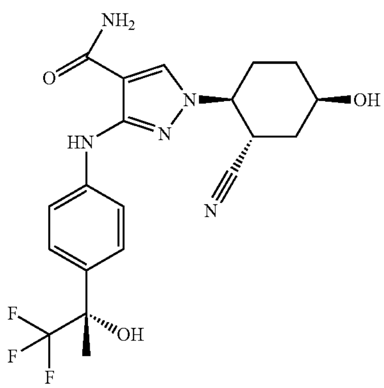 [SMILES: C[C@](O)(c1ccc(Nc2nn([C@H]3CC[C@@H](O)C[C@@H]3C#N)cc2C(N)=O)cc1)C(F)(F)F] | 1-[(1S,2S,4R or 1R,2R,4S)-2-cyano-4-hydroxycyclohexyl]-3-({4-[(1S or 1R)-2,2,2-trifluoro-1-hydroxy-1-methylethyl]phenyl}amino)-1H-pyrazole-4-carboxamide | Cal'd 438, found 438 |
| 25-9 | 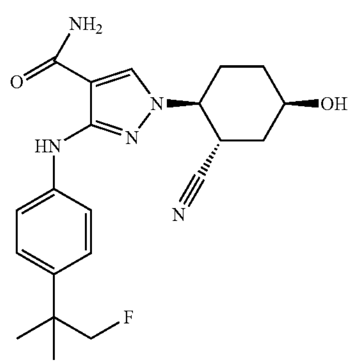 [SMILES: CC(C)(CF)c1ccc(Nc2nn([C@H]3CC[C@@H](O)C[C@@H]3C#N)cc2C(N)=O)cc1] | 1-[(1S,2S,4R or 1R,2R,4S)-2-cyano-4-hydroxycyclohexyl]-3-{[4-(2-fluoro-1,1-dimethylethyl)phenyl]amino}-1H-pyrazole-4-carboxamide | Cal'd 400, found 400 |
| 25-10 | 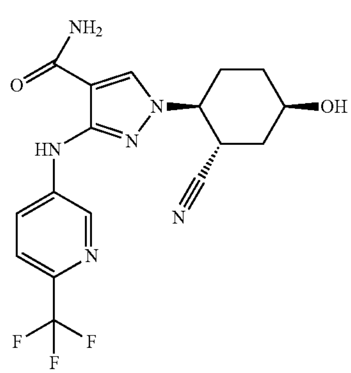 [SMILES: N#C[C@H]1C[C@H](O)CC[C@@H]1n1cc(C(N)=O)c(Nc2ccc(C(F)(F)F)nc2)n1] | 1-[(1S,2S,4R or 1R,2R,4S)-2-cyano-4-hydroxycyclohexyl]-3-{[6-(trifluoromethyl)pyridin-3-yl]amino}-1H-pyrazole-4-carboxamide | Cal'd 395, found 395 |

TABLE 20-continued

| Example | Structure | Compound Name | Exact Mass [M + H]+ |
|---|---|---|---|
| 25-11 | 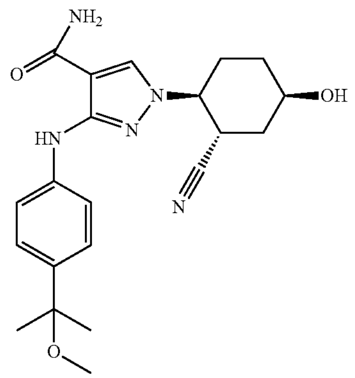 [SMILES: COC(C)(C)c1ccc(Nc2nn([C@H]3CC[C@@H](O)C[C@@H]3C#N)cc2C(N)=O)cc1] | 1-[(1S,2S,4R or 1R,2R,4S)-2-cyano-4-hydroxycyclohexyl]-3-{[4-(1-methoxy-1-methylethyl)phenyl]amino}-1H-pyrazole-4-carboxamide | Cal'd 398, found 398 |
| 25-12 | 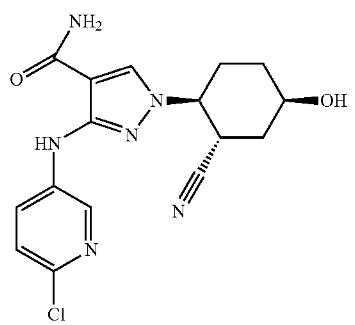 [SMILES: N#C[C@H]1C[C@H](O)CC[C@@H]1n1cc(C(N)=O)c(Nc2ccc(Cl)nc2)n1] | 3-[(6-chloropyridin-3-yl)amino]-1-[(1S,2S,4R or 1R,2R,4S)-2-cyano-4-hydroxycyclohexyl]-1H-pyrazole-4-carboxamide | Cal'd 361, found 361 |
| 25-13 | 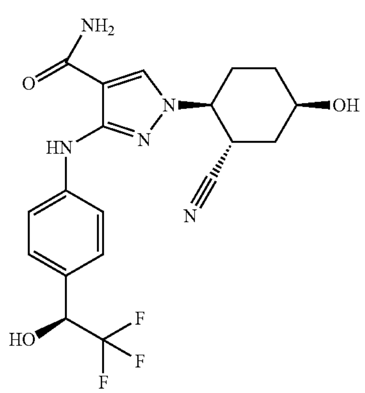 [SMILES: N#C[C@H]1C[C@H](O)CC[C@@H]1n1cc(C(N)=O)c(Nc2ccc([C@H](O)C(F)(F)F)cc2)n1] | 1-[(1S,2S,4R or 1R,2R,4S)-2-cyano-4-hydroxycyclohexyl]-3-({4-[(1S or 1R)-2,2,2-trifluoro-1-hydroxyethyl]phenyl}amino)-1H-pyrazole-4-carboxamide | Cal'd 424, found 424 |
| 25-14 | 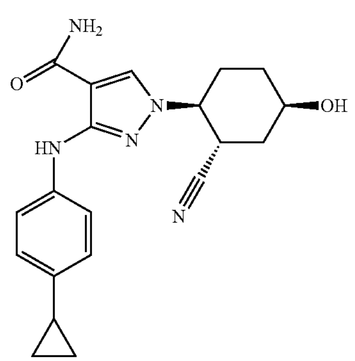 [SMILES: N#C[C@H]1C[C@H](O)CC[C@@H]1n1cc(C(N)=O)c(Nc2ccc(C3CC3)cc2)n1] | 1-[(1S,2S,4R or 1R,2R,4S)-2-cyano-4-hydroxycyclohexyl]-3-[(4-cyclopropylphenyl)amino]-1H-pyrazole-4-carboxamide | Cal'd 366, found 366 |

TABLE 20-continued

| Example | Structure | Compound Name | Exact Mass [M + H]+ |
|---|---|---|---|
| 25-15 | 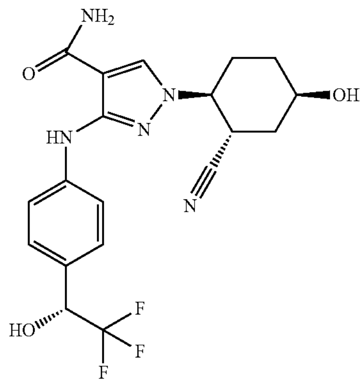 [SMILES: N#C[C@H]1C[C@H](O)CC[C@@H]1n1cc(C(N)=O)c(Nc2ccc([C@@H](O)C(F)(F)F)cc2)n1] | 1-[(1S,2S,4R or 1R,2R,4S)-2-cyano-4-hydroxycyclohexyl]-3-({4-[(1R or 1S)-2,2,2-trifluoro-1-hydroxyethyl]phenyl}amino)-1H-pyrazole-4-carboxamide | Cal'd 424, found 424 |
| 25-16 | 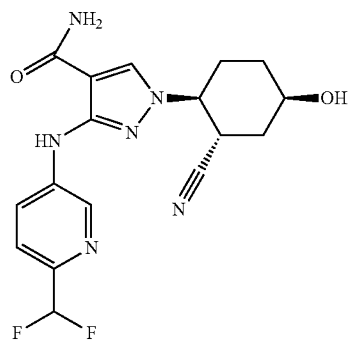 [SMILES: N#C[C@H]1C[C@H](O)CC[C@@H]1n1cc(C(N)=O)c(Nc2ccc(C(F)F)nc2)n1] | 1-[(1S,2S,4R or 1R,2R,4S)-2-cyano-4-hydroxycyclohexyl]-3-{[6-(difluoromethyl)pyridin-3-yl]amino}-1H-pyrazole-4-carboxamide | Cal'd 377, found 377 |
| 25-17 | 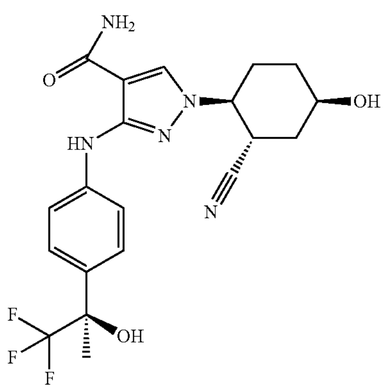 [SMILES: C[C@@](O)(c1ccc(Nc2nn([C@H]3CC[C@@H](O)C[C@@H]3C#N)cc2C(N)=O)cc1)C(F)(F)F] | 1-[(1S,2S,4R or 1R,2R,4S)-2-cyano-4-hydroxycyclohexyl]-3-({4-[(1R)-2,2,2-trifluoro-1-hydroxy-1-methylethyl]phenyl}amino)-1H-pyrazole-4-carboxamide | Cal'd 438, found 438 |
| 25-20 | 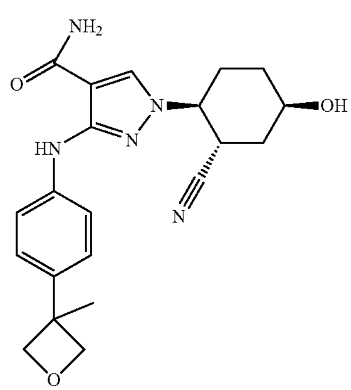 [SMILES: CC1(c2ccc(Nc3nn([C@H]4CC[C@@H](O)C[C@@H]4C#N)cc3C(N)=O)cc2)COC1] | 1-[(1S,2S,4R or 1R,2R,4S)-2-cyano-4-hydroxycyclohexyl]-3-{[4-(3-methyloxetan-3-yl)phenyl]amino}-1H-pyrazole-4-carboxamide | Cal'd 396, found 396 |

TABLE 20-continued

| Example | Structure | Compound Name | Exact Mass [M + H]+ |
|---|---|---|---|
| 25-21 | 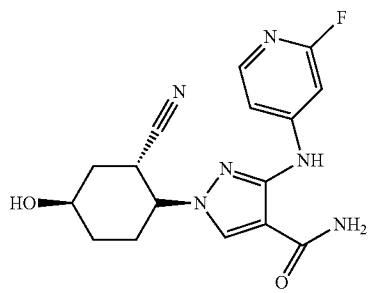 | 1-[(1S,2S,4R or 1R,2R,4S)-2-cyano-4-hydroxycyclohexyl]-3-[(2-fluoropyridin-4-yl)amino]-1H-pyrazole-4-carboxamide | Cal'd 345, found 345 |
| 25-22 | 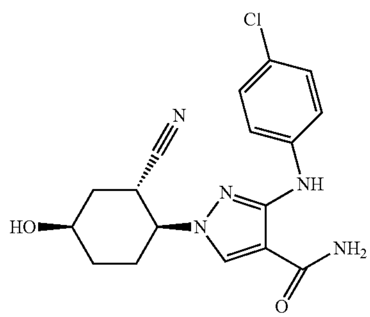 [SMILES: N#C[C@H]1C[C@H](O)CC[C@@H]1n1cc(C(N)=O)c(Nc2ccc(Cl)cc2)n1] | 3-[(4-chlorophenyl)amino]-1-[(1S,2S,4R or 1R,2R,4S)-2-cyano-4-hydroxycyclohexyl]-1H-pyrazole-4-carboxamide | Cal'd 360, found 360 |
| 25-23 | 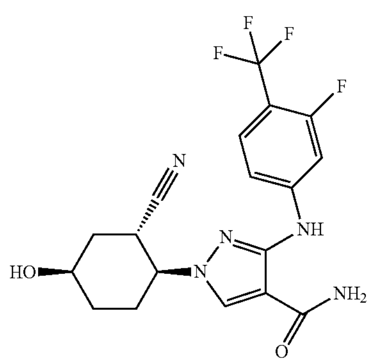 [SMILES: N#C[C@H]1C[C@H](O)CC[C@@H]1n1cc(C(N)=O)c(Nc2ccc(C(F)(F)F)c(F)c2)n1] | 1-[(1S,2S,4R or 1R,2R,4S)-2-cyano-4-hydroxycyclohexyl]-3-{[3-fluoro-4-(trifluoromethyl)phenyl]amino}-1H-pyrazole-4-carboxamide | Cal'd 412, found 412 |
| 25-24 | 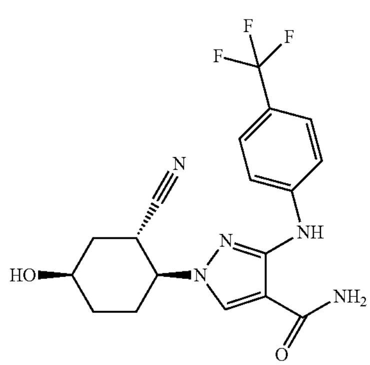 [SMILES: N#C[C@H]1C[C@H](O)CC[C@@H]1n1cc(C(N)=O)c(Nc2ccc(C(F)(F)F)cc2)n1] | 1-[(1S,2S,4R or 1R,2R,4S)-2-cyano-4-hydroxycyclohexyl]-3-{[4-(trifluoromethyl)phenyl]amino}-1H-pyrazole-4-carboxamide | Cal'd 394, found 394 |

TABLE 20-continued

| Example | Structure | Compound Name | Exact Mass [M + H]+ |
|---|---|---|---|
| 25-25 | 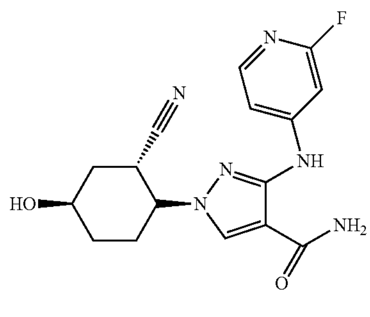 | 1-[(1S,2S,4R or 1R,2R,4S)-2-cyano-4-hydroxycyclohexyl]-3-[2-fluoropyridin-4-yl)amino]-1H-pyrazole-4-carboxamide | Cal'd 345, found 345 |
| 25-26 | 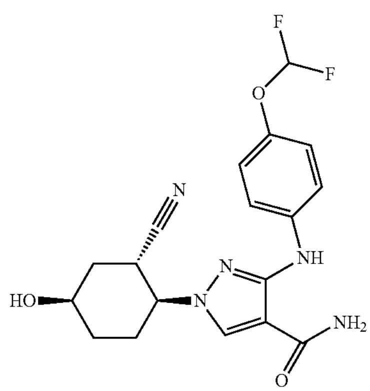 | 1-[(1S,2S,4R or 1R,2R,4S)-2-cyano-4-hydroxycyclohexyl]-3-{[4-(difluoromethoxy)phenyl]amino}-1H-pyrazole-4-carboxamide | Cal'd 392, found 392 |
| 25-27 | 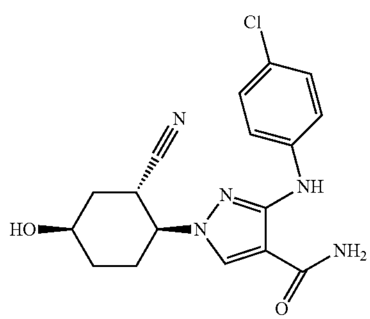 [SMILES: N#C[C@H]1C[C@H](O)CC[C@@H]1n1cc(C(N)=O)c(Nc2ccc(Cl)cc2)n1] | 3-[(4-chlorophenyl)amino]-1-[(1S,2S,4R or 1R,2R,4S)-2-cyano-4-hydroxycyclohexyl]-1H-pyrazole-4-carboxamide | Cal'd 360, found 360 |
| 25-28 | 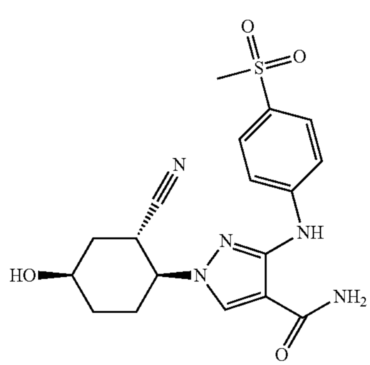 [SMILES: CS(=O)(=O)c1ccc(Nc2nn([C@H]3CC[C@@H](O)C[C@@H]3C#N)cc2C(N)=O)cc1] | 1-[(1S,2S,4R or 1R,2R,4S)-2-cyano-4-hydroxycyclohexyl]-3-{[4-(methylsulfonyl)phenyl]amino}-1H-pyrazole-4-carboxamide | Cal'd 404, found 404 |

TABLE 20-continued

| Example | Structure | Compound Name | Exact Mass [M + H]+ |
|---------|-----------|---------------|---------------------|
| 25-29 | 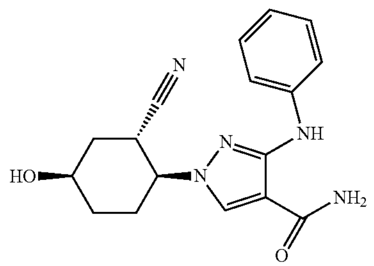 [SMILES: N#C[C@H]1C[C@H](O)CC[C@@H]1n1cc(C(N)=O)c(Nc2ccccc2)n1] | 1-[(1S,2S,4R or 1R,2R,4S)-2-cyano-4-hydroxycyclohexyl]-3-(phenylamino)-1H-pyrazole-4-carboxamide | Cal'd 326, found 326 |

Scheme #51

Example #26-1, 26-2, 26-3, and 26-4

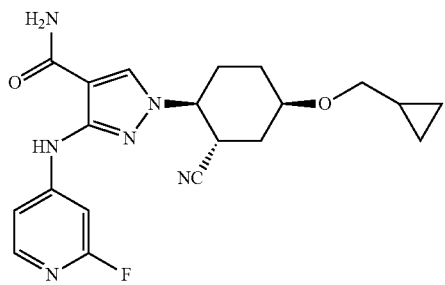 [SMILES: N#C[C@H]1C[C@H](OCC2CC2)CC[C@@H]1n1cc(C(N)=O)c(Nc2ccnc(F)c2)n1]

1-[(1S,2S,4R or 1R,2R,4S)-2-Cyano-4-(cyclopropyl-methoxy)cyclohexyl]-3-[(2-fluoropyridin-4-yl)amino]-1H-pyrazole-4-carboxamide Example #26-1

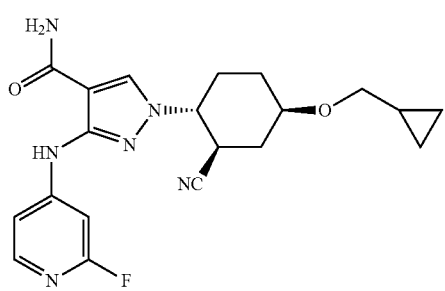 [SMILES: N#C[C@@H]1C[C@H](OCC2CC2)CC[C@H]1n1cc(C(N)=O)c(Nc2ccnc(F)c2)n1]

1-[(1R,2R,4R or 1S,2S,4S)-2-Cyano-4-(cyclopropyl-methoxy)cyclohexyl]-3-[(2-fluoropyridin-4-yl)amino]-1H-pyrazole-4-carboxamide Example #26-2

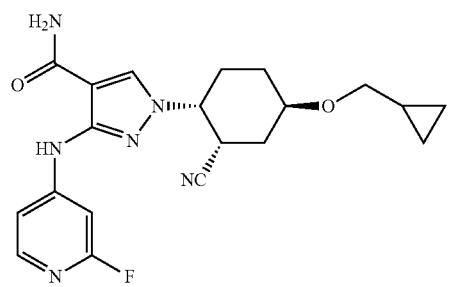 [SMILES: N#C[C@H]1C[C@H](OCC2CC2)CC[C@H]1n1cc(C(N)=O)c(Nc2ccnc(F)c2)n1]

1-[(1R,2S,4R or 1S,2R,4S)-2-Cyano-4-(cyclopropyl-methoxy)cyclohexyl]-3-[(2-fluoropyridin-4-yl)amino]-1H-pyrazole-4-carboxamide Example #26-3

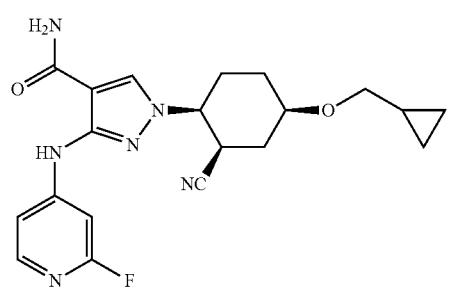 [SMILES: N#C[C@@H]1C[C@H](OCC2CC2)CC[C@@H]1n1cc(C(N)=O)c(Nc2ccnc(F)c2)n1]

1-[(1S,2R,4R) or (1R,2S,4R)-2-Cyano-4-(cyclopropylmethoxy)cyclohexyl]-3-[(2-fluoropyridin-4-yl)amino]-1H-pyrazole-4-carboxamide Example #26-4

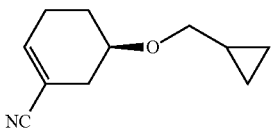 [SMILES: N#CC1=CCC[C@@H](OCC2CC2)C1]

Step A: (R or S)-5-(Cyclopropylmethoxy)cyclohex-1-enecarbonitrile

To the solution of (R or S)-5-Hydroxycyclohex-1-enecarbonitrile (Intermediate #40, 2.0 g, 16 mmol) in N,N-dimethylformamide (10 mL) was added sodium hydride (850 mg, 21 mmol, 60% dispersion in oil) at 0° C. The resulting suspension was stirred at ambient temperature for 30 minutes before the addition of bromomethylcyclopropane (3.3 g, 24 mmol). The mixture was then stirred at 75° C. for 6 hours, and diluted with EtOAc (50 mL). The organic solution was washed with brine (2×10 mL), dried over anhydrous sodium sulfate, filtered and concentrated in vacuo. The crude residue was purified by MPLC on Silica gel (eluting with 2-5% EtOAc/hexane) to afford the title compound as a yellow oil. $^1$H NMR (300 MHz, CDCl$_3$) δ 6.63-6.62 (m, 1H), 3.69-3.66 (m, 1H), 3.34-3.32 (m, 2H), 2.54-2.49 (m, 1H), 2.38-2.30 (m, 1H), 2.29-2.24 (m, 2H), 1.85-1.83 (m, 1H), 1.75-1.72 (m, 1H), 1.08-1.04 (m, 1H), 0.59-0.54 (m, 2H), 0.24-0.20 (1,2H).

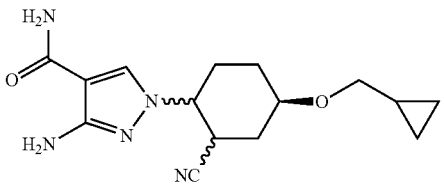 [SMILES: N#CC1C[C@H](OCC2CC2)CCC1n1cc(C(N)=O)c(N)n1]

Step B: 3-Amino-1-((4R or 4S)-2-cyano-4-(cyclopropylmethoxy)cyclohexyl)-1H-pyrazole-4-carboxamide A solution of (R or S)-5-(cyclopropylmethoxy)cyclohex-1-ene-1-carbonitrile (800 mg, 4.5 mmol), 3-amino-1H-pyrazole-4-carboxamide (1.1 g, 8.9 mmol) and DBU (1.4 g, 9.0 mmol) in ethanol (8 mL) was refluxed under nitrogen overnight, and then concentrated in vacuo. The crude residue was purified by MPLC on Silica gel (eluting with 1-2% MeOH/DCM) to afford the title compound as a mixture of diastereomers. MS ESI: [M+H]$^+$ m/z 304.

Step C: 1-[(1S,2S,4R or 1R,2R,4S)-2-Cyano-4-(cyclopropylmethoxy)cyclohexyl]-3-[(2-fluoropyridin-4-yl)amino]-1H-pyrazole-4-carboxamide and 1-[(1R,2R,4R or 1S,2S,4S)-2-cyano-4-(cyclopropylmethoxy)cyclohexyl]-3-[(2-fluoropyridin-4-yl)amino]-1H-pyrazole-4-carboxamide and 1-[(1R,2S,4R or 1S,2R,4S)-2-cyano-4-(cyclopropylmethoxy)cyclohexyl]-3-[(2-fluoropyridin-4-yl)amino]-1H-pyrazole-4-carboxamide and 1-[(1S,2R,4R) or (1R,2S,4R)-2-cyano-4-(cyclopropylmethoxy)cyclohexyl]-3-[(2-fluoropyridin-4-yl)amino]-1H-pyrazole-4-carboxamide A mixture of 3-amino-1-((4R or 4S)-2-cyano-4-(cyclopropylmethoxy)cyclohexyl)-1H-pyrazole-4-carboxamide (860 mg, 2.8 mmol), 4-bromo-2-fluoropyridine (490 mg, 2.8 mmol), KOAc (550 mg, 5.6 mmol), Pd$_2$(dba)$_3$.CHCl$_3$ (290 mg, 0.28 mmol) and t-Bu X-Phos (240 mg, 0.57 mmol) in 2-propanol (8 mL) was degassed with bubbling nitrogen for 15 minutes, then stirred at 60° C. for 2 hours under nitrogen. The mixture was cooled to ambient temperature and concentrated in vacuo. The crude residue was purified by MPLC on Silica gel (eluting with 1-2% MeOH/DCM) to afford the title compound as a mixture of 4 diastereomers. This mixture was then separated by preparative reverse-phase HPLC (using a gradient elution of 40-60% MeCN/water with 0.05% NH$_3$.H$_2$O) to afford the major isomer 1-[(1S,2S,4R or 1R,2R,4S)-2-cyano-4-(cyclopropylmethoxy)cyclohexyl]-3-[(2-fluoropyridin-4-yl)amino]-1H-pyrazole-4-carboxamide (Example #26-1) as an off-white solid, the minor isomer 1-[(1R,2R,4R or 1S,2S,4S)-2-cyano-4-(cyclopropylmethoxy)cyclohexyl]-3-[(2-fluoropyridin-4-yl)amino]-1H-pyrazole-4-carboxamide (Example #26-2) as an off-white solid, and a mixture containing the remaining 2 diastereomers. This mixture was further resolved to the constituent diastereomers via preparative chiral HPLC (Chiralpak IC, 2×25 cm; Mobile phase: 50% EtOH/hexane with 0.1% TEA) to afford 1-[(1R,2S,4R or 1S,2R,4S)-2-cyano-4-(cyclopropylmethoxy)cyclohexyl]-3-[(2-fluoropyridin-4-yl)amino]-1H-pyrazole-4-carboxamide (Example 26-3) and 1-[(1S,2R,4R or 1R,2S,4R)-2-cyano-4-(cyclopropylmethoxy)cyclohexyl]-3-[(2-fluoropyridin-4-yl)amino]-1H-pyrazole-4-carboxamide (Example 26-4).

Example 26-1

1-[(1S,2S,4R or 1R,2R,4S)-2-cyano-4-(cyclopropylmethoxy)cyclohexyl]-3-[(2-fluoropyridin-4-yl)amino]-1H-pyrazole-4-carboxamide: $^1$H NMR (400 MHz, CD$_3$OD) δ 8.23 (s, 1H), 7.92 (d, J=6.0 Hz, 1H), 7.50 (s, 1H), 7.22 (d, J=5.6 Hz, 1H), 4.41-4.39 (m, 1H), 3.80-3.78 (m, 1H), 3.67-3.61 (m, 1H), 3.41-3.33 (m, 2H), 2.48-2.39 (m, 2H), 2.17-2.13 (m, 1H), 2.00-1.89 (m, 2H), 1.67-1.66 (m, 1H), 1.16-1.13 (m, 1H), 0.63-0.58 (m, 2H), 0.34-0.30 (m, 2H). MS ESI: [M+H]$^+$ m/z 399.

Example 26-2

1-[(1R,2R,4R or 1S,2S,4S)-2-cyano-4-(cyclopropylmethoxy)cyclohexyl]-3-[(2-fluoropyridin-4-yl)amino]-1H-pyrazole-4-carboxamide: ¹H NMR (400 MHz, CD₃OD) δ 8.21 (s, 1H), 7.92 (d, J=6.0 Hz, 1H), 7.43 (s, 1H), 7.25 (d, J=6.0 Hz, 1H), 4.41-4.39 (m, 1H), 3.60-3.46 (m, 2H), 3.43-3.32 (m, 2H), 2.60-2.57 (m, 1H), 2.26-2.13 (m, 3H), 1.78-1.72 (m, 1H), 1.69-1.50 (m, 1H), 1.10-1.06 (m, 1H), 0.58-0.54 (m, 2H), 0.27-0.23 (m, 2H). MS ESI: [M+H]⁺ m/z 399.

Example 26-3

1-[(1R,2S,4R or 1S,2R,4S)-2-cyano-4-(cyclopropylmethoxy)cyclohexyl]-3-[(2-fluoropyridin-4-yl)amino]-1H-pyrazole-4-carboxamide: ¹H NMR (300 MHz, CD₃OD) δ 8.21 (s, 1H), 7.94 (d, J=6.0 Hz, 1H), 7.52 (s, 1H), 7.27 (d, J=6.0 Hz, 1H), 4.56-4.52 (m, 1H), 3.80-3.78 (m, 2H), 3.55-3.34 (m, 2H), 2.57-2.49 (m, 2H), 2.26-2.25 (m, 1H), 2.31-1.97 (m, 2H), 1.83-1.73 (m, 1H), 1.14-1.12 (m, 1H), 0.58-0.53 (m, 2H), 0.39-0.30 (m, 2H). MS ESI: [M+H]⁺ m/z 399.

Example 26-4

1-[(1S,2R,4R or 1R,2S,4S)-2-cyano-4-(cyclopropylmethoxy)cyclohexyl]-3-[(2-fluoropyridin-4-yl)amino]-1H-pyrazole-4-carboxamide: ¹H NMR (300 MHz, CD₃OD) δ 8.38 (s, 1H), 7.86 (d, J=6.0 Hz, 1H), 7.46 (s, 1H), 7.21 (d, J=6.0 Hz, 1H), 4.49-4.46 (m, 1H), 3.85-3.84 (m, 1H), 3.71-3.62 (m, 1H), 3.39-3.37 (m, 2H), 2.44-2.40 (m, 1H), 2.30-2.22 (m, 3H), 1.85-1.77 (m, 1H), 1.58-1.47 (m, 1H), 1.03-1.00 (m, 1H), 0.53-0.48 (m, 2H), 0.24-0.19 (m, 2H). MS ESI: [M+H]⁺ m/z 399.

The following compounds found in TABLE 21 were prepared according to Scheme #51 following similar procedures described for Example #26-1-4, which can be achieved by those of ordinary skill in the art of organic synthesis.

TABLE 21

| Example | Structure | Compound Name | Exact Mass [M + H]+ |
|---|---|---|---|
| 26-5 | 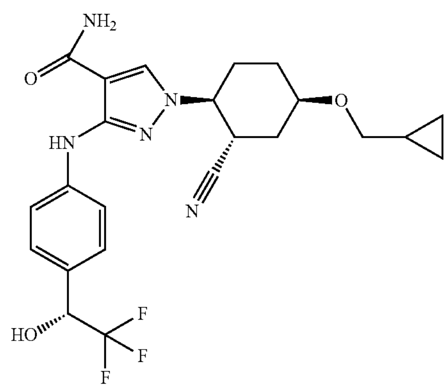 [SMILES: N#C[C@H]1C[C@H](OCC2CC2)CC[C@@H]1n1cc(C(N)=O)c(Nc2ccc([C@@H](O)C(F)(F)F)cc2)n1] | 1-[(1S,2S,4R or 1R,2R,4S)-2-cyano-4-(cyclopropylmethoxy)cyclohexyl]-3-({4-[(1R or 1S)-2,2,2-trifluoro-1-hydroxyethyl]phenyl}amino)-1H-pyrazole-4-carboxamide | Cal'd 478, found 478 |
| 26-6 | 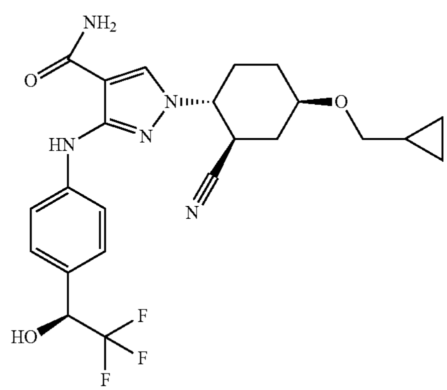 [SMILES: N#C[C@@H]1C[C@H](OCC2CC2)CC[C@H]1n1cc(C(N)=O)c(Nc2ccc([C@H](O)C(F)(F)F)cc2)n1] | 1-[(1R,2R,4R or 1S,2S,4S)-2-cyano-4-(cyclopropylmethoxy)cyclohexyl]-3-({4-[(1S or 1R)-2,2,2-trifluoro-1-hydroxyethyl]phenyl}amino)-1H-pyrazole-4-carboxamide | Cal'd 478, found 478 |

TABLE 21-continued

| Example | Structure | Compound Name | Exact Mass [M + H]+ |
|---|---|---|---|
| 26-7 | 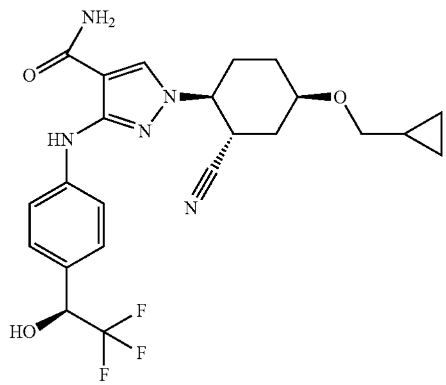 [SMILES: N#C[C@H]1C[C@H](OCC2CC2)CC[C@@H]1n1cc(C(N)=O)c(Nc2ccc([C@H](O)C(F)(F)F)cc2)n1] | 1-[(1S,2S,4R or 1R,2R,4S)-2-cyano-4-(cyclopropylmethoxy)cyclohexyl]-3-({4-[(1S or 1R)-2,2,2-trifluoro-1-hydroxyethyl]phenyl}amino)-1H-pyrazole-4-carboxamide | Cal'd 478, found 478 |
| 26-8 | 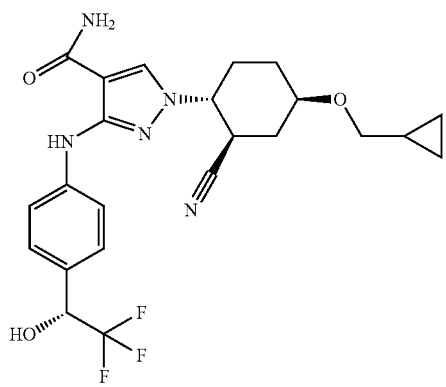 [SMILES: N#C[C@@H]1C[C@H](OCC2CC2)CC[C@H]1n1cc(C(N)=O)c(Nc2ccc([C@@H](O)C(F)(F)F)cc2)n1] | 1-[(1R,2R,4R or 1S,2S,4S)-2-cyano-4-(cyclopropylmethoxy)cyclohexyl]-3-({4-[(1R or 1S)-2,2,2-trifluoro-1-hydroxyethyl]phenyl}amino)-1H-pyrazole-4-carboxamide | Cal'd 478, found 478 |
| 26-9 | 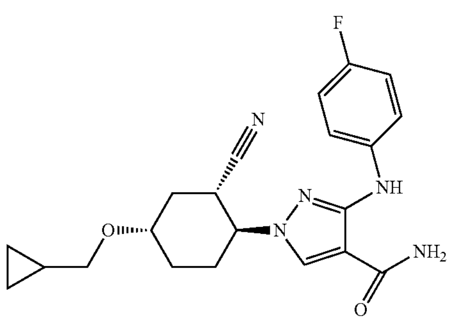 [SMILES: N#C[C@H]1C[C@@H](OCC2CC2)CC[C@@H]1n1cc(C(N)=O)c(Nc2ccc(F)cc2)n1] | 1-[(1S,2S,4S or 1R,2R,4R)-2-cyano-4-(cyclopropylmethoxy)cyclohexyl]-3-[(4-fluorophenyl)amino]-1H-pyrazole-4-carboxamide | Cal'd 398, found 398 |
| 26-10 | 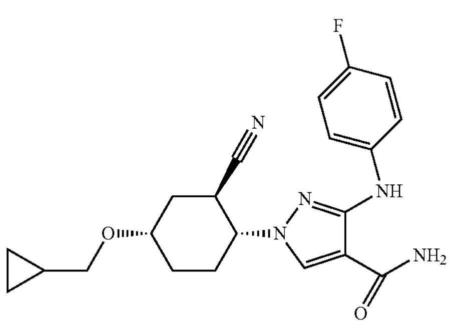 [SMILES: N#C[C@@H]1C[C@@H](OCC2CC2)CC[C@H]1n1cc(C(N)=O)c(Nc2ccc(F)cc2)n1] | 1-[(1R,2R,4S or 1S,2S,4R)-2-cyano-4-(cyclopropylmethoxy)cyclohexyl]-3-[(4-fluorophenyl)amino]-1H-pyrazole-4-carboxamide | Cal'd 398, found 398 |

TABLE 21-continued

| Example | Structure | Compound Name | Exact Mass [M + H]+ |
|---|---|---|---|
| 26-11 | 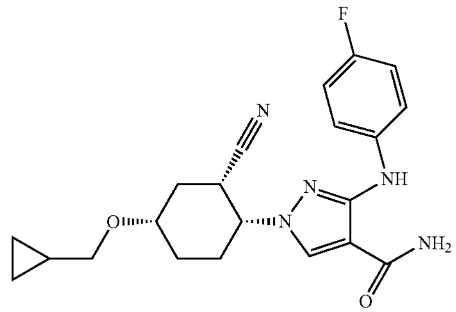 [SMILES: N#C[C@H]1C[C@@H](OCC2CC2)CC[C@H]1n1cc(C(N)=O)c(Nc2ccc(F)cc2)n1] | 1-[(1R,2S,4S or 1S,2R,4R)-2-cyano-4-(cyclopropylmethoxy)cyclohexyl]-3-[(4-fluorophenyl)amino]-1H-pyrazole-4-carboxamide | Cal'd 398, found 398 |

Scheme #40

Example #27-1 and #27-2

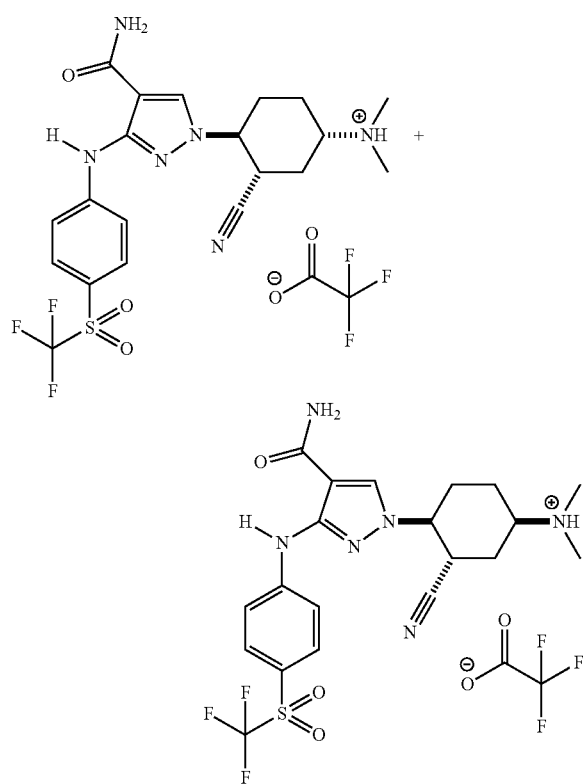

1-[(1S,3S,4S and 1R,3R,4R)-4-[4-carbamoyl-3-({4-[(trifluoromethyl)sulfonyl]phenyl}amino)-1H-pyrazol-1-yl]-3-cyano-N,N-dimethylcyclohexanaminium trifluoroacetate and 1-[(1R,3S,4S and 1S,3R,4R)-4-[4-carbamoyl-3-({4-[(trifluoromethyl)sulfonyl]phenyl}amino)-1H-pyrazol-1-yl]-3-cyano-N,N-dimethylcyclohexanaminium trifluoroacetate 1-[(1S,2S,4R and 1R,2R,4S)-2-Cyano-4-hydroxycyclohexyl]-3-({4-[(trifluoromethyl)sulfonyl]phenyl}amino)-1H-pyrazole-4-carboxamide (0.40 g, 0.87 mmol) was dissolved in DCM (2.19 mL):MeCN (2.19 mL). NMO (242 mg, 1.79 mmol) and 4 Å molecular sieves (200 mg/mmol) were added and the reaction mixture was allowed to stir at ambient temperature for 15 minutes. TPAP (62 mg, 0.17 mmol) was added to the reaction mixture and it was allowed to stir at ambient temperature for 1 hour. The reaction mixture was then purified directly by MPLC on silica gel (using a gradient elution of 80-100%, EtOAc/hexanes). Desired fractions were identified, combined, and concentrated in vacuo. The residue was dissolved in MeOH (0.33 mL) and THF (0.33 mL). Dimethylamine (0.33 mL, 0.66 mmol, 2.0 M in THF), acetic acid (0.034 mL, 0.66 mmol) and sodium cyanoborohydride (10 mg, 0.16 mmol) were then added sequentially at ambient temperature. The resulting mixture was allowed to stir at ambient temperature for 18 hours before the reaction mixture was concentrated in vacuo. The residue was purified by reverse-phase preparative HPLC (using a gradient elution of MeCN/water, with 0.1% v/v TFA modifier). Desired fractions were identified, combined, and lyophilized to afford the title compounds:

Example #27-1

1-[(1S,3S,4S and 1R,3R,4R)-4-[4-carbamoyl-3-({4-[(trifluoromethyl)sulfonyl]phenyl}amino)-1H-pyrazol-1-yl]-3-cyano-N,N-dimethylcyclohexanaminium trifluoroacetate. $^1$HNMR (500 MHz, DMSO-$d_6$): δ 9.98 (s, 1H), 9.53 (s, 1H), 8.41 (s, 1H), 7.92-7.86 (m, 4H), 7.81 (s, 1H), 7.39 (s, 1H), 4.71-4.66 (m, 1H), 4.04-3.99 (m, 1H), 3.49-3.45 (m, 1H), 2.86 (d, J=4.5 Hz, 3H), 2.81 (d, J=4.0 Hz, 3H), 2.30-2.19 (m, 3H), 2.11-1.97 (m, 3H). LRMS (ESI) calc'd for $C_{20}H_{23}F_3N_6O_3S$ [M+H]$^+$: 485. Found: 485.

Example #27-2

1-[(1R,3S,4S and 1S,3R,4R)-4-[4-carbamoyl-3-({4-[(trifluoromethyl)sulfonyl]phenyl}amino)-1H-pyrazol-1-yl]-3-cyano-N,N-dimethylcyclohexanaminium trifluoroacetate $^1$HNMR (500 MHz, DMSO-$d_6$): δ 10.0 (s, 1H), 9.91 (s, 1H), 8.33 (s, 1H), 7.93-7.85 (m, 5H), 7.39 (s, 1H), 4.57 (td, 11.5, 3.7 Hz, 1H), 3.61 (td, J=12.0, 3.3 Hz, 1H), 3.45-3.38 (m, 1H), 2.82-2.76 (m, 6H), 2.17-1.97 (m, 5H), 1.72 (m, 1H). LRMS (ESI) calc'd for $C_{20}H_{23}F_3N_6O_3S$ [M+H]$^+$: 485. Found: 485.

The following compounds shown in TABLE 22 were prepared according to Scheme #40 following similar procedures described for Example #27-1 and 27-2, which can be achieved by those of ordinary skill in the art of organic synthesis.

TABLE 22

| Example | Structure | Compound Name | Exact Mass [M + H]+ |
|---|---|---|---|
| 27-3 | 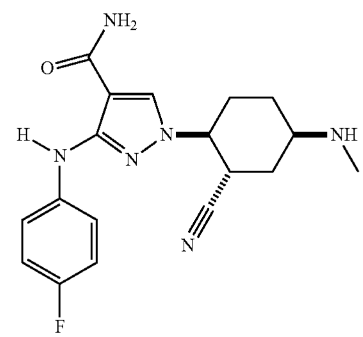 | 1-[(1S,2S,4R and 1R,2R,4S)-2-cyano-4-(methylamino)cyclohexyl]-3-[(4-fluorophenyl)amino]-1H-pyrazole-4-carboxamide | Cal'd 357, found 357 |
| 27-4 | 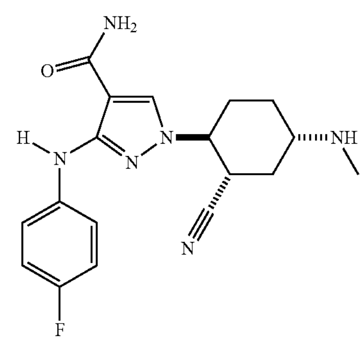 | 1-[(1S,2S,4S and 1R,2R,4R)-2-cyano-4-(methylamino)cyclohexyl]-3-[(4-fluorophenyl)amino]-1H-pyrazole-4-carboxamide | Cal'd 357, found 357 |
| 27-5 | 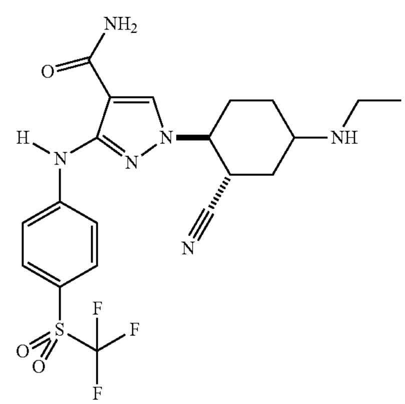 | 1-[(1S,2S and 1R,2R)-2-cyano-4-(ethylamino)cyclohexyl]-3-({4-[(trifluoromethyl)sulfonyl]phenyl}amino)-1H-pyrazole-4-carboxamide | Cal'd 485, found 485 |
| 27-6 | 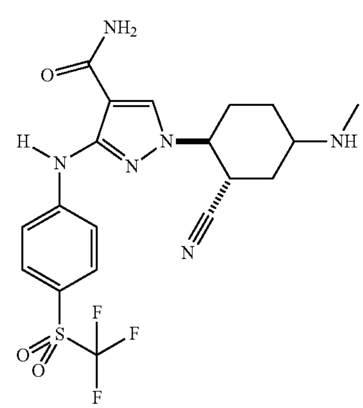 | 1-[(1S,2S and 1R,2R)-2-cyano-4-(methylamino)cyclohexyl]-3-({4-[(trifluoromethyl)sulfonyl]phenyl}amino)-1H-pyrazole-4-carboxamide | Cal'd 471, found 471 |

TABLE 22-continued

| Example | Structure | Compound Name | Exact Mass [M + H]+ |
|---|---|---|---|
| 27-7 | 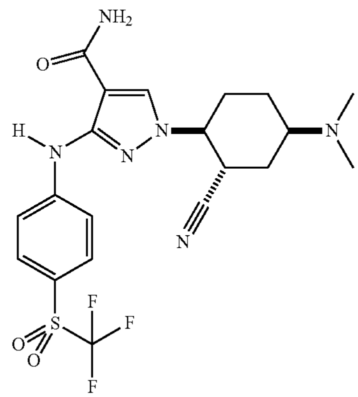 | 1-[(1S,2S,4R and 1R,2R,4S)-2-cyano-4-(dimethylamino)cyclohexyl]-3-({4-[(trifluoromethyl)sulfonyl]phenyl}amino)-1H-pyrazole-4-carboxamide | Cal'd 485, found 485 |
| 27-8 | 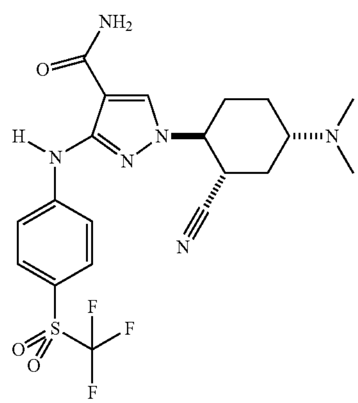 | 1-[(1S,2S,4S and 1R,2R,4R)-2-cyano-4-(dimethylamino)cyclohexyl]-3-({4-[(trifluoromethyl)sulfonyl]phenyl}amino)-1H-pyrazole-4-carboxamide | Cal'd 485, found 485 |
| 27-9 | 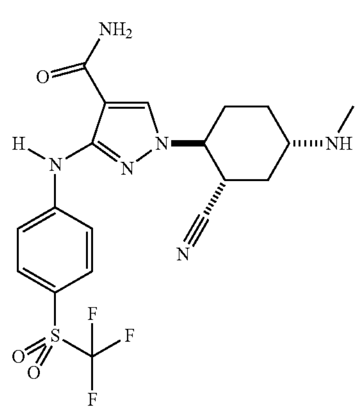 | 1-[(1S,2S,4S and 1R,2R,4R)-2-cyano-4-(methylamino)cyclohexyl]-3-({4-[(trifluoromethyl)sulfonyl]phenyl}amino)-1H-pyrazole-4-carboxamide | Cal'd 471, found 471 |

TABLE 22-continued

| Example | Structure | Compound Name | Exact Mass [M + H]+ |
|---|---|---|---|
| 27-10 | 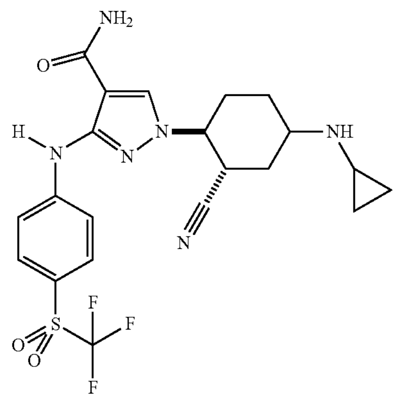 | 1-[(1S,2S and 1R,2R)-2-cyano-4-(cyclopropylamino)cyclohexyl]-3-({4-[(trifluoromethyl)sulfonyl]phenyl}amino)-1H-pyrazole-4-carboxamide | Cal'd 497, found 497 |
| 27-11 | 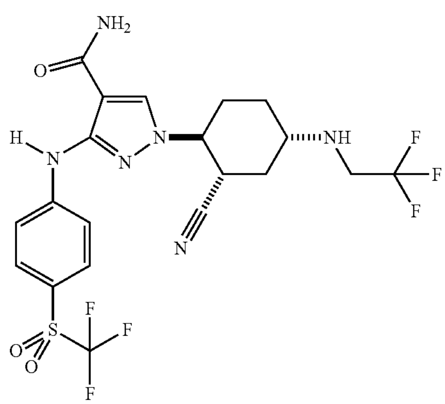 | 1-{(1S,2S,4S and 1R,2R,4R)-2-cyano-4-[(2,2,2-trifluoroethyl)amino]cyclohexyl}-3-({4-[(trifluoromethyl)sulfonyl]phenyl}amino)-1H-pyrazole-4-carboxamide | Cal'd 539, found 539 |
| 27-12 | 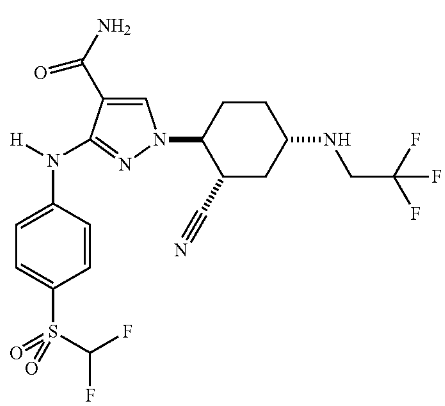 | 1-{(1S,2S,4S and 1R,2R,4R)-2-cyano-4-[(2,2,2-trifluoroethyl)amino]cyclohexyl}-3-({4-[(difluoromethyl)sulfonyl]phenyl}amino)-1H-pyrazole-4-carboxamide | Cal'd 521, found 521 |

TABLE 22-continued

| Example | Structure | Compound Name | Exact Mass [M + H]+ |
|---|---|---|---|
| 27-13 | 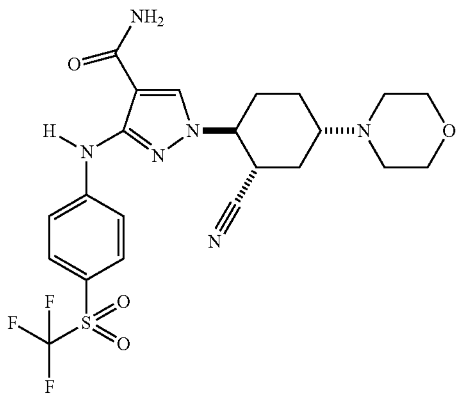 | 1-[(1S,2S,4S and 1R,2R,4R)-2-cyano-4-(morpholin-4-yl)cyclohexyl]-3-({4-[(trifluoromethyl)sulfonyl]phenyl}amino)-1H-pyrazole-4-carboxamide | Cal'd 527, found 527 |
| 27-14 | 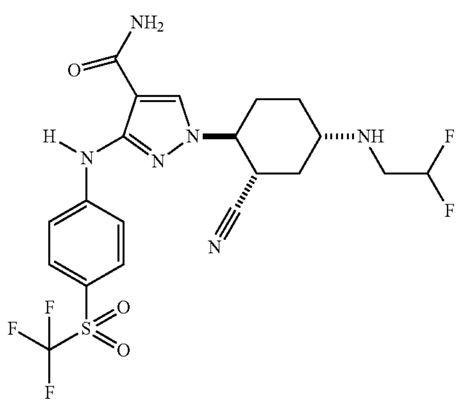 | 1-{(1S,2S,4S and 1R,2R,4R)-2-cyano-4-[(2,2-difluoroethyl)amino]cyclohexyl}-3-({4-[(trifluoromethyl)sulfonyl]phenyl}amino)-1H-pyrazole-4-carboxamide | Cal'd 521, found 521 |
| 27-15 | 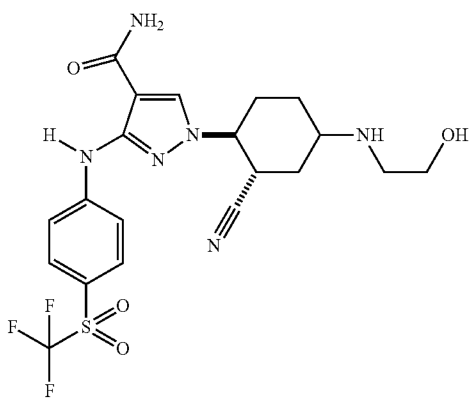 | 1-{(1S,2S and 1R,2R)-2-cyano-4-[(2-hydroxyethyl)amino]cyclohexyl}-3-({4-[(trifluoromethyl)sulfonyl]phenyl}amino)-1/f-pyrazole-4-carboxamide_ 1-{(1S,2S,4S and 1R,2R,4R)-2-cyano-4-[(2-methoxyethyl)amino] cyclohexyl}-3-({4-[(trifluoromethyl)sulfonyl]phenyl}amino)-1//-pyrazole-4-carboxamide | Cal'd 501, found 501 |

TABLE 22-continued

| Example | Structure | Compound Name | Exact Mass [M + H]+ |
|---|---|---|---|
| 27-16 | 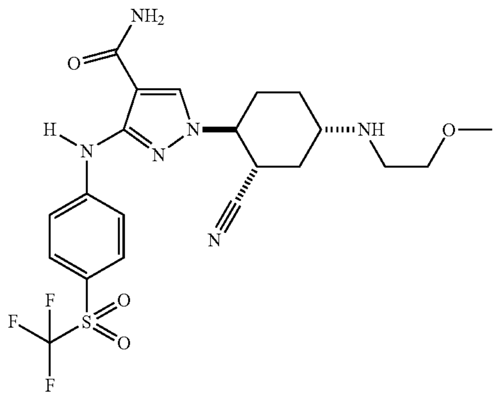 | 1-{(1S,2S,4S and 1R,2R,4R)-2-cyano-4-[(2-methoxyethyl)amino]cyclohexyl}-3-({4-[(trifluoromethyl)sulfonyl]phenyl)amino)-1H-pyrazole-4-carboxamide | Cal'd 515, found 515 |
| 27-17 | 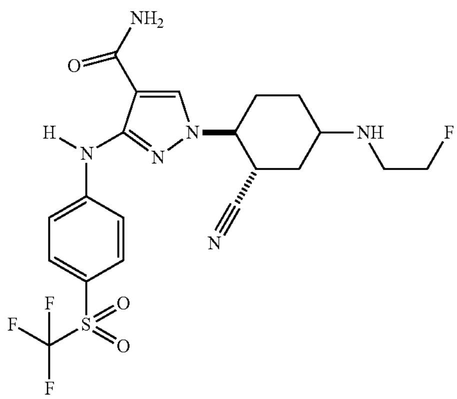 | 1-{(1S,2S and 1R,2R)-2-cyano-4-[(2-fluoroethyl)amino]cyclohexyl}-3-({4-[(trifluoromethyl)sulfonyl]phenyl)amino)-1H-pyrazole-4-carboxamide | Cal'd 503, found 503 |

Scheme #54

Example #28-1

1-{(1S,2S and 1R,2R)-2-cyano-4-[(2-fluoroethyl)amino]cyclohexyl}-3-({4-[(trifluoromethyl)sulfonyl]phenyl)amino)-1H-pyrazole-4-carboxamide

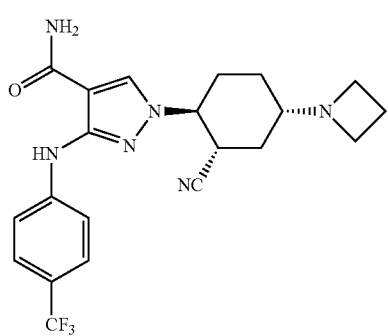 [SMILES: N#C[C@H]1C[C@@H](N2CCC2)CC[C@@H]1n1cc(C(N)=O)c(Nc2ccc(C(F)(F)F)cc2)n1]

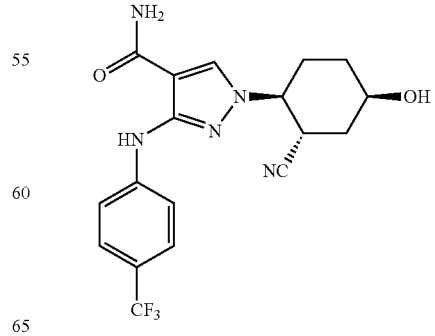

Step A: 1-((1S,2S,4R or 1R,2R,4S)-2-cyano-4-hydroxycyclohexyl)-3-((4-(trifluoromethyl)phenyl)amino)-1H-pyrazole-4-carboxamide A mixture of 3-amino-1-((1S,2S and 1R,2R)-2-cyano-4-hydroxycyclohexyl)-1H-pyrazole-4-carboxamide (Intermediates 48-1 and 48-2, 150 g, 602 mmol), 4-bromobenzotrifluoride (0.101 L, 722 mmol), Pd$_2$(dba)$_3$ (27.6 g, 30.1 mmol), 2-di-tert-butylphosphino-2',4',6'-triisopropylbiphenyl (28.1 g, 66.2 mmol), and potassium acetate (89 g, 903 mmol) in 2-propanol (1.5 L) was degassed and stirred at 80° C. for 2.5 hours. After cooling to ambient temperature, the reaction mixture was diluted with 1 L of EtOAc, stirred for 30 minutes, filtered through a celite pad and washed with EtOAc (500 mL×2). The filtrate was adsorbed on silica gel in vacuo and purified by column chromatography on silica gel (eluting with 0-8% MeOH/DCM) to give 1-((1S,2S,4R and 1R,2R,4S)-2-cyano-4-hydroxycyclohexyl)-3-((4-(trifluoromethyl)phenyl)amino)-1H-pyrazole-4-carboxamide as a pale yellow solid. This racemic mixture was chirally resolved via Chiral SFC column chromatography (Chiral Technology OZ-H 2.1× 25 cm, 5 uM) to afford the title compound as the second enantiomer to elute, Intermediate A of Example 28-1. $^1$H NMR (400 MHz, CD$_3$OD) δ 1.73 (1H, t, J=14. Hz), 1.87-1.85 (1H, m), 1.98-1.96 (2H, m), 2.25 (1H, dd, J=14, 3.5 Hz), 2.46 (1H, qd, J=13, 3.6 Hz), 3.68-3.65 (1H, m), 4.10 (1H, s), 4.30 (1H, td, J=11.5, 3.9 Hz), 7.50 (2H, d, J=8.4 Hz), 7.67 (2H, d, J=8.4 Hz), 8.14 (1H, s). MS ESI: [M+H]$^+$ m/z 394.

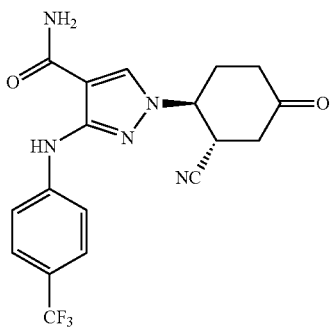 [SMILES: N#C[C@H]1CC(=O)CC[C@@H]1n1cc(C(N)=O)c(Nc2ccc(C(F)(F)F)cc2)n1]

Step B: 1-((1S,2S or 1R,2R)-2-Cyano-4-oxocyclohexyl)-3-((4-(trifluoromethyl)phenyl)amino)-1H-pyrazole-4-carboxamide To a solution of 1-((1S,2S,4R or 1R,2R,4S)-2-cyano-4-hydroxycyclohexyl)-3-((4-(trifluoromethyl)phenyl)amino)-1H-pyrazole-4-carboxamide (61.2 g, 156 mmol) in DMSO (612 mL) was added TEA (65.1 mL, 467 mmol), followed by sulfur trioxide-pyridine complex (74.3 g, 467 mmol) in one portion at ambient temperature (slightly exothermic). The reaction mixture was stirred at ambient temperature for 16 hours. The reaction mixture was diluted with EtOAc (3000 mL), washed sequentially with saturated aqueous NaHCO$_3$ (1500 mL), water (1000 mL) and brine (500 mL×2). The aqueous layer was back extracted with EtOAc (500 mL×2), and the combined organic layers were then dried over anhydrous Na$_2$SO$_4$ and concentrated in vacuo. The residue was purified by column chromatography on silica gel (eluting with 0-8% MeOH/DCM) to give the title compound as an off-white solid. $^1$H NMR (400 MHz, Acetone-d$_6$) δ 2.41-2.40 (1H, m), 2.53-2.51 (1H, m), 2.61 (1H, tdd, J=13.4, 11.1, 4.48 Hz), 2.79 (2H, m), 3.00 (1H, dd, J=15, 13 Hz), 4.07-4.06 (1H, m), 5.04 (1H, td, J=10.9, 4. Hz), 6.65 (1H, br s), 7.30 (1H, br s), 7.54 (2H, d, J=8.5 Hz), 7.79 (2H, d, J=8.5 Hz), 8.36 (1H, s), 9.61 (1H, s). MS ESI: [M+H]$^+$ m/z 392;

Step C: 1-((1S,2S,4S or 1R,2R,4R)-4-(azetidin-1-yl)-2-cyanocyclohexyl)-3-((4-(trifluoromethyl)phenyl)amino)-1H-pyrazole-4-carboxamide To a solution of 1-((1S,2S or 1R,2R)-2-cyano-4-oxocyclohexyl)-3-((4-(trifluoromethyl)phenyl)amino)-1H-pyrazole-4-carboxamide (54.0 g, 138 mmol) and azetidine hydrochloride (38.7 g, 414 mmol) in MeOH (540 mL) was added TEA (57.7 mL, 414 mmol), and acetic acid (118 mL, 2070 mmol), followed by sodium triacetoxyborohydride (58.5 g, 276 mmol) at 0° C. in two portions (slightly exothermic). The reaction mixture was then stirred at 0° C. for 2 hours. After removal of all the volatiles in vacuo, the residue was diluted with EtOAc (1500 mL) and basified with saturated aqueous Na$_2$CO$_3$. A white precipitate formed and was filtered. The filtrate was partitioned and the aqueous layer was extracted with EtOAc (300 mL×2). The combined EtOAc layers were washed with brine, dried over anhydrous sodium sulfate, and filtered. The white precipitate was slurried in MeOH (300 mL) for 15 minutes and filtered again. The MeOH filtrate was combined with the EtOAc layer and concentrated in vacuo. The residue was purified by column chromatography on silica gel (eluting with 0-10% MeOH/EtOAc with 3 vol % aqueous NH$_4$OH) to give the title compound as a pale yellow solid. $^1$H NMR (400 MHz, DMSO-d$_6$): δ 1.12-1.10 (1H, m), 1.37 (1H, q, J=12 Hz), 1.75 (1H, d, J=12. Hz), 1.93-1.85 (4H, m), 2.11-2.07 (2H, m), 3.07 (4H, t, J=7 Hz), 3.33 (1H, td, J=8 Hz), 4.41 (1H, td, J=11, 4.08 Hz), 7.21 (1H, br s), 7.54 (2H, d, J=8 Hz), 7.67 (2H, d, J=8 Hz), 7.72 (1H, br s), 8.22 (1H, s), 9.49 (1H, s). MS ESI: [M+H]$^+$ m/z 433.

Scheme #36 and 41

Example #28-2 and #28-3

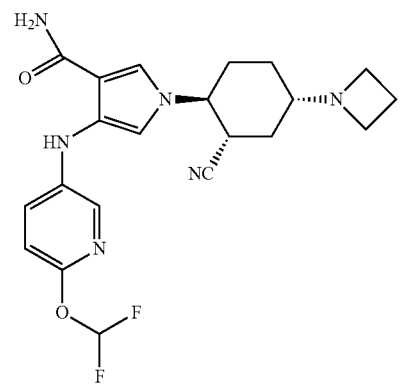

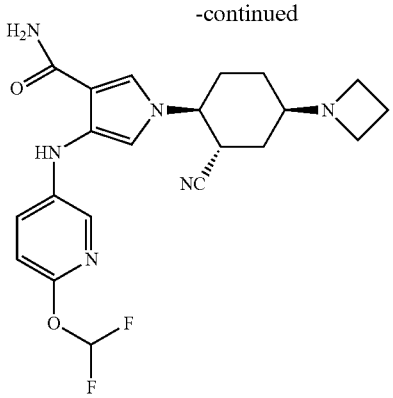

1-[(1S,2S,4R or 1R,2R,4S)-4-(Azetidin-1-yl)-2-cyanocyclohexyl]-3-{[6-(difluoromethoxy)pyridin-3-yl]amino}-1H-pyrazole-4-carboxamide and 1-[(1S,2S,4S or 1R,2R,4R)-4-(azetidin-1-yl)-2-cyanocyclohexyl]-3-{[6-(difluoromethoxy)pyridin-3-yl]amino}-1H-pyrazole-4-carboxamide

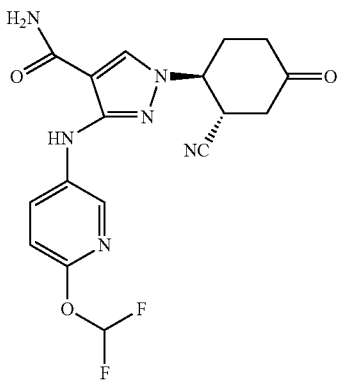 [SMILES: N#C[C@H]1CC(=O)CC[C@@H]1n1cc(C(N)=O)c(Nc2ccc(OC(F)F)nc2)n1]

Step A: 1-[(1S,2S or 1R,2R)-2-Cyano-4-oxocyclohexyl]-3-{[6-(difluoromethoxy)pyridin-3-yl]amino}-1H-pyrazole-4-carboxamide To a solution of 1-[(1S,2S,4R or 1R,2R,4S)-2-cyano-4-hydroxycyclohexyl]-3-{[6-(difluoromethoxy)pyridin-3-yl]amino}-1H-pyrazole-4-carboxamide (Example #25-26, 386 mg, 0.984 mmol) in DMSO (2 mL) was added stabilized 2-iodoxybenzoic acid (413 mg, 1.48 mmol). The resulting slurry was heated to 50° C. for 5 hours. The reaction mixture was cooled to ambient temperature, diluted with EtOAc and washed with saturated aqueous sodium thiosulfate. The organic layer was collected, dried over anhydrous MgSO$_4$, filtered, and concentrated in vacuo to afford the title compound, (Intermediate A of Example #28-2). LRMS (ESI) calc'd for C$_{17}$H$_{17}$F$_2$N$_6$O$_3$ [M+H]$^+$: 391. Found: 391+ [M+H$_2$O]$^+$: 409.

Step B: 1-[(1S,2S,4R or 1R,2R,4S)-4-(Azetidin-1-yl)-2-cyanocyclohexyl]-3-{[6-(difluoromethoxy)pyridin-3-yl]amino}-1H-pyrazole-4-carboxamide and 1-[(1S,2S,4S or 1R,2R,4R)-4-(azetidin-1-yl)-2-cyanocyclohexyl]-3-{[6-(difluoromethoxy)pyridin-3-yl]amino}-1H-pyrazole-4-carboxamide To a solution of 1-[(1S,2S or 1R,2R)-2-cyano-4-oxocyclohexyl]-3-{[6-(difluoromethoxy)pyridin-3-yl]amino}-1H-pyrazole-4-carboxamide (Intermediate A of Example #28-2, 100 mg, 0.256 mmol) in THF (1 mL) and MeOH (1 mL) were added azetidine hydrogen chloride salt (240 mg, 2.56 mmol) and triethylamine (0.357 mL, 2.56 mmol). The reaction mixture was stirred for 10 minutes, then acetic acid (0.147 mL, 2.56 mmol) was added. The mixture was stirred for another 10 minutes then sodium cyanoborohydride (40 mg, 0.64 mmol) was added and stirring continued for 14 hours. The reaction mixture was filtered, and the filtrate was purified directly by reverse phase HPLC (using a gradient elution of MeCN/water with 0.1% TFA) to afford the title compounds.

Example #28-2

1-[(1S,2S,4R or 1R,2R,4S)-4-(azetidin-1-yl)-2-cyanocyclohexyl]-3-{[6-(difluoromethoxy)pyridin-3-yl]amino}-1H-pyrazole-4-carboxamide. $^1$H NMR (500 MHz, CD$_3$OD): δ 8.53 (d, J=3 Hz, 1H), 8.17 (s, 1H), 8.12-8.09 (dd, J=9, 3 Hz, 1H), 7.55-7.25 (t, J=74 Hz, 1H), 6.93 (d, J=9 Hz, 1H), 4.30-4.25 (td, J=11, 4 Hz, 1H), 3.68-3.63 (td, J=11, 3 Hz, 1H), 3.30-3.29 (m, 4H), 2.60 (m, 1H), 2.33-2.30 (1H), 2.14-2.09 (m, 3H), 1.90-1.811 (m, 3H), 1.62 (m, 1H). LRMS (ESI) calc'd for C$_{20}$H$_{24}$F$_2$N$_7$O$_2$ [M+H]$^+$: 432. Found: 432.

Example #28-3

1-[(1S,2S,4S or 1R,2R,4R)-4-(azetidin-1-yl)-2-cyanocyclohexyl]-3-{[6-(difluoromethoxy)pyridin-3-yl]amino}-1H-pyrazole-4-carboxamide. $^1$H NMR (500 MHz, CD$_3$OD): δ 8.51 (d, J=3 Hz, 1H), 8.13 (s, 1H), 8.07-8.05 (dd, J=9, 3 Hz, 1H), 7.38 (t, J=74 Hz, 1H), 6.89 (d, J=9 Hz, 1H), 4.30 (m, 1H), 3.46-3.42 (m, 5H), 2.50 (m, 1H), 2.35 (m, 1H), 2.17-2.09 (m, 4H), 2.00 (m, 1H), 1.50-1.48 (m, 1H), 1.251 (m, 1H). LRMS (ESI) calc'd for C$_{20}$H$_{24}$F$_2$N$_7$O$_2$ [M+H]$^+$: 432. Found: 432.

Scheme #36 and 42

Example #28-4

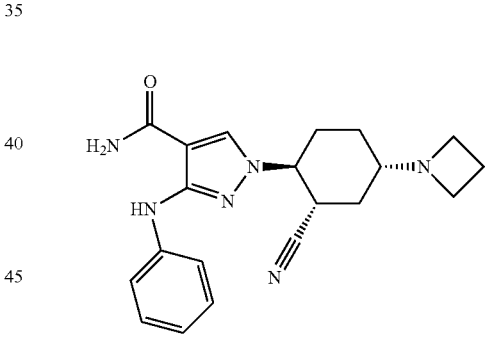

1-((1R,2R,4R or 1S,2S,4S)-4-(Azetidin-1-yl)-2-cyanocyclohexyl)-3-(phenylamino)-1H-pyrazole-4-carboxamide

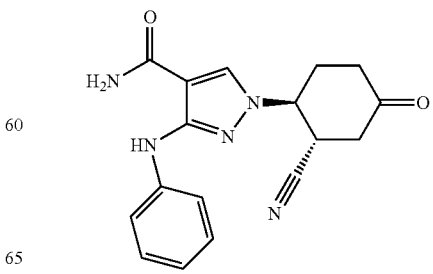

Step A: 1-((1R,2R or 1S,2S)-2-Cyano-4-oxocyclohexyl)-3-(phenylamino)-1H-pyrazole-4-carboxamide The title compound was prepared using methods similar to those described for the preparation of Intermediate A of Example #28-2; using 1-[(1S,2S,4R or 1R,2R,4S)-2-cyano-4-hydroxycyclohexyl]-3-(phenylamino)-1H-pyrazole-4-carboxamide (Example #25-29) as a starting material. LRMS (ESI) calc'd for $C_{17}H_{17}N_5O_2$ [M+H]$^+$: 324. Found: 324.

Step B: 1-((1R,2R,4R or 1S,2S,4S)-4-(Azetidin-1-yl)-2-cyanocyclohexyl)-3-(phenylamino)-1H-pyrazole-4-carboxamide 1-((1R,2R or 1S,2S)-2-Cyano-4-oxocyclohexyl)-3-(phenylamino)-1H-pyrazole-4-carboxamide (0.50 g, 1.5 mmol) was stirred in 1:1 THF:MeOH (31 mL) at 0° C. and azetidine hydrochloride (0.72 g, 7.7 mmol) was added, followed by TEA (0.78 g, 7.7 mmol), acetic acid (0.93 g, 15 mmol), and sodium triacetoxyborohydride (0.98 g, 4.6 mmol). The resulting mixture was stirred at 0° C. for 30 minutes, then concentrated in vacuo, partitioned between EtOAc and saturated aqueous NaHCO$_3$. The organic layer was washed with brine, dried over anhydrous Na$_2$SO$_4$, filtered, and concentrated in vacuo. The residue was purified by MPLC on silica gel (using a gradient elution of 0-15% MeOH/EtOAc with 3% NH$_4$OH). Desired fractions were identified, combined, and concentrated in vacuo to afford the title compound. LRMS (ESI) calc'd for $C_{20}H_{24}N_6O$ [M+H]$^+$: 365. Found: 365. $^1$H NMR (500 MHz, DMSO-d$_6$): δ 9.15 (s, 1H); 8.19 (s, 1H); 7.66 (br s, 1H); 7.49 (d, J=8.1 Hz, 2H); 7.24 (t, J=7.7 Hz, 2H); 7.14 (br s, 1H); 6.82 (t, J=7.3 Hz, 1H); 4.39 (td, J=11.2, 4.2 Hz, 1H); 3.09 (t, J=7.0 Hz, 4H); 2.09-2.17 (m, 2H); 1.84-1.98 (m, 5H); 1.74-1.80 (m, 1H); 1.36-1.38 (m, 1H); 1.06-1.14 (m, 1H).

Scheme #36 and 43

Example #28-5

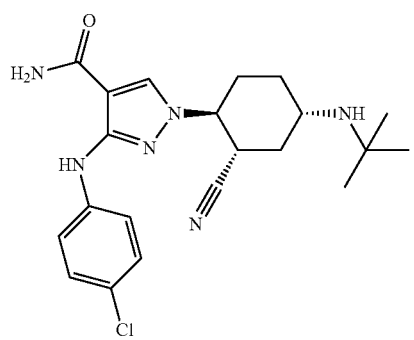 [SMILES: CC(C)(C)N[C@H]1CC[C@H](n2cc(C(N)=O)c(Nc3ccc(Cl)cc3)n2)[C@@H](C#N)C1]

1-((1R,2R,4R or 1S,2S,4S)-4-(tert-Butylamino)-2-cyanocyclohexyl)-3-((4-chlorophenyl)amino)-1H-pyrazole-4-carboxamide

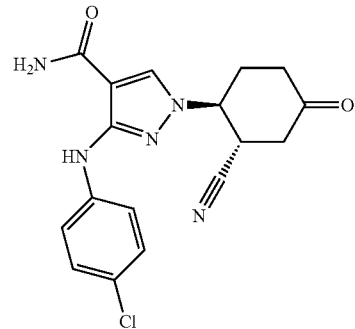 [SMILES: N#C[C@H]1CC(=O)CC[C@@H]1n1cc(C(N)=O)c(Nc2ccc(Cl)cc2)n1]

Step A: 3-((4-Chlorophenyl)amino)-1-((1R,2R or 1S,2S)-2-cyano-4-oxocyclohexyl)-1H-pyrazole-4-carboxamide To a solution of 3-[(4-chlorophenyl)amino]-1-[(1S,2S,4R or 1R,2R,4S)-2-cyano-4-hydroxycyclohexyl]-1H-pyrazole-4-carboxamide (Example 25-22) (5.0 g, 14 mmol) in DMSO (99 mL) was added IBX (17.3 g, 27.8 mmol). The resulting mixture was heated to 50° C. for 2.5 hours, then cooled to ambient temperature and stirred with saturated aqueous sodium thiosulfate and saturated aqueous NaHCO$_3$ for 30 minutes. The mixture was extracted with EtOAc (3×). The combined organic layers were washed with saturated aqueous NaHCO$_3$, brine, dried over anhydrous Na$_2$SO$_4$, filtered, and concentrated in vacuo. The residue was purified by MPLC on silica gel (using a gradient elution of 0-80% EtOAc/hexanes). Desired fractions were identified, combined, and concentrated in vacuo to afford the title compound. LRMS (ESI) calc'd for $C_{17}H_{16}ClN_5O_2$ [M+H]$^+$: 358. Found: 358.

Step B: 1-((1R,2R,4R or 1S,2S,4S)-4-(tert-Butylamino)-2-cyanocyclohexyl)-3-((4-chlorophenyl)amino)-1H-pyrazole-4-carboxamide 3-((4-Chlorophenyl)amino)-1-((1R,2R or 1S,2S)-2-cyano-4-oxocyclohexyl)-1H-pyrazole-4-carboxamide (100 mg, 0.28 mmol) was stirred in THF (2.8 mL) at ambient temperature and tert-butylamine (25 mg, 0.34 mmol), and titanium (IV) isopropoxide (175 mg, 0.62 mmol) was added. The resulting mixture was stirred at ambient temperature for 20 hours. MeOH (2.3 mL) was added and stirring continued for 30 minutes before sodium borohydride (11 mg, 0.28 mmol) was added. The resulting mixture was stirred at ambient temperature for 1 hour. The mixture was partitioned between EtOAc and 0.5 M aqueous NaOH. The organic layer was washed with brine, dried over anhydrous Na$_2$SO$_4$, filtered, and concentrated in vacuo. The residue was purified by MPLC on silica gel (10% MeOH/EtOAc with 1% NH$_4$OH stepping to 2% NH$_4$OH after the first diastereomer elutes). Desired fractions were identified, combined, and concentrated in vacuo to afford the title compound. LRMS (ESI) calc'd for $C_{21}H_{27}ClN_6O$ [M+H]$^+$: 415. Found: 415. $^1$H NMR (500 MHz, CD$_3$OD): δ 8.10 (s, 1H); 7.53-7.54 (m, 2H); 7.21-7.22 (m, 2H); 4.23-4.24 (m, 1H); 3.49-3.50 (m, 1H); 2.84 (tt, J=11.5, 3.9 Hz, 1H); 2.34 (dd, J=12.9, 3.6 Hz, 1H);

2.18-2.20 (m, 1H); 2.01 (s, 2H); 1.67 (q, J=12.3 Hz, 1H); 1.43-1.45 (m, 1H); 1.15 (s, 9H).

Scheme #36 and 44

Example #28-6

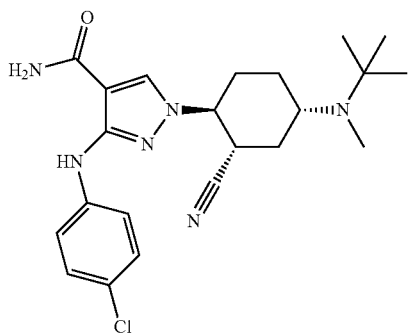 [SMILES: CN([C@H]1CC[C@H](n2cc(C(N)=O)c(Nc3ccc(Cl)cc3)n2)[C@@H](C#N)C1)C(C)(C)C]

1-((1S,2S,4S or 1R,2R,4R)-4-(tert-butyl(methyl) amino)-2-cyanocyclohexyl)-3-((4-chlorophenyl) amino)-1H-pyrazole-4-carboxamide 1-((1R,2R,4R or 1S,2S,4S)-4-(tert-Butylamino)-2-cyano-cyclohexyl)-3-((4-chlorophenyl)amino)-1H-pyrazole-4-carboxamide (Example 28-5) (7.0 mg, 0.017 mmol) was stirred in 1:1 THF:MeOH (0.34 mL) at ambient temperature and sodium cyanoborohydride (1.6 mg, 0.025 mmol), acetic acid (0.0015 mL, 0.025 mmol), and aqueous formaldehyde (0.0019 mL, 0.025 mmol, 37% in water) were added. The resulting mixture was stirred at ambient temperature for 30 minutes, then concentrated in vacuo and partitioned between EtOAc and saturated aqueous $NaHCO_3$. The organic layer was dried over anhydrous $Na_2SO_4$, filtered, and concentrated in vacuo to afford the title compound.

LRMS (ESI) calc'd for $C_{22}H_{30}ClN_6O$ [M+H]$^+$: 429. Found: 429.

$^1$H NMR (500 MHz, $CD_3OD$): δ 8.10 (s, 1H), 7.54 (d, J=9.0 Hz, 2H) 7.23 (d, J=9.0 Hz, 2H), 4.22 (td, J=11.5, 4.3 Hz, 1H), 3.52 (td, J=12.5, 3.5 Hz, 1H), 3.16-3.12 (m, 1H), 2.29 (s, 3H), 2.20-2.05 (m, 3H), 2.00-1.82 (m, 2H), 1.74 (qd, J=12.7, 3.7 Hz, 1H), 1.17 (s, 9H).

The following compounds shown in TABLE 23 were prepared according to Scheme #36 and 40, 41, 42, 43, and 44 following similar procedures described for Examples #28-1, 28-2, 28-3, 28-4, 28-5, and 28-6, which can be achieved by those of ordinary skill in the art of organic synthesis. As an alternative to using chiral stationary phase chromatography, according to Scheme #36, chiral alcohol Intermediate #40 could be utilized thus providing chiral intermediate ketones, and non-racemic diastereomeric reductive amination products.

TABLE 23

| Example | Method | Structure | Compound Name | Exact Mass [M + H]+ |
|---|---|---|---|---|
| 28-7 | 40 | 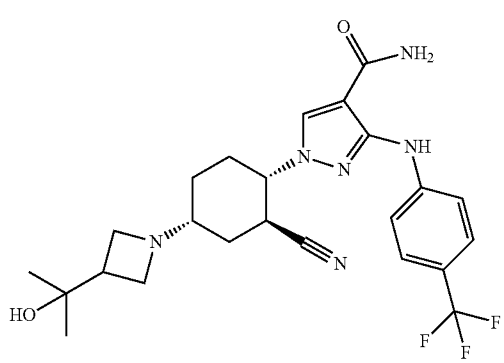 [SMILES: CC(C)(O)C1CN([C@@H]2CC[C@H](n3cc(C(N)=O)c(Nc4ccc(C(F)(F)F)cc4)n3)[C@@H](C#N)C2)C1] | 1-{(1S,2S,4R or 1R,2R,4S)-2-cyano-4-[3-(1-hydroxy-1-methylethyl)azetidin-1-yl]cyclohexyl}-3-{[4-(trifluoromethyl)phenyl]amino}-1H-pyrazole-4-carboxamide | Calc'd 491, found 491 |
| 28-8 | 40 | 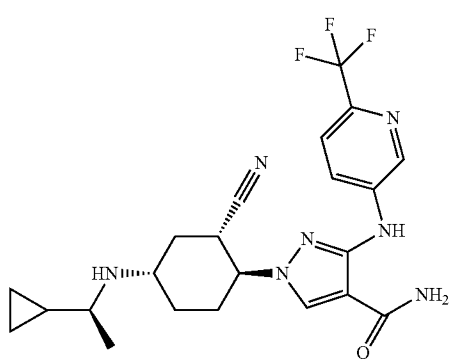 [SMILES: C[C@H](N[C@H]1CC[C@H](n2cc(C(N)=O)c(Nc3ccc(C(F)(F)F)nc3)n2)[C@@H](C#N)C1)C1CC1] | 1-[(1S,2S,4S or 1R,2R,4R)-2-cyano-4-{[(1S)-1-cyclopropylethyl]amino}cyclohexyl]-3-{[6-(trifluoromethyl)pyridin-3-yl]amino}-1H-pyrazole-4-carboxamide | Calc'd 462, found 462 |

TABLE 23-continued

| Example | Method | Structure | Compound Name | Exact Mass [M + H]+ |
|---|---|---|---|---|
| 28-9 | 40 | 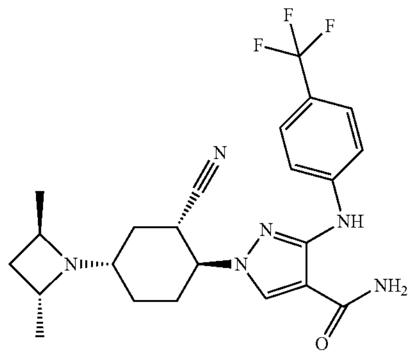 [SMILES: C[C@@H]1C[C@@H](C)N1[C@H]1CC[C@H](n2cc(C(N)=O)c(Nc3ccc(C(F)(F)F)cc3)n2)[C@@H](C#N)C1] | 1-{(1S,2S,4S or 1R,2R,4R)-2-cyano-4-[(2R,4R or 2S,4S)-2,4-dimethylazetidin-1-yl]cyclohexyl}-3-{[4-(trifluoromethyl)phenyl]amino}-1H-pyrazole-4-carboxamide | Calc'd 461, found 461 |
| 28-10 | 40 | 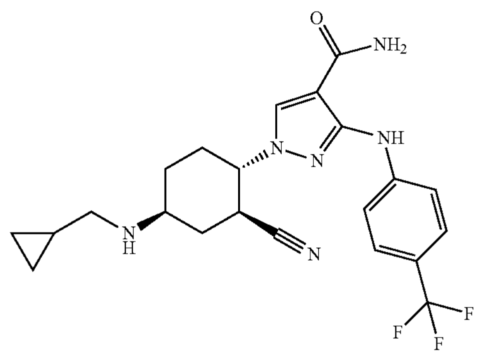 [SMILES: N#C[C@H]1C[C@@H](NCC2CC2)CC[C@@H]1n1cc(C(N)=O)c(Nc2ccc(C(F)(F)F)cc2)n1] | 1-{(1S,2S,4S or 1R,2R,4R)-2-cyano-4-[(cyclopropylmethyl)amino]cyclohexyl}-3-{[4-(trifluoromethyl)phenyl]amino}-1H-pyrazole-4-carboxamide | Calc'd 447, found 447 |
| 28-11 | 41 | 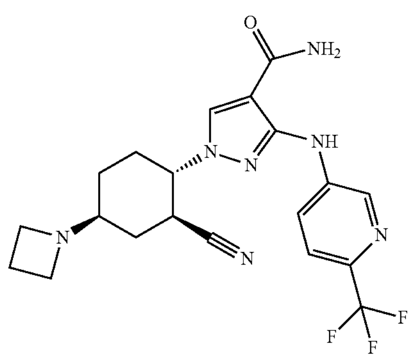 [SMILES: N#C[C@H]1C[C@@H](N2CCC2)CC[C@@H]1n1cc(C(N)=O)c(Nc2ccc(C(F)(F)F)nc2)n1] | 1-[(1S,2S,4S or 1R,2R,4R)-4-azetidin-1-yl-2-cyanocyclohexyl]-3-{[6-(trifluoromethyl)pyridin-3-yl]amino}-1H-pyrazole-4-carboxamide | Calc'd 434, found 434 |
| 28-12 | 41 | 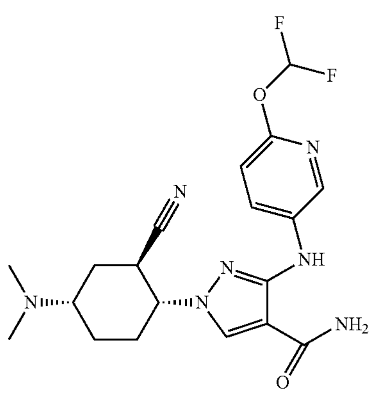 [SMILES: CN(C)[C@H]1CC[C@@H](n2cc(C(N)=O)c(Nc3ccc(OC(F)F)nc3)n2)[C@H](C#N)C1] | 1-[(1R,2R,4S or 1S,2S,4R)-2-cyano-4-(dimethylamino)cyclohexyl]-3-{[6-(difluoromethoxy)pyridin-3-yl]amino}-1H-pyrazole-4-carboxamide | Calc'd 420, found 420 |

TABLE 23-continued

| Example | Method | Structure | Compound Name | Exact Mass [M + H]+ |
|---|---|---|---|---|
| 28-13 | 41 | 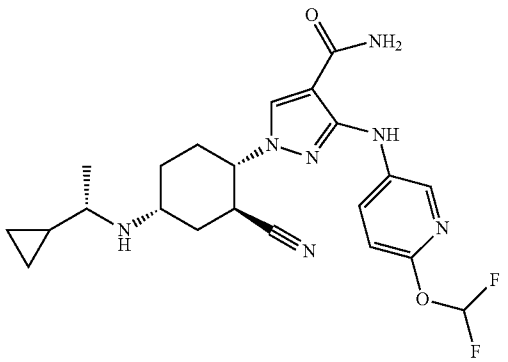 [SMILES: C[C@H](N[C@@H]1CC[C@H](n2cc(C(N)=O)c(Nc3ccc(OC(F)F)nc3)n2)[C@@H](C#N)C1)C1CC1] | 1-[(1S,2S,4R or 1R,2R,4S)-2-cyano-4-{[(1S)-1-cyclopropylethyl]amino}cyclohexyl]-3-{[6-(difluoromethoxy)pyridin-3-yl]amino}-1H-pyrazole-4-carboxamide | Calc'd 460, found 460 |
| 28-14 | 41 | 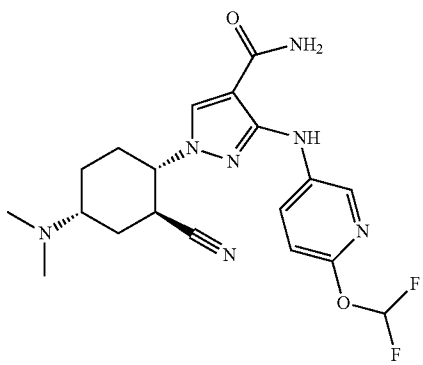 [SMILES: CN(C)[C@@H]1CC[C@H](n2cc(C(N)=O)c(Nc3ccc(OC(F)F)nc3)n2)[C@@H](C#N)C1] | 1-[(1S,2S,4R or 1R,2R,4S)-2-cyano-4-(dimethylamino)cyclohexyl]-3-{[6-(difluoromethoxy)pyridin-3-yl]amino}-1H-pyrazole-4-carboxamide | Calc'd 420, found 420 |
| 28-15 | 40 | 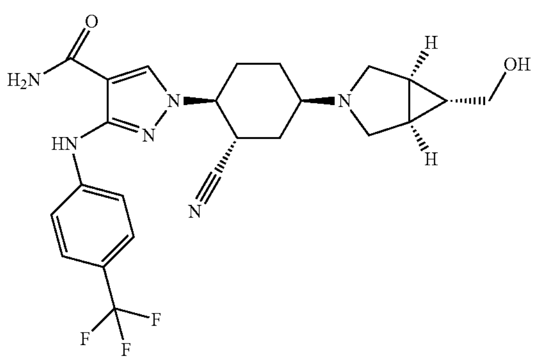 [SMILES: N#C[C@H]1C[C@H](N2C[C@@H]3[C@@H](CO)[C@@H]3C2)CC[C@@H]1n1cc(C(N)=O)c(Nc2ccc(C(F)(F)F)cc2)n1] | 1-{(1S,2S,4R or 1R,2R,4S)-2-cyano-4-[(1R,5S,6R or 1S,5R,6S)-6-(hydroxymethyl)-3-azabicyclo[3.1.0]hex-3-yl]cyclohexyl}-3-{[4-(trifluoromethyl)phenyl]amino}-1H-pyrazole-4-carboxamide | Calc'd 489, found 489 |
| 28-16 | 40 | 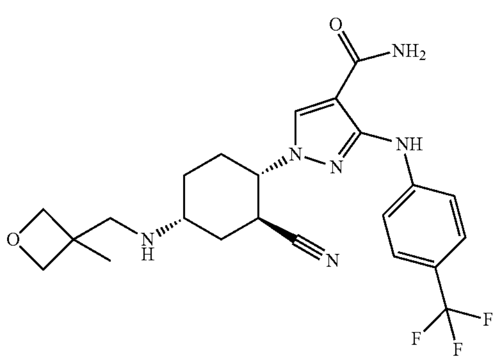 [SMILES: CC1(CN[C@@H]2CC[C@H](n3cc(C(N)=O)c(Nc4ccc(C(F)(F)F)cc4)n3)[C@@H](C#N)C2)COC1] | 1-[(1S,2S,4R or 1R,2R,4S)-2-cyano-4-{[(3-methyloxetan-3-yl)methyl]amino}cyclohexyl]-3-{[4-(trifluoromethyl)phenyl]amino}-1H-pyrazole-4-carboxamide | Calc'd 477, found 477 |

TABLE 23-continued

| Example | Method | Structure | Compound Name | Exact Mass [M + H]+ |
|---|---|---|---|---|
| 28-17 | 40 | 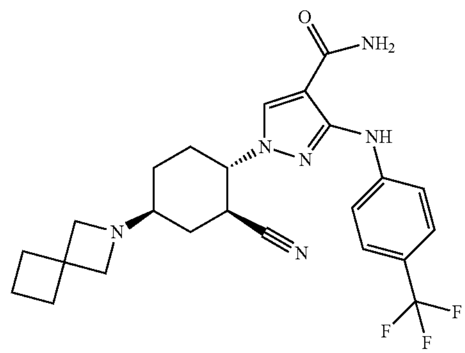 [SMILES: N#C[C@H]1C[C@@H](N2CC3(CCC3)C2)CC[C@@H]1n1cc(C(N)=O)c(Nc2ccc(C(F)(F)F)cc2)n1] | 1-[(1S,2S,4S or 1R,2R,4R)-4-(2-azaspiro[3.3]hept-2-yl)-2-cyanocyclohexyl]-3-{[4-(trifluoromethyl)phenyl]amino}-1H-pyrazole-4-carboxamide | Calc'd 473, found 473 |
| 28-18 | 41 | 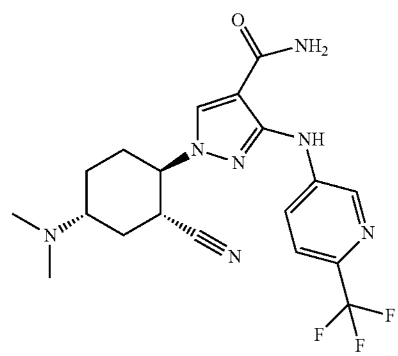 [SMILES: CN(C)[C@@H]1CC[C@@H](n2cc(C(N)=O)c(Nc3ccc(C(F)(F)F)nc3)n2)[C@H](C#N)C1] | 1-[(1R,2R,4R or 1S,2S,4S)-2-cyano-4-(dimethylamino)cyclohexyl]-3-{[6-(trifluoromethyl)pyridin-3-yl]amino}-1H-pyrazole-4-carboxamide | Calc'd 422, found 422 |
| 28-19 | 41 | 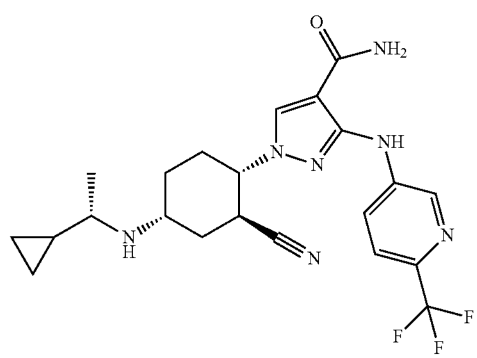 [SMILES: C[C@H](N[C@@H]1CC[C@H](n2cc(C(N)=O)c(Nc3ccc(C(F)(F)F)nc3)n2)[C@@H](C#N)C1)C1CC1] | 1-[(1S,2S,4R or 1R,2R,4S)-2-cyano-4-{[(1S)-1-cyclopropylethyl]amino}cyclohexyl]-3-{[6-(trifluoromethyl)pyridin-3-yl]amino}-1H-pyrazole-4-carboxamide | Calc'd 462, found 462 |
| 28-20 | 40 | 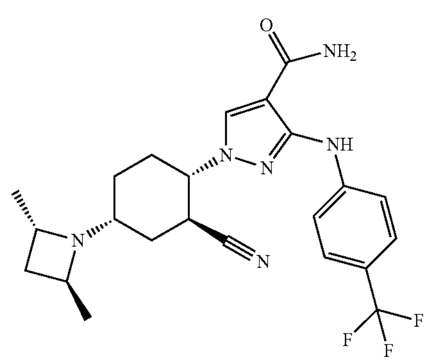 [SMILES: C[C@H]1C[C@H](C)N1[C@@H]1CC[C@H](n2cc(C(N)=O)c(Nc3ccc(C(F)(F)F)cc3)n2)[C@@H](C#N)C1] | 1-{(1S,2S,4R or 1R,2R,4S)-2-cyano-4-[(2S,4S or 2R,4R)-2,4-dimethylazetidin-1-yl]cyclohexyl}-3-{[4-(trifluoromethyl)phenyl]amino}-1H-pyrazole-4-carboxamide | Calc'd 461, found 461 |

TABLE 23-continued

| Example | Method | Structure | Compound Name | Exact Mass [M + H]+ |
|---|---|---|---|---|
| 28-21 | 40 | 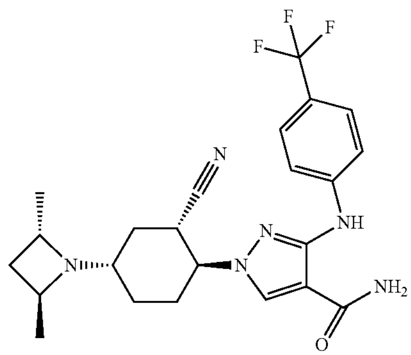 [SMILES: C[C@H]1C[C@H](C)N1[C@H]1CC[C@H](n2cc(C(N)=O)c(Nc3ccc(C(F)(F)F)cc3)n2)[C@@H](C#N)C1] | 1-{(1S,2S,4S or 1R,2R,4R)-2-cyano-4-[(2S,4S or 2R,4R)-2,4-dimethylazetidin-1-yl]cyclohexyl}-3-{[4-(trifluoromethyl)phenyl]amino}-1H-pyrazole-4-carboxamide | Calc'd 461, found 461 |
| 28-22 | 41 | 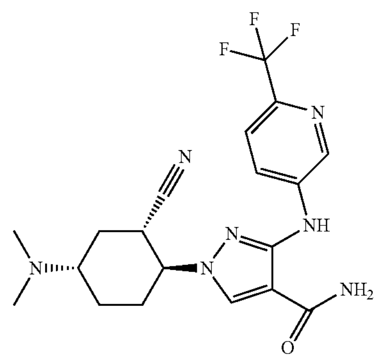 [SMILES: CN(C)[C@H]1CC[C@H](n2cc(C(N)=O)c(Nc3ccc(C(F)(F)F)nc3)n2)[C@@H](C#N)C1] | 1-[(1S,2S,4S or 1R,2R,4R)-2-cyano-4-(dimethylamino)cyclohexyl]-3-{[6-(trifluoromethyl)pyridin-3-yl]amino}-1H-pyrazole-4-carboxamide | Calc'd 422, found 422 |
| 28-23 | 40 | 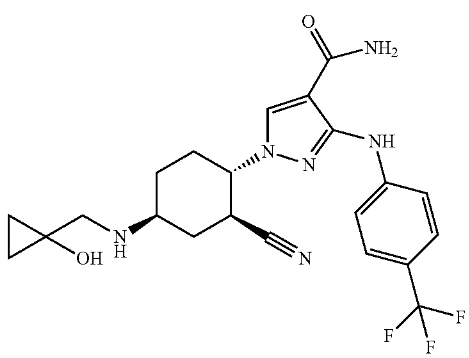 [SMILES: N#C[C@H]1C[C@@H](NCC2(O)CC2)CC[C@@H]1n1cc(C(N)=O)c(Nc2ccc(C(F)(F)F)cc2)n1] | 1-[(1S,2S,4S or 1R,2R,4R)-2-cyano-4-{[(1-hydroxycyclopropyl)methyl]amino}cyclohexyl]-3-{[4-(trifluoromethyl)phenyl]amino}-1H-pyrazole-4-carboxamide | Calc'd 463, found 463 |
| 28-24 | 40 | 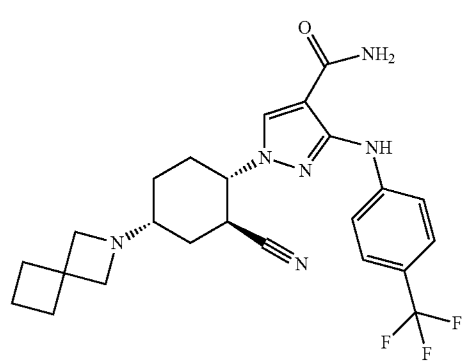 [SMILES: N#C[C@H]1C[C@H](N2CC3(CCC3)C2)CC[C@@H]1n1cc(C(N)=O)c(Nc2ccc(C(F)(F)F)cc2)n1] | 1-[(1S,2S,4R or 1R,2R,4S)-4-(2-azaspiro[3.3]hept-2-yl)-2-cyanocyclohexyl]-3-{[4-(trifluoromethyl)phenyl]amino}-1H-pyrazole-4-carboxamide | Calc'd 473, found 473 |

TABLE 23-continued

| Example | Method | Structure | Compound Name | Exact Mass [M + H]+ |
|---|---|---|---|---|
| 28-25 | 41 | 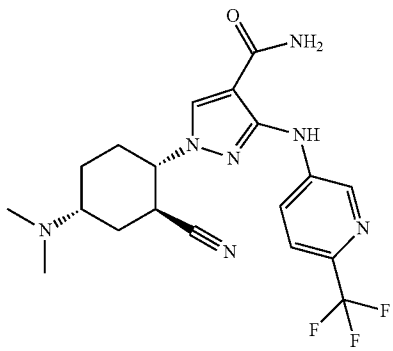 [SMILES: CN(C)[C@@H]1CC[C@H](n2cc(C(N)=O)c(Nc3ccc(C(F)(F)F)nc3)n2)[C@@H](C#N)C1] | 1-[(1S,2S,4R or 1R,2R,4S)-2-cyano-4-(dimethylamino)cyclohexyl]-3-{[6-(trifluoromethyl)pyridin-3-yl]amino}-1H-pyrazole-4-carboxamide | Calc'd 422, found 422 |
| 28-26 | 40 | 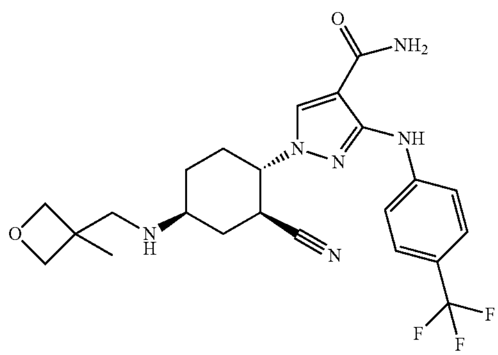 [SMILES: CC1(CN[C@H]2CC[C@H](n3cc(C(N)=O)c(Nc4ccc(C(F)(F)F)cc4)n3)[C@@H](C#N)C2)COC1] | 1-[(1S,2S,4S or 1R,2R,4R)-2-cyano-4-{[(3-methyloxetan-3-yl)methyl]amino}cyclohexyl]-3-{[4-(trifluoromethyl)phenyl]amino}-1H-pyrazole-4-carboxamide | Calc'd 477, found 477 |
| 28-27 | 41 | 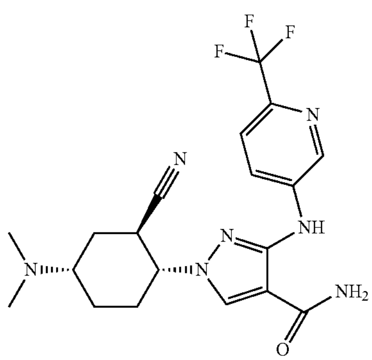 [SMILES: CN(C)[C@H]1CC[C@@H](n2cc(C(N)=O)c(Nc3ccc(C(F)(F)F)nc3)n2)[C@H](C#N)C1] | 1-[(1R,2R,4S or 1S,2S,4R)-2-cyano-4-(dimethylamino)cyclohexyl]-3-{[6-(trifluoromethyl)pyridin-3-yl]amino}-1H-pyrazole-4-carboxamide | Calc'd 422, found 422 |
| 28-28 | 40 | 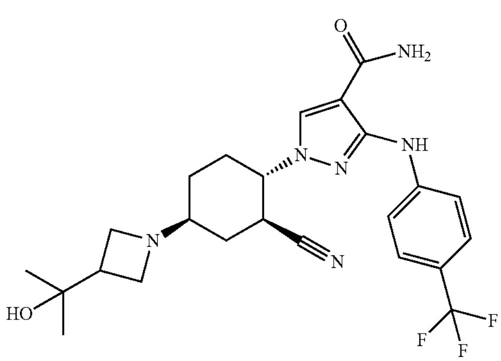 [SMILES: CC(C)(O)C1CN([C@H]2CC[C@H](n3cc(C(N)=O)c(Nc4ccc(C(F)(F)F)cc4)n3)[C@@H](C#N)C2)C1] | 1-{(1S,2S,4S or 1R,2R,4R)-2-cyano-4-[3-(1-hydroxy-1-methylethyl)azetidin-1-yl]cyclohexyl}-3-{[4-(trifluoromethyl)phenyl]amino}-1H-pyrazole-4-carboxamide | Calc'd 491, found 491 |

TABLE 23-continued

| Example | Method | Structure | Compound Name | Exact Mass [M + H]+ |
|---|---|---|---|---|
| 28-30 | 40 | 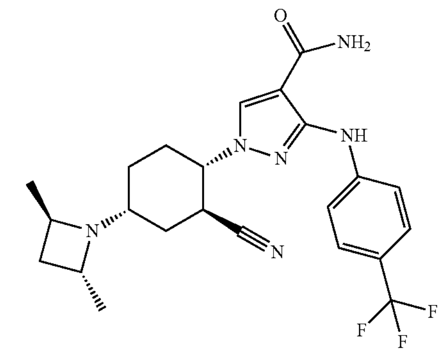 [SMILES: C[C@@H]1C[C@@H](C)N1[C@@H]1CC[C@H](n2cc(C(N)=O)c(Nc3ccc(C(F)(F)F)cc3)n2)[C@@H](C#N)C1] | 1-{(1S,2S,4R or 1R,2R,4S)-2-cyano-4-[(2R,4R or 2S,4S)-2,4-dimethylazetidin-1-yl]cyclohexyl}-3-{[4-(trifluoromethyl)phenyl]amino}-1H-pyrazole-4-carboxamide | Calc'd 461, found 461 |
| 28-31 | 41 | 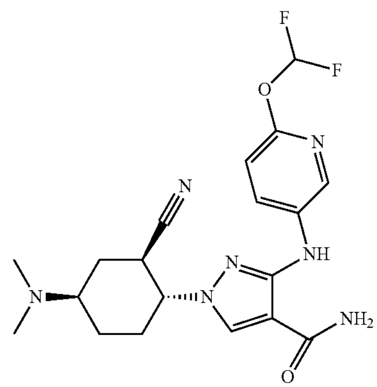 [SMILES: CN(C)[C@@H]1CC[C@@H](n2cc(C(N)=O)c(Nc3ccc(OC(F)F)nc3)n2)[C@H](C#N)C1] | 1-[(1R,2R,4R pr 1S,2S,4S)-2-cyano-4-(dimethylamino)cyclohexyl]-3-{[6-(difluoromethoxy)pyridin-3-yl]amino}-1H-pyrazole-4-carboxamide | Calc'd 420, found 420 |
| 28-32 | 41 | 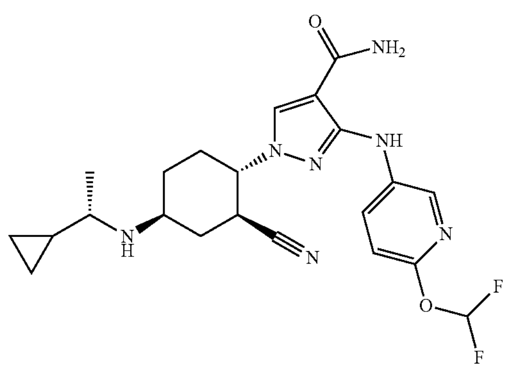 [SMILES: C[C@H](N[C@H]1CC[C@H](n2cc(C(N)=O)c(Nc3ccc(OC(F)F)nc3)n2)[C@@H](C#N)C1)C1CC1] | 1-[(1S,2S,4S or 1R,2R,4R)-2-cyano-4-{[(1S)-1-cyclopropylethyl]amino}cyclohexyl]-3-{[6-(difluoromethoxy)pyridin-3-yl]amino}-1H-pyrazole-4-carboxamide | Calc'd 460, found 460 |
| 28-33 | 41 | 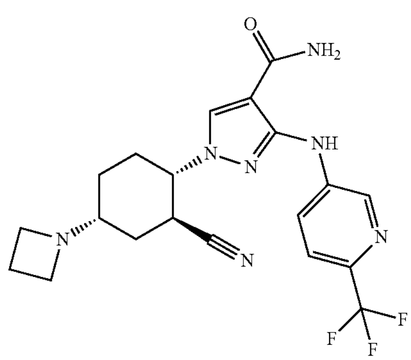 [SMILES: N#C[C@H]1C[C@H](N2CCC2)CC[C@@H]1n1cc(C(N)=O)c(Nc2ccc(C(F)(F)F)nc2)n1] | 1-[(1S,2S,4R or 1R,2R,4S)-4-azetidin-1-yl-2-cyanocyclohexyl]-3-{[6-(trifluoromethyl)pyridin-3-yl]amino}-1H-pyrazole-4-carboxamide | Calc'd 434, found 434 |

TABLE 23-continued

| Example | Method | Structure | Compound Name | Exact Mass [M + H]+ |
|---|---|---|---|---|
| 28-34 | 40 | 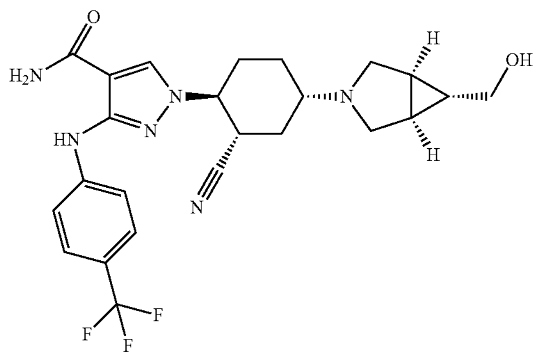 [SMILES: N#C[C@H]1C[C@@H](N2C[C@@H]3[C@@H](CO)[C@@H]3C2)CC[C@@H]1n1cc(C(N)=O)c(Nc2ccc(C(F)(F)F)cc2)n1] | 1-{(1S,2S,4S or 1R,2R,4R)-2-cyano-4-[(1R,5S,6S or 1S,5R,6R)-6-(hydroxymethyl)-3-azabicyclo[3.1.0]hex-3-yl]cyclohexyl}-3-{[4-(trifluoromethyl)phenyl]amino}-1H-pyrazole-4-carboxamide | Calc'd 489, found 489 |
| 28-35 | 40 | 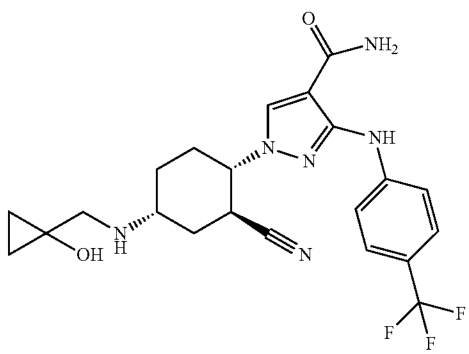 [SMILES: N#C[C@H]1C[C@H](NCC2(O)CC2)CC[C@@H]1n1cc(C(N)=O)c(Nc2ccc(C(F)(F)F)cc2)n1] | 1-[(1S,2S,4R or 1R,2R,4S)-2-cyano-4-{[(1-hydroxycyclopropyl)methyl]amino}cyclohexyl]-3-{[4-(trifluoromethyl)phenyl]amino}-1H-pyrazole-4-carboxamide | Calc'd 463, found 463 |
| 28-36 | 40 | 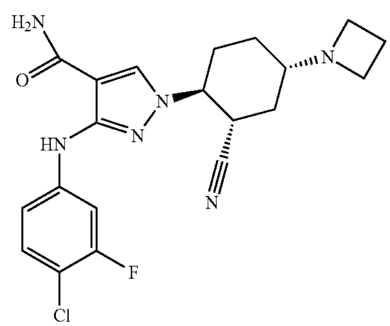 [SMILES: N#C[C@H]1C[C@@H](N2CCC2)CC[C@@H]1n1cc(C(N)=O)c(Nc2ccc(Cl)c(F)c2)n1] | 1-[(1S,2S,4S or 1R,2R,4R)-4-azetidin-1-yl-2-cyanocyclohexyl]-3-[(4-chloro-3-fluorophenyl)amino]-1H-pyrazole-4-carboxamide | Calc'd 417, found 417 |
| 28-37 | 40 | 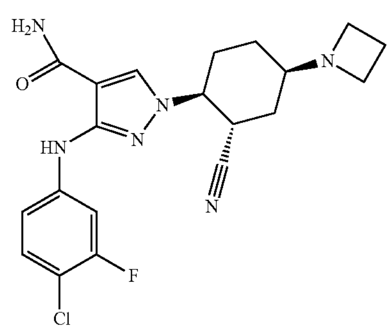 [SMILES: N#C[C@H]1C[C@H](N2CCC2)CC[C@@H]1n1cc(C(N)=O)c(Nc2ccc(Cl)c(F)c2)n1] | 1-[(1S,2S,4R or 1R,2R,4S)-4-azetidin-1-yl-2-cyanocyclohexyl]-3-[(4-chloro-3-fluorophenyl)amino]-1H-pyrazole-4-carboxamide | Calc'd 417, found 417 |

TABLE 23-continued

| Example | Method | Structure | Compound Name | Exact Mass [M + H]+ |
|---|---|---|---|---|
| 28-38 | 40 | 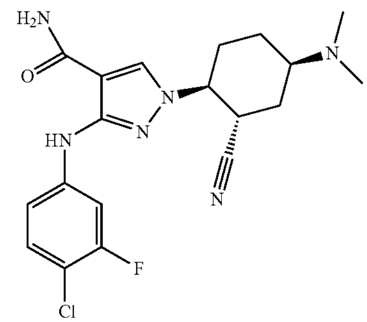 [SMILES: CN(C)[C@@H]1CC[C@H](n2cc(C(N)=O)c(Nc3ccc(Cl)c(F)c3)n2)[C@@H](C#N)C1] | 3-[(4-chloro-3-fluorophenyl)amino]-1-[(1S,2S,4R or 1R,2R,4S)-2-cyano-4-(dimethylamino)cyclohexyl]-1H-pyrazole-4-carboxamide | Calc'd 405, found 405 |
| 28-39 | 40 | 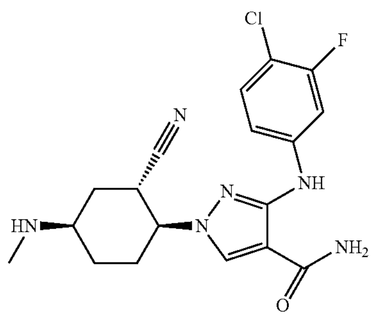 [SMILES: CN[C@@H]1CC[C@H](n2cc(C(N)=O)c(Nc3ccc(Cl)c(F)c3)n2)[C@@H](C#N)C1] | 3-[(4-chloro-3-fluorophenyl)amino]-1-[(1S,2S,4R or 1R,2R,4S)-2-cyano-4-(methylamino)cyclohexyl]-1H-pyrazole-4-carboxamide | Calc'd 391, found 391 |
| 28-40 | 41 | 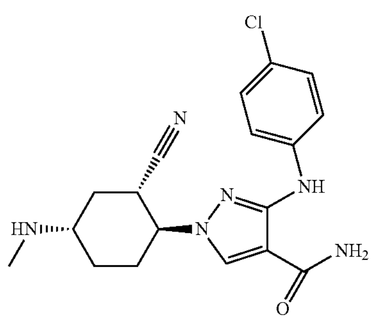 [SMILES: CN[C@H]1CC[C@H](n2cc(C(N)=O)c(Nc3ccc(Cl)cc3)n2)[C@@H](C#N)C1] | 3-[(4-chlorophenyl)amino]-1-[(1S,2S,4S or 1R,2R,4R)-2-cyano-4-(methylamino)cyclohexyl]-1H-pyrazole-4-carboxamide | Calc'd 373, found 373 |
| 28-41 | 40 | 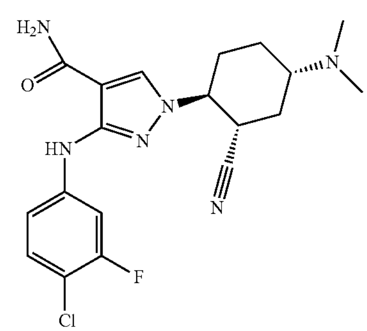 [SMILES: CN(C)[C@H]1CC[C@H](n2cc(C(N)=O)c(Nc3ccc(Cl)c(F)c3)n2)[C@@H](C#N)C1] | 3-[(4-chloro-3-fluorophenyl)amino]-1-[(1S,2S,4S or 1R,2R,4R)-2-cyano-4-(dimethylamino)cyclohexyl]-1H-pyrazole-4-carboxamide | Calc'd 405, found 405 |

TABLE 23-continued

| Example | Method | Structure | Compound Name | Exact Mass [M + H]+ |
|---|---|---|---|---|
| 28-42 | 41 | 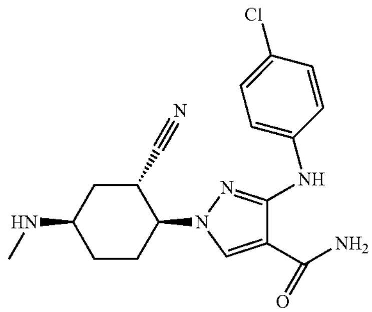 [SMILES: CN[C@@H]1CC[C@H](n2cc(C(N)=O)c(Nc3ccc(Cl)cc3)n2)[C@@H](C#N)C1] | 3-[(4-chlorophenyl)amino]-1-[(1S,2S,4R or 1R,2R,4S)-2-cyano-4-(methylamino)cyclohexyl]-1H-pyrazole-4-carboxamide | Calc'd 373, found 373 |
| 28-43 | 40 | 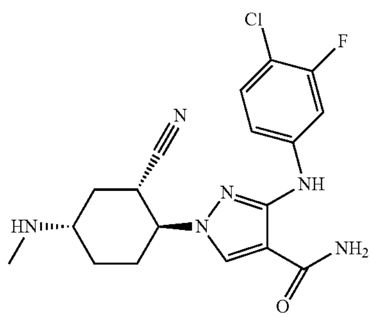 [SMILES: CN[C@H]1CC[C@H](n2cc(C(N)=O)c(Nc3ccc(Cl)c(F)c3)n2)[C@@H](C#N)C1] | 3-[(4-chloro-3-fluorophenyl)amino]-1-[(1S,2S,4S or 1R,2R,4R)-2-cyano-4-(methylamino)cyclohexyl]-1H-pyrazole-4-carboxamide | Calc'd 391, found 391 |
| 28-44 | 40 | 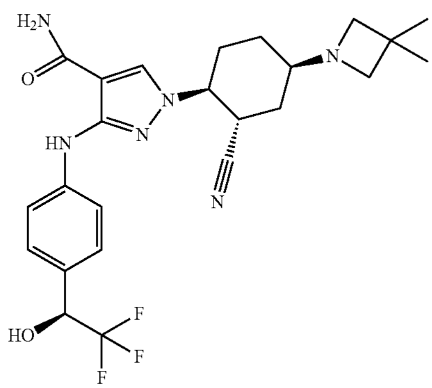 [SMILES: CC1(C)CN([C@@H]2CC[C@H](n3cc(C(N)=O)c(Nc4ccc([C@H](O)C(F)(F)F)cc4)n3)[C@@H](C#N)C2)C1] | 1-[(1S,2S,4R or 1R,2R,4S)-2-cyano-4-(3,3-dimethylazetidin-1-yl)cyclohexyl]-3-({4-[(1S or 1R)-2,2,2-trifluoro-1-hydroxyethyl]phenyl}amino)-1H-pyrazole-4-carboxamide | Calc'd 491, found 491 |
| 28-45 | 40 | 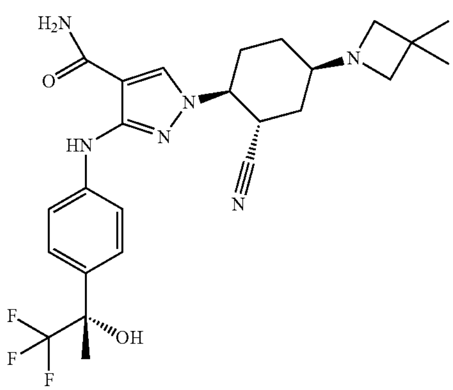 [SMILES: CC1(C)CN([C@@H]2CC[C@H](n3cc(C(N)=O)c(Nc4ccc([C@](C)(O)C(F)(F)F)cc4)n3)[C@@H](C#N)C2)C1] | 1-[(1S,2S,4R or 1R,2R,4S)-2-cyano-4-(3,3-dimethylazetidin-1-yl)cyclohexyl]-3-({4-[(1S or 1R)-2,2,2-trifluoro-1-hydroxy-1-methylethyl]phenyl}amino)-1H-pyrazole-4-carboxamide | Calc'd 505, found 505 |

TABLE 23-continued

| Example | Method | Structure | Compound Name | Exact Mass [M + H]+ |
|---|---|---|---|---|
| 28-47 | 40 | 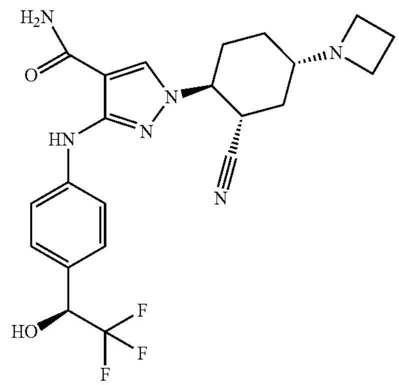 [SMILES: N#C[C@H]1C[C@@H](N2CCC2)CC[C@@H]1n1cc(C(N)=O)c(Nc2ccc([C@H](O)C(F)(F)F)cc2)n1] | 1-[(1S,2S,4S or 1R,2R,4R)-4-azetidin-1-yl-2-cyanocyclohexyl]-3-({4-[(1S or 1R)-2,2,2-trifluoro-1-hydroxyethyl]phenyl}amino)-1H-pyrazole-4-carboxamide | Calc'd 463, found 463 |
| 28-48 | 40 | 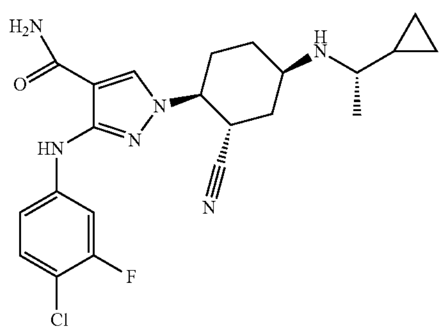 [SMILES: C[C@H](N[C@@H]1CC[C@H](n2cc(C(N)=O)c(Nc3ccc(Cl)c(F)c3)n2)[C@@H](C#N)C1)C1CC1] | 3-[(4-chloro-3-fluorophenyl)amino]-1-[(1S,2S,4R or 1R,2R,4S)-2-cyano-4-{[(1S or 1R)-1-cyclopropylethyl]amino}cyclohexyl]-1H-pyrazole-4-carboxamide | Calc'd 445, found 445 |
| 28-49 | 40 | 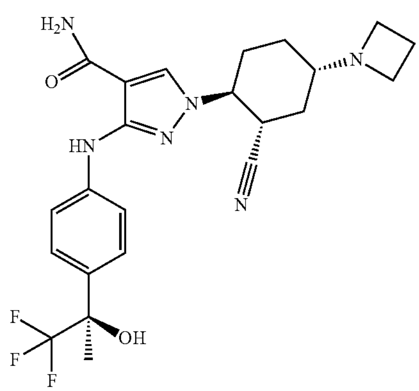 [SMILES: C[C@@](O)(c1ccc(Nc2nn([C@H]3CC[C@H](N4CCC4)C[C@@H]3C#N)cc2C(N)=O)cc1)C(F)(F)F] | 1-[(1S,2S,4S or 1R,2R,4R)-4-azetidin-1-yl-2-cyanocyclohexyl]-3-({4-[(1R or 1S)-2,2,2-trifluoro-1-hydroxy-1-methylethyl]phenyl}amino)-1H-pyrazole-4-carboxamide | Calc'd 477, found 477 |
| 28-50 | 40 | 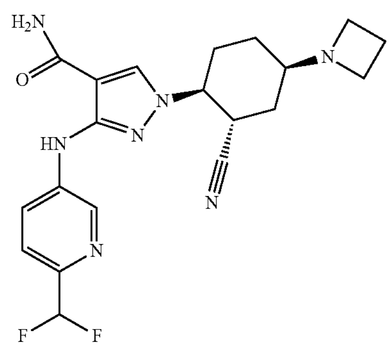 [SMILES: N#C[C@H]1C[C@H](N2CCC2)CC[C@@H]1n1cc(C(N)=O)c(Nc2ccc(C(F)F)nc2)n1] | 1-[(1S,2S,4R or 1R,2R,4S)-4-azetidin-1-yl-2-cyanocyclohexyl]-3-{[6-(difluoromethyl)pyridin-3-yl]amino}-1H-pyrazole-4-carboxamide | Calc'd 416, found 416 |

TABLE 23-continued

| Example | Method | Structure | Compound Name | Exact Mass [M + H]+ |
|---|---|---|---|---|
| 28-51 | 40 | 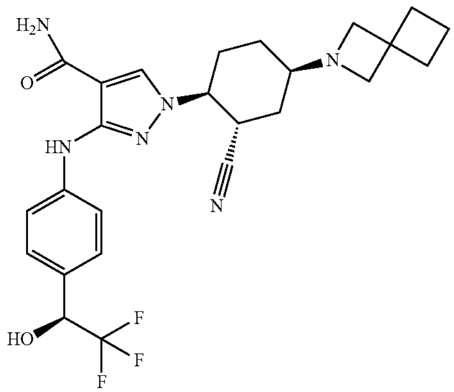 [SMILES: N#C[C@H]1C[C@H](N2CC3(CCC3)C2)CC[C@@H]1n1cc(C(N)=O)c(Nc2ccc([C@H](O)C(F)(F)F)cc2)n1] | 1-[(1S,2S,4R or 1R,2R,4S)-4-(2-azaspiro[3.3]hept-2-yl)-2-cyanocyclohexyl]-3-({4-[(1S or 1R)-2,2,2-trifluoro-1-hydroxyethyl]phenyl}amino)-1H-pyrazole-4-carboxamide | Calc'd 503, found 503 |
| 28-52 | 40 | 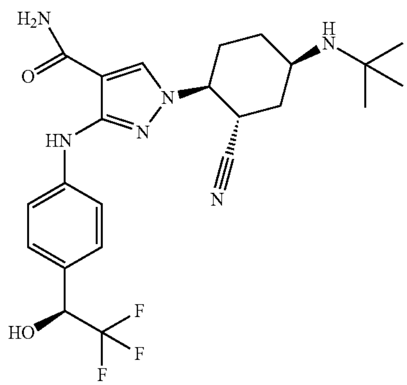 [SMILES: CC(C)(C)N[C@@H]1CC[C@H](n2cc(C(N)=O)c(Nc3ccc([C@H](O)C(F)(F)F)cc3)n2)[C@@H](C#N)C1] | 1-[(1S,2S,4R or 1R,2R,4S)-4-(tert-butylamino)-2-cyanocyclohexyl]-3-({4-[(1S or 1R)-2,2,2-trifluoro-1-hydroxyethyl]phenyl}amino)-1H-pyrazole-4-carboxamide | Calc'd 479, found 479 |
| 28-53 | 40 | 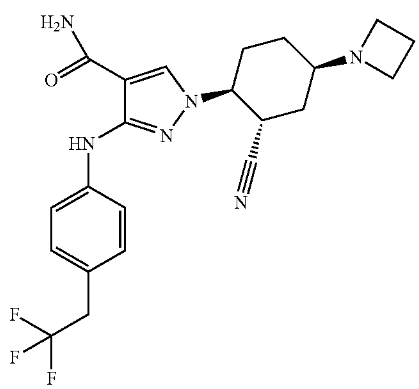 [SMILES: N#C[C@H]1C[C@H](N2CCC2)CC[C@@H]1n1cc(C(N)=O)c(Nc2ccc(CC(F)(F)F)cc2)n1] | 1-[(1S,2S,4R or 1R,2R,4S)-4-azetidin-1-yl-2-cyanocyclohexyl]-3-{[4-(2,2,2-trifluoroethyl)phenyl]amino}-1H-pyrazole-4-carboxamide | Calc'd 447, found 447 |
| 28-54 | 40 | 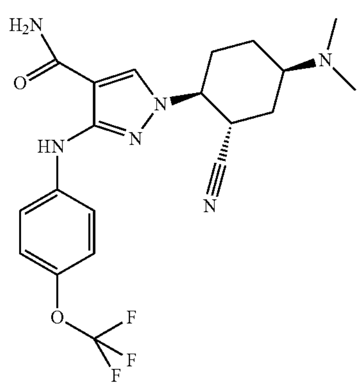 [SMILES: CN(C)[C@@H]1CC[C@H](n2cc(C(N)=O)c(Nc3ccc(OC(F)(F)F)cc3)n2)[C@@H](C#N)C1] | 1-[(1S,2S,4R or 1R,2R,4S)-2-cyano-4-(dimethylamino)cyclohexyl]-3-{[4-(trifluoromethoxy)phenyl]amino}-1H-pyrazole-4-carboxamide | Calc'd 437, found 437 |

TABLE 23-continued

| Example | Method | Structure | Compound Name | Exact Mass [M + H]+ |
|---|---|---|---|---|
| 28-55 | 40 | 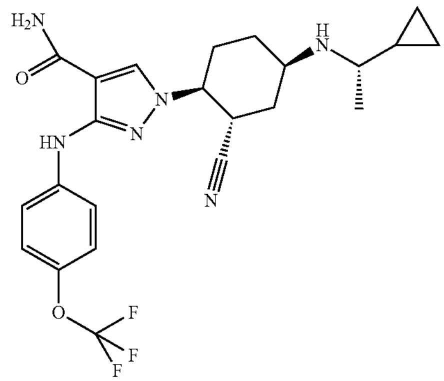 [SMILES: C[C@H](N[C@@H]1CC[C@H](n2cc(C(N)=O)c(Nc3ccc(OC(F)(F)F)cc3)n2)[C@@H](C#N)C1)C1CC1] | 1-[(1S,2S,4R or 1R,2R,4S)-2-cyano-4-{[(1S)-1-cyclopropylethyl]amino}cyclohexyl]-3-{[4-(trifluoromethoxy)phenyl]amino}-1H-pyrazole-4-carboxamide | Calc'd 477, found 477 |
| 28-57 | 40 | 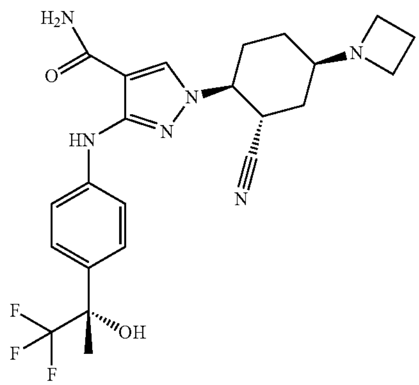 [SMILES: C[C@](O)(c1ccc(Nc2nn([C@H]3CC[C@@H](N4CCC4)C[C@@H]3C#N)cc2C(N)=O)cc1)C(F)(F)F] | 1-[(1S,2S,4R or 1R,2R,4S)-4-azetidin-1-yl-2-cyanocyclohexyl]-3-({4-[(1S or 1R)-2,2,2-trifluoro-1-hydroxy-1-methylethyl]phenyl}amino)-1H-pyrazole-4-carboxamide | Calc'd 477, found 477 |
| 28-58 | 40 | 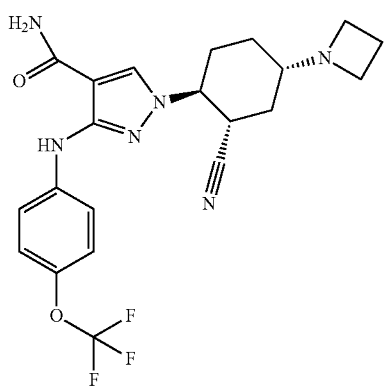 [SMILES: N#C[C@H]1C[C@@H](N2CCC2)CC[C@@H]1n1cc(C(N)=O)c(Nc2ccc(OC(F)(F)F)cc2)n1] | 1-[(1S,2S,4S or 1R,2R,4R)-4-azetidin-1-yl-2-cyanocyclohexyl]-3-{[4-(trifluoromethoxy)phenyl]amino}-1H-pyrazole-4-carboxamide | Calc'd 449, found 449 |
| 28-60 | 40 | 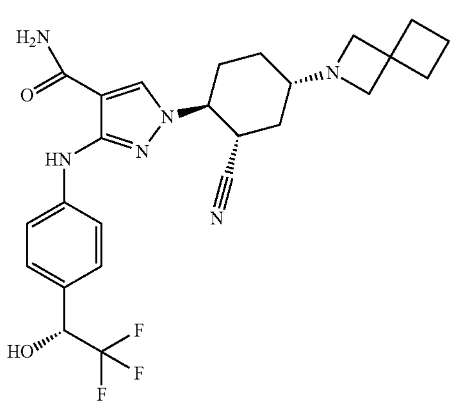 [SMILES: N#C[C@H]1C[C@@H](N2CC3(CCC3)C2)CC[C@@H]1n1cc(C(N)=O)c(Nc2ccc([C@@H](O)C(F)(F)F)cc2)n1] | 1-[(1S,2S,4S or 1R,2R,4R)-4-(2-azaspiro[3.3]hept-2-yl)-2-cyanocyclohexyl]-3-({4-[(1R or 1S)-2,2,2-trifluoro-1-hydroxyethyl]phenyl}amino)-1H-pyrazole-4-carboxamide | Calc'd 503, found 503 |

TABLE 23-continued

| Example | Method | Structure | Compound Name | Exact Mass [M + H]+ |
|---|---|---|---|---|
| 28-61 | 40 | 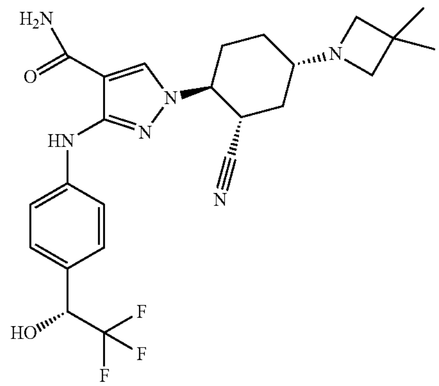 [SMILES: CC1(C)CN([C@H]2CC[C@H](n3cc(C(N)=O)c(Nc4ccc([C@@H](O)C(F)(F)F)cc4)n3)[C@@H](C#N)C2)C1] | 1-[(1S,2S,4S or 1R,2R,4R)-2-cyano-4-(3,3-dimethylazetidin-1-yl)cyclohexyl]-3-({4-[(1R or 1S)-2,2,2-trifluoro-1-hydroxyethyl]phenyl}amino)-1H-pyrazole-4-carboxamide | Calc'd 491, found 491 |
| 28-62 | 40 | 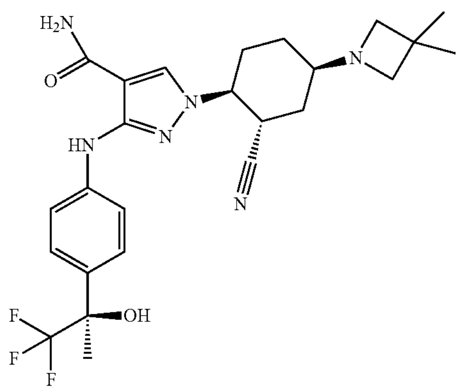 [SMILES: CC1(C)CN([C@@H]2CC[C@H](n3cc(C(N)=O)c(Nc4ccc([C@@](C)(O)C(F)(F)F)cc4)n3)[C@@H](C#N)C2)C1] | 1-[(1S,2S,4R or 1R,2R,4S)-2-cyano-4-(3,3-dimethylazetidin-1-yl)cyclohexyl]-3-({4-[(1R or 1S)-2,2,2-trifluoro-1-hydroxy-1-methylethyl]phenyl}amino)-1H-pyrazole-4-carboxamide | Calc'd 505, found 505 |
| 28-63 | 40 | 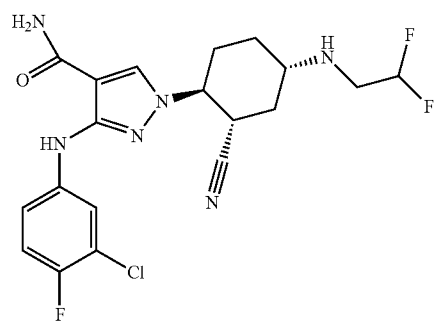 [SMILES: N#C[C@H]1C[C@@H](NCC(F)F)CC[C@@H]1n1cc(C(N)=O)c(Nc2ccc(F)c(Cl)c2)n1] | 3-[(3-chloro-4-fluorophenyl)amino]-1-{(1S,2S,4S or 1R,2R,4R)-2-cyano-4-[(2,2-difluoroethyl)amino]cyclohexyl}-1H-pyrazole-4-carboxamide | Calc'd 441, found 441 |
| 28-65 | 40 | 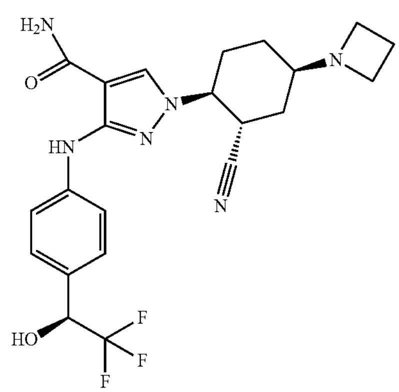 [SMILES: N#C[C@H]1C[C@H](N2CCC2)CC[C@@H]1n1cc(C(N)=O)c(Nc2ccc([C@H](O)C(F)(F)F)cc2)n1] | 1-[(1S,2S,4R or 1R,2R,4S)-4-azetidin-1-yl-2-cyanocyclohexyl]-3-({4-[(1S or 1R)-2,2,2-trifluoro-1-hydroxyethyl]phenyl}amino)-1H-pyrazole-4-carboxamide | Calc'd 463, found 463 |

TABLE 23-continued

| Example | Method | Structure | Compound Name | Exact Mass [M + H]+ |
|---|---|---|---|---|
| 28-66 | 40 | 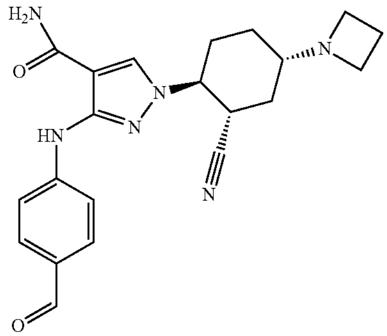 [SMILES: N#C[C@H]1C[C@@H](N2CCC2)CC[C@@H]1n1cc(C(N)=O)c(Nc2ccc(C=O)cc2)n1] | 1-[(1S,2S,4S or 1R,2R,4R)-4-azetidin-1-yl-2-cyanocyclohexyl]-3-[(4-formylphenyl)amino]-1H-pyrazole-4-carboxamide | Calc'd 393, found 393 |
| 28-68 | 40 | 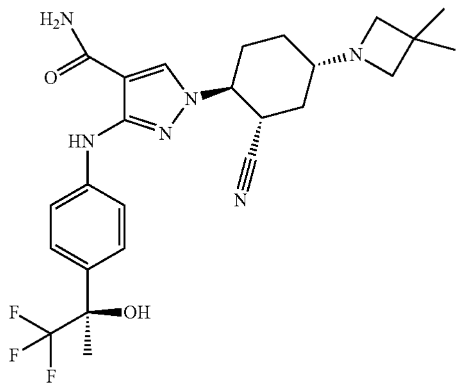 [SMILES: CC1(C)CN([C@H]2CC[C@H](n3cc(C(N)=O)c(Nc4ccc([C@@](C)(O)C(F)(F)F)cc4)n3)[C@@H](C#N)C2)C1] | 1-[(1S,2S,4S or 1R,2R,4R)-2-cyano-4-(3,3-dimethylazetidin-1-yl)cyclohexyl]-3-({4-[(1R or 1S)-2,2,2-trifluoro-1-hydroxy-1-methylethyl]phenyl}amino)-1H-pyrazole-4-carboxamide | Calc'd 505, found 505 |
| 28-69 | 40 | 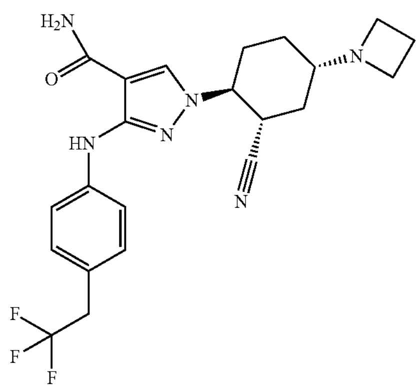 [SMILES: N#C[C@H]1C[C@@H](N2CCC2)CC[C@@H]1n1cc(C(N)=O)c(Nc2ccc(CC(F)(F)F)cc2)n1] | 1-[(1S,2S,4S or 1R,2R,4R)-4-azetidin-1-yl-2-cyanocyclohexyl]-3-{[4-(2,2,2-trifluoroethyl)phenyl]amino}-1H-pyrazole-4-carboxamide | Calc'd 447, found 447 |
| 28-70 | 40 | 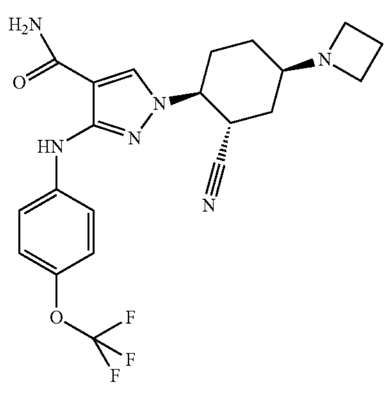 [SMILES: N#C[C@H]1C[C@H](N2CCC2)CC[C@@H]1n1cc(C(N)=O)c(Nc2ccc(OC(F)(F)F)cc2)n1] | 1-[(1S,2S,4R or 1R,2R,4S)-4-azetidin-1-yl-2-cyanocyclohexyl]-3-{[4-(trifluoromethoxy)phenyl]amino}-1H-pyrazole-4-carboxamide | Calc'd 449, found 449 |

TABLE 23-continued

| Example | Method | Structure | Compound Name | Exact Mass [M + H]+ |
|---|---|---|---|---|
| 28-71 | 40 | 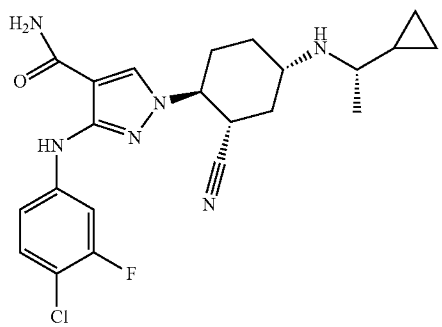 [SMILES: C[C@H](N[C@H]1CC[C@H](n2cc(C(N)=O)c(Nc3ccc(Cl)c(F)c3)n2)[C@@H](C#N)C1)C1CC1] | 3-[(4-chloro-3-fluorophenyl)amino]-1-[(1S,2S,4S or 1R,2R,4R)-2-cyano-4-{[(1S or 1R)-1-cyclopropylethyl]amino}cyclohexyl]-1H-pyrazole-4-carboxamide | Calc'd 445, found 445 |
| 28-72 | 40 | 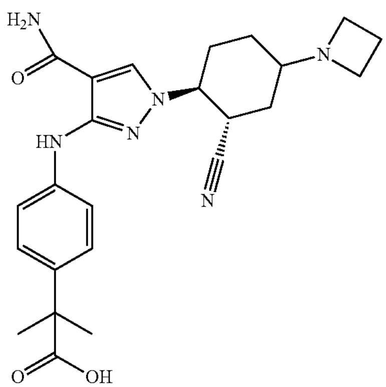 [SMILES: CC(C)(C(=O)O)c1ccc(Nc2nn([C@H]3CCC(N4CCC4)C[C@@H]3C#N)cc2C(N)=O)cc1] | 2-[4-({1-[(1S,2S or 1R,2R)-4-azetidin-1-yl-2-cyanocyclohexyl]-4-carbamoyl-1H-pyrazol-3-yl}amino)phenyl]-2-methylpropanoic acid | Calc'd 451, found 451 |
| 28-75 | 40 | 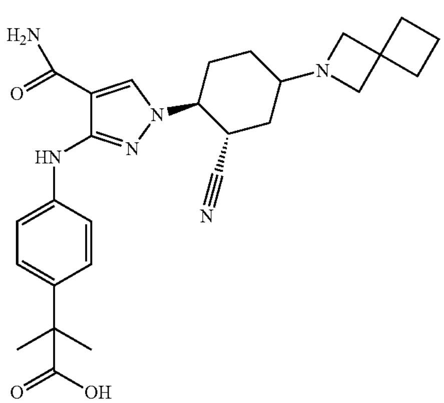 [SMILES: CC(C)(C(=O)O)c1ccc(Nc2nn([C@H]3CCC(N4CC5(CCC5)C4)C[C@@H]3C#N)cc2C(N)=O)cc1] | 2-[4-({1-[(1S,2S,4R or 1R,2R,4S)-4-(2-azaspiro[3.3]hept-2-yl)-2-cyanocyclohexyl]-4-carbamoyl-1H-pyrazol-3-yl}amino)phenyl]-2-methylpropanoic acid | Calc'd 491, found 491 |
| 28-76 | 40 | 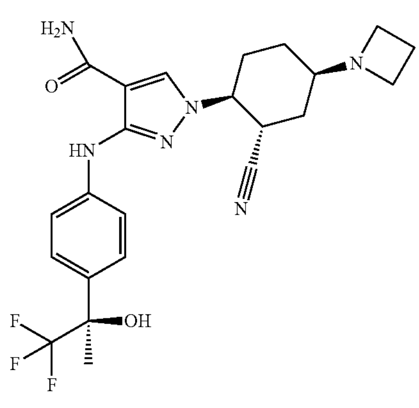 [SMILES: C[C@@](O)(c1ccc(Nc2nn([C@H]3CC[C@@H](N4CCC4)C[C@@H]3C#N)cc2C(N)=O)cc1)C(F)(F)F] | 1-[(1S,2S,4R or 1R,2R,4S)-4-azetidin-1-yl-2-cyanocyclohexyl]-3-({4-[(1R or 1S)-2,2,2-trifluoro-1-hydroxy-1-methylethyl]phenyl}amino)-1H-pyrazole-4-carboxamide | Calc'd 477, found 477 |

TABLE 23-continued

| Example | Method | Structure | Compound Name | Exact Mass [M + H]+ |
|---|---|---|---|---|
| 28-77 | 40 | 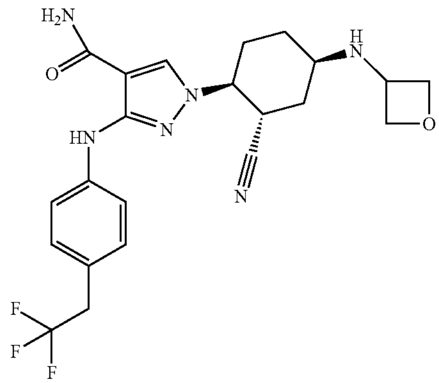 [SMILES: N#C[C@H]1C[C@H](NC2COC2)CC[C@@H]1n1cc(C(N)=O)c(Nc2ccc(CC(F)(F)F)cc2)n1] | 1-[(1S,2S,4R or 1R,2R,4S)-2-cyano-4-(oxetan-3-ylamino)cyclohexyl]-3-{[4-(2,2,2-trifluoroethyl)phenyl]amino}-1H-pyrazole-4-carboxamide | Calc'd 463, found 463 |
| 28-78 | 40 | 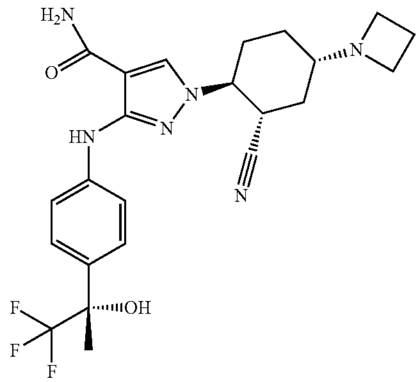 [SMILES: C[C@](O)(c1ccc(Nc2nn([C@H]3CC[C@H](N4CCC4)C[C@@H]3C#N)cc2C(N)=O)cc1)C(F)(F)F] | 1-[(1S,2S,4S or 1R,2R,4R)-4-azetidin-1-yl-2-cyanocyclohexyl]-3-({4-[(1S or 1R)-2,2,2-trifluoro-1-hydroxy-1-methylethyl]phenyl}amino)-1H-pyrazole-4-carboxamide | Calc'd 477, found 477 |
| 28-79 | 40 | 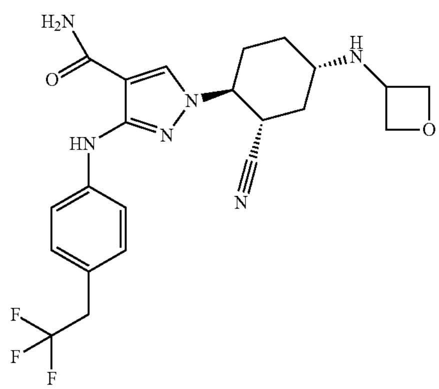 [SMILES: N#C[C@H]1C[C@@H](NC2COC2)CC[C@@H]1n1cc(C(N)=O)c(Nc2ccc(CC(F)(F)F)cc2)n1] | 1-[(1S,2S,4S or 1R,2R,4R)-2-cyano-4-(oxetan-3-ylamino)cyclohexyl]-3-{[4-(2,2,2-trifluoroethyl)phenyl]amino}-1H-pyrazole-4-carboxamide | Calc'd 463, found 463 |
| 28-80 | 40 | 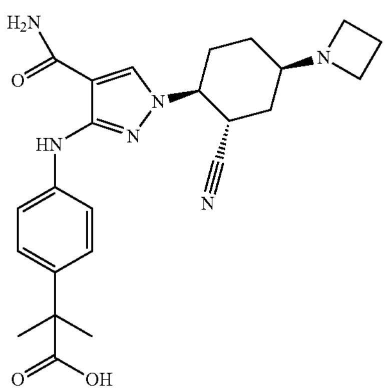 [SMILES: CC(C)(C(=O)O)c1ccc(Nc2nn([C@H]3CC[C@@H](N4CCC4)C[C@@H]3C#N)cc2C(N)=O)cc1] | 2-[4-({1-[(1S,2S,4R or 1R,2R,4S)-4-azetidin-1-yl-2-cyanocyclohexyl]-4-carbamoyl-1H-pyrazol-3-yl}amino)phenyl]-2-methylpropanoic acid | Calc'd 451, found 451 |

TABLE 23-continued

| Example | Method | Structure | Compound Name | Exact Mass [M + H]+ |
|---|---|---|---|---|
| 28-81 | 40 | 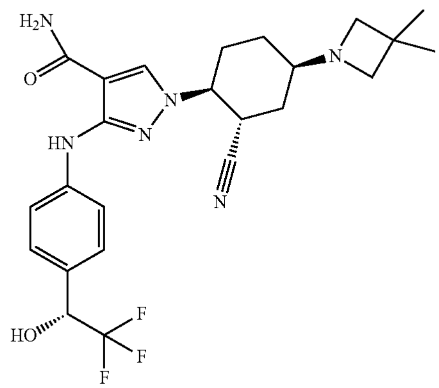 [SMILES: CC1(C)CN([C@@H]2CC[C@H](n3cc(C(N)=O)c(Nc4ccc([C@@H](O)C(F)(F)F)cc4)n3)[C@@H](C#N)C2)C1] | 1-[(1S,2S,4R or 1R,2R,4S)-2-cyano-4-(3,3-dimethylazetidin-1-yl)cyclohexyl]-3-({4-[(1R or 1S)-2,2,2-trifluoro-1-hydroxyethyl]phenyl}amino)-1H-pyrazole-4-carboxamide | Calc'd 491, found 491 |
| 28-83 | 40 | 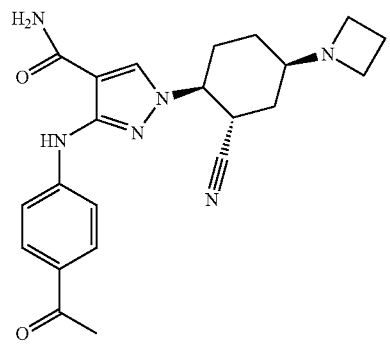 [SMILES: CC(=O)c1ccc(Nc2nn([C@H]3CC[C@@H](N4CCC4)C[C@@H]3C#N)cc2C(N)=O)cc1] | 3-[(4-acetylphenyl)amino]-1-[(1S,2S,4R or 1R,2R,4S)-4-azetidin-1-yl-2-cyanocyclohexyl]-1H-pyrazole-4-carboxamide | Calc'd 407, found 407 |
| 28-84 | 40 | 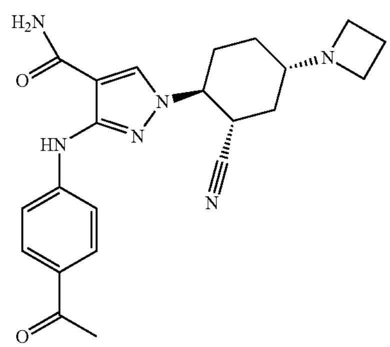 [SMILES: CC(=O)c1ccc(Nc2nn([C@H]3CC[C@H](N4CCC4)C[C@@H]3C#N)cc2C(N)=O)cc1] | 3-[(4-acetylphenyl)amino]-1-[(1S,2S,4S or 1R,2R,4R)-4-azetidin-1-yl-2-cyanocyclohexyl]-1H-pyrazole-4-carboxamide | Calc'd 407, found 407 |
| 28-85 | 40 | 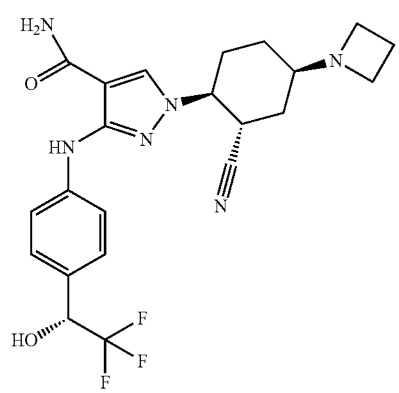 [SMILES: N#C[C@H]1C[C@H](N2CCC2)CC[C@@H]1n1cc(C(N)=O)c(Nc2ccc([C@@H](O)C(F)(F)F)cc2)n1] | 1-[(1S,2S,4R or 1R,2R,4S)-4-azetidin-1-yl-2-cyanocyclohexyl]-3-({4-[(1R or 1S)-2,2,2-trifluoro-1-hydroxyethyl]phenyl}amino)-1H-pyrazole-4-carboxamide | Calc'd 463, found 463 |

TABLE 23-continued

| Example | Method | Structure | Compound Name | Exact Mass [M + H]+ |
|---------|--------|-----------|---------------|---------------------|
| 28-86 | 40 | 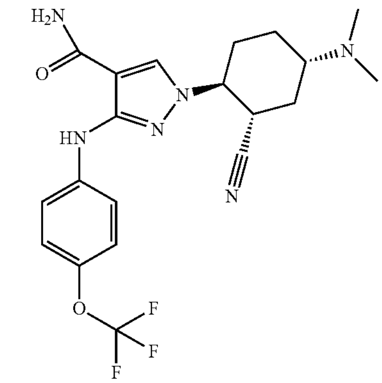 [SMILES: CN(C)[C@H]1CC[C@H](n2cc(C(N)=O)c(Nc3ccc(OC(F)(F)F)cc3)n2)[C@@H](C#N)C1] | 1-[(1S,2S,4S or 1R,2R,4R)-2-cyano-4-(dimethylamino)cyclohexyl]-3-{[4-(trifluoromethoxy)phenyl]amino}-1H-pyrazole-4-carboxamide | Calc'd 437, found 437 |
| 28-87 | 40 | 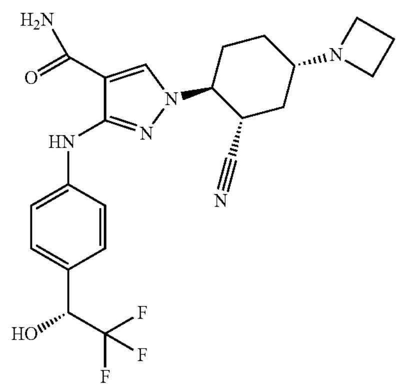 [SMILES: N#C[C@H]1C[C@@H](N2CCC2)CC[C@@H]1n1cc(C(N)=O)c(Nc2ccc([C@@H](O)C(F)(F)F)cc2)n1] | 1-[(1S,2S,4S or 1R,2R,4R)-4-azetidin-1-yl-2-cyanocyclohexyl]-3-({4-[(1R or 1S)-2,2,2-trifluoro-1-hydroxyethyl]phenyl}amino)-1H-pyrazole-4-carboxamide | Calc'd 463, found 463 |
| 28-88 | 40 | 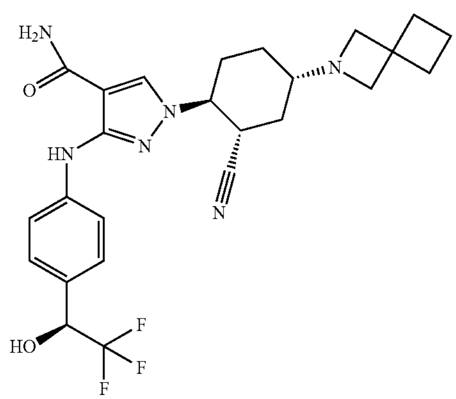 [SMILES: N#C[C@H]1C[C@@H](N2CC3(CCC3)C2)CC[C@@H]1n1cc(C(N)=O)c(Nc2ccc([C@H](O)C(F)(F)F)cc2)n1] | 1-[(1S,2S,4S or 1R,2R,4R)-4-(2-azaspiro[3.3]hept-2-yl)-2-cyanocyclohexyl]-3-({4-[(1S or 1R)-2,2,2-trifluoro-1-hydroxyethyl]phenyl}amino)-1H-pyrazole-4-carboxamide | Calc'd 503, found 503 |
| 28-89 | 40 | 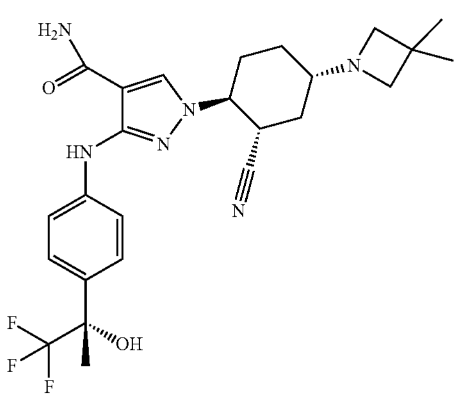 [SMILES: CC1(C)CN([C@H]2CC[C@H](n3cc(C(N)=O)c(Nc4ccc([C@](C)(O)C(F)(F)F)cc4)n3)[C@@H](C#N)C2)C1] | 1-[(1S,2S,4S or 1R,2R,4R)-2-cyano-4-(3,3-dimethylazetidin-1-yl)cyclohexyl]-3-({4-[(1S or 1R)-2,2,2-trifluoro-1-hydroxy-1-methylethyl]phenyl}amino)-1H-pyrazole-4-carboxamide | Calc'd 505, found 505 |

TABLE 23-continued

| Example | Method | Structure | Compound Name | Exact Mass [M + H]+ |
|---|---|---|---|---|
| 28-90 | 40 | 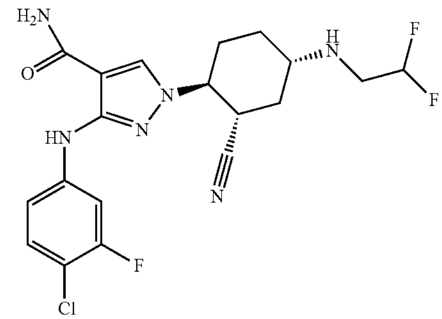 [SMILES: N#C[C@H]1C[C@@H](NCC(F)F)CC[C@@H]1n1cc(C(N)=O)c(Nc2ccc(Cl)c(F)c2)n1] | 3-[(4-chloro-3-fluorophenyl)amino]-1-{(1S,2S,4S or 1R,2R,4R)-2-cyano-4-[(2,2-difluoroethyl)amino]cyclohexyl}-1H-pyrazole-4-carboxamide | Calc'd 441, found 441 |
| 28-91 | 40 | 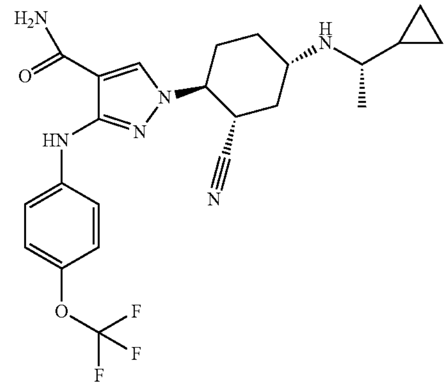 [SMILES: C[C@H](N[C@H]1CC[C@H](n2cc(C(N)=O)c(Nc3ccc(OC(F)(F)F)cc3)n2)[C@@H](C#N)C1)C1CC1] | 1-[(1S,2S,4S or 1R,2R,4R)-2-cyano-4-{[(1S)-1-cyclopropylethyl]amino}cyclohexyl]-3-{[4-(trifluoromethoxy)phenyl]amino}-1H-pyrazole-4-carboxamide | Calc'd 477, found 477 |
| 28-92 | 40 | 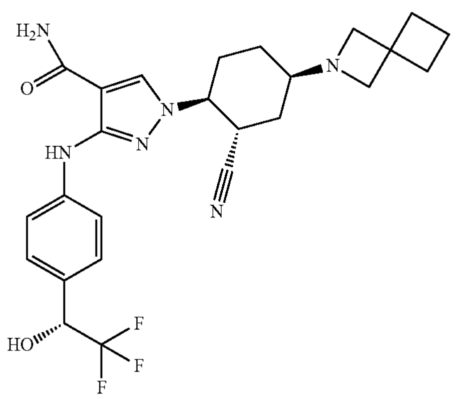 [SMILES: N#C[C@H]1C[C@H](N2CC3(CCC3)C2)CC[C@@H]1n1cc(C(N)=O)c(Nc2ccc([C@@H](O)C(F)(F)F)cc2)n1] | 1-[(1S,2S,4R or 1R,2R,4S)-4-(2-azaspiro[3.3]hept-2-yl)-2-cyanocyclohexyl]-3-({4-[(1R or 1S)-2,2,2-trifluoro-1-hydroxyethyl]phenyl}amino)-1H-pyrazole-4-carboxamide | Calc'd 503, found 503 |
| 28-93 | 40 | 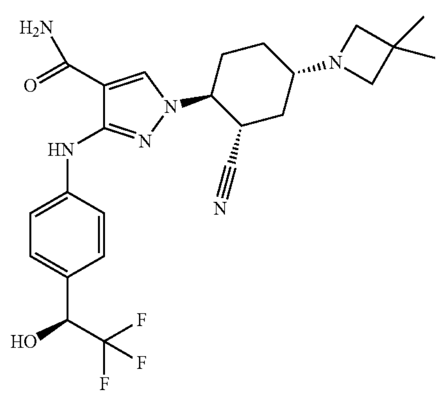 [SMILES: CC1(C)CN([C@H]2CC[C@H](n3cc(C(N)=O)c(Nc4ccc([C@H](O)C(F)(F)F)cc4)n3)[C@@H](C#N)C2)C1] | 1-[(1S,2S,4S or 1R,2R,4R)-2-cyano-4-(3,3-dimethylazetidin-1-yl)cyclohexyl]-3-({4-[(1S or 1R)-2,2,2-trifluoro-1-hydroxyethyl]phenyl}amino)-1H-pyrazole-4-carboxamide | Calc'd 491, found 491 |

TABLE 23-continued

| Example | Method | Structure | Compound Name | Exact Mass [M + H]+ |
|---|---|---|---|---|
| 28-94 | 40 | 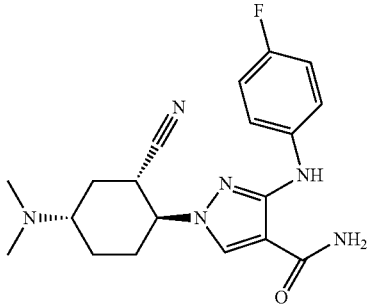 [SMILES: CN(C)[C@H]1CC[C@H](n2cc(C(N)=O)c(Nc3ccc(F)cc3)n2)[C@@H](C#N)C1] | 1-[(1S,2S,4S or 1R,2R,4S)-2-cyano-4-(dimethylamino)cyclohexyl]-3-[(4-fluorophenyl)amino]-1H-pyrazole-4-carboxamide | Calc'd 371, found 371 |
| 28-95 | 40 | 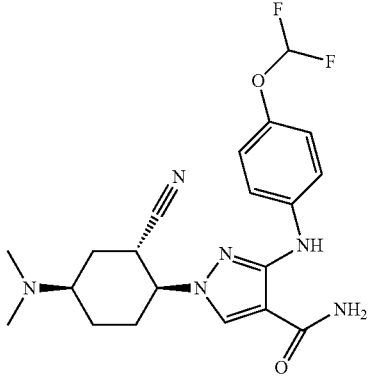 [SMILES: CN(C)[C@@H]1CC[C@H](n2cc(C(N)=O)c(Nc3ccc(OC(F)F)cc3)n2)[C@@H](C#N)C1] | 1-[(1S,2S,4R or 1R,2R,4S)-2-cyano-4-(dimethylamino)cyclohexyl]-3-{[4-(difluoromethoxy)phenyl]amino}-1H-pyrazole-4-carboxamide | Calc'd 419, found 419 |
| 28-96 | 41 | 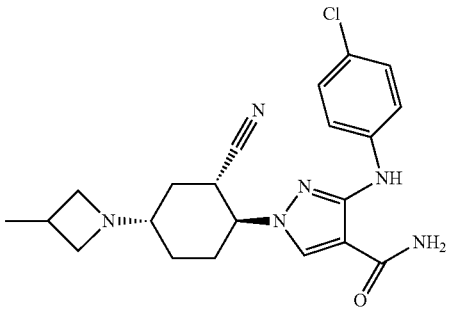 [SMILES: CC1CN([C@H]2CC[C@H](n3cc(C(N)=O)c(Nc4ccc(Cl)cc4)n3)[C@@H](C#N)C2)C1] | 3-[(4-chlorophenyl)amino]-1-[(1S,2S,4S or 1R,2R,4R)-2-cyano-4-(3-methylazetidin-1-yl)cyclohexyl]-1H-pyrazole-4-carboxamide | Calc'd 413, found 413 |
| 28-97 | 40 | 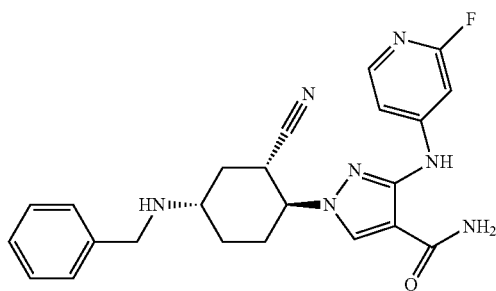 [SMILES: N#C[C@H]1C[C@@H](NCc2ccccc2)CC[C@@H]1n1cc(C(N)=O)c(Nc2ccnc(F)c2)n1] | 1-[(1S,2S,4S or 1R,2R,4R)-4-(benzylamino)-2-cyanocyclohexyl]-3-[(2-fluoropyridin-4-yl)amino]-1H-pyrazole-4-carboxamide | Calc'd 434, found 434 |

TABLE 23-continued

| Example | Method | Structure | Compound Name | Exact Mass [M + H]+ |
|---|---|---|---|---|
| 28-98 | 41 | 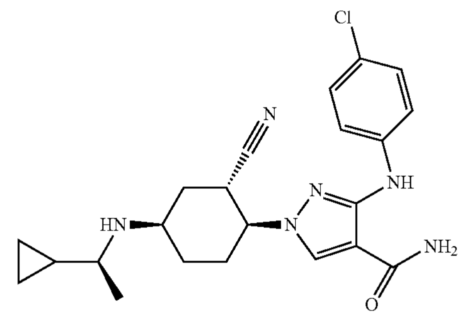 [SMILES: C[C@H](N[C@@H]1CC[C@H](n2cc(C(N)=O)c(Nc3ccc(Cl)cc3)n2)[C@@H](C#N)C1)C1CC1] | 3-[(4-chlorophenyl)amino]-1-[(1S,2S,4R or 1R,2R,4S)-2-cyano-4-{[(1S)-1-cyclopropylethyl]amino}cyclohexyl]-1H-pyrazole-4-carboxamide | Calc'd 427, found 427 |
| 28-99 | 41 | 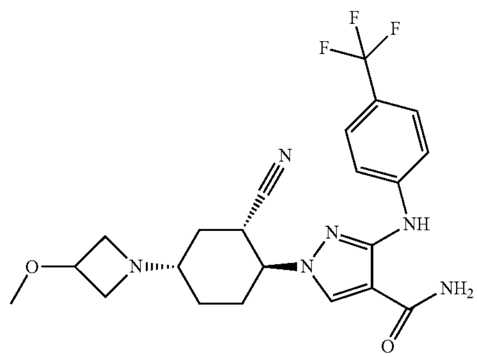 [SMILES: COC1CN([C@H]2CC[C@H](n3cc(C(N)=O)c(Nc4ccc(C(F)(F)F)cc4)n3)[C@@H](C#N)C2)C1] | 1-[(1S,2S,4S or 1R,2R,4R)-2-cyano-4-(3-methoxyazetidin-1-yl)cyclohexyl]-3-{[4-(trifluoromethyl)phenyl]amino}-1H-pyrazole-4-carboxamide | Calc'd 463, found 463 |
| 28-100 | 41 | 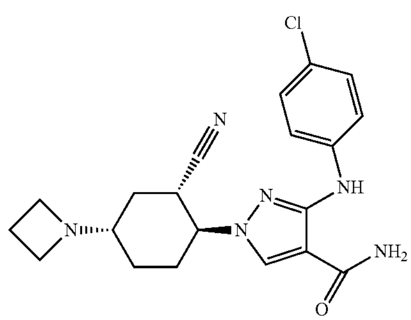 [SMILES: N#C[C@H]1C[C@@H](N2CCC2)CC[C@@H]1n1cc(C(N)=O)c(Nc2ccc(Cl)cc2)n1] | 1-[(1S,2S,4S or 1R,2R,4R)-4-azetidin-1-yl-2-cyanocyclohexyl]-3-[(4-chlorophenyl)amino]-1H-pyrazole-4-carboxamide | Calc'd 399, found 399 |
| 28-101 | 41 | 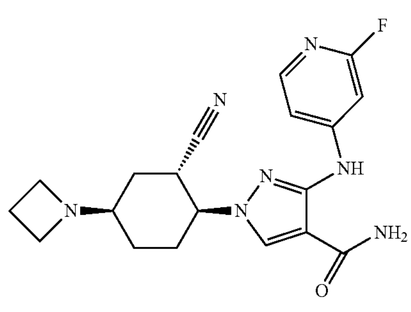 [SMILES: N#C[C@H]1C[C@H](N2CCC2)CC[C@@H]1n1cc(C(N)=O)c(Nc2ccnc(F)c2)n1] | 1-[(1S,2S,4R or 1R,2R,4S)-4-azetidin-1-yl-2-cyanocyclohexyl]-3-[(2-fluoropyridin-4-yl)amino]-1H-pyrazole-4-carboxamide | Calc'd 384, found 384 |

TABLE 23-continued

| Example | Method | Structure | Compound Name | Exact Mass [M + H]+ |
|---|---|---|---|---|
| 28-102 | 40 | 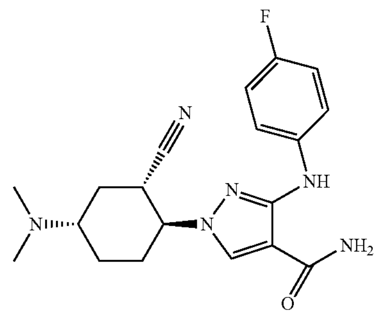 [SMILES: CN(C)[C@H]1CC[C@H](n2cc(C(N)=O)c(Nc3ccc(F)cc3)n2)[C@@H](C#N)C1] | 1-[(1S,2S,4S or 1R,2R,4R)-2-cyano-4-(dimethylamino)cyclohexyl]-3-[(4-fluorophenyl)amino]-1H-pyrazole-4-carboxamide | Calc'd 371, found 371 |
| 28-103 | 40 | 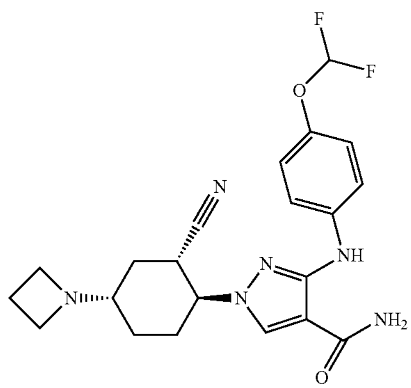 [SMILES: N#C[C@H]1C[C@@H](N2CCC2)CC[C@@H]1n1cc(C(N)=O)c(Nc2ccc(OC(F)F)cc2)n1] | 1-[(1S,2S,4S or 1R,2R,4R)-4-azetidin-1-yl-2-cyanocyclohexyl]-3-{[4-(difluoromethoxy)phenyl]amino}-1H-pyrazole-4-carboxamide | Calc'd 431, found 431 |
| 28-104 | 40 | 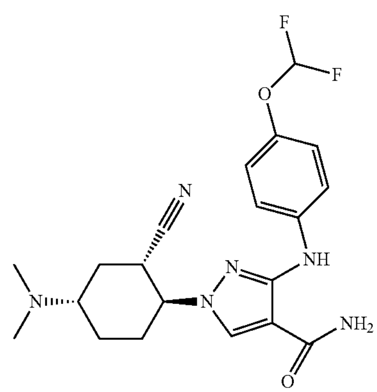 [SMILES: CN(C)[C@H]1CC[C@H](n2cc(C(N)=O)c(Nc3ccc(OC(F)F)cc3)n2)[C@@H](C#N)C1] | 1-[(1S,2S,4S or 1R,2R,4R)-2-cyano-4-(dimethylamino)cyclohexyl]-3-{[4-(difluoromethoxy)phenyl]amino}-1H-pyrazole-4-carboxamide | Calc'd 419, found 419 |
| 28-105 | 41 | 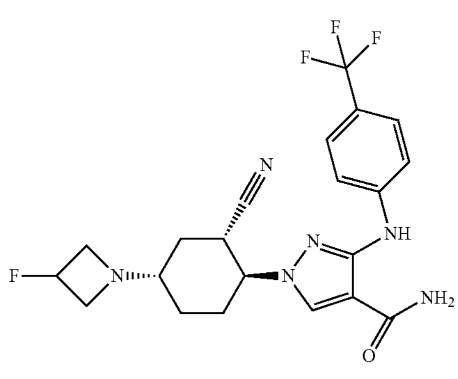 [SMILES: N#C[C@H]1C[C@@H](N2CC(F)C2)CC[C@@H]1n1cc(C(N)=O)c(Nc2ccc(C(F)(F)F)cc2)n1] | 1-[(1S,2S,4S or 1R,2R,4R)-2-cyano-4-(3-fluoroazetidin-1-yl)cyclohexyl]-3-{[4-(trifluoromethyl)phenyl]amino}-1H-pyrazole-4-carboxamide | Calc'd 451, found 451 |

TABLE 23-continued

| Example | Method | Structure | Compound Name | Exact Mass [M + H]+ |
|---|---|---|---|---|
| 28-106 | 40 | 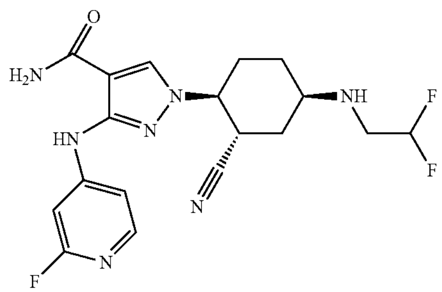 [SMILES: N#C[C@H]1C[C@H](NCC(F)F)CC[C@@H]1n1cc(C(N)=O)c(Nc2ccnc(F)c2)n1] | 1-{(1S,2S,4R or 1R,2R,4S)-2-cyano-4-[(2,2-difluoroethyl)amino]cyclohexyl}-3-[(2-fluoropyridin-4-yl)amino]-1H-pyrazole-4-carboxamide | Calc'd 408, found 408 |
| 28-107 | 40 | 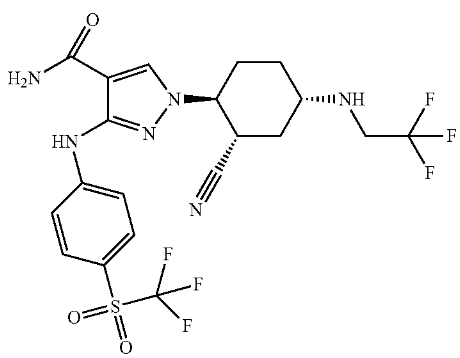 [SMILES: N#C[C@H]1C[C@@H](NCC(F)(F)F)CC[C@@H]1n1cc(C(N)=O)c(Nc2ccc(S(=O)(=O)C(F)(F)F)cc2)n1] | 1-{(1S,2S,4S or 1R,2R,4R)-2-cyano-4-[(2,2,2-trifluoroethyl)amino]cyclohexyl}-3-({4-[(trifluoromethyl)sulfonyl]phenyl}amino)-1H-pyrazole-4-carboxamide | Calc'd 539, found 539 |
| 28-108 | 40 | 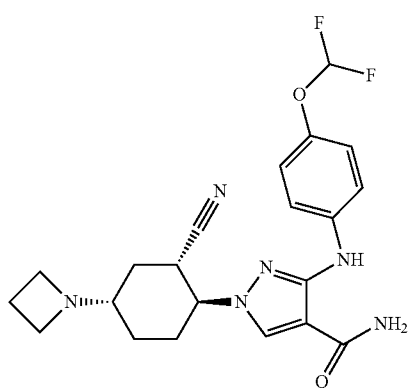 [SMILES: N#C[C@H]1C[C@@H](N2CCC2)CC[C@@H]1n1cc(C(N)=O)c(Nc2ccc(OC(F)F)cc2)n1] | 1-[(1S,2S,4S or 1R,2R,4R)-4-azetidin-1-yl-2-cyanocyclohexyl]-3-{[4-(difluoromethoxy)phenyl]amino}-1H-pyrazole-4-carboxamide | Calc'd 431, found 431 |
| 28-109 | 41 | 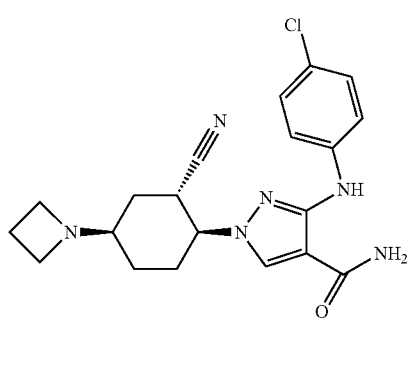 [SMILES: N#C[C@H]1C[C@H](N2CCC2)CC[C@@H]1n1cc(C(N)=O)c(Nc2ccc(Cl)cc2)n1] | 1-[(1S,2S,4R or 1R,2R,4S)-4-azetidin-1-yl-2-cyanocyclohexyl]-3-[(4-chlorophenyl)amino]-1H-pyrazole-4-carboxamide | Calc'd 399, found 399 |

TABLE 23-continued

| Example | Method | Structure | Compound Name | Exact Mass [M + H]+ |
|---|---|---|---|---|
| 28-110 | 41 | 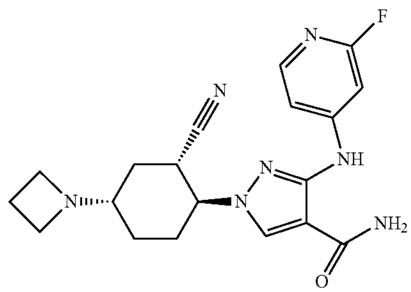 [SMILES: N#C[C@H]1C[C@@H](N2CCC2)CC[C@@H]1n1cc(C(N)=O)c(Nc2ccnc(F)c2)n1] | 1-[(1S,2S,4S or 11R,2R,4R)-4-azetidin-1-yl-2-cyanocyclohexyl]-3-[(2-fluoropyridin-4-yl)amino]-1H-pyrazole-4-carboxamide | Calc'd 384, found 384 |
| 28-111 | 41 | 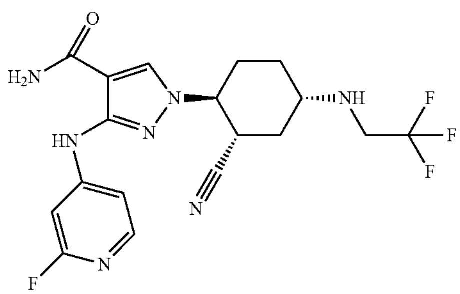 [SMILES: N#C[C@H]1C[C@@H](NCC(F)(F)F)CC[C@@H]1n1cc(C(N)=O)c(Nc2ccnc(F)c2)n1] | 1-{(1S,2S,4S or 1R,2R,4R)-2-cyano-4-[(2,2,2-trifluoroethyl)amino]cyclohexyl}-3-[(2-fluoropyridin-4-yl)amino]-1H-pyrazole-4-carboxamide | Calc'd 426, found 426 |
| 28-112 | 40 | 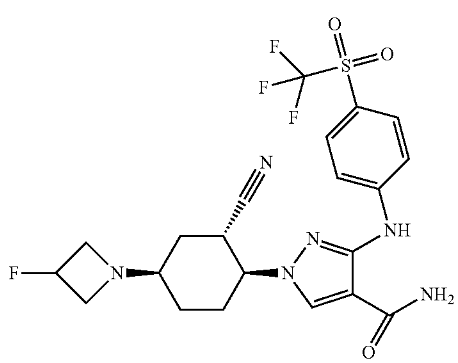 [SMILES: N#C[C@H]1C[C@H](N2CC(F)C2)CC[C@@H]1n1cc(C(N)=O)c(Nc2ccc(S(=O)(=O)C(F)(F)F)cc2)n1] | 1-[(1S,2S,4R or 1R,2R,4S)-2-cyano-4-(3-fluoroazetidin-1-yl)cyclohexyl]-3-({4-[(trifluoromethyl)sulfonyl]phenyl}amino)-1H-pyrazole-4-carboxamide | Calc'd 515, found 515 |
| 28-113 | 40 | 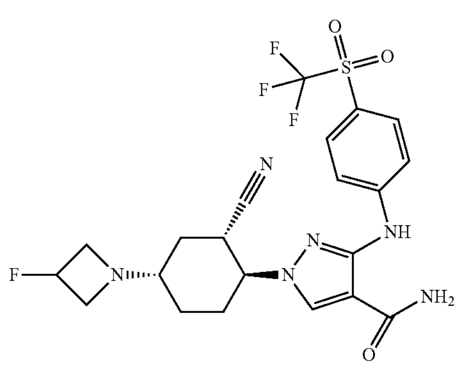 [SMILES: N#C[C@H]1C[C@@H](N2CC(F)C2)CC[C@@H]1n1cc(C(N)=O)c(Nc2ccc(S(=O)(=O)C(F)(F)F)cc2)n1] | 1-[(1S,2S,4S or 1R,2R,4R)-2-cyano-4-(3-fluoroazetidin-1-yl)cyclohexyl]-3-({4-[(trifluoromethyl)sulfonyl]phenyl}amino)-1H-pyrazole-4-carboxamide | Calc'd 515, found 515 |

TABLE 23-continued

| Example | Method | Structure | Compound Name | Exact Mass [M + H]+ |
|---|---|---|---|---|
| 28-114 | 40 | 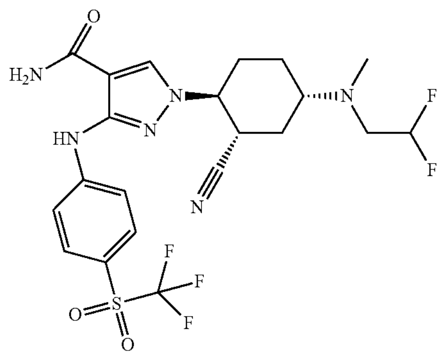 [SMILES: CN(CC(F)F)[C@H]1CC[C@H](n2cc(C(N)=O)c(Nc3ccc(S(=O)(=O)C(F)(F)F)cc3)n2)[C@@H](C#N)C1] | 1-{(1S,2S,4S or 1R,2R,4R)-2-cyano-4-[(2,2-difluoroethyl)(methyl)amino]cyclohexyl}-3-({4-[(trifluoromethyl)sulfonyl]phenyl}amino)-1H-pyrazole-4-carboxamide | Calc'd 535, found 535 |
| 28-115 | 40 | 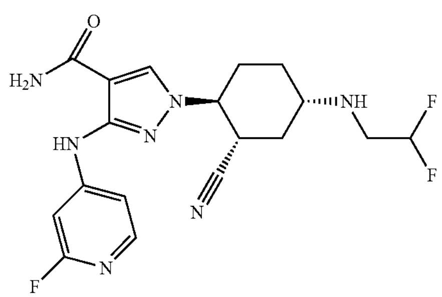 [SMILES: N#C[C@H]1C[C@@H](NCC(F)F)CC[C@@H]1n1cc(C(N)=O)c(Nc2ccnc(F)c2)n1] | 1-{(1S,2S,4S or 1R,2R,4R)-2-cyano-4-[(2,2-difluoroethyl)amino]cyclohexyl}-3-[(2-fluoropyridin-4-yl)amino]-1H-pyrazole-4-carboxamide | Calc'd 408, found 408 |
| 28-116 | 40 | 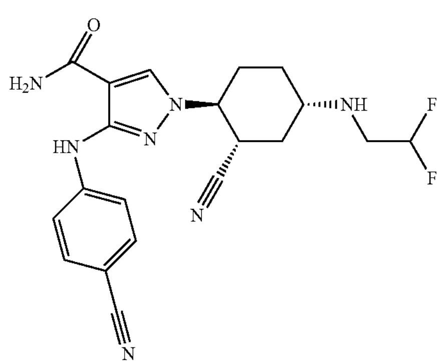 [SMILES: N#Cc1ccc(Nc2nn([C@H]3CC[C@H](NCC(F)F)C[C@@H]3C#N)cc2C(N)=O)cc1] | 1-{(1S,2S,4S or 1R,2R,4R)-2-cyano-4-[(2,2-difluoroethyl)amino]cyclohexyl}-3-[(4-cyanophenyl)amino]-1H-pyrazole-4-carboxamide | Calc'd 414, found 414 |
| 28-117 | 41 | 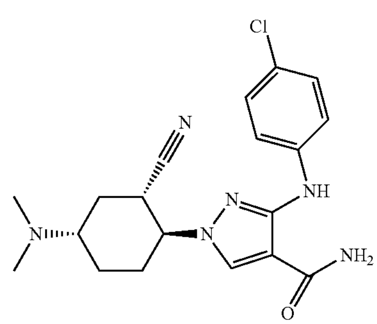 | 3-[(4-chlorophenyl)amino]-1-[(1S,2S,4S or 1R,2R,4R)-2-cyano-4-(dimethylamino)cyclohexyl]-1H-pyrazole-4-carboxamide | Calc'd 387, found 387 |

TABLE 23-continued

| Example | Method | Structure | Compound Name | Exact Mass [M + H]+ |
|---|---|---|---|---|
| 28-118 | 40 | 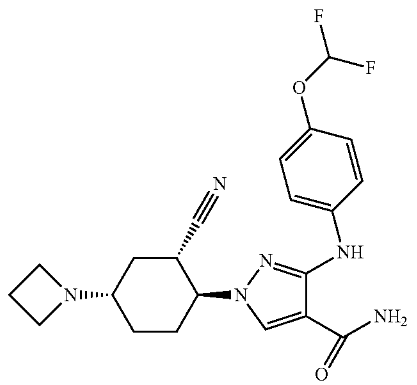 [SMILES: N#C[C@H]1C[C@@H](N2CCC2)CC[C@@H]1n1cc(C(N)=O)c(Nc2ccc(OC(F)F)cc2)n1] | 1-[(1S,2S,4S or 1R,2R,4R)-4-azetidin-1-yl-2-cyanocyclohexyl]-3-{[4-(difluoromethoxy)phenyl]amino}-1H-pyrazole-4-carboxamide | Calc'd 431, found 431 |
| 28-119 | 41 | 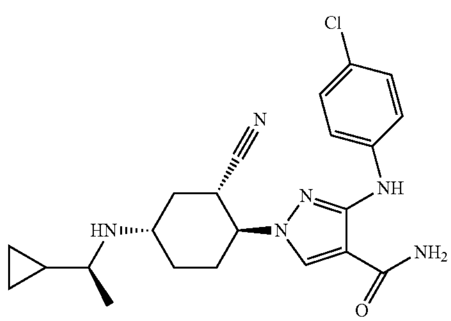 [SMILES: C[C@H](N[C@H]1CC[C@H](n2cc(C(N)=O)c(Nc3ccc(Cl)cc3)n2)[C@@H](C#N)C1)C1CC1] | 3-[(4-chlorophenyl)amino]-1-[(1S,2S,4S or 1R,2R,4R)-2-cyano-4-{[(1R)-1-cyclopropylethyl]amino}cyclohexyl]-1H-pyrazole-4-carboxamide | Calc'd 427, found 427 |
| 28-120 | 41 | 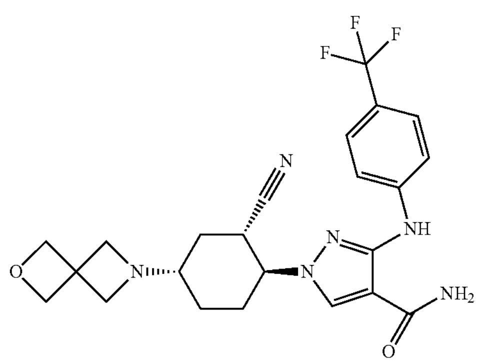 [SMILES: N#C[C@H]1C[C@@H](N2CC3(COC3)C2)CC[C@@H]1n1cc(C(N)=O)c(Nc2ccc(C(F)(F)F)cc2)n1] | 1-[(1S,2S,4S or 1R,2R,4R)-2-cyano-4-(2-oxa-6-azaspiro[3.3]hept-6-yl)cyclohexyl]-3-{[4-(trifluoromethyl)phenyl]amino}-1H-pyrazole-4-carboxamide | Calc'd 475, found 475 |
| 28-121 | 41 | 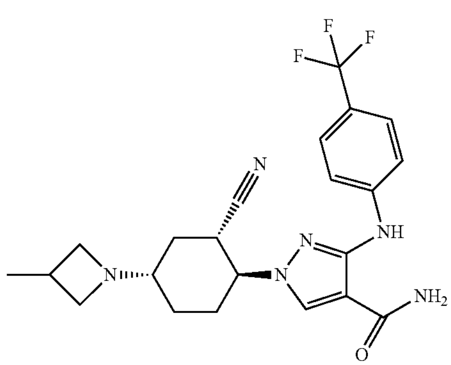 [SMILES: CC1CN([C@H]2CC[C@H](n3cc(C(N)=O)c(Nc4ccc(C(F)(F)F)cc4)n3)[C@@H](C#N)C2)C1] | 1-[(1S,2S,4S or 1R,2R,4R)-2-cyano-4-(3-methylazetidin-1-yl)cyclohexyl]-3-{[4-(trifluoromethyl)phenyl]amino}-1H-pyrazole-4-carboxamide | Calc'd 447, found 447 |

TABLE 23-continued

| Example | Method | Structure | Compound Name | Exact Mass [M + H]+ |
|---|---|---|---|---|
| 28-122 | 40 | 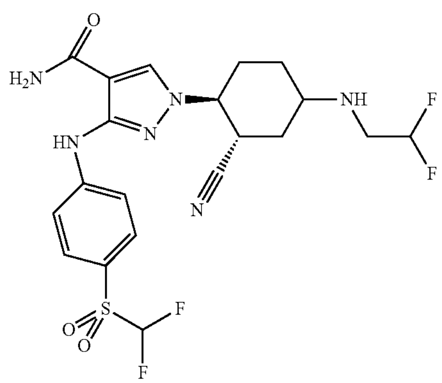 [SMILES: N#C[C@H]1CC(NCC(F)F)CC[C@@H]1n1cc(C(N)=O)c(Nc2ccc(S(=O)(=O)C(F)F)cc2)n1] | 1-{(1S,2S or 1R,2R)-2-cyano-4-[(2,2-difluoroethyl)amino]cyclohexyl}-3-({4-[(difluoromethyl)sulfonyl]phenyl}amino)-1H-pyrazole-4-carboxamide | Calc'd 503, found 503 |
| 28-123 | 40 | 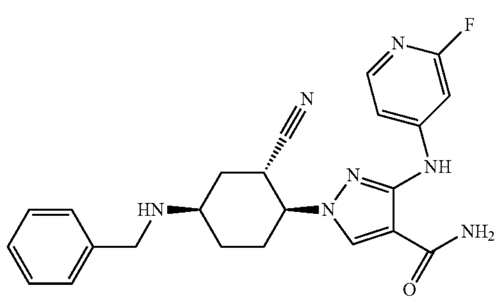 [SMILES: N#C[C@H]1C[C@H](NCc2ccccc2)CC[C@@H]1n1cc(C(N)=O)c(Nc2ccnc(F)c2)n1] | 1-[(1S,2S,4R or 1R,2R,4S)-4-(benzylamino)-2-cyanocyclohexyl]-3-[(2-fluoropyridm-4-yl)amino]-1H-pyrazole-4-carboxamide | Calc'd 434, found 434 |
| 28-124 | 41 | 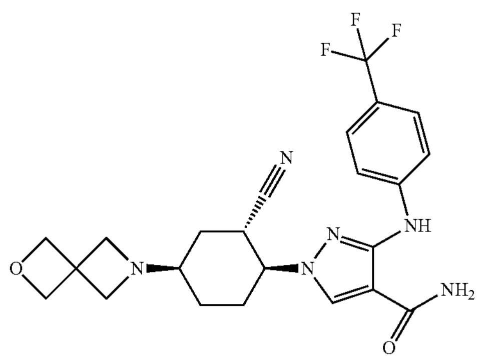 [SMILES: N#C[C@H]1C[C@H](N2CC3(COC3)C2)CC[C@@H]1n1cc(C(N)=O)c(Nc2ccc(C(F)(F)F)cc2)n1] | 1-[(1S,2S,4R or 1R,2R,4S)-2-cyano-4-(2-oxa-6-azaspiro[3.3]hept-6-yl)cyclohexyl]-3-{[4-(trifluoromethyl)phenyl]amino}-1H-pyrazole-4-carboxamide | Calc'd 475, found 475 |
| 28-125 | 41 | 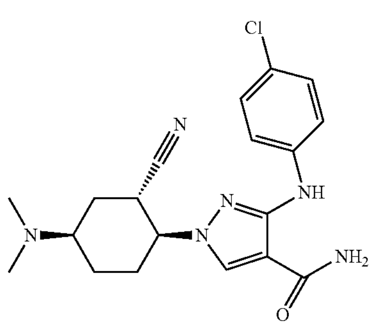 [SMILES: CN(C)[C@@H]1CC[C@H](n2cc(C(N)=O)c(Nc3ccc(Cl)cc3)n2)[C@@H](C#N)C1] | 3-[(4-chlorophenyl)amino]-1-[(1S,2S,4R or 1R,2R,4S)-2-cyano-4-(dimethylamino)cyclohexyl]-1H-pyrazole-4-carboxamide | Calc'd 387, found 387 |

TABLE 23-continued

| Example | Method | Structure | Compound Name | Exact Mass [M + H]+ |
|---|---|---|---|---|
| 28-126 | 40 | 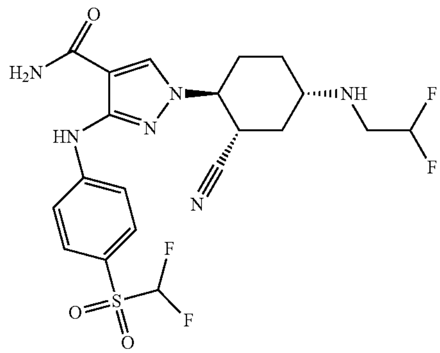 [SMILES: N#C[C@H]1C[C@@H](NCC(F)F)CC[C@@H]1n1cc(C(N)=O)c(Nc2ccc(S(=O)(=O)C(F)F)cc2)n1] | 1-{(1S,2S,4S or 1R,2R,4R)-2-cyano-4-[(2,2-difluoroethyl)amino]cyclohexyl}-3-({4-[(difluoromethyl)sulfonyl]phenyl}amino)-1H-pyrazole-4-carboxamide | Calc'd 503, found 503 |
| 28-127 | 40 | 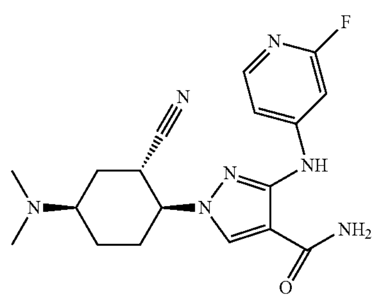 [SMILES: CN(C)[C@@H]1CC[C@H](n2cc(C(N)=O)c(Nc3ccnc(F)c3)n2)[C@@H](C#N)C1] | 1-[(1S,2S,4R or 1R,2R,4S)-2-cyano-4-(dimethylamino)cyclohexyl]-3-[(2-fluoropyridin-4-yl)amino]-1H-pyrazole-4-carboxamide | Calc'd 372, found 372 |
| 28-128 | 40 | 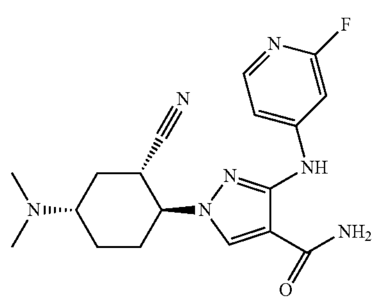 [SMILES: CN(C)[C@H]1CC[C@H](n2cc(C(N)=O)c(Nc3ccnc(F)c3)n2)[C@@H](C#N)C1] | 1-[(1S,2S,4S or 1R,2R,4R)-2-cyano-4-(dimethylamino)cyclohexyl]-3-[(2-fluoropyridin-4-yl)amino]-1H-pyrazole-4-carboxamide | Calc'd 372, found 372 |
| 28-129 | 40 | 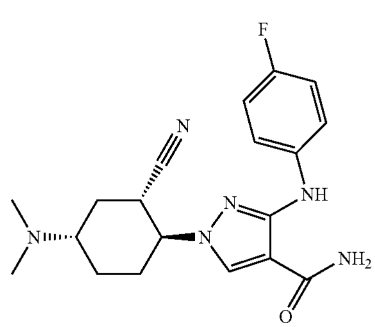 [SMILES: CN(C)[C@H]1CC[C@H](n2cc(C(N)=O)c(Nc3ccc(F)cc3)n2)[C@@H](C#N)C1] | 1-[(1S,2S,4S or 1R,2R,4R)-2-cyano-4-(dimethylamino)cyclohexyl]-3-[(4-fluorophenyl)amino]-1H-pyrazole-4-carboxamide | Calc'd 371, found 371 |

TABLE 23-continued

| Example | Method | Structure | Compound Name | Exact Mass [M + H]+ |
|---|---|---|---|---|
| 28-130 | 41 | 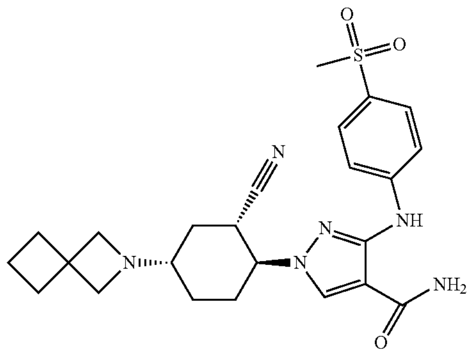 [SMILES: CS(=O)(=O)c1ccc(Nc2nn([C@H]3CC[C@H](N4CC5(CCC5)C4)C[C@@H]3C#N)cc2C(N)=O)cc1] | 1-[(1S,2S,4S or 1R,2R,4R)-4-(2-azaspiro[3.3]hept-2-yl)-2-cyanocyclohexyl]-3-{[4-(methylsulfonyl)phenyl]amino}-1H-pyrazole-4-carboxamide | Calc'd 483, found 483 |
| 28-131 | 41 | 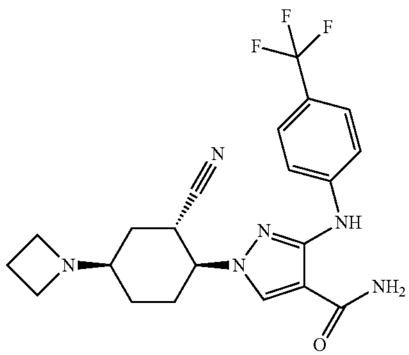 [SMILES: N#C[C@H]1C[C@H](N2CCC2)CC[C@@H]1n1cc(C(N)=O)c(Nc2ccc(C(F)(F)F)cc2)n1] | 1-[(1S,2S,4R or 1R,2R,4S)-4-azetidin-1-yl-2-cyanocyclohexyl]-3-{[4-(trifluoromethyl)phenyl]amino}-1H-pyrazole-4-carboxamide | Calc'd 433, found 433 |
| 28-133 | 41 | 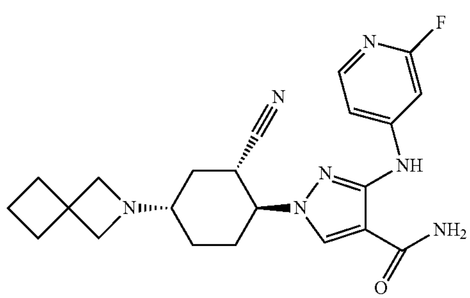 [SMILES: N#C[C@H]1C[C@@H](N2CC3(CCC3)C2)CC[C@@H]1n1cc(C(N)=O)c(Nc2ccnc(F)c2)n1] | 1-[(1S,2S,4S or 1R,2R,4R)-4-(2-azaspiro[3.3]hept-2-yl)-2-cyanocyclohexyl]-3-[(2-fluoropyridin-4-yl)amino]-1H-pyrazole-4-carboxamide | Calc'd 424, found 424 |
| 28-134 | 41 | 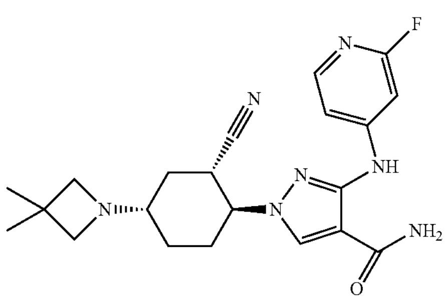 [SMILES: CC1(C)CN([C@H]2CC[C@H](n3cc(C(N)=O)c(Nc4ccnc(F)c4)n3)[C@@H](C#N)C2)C1] | 1-[(1S,2S,4S or 1R,2R,4R )-2-cyano-4-(3,3-dimethylazetidin-1-yl)cyclohexyl]-3-[(2-fluoropyridin-4-yl)amino]-1H-pyrazole-4-carboxamide | Calc'd 412, found 412 |
| 28-135 | 42 | 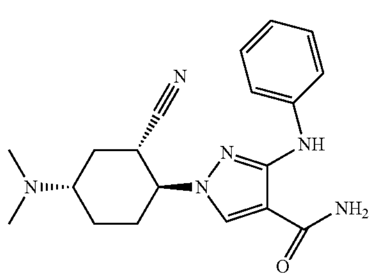 [SMILES: CN(C)[C@H]1CC[C@H](n2cc(C(N)=O)c(Nc3ccccc3)n2)[C@@H](C#N)C1] | 1-[(1S,2S,4S or 1R,2R,4R)-2-cyano-4-(dimethylamino)cyclohexyl]-3-(phenylamino)-1H-pyrazole-4-carboxamide | Calc'd 353, found 353 |

TABLE 23-continued

| Example | Method | Structure | Compound Name | Exact Mass [M + H]+ |
|---|---|---|---|---|
| 28-136 | 42 | 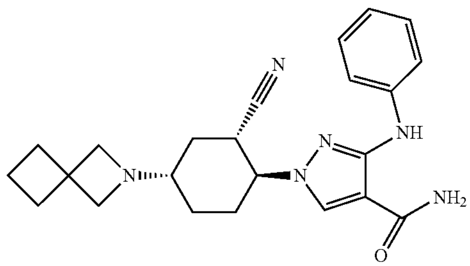 [SMILES: N#C[C@H]1C[C@@H](N2CC3(CCC3)C2)CC[C@@H]1n1cc(C(N)=O)c(Nc2ccccc2)n1] | 1-[(1S,2S,4S or 1R,2R,4R)-4-(2-azaspiro[3.3]hept-2-yl)-2-cyanocyclohexyl]-3-(phenylamino)-1H-pyrazole-4-carboxamide | Calc'd 405, found 405 |
| 28-137 | 41 | 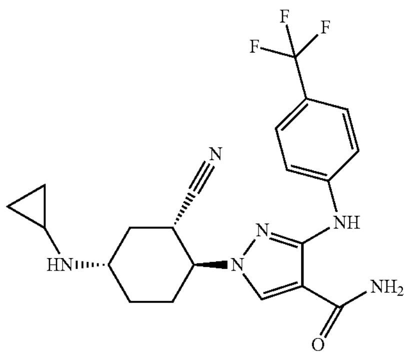 [SMILES: N#C[C@H]1C[C@@H](NC2CC2)CC[C@@H]1n1cc(C(N)=O)c(Nc2ccc(C(F)(F)F)cc2)n1] | 1-[(1S,2S,4S or 1R,2R,4R)-2-cyano-4-(cyclopropylamino)cyclohexyl]-3-{[4-(trifluoromethyl)phenyl]amino}-1H-pyrazole-4-carboxamide | Calc'd 433, found 433 |
| 28-138 | 41 | 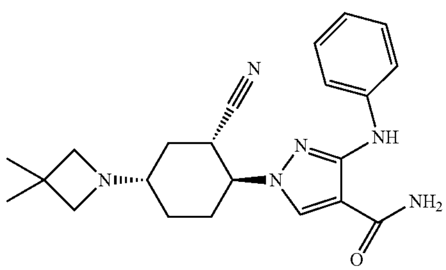 [SMILES: CC1(C)CN([C@H]2CC[C@H](n3cc(C(N)=O)c(Nc4ccccc4)n3)[C@@H](C#N)C2)C1] | 1-[(1S,2S,4S or 1R,2R,4R)-2-cyano-4-(3,3-dimethylazetidin-1-yl)cyclohexyl]-3-(phenylamino)-1H-pyrazole-4-carboxamide | Calc'd 393, found 393 |
| 28-139 | 41 | 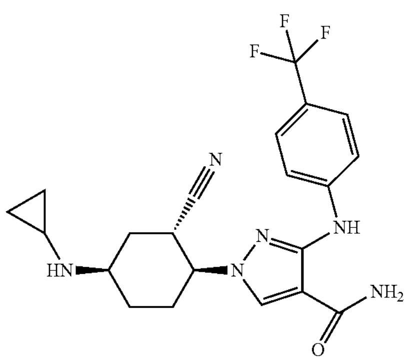 [SMILES: N#C[C@H]1C[C@H](NC2CC2)CC[C@@H]1n1cc(C(N)=O)c(Nc2ccc(C(F)(F)F)cc2)n1] | 1-[(1S,2S,4R or 1R,2R,4R)-2-cyano-4-(cyclopropylamino)cyclohexyl]-3-{[4-(trifluoromethyl)phenyl]amino}-1H-pyrazole-4-carboxamide | Calc'd 433, found 433 |
| 28-141 | 41 | 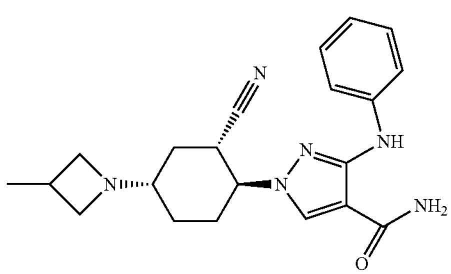 [SMILES: CC1CN([C@H]2CC[C@H](n3cc(C(N)=O)c(Nc4ccccc4)n3)[C@@H](C#N)C2)C1] | 1-[(1S,2S,4S or 1R,2R,4R)-2-cyano-4-(3-methylazetidin-1-yl)cyclohexyl]-3-(phenylamino)-1H-pyrazole-4-carboxamide | Calc'd 379, found 379 |

TABLE 23-continued

| Example | Method | Structure | Compound Name | Exact Mass [M + H]+ |
|---|---|---|---|---|
| 28-142 | 41 | 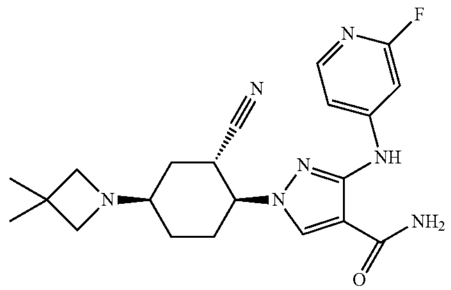 [SMILES: CC1(C)CN([C@@H]2CC[C@H](n3cc(C(N)=O)c(Nc4ccnc(F)c4)n3)[C@@H](C#N)C2)C1] | 1-[(1S,2S,4R or 1R,2R,4S)-2-cyano-4-(3,3-dimethylazetidin-1-yl)cyclohexyl]-3-[(2-fluoropyridin-4-yl)amino]-1H-pyrazole-4-carboxamide | Calc'd 412, found 412 |
| 28-143 | 41 | 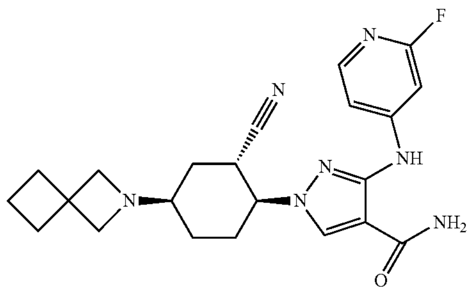 [SMILES: N#C[C@H]1C[C@H](N2CC3(CCC3)C2)CC[C@@H]1n1cc(C(N)=O)c(Nc2ccnc(F)c2)n1] | 1-[(1S,2S,4R or 1R,2R,4S)-4-(2-azaspiro[3.3]hept-2-yl)-2-cyanocyclohexyl]-3-[(2-fluoropyridin-4-yl)amino]-1H-pyrazole-4-carboxamide | Calc'd 424, found 424 |
| 28-144 | 41 | 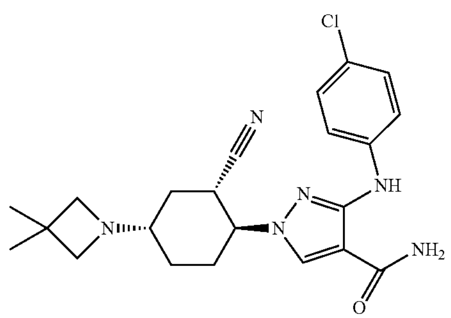 [SMILES: CC1(C)CN([C@H]2CC[C@H](n3cc(C(N)=O)c(Nc4ccc(Cl)cc4)n3)[C@@H](C#N)C2)C1] | 3-[(4-chlorophenyl)amino]-1-[(1S,2S,4S or 1R,2R,4R)-2-cyano-4-(3,3-dimethylazetidin-1-yl)cyclohexyl]-1H-pyrazole-4-carboxamide | Calc'd 427, found 427 |
| 28-145 | 41 | 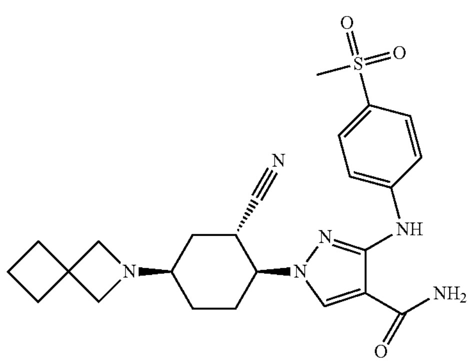 [SMILES: CS(=O)(=O)c1ccc(Nc2nn([C@H]3CC[C@@H](N4CC5(CCC5)C4)C[C@@H]3C#N)cc2C(N)=O)cc1] | 1-[(1S,2S,4R or 1R,2R,4S)-4-(2-azaspiro[3.3]hept-2-yl)-2-cyanocyclohexyl]-3-{[4-(methylsulfonyl)phenyl]amino}-1H-pyrazole-4-carboxamide | Calc'd 483, found 483 |
| 28-146 | 41 | 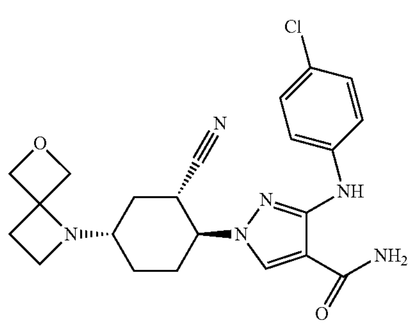 [SMILES: N#C[C@H]1C[C@@H](N2CCC23COC3)CC[C@@H]1n1cc(C(N)=O)c(Nc2ccc(Cl)cc2)n1] | 3-[(4-chlorophenyl)amino]-1-[(1S,2S,4S or 1R,2R,4R)-2-cyano-4-(6-oxa-1-azaspiro[3.3]hept-1-yl)cyclohexyl]-1H-pyrazole-4-carboxamide | Calc'd 441, found 441 |

TABLE 23-continued

| Example | Method | Structure | Compound Name | Exact Mass [M + H]+ |
|---|---|---|---|---|
| 28-147 | 40 | 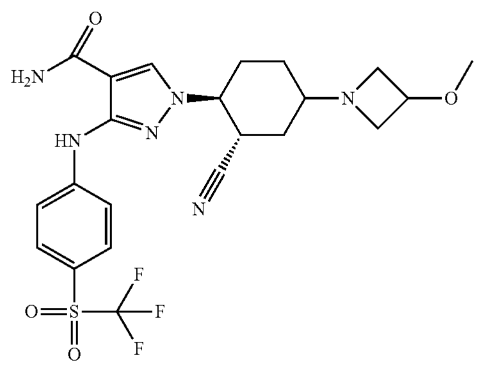 [SMILES: COC1CN(C2CC[C@H](n3cc(C(N)=O)c(Nc4ccc(S(=O)(=O)C(F)(F)F)cc4)n3)[C@@H](C#N)C2)C1] | 1-[(1S,2S or 1R,2R)-2-cyano-4-(3-methoxyazetidin-1-yl)cyclohexyl]-3-({4-[(trifluoromethyl)sulfonyl]phenyl}amino)-1H-pyrazole-4-carboxamide | Calc'd 527, found 527 |
| 28-148 | 40 | 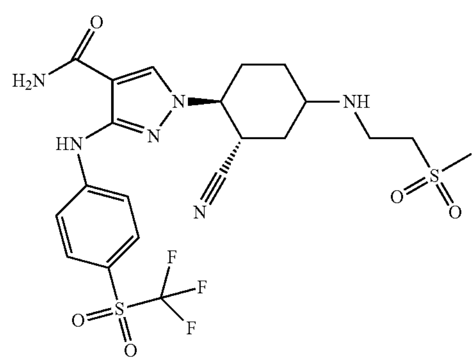 [SMILES: CS(=O)(=O)CCNC1CC[C@H](n2cc(C(N)=O)c(Nc3ccc(S(=O)(=O)C(F)(F)F)cc3)n2)[C@@H](C#N)C1] | 1-[(1S,2S or 1R,2R)-2-cyano-4-{[2-(methylsulfonyl)ethyl]amino}cyclohexyl]-3-({4-[(trifluoromethyl)sulfonyl]phenyl}amino)-1H-pyrazole-4-carboxamide | Calc'd 563, found 563 |
| 28-149 | 40 | 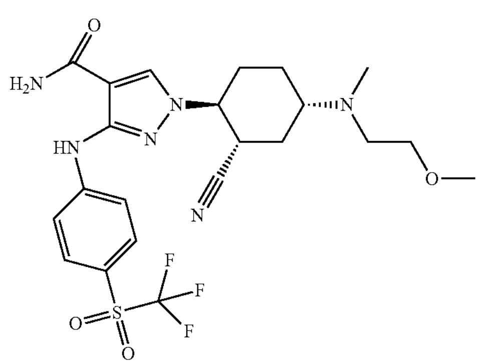 [SMILES: COCCN(C)[C@H]1CC[C@H](n2cc(C(N)=O)c(Nc3ccc(S(=O)(=O)C(F)(F)F)cc3)n2)[C@@H](C#N)C1] | 1-{(1S,2S,4S or 1R,2R,4R)-2-cyano-4-[(2-methoxyethyl)(methyl)amino]cyclohexyl}-3-({4-[(trifluoromethyl)sulfonyl]phenyl}amino)-1H-pyrazole-4-carboxamide | Calc'd 529, found 529 |
| 28-150 | 40 | 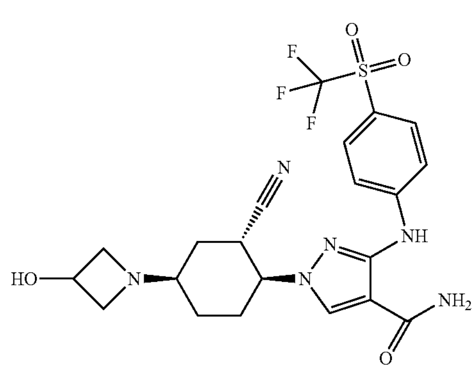 [SMILES: N#C[C@H]1C[C@H](N2CC(O)C2)CC[C@@H]1n1cc(C(N)=O)c(Nc2ccc(S(=O)(=O)C(F)(F)F)cc2)n1] | 1-[(1S,2S,4R or 1R,2R,4S)-2-cyano-4-(3-hydroxyazetidin-1-yl)cyclohexyl]-3-({4-[(trifluoromethyl)sulfonyl]phenyl}amino)-1H-pyrazole-4-carboxamide | Calc'd 513, found 513 |

TABLE 23-continued

| Example | Method | Structure | Compound Name | Exact Mass [M + H]+ |
|---|---|---|---|---|
| 28-151 | 40 | 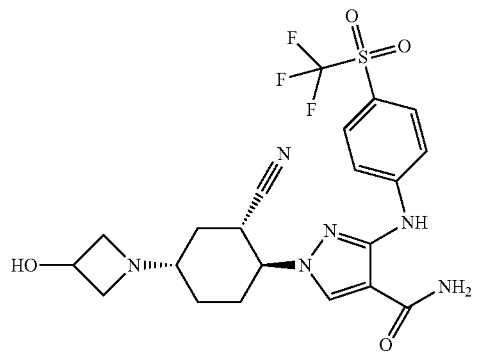 [SMILES: N#C[C@H]1C[C@@H](N2CC(O)C2)CC[C@@H]1n1cc(C(N)=O)c(Nc2ccc(S(=O)(=O)C(F)(F)F)cc2)n1] | 1-[(1S,2S,4S or 1R,2R,4R)-2-cyano-4-(3-hydroxyazetidin-1-yl)cyclohexyl]-3-({4-[(trifluoromethyl)sulfonyl]phenyl}amino)-1H-pyrazole-4-carboxamide | Calc'd 513, found 513 |
| 28-152 | 40 | 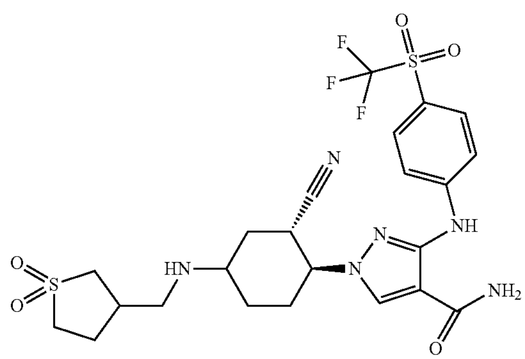 [SMILES: N#C[C@H]1CC(NCC2CCS(=O)(=O)C2)CC[C@@H]1n1cc(C(N)=O)c(Nc2ccc(S(=O)(=O)C(F)(F)F)cc2)n1] | 1-[(1S,2S or 1R,2R)-2-cyano-4-{[(1,1-dioxidotetrahydrothiophen-3-yl)methyl]amino}cyclohexyl]-3-({4-[(trifluoromethyl)sulfonyl]phenyl}amino)-1H-pyrazole-4-carboxamide | Calc'd 589, found 589 |
| 28-153 | 40 | 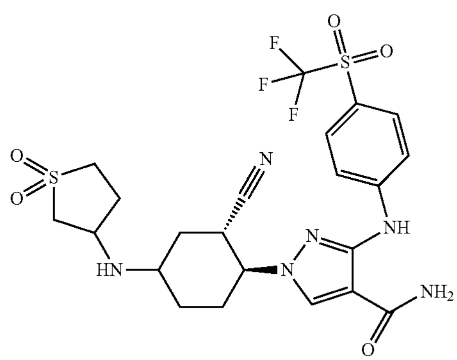 [SMILES: N#C[C@H]1CC(NC2CCS(=O)(=O)C2)CC[C@@H]1n1cc(C(N)=O)c(Nc2ccc(S(=O)(=O)C(F)(F)F)cc2)n1] | 1-{(1S,2S or 1R,2R)-2-cyano-4-[(1,1-dioxidotetrahydrothiophen-3-yl)amino]cyclohexyl}-3-({4-[(trifluoromethyl)sulfonyl]phenyl}amino)-1H-pyrazole-4-carboxamide | Calc'd 575, found 575 |
| 28-154 | 40 | 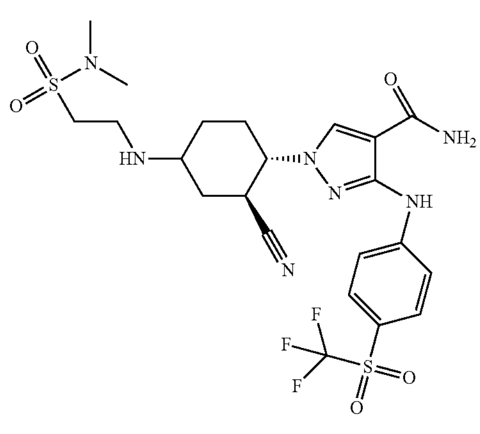 [SMILES: CN(C)S(=O)(=O)CCNC1CC[C@H](n2cc(C(N)=O)c(Nc3ccc(S(=O)(=O)C(F)(F)F)cc3)n2)[C@@H](C#N)C1] | 1-[(1S,2S or 1R,2R)-2-cyano-4-{[2-(dimethylsulfamoyl)ethyl]amino}cyclohexyl]-3-({4-[(trifluoromethyl)sulfonyl]phenyl}amino)-1H-pyrazole-4-carboxamide | Calc'd 592, found 592 |

TABLE 23-continued

| Example | Method | Structure | Compound Name | Exact Mass [M + H]+ |
|---|---|---|---|---|
| 28-155 | 40 | 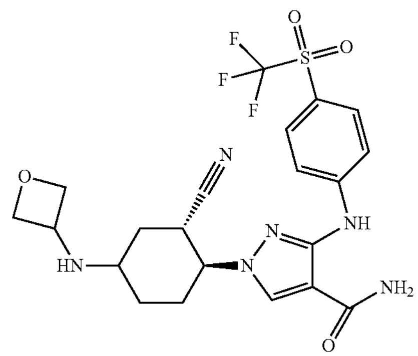 [SMILES: N#C[C@H]1CC(NC2COC2)CC[C@@H]1n1cc(C(N)=O)c(Nc2ccc(S(=O)(=O)C(F)(F)F)cc2)n1] | 1-[(1S,2S or 1R,2R)-2-cyano-4-(oxetan-3-ylamino)cyclohexyl]-3-({4-[(trifluoromethyl)sulfonyl]phenyl}amino)-1H-pyrazole-4-carboxamide | Calc'd 513, found 513 |
| 28-156 | 40 | 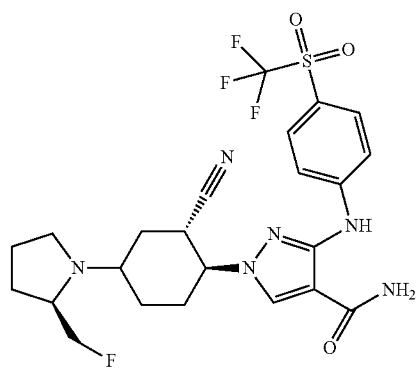 [SMILES: N#C[C@H]1CC(N2CCC[C@@H]2CF)CC[C@@H]1n1cc(C(N)=O)c(Nc2ccc(S(=O)(=O)C(F)(F)F)cc2)n1] | 1-{(1S,2S or 1R,2R)-2-cyano-4-[(2R)-2-(fluoromethyl)pyrrolidin-1-yl]cyclohexyl}-3-({4-[(trifluoromethyl)sulfonyl]phenyl}amino)-1H-pyrazole-4-carboxamide | Calc'd 543, found 543 |
| 28-157 | 40 | 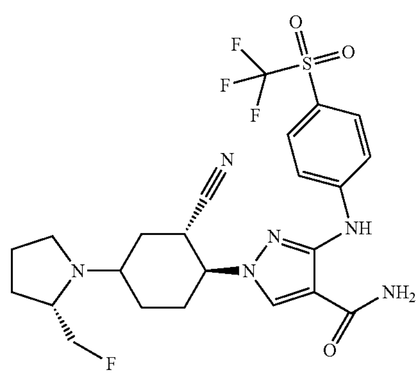 [SMILES: N#C[C@H]1CC(N2CCC[C@H]2CF)CC[C@@H]1n1cc(C(N)=O)c(Nc2ccc(S(=O)(=O)C(F)(F)F)cc2)n1] | 1-{(1S,2S or 1R,2R)-2-cyano-4-[(2S)-2-(fluoromethyl)pyrrolidin-1-yl]cyclohexyl}-3-({4-[(trifluoromethyl)sulfonyl]phenyl}amino)-1H-pyrazole-4-carboxamide | Calc'd 543, found 543 |
| 28-158 | 40 | 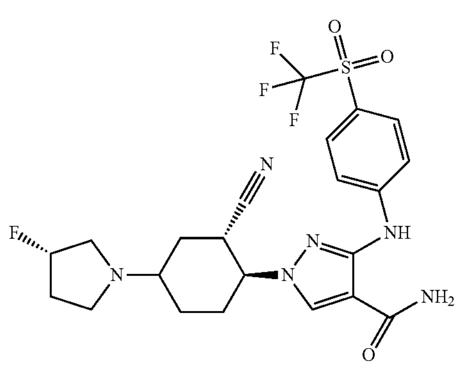 [SMILES: N#C[C@H]1CC(N2CC[C@H](F)C2)CC[C@@H]1n1cc(C(N)=O)c(Nc2ccc(S(=O)(=O)C(F)(F)F)cc2)n1] | 1-{(1S,2S or 1R,2R)-2-cyano-4-[(3S)-3-fluoropyrrolidin-1-yl]cyclohexyl}-3-({4-[(trifluoromethyl)sulfonyl]phenyl}amino)-1H-pyrazole-4-carboxamide | Calc'd 529, found 529 |

TABLE 23-continued

| Example | Method | Structure | Compound Name | Exact Mass [M + H]+ |
|---|---|---|---|---|
| 28-159 | 40 | 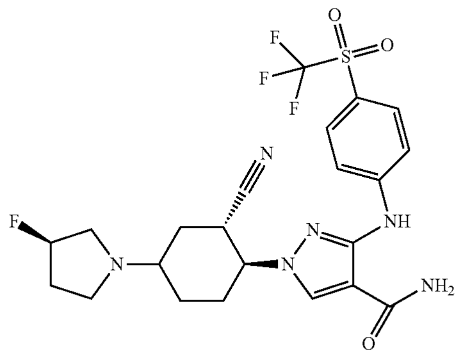 [SMILES: N#C[C@H]1CC(N2CC[C@@H](F)C2)CC[C@@H]1n1cc(C(N)=O)c(Nc2ccc(S(=O)(=O)C(F)(F)F)cc2)n1] | 1-{(1S,2S or 1R,2R)-2-cyano-4-[(3R)-3-fluoropyrrolidin-1-yl]cyclohexyl}-3-({4-[(trifluoromethyl)sulfonyl]phenyl}amino)-1H-pyrazole-4-carboxamide | Calc'd 529, found 529 |
| 28-160 | 40 | 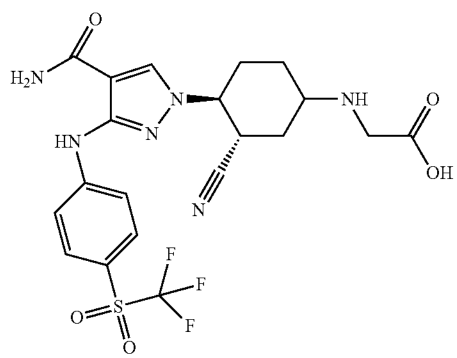 [SMILES: N#C[C@H]1CC(NCC(=O)O)CC[C@@H]1n1cc(C(N)=O)c(Nc2ccc(S(=O)(=O)C(F)(F)F)cc2)n1] | N-{(3S,4S or 3R,4R)-4-[4-carbamoyl-3-({4-[(trifluoromethyl)sulfonyl]phenyl}amino)-1H-pyrazol-1-yl]-3-cyanocyclohexyl}glycine | Calc'd 515, found 515 |
| 28-164 | 40 | 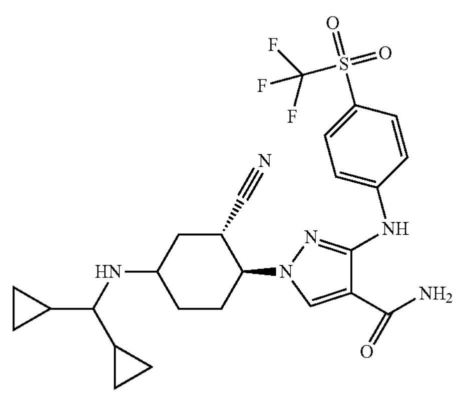 | 1-{(1S,2S,4R or 1R,2R,4S)-2-cyano-4-[(dicyclopropylmethyl)amino]cyclohexyl}-3-({4-[(trifluoromethyl)sulfonyl]phenyl}amino)-1H-pyrazole-4-carboxamide | Calc'd 551, found 551 |
| 28-165 | 40 | 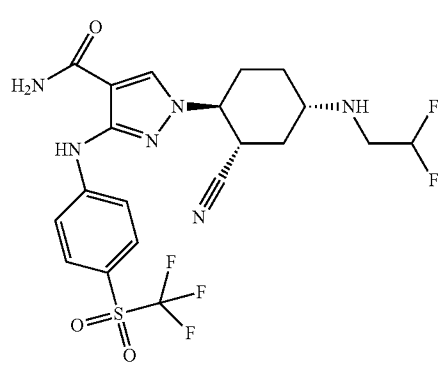 [SMILES: N#C[C@H]1C[C@@H](NCC(F)F)CC[C@@H]1n1cc(C(N)=O)c(Nc2ccc(S(=O)(=O)C(F)(F)F)cc2)n1] | 1-{(1S,2S,4S or 1R,2R,4R)-2-cyano-4-[(2,2-difluoroethyl)amino]cyclohexyl}-3-({4-[(trifluoromethyl)sulfonyl]phenyl}amino)-1H-pyrazole-4-carboxamide | Calc'd 521, found 521 |

TABLE 23-continued

| Example | Method | Structure | Compound Name | Exact Mass [M + H]+ |
|---|---|---|---|---|
| 28-166 | 40 | 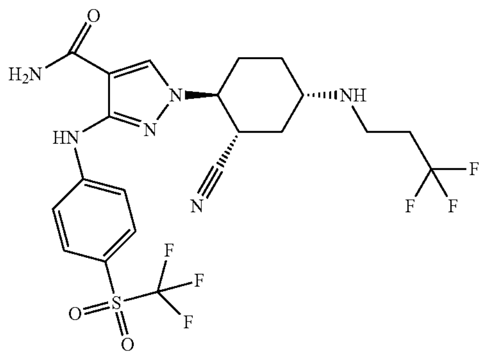 [SMILES: N#C[C@H]1C[C@@H](NCCC(F)(F)F)CC[C@@H]1n1cc(C(N)=O)c(Nc2ccc(S(=O)(=O)C(F)(F)F)cc2)n1] | 1-{(1S,2S,4S or 1R,2R,4R)-2-cyano-4-[(3,3,3-trifluoropropyl)amino]cyclohexyl}-3-({4-[(trifluoromethyl)sulfonyl]phenyl}amino)-1H-pyrazole-4-carboxamide | Calc'd 553, found 553 |
| 28-167 | 40 | 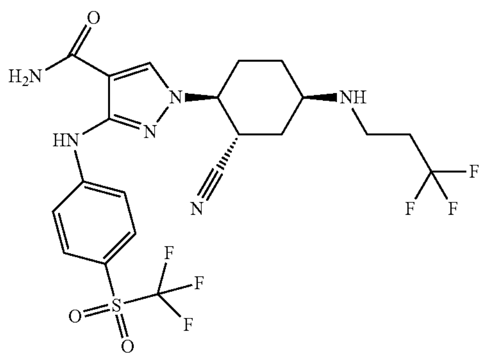 [SMILES: N#C[C@H]1C[C@H](NCCC(F)(F)F)CC[C@@H]1n1cc(C(N)=O)c(Nc2ccc(S(=O)(=O)C(F)(F)F)cc2)n1] | 1-{(1S,2S,4R or 1R,2R,4S)-2-cyano-4-[(3,3,3-trifluoropropyl)amino]cyclohexyl}-3-({4-[(trifluoromethyl)sulfonyl]phenyl}amino)-1H-pyrazole-4-carboxamide | Calc'd 553, found 553 |
| 28-168 | 40 | 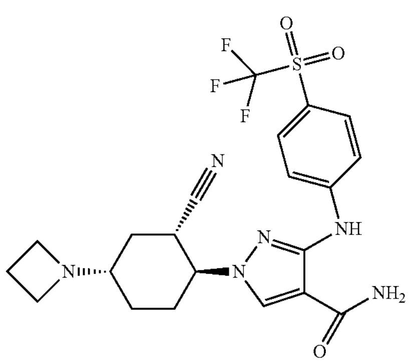 [SMILES: N#C[C@H]1C[C@@H](N2CCC2)CC[C@@H]1n1cc(C(N)=O)c(Nc2ccc(S(=O)(=O)C(F)(F)F)cc2)n1] | 1-[(1S,2S,4S or 1R,2R,4R)-4-azetidin-1-yl-2-cyanocyclohexyl]-3-({4-[(trifluoromethyl)sulfonyl]phenyl}amino)-1H-pyrazole-4-carboxamide | Calc'd 497, found 497 |
| 28-169 | 40 | 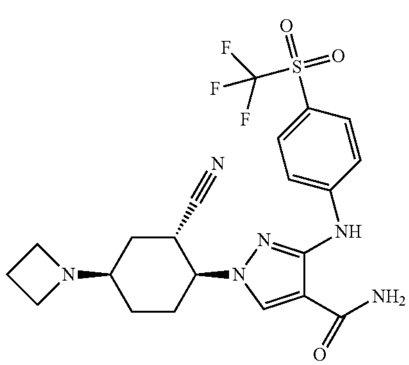 [SMILES: N#C[C@H]1C[C@H](N2CCC2)CC[C@@H]1n1cc(C(N)=O)c(Nc2ccc(S(=O)(=O)C(F)(F)F)cc2)n1] | 1-[(1S,2S,4R or 1R,2R,4S)-4-azetidin-1-yl-2-cyanocyclohexyl]-3-({4-[(trifluoromethyl)sulfonyl]phenyl}amino)-1H-pyrazole-4-carboxamide | Calc'd 497, found 497 |

TABLE 23-continued

| Example | Method | Structure | Compound Name | Exact Mass [M + H]+ |
|---|---|---|---|---|
| 28-170 | 40 | 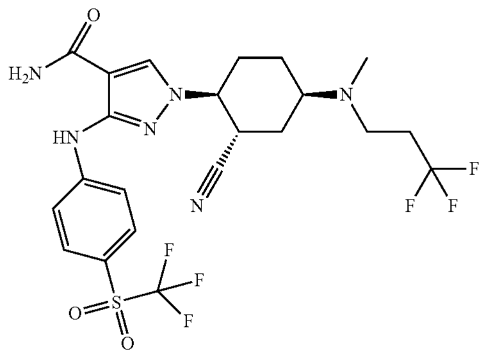 [SMILES: CN(CCC(F)(F)F)[C@@H]1CC[C@H](n2cc(C(N)=O)c(Nc3ccc(S(=O)(=O)C(F)(F)F)cc3)n2)[C@@H](C#N)C1] | 1-{(1S,2S,4R or 1R,2R,4S)-2-cyano-4-[methyl(3,3,3-trifluoropropyl)amino]cyclohexyl}-3-({4-[(trifluoromethyl)sulfonyl]phenyl]amino)-1H-pyrazole-4-carboxamide | Calc'd 567, found 567 |
| 28-171 | 40 | 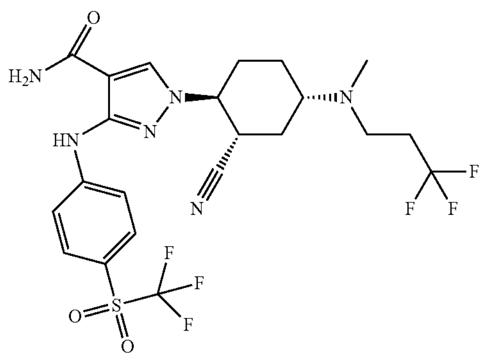 [SMILES: CN(CCC(F)(F)F)[C@H]1CC[C@H](n2cc(C(N)=O)c(Nc3ccc(S(=O)(=O)C(F)(F)F)cc3)n2)[C@@H](C#N)C1] | 1-{(1S,2S,4S or 1R,2R,4R)-2-cyano-4-[methyl(3,3,3-trifluoropropyl)amino]cyclohexyl}-3-({4-[(trifluoromethyl)sulfonyl]phenyl}amino)-1H-pyrazole-4-carboxamide | Calc'd 567, found 567 |
| 28-172 | 40 | 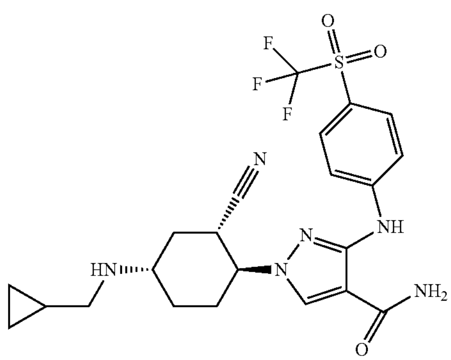 [SMILES: N#C[C@H]1C[C@@H](NCC2CC2)CC[C@@H]1n1cc(C(N)=O)c(Nc2ccc(S(=O)(=O)C(F)(F)F)cc2)n1] | 1-{(1S,2S,4S or 1R,2R,4R)-2-cyano-4-[(cyclopropylmethyl)amino]cyclohexyl}-3-({4-[(trifluoromethyl)sulfonyl]phenyl}amino)-1H-pyrazole-4-carboxamide | Calc'd 511, found 511 |
| 28-173 | 40 | 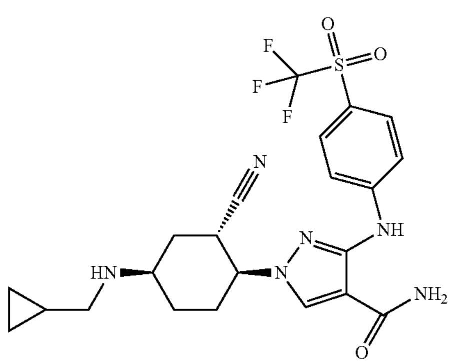 [SMILES: N#C[C@H]1C[C@H](NCC2CC2)CC[C@@H]1n1cc(C(N)=O)c(Nc2ccc(S(=O)(=O)C(F)(F)F)cc2)n1] | 1-{(1S,2S,4R or 1R,2R,4S)-2-cyano-4-[(cyclopropylmethyl)amino]cyclohexyl}-3-({4-[(trifluoromethyl)sulfonyl]phenyl}amino)-1H-pyrazole-4-carboxamide | Calc'd 511, found 511 |

TABLE 23-continued

| Example | Method | Structure | Compound Name | Exact Mass [M + H]+ |
|---|---|---|---|---|
| 28-174 | 40 | 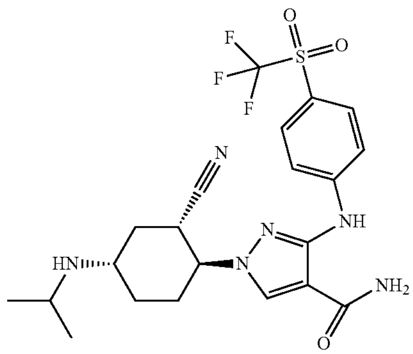 [SMILES: CC(C)N[C@H]1CC[C@H](n2cc(C(N)=O)c(Nc3ccc(S(=O)(=O)C(F)(F)F)cc3)n2)[C@@H](C#N)C1] | 1-{(1S,2S,4S or 1R,2R,4R)-2-cyano-4-[(1-methylethyl)amino]cyclohexy}-3-({4-[(trifluoromethyl)sulfonyl]phenyl}amino)-1H-pyrazole-4-carboxamide | Calc'd 499, found 499 |
| 28-175 | 40 | 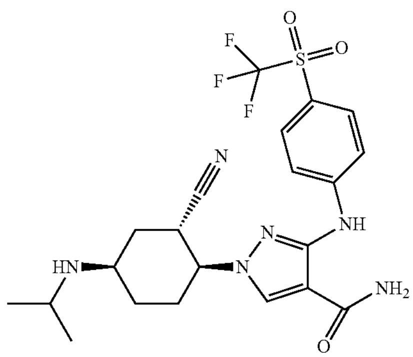 [SMILES: CC(C)N[C@@H]1CC[C@H](n2cc(C(N)=O)c(Nc3ccc(S(=O)(=O)C(F)(F)F)cc3)n2)[C@@H](C#N)C1] | 1-{(1S,2S,4R or 1R,2R,4S)-2-cyano-4-[(1-methylethyl)amino]cyclohexyl}-3-({4-[(trifluoromethyl)sulfonyl]phenyl}amino)-1H-pyrazole-4-carboxamide | Calc'd 499, found 499 |
| 28-176 | 40 | 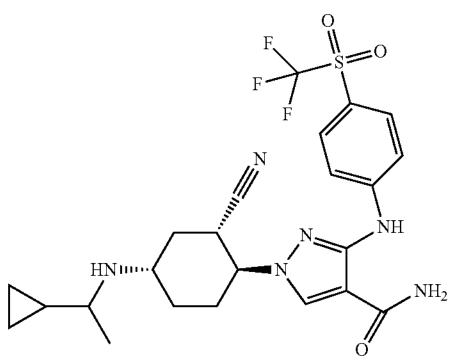 [SMILES: CC(N[C@H]1CC[C@H](n2cc(C(N)=O)c(Nc3ccc(S(=O)(=O)C(F)(F)F)cc3)n2)[C@@H](C#N)C1)C1CC1] | 1-[(1S,2S,4S or 1R,2R,4R)-2-cyano-4-{[(1R)-1-cyclopropylethyl]amino}cyclohexyl]-3-({4-[(trifluoromethyl)sulfonyl]phenyl}amino)-1H-pyrazole-4-carboxamide | Calc'd 525, found 525 |
| 28-177 | 40 | 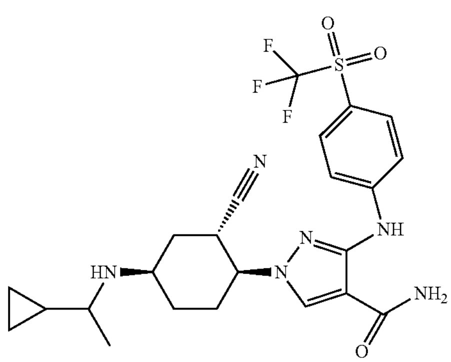 [SMILES: CC(N[C@@H]1CC[C@H](n2cc(C(N)=O)c(Nc3ccc(S(=O)(=O)C(F)(F)F)cc3)n2)[C@@H](C#N)C1)C1CC1] | 1-[(1S,2S,4R or 1R,2R,4S)-2-cyano-4-{[(1S)-1-cyclopropylethyl]amino}cyclohexyl]-3-({4-[(trifluoromethyl)sulfonyl]phenyl}amino)-1H-pyrazole-4-carboxamide | Calc'd 525, found 525 |

TABLE 23-continued

| Example | Method | Structure | Compound Name | Exact Mass [M + H]+ |
|---|---|---|---|---|
| 28-178 | 40 | 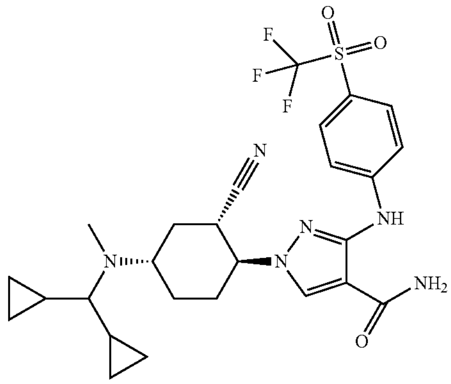 [SMILES: CN(C(C1CC1)C1CC1)[C@H]1CC[C@H](n2cc(C(N)=O)c(Nc3ccc(S(=O)(=O)C(F)(F)F)cc3)n2)[C@@H](C#N)C1] | 1-{(1S,2S,4S or 1R,2R,4R)-2-cyano-4-[(dicyclopropyl-methyl)(methyl)amino]cyclo-hexyl}-3-({4-[(trifluoromethyl)sulfonyl]phen-yl}amino)-1H-pyrazole-4-carboxamide | Calc'd 565, found 565 |
| 28-179 | 40 | 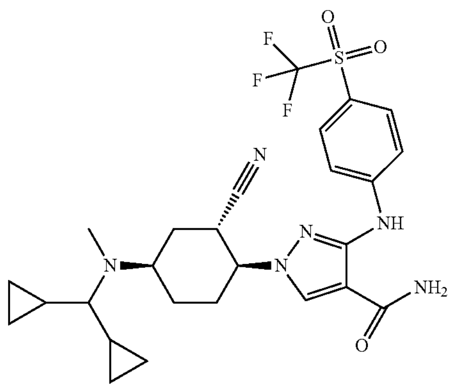 [SMILES: CN(C(C1CC1)C1CC1)[C@@H]1CC[C@H](n2cc(C(N)=O)c(Nc3ccc(S(=O)(=O)C(F)(F)F)cc3)n2)[C@@H](C#N)C1] | 1-{(1S,2S,4R or 1R,2R,4S)-2-cyano-4-[(dicyclopropyl-methyl)(methyl)amino]cyclo-hexyl}-3-({4-[(trifluoromethyl)sulfonyl]phen-yl}amino)-1H-pyrazole-4-carboxamide | Calc'd 565, found 565 |
| 28-180 | 40 | 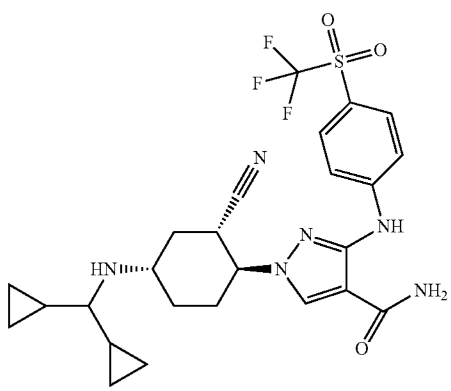 | 1-{(1S,2S,4S or 1R,2R,4R)-2-cyano-4-[(dicyclopropyl-methyl)amino]cyclohexyl}-3-({4-[(trifluoro-methyl)sulfonyl]phenyl}amino)-1H-pyrazole-4-carboxamide | Calc'd 551, found 551 |
| 28-181 | 40 | 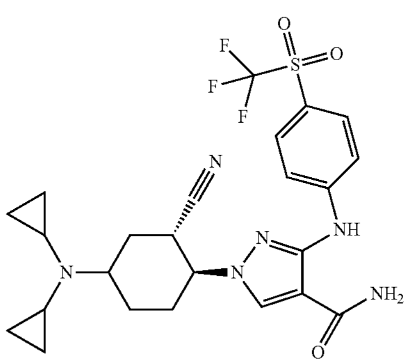 [SMILES: N#C[C@H]1CC(N(C2CC2)C2CC2)CC[C@@H]1n1cc(C(N)=O)c(Nc2ccc(S(=O)(=O)C(F)(F)F)cc2)n1] | 1-[(1S,2S or 1R,2R)-2-cyano-4-(dicyclopropylamino)cyclohexyl]-3-({4-[(trifluoro-methyl)sulfonyl]phenyl}amino)-1H-pyrazole-4-carboxamide | Calc'd 537, found 537 |

TABLE 23-continued

| Example | Method | Structure | Compound Name | Exact Mass [M + H]+ |
|---|---|---|---|---|
| 28-182 | 40 | 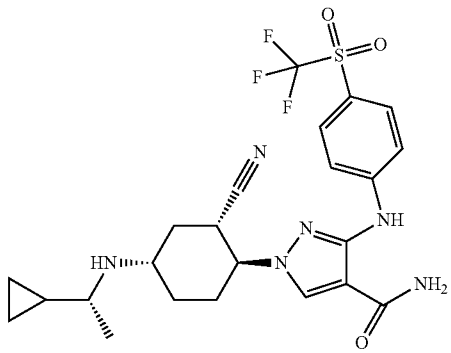 [SMILES: C[C@@H](N[C@H]1CC[C@H](n2cc(C(N)=O)c(Nc3ccc(S(=O)(=O)C(F)(F)F)cc3)n2)[C@@H](C#N)C1)C1CC1] | 1-[(1S,2S,4S or 1R,2R,4R)-2-cyano-4-{[(1R)-1-cyclopropylethyl]amino}cyclohexyl]-3-({4-[(trifluoromethyl)sulfonyl]phenyl}amino)-1H-pyrazole-4-carboxamide | Calc'd 525, found 525 |
| 28-183 | 40 | 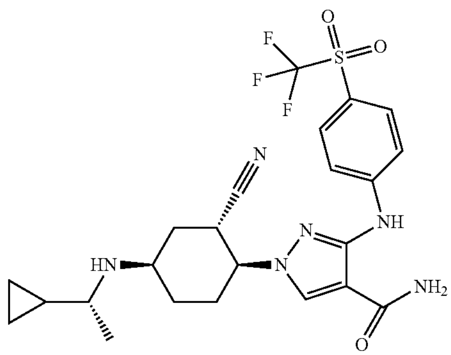 [SMILES: C[C@@H](N[C@@H]1CC[C@H](n2cc(C(N)=O)c(Nc3ccc(S(=O)(=O)C(F)(F)F)cc3)n2)[C@@H](C#N)C1)C1CC1] | 1-{(1S,2S,4R or 1R,2R,4S)-2-cyano-4-[(1-cyclopropylethyl)amino]cyclohexyl}-3-({4-[(trifluoromethyl)sulfonyl]phenyl}amino)-1H-pyrazole-4-carboxamide | Calc'd 525, found 525 |
| 28-184 | 40 | 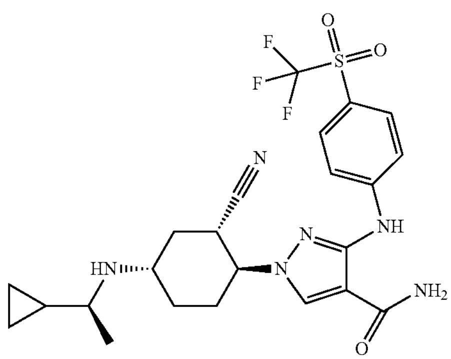 [SMILES: C[C@H](N[C@H]1CC[C@H](n2cc(C(N)=O)c(Nc3ccc(S(=O)(=O)C(F)(F)F)cc3)n2)[C@@H](C#N)C1)C1CC1] | 1-{(1S,2S,4S or 1R,2R,4R)-2-cyano-4-[(1-cyclopropylethyl)amino]cyclohexyl}-3-({4-[(trifluoromethyl)sulfonyl]phenyl}amino)-1H-pyrazole-4-carboxamide | Calc'd 525, found 525 |
| 28-185 | 40 | 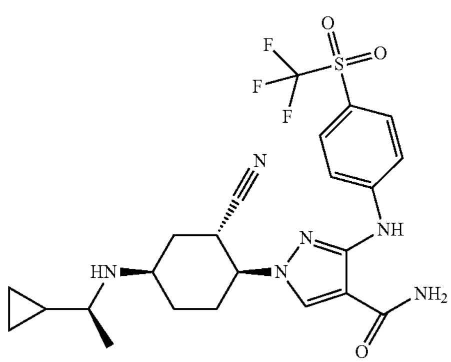 [SMILES: C[C@H](N[C@@H]1CC[C@H](n2cc(C(N)=O)c(Nc3ccc(S(=O)(=O)C(F)(F)F)cc3)n2)[C@@H](C#N)C1)C1CC1] | 1-[(1S,2S,4R or 1R,2R,4S)-2-cyano-4-{[(1S)-1-cyclopropylethyl]amino}cyclohexyl]-3-({4-[(trifluoromethyl)sulfonyl]phenyl}amino)-1H-pyrazole-4-carboxamide | Calc'd 525, found 525 |

TABLE 23-continued

| Example | Method | Structure | Compound Name | Exact Mass [M + H]+ |
|---|---|---|---|---|
| 28-186 | 40 | 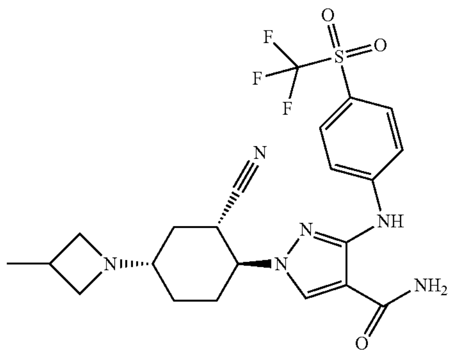 [SMILES: CC1CN([C@H]2CC[C@H](n3cc(C(N)=O)c(Nc4ccc(S(=O)(=O)C(F)(F)F)cc4)n3)[C@@H](C#N)C2)C1] | 1-[(1S,2S,4S or 1R,2R,4R)-2-cyano-4-(3-methylazetidin-1-yl)cyclohexyl]-3-({4-[(trifluoromethyl)sulfonyl]phenyl}amino)-1H-pyrazole-4-carboxamide | Calc'd 511, found 511 |
| 28-187 | 40 | 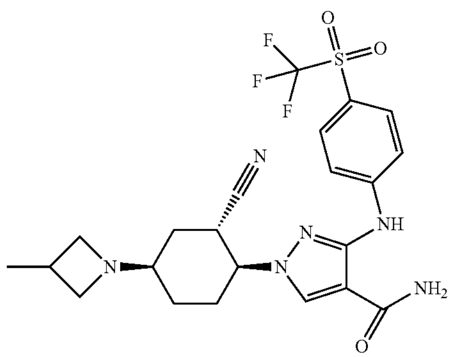 [SMILES: CC1CN([C@@H]2CC[C@H](n3cc(C(N)=O)c(Nc4ccc(S(=O)(=O)C(F)(F)F)cc4)n3)[C@@H](C#N)C2)C1] | 1-[(1S,2S,4R or 1R,2R,4S)-2-cyano-4-(3-methylazetidin-1-yl)cyclohexyl]-3-({4-[(trifluoromethyl)sulfonyl]phenyl}amino)-1H-pyrazole-4-carboxamide | Calc'd 511, found 511 |
| 28-188 | 40 | 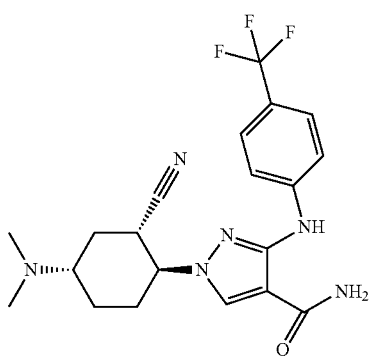 [SMILES: CN(C)[C@H]1CC[C@H](n2cc(C(N)=O)c(Nc3ccc(C(F)(F)F)cc3)n2)[C@@H](C#N)C1] | 1-[(1S,2S,4S or 1R,2R,4R)-2-cyano-4-(dimethylamino)cyclohexyl]-3-{[4-(trifluoromethyl)phenyl]amino}-1H-pyrazole-4-carboxamide | Calc'd 421, found 421 |
| 28-189 | 40 | 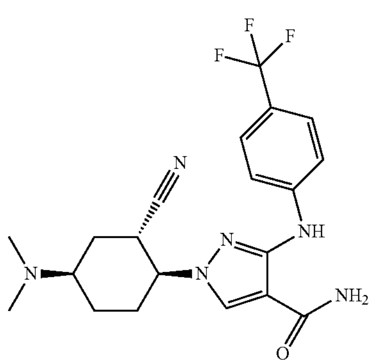 [SMILES: CN(C)[C@@H]1CC[C@H](n2cc(C(N)=O)c(Nc3ccc(C(F)(F)F)cc3)n2)[C@@H](C#N)C1] | 1-[(1S,2S,4R or 1R,2R,4S)-2-cyano-4-(dimethylamino)cyclohexyl]-3-{[4-(trifluoromethyl)phenyl]amino}-1H-pyrazole-4-carboxamide | Calc'd 421, found 421 |

TABLE 23-continued

| Example | Method | Structure | Compound Name | Exact Mass [M + H]+ |
|---|---|---|---|---|
| 28-190 | 40 | 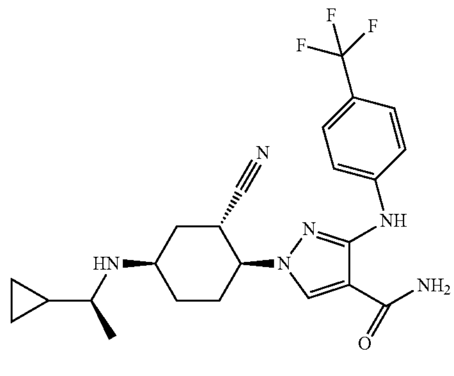 [SMILES: C[C@H](N[C@@H]1CC[C@H](n2cc(C(N)=O)c(Nc3ccc(C(F)(F)F)cc3)n2)[C@@H](C#N)C1)C1CC1] | 1-[(1S,2S,4R or 1R,2R,4S)-2-cyano-4-{[(1S)-1-cyclopropylethyl]amino}cyclohexyl]-3-{[4-(trifluoromethyl)phenyl]amino}-1H-pyrazole-4-carboxamide | Calc'd 461, found 461 |
| 28-191 | 40 | 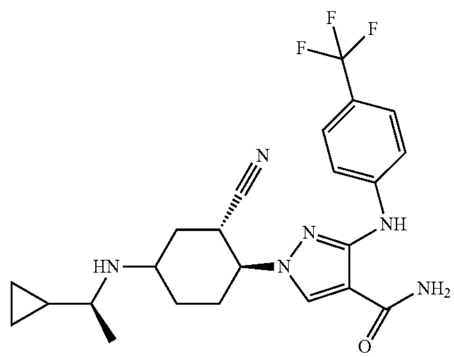 [SMILES: C[C@H](NC1CC[C@H](n2cc(C(N)=O)c(Nc3ccc(C(F)(F)F)cc3)n2)[C@@H](C#N)C1)C1CC1] | 1-[(1S,2S or 1R,2R)-2-cyano-4-{[(1S)-1-cyclopropylethyl]amino}cyclohexyl]-3-{[4-(trifluoromethyl)phenyl]amino}-1H-pyrazole-4-carboxamide | Calc'd 461, found 461 |
| 28-192 | 41 | 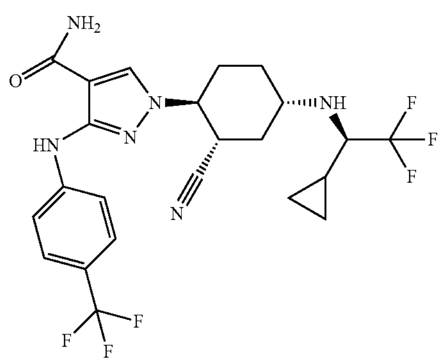 [SMILES: N#C[C@H]1C[C@@H](N[C@H](C2CC2)C(F)(F)F)CC[C@@H]1n1cc(C(N)=O)c(Nc2ccc(C(F)(F)F)cc2)n1] | 1-[(1S,2S,4S or 1R,2R,4R)-2-cyano-4-{[(1S)-1-cyclopropyl-2,2,2-trifluoroethyl]amino}cyclohexyl]-3-{[4-(trifluoromethyl)phenyl]amino}-1H-pyrazole-4-carboxamide | Calc'd 515, found 515 |
| 28-193 | 41 | 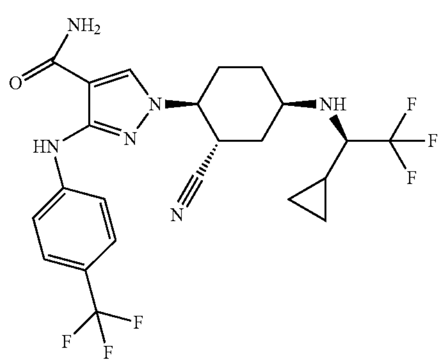 [SMILES: N#C[C@H]1C[C@H](N[C@H](C2CC2)C(F)(F)F)CC[C@@H]1n1cc(C(N)=O)c(Nc2ccc(C(F)(F)F)cc2)n1] | 1-[(1S,2S,4R or 1R,2R,4S)-2-cyano-4-{[(1R)-1-cyclopropyl-2,2,2-trifluoroethyl]amino}cyclohexyl]-3-{[4-(trifluoromethyl)phenyl]amino}-1H-pyrazole-4-carboxamide | Calc'd 515, found 515 |

TABLE 23-continued

| Example | Method | Structure | Compound Name | Exact Mass [M + H]+ |
|---|---|---|---|---|
| 28-194 | 41 | 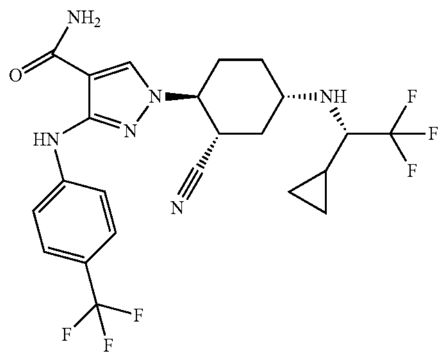 [SMILES: N#C[C@H]1C[C@@H](N[C@@H](C2CC2)C(F)(F)F)CC[C@@H]1n1cc(C(N)=O)c(Nc2ccc(C(F)(F)F)cc2)n1] | 1-[(1S,2S,4S or 1R,2R,4R)-2-cyano-4-{[(1S)-1-cyclopropyl-2,2,2-trifluoroethyl]amino}cyclohexyl]-3-{[4-(trifluoromethyl)phenyl]amino}-1H-pyrazole-4-carboxamide | Calc'd 515, found 515 |
| 28-195 | 41 | 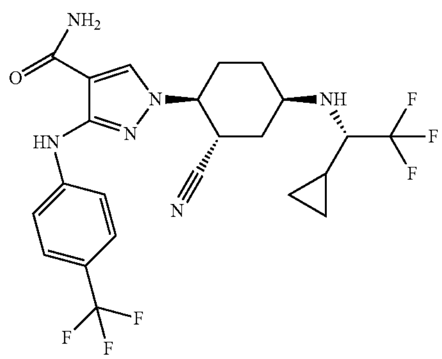 [SMILES: N#C[C@H]1C[C@H](N[C@@H](C2CC2)C(F)(F)F)CC[C@@H]1n1cc(C(N)=O)c(Nc2ccc(C(F)(F)F)cc2)n1] | 1-[(1S,2S,4R or 1R,2R,4S)-2-cyano-4-{[(1R)-1-cyclopropyl-2,2,2-trifluoroethyl]amino}cyclohexyl]-3-{[4-(trifluoromethyl)phenyl]amino}-1H-pyrazole-4-carboxamide | Calc'd 515, found 515 |
| 28-196 | 40 | 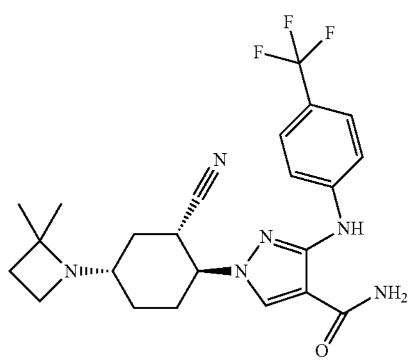 [SMILES: CC1(C)CCN1[C@H]1CC[C@H](n2cc(C(N)=O)c(Nc3ccc(C(F)(F)F)cc3)n2)[C@@H](C#N)C1] | 1-[(1S,2S,4S or 1R,2R,4R)-2-cyano-4-(2,2-dimethylazetidin-1-yl)cyclohexyl]-3-{[4-(trifluoromethyl)phenyl]amino}-1H-pyrazole-4-carboxamide | Calc'd 461, found 461 |
| 28-197 | 40 | 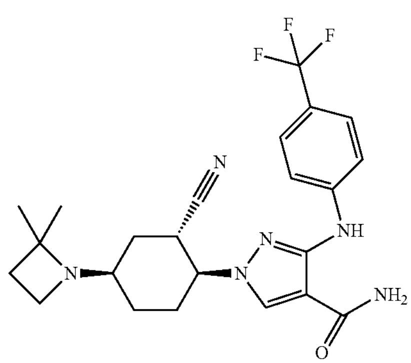 [SMILES: CC1(C)CCN1[C@@H]1CC[C@H](n2cc(C(N)=O)c(Nc3ccc(C(F)(F)F)cc3)n2)[C@@H](C#N)C1] | 1-[(1S,2S,4R or 1R,2R,4S)-2-cyano-4-(2,2-dimethylazetidin-1-yl)cyclohexyl]-3-{[4-(trifluoromethyl)phenyl]amino}-1H-pyrazole-4-carboxamide | Calc'd 461, found 461 |

TABLE 23-continued

| Example | Method | Structure | Compound Name | Exact Mass [M + H]+ |
|---|---|---|---|---|
| 28-198 | 40 | 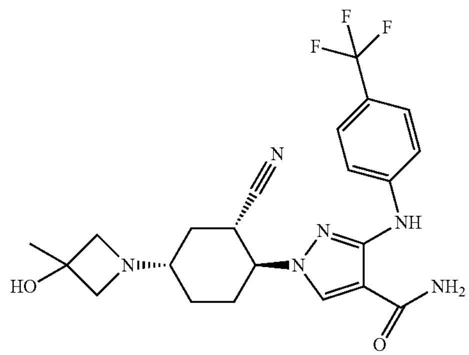 [SMILES: CC1(O)CN([C@H]2CC[C@H](n3cc(C(N)=O)c(Nc4ccc(C(F)(F)F)cc4)n3)[C@@H](C#N)C2)C1] | 1-[(1S,2S,4S or 1R,2R,4R)-2-cyano-4-(3-hydroxy-3-methylazetidin-1-yl)cyclohexyl]-3-{[4-(trifluoromethyl)phenyl]amino}-1H-pyrazole-4-carboxamide | Calc'd 463, found 463 |
| 28-199 | 40 | 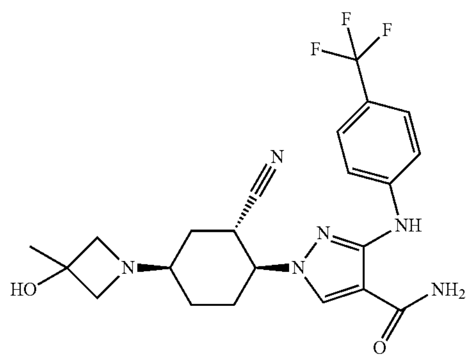 [SMILES: CC1(O)CN([C@@H]2CC[C@H](n3cc(C(N)=O)c(Nc4ccc(C(F)(F)F)cc4)n3)[C@@H](C#N)C2)C1] | 1-[(1S,2S,4R or 1R,2R,4S)-2-cyano-4-(3-hydroxy-3-methylazetidin-1-yl)cyclohexyl]-3-{[4-(trifluoromethyl)phenyl]amino}-1H-pyrazole-4-carboxamide | Calc'd 463, found 463 |
| 28-200 | 40 | 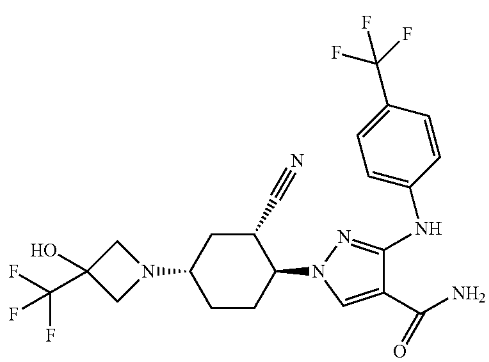 [SMILES: N#C[C@H]1C[C@@H](N2CC(O)(C(F)(F)F)C2)CC[C@@H]1n1cc(C(N)=O)c(Nc2ccc(C(F)(F)F)cc2)n1] | 1-{(1S,2S,4S or 1R,2R,4R)-2-cyano-4-[3-hydroxy-3-(trifluoromethyl)azetidin-1-yl]cyclohexyl}-3-{[4-(trifluoromethyl)phenyl]amino}-nvrazole-4-carboxamide | Calc'd 517, found 517 |
| 28-201 | 40 | 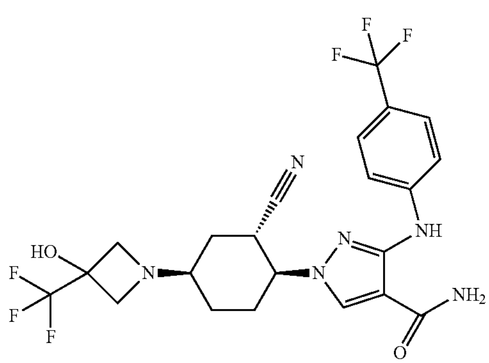 [SMILES: N#C[C@H]1C[C@H](N2CC(O)(C(F)(F)F)C2)CC[C@@H]1n1cc(C(N)=O)c(Nc2ccc(C(F)(F)F)cc2)n1] | 1-{(1S,2S,4R or 1R,2R,4S)-2-cyano-4-[3-hydroxy-3-(trifluoromethyl)azetidin-1-yl]cyclohexyl}-3-{[4-(trifluoromethyl)phenyl]amino}-1H-pyrazole-4-carboxamide | Calc'd 517, found 517 |

TABLE 23-continued

| Example | Method | Structure | Compound Name | Exact Mass [M + H]+ |
|---|---|---|---|---|
| 28-202 | 40 | 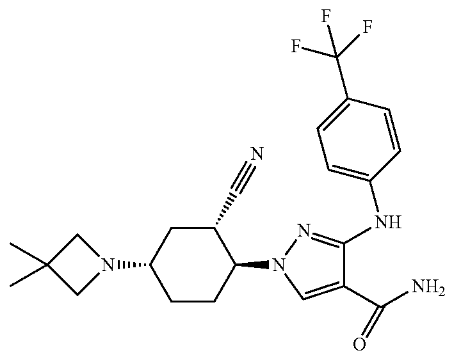 [SMILES: CC1(C)CN([C@H]2CC[C@H](n3cc(C(N)=O)c(Nc4ccc(C(F)(F)F)cc4)n3)[C@@H](C#N)C2)C1] | 1-[(1S,2S,4S or 1R,2R,4R)-2-cyano-4-(3,3-dimethylazetidin-1-yl)cyclohexyl]-3-{[4-(trifluoromethyl)phenyl]amino}-1H-pyrazole-4-carboxamide | Calc'd 461, found 461 |
| 28-203 | 40 | 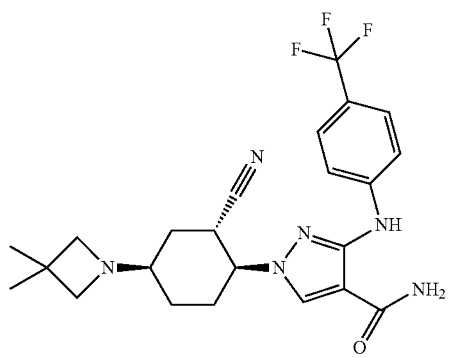 [SMILES: CC1(C)CN([C@@H]2CC[C@H](n3cc(C(N)=O)c(Nc4ccc(C(F)(F)F)cc4)n3)[C@@H](C#N)C2)C1] | 1-[(1S,2S,4R or 1R,2R,4S)-2-cyano-4-(3,3-dimethylazetidin-1-yl)cyclohexyl]-3-{[4-(trifluoromethyl)phenyl]amino}-1H-pyrazole-4-carboxamide | Calc'd 461, found 461 |
| 28-204 | 43 | 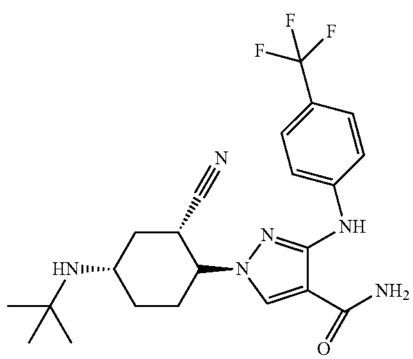 | 1-[(1S,2S,4S or 1R,2R,4R)-4-(tert-butylamino)-2-cyanocyclohexyl]-3-{[4-(trifluoromethyl)phenyl]amino}-1H-pyrazole-4-carboxamide | Calc'd 449, found 449 |
| 28-205 | 43 | 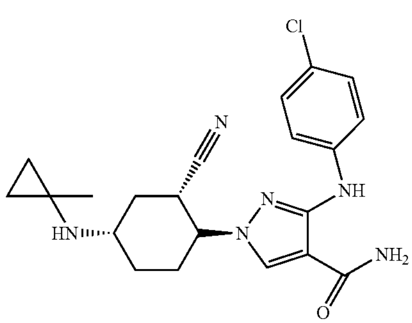 | 3-[(4-chlorophenyl)amino]-1-{(1S,2S,4S or 1R,2R,4R,)-2-cyano-4-[(1-methylcyclopropyl)amino]cyclohexyl}-1H-pyrazole-4-carboxamide | Calc'd 413, found 413 |

TABLE 23-continued

| Example | Method | Structure | Compound Name | Exact Mass [M + H]+ |
|---|---|---|---|---|
| 28-206 | 43 | 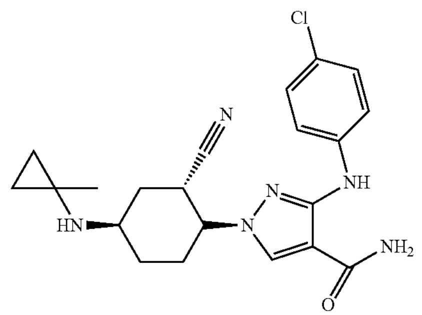 | 3-[(4-chlorophenyl)amino]-1-{(1S,2S,4R or 1R,2R,4S)-2-cyano-4-[(1-methylcyclopropyl)amino]cyclohexyl}-1H-pyrazole-4-carboxamide | Calc'd 413, found 413 |
| 28-207 | 43 | 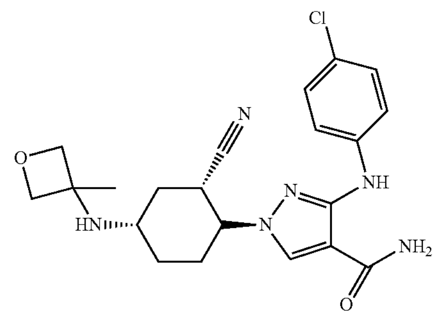 | 3-[(4-chlorophenyl)amino]-1-{(1S,2S,4S or 1R,2R,4R)-2-cyano-4-[(3-methyloxetan-3-yl)amino]cyclohexyl}-1H-pyrazole-4-carboxamide | Calc'd 429, found 429 |
| 28-208 | 43 | 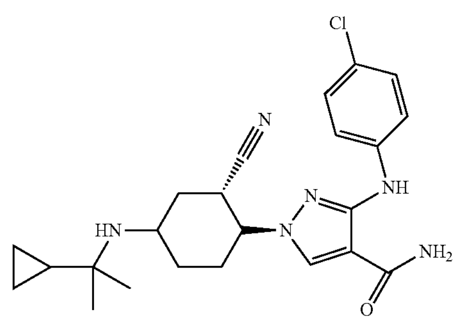 | 3-[(4-chlorophenyl)amino]-1-{(1S,2S or 1R,2R)-2-cyano-4-[(1-cyclopropyl-1-methylethyl)amino]cyclohexyl}-1H-pyrazole-4-carboxamide | Calc'd 441, found 441 |
| 28-209 | 43 | 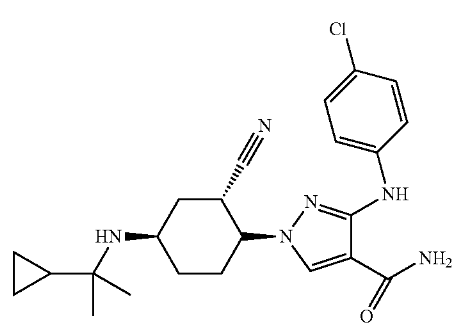 | 3-[(4-chlorophenyl)amino]-1-{(1S,2S,4R or 1R,2R,4S)-2-cyano-4-[(1-cyclopropyl-1-methylethyl)amino]cyclohexyl}-1H-pyrazole-4-carboxamide | Calc'd 441, found 441 |

TABLE 23-continued

| Example | Method | Structure | Compound Name | Exact Mass [M + H]+ |
|---|---|---|---|---|
| 28-210 | 43 | 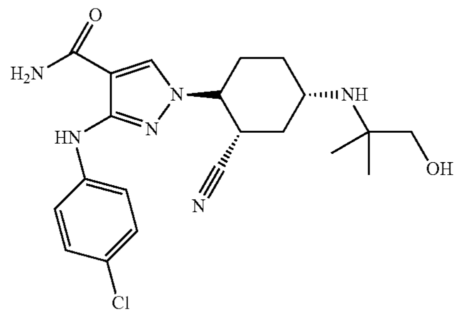 | 3-[(4-chlorophenyl)amino]-1-{(1S,2S,4S or 1R,2R,4R)-2-cyano-4-[(2-hydroxy-1,1-dimethylethyl)amino]cyclohexyl}-1H-pyrazole-4-carboxamide | Calc'd 431, found 431 |
| 28-211 | 43 | 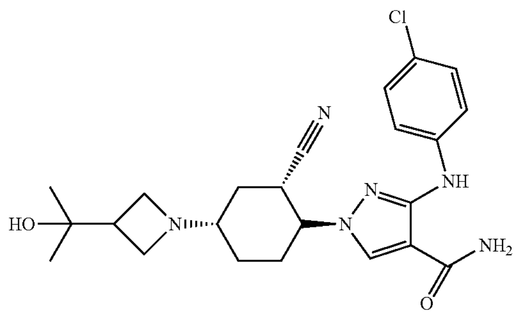 | 3-[(4-chlorophenyl)amino]-1-{(1S,2S,4S or 1R,2R,4R)-2-cyano-4-[3-(1-hydroxy-1-methylethyl)azetidin-1-yl]cyclohexyl}-1H-pyrazole-4-carboxamide | Calc'd 457, found 457 |
| 28-212 | 43 | 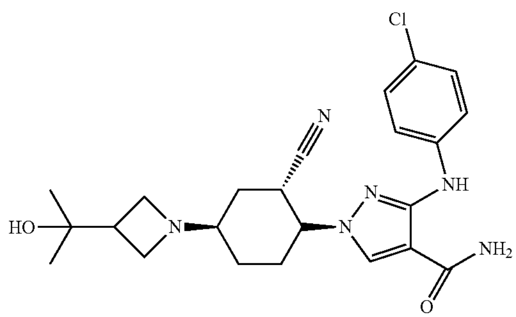 | 3-[(4-chlorophenyl)amino]-1-{(1S,2S,4R or 1R,2R,4S)-2-cyano-4-[3-(1-hydroxy-1-methylethyl)azetidin-1-yl]cyclohexyl}-1H-pyrazole-4-carboxamide | Calc'd 457, found 457 |
| 28-213 | 43 | 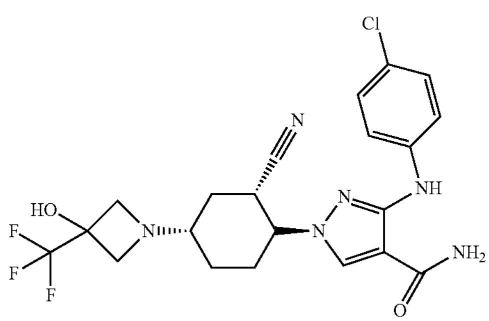 | 3-[(4-chlorophenyl)amino]-1-{(1S,2S,4S or 1R,2R,4R)-2-cyano-4-[3-hydroxy-3-(trifluoromethyl)azetidin-1-yl]cyclohexyl}-1H-pyrazole-4-carboxamide | Calc'd 483, found 483 |
| 28-214 | 43 | 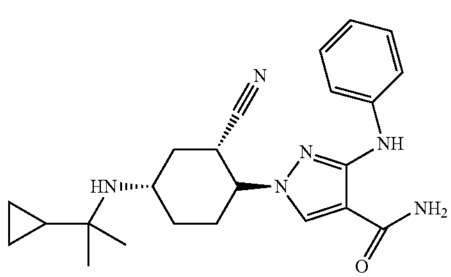 | 1-{(1S,2S,4S or 1R,2R,4R)-2-cyano-4-[(1-cyclopropyl-1-methylethyl)amino]cyclohexyl}-3-(phenylamino)-1H-pyrazole-4-carboxamide | Calc'd 407, found 407 |

TABLE 23-continued

| Example | Method | Structure | Compound Name | Exact Mass [M + H]+ |
|---|---|---|---|---|
| 28-215 | 43 | 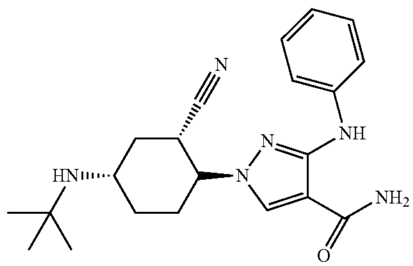 | 1-[(1S,2S,4S or 1R,2R,4R)-4-(tert-butylamino)-2-cyanocyclohexyl]-3-(phenylamino)-1H-pyrazole-4-carboxamide | Calc'd 381, found 381 |
| 28-216 | 43 | 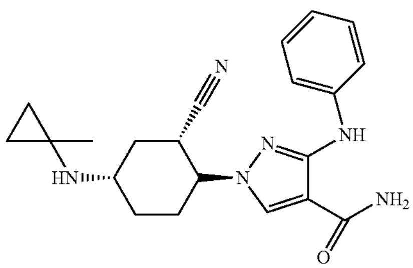 | 1-{(1S,2S,4S or 1R,2R,4R)-2-cyano-4-[(1-methylcyclopropyl)amino]cyclohexyl}-3-(phenylamino)-1H-pyrazole-4-carboxamide | Calc'd 379, found 379 |
| 28-217 | 43 | 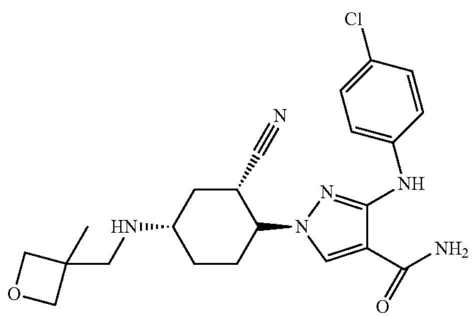 | 3-[(4-chlorophenyl)amino]-1-[(1S,2S,4S or 1R,2R,4R)-2-cyano-4-{[(3-methyloxetan-3-yl)methyl]amino}cyclohexyl]-1H-pyrazole-4-carboxamide | Calc'd 443, found 443 |
| 28-218 | 43 | 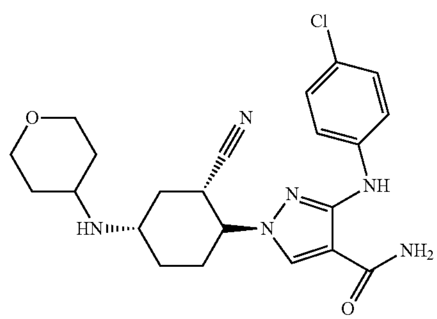 | 3-[(4-chlorophenyl)amino]-1-[(1S,2S,4S or 1R,2R,4R)-2-cyano-4-(tetrahydro-2H-pyran-4-ylamino)cyclohexyl]-1H-pyrazole-4-carboxamide | Calc'd 443, found 443 |
| 28-219 | 43 | 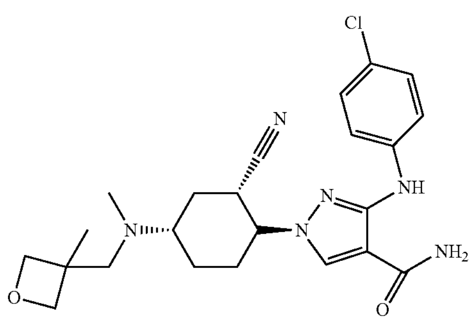 | 3-[(4-chlorophenyl)amino]-1-[(1S,2S,4S or 1R,2R,4R)-2-cyano-4-{methyl[(3-methyloxetan-3-yl)methyl]amino}cyclohexyl]-1H-pyrazole-4-carboxamide | Calc'd 457, found 457 |

TABLE 23-continued

| Example | Method | Structure | Compound Name | Exact Mass [M + H]+ |
|---|---|---|---|---|
| 28-220 | 43 | 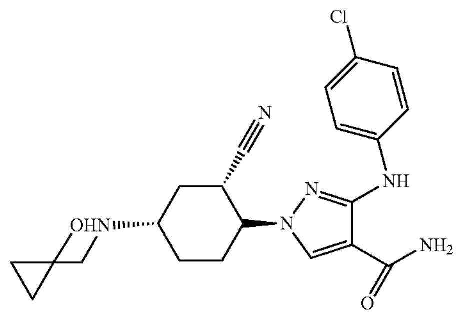 | 3-[(4-chlorophenyl)amino]-1-[(1S,2S,4S or 1R,2R,4R)-2-cyano-4-{[(1-hydroxycyclo-propyl)methyl]amino}cyclohexyl]-1H-pyrazole-4-carboxamide | Calc'd 429, found 429 |
| 28-221 | 43 | 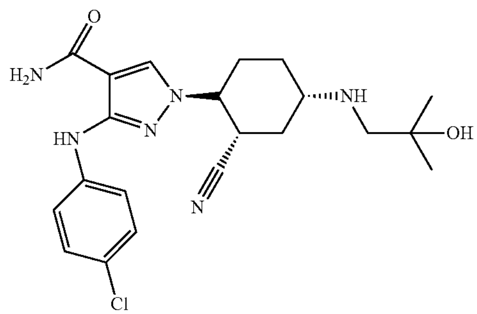 | 3-[(4-chlorophenyl)amino]-1-{(1S,2S,4S or 1R,2R,4R)-2-cyano-4-[(2-hydroxy-2-methylpropyl)amino]cyclo-hexyl}-1H-pyrazole-4-carboxamide | Calc'd 431, found 431 |
| 28-222 | 43 | 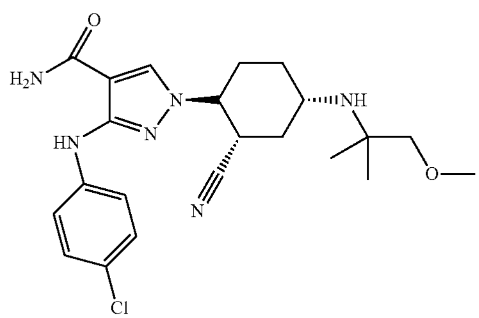 | 3-[(4-chlorophenyl)amino]-1-{(1S,2S,4S or 1R,2R,4R)-2-cyano-4-[(2-methoxy-1,1-dimethylethyl)amino]cyclo-hexyl}-1H-pyrazole-4-carboxamide | Calc'd 445, found 445 |
| 28-223 | 43 | 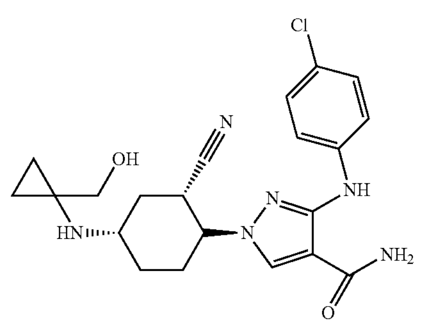 | 3-[(4-chlorophenyl)amino]-1-[(1S,2S,4S or 1R,2R,4R)-2-cyano-4-{[1-(hydroxymethyl)cyclopropyl]a-mino}cyclohexyl]-1H-pyrazole-4-carboxamide | Calc'd 429, found 429 |

TABLE 23-continued

| Example | Method | Structure | Compound Name | Exact Mass [M + H]+ |
|---|---|---|---|---|
| 28-224 | 41 | 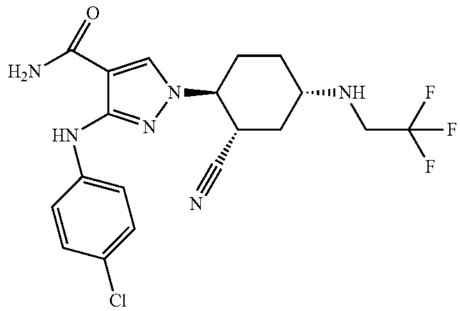 [SMILES: N#C[C@H]1C[C@@H](NCC(F)(F)F)CC[C@@H]1n1cc(C(N)=O)c(Nc2ccc(Cl)cc2)n1] | 3-[(4-chlorophenyl)amino]-1-{(1S,2S,4S or 1R,2R,4R)-2-cyano-4-[(2,2,2-trifluoroethyl)amino]cyclohexyl}-1H-pyrazole-4-carboxamide | Calc'd 441, found 441 |
| 28-225 | 41 | 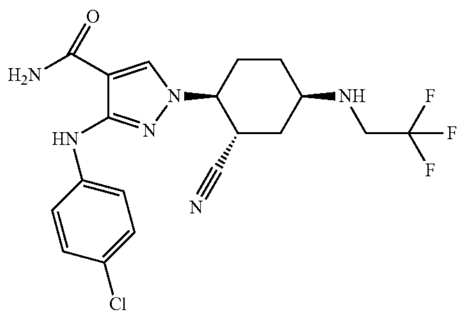 [SMILES: N#C[C@H]1C[C@H](NCC(F)(F)F)CC[C@@H]1n1cc(C(N)=O)c(Nc2ccc(Cl)cc2)n1] | 3-[(4-chlorophenyl)amino]-1-{(1S,2S,4R or 1R,2R,4S)-2-cyano-4-[(2,2,2-trifluoroethyl)amino]cyclohexyl}-1H-pyrazole-4-carboxamide | Calc'd 441, found 441 |
| 28-226 | 41 | 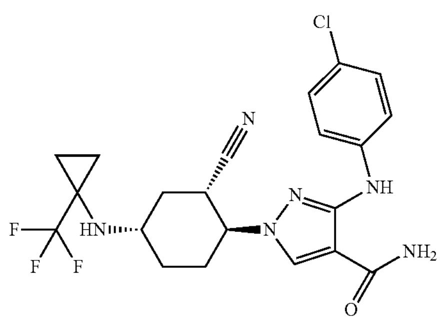 [SMILES: N#C[C@H]1C[C@@H](NC2(C(F)(F)F)CC2)CC[C@@H]1n1cc(C(N)=O)c(Nc2ccc(Cl)cc2)n1] | 3-[(4-chlorophenyl)amino]-1-[(1S,2S,4S or 1R,2R,4R)-2-cyano-4-{[1-(trifluoromethyl)cyclopropyl]amino}cyclohexyl]-1H-pyrazole-4-carboxamide | Calc'd 467, found 467 |
| 28-227 | 41 | 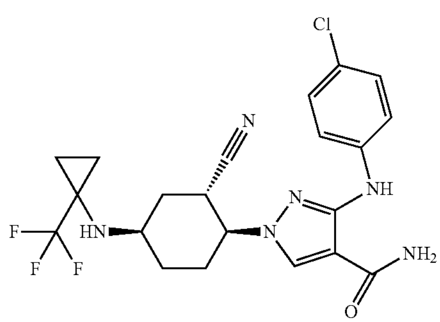 [SMILES: N#C[C@H]1C[C@H](NC2(C(F)(F)F)CC2)CC[C@@H]1n1cc(C(N)=O)c(Nc2ccc(Cl)cc2)n1] | 3-[(4-chlorophenyl)amino]-1-[(1S,2S,4R or 1R,2R,4S)-2-cyano-4-{[1-(trifluoromethyl)cyclopropyl]amino}cyclohexyl]-1H-pyrazole-4-carboxamide | Calc'd 467, found 467 |

TABLE 23-continued

| Example | Method | Structure | Compound Name | Exact Mass [M + H]+ |
|---|---|---|---|---|
| 28-228 | 43 | 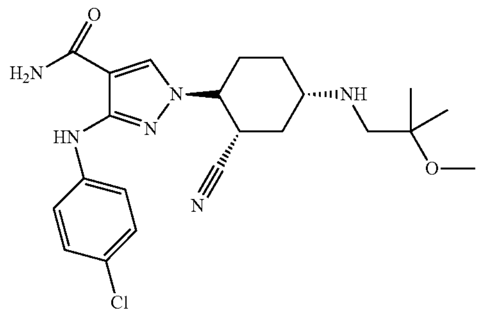 | 3-[(4-chlorophenyl)amino]-1-{(1S,2S,4S or 1R,2R,4R)-2-cyano-4-[(2-methoxy-2-methylpropyl)amino]cyclohexyl}-1H-pyrazole-4-carboxamide | Calc'd 445, found 445 |
| 28-229 | 44 | 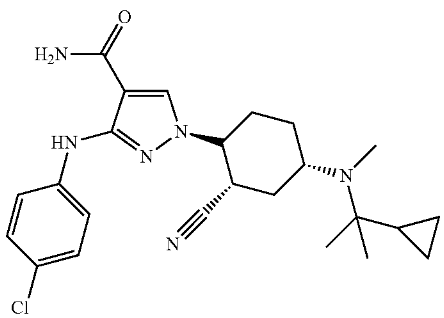 | 3-[(4-chlorophenyl)amino]-1-{(1S,2S,4S or 1R,2R,4R)-2-cyano-4-[(1-cyclopropyl-1-methylethyl)(methyl)amino]cyclohexyl}-1H-pyrazole-4-carboxamide | Calc'd 455, found 455 |
| 28-230 | 43 | 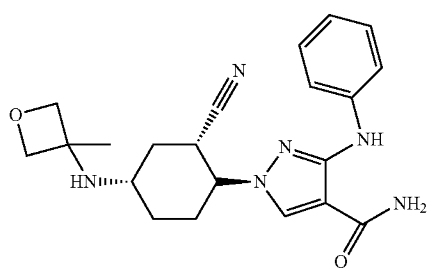 | 1-{(1S,2S,4S or 1R,2R,4R)-2-cyano-4-[(3-methyloxetan-3-yl)amino]cyclohexyl}-3-(phenylamino)-1H-pyrazole-4-carboxamide | Calc'd 395, found 395 |
| 28-231 | 43 | 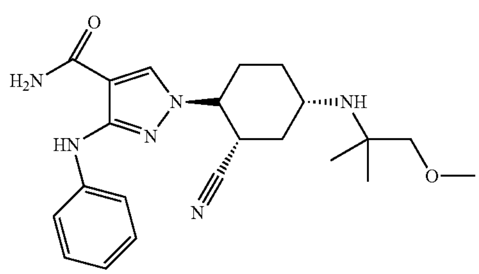 | 1-{(1S,2S,4S or 1R,2R,4R)-2-cyano-4-[(2-methoxy-1,1-dimethylethyl)amino]cyclohexyl}-3-(phenylamino)-1H-pyrazole-4-carboxamide | Calc'd 411, found 411 |
| 28-232 | 44 | 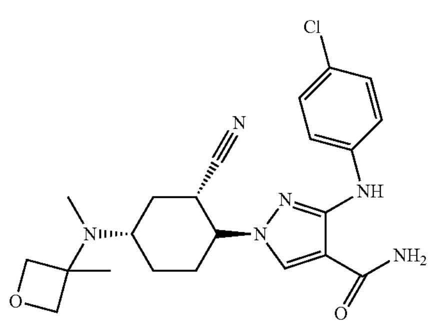 | 3-[(4-chlorophenyl)amino]-1-{(1S,2S,4S or 1R,2R,4R)-2-cyano-4-[methyl(3-methyloxetan-3-yl)amino]cyclohexyl}-1H-pyrazole-4-carboxamide | Calc'd 443, found 443 |

TABLE 23-continued

| Example | Method | Structure | Compound Name | Exact Mass [M + H]+ |
|---|---|---|---|---|
| 28-233 | 44 | 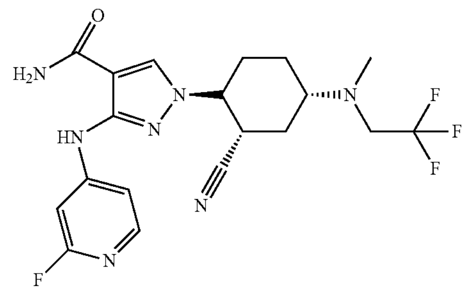 | 1-{(1S,2S,4S or 1R,2R,4R)-2-cyano-4-[methyl(2,2,2-trifluoroethyl)amino]cyclohexyl}-3-[(2-fluoropyridin-4-yl)amino]-1H-pyrazole-4-carboxamide | Calc'd 440, found 440 |
| 28-234 | 44 | 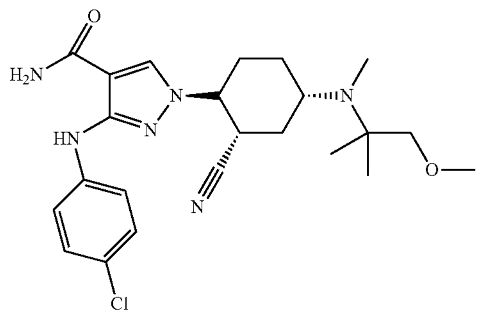 | 3-[(4-chlorophenyl)amino]-1-{(1S,2S,4S or 1R,2R,4R)-2-cyano-4-[(2-methoxy-1,1-dimethylethyl)(methyl)amino]cyclohexyl}-1H-pyrazole-4-carboxamide | Calc'd 459, found 459 |
| 28-235 | 43 | 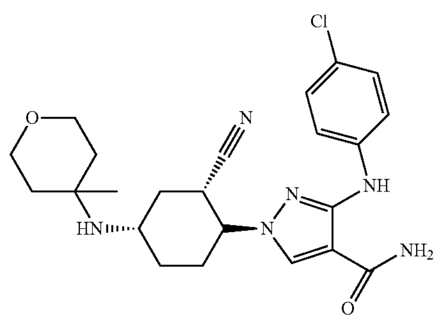 | 3-[(4-chlorophenyl)amino]-1-{(1S,2S,4S or 1R,2R,4R)-2-cyano-4-[(4-methyltetrahydro-2H-pyran-4-yl)amino]cyclohexyl}-1H-pyrazole-4-carboxamide | Calc'd 457, found 457 |
| 28-236 | 43 | 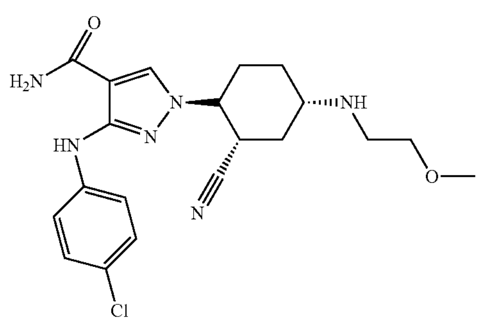 | 3-[(4-chlorophenyl)amino]-1-{(1S,2S,4S or 1R,2R,4R)-2-cyano-4-[(2-methoxyethyl)amino]cyclohexyl}-1H-pyrazole-4-carboxamide | Calc'd 417, found 417 |
| 28-237 | 43 | 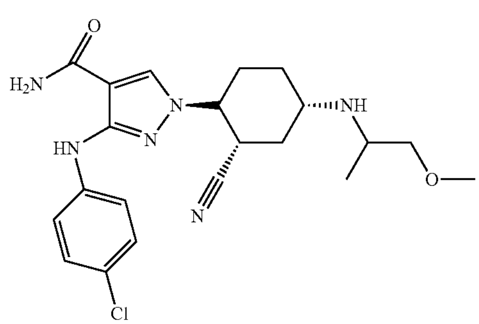 | 3-[(4-chlorophenyl)amino]-1-[(1S,2S,4S or 1R,2R,4R)-2-cyano-4-{[(1S)-2-methoxy-1-methylethyl]amino}cyclohexyl]-1H-pyrazole-4-carboxamide | Calc'd 431, found 431 |

TABLE 23-continued

| Example | Method | Structure | Compound Name | Exact Mass [M + H]+ |
|---|---|---|---|---|
| 28-238 | 43 | 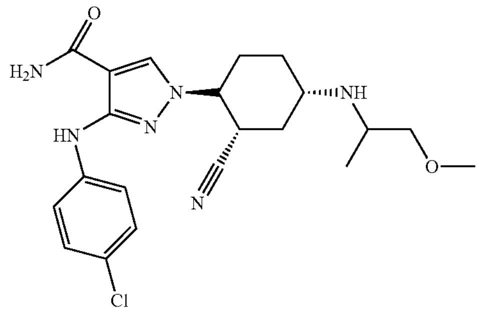 | 3-[(4-chlorophenyl)amino]-1-[(1S,2S,4S or 1R,2R,4R)-2-cyano-4-{[(1S)-2-methoxy-1-methylethyl]amino}cyclohexyl]-1H-pyrazole-4-carboxamide | Calc'd 431, found 431 |
| 28-239 | 44 | 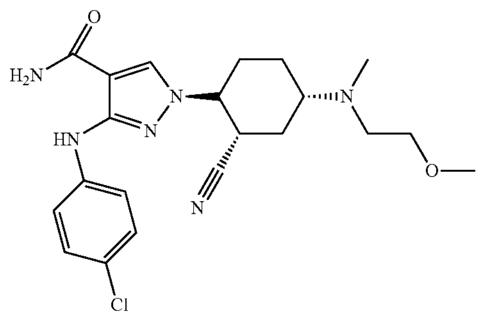 | 3-[(4-chlorophenyl)amino]-1-{(1S,2S,4S or 1R,2R,4R)-2-cyano-4-[(2-methoxyethyl)(methyl)amino]cyclohexyl}-1H-pyrazole-4-carboxamide | Calc'd 431, found 431 |
| 28-240 | 44 | 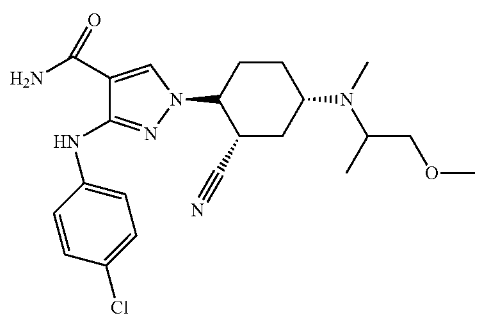 | 3-[(4-chlorophenyl)amino]-1-[(1S,2S,4S or 1R,2R,4R)-2-cyano-4-{[(1S or 1R)-2-methoxy-1-methylethyl](methyl)amino}cyclohexyl]-1H-pyrazole-4-carboxamide | Calc'd 445, found 445 |
| 28-241 | 44 | 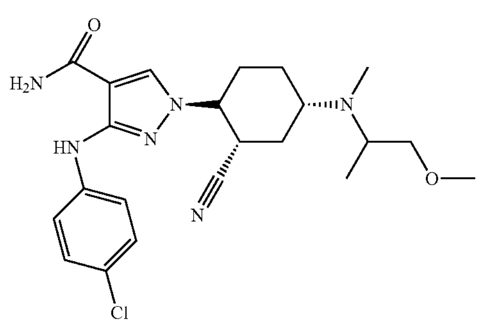 | 3-[(4-chlorophenyl)amino]-1-[(1R,2S,4S1S,2S,4S or 1R,2R,4R)-2-cyano-4-{[(1S or 1R)-2-methoxy-1-methylethyl](methyl)amino}cyclohexyl]-1H-pyrazole-4-carboxamide | Calc'd 445, found 445 |

Scheme #56

Example #29

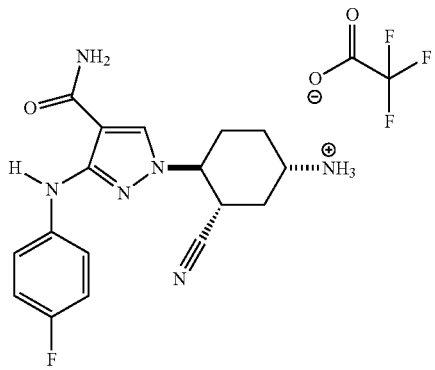

Step A-C: (1S,3S,4S and 1R,3R,4R)-4-{4-Carbamoyl-3-[(4-fluorophenyl)amino]-1H-pyrazol-1-yl}-3-cyanocyclohexanaminium trifluoroacetate 1-[(1S,2S,4R and 1R,2R,4S)-2-cyano-4-hydroxycyclohexyl]-3-[(fluorophenyl)amino]-1H-pyrazole-4-carboxamide (Example #5, 50 mg, 0.15 mmol) was dissolved in DCM (1.5 mL) and cooled to 0° C. TEA (0.041 mL, 0.29 mmol) and methanesulfonyl chloride (0.014 mL, 0.18 mmol) were added sequentially and the reaction mixture was maintained at 0° C. for 10 minutes. The reaction mixture was then partitioned between saturated aqueous NaHCO$_3$ and EtOAc, the layers were separated, and the organic layer was washed with brine, dried over anhydrous Na$_2$SO$_4$, filtered, and concentrated in vacuo. The crude residue, which was carried on without further purification, was dissolved in DMF (0.72 mL) followed by the addition of sodium azide (94 mg, 1.5 mmol). The reaction mixture was heated to 90° C. for 16 hours. After cooling to ambient temperature the reaction mixture was partitioned between water and EtOAc. The layers were separated, and the organic layer was washed with brine, dried over anhydrous Na$_2$SO$_4$, filtered, and concentrated in vacuo. The crude residue, which was carried on without further purification, was dissolved in THF (1.9 mL). Triphenylphosphine (145 mg, 0.554 mmol) and water (0.033 mL, 1.9 mmol) were added and the reaction mixture was heated to 55° C. for 20 hours. The reaction mixture was then allowed to cool to ambient temperature, filtered, and purified by reverse phase preparative HPLC (using a gradient elution of 20-60% MeCN/water, with 0.1% v/v TFA modifier). Desired fractions were identified, combined, and lyophilized to afford the title compound. $^1$H NMR (DMSO-d$_6$): δ 9.13 (s, 1H), 8.21 (s, 1H), 8.04 (br s, 3H), 7.70 (br s, 1H), 7.53 (m, 2H), 7.17 (br s, 1H), 7.05 (m, 2H), 4.49 (ddd, J=11.5, 11.5, 4 Hz, 1H), 3.58 (ddd, J=13, 13, 4 Hz, 1H), 3.28 (br s, 1H), 2.37 (d, J=11.5 Hz, 1H), 2.01 (m, 3H), 1.84 (ddd, J=12.5, 12.5, 12.5 Hz, 1H), 1.55 (m, 1H).

LRMS (ESI) calc'd for C$_{17}$H$_{19}$FN$_6$O [M+H]$^+$: 343. Found: 343.

Scheme #50

Example #30-1

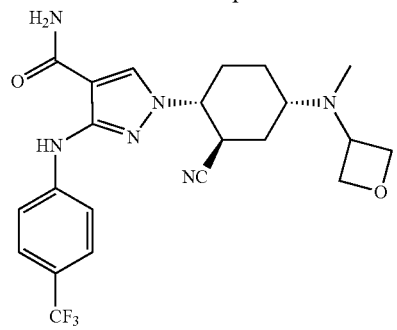

1-{(1R,2R,4S or 1S,2S,4R)-2-Cyano-4-[methyl(oxetan-3-yl)amino]cyclohexyl}-3-{[4-(trifluoromethyl)phenyl]amino}-1H-pyrazole-4-carboxamide

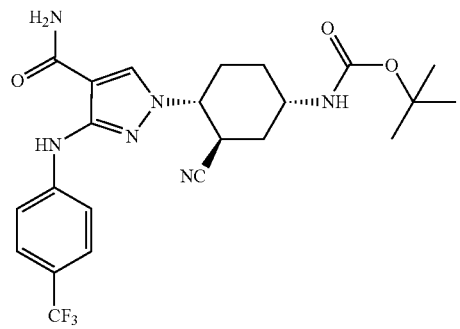 [SMILES: CC(C)(C)OC(=O)N[C@H]1CC[C@@H](n2cc(C(N)=O)c(Nc3ccc(C(F)(F)F)cc3)n2)[C@H](C#N)C1]

Step A: tert-Butyl((1S,3R,4R or 1R,2S,4S)-4-(4-carbamoyl-3-((4-(trifluoromethyl)phenyl)amino)-1H-pyrazol-1-yl)-3-cyanocyclohexyl)carbamate To a solution of tert-butyl[(1R,3S,4S and 1S,3R,4R)-4-(3-amino-4-carbamoyl-1H-pyrazol-1-yl)-3-cyanocyclohexyl] carbamate (4.74 g, 13.6 mmol) in 2-propanol (68 mL), were added 1-bromo-4-(trifluoromethyl)benzene (3.67 g, 16.3 mmol), potassium acetate (2.67 g, 27.2 mmol), tetramethyl t-butyl X-Phos (1.96 g, 4.08 mmol), and Pd$_2$ dba$_3$ (1.87 g, 2.04 mmol). The reaction was degassed by bubbling argon gas for 10 minutes, sealed, and heated to 90° C. for 14 hours. The reaction mixture was cooled to ambient temperature and partitioned between EtOAc and brine. The organic layer was collected, dried over anhydrous MgSO$_4$, filtered, and concentrated in vacuo. The residue was purified by MPLC on silica gel (Using a gradient elution of 0-100% EtOAc/hexanes) to afford tert-butyl[(1R,3S,4S and 1S,3R,4R)-4-(4-carbamoyl-3-{[4-(trifluoromethyl)phenyl]amino}-1H-pyrazol-1-yl)-3-cyanocyclohexyl]carbamate as a racemic mixture. The racemate was resolved via chiral SFC chromatography (Chiral Technology IC 2.1×25 cm column, mobile phase: 15%/85% Methanol/CO$_2$) to afford the separated enantiomers.

Intermediate A of Example #30-1: The $2^{nd}$ enantiomer to elute; $^1$H NMR (500 MHz, DMSO-d$_6$): δ 9.45 (s, 1H), 8.27 (s, 1H), 7.69 (d, J=9 Hz, 2H), 7.53 (d, J=9 Hz, 2H), 7.20 (s, 2H), 4.45-4.40 (td, J=10.8, 3.6 Hz, 1H), 3.70 (m, 1H), 3.64-3.60 (td, J=11.4, 3.6 Hz, 1H), 2.09-1.94 (m, 3H), 1.83-1.80 (m, 2H), 1.68-1.63 (m, 1H), 1.38 (s, 9H). LRMS (ESI) calc'd for C$_{23}$H$_{28}$F$_3$N$_6$O$_3$ [M+H]$^+$: 493. Found: 493.

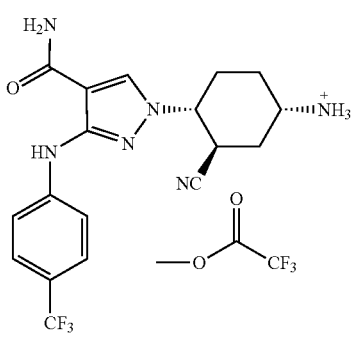

Step B: (1R,3S,4S or 1S,3R,4R)-4-(4-carbamoyl-3-{[4-(trifluoromethyl)phenyl]amino}-1H-pyrazol-1-yl)-3-cyanocyclohexanaminium trifluoroacetate tert-Butyl((1S,3R,4R or 1R,2S,4S)-4-(4-carbamoyl-3-((4-(trifluoromethyl)phenyl)amino)-1H-pyrazol-1-yl)-3-cyanocyclohexyl)carbamate (Intermediate B of Example #30-1, 640 mg, 1.30 mmol) was dissolved in DCM (3 mL) at 0° C. and TFA (3 mL) was added. The solution was stirred for 1 hour then concentrated in vacuo to afford the title compound. LRMS (ESI) calc'd for $C_{18}H_{20}F_3N_6O$ [M+H]$^+$: 393. Found: 393.

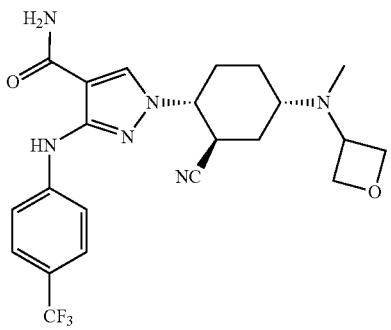 [SMILES: CN(C1COC1)[C@H]1CC[C@@H](n2cc(C(N)=O)c(Nc3ccc(C(F)(F)F)cc3)n2)[C@H](C#N)C1]

Step C: 1-{(1R,2R,4S or 1S,2S,4R)-2-Cyano-4-[methyl(oxetan-3-yl)amino]cyclohexyl}-3-{[4-(trifluoromethyl)phenyl]amino}-1H-pyrazole-4-carboxamide To a solution of (1R,3S,4S or 1S,3R,4R)-4-(4-carbamoyl-3-{[4-(trifluoromethyl)phenyl]amino}-1H-pyrazol-1-yl)-3-cyanocyclohexanaminium trifluoroacetate (30 mg, 0.059 mmol) in DMF (0.5 mL) and MeOH (0.5 mL) were added oxetan-3-one (21 mg, 0.30 mmol) and stirred for 15 minutes followed by sodium cyanoborohydride (9 mg, 0.3 mmol). Additional oxetan-3-one (13 mg, 0.18 mmol) was added and the reaction mixture was stirred for 15 minutes then additional sodium cyanoborohydride (9 mg, 0.3 mmol) was added. After 30 minutes formaldehyde (48 mg, 0.59 mmol) was added and the mixture was stirred for 15 minutes before additional sodium cyanoborohydride (9 mg, 0.3 mmol) was added. The reaction was stirred for 1 hour then filtered and purified directly by reverse phase HPLC to afford the title compound. $^1$H NMR (500 MHz, CD$_3$OD): δ 8.22 (s, 1H), 7.68 (d, J=9 Hz, 2H) 7.53 (d, 8.5 Hz, 2H), 4.74-4.64 (m, 4H), 4.47 (m, 1H), 4.04-4.02 (m, 1H), 3.86 (m, 1H), 2.65 (m, 1H), 2.40 (m, 1H), 2.24 (s, 3H), 2.16 (m, 1H), 2.06 (m, 1H), 1.97-1.88 (m 2H), 1.70 (m, 1H). LRMS (ESI) calc'd for $C_{22}H_{26}F_3N_6O_2$ [M+H]$^+$: 463. Found: 463.

The following compounds shown in TABLE 24 were prepared according to Scheme #50 following similar procedures described for Example #30-1 which can be achieved by those of ordinary skill in the art of organic synthesis.

TABLE 24

| Example | Structure | Compound Name | Exact Mass [M + H]+ |
|---|---|---|---|
| 30-2 | 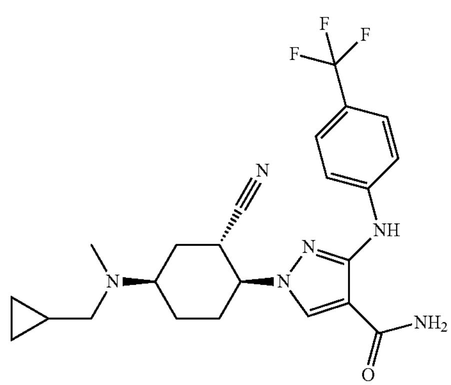 [SMILES: CN(CC1CC1)[C@@H]1CC[C@H](n2cc(C(N)=O)c(Nc3ccc(C(F)(F)F)cc3)n2)[C@@H](C#N)C1] | 1-{(1S,2S,4R or 1R,2R,4S)-2-cyano-4-[(cyclopropylmethyl)(methyl)amino]cyclohexyl}-3-{[4-(trifluoromethyl)phenyl]amino}-1H-pyrazole-4-carboxamide | Calc'd 461, found 461 |

TABLE 24-continued

| Example | Structure | Compound Name | Exact Mass [M + H]+ |
|---|---|---|---|
| 30-4 | 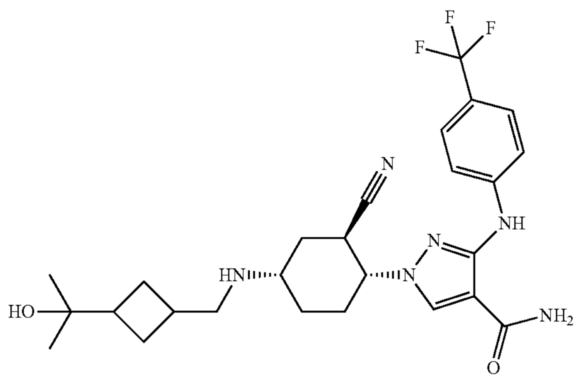 [SMILES: CC(C)(O)C1CC(CN[C@H]2CC[C@@H](n3cc(C(N)=O)c(Nc4ccc(C(F)(F)F)cc4)n3)[C@H](C#N)C2)C1] | 1-[(1R,2R,4S or 1S,2S,4R)-2-cyano-4-({[3-(1-hydroxy-1-methylethyl)cyclobutyl]methyl}amino)cyclohexyl]-3-{[4-(trifluoromethyl)phenyl]amino}-1H-pyrazole-4-carboxamide | Calc'd 519, found 519 |
| 30-5 | 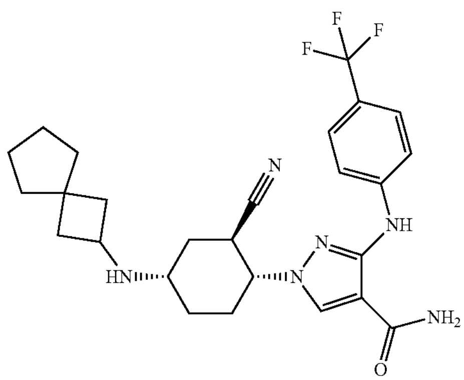 [SMILES: N#C[C@@H]1C[C@@H](NC2CC3(CCCC3)C2)CC[C@H]1n1cc(C(N)=O)c(Nc2ccc(C(F)(F)F)cc2)n1] | 1-[(1R,2R,4S or 1S,2S,4R)-2-cyano-4-(spiro[3.4]oct-2-ylamino)cyclohexyl]-3-{[4-(trifluoromethyl)phenyl]amino}-1H-pyrazole-4-carboxamide | Calc'd 501, found 501 |
| 30-6 | 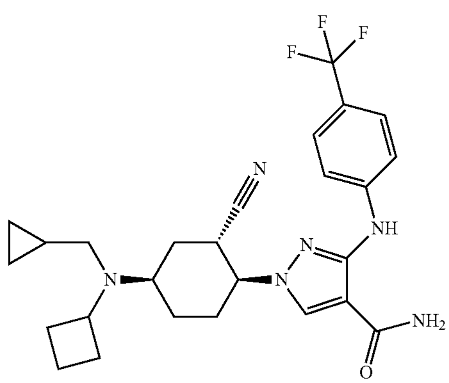 [SMILES: N#C[C@H]1C[C@H](N(CC2CC2)C2CCC2)CC[C@@H]1n1cc(C(N)=O)c(Nc2ccc(C(F)(F)F)cc2)n1] | 1-{(1S,2S,4R or 1R,2R,4S)-2-cyano-4-[cyclobutyl(cyclopropylmethyl)amino]cyclohexyl}-3-{[4-(trifluoromethyl)phenyl]amino}-1H-pyrazole-4-carboxamide | Calc'd 501, found 501 |
| 30-7 | 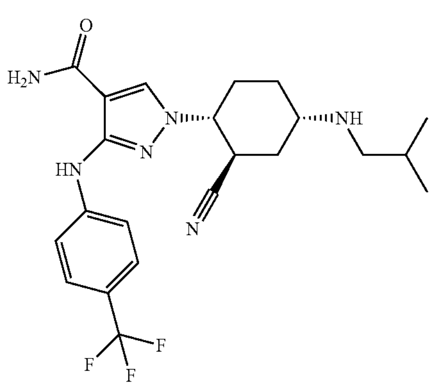 [SMILES: CC(C)CN[C@H]1CC[C@@H](n2cc(C(N)=O)c(Nc3ccc(C(F)(F)F)cc3)n2)[C@H](C#N)C1] | 1-{(1R,2R,4S or 1S,2S,4R)-2-cyano-4-[(2-methylpropyl)amino]cyclohexyl}-3-{[4-(trifluoromethyl)phenyl]amino}-1H-pyrazole-4-carboxamide | Calc'd 449, found 449 |

TABLE 24-continued

| Example | Structure | Compound Name | Exact Mass [M + H]+ |
|---|---|---|---|
| 30-8 | 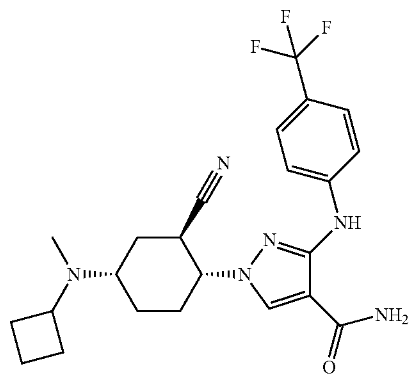 [SMILES: CN(C1CCC1)[C@H]1CC[C@@H](n2cc(C(N)=O)c(Nc3ccc(C(F)(F)F)cc3)n2)[C@H](C#N)C1] | 1-{(1R,2R,4S or 1S,2S,4R)-2-cyano-4-[cyclobutyl(methyl)amino]cyclohexyl}-3-{[4-(trifluoromethyl)phenyl]amino}-1H-pyrazole-4-carboxamide | Calc'd 461, found 461 |
| 30-9 | 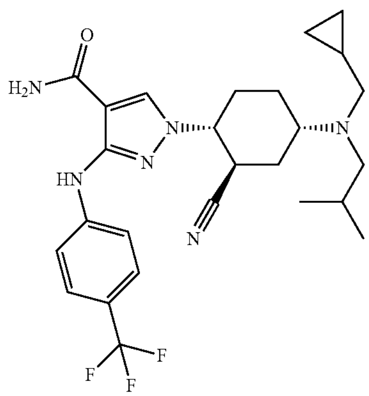 [SMILES: CC(C)CN(CC1CC1)[C@H]1CC[C@@H](n2cc(C(N)=O)c(Nc3ccc(C(F)(F)F)cc3)n2)[C@H](C#N)C1] | 1-{(1R,2R,4S or 1S,2S,4R)-2-cyano-4-[(cyclopropylmethyl)(2-methylpropyl)amino]cyclohexyl}-3-{[4-(trifluoromethyl)phenyl]amino}-1H-pyrazole-4-carboxamide | Calc'd 503, found 503 |
| 30-10 | 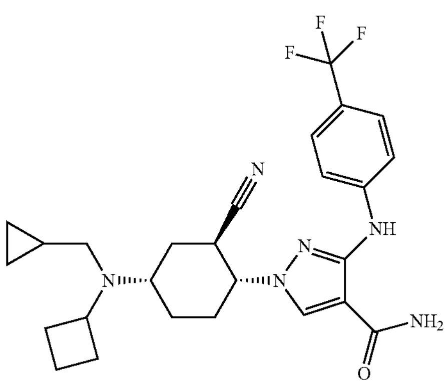 [SMILES: N#C[C@@H]1C[C@@H](N(CC2CC2)C2CCC2)CC[C@H]1n1cc(C(N)=O)c(Nc2ccc(C(F)(F)F)cc2)n1] | 1-{(1R,2R,4S or 1S,2R,4R)-2-cyano-4-[cyclobutyl(cyclopropylmethyl)amino]cyclohexyl}-3-{[4-(trifluoromethyl)phenyl]amino}-1H-pyrazole-4-carboxamide | Calc'd 501, found 501 |
| 30-12 | 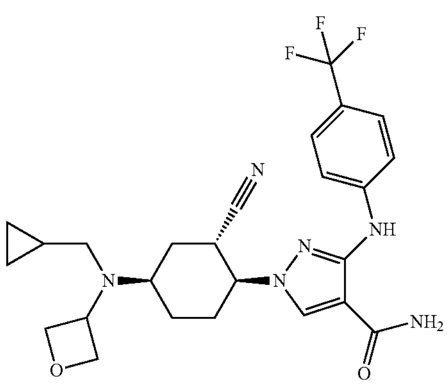 | 1-{(1S,2S,4R or 1R,2R,4S)-2-cyano-4-[(cyclopropylmethyl)(oxetan-3-yl)amino]cyclohexyl}-3-{[4-(trifluoromethyl)phenyl]amino}-1H-pyrazole-4-carboxamide | Calc'd 503, found 503 |

TABLE 24-continued

| Example | Structure | Compound Name | Exact Mass [M + H]+ |
|---|---|---|---|
| 30-13 | 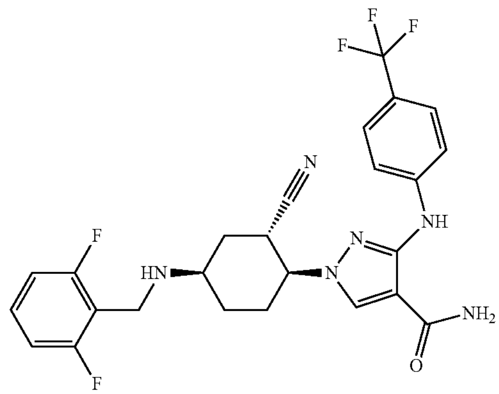 [SMILES: N#C[C@H]1C[C@H](NCc2c(F)cccc2F)CC[C@@H]1n1cc(C(N)=O)c(Nc2ccc(C(F)(F)F)cc2)n1] | 1-{(1S,2S,4R or 1R,2R,4S)-2-cyano-4-[(2,6-difluoro-benzyl)amino]cyclohexyl}-3-{[4-(trifluoromethyl)phenyl]amino}-1H-pyrazole-4-carboxamide | Calc'd 519, found 519 |
| 30-14 | 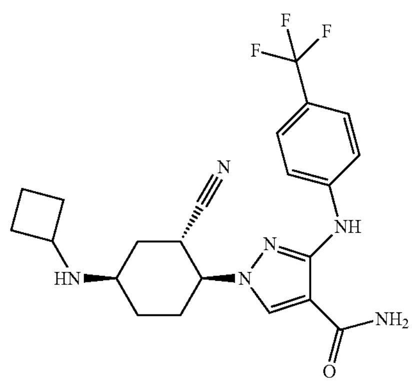 [SMILES: N#C[C@H]1C[C@H](NC2CCC2)CC[C@@H]1n1cc(C(N)=O)c(Nc2ccc(C(F)(F)F)cc2)n1] | 1-[(1S,2S,4R or 1R,2R,4S)-2-cyano-4-(cyclobutylamino)cyclohexyl]-3-{[4-(trifluoro-methyl)phenyl]amino}-1H-pyrazole-4-carboxamide | Calc'd 447, found 447 |
| 30-15 | 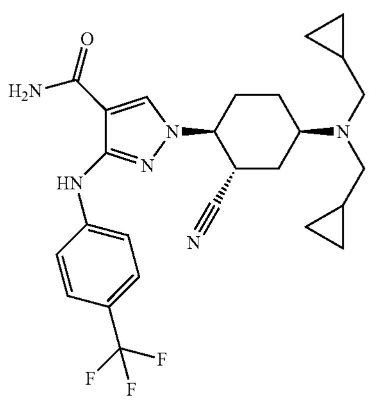 [SMILES: N#C[C@H]1C[C@H](N(CC2CC2)CC2CC2)CC[C@@H]1n1cc(C(N)=O)c(Nc2ccc(C(F)(F)F)cc2)n1] | 1-{(1S,2S,4R or 1R,2R,4S)-4-[bis(cyclopropylmethyl)amino]-2-cyanocyclohexyl}-3-{[4-(trifluoromethyl)phenyl]amino}-1H-pyrazole-4-carboxamide | Calc'd 501, found 501 |
| 30-16 | 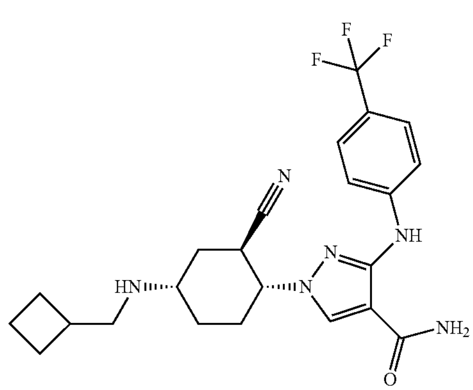 [SMILES: N#C[C@@H]1C[C@@H](NCC2CCC2)CC[C@H]1n1cc(C(N)=O)c(Nc2ccc(C(F)(F)F)cc2)n1] | 1-{(1R,2R,4S or 1S,2S,4R)-2-cyano-4-[(cyclobutyl-methyl)amino]cyclohexyl}-3-{[4-(trifluoro-methyl)phenyl]amino}-1H-pyrazole-4-carboxamide | Calc'd 461, found 461 |

TABLE 24-continued

| Example | Structure | Compound Name | Exact Mass [M + H]+ |
|---|---|---|---|
| 30-17 | 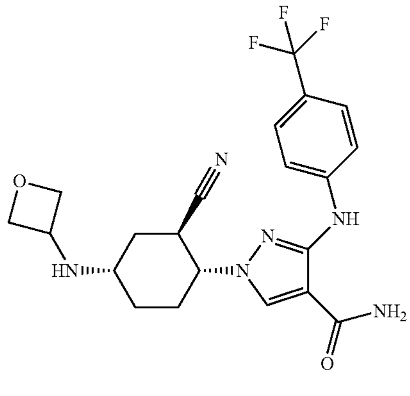 [SMILES: N#C[C@@H]1C[C@@H](NC2COC2)CC[C@H]1n1cc(C(N)=O)c(Nc2ccc(C(F)(F)F)cc2)n1] | 1-[(1R,2R,4S or 1S,2S,4R)-2-cyano-4-(oxetan-3-ylamino)cyclohexyl]-3-{[4-(trifluoromethyl)phenyl]amino}-1H-pyrazole-4-carboxamide | Calc'd 449, found 449 |
| 30-18 | 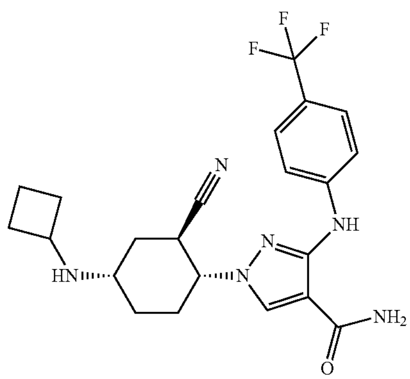 [SMILES: N#C[C@@H]1C[C@@H](NC2CCC2)CC[C@H]1n1cc(C(N)=O)c(Nc2ccc(C(F)(F)F)cc2)n1] | 1-[(1R,2R,4S or 1S,2S,4R)-2-cyano-4-(cyclobutyl-amino)cyclohexyl]-3-{[4-(trifluoromethyl)phenyl]amino}-1H-pyrazole-4-carboxamide | Calc'd 447, found 447 |

Scheme #45

Example #31-1

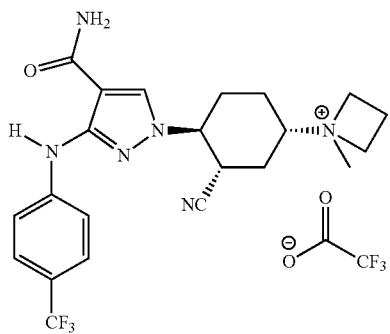 [SMILES: C[N+]1([C@H]2CC[C@H](n3cc(C(N)=O)c(Nc4ccc(C(F)(F)F)cc4)n3)[C@@H](C#N)C2)CCC1 ; O=C([O-])C(F)(F)F]

1-((1S,3S,4S or 1R,3R,4R)-4-(4-carbamoyl-3-((4-(trifluoromethyl)phenyl)amino)-1H-pyrazol-1-yl)-3-cyanocyclohexyl)-1-methylazetidin-1-ium 2,2,2-trifluoroacetate Iodomethane (0.011 mL, 0.17 mmol) was added to a mixture of 1-((1S,2S,4S or 1R,2R,4R)-4-(Azetidin-1-yl)-2-cyanocyclohexyl)-3-((4-(trifluoromethyl)phenyl)amino)-1H-pyrazole-4-carboxamide (Example #28-1, 15 mg, 0.034 mmol) and DIPEA (0.006 mL, 0.03 mmol) in MeCN (0.70 mL) at 23° C. The reaction mixture was stirred at 23° C. for 2 hours, and was then purified directly by reverse-phase preparative HPLC (using a gradient elution of MeCN/water, with 0.1% v/v TFA modifier). Desired fractions were identified, combined, and lyophilized to afford the title compound. $^1$H NMR (500 MHz, DMSO-d$_6$): δ 9.59 (s, 1H), 8.30 (s, 1H), 7.82 (s, 1H), 7.10 (d, J=8.5 Hz, 2H), 7.56 (d, J=8.5 Hz, 2H), 7.31 (s, 1H), 4.60-4.49 (m, 3H), 4.11-3.90 (m, 2H), 3.80-3.48 (m, 4H), 2.78-2.70 (m, 1H), 2.40-2.37 (m, 1H), 2.29-2.23 (m, 1H), 2.19-2.16 (m, 1H), 2.10-1.96 (m, 3H), 1.68-1.62 (m, 1H). LRMS (ESI) calc'd for $C_{22}H_{26}F_3N_6O^+$ [M]$^+$: 447. Found: 447.

The following compounds shown in TABLE 25 were prepared according to Scheme #45 following similar procedures described for Example #31-1 which can be achieved by those of ordinary skill in the art of organic synthesis.

TABLE 25

| Example | Structure | Compound Name | Exact Mass [M + H]+ |
|---|---|---|---|
| 31-2 | 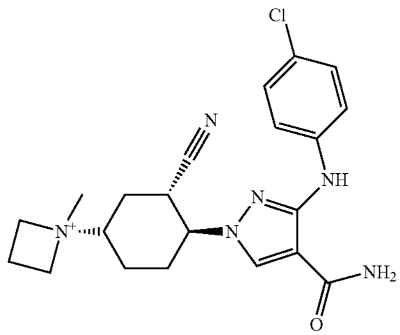 | 1-[(1S,3S,4S)-4-{4-carbamoyl-3-[(4-chlorophenyl)amino]-1H-pyrazol-1-yl}-3-cyanocyclohexyl]-1-methylazetidinium | Calc'd 413, found 413 |
| 31-3 | 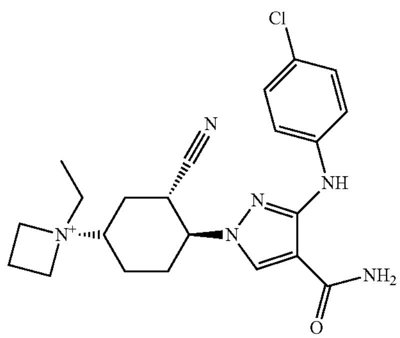 | 1-[(1S,3S,4S)-4-{4-carbamoyl-3-[(4-chlorophenyl)amino]-1H-pyrazol-1-yl}-3-cyanocyclohexyl]-1-ethylazetidinium | Calc'd 427, found 427 |
| 31-4 | 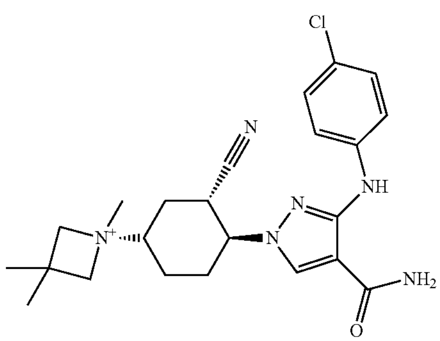 | 1-[(1S,3S,4S)-4-{4-carbamoyl-3-[(4-chlorophenyl)amino]-1H-pyrazol-1-yl}-3-cyanocyclohexyl]-1,3,3-trimethylazetidinium | Calc'd 441, found 441 |
| 31-5 | 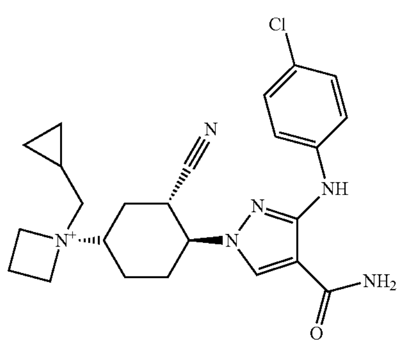 | 1-[(1S,3S,4S)-4-{4-carbamoyl-3-[(4-chlorophenyl)amino]-1H-pyrazol-1-yl}-3-cyanocyclohexyl]-1-(cyclopropylmethyl)azetidinium | Calc'd 453, found 453 |

Scheme #38

Example #32-1

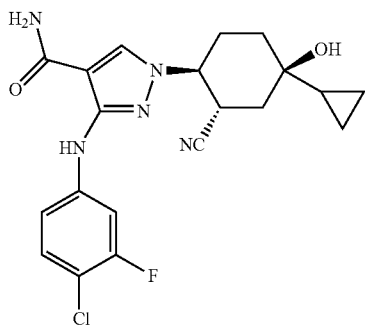 [SMILES: N#C[C@H]1C[C@@](O)(C2CC2)CC[C@@H]1n1cc(C(N)=O)c(Nc2ccc(Cl)c(F)c2)n1]

3-[(4-Chloro-3-fluorophenyl)amino]-1-[(1S,2S,4S or 1R,2R,4R)-2-cyano-4-cyclopropyl-4-hydroxycyclohexyl]-1H-pyrazole-4-carboxamide

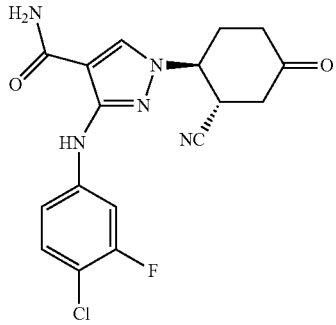 [SMILES: N#C[C@H]1CC(=O)CC[C@@H]1n1cc(C(N)=O)c(Nc2ccc(Cl)c(F)c2)n1]

Step A: 3-((4-Chloro-3-fluorophenyl)amino)-1-((1S, 2S or 1R,2R)-2-cyano-4-oxocyclohexyl)-1H-pyrazole-4-carboxamide According to the oxidation protocol described for Example #27-1 and #27-2,3-[(4-chloro-3-fluorophenyl)amino]-1-[(1S,2S,4R or 1R,2R,4S)-2-cyano-4-hydroxycyclohexyl]-1H-pyrazole-4-carboxamide (Example #25-3) was converted to 3-[(4-chloro-3-fluorophenyl)amino]-1-[(1S,2S or 1R,2R)-2-cyano-4-oxocyclohexyl]-1H-pyrazole-4-carboxamide under the action of TPAP and NMO. LRMS (ESI) calc'd for $C_{17}H_{15}ClFN_5O_2$ [M+H]$^+$: 376. Found: 376.

Step B: 3-[(4-Chloro-3-fluorophenyl)amino]-1-[(1S, 2S,4S or 1R,2R,4R)-2-cyano-4-cyclopropyl-4-hydroxycyclohexyl]-1H-pyrazole-4-carboxamide To a solution of 3-[(4-chloro-3-fluorophenyl)amino]-1-[(1S,2S or 1R,2R)-2-cyano-4-oxocyclohexyl]-1H-pyrazole-4-carboxamide (209 mg, 0.556 mmol) in THF (5.6 mL) at −78° C. under argon was added cyclopropyl magnesium bromide solution (6.67 mL, 3.34 mmol, 0.5 M in THF) dropwise. The solution was maintained at −78° C. for 45 minutes then another 3 eq. cyclopropyl magnesium bromide (3.33 mL, 1.67 mmol, 0.5 M in THF) was added dropwise. The solution was stirred at −78° C. for 1 hour then warmed to −30° C. and quenched with saturated aqueous ammonium chloride followed by warming to ambient temperature. The solution was taken up in EtOAc. The organic layer was washed with water, dried over anhydrous $MgSO_4$, filtered, and concentrated in vacuo. The reaction mixture was purified by MPLC on silica gel (using a gradient elution of 0-8% MeOH/DCM) to afford a mixture of diastereomers. The diastereomers were separated by reverse phase preparative HPLC to afford the title compound. $^1$H NMR (500 MHz, $CD_3OD$): δ 8.15 (s, 1H), 7.78-7.75 (dd, J=13, 3 Hz, 1H), 7.27-7.23 (t, J=9 Hz, 1H), 7.12-7.09 (m 1H), 4.35-4.30 (td, J=12, 4 Hz, 1H), 3.68-3.62 (m, 1H), 2.47-2.42 (qd, J=13, 4 Hz, 1H), 2.15-2.10 (dt, J=14, 4 Hz, 1H), 1.98-190 (m, 2H), 1.82-1.78 (m, 1H), 1.72-1.65 (td, J=14, 5 Hz, 1H), 0.92-0.87 (m, 1H), 0.437-0.360 (m, 3H). LRMS (ESI) calc'd for $C_{20}H_{22}ClFN_5O_2$ [M+H]$^+$: 418. Found: 418.

The following compounds shown in TABLE 26 were prepared according to Scheme #38 following similar procedures described for Example #32-1 which can be achieved by those of ordinary skill in the art of organic synthesis.

TABLE 26

| Example | Structure | Compound Name | Exact Mass [M + H]$^+$ |
|---|---|---|---|
| 32-2 | 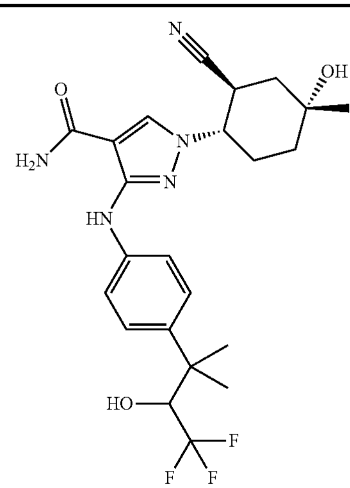 | 1-[(1S,2S,4R or 1R,2R,4S)-2-cyano-4-hydroxy-4-methylcyclohexyl]-3-{[4-(3,3,3-trifluoro-(2R or 2S)-hydroxy-1,1-dimethylpropyl)phenyl]amino}-1H-pyrazole-4-carboxamide | Calc'd 480, found 480 |

TABLE 26-continued

| Example | Structure | Compound Name | Exact Mass [M + H]+ |
|---|---|---|---|
| 32-3 | 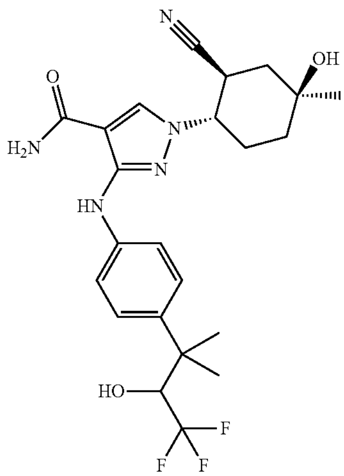 [SMILES: CC(C)(c1ccc(Nc2nn([C@H]3CC[C@](C)(O)C[C@@H]3C#N)cc2C(N)=O)cc1)C(O)C(F)(F)F] | 1-[(1S,2S,4S or 1R,2R,4R)-2-cyano-4-hydroxy-4-methylcyclohexyl]-3-{[4-(3,3,3-trifluoro-(2R or 2S)-hydroxy-1,1-dimethylpropyl)phenyl]amino}-1H-pyrazole-4-carboxamide | Calc'd 480, found 480 |
| 32-4 | 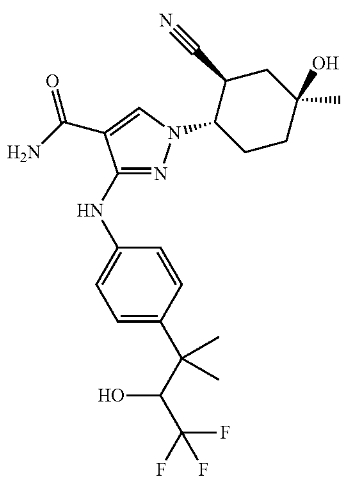 [SMILES: CC(C)(c1ccc(Nc2nn([C@H]3CC[C@](C)(O)C[C@@H]3C#N)cc2C(N)=O)cc1)C(O)C(F)(F)F] | 1-[(1S,2S,4S or 1R,2R,4R)-2-cyano-4-hydroxy-4-methylcyclohexyl]-3-{[4-(3,3,3-trifluoro-(2R or 2S)-hydroxy-1,1-dimethylpropyl)phenyl]amino}-1H-pyrazole-4-carboxamide | Calc'd 480, found 480 |
| 32-5 | 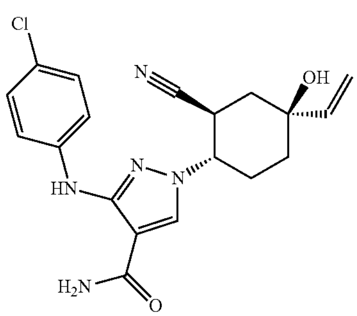 [SMILES: C=C[C@]1(O)CC[C@H](n2cc(C(N)=O)c(Nc3ccc(Cl)cc3)n2)[C@@H](C#N)C1] | 3-[(4-chlorophenyl)amino]-1-[(1S,2S,4S or 1R,2R,4R)-2-cyano-4-ethenyl-4-hydroxycyclohexyl]-1H-pyrazole-4-carboxamide | Calc'd 386, found 386 |

TABLE 26-continued

| Example | Structure | Compound Name | Exact Mass [M + H]⁺ |
|---|---|---|---|
| 32-6 | 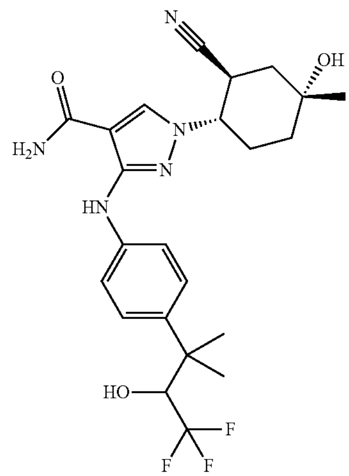 [SMILES: CC(C)(c1ccc(Nc2nn([C@H]3CC[C@@](C)(O)C[C@@H]3C#N)cc2C(N)=O)cc1)C(O)C(F)(F)F] | 1-[(1S,2S,4R or 1R,2R,4R)-2-cyano-4-hydroxy-4-methylcyclohexyl]-3-{[4-(3,3,3-trifluoro-(2R or 2S)-hydroxy-1,1-dimethylpropyl)phenyl]amino}-1H-pyrazole-4-carboxamide | Calc'd 480, found 480 |
| 32-7 | 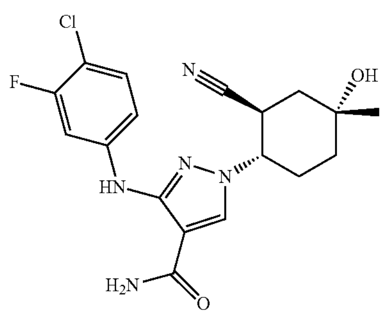 [SMILES: C[C@@]1(O)CC[C@H](n2cc(C(N)=O)c(Nc3ccc(Cl)c(F)c3)n2)[C@@H](C#N)C1] | 3-[(4-chloro-3-fluorophenyl)amino]-1-[(1S,2S,4R or 1R,2R,4S)-2-cyano-4-hydroxy-4-methylcyclohexyl]-1H-pyrazole-4-carboxamide | Calc'd 392, found 392 |
| 32-8 | 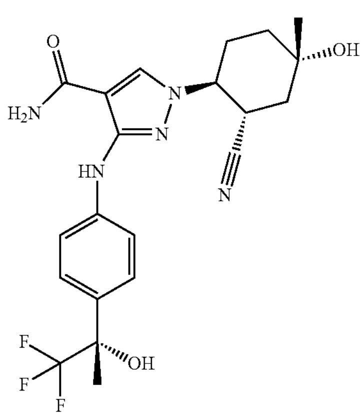 [SMILES: C[C@]1(O)CC[C@H](n2cc(C(N)=O)c(Nc3ccc([C@](C)(O)C(F)(F)F)cc3)n2)[C@@H](C#N)C1] | 1-[(1S,2S,4S or 1R,2R,4R)-2-cyano-4-hydroxy-4-methylcyclohexyl]-3-({4-[(1S or 1R)-2,2,2-trifluoro-1-hydroxy-1-methylethyl]phenyl}amino)-1H-pyrazole-4-carboxamide | Calc'd 452, found 452 |

TABLE 26-continued

| Example | Structure | Compound Name | Exact Mass [M + H]+ |
|---|---|---|---|
| 32-9 | 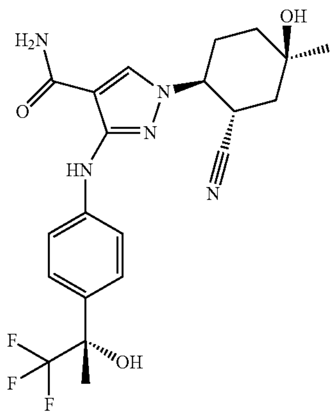 [SMILES: C[C@@]1(O)CC[C@H](n2cc(C(N)=O)c(Nc3ccc([C@](C)(O)C(F)(F)F)cc3)n2)[C@@H](C#N)C1] | 1-[(1S,2S,4R or 1R,2R,4S)-2-cyano-4-hydroxy-4-methylcyclohexyl]-3-({4-[(1S or 1R)-2,2,2-trifluoro-1-hydroxy-1-methylethyl]phenyl}amino)-1H-pyrazole-4-carboxamide | Calc'd 452, found 452 |
| 32-10 | 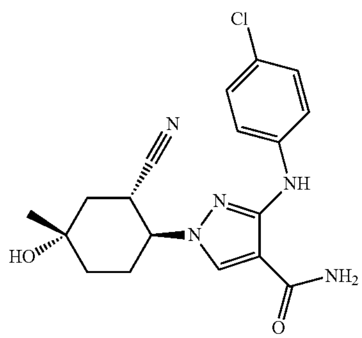 [SMILES: C[C@]1(O)CC[C@H](n2cc(C(N)=O)c(Nc3ccc(Cl)cc3)n2)[C@@H](C#N)C1] | 3-[(4-chlorophenyl)amino]-1-[(1S,2S,4S or 1R,2R,4R)-2-cyano-4-hydroxy-4-methylcyclohexyl]-1H-pyrazole-4-carboxamide | Calc'd 374, found 374 |
| 32-11 | 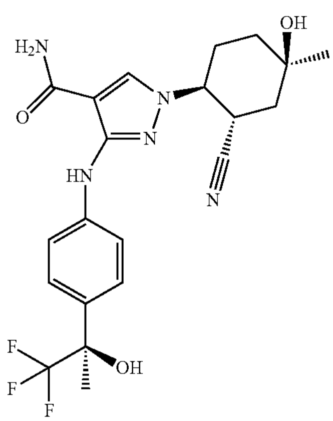 [SMILES: C[C@@]1(O)CC[C@H](n2cc(C(N)=O)c(Nc3ccc([C@@](C)(O)C(F)(F)F)cc3)n2)[C@@H](C#N)C1] | 1-[(1S,2S,4R or 1R,2R,4S)-2-cyano-4-hydroxy-4-methylcyclohexyl]-3-({4-[(1R or 1S)-2,2,2-trifluoro-1-hydroxy-1-methylethyl]phenyl}amino)-1H-pyrazole-4-carboxamide | Calc'd 452, found 452 |
| 32-12 | 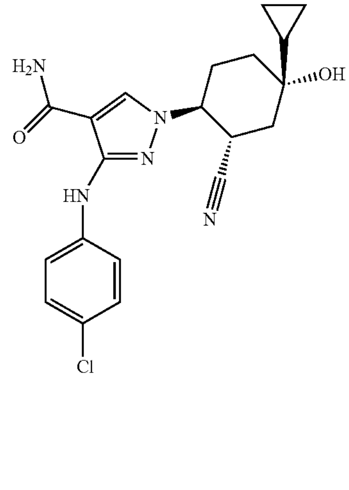 [SMILES: N#C[C@H]1C[C@](O)(C2CC2)CC[C@@H]1n1cc(C(N)=O)c(Nc2ccc(Cl)cc2)n1] | 3-[(4-chlorophenyl)aminol-1-[(1S,2S,4S or 1R,2R,4R)-2-cyano-4-cyclopropyl-4-hydroxycyclohexyl]-1H-pyrazole-4-carboxamide | Calc'd 400, found 400 |

TABLE 26-continued

| Example | Structure | Compound Name | Exact Mass [M + H]+ |
|---|---|---|---|
| 32-13 | 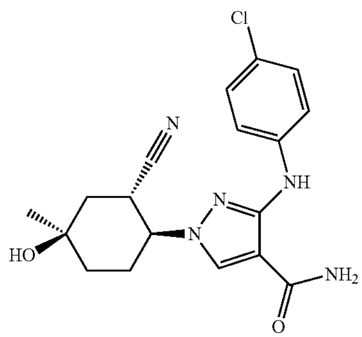 [SMILES: C[C@@]1(O)CC[C@H](n2cc(C(N)=O)c(Nc3ccc(Cl)cc3)n2)[C@@H](C#N)C1] | 3-[(4-chlorophenyl)amino]-1-[(1S,2S,4R or 1R,2R,4S)-2-cyano-4-hydroxy-4-methylcyclohexyl]-1H-pyrazole-4-carboxamide | Calc'd 374, found 374 |
| 32-14 | 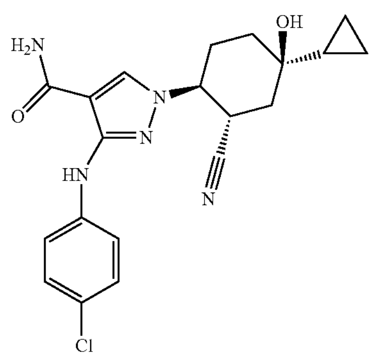 [SMILES: N#C[C@H]1C[C@@](O)(C2CC2)CC[C@@H]1n1cc(C(N)=O)c(Nc2ccc(Cl)cc2)n1] | 3-[(4-chlorophenyl)amino]-1-[(1S,2S,4R or 1R,2R,4S)-2-cyano-4-cyclopropyl-4-hydroxycyclohexyl]-1H-pyrazole-4-carboxamide | Calc'd 400, found 400 |
| 32-15 | 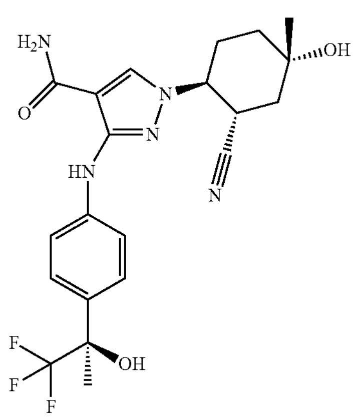 [SMILES: C[C@]1(O)CC[C@H](n2cc(C(N)=O)c(Nc3ccc([C@@](C)(O)C(F)(F)F)cc3)n2)[C@@H](C#N)C1] | 1-[(1S,2S,4S or 1R,2R,4R)-2-cyano-4-hydroxy-4-methylcyclohexyl]-3-({4-[(1R or 1S)-2,2,2-trifluoro-1-hydroxy-1-methylethyl]phenyl}amino)-1H-pyrazole-4-carboxamide | Calc'd 452, found 452 |
| 32-16 | 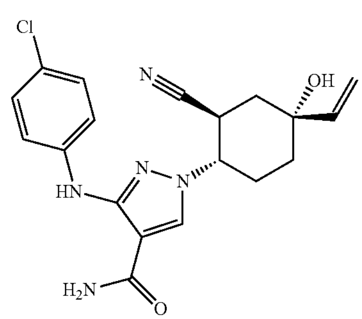 [SMILES: C=C[C@@]1(O)CC[C@H](n2cc(C(N)=O)c(Nc3ccc(Cl)cc3)n2)[C@@H](C#N)C1] | 3-[(4-chlorophenyl)amino]-1-[(1S,2S,4R or 1R,2R,4S)-2-cyano-4-ethenyl-4-hydroxycyclohexyl]-1H-pyrazole-4-carboxamide | Calc'd 386, found 386 |

TABLE 26-continued

| Example | Structure | Compound Name | Exact Mass [M + H]+ |
|---|---|---|---|
| 32-17 | 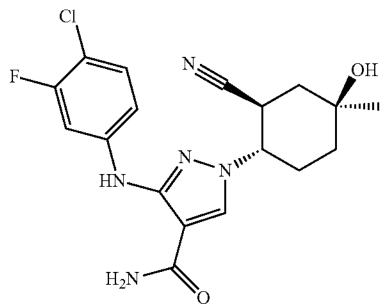 [SMILES: C[C@]1(O)CC[C@H](n2cc(C(N)=O)c(Nc3ccc(Cl)c(F)c3)n2)[C@@H](C#N)C1] | 3-[(4-chloro-3-fluorophenyl)amino]-1-[(1S,2S,4S or 1R,2R,4R)-2-cyano-4-hydroxy-4-methylcyclohexyl]-1H-pyrazole-4-carboxamide | Calc'd 392, found 392 |

Scheme #39

Example #33-1

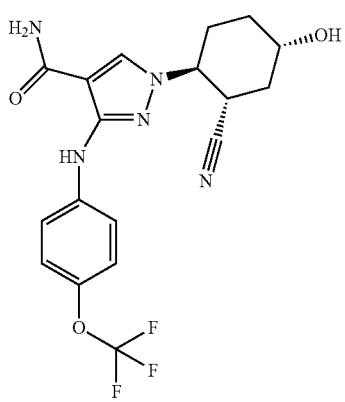 [SMILES: N#C[C@H]1C[C@@H](O)CC[C@@H]1n1cc(C(N)=O)c(Nc2ccc(OC(F)(F)F)cc2)n1]

1-((1S,2S,4S or 1R,2R,4R)-2-Cyano-4-hydroxycyclohexyl)-3-((4-(trifluoromethoxy)phenyl)amino)-1H-pyrazole-4-carboxamide According to oxidation protocol described for Example #27-1 and 27-#2, 1-[(1S,2S,4R or 1R,2R,4S)-2-cyano-4-hydroxycyclohexyl]-3-{[4-(trifluoromethoxy)phenyl]amino}-1H-pyrazole-4-carboxamide (Example #25-5) was converted to 1-((1S,2S or 1R,2R)-2-cyano-4-oxocyclohexyl)-3-((4-(trifluoromethoxy)phenyl)amino)-1H-pyrazole-4-carboxamide under the action of TPAP and NMO.

1-((1S,2S or 1R,2R)-2-cyano-4-oxocyclohexyl)-3-((4-(trifluoromethoxy)phenyl)amino)-1H-pyrazole-4-carboxamide (1.35 g, 3.31 mmol) was dissolved in methanol (16 mL) and sodium borohydride (0.125 g, 3.31 mmol) was added. The resulting mixture was stirred for 1 hour. The reaction mixture was diluted with EtOAc and the organic layer was collected, washed with water, brine, dried over anhydrous $MgSO_4$, and concentrated in vacuo. The residue was purified by MPLC on silica gel (using a gradient elution of 0-10% MeOH/DCM) to afford mixture of diastereomers. The diastereomers were separated by chiral SFC purification (Chiral Technology IB 2.1×25 cm, 5 uM column, mobile phase: 20% methanol/$CO_2$) to afford the title compound. $^1$H NMR (500 MHz, DMSO-$d_6$) δ 9.26 (s, 1H), 8.22 (s, 1H), 7.69 (br, 1H), 7.62-7.60 (d, 2H), 7.22-7.21 (d, 2H), 7.18 (br, 1H), 5.00-4.99 (d, 1H), 4.45-4.39 (m, 1H), 3.60-3.55 (m, 1H), 3.44-3.39 (m, 1H), 2.24-2.22 (m, 1H), 1.93-1.88 (m, 3H), 1.69-1.61 (m, 1H), 1.45-1.37 (m, 1H). LRMS (ESI) calc'd [M+H]+: 410. Found: 410.

The following compounds shown in TABLE 27 were prepared according to Scheme #39 following similar procedures described for Example #33-1, which can be achieved by those of ordinary skill in the art of organic synthesis.

TABLE 27

| Example | Structure | Compound Name | Exact Mass [M + H]+ |
|---|---|---|---|
| 33-2 | 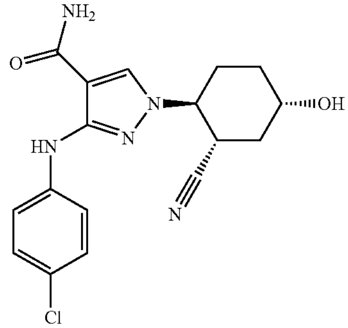 [SMILES: N#C[C@H]1C[C@@H](O)CC[C@@H]1n1cc(C(N)=O)c(Nc2ccc(Cl)cc2)n1] | 3-[(4-chlorophenyl)amino]-1-[(1S,2S,4S or 1R,2R,4R)-2-cyano-4-hydroxycyclohexyl]-1H-pyrazole-4-carboxamide | Calc'd 360, found 360 |

TABLE 27-continued

| Example | Compound Name | Exact Mass [M + H]+ |
|---|---|---|
| 33-3 | 3-[(4-chloro-3-fluorophenyl)amino]-1-[(1S,2S,4S or 1R,2R,4R)-2-cyano-4-hydroxycyclohexyl]-1H-pyrazole-4-carboxamide | Calc'd 378, found 378 |
| 33-4 | 1-[(1S,2S,4S or 1R,2R,4R)-2-cyano-4-hydroxycyclohexyl]-3-{[4-(trifluoromethyl)phenyl]amino}-1H-pyrazole-4-carboxamide | Calc'd 394, found 394 |
| 33-5 | 1-[(1S,2S,4S or 1R,2R,4R)-2-cyano-4-hydroxycyclohexyl]-3-({4-[(trifluoromethyl)sulfonyl]phenyl}amino)-1H-pyrazole-4-carboxamide | Calc'd 458, found 458 |
| 33-6 | 1-[(1S,2S,4S or 1R,2R,4R)-2-cyano-4-hydroxycyclohexyl]-3-[(4-cyanophenyl)amino]-1H-pyrazole-4-carboxamide | Calc'd 351, found 351 |

TABLE 27-continued

| Example | Structure | Compound Name | Exact Mass [M + H]+ |
|---|---|---|---|
| 33-7 | 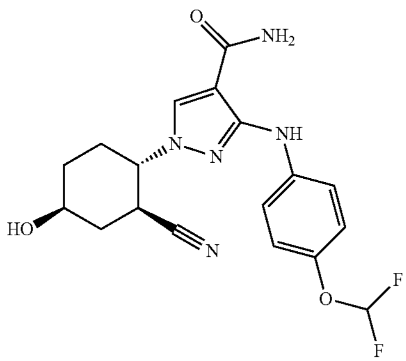 [SMILES: N#C[C@H]1C[C@@H](O)CC[C@@H]1n1cc(C(N)=O)c(Nc2ccc(OC(F)F)cc2)n1] | 1-[(1S,2S,4S or 1R,2R,4R)-2-cyano-4-hydroxycyclohexyl]-3-{[4-(difluoromethoxy)phenyl]amino}-1H-pyrazole-4-carboxamide | Calc'd 392, found 392 |
| 33-8 | 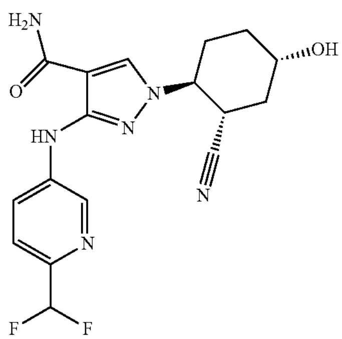 [SMILES: N#C[C@H]1C[C@@H](O)CC[C@@H]1n1cc(C(N)=O)c(Nc2ccc(C(F)F)nc2)n1] | 1-[(1S,2S,4S or 1R,2R,4R)-2-cyano-4-hydroxycyclohexyl)-3-{[6-(difluoromethyl)pyridin-3-yl]amino}-1H-pyrazole-4-carboxamide | Calc'd 377, found 377 |
| 33-9 | 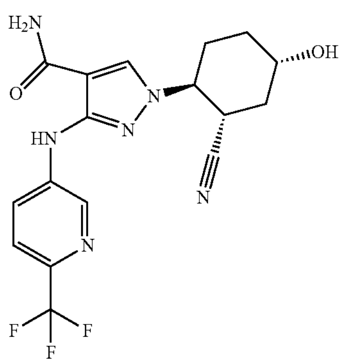 [SMILES: N#C[C@H]1C[C@@H](O)CC[C@@H]1n1cc(C(N)=O)c(Nc2ccc(C(F)(F)F)nc2)n1] | 1-[(1S,2S,4S or 1R,2R,4R)-2-cyano-4-hydroxycyclohexyl]-3-{[6-(trifluoromethyl)pyridin-3-yl]amino}-1H-pyrazole-4-carboxamide | Calc'd 395, found 395 |
| 33-10 | 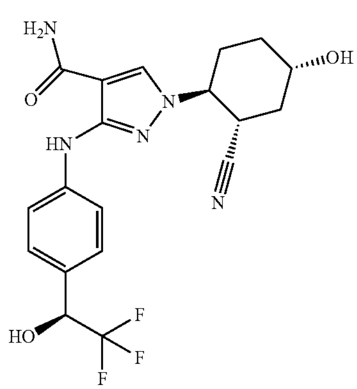 [SMILES: N#C[C@H]1C[C@@H](O)CC[C@@H]1n1cc(C(N)=O)c(Nc2ccc([C@H](O)C(F)(F)F)cc2)n1] | 1-[(1S,2S,4S or 1R,2R,4R)-2-cyano-4-hydroxycyclohexyl]-3-({4-[(1S)-2,2,2-trifluoro-1-hydroxyethyl]phenyl}amino)-1H-pyrazole-4-carboxamide | Calc'd 424, found 424 |

TABLE 27-continued

| Example | Structure | Compound Name | Exact Mass [M + H]+ |
|---|---|---|---|
| 33-11 | 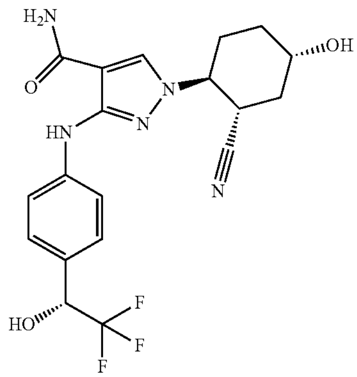 [SMILES: N#C[C@H]1C[C@@H](O)CC[C@@H]1n1cc(C(N)=O)c(Nc2ccc([C@@H](O)C(F)(F)F)cc2)n1] | 1-[(1S,2S,4S or 1R,2R,4R)-2-cyano-4-hydroxycyclohexyl]-3-({4-[(1R or 1S)-2,2,2-trifluoro-1-hydroxyethyl]phenyl}amino)-1H-pyrazole-4-carboxamide | Calc'd 424, found 424 |
| 33-12 | 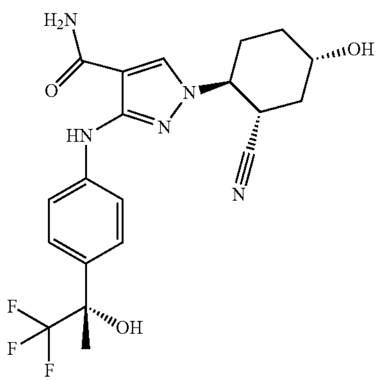 [SMILES: C[C@](O)(c1ccc(Nc2nn([C@H]3CC[C@H](O)C[C@@H]3C#N)cc2C(N)=O)cc1)C(F)(F)F] | 1-[(1S,2S,4S or 1R,2R,4R)-2-cyano-4-hydroxycyclohexyl]-3-({4-[(1S or 1R)-2,2,2-trifluoro-1-hydroxy-1-methylethyl]phenyl}amino)-1H-pyrazole-4-carboxamide | Calc'd 438, found 438 |
| 33-13 | 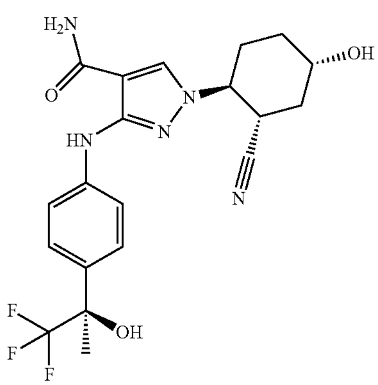 [SMILES: C[C@@](O)(c1ccc(Nc2nn([C@H]3CC[C@H](O)C[C@@H]3C#N)cc2C(N)=O)cc1)C(F)(F)F] | 1-[(1S,2S,4S or 1R,2R,4R)-2-cyano-4-hydroxycyclohexyl]-3-({4-[(1R or 1S)-2,2,2-trifluoro-1-hydroxy-1-methylethyl]phenyl}amino)-1H-pyrazole-4-carboxamide | Calc'd 438, found 438 |
| 33-14 | 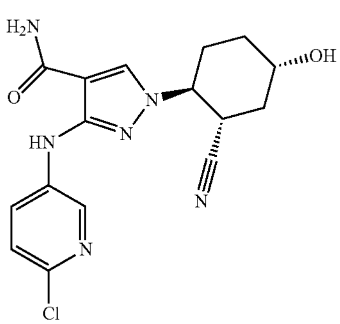 [SMILES: N#C[C@H]1C[C@@H](O)CC[C@@H]1n1cc(C(N)=O)c(Nc2ccc(Cl)nc2)n1] | 3-[(6-chloropyridin-3-yl)amino]-1-[(1S,2S,4S or 1R,2R,4R)-2-cyano-4-hydroxycyclohexyl]-1H-pyrazole-4-carboxamide | Calc'd 361, found 361 |

TABLE 27-continued

| Example | Structure | Compound Name | Exact Mass [M + H]+ |
|---|---|---|---|
| 33-15 | 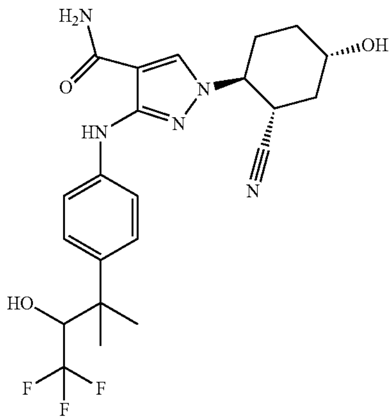 [SMILES: CC(C)(c1ccc(Nc2nn([C@H]3CC[C@H](O)C[C@@H]3C#N)cc2C(N)=O)cc1)C(O)C(F)(F)F] | 1-[(1S,2S,4S or 1R,2R,4R)-2-cyano-4-hydroxycyclohexyl]-3-{[4-(3,3,3-trifluoro-(2R or 2S)-hydroxy-1,1-dimethylpropyl)phenyl]amino}-1H-pyrazole-4-carboxamide | Calc'd 466, found 466 |
| 33-16 | 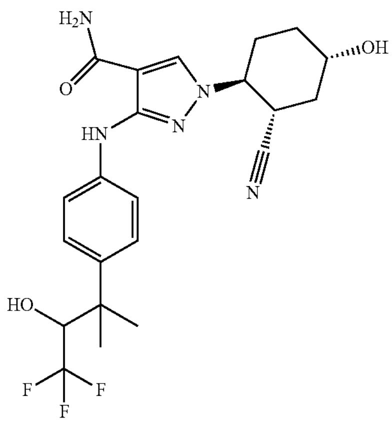 [SMILES: CC(C)(c1ccc(Nc2nn([C@H]3CC[C@H](O)C[C@@H]3C#N)cc2C(N)=O)cc1)C(O)C(F)(F)F] | 1-[(1S,2S,4S or 1R,2R,4R)-2-cyano-4-hydroxycyclohexyl]-3-{[4-(3,3,3-trifluoro-(2R or 2S)-hydroxy-1,1-dimethylpropyl)phenyl]amino}-1H-pyrazole-4-carboxamide | Calc'd 466, found 466 |
| 33-18 | 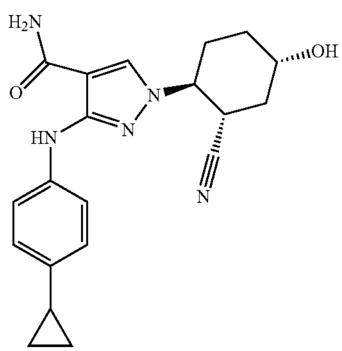 [SMILES: N#C[C@H]1C[C@@H](O)CC[C@@H]1n1cc(C(N)=O)c(Nc2ccc(C3CC3)cc2)n1] | 1-[(1S,2S,4S or 1R,2R,4R)-2-cyano-4-hydroxycyclohexyl]-3-[(4-cyclopropylphenyl)amino]-1H-pyrazole-4-carboxamide | Calc'd 366, found 366 |
| 33-19 | 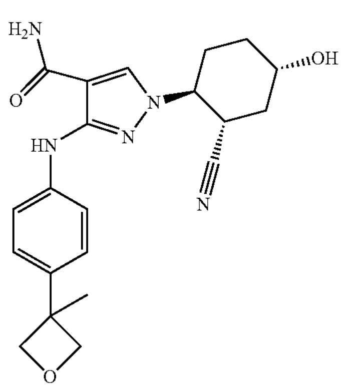 [SMILES: CC1(c2ccc(Nc3nn([C@H]4CC[C@H](O)C[C@@H]4C#N)cc3C(N)=O)cc2)COC1] | 1-[(1S,2S,4S or 1R,2R,4R)-2-cyano-4-hydroxycyclohexyl]-3-{[4-(3-methyloxetan-3-yl)phenyl]amino}-1H-pyrazole-4-carboxamide | Calc'd 396, found 396 |

TABLE 27-continued

| Example | Structure | Compound Name | Exact Mass [M + H]+ |
|---|---|---|---|
| 33-20 | 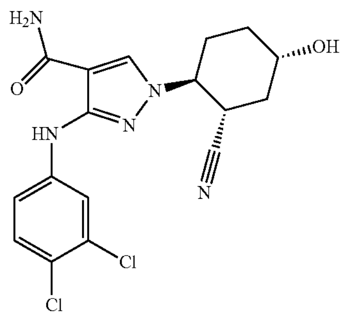 [SMILES: N#C[C@H]1C[C@@H](O)CC[C@@H]1n1cc(C(N)=O)c(Nc2ccc(Cl)c(Cl)c2)n1] | 1-[(1S,2S,4S or 1R,2R,4R)-2-cyano-4-hydroxycyclohexyl]-3-[(3,4-dichlorophenyl)amino]-1H-pyrazole-4-carboxamide | Calc'd 394, found 394 |
| 33-21 | 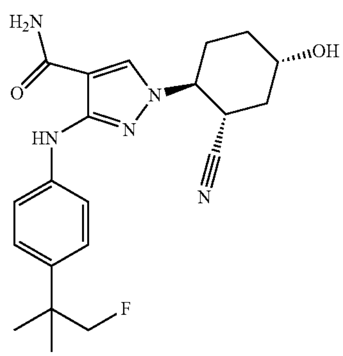 [SMILES: CC(C)(CF)c1ccc(Nc2nn([C@H]3CC[C@H](O)C[C@@H]3C#N)cc2C(N)=O)cc1] | 1-[(1S,2S,4S or 1R,2R,4R)-2-cyano-4-hydroxycyclohexyl]-3-{[4-(2-fluoro-1,1-dimethylethyl)phenyl]amino}-1H-pyrazole-4-carboxamide | Calc'd 400, found 400 |
| 25-2 | 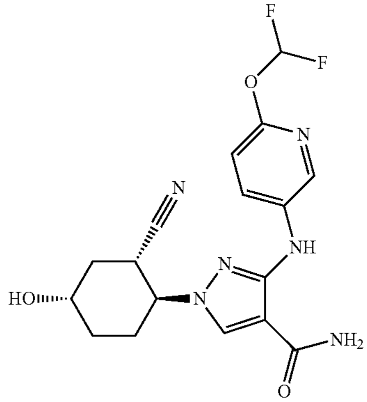 [SMILES: N#C[C@H]1C[C@@H](O)CC[C@@H]1n1cc(C(N)=O)c(Nc2ccc(OC(F)F)nc2)n1] | 1-[(1S,2S,4S or 1R,2R,4R)-2-cyano-4-hydroxycyclohexyl)-3-{[6-(difluoromethoxy)pyridin-3-yl]amino}-1H-pyrazole-4-carboxamide | Calc'd 393, found 393 |

Scheme #52

Example #34-1

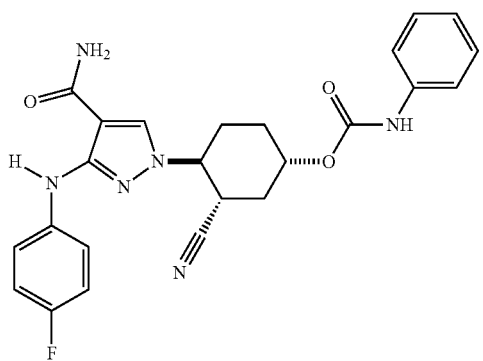

(1S,3S,4S and 1R,3R,4R)-4-{4-Carbamoyl-3-[(4-fluorophenyl)amino]-1H-pyrazol-1-yl}-3-cyanocyclohexyl phenylcarbamate To a solution of 1-[(1S,2S,4S and 1R,2R,4R)-2-cyano-4-hydroxycyclohexyl]-3-[(4-fluorophenyl)amino]-1H-pyrazole-4-carboxamide (25 mg, 0.073 mmol) in THF (0.73 mL) was added DMAP (9 mg, 0.07 mmol) and phenyl isocyanate (0.05 mL, 0.4 mmol). The resulting mixture was allowed to stir at ambient temperature for 24 hours. The reaction mixture was then partitioned between 0.5 N aqueous HCl and EtOAc. The organic layer was washed sequentially with water and brine. The combined organic extracts were dried over anhydrous $Na_2SO_4$, filtered, and concentrated in vacuo. The residue was purified by reverse phase preparative HPLC (using a gradient elution of 50-85% MeCN/water, with 0.1% v/v TFA modifier). Desired fractions were combined, partitioned between saturated aqueous $NaHCO_3$ and EtOAc. The organic layer was collected, dried over anhydrous $Na_2SO_4$, filtered, and concentrated in vacuo to afford the title compound. $^1$H NMR (DMSO-$d_6$): δ 9.71 (s, 1H), 9.12 (s, 1H), 8.21 (s, 1H), 7.70 (br s, 1H), 7.56 (m, 2H), 7.46 (d, J=7.5 Hz, 2H), 7.27 (dd, J=7.5, 7.5 Hz, 2H), 7.16 (br s, 1H), 7.07 (m, 2H), 6.98 (dd, J=7.5, 7.5, Hz, 1H), 4.80 (m, 1H), 4.56 (m, 1H), 3.63 (m, 1H), 2.44 (m, 1H), 2.12-1.93 (m, 4H), 1.65 (m, 1H). LRMS (ESI) calc'd for $C_{24}H_{23}FN_6O_3$ [M+H]$^+$: 463. Found: 463.

The following compounds shown in TABLE 28 were prepared according to Scheme #52 following similar procedures described for Example #34-1, which can be achieved by those of ordinary skill in the art of organic synthesis.

TABLE 28

| Example | Structure | Compound Name | Exact Mass [M + H]$^+$ |
|---|---|---|---|
| 34-2 | 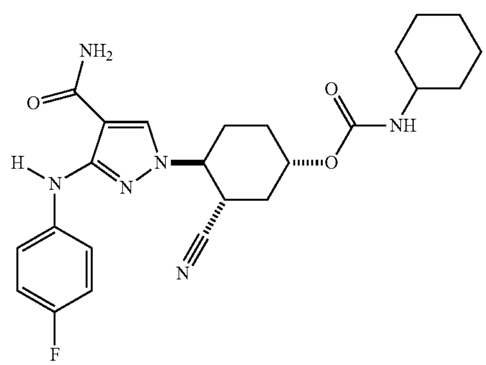 | (1S,3S,4S and 1R,3R,4R)-4-{4-carbamoyl-3-[(4-fluorophenyl)amino]-1H-pyrazol-1-yl}-3-cyanocyclohexyl cyclohexylcarbamate | Calc'd 469, Found 469 |
| 34-3 | 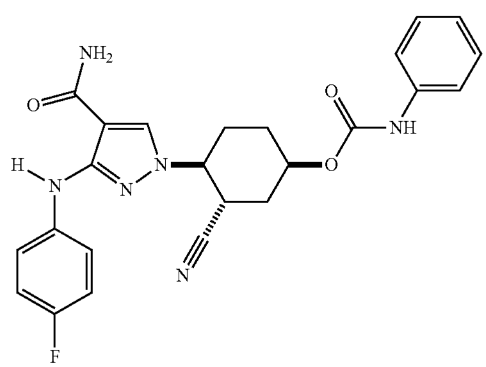 | (1R,3S,4S and 1S,3R,4R)-4-{4-carbamoyl-3-[(4-fluorophonyl)aminol-1H-pyrazol-1-yl}-3-cyanocyclohexyl phenylcarbamate | Calc'd 463, Found 463 |

TABLE 28-continued

| Example | Structure | Compound Name | Exact Mass [M + H]+ |
|---|---|---|---|
| 34-4 | 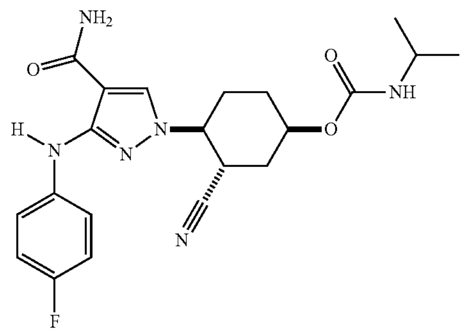 | (1R,3S,4S and 1S,3R,4R)-4-{4-carbamoyl-3-[(4-fluorophenyl)amino]-1H-pyrazol-1-yl}-3-cyanocyclohexyl propan-2-ylcarbamate | Calc'd 429, Found 429 |
| 34-5 | 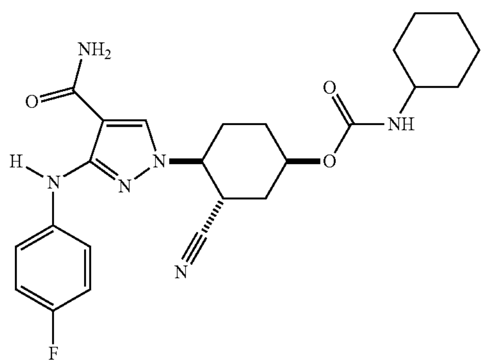 | (1R,3S,4S and 1S,3R,4R)-4-{4-carbamoyl-3-[(4-fluorophenyl)amino]-1H-pyrazol-1-yl}-3-cyanocyclohexyl cyclohexylcarbamate | Calc'd 469, Found 469 |
| 34-6 | 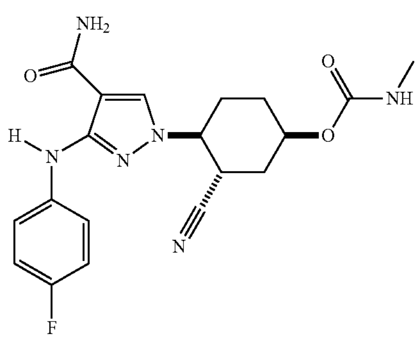 | (1R,3S,4S and 1S,3R,4R)-4-{4-carbamoyl-3-[(4-fluorophenyl)aminol-1H-pyrazol-1-yl}-3-cyanocyclohexyl methylcarbamate | Calc'd 401, Found 401 |
| 34-7 | 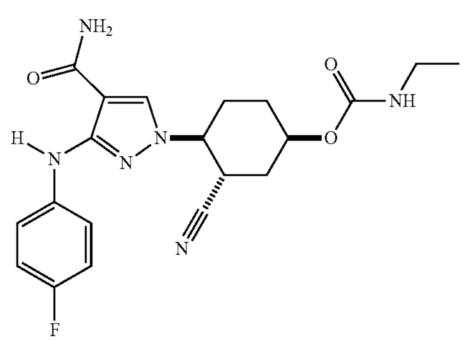 | (1R,3S,4S and 1S,3R,4R)-4-{4-carbamoyl-3-[(4-fluorophenyl)aminol-1H-pyrazol-1-yl}-3-cyanocyclohexyl ethylcarbamate | Calc'd 415, Found 415 |

TABLE 28-continued

| Example | Structure | Compound Name | Exact Mass [M + H]+ |
|---|---|---|---|
| 34-8 | 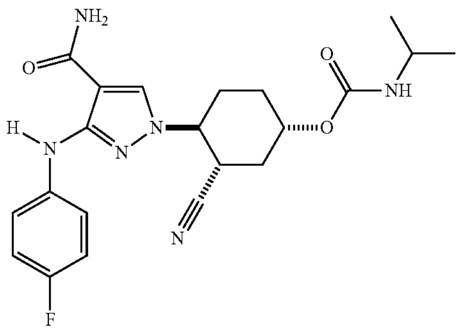 | (1S,3S,4S and 1R,3R,4R)-4-{4-carbamoyl-3-[(4-fluorophenyl)amino]-1H-pyrazol-1-yl}-3-cyanocyclohexyl propan-2-ylcarbamate | Calc'd 429, Found 429 |
| 34-9 | 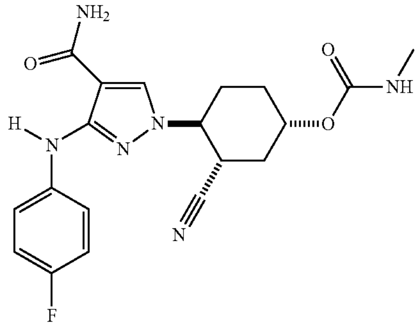 | (1S,3S,4S and 1R,3R,4R)-4-{4-carbamoyl-3-[(4-fluorophenyl)aminol-1H-pyrazol-1-yl}-3-cyanocyclohexyl methylcarbamate | Calc'd 401, Found 401 |

Scheme #48

Example #35-1 and 35-2

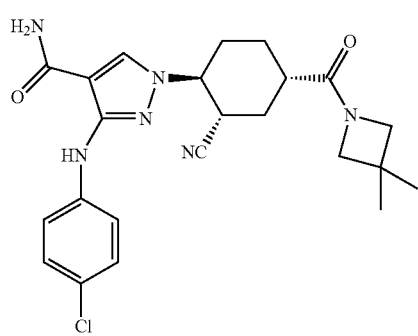

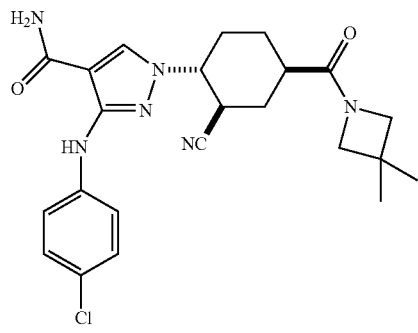

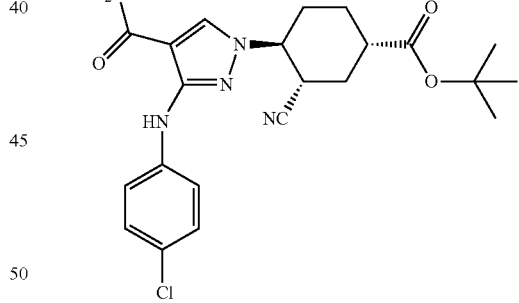

3-((4-chlorophenyl)amino)-1-((1S,2S,4S or 1R,2R,4R)-2-cyano-4-(3,3-dimethylazetidine-1-carbonyl)cyclohexyl)-1H-pyrazole-4-carboxamide Step A: (1S,3S,4S and 1R,3R,4R)-tert-Butyl 4-(4-carbamoyl-3-((4-chlorophenyl)amino)-1H-pyrazol-1-yl)-3-cyanocyclohexanecarboxylate A solution of (1S,3S,4S and 1R,3R,4R)-t-butyl 4-(3-amino-4-carbamoyl-1H-pyrazol-1-yl)-3-cyanocyclohexane-1-carboxylate (Intermediate #47-4, 11 g, 33 mmol), 1-bromo-4-chlorobenzene (9.2 g, 48 mmol), KOAc (9.4 g, 96 mmol), Pd$_2$(dba)$_3$·CHCl$_3$ (4.9 g, 5.0 mmol) and t-Butyl X-Phos (4.1 g, 10 mmol) in iso-propanol (100 mL) was degassed with bubbling N$_2$ gas for 15 minutes and then stirred at 85° C. under nitrogen for 16 hours, and then concentrated in vacuo. The crude residue was purified by MPLC on Silica gel (eluting with 1-2% MeOH/DCM). Desired fractions were identified, combined, and concentrated in vacuo. The residue was further purified by reverse-phase preparative HPLC (using a gradient elution of 40-60% MeCN/water with 0.5% ammonia in 20) to afford the title compound. $^1$H NMR (400 MHz, CD$_3$OD) δ 8.13 (s, 1H), 7.54 (d, J=9.2 Hz, 2H), 7.24 (d, J=8.8 Hz, 2H), 4.32-4.30 (m, 1H), 3.49-3.42 (m, 1H), 2.51-2.47 (m, 2H), 2.20-2.13 (m, 3H), 1.95-1.82 (m, 1H), 1.66-1.59 (m, 1H), 1.50 (s, 9H). MS ESI: [M+H]$^+$ m/z 444.

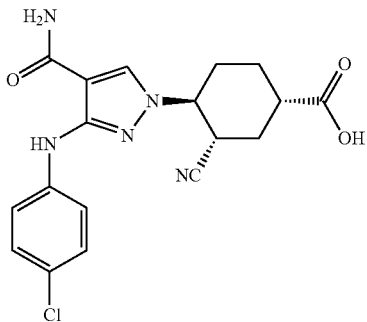 [SMILES: N#C[C@H]1C[C@@H](C(=O)O)CC[C@@H]1n1cc(C(N)=O)c(Nc2ccc(Cl)cc2)n1]

Step B: (1S,3S,4S and 1R,3R,4R)-4-(4-Carbamoyl-3-((4-chlorophenyl)amino)-1H-pyrazol-1-yl)-3-cyanocyclohexanecarboxylic acid To a solution of (1S,3S,4S and 1R,3R,4R)-t-butyl 4-[4-carbamoyl-3-[(4-chlorophenyl)amino]-1H-pyrazol-1-yl]-3-cyanocyclohexane-1-carboxylate (500 mg, 1.1 mmol) in DCM (4 mL) was added TFA (2 mL) at 0° C. The resulting solution was stirred at ambient temperature for 16 hours and then concentrated in vacuo to afford the title compound as an off-white solid, which was used directly without further purification. $^1$H NMR (400 MHz, CD$_3$OD) δ 8.14 (s, 1H), 7.58-7.53 (m, 2H), 7.26-7.21 (m, 2H), 4.32-4.30 (m, 1H), 3.50-3.46 (m, 1H), 2.58-2.48 (m, 2H), 2.33-2.15 (m, 3H), 1.98-1.88 (m, 1H), 1.77-1.64 (m, 1H). MS ESI: [M+H]$^+$ m/z 388.

Step C: 3-((4-Chlorophenyl)amino)-1-((1S,2S,4S or 1R,2R,4R)-2-cyano-4-(3,3-dimethylazetidine-1-carbonyl)cyclohexyl)-1H-pyrazole-4-carboxamide To a solution of the crude acid (1S,3S,4S and 1R,3R,4R)-4-[4-carbamoyl-3-[(4-chlorophenyl)amino]-1H-pyrazol-1-yl]-3-cyanocyclohexane 1-carboxylic acid (200 mg, 0.5 mmol) in DMF (4 mL) were sequentially added 3,3-dimethylazetidin-1-ium chloride (75 mg, 0.62 mmol), EDC (120 mg, 0.62 mmol), HOBt (83 mg, 0.61 mmol) and triethylamine (120 mg, 1.2 mmol). The resulting solution was stirred at ambient temperature for 16 hours before it was concentrated in vacuo. The crude residue was partitioned between DCM (10 mL) and water (2 mL). The organic solution was washed with saturated aqueous NaHCO$_3$ (2×2 mL), dried over anhydrous sodium sulfate, filtered and concentrated in vacuo. The crude residue was purified by MPLC on Silica gel (eluting with 2-5% MeOH/DCM) to afford a racemic mixture of 3-(4-chlorophenylamino)-1-((1S,2S,4S and 1R,2R,4R)-2-cyano-4-(3,3-dimethylazetidine-1-carbonyl)cyclohexyl)-1H-pyrazole-4-carboxamide, which was then resolved to the constituent enantiomers by preparative chiral HPLC (Chiralpak IC, 2*25 cm; Mobile phase: 30% ethanol (0.2% DEA)/hexane (0.1% DEA)] to afford the title compounds as single enantiomers.

Example #35-1

1$^{st}$ enantiomer to elute; 3-(4-chlorophenylamino)-1-((1S,2S,4S or 1R,2R,4R)-2-cyano-4-(3,3-dimethylazetidine-1-carbonyl)cyclohexyl)-1H-pyrazole-4-carboxamide. $^1$H NMR (300 MHz, CD$_3$OD) δ 8.02 (s, 1H), 7.54 (d, J=9.0 Hz, 2H), 7.23 (d, J=9.0 Hz, 2H), 4.34-4.27 (m, 1H), 4.02-3.94 (m, 2H), 3.67 (s, 2H), 3.48-3.43 (m, 1H), 2.58-2.53 (m, 1H), 2.29-2.12 (m, 3H), 2.01-1.97 (m, 2H), 1.71-1.67 (m, 1H), 1.30 (s, 6H). MS ESI: [M+H]$^+$ m/z 455.

Example #35-2

2$^{nd}$ enantiomer to elute; 3-(4-chlorophenylamino)-1-((1R,2R,4R or 1S,2S,4S)-2-cyano-4-(3,3-dimethylazetidine-1-carbonyl)cyclohexyl)-1H-pyrazole-4-carboxamide: $^1$H NMR (300 MHz, CD$_3$OD) δ 8.02 (s, 1H), 7.54 (d, J=8.7 Hz, 2H), 7.23 (d, J=9.0 Hz, 2H), 4.35-4.28 (m, 1H), 4.04-3.96 (m, 2H), 3.68 (s, 2H), 3.54-3.45 (m, 1H), 2.59-2.54 (m, 1H), 2.30-2.14 (m, 3H), 2.03-1.94 (m, 2H), 1.72-1.68 (m, 1H), 1.30 (s, 6H). MS ESI: [M+H]$^+$ m/z 455.

The following compounds shown in TABLE 29 were prepared according to Scheme #48 following similar procedures described for Example #35-1 and 35-2, which can be achieved by those of ordinary skill in the art of organic synthesis.

TABLE 29

| Example | Structure | Compound Name | Exact Mass [M + H]+ |
|---------|-----------|---------------|---------------------|
| 35-3 | 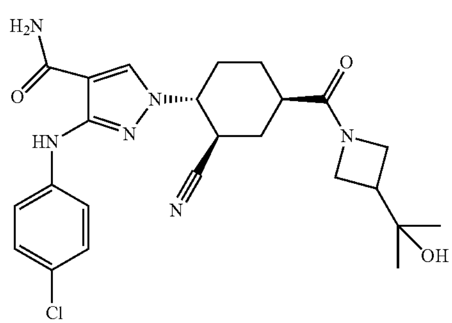 [SMILES: CC(C)(O)C1CN(C(=O)[C@@H]2CC[C@@H](n3cc(C(N)=O)c(Nc4ccc(Cl)cc4)n3)[C@H](C#N)C2)C1] | 3-[(4-chlorophenyl)amino]-1-[(1R,2R,4R or 1S,2S,4S)-2-cyano-4-{[3-(1-hydroxy-1-methylethyl)azetidin-1-yl]carbonyl}cyclohexyl]-1H-pyrazole-4-carboxamide | Calc'd 485, found 485 |

TABLE 29-continued

| Example | Structure | Compound Name | Exact Mass [M + H]+ |
|---|---|---|---|
| 35-4 | 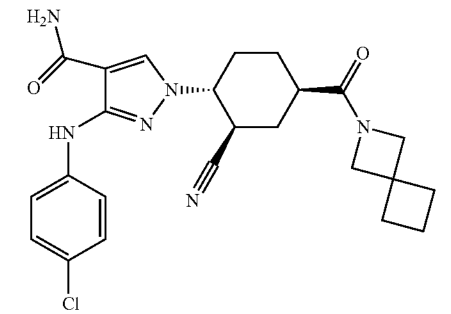 [SMILES: N#C[C@@H]1C[C@H](C(=O)N2CC3(CCC3)C2)CC[C@H]1n1cc(C(N)=O)c(Nc2ccc(Cl)cc2)n1] | 1-[(1R,2R,4R or 1S,2S,4S)-4-(2-azaspiro[3.3]hept-2-ylcarbonyl)-2-cyanocyclohexyl]-3-[(4-chlorophenyl)amino]-1H-pyrazole-4-carboxamide | Calc'd 467, found 467 |
| 35-5 | 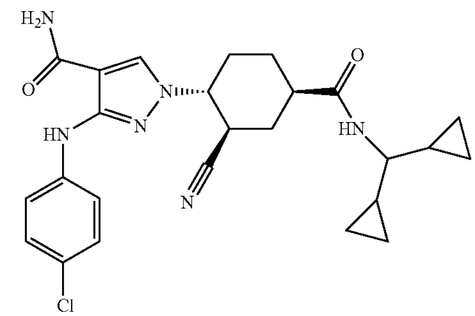 [SMILES: N#C[C@@H]1C[C@H](C(=O)NC(C2CC2)C2CC2)CC[C@H]1n1cc(C(N)=O)c(Nc2ccc(Cl)cc2)n1] | 3-[(4-chlorophenyl)amino]-1-{(1R,2R,4R or 1S,2S,4S)-2-cyano-4-[(dicyclopropylmethyl)carbamoyl]cyclohexyl}-1H-pyrazole-4-carboxamide | Calc'd 481, found 481 |
| 35-6 | 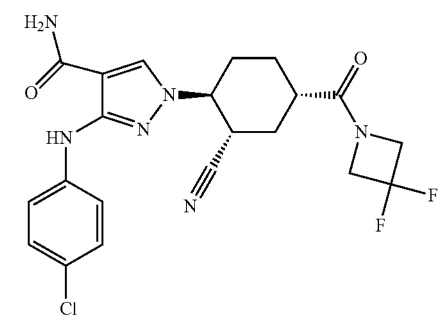 [SMILES: N#C[C@H]1C[C@@H](C(=O)N2CC(F)(F)C2)CC[C@@H]1n1cc(C(N)=O)c(Nc2ccc(Cl)cc2)n1] | 3-[(4-chlorophenyl)amino]-1-{(1S,2S,4S or 1R,2R,4R)-2-cyano-4-[(3,3-difluoroazetidin-1-yl)carbonyl]cyclohexyl}-1H-pyrazole-4-carboxamide | Calc'd 463, found 463 |
| 35-7 | 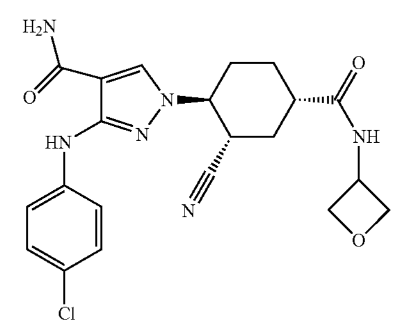 [SMILES: N#C[C@H]1C[C@@H](C(=O)NC2COC2)CC[C@@H]1n1cc(C(N)=O)c(Nc2ccc(Cl)cc2)n1] | 3-[(4-chlorophenyl)amino]-1-[(1S,2S,4S or 1R,2R,4R)-2-cyano-4-(oxetan-3-ylcarbamoyl)cyclohexyl]-1H-pyrazole-4-carboxamide | Calc'd 443, found 443 |

TABLE 29-continued

| Example | Structure | Compound Name | Exact Mass [M + H]+ |
|---|---|---|---|
| 35-8 | 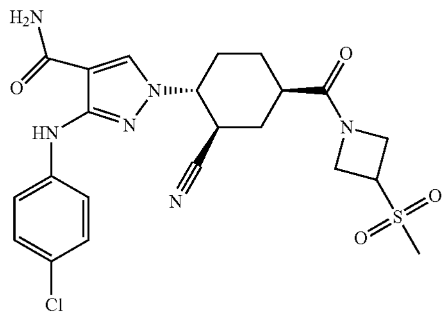 [SMILES: CS(=O)(=O)C1CN(C(=O)[C@@H]2CC[C@@H](n3cc(C(N)=O)c(Nc4ccc(Cl)cc4)n3)[C@H](C#N)C2)C1] | 3-[(4-chlorophenyl)amino]-1-[(1R,2R,4R or 1S,2S,4S)-2-cyano-4-{[3-(methylsulfonyl)azetidin-1-yl]carbonyl}cyclohexyl]-1H-pyrazole-4-carboxamide | Calc'd 505, found 505 |
| 35-9 | 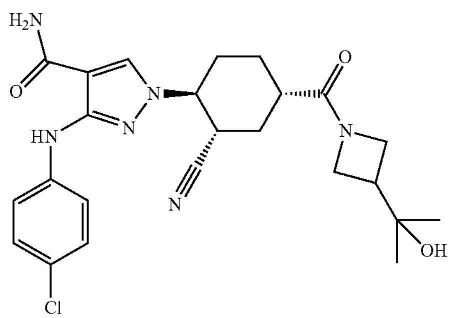 [SMILES: CC(C)(O)C1CN(C(=O)[C@H]2CC[C@H](n3cc(C(N)=O)c(Nc4ccc(Cl)cc4)n3)[C@@H](C#N)C2)C1] | 3-[(4-chlorophenyl)amino]-1-[(1S,2S,4S or 1R,2R,4R)-2-cyano-4-{[3-(1-hydroxy-1-methylethyl)azetidin-1-yl]carbonyl}cyclohexyl]-1H-pyrazole-4-carboxamide | Calc'd 485, found 485 |
| 35-10 | 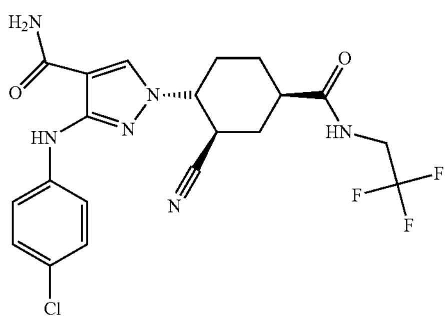 | 3-[(4-chlorophenyl)amino]-1-{(1R,2R,4R or 1S,2S,4S)-2-cyano-4-[(2,2,2-trifluoroethyl)carbamoyl]cyclohexyl}-1H-pyrazole-4-carboxamide | Calc'd 469, found 469 |
| 35-11 | 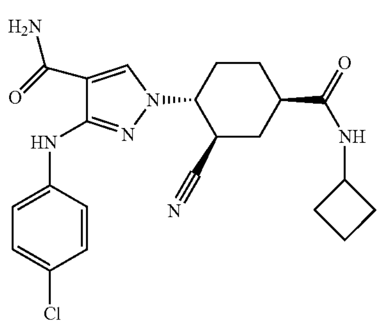 [SMILES: N#C[C@@H]1C[C@H](C(=O)NC2CCC2)CC[C@H]1n1cc(C(N)=O)c(Nc2ccc(Cl)cc2)n1] | 3-[(4-chlorophenyl)amino]-1-[(1R,2R,4R or 1S,2S,4S)-2-cyano-4-(cyclobutylcarbamoyl)cyclohexyl]-1H-pyrazole-4-carboxamide | Calc'd 441, found 441 |

TABLE 29-continued

| Example | Compound Name | Exact Mass [M + H]+ |
|---|---|---|
| 35-12 | 3-[(4-chlorophenyl)amino]-1-[(1S,2S,4S or 1R,2R,4R)-2-cyano-4-(cyclobutylcarbamoyl)cyclohexyl]-1H-pyrazole-4-carboxamide | Calc'd 441, found 441 |
| 35-13 | 3-[(4-chlorophenyl)amino]-1-[(1R,2R,4R or 1S,2S,4S)-2-cyano-4-(oxetan-3-ylcarbamoyl)cyclohexyl]-1H-pyrazole-4-carboxamide | Calc'd 443, found 443 |
| 35-14 | 3-[(4-chlorophenyl)amino]-1-[(1S,2S,4S or 1R,2R,4R)-2-cyano-4-{[(1R)-1-cyclopropyl-2,2,2-trifluoroethyl]carbamoyl}cyclohexyl]-1H-pyrazole-4-carboxamide | Calc'd 509, found 509 |
| 35-15 | 3-[(4-chlorophenyl)amino]-1-{(1R,2R,4R or 1S,2S,4S)-2-cyano-4-[(3,3-difluoroazetidin-1-yl)carbonyl]cyclohexyl}-1H-pyrazole-4-carboxamide | Calc'd 463, found 463 |

TABLE 29-continued

| Example | Structure | Compound Name | Exact Mass [M + H]+ |
|---|---|---|---|
| 35-16 | 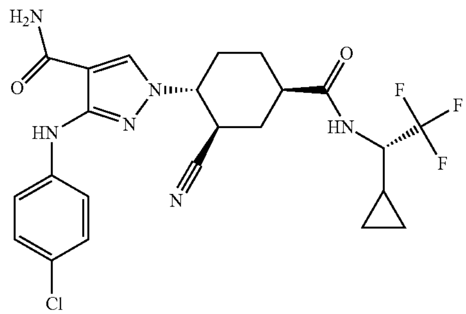 [SMILES: N#C[C@@H]1C[C@H](C(=O)N[C@@H](C2CC2)C(F)(F)F)CC[C@H]1n1cc(C(N)=O)c(Nc2ccc(Cl)cc2)n1] | 3-[(4-chlorophenyl)amino]-1-[(1R,2R,4R or 1S,2S,4S)-2-cyano-4-{[(1S)-1-cyclopropyl-2,2,2-trifluoroethyl]carbamoyl}cyclohexyl]-1H-pyrazole-4-carboxamide | Calc'd 509, found 509 |
| 35-17 | 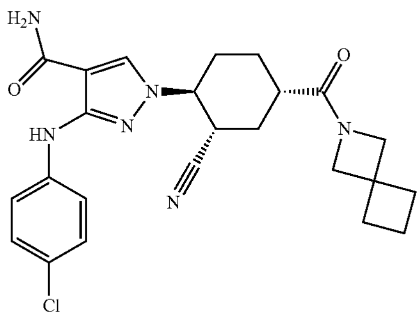 [SMILES: N#C[C@H]1C[C@@H](C(=O)N2CC3(CCC3)C2)CC[C@@H]1n1cc(C(N)=O)c(Nc2ccc(Cl)cc2)n1] | 1-[(1S,2S,4S or 1R,2R,4R)-4-(2-azaspiro[3.3]hept-2-ylcarbonyl)-2-cyanocyclohexyl]-3-[(4-chlorophenyl)amino]-1H-pyrazole-4-carboxamide | Calc'd 467, found 467 |
| 35-18 | 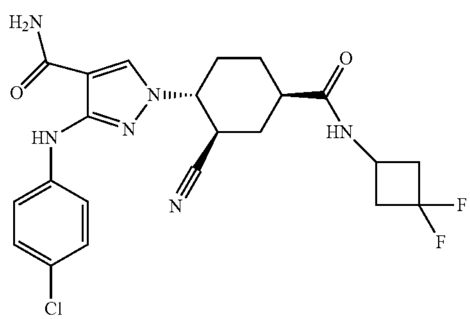 [SMILES: N#C[C@@H]1C[C@H](C(=O)NC2CC(F)(F)C2)CC[C@H]1n1cc(C(N)=O)c(Nc2ccc(Cl)cc2)n1] | 3-[(4-chlorophenyl)amino]-1-{(1R,2R,4R or 1S,2S,4S)-2-cyano-4-[(3,3-difluorocyclobutyl)carbamoyl]cyclohexyl}-1H-pyrazole-4-carboxamide | Calc'd 477, found 477 |
| 35-19 | 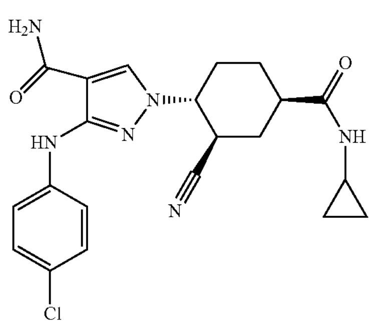 [SMILES: N#C[C@@H]1C[C@H](C(=O)NC2CC2)CC[C@H]1n1cc(C(N)=O)c(Nc2ccc(Cl)cc2)n1] | 3-[(4-chlorophenyl)amino]-1-[(1R,2R,4R or 1S,2S,4S)-2-cyano-4-(cyclopropylcarbamoyl)cyclohexyl]-1H-pyrazole-4-carboxamide | Calc'd 427, found 427 |

TABLE 29-continued

| Example | Structure | Compound Name | Exact Mass [M + H]+ |
|---|---|---|---|
| 35-20 | 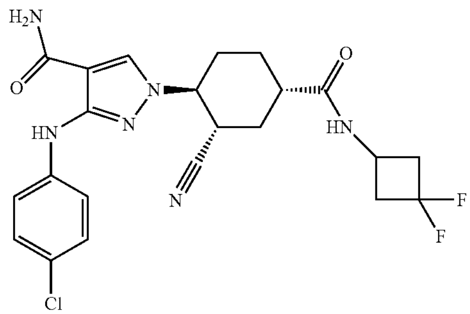 [SMILES: N#C[C@H]1C[C@@H](C(=O)NC2CC(F)(F)C2)CC[C@@H]1n1cc(C(N)=O)c(Nc2ccc(Cl)cc2)n1] | 3-[(4-chlorophenyl)amino]-1-{(1S,2S,4S or 1R,2R,4R)-2-cyano-4-[(3,3-difluorocyclobutyl)carbamoyl]cyclohexyl}-1H-pyrazole-4-carboxamide | Calc'd 477, found 477 |
| 35-21 | 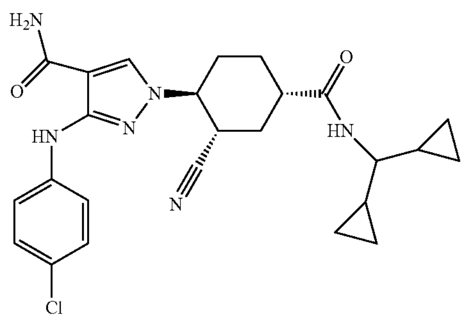 [SMILES: N#C[C@H]1C[C@@H](C(=O)NC(C2CC2)C2CC2)CC[C@@H]1n1cc(C(N)=O)c(Nc2ccc(Cl)cc2)n1] | 3-[(4-chlorophenyl)amino]-1-{(1S,2S,4S or 1R,2R,4R)-2-cyano-4-[(dicyclopropylmethyl)carbamoyl]cyclohexyl}-1H-pyrazole-4-carboxamide | Calc'd 481, found 481 |
| 35-22 | 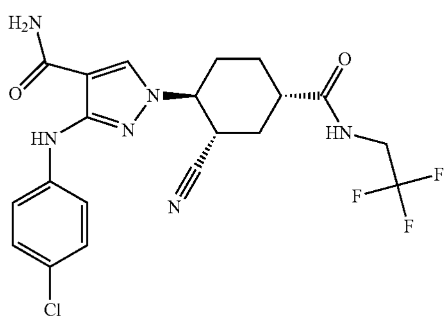 [SMILES: N#C[C@H]1C[C@@H](C(=O)NCC(F)(F)F)CC[C@@H]1n1cc(C(N)=O)c(Nc2ccc(Cl)cc2)n1] | 3-[(4-chlorophenyl)amino]-1-{(1S,2S,4S or 1R,2R,4R)-2-cyano-4-[(2,2,2-trifluoroethyl)carbamoyl]cyclohexyl}-1H-pyrazole-4-carboxamide | Calc'd 469, found 469 |
| 35-23 | 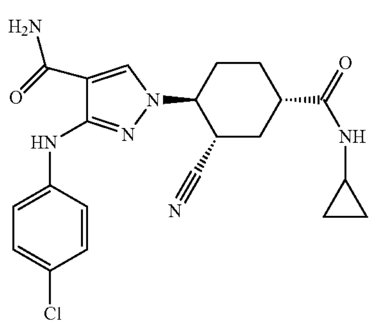 [SMILES: N#C[C@H]1C[C@@H](C(=O)NC2CC2)CC[C@@H]1n1cc(C(N)=O)c(Nc2ccc(Cl)cc2)n1] | 3-[(4-chlorophenyl)amino]-1-[(1S,2S,4S or 1R,2R,4R)-2-cyano-4-(cyclopropylcarbamoyl)cyclohexyl]-1H-pyrazole-4-carboxamide | Calc'd 427, found 427 |

TABLE 29-continued

| Example | Structure | Compound Name | Exact Mass [M + H]+ |
|---|---|---|---|
| 35-24 | 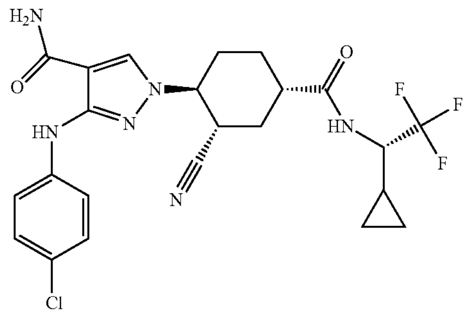 [SMILES: N#C[C@H]1C[C@@H](C(=O)N[C@@H](C2CC2)C(F)(F)F)CC[C@@H]1n1cc(C(N)=O)c(Nc2ccc(Cl)cc2)n1] | 3-[(4-chlorophenyl)amino]-1-[(1S,2S,4S or 1R,2R,4R)-2-cyano-4-{[(1S)-1-cyclopropyl-2,2,2-trifluoroethyl]carbamoyl}cyclohexyl]-1H-pyrazole-4-carboxamide | Calc'd 509, found 509 |
| 35-25 | 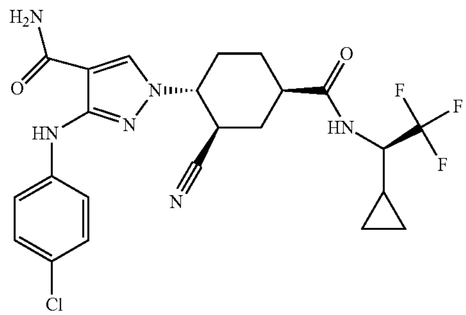 [SMILES: N#C[C@@H]1C[C@H](C(=O)N[C@H](C2CC2)C(F)(F)F)CC[C@H]1n1cc(C(N)=O)c(Nc2ccc(Cl)cc2)n1] | 3-[(4-chlorophenyl)amino]-1-[(1R,2R,4R or 1S,2S,4S)-2-cyano-4-{[(1R)-1-cyclopropyl-2,2,2-trifluoroethyl]carbamoyl}cyclohexyl]-1H-pyrazole-4-carboxamide | Calc'd 509, found 509 |
| 35-26 | 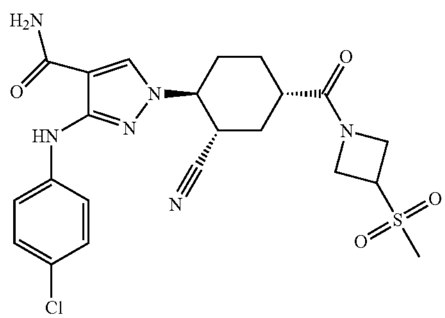 [SMILES: CS(=O)(=O)C1CN(C(=O)[C@H]2CC[C@H](n3cc(C(N)=O)c(Nc4ccc(Cl)cc4)n3)[C@@H](C#N)C2)C1] | 3-[(4-chlorophenyl)amino]-1-[(1S,2S,4S or 1R,2R,4R)-2-cyano-4-{[3-(methylsulfonyl)azetidin-1-yl]carbonyl}cyclohexyl]-1H-pyrazole-4-carboxamide | Calc'd 505, found 505 |
| 35-27 | 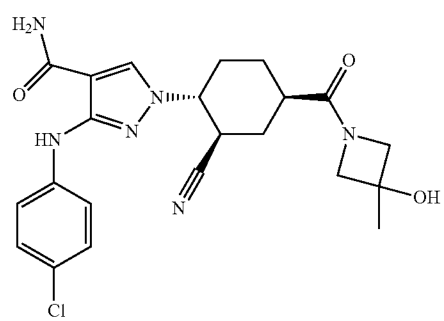 [SMILES: CC1(O)CN(C(=O)[C@@H]2CC[C@@H](n3cc(C(N)=O)c(Nc4ccc(Cl)cc4)n3)[C@H](C#N)C2)C1] | 3-[(4-chlorophenyl)amino]-1-{(1R,2R,4R or 1S,2S,4S)-2-cyano-4-[(3-hydroxy-3-methylazetidin-1-yl)carbonyl]cyclohexyl}-1H-pyrazole-4-carboxamide | Calc'd 457, found 457 |
| 35-28 | 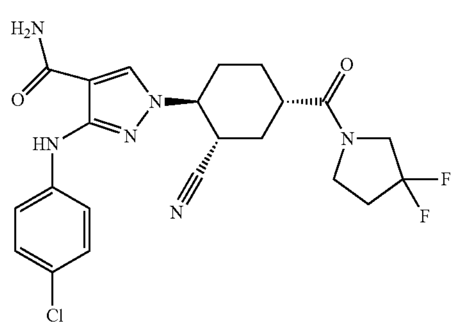 [SMILES: N#C[C@H]1C[C@@H](C(=O)N2CCC(F)(F)C2)CC[C@@H]1n1cc(C(N)=O)c(Nc2ccc(Cl)cc2)n1] | 3-[(4-chlorophenyl)amino]-1-{(1S,2S,4S or 1R,2R,4R)-2-cyano-4-[(3,3-difluoropyrrolidin-1-yl)carbonyl]cyclohexyl}-1H-pyrazole-4-carboxamide | Calc'd 477, found 477 |

TABLE 29-continued

| Example | Structure | Compound Name | Exact Mass [M + H]+ |
|---|---|---|---|
| 35-29 | 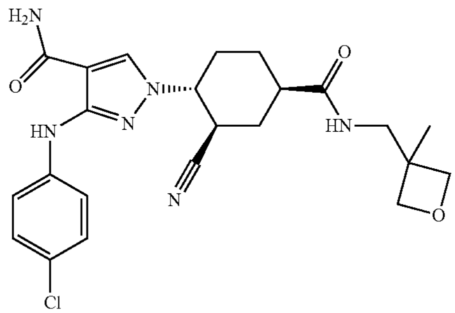 [SMILES: CC1(CNC(=O)[C@@H]2CC[C@@H](n3cc(C(N)=O)c(Nc4ccc(Cl)cc4)n3)[C@H](C#N)C2)COC1] | 3-[(4-chlorophenyl)amino]-1-[(1R,2R,4R or 1S,2S,4S)-2-cyano-4-{[(3-methyloxetan-3-yl)methyl]carbamoyl}cyclohexyl]-1H-pyrazole-4-carboxamide | Calc'd 471, found 471 |
| 35-30 | 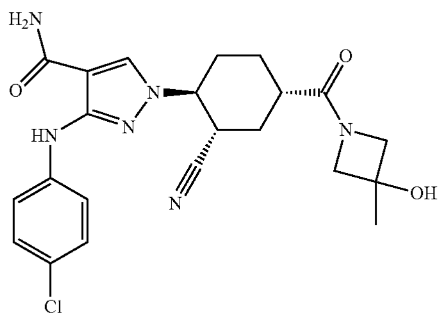 [SMILES: CC1(O)CN(C(=O)[C@H]2CC[C@H](n3cc(C(N)=O)c(Nc4ccc(Cl)cc4)n3)[C@@H](C#N)C2)C1] | 3-[(4-chlorophenyl)amino]-1-{(1S,2S,4S or 1R,2R,4R)-2-cyano-4-[(3-hydroxy-3-methylazetidin-1-yl)carbonyl]cyclohexyl}-1H-pyrazole-4-carboxamide | Calc'd 457, found 457 |
| 35-31 | 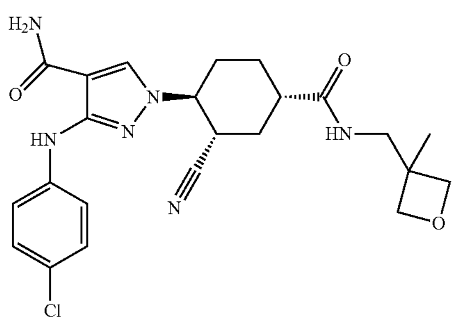 [SMILES: CC1(CNC(=O)[C@H]2CC[C@H](n3cc(C(N)=O)c(Nc4ccc(Cl)cc4)n3)[C@@H](C#N)C2)COC1] | 3-[(4-chlorophenyl)amino]-1-[(1S,2S,4S or 1R,2R,4R)-2-cyano-4-{[(3-methyloxetan-3-yl)methyl]carbamoyl}cyclohexyl]-1H-pyrazole-4-carboxamide | Calc'd 471, found 471 |
| 35-32 | 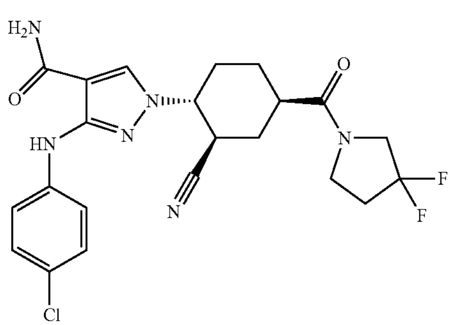 [SMILES: N#C[C@@H]1C[C@H](C(=O)N2CCC(F)(F)C2)CC[C@H]1n1cc(C(N)=O)c(Nc2ccc(Cl)cc2)n1] | 3-[(4-chlorophenyl)amino]-1-{(1R,2R,4R or 1S,2S,4S)-2-cyano-4-[(3,3-difluoropyrrolidin-1-yl)carbonyl]cyclohexyl}-1H-pyrazole-4-carboxamide | Calc'd 477, found 477 |

TABLE 29-continued

| Example | Structure | Compound Name | Exact Mass [M + H]+ |
|---|---|---|---|
| 35-33 | 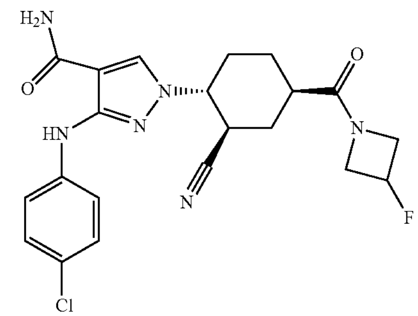 [SMILES: N#C[C@@H]1C[C@H](C(=O)N2CC(F)C2)CC[C@H]1n1cc(C(N)=O)c(Nc2ccc(Cl)cc2)n1] | 3-[(4-chlorophenyl)amino]-1-{(1R,2R,4R or 1S,2S,4S)-2-cyano-4-[(3-fluoroazetidin-1-yl)carbonyl]cyclohexyl}-1H-pyrazole-4-carboxamide | Calc'd 445, found 445 |
| 35-34 | 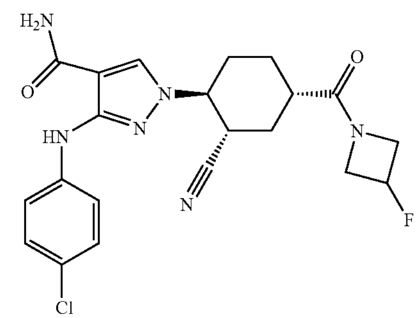 [SMILES: N#C[C@H]1C[C@@H](C(=O)N2CC(F)C2)CC[C@@H]1n1cc(C(N)=O)c(Nc2ccc(Cl)cc2)n1] | 3-[(4-chlorophenyl)amino]-1-{(1S,2S,4S or 1R,2R,4R)-2-cyano-4-[(3-fluoroazetidin-1-yl)carbonyl]cyclohexyl}-1H-pyrazole-4-carboxamide | Calc'd 445, found 445 |
| 35-35 | 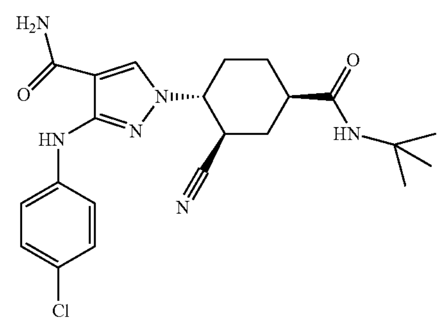 [SMILES: CC(C)(C)NC(=O)[C@@H]1CC[C@@H](n2cc(C(N)=O)c(Nc3ccc(Cl)cc3)n2)[C@H](C#N)C1] | 1-[(1R,2R,4R or 1S,2S,4S)-4-(tert-butylcarbamoyl)-2-cyanocyclohexyl]-3-[(4-chlorophenyl)amino]-1H-pyrazole-4-carboxamide | Calc'd 443, found 443 |
| 35-36 | 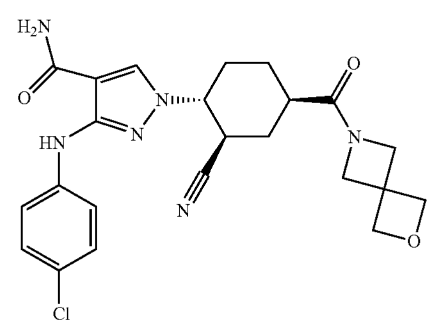 [SMILES: N#C[C@@H]1C[C@H](C(=O)N2CC3(COC3)C2)CC[C@H]1n1cc(C(N)=O)c(Nc2ccc(Cl)cc2)n1] | 3-[(4-chlorophenyl)amino]-1-[(1R,2R,4R or 1S,2S,4S)-2-cyano-4-(2-oxa-6-azaspiro[3.3]hept-6-ylcarbonyl)cyclohexyl]-1H-pyrazole-4-carboxamide | Calc'd 469, found 469 |

TABLE 29-continued

| Example | Structure | Compound Name | Exact Mass [M + H]+ |
|---|---|---|---|
| 35-37 | 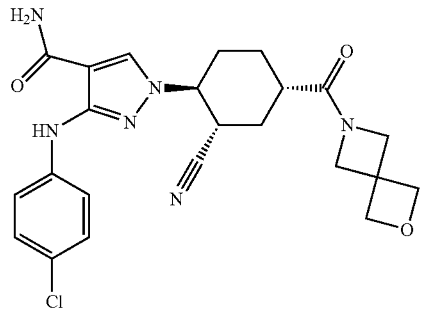 | 3-[(4-chlorophenyl)amino]-1-[(1S,2S,4S or 1R,2R,4R)-2-cyano-4-(2-oxa-6-azaspiro[3.3]hept-6-ylcarbonyl)cyclohexyl]-1H-pyrazole-4-carboxamide | Calc'd 469, found 469 |

Scheme #49

Example #36-1 and 36-2

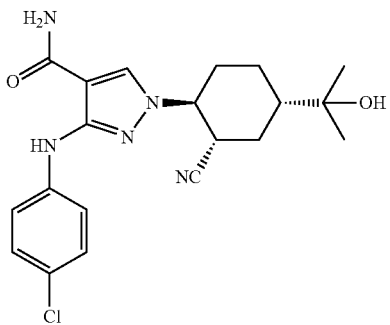 [SMILES: CC(C)(O)[C@H]1CC[C@H](n2cc(C(N)=O)c(Nc3ccc(Cl)cc3)n2)[C@@H](C#N)C1]

3-(4-Chlorophenylamino)-1-((1S,2S,4S or 1R,2R,4R)-2-cyano-4-(2-hydroxypropan-2-yl)cyclohexyl)-1H-pyrazole-4-carboxamide

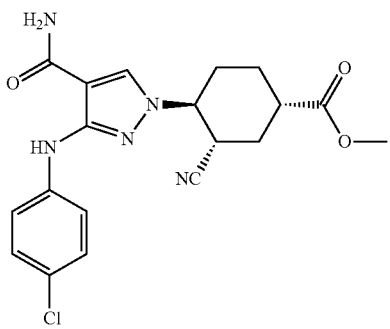 [SMILES: COC(=O)[C@H]1CC[C@H](n2cc(C(N)=O)c(Nc3ccc(Cl)cc3)n2)[C@@H](C#N)C1]

Step A: (1S,3S,4S and 1R,3R,4R)-methyl 4-(4-carbamoyl-3-((4-chlorophenyl)amino)-1H-pyrazol-1-yl)-3-cyanocyclohexanecarboxylate To a solution of the crude acid (1S,3S,4S and 1R,3R,4R)-4-[4-carbamoyl-3-[(4-chlorophenyl)amino]-1H-pyrazol-1-yl]-3-cyanocyclohexane-1-carboxylic acid (Example #35-1 Step C, 500 mg, 1.3 mmol) in MeOH (5 mL) were sequentially added EDC (324 mg, 1.7 mmol) and HOBt (210 mg, 1.6 mmol). The resulting solution was stirred at ambient temperature overnight before it was concentrated in vacuo. The crude residue was partitioned between DCM (20 mL) and water (5 mL). The organic solution was washed with saturated aqueous NaHCO$_3$ (2×5 mL), dried over anhydrous sodium sulfate, filtered and concentrated in vacuo. The crude residue was purified by MPLC on Silica gel (eluting with 2-4% MeOH/DCM) to afford the title compound. $^1$H NMR (400 MHz, CD$_3$OD) δ 8.13 (s, 1H), 7.55 (d, J=8.8 Hz, 2H), 7.24 (d, J=9.2 Hz, 2H), 4.35-4.28 (m, 1H), 3.74 (s, 3H), 3.52-3.34 (m, 1H), 2.68-2.62 (m, 1H), 2.55-2.52 (m, 1H), 2.24-2.16 (m, 3H), 2.00-1.90 (m, 1H), 1.73-1.70 (m, 1H). MS ESI: [M+H]$^+$ m/z 401.

Step B: 3-(4-Chlorophenylamino)-1-((1S,2S,4S or 1R,2R,4R)-2-cyano-4-(2-hydroxypropan-2-yl)cyclohexyl)-1H-pyrazole-4-carboxamide To a solution of methyl (1S,3S,4S and 1R,3R,4R)-4-[4-carbamoyl-3-[(4-chlorophenyl)amino]-1H-pyrazol-1-yl]-3-cyanocyclohexane-1-carboxylate (100 mg, 0.25 mmol) in THF (8 mL) under nitrogen was added MeMgBr (1.8 mL, 2.5 mmol, 1.4N in THF) dropwise at −15° C. The resulting solution was stirred at ambient temperature for 3 hours before the addition of saturated aqueous NH$_4$Cl (10 mL) at 0° C. The mixture was vigorously stirred at ambient temperature for 10 minutes, and then extracted with EtOAc (3×30 mL). The combined organic layers were dried over anhydrous sodium sulfate, filtered and concentrated in vacuo. The crude residue was purified by MPLC on Silica gel (eluting with 2-5% MeOH/DCM) to afford a racemic mixture of 3-(4-chlorophenylamino)-1-((1S,2S,4S and 1R,2R,4R)-2-cyano-4-(2-hydroxypropan-2-yl)cyclohexyl)-1H-pyrazole-4-carboxamide, which was then resolved to the constituent enantiomers by preparative chiral HPLC (Chiralpak IC, 2*25 cm; Mobile phase: 30% ethanol/hexane (0.1% TEA)] to afford the title compounds as single enantiomers.

Example 36-1

1$^{st}$ enantiomer to elute; 3-(4-chlorophenylamino)-1-((1S,2S,4S or 1R,2R,4R)-2-cyano-4-(2-hydroxypropan-2-yl)cyclohexyl)-1H-pyrazole-4-carboxamide: MS ESI: [M+H]$^+$ m/z 402.1; $^1$H NMR (400 MHz, CD$_3$OD) δ 8.13 (s, 1H), 7.54 (d, J=8.8 Hz, 2H), 7.24 (d, J=8.8 Hz, 2H), 4.28-4.22 (m, 1H), 3.39-3.35 (m, 1H), 2.44-2.41 (m, 1H), 2.19-2.03 (m, 3H), 1.70-1.59 (m, 2H), 1.56-1.45 (m, 1H), 1.22 (s, 6H).

Example 36-2

$2^{nd}$ enantiomer to elute; 3-(4-chlorophenylamino)-1-((1R,2R,4R or 1S,2S,4S)-2-cyano-4-(2-hydroxypropan-2-yl)cyclohexyl)-1H-pyrazole-4-carboxamide: $^1$H NMR (400 MHz, CD$_3$OD) δ 8.13 (s, 1H), 7.55 (d, J=8.8 Hz, 2H), 7.24 (d, J=8.8 Hz, 2H), 4.28-4.22 (m, 1H), 3.39-3.32 (m, 1H), 2.44-2.41 (m, 1H), 2.19-2.03 (m, 3H), 1.70-1.57 (m, 2H), 1.54-1.45 (m, 1H), 1.23 (s, 6H). MS ESI: [M+H]$^+$ m/z 402.

Example #37

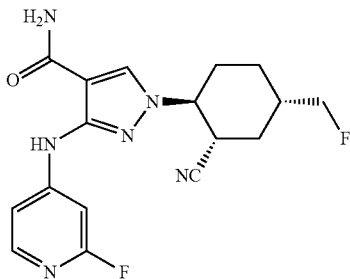 [SMILES: N#C[C@H]1C[C@@H](CF)CC[C@@H]1n1cc(C(N)=O)c(Nc2ccnc(F)c2)n1]

1-[(1S,2S,4S and 1R,2R,4R)-2-Cyano-4-(fluoromethyl)cyclohexyl]-3-[(2-fluoropyridin-4-yl)amino]-1H-pyrazole-4-carboxamide

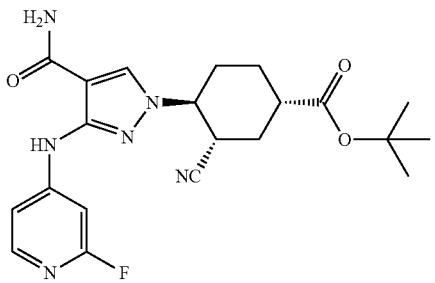 [SMILES: CC(C)(C)OC(=O)[C@H]1CC[C@H](n2cc(C(N)=O)c(Nc3ccnc(F)c3)n2)[C@@H](C#N)C1]

Step A: (1S,3S,4S and 1R,3R,4R)-tert-butyl 4-(4-carbamoyl-3-((2-fluoropyridin-4-yl)amino)-1H-pyrazol-1-yl)-3-cyanocyclohexanecarboxylate To a solution of tert-butyl (1S,3S,4S and 1R,3R,4R)-4-(3-amino-4-carbamoyl-1H-pyrazol-1-yl)-3-cyanocyclohexanecarboxylate (Intermediate 47-4, 409 mg, 1.23 mmol) in dioxane (10 mL) were added potassium acetate (781 mg, 3.68 mmol), 4-bromo-2-fluoropyridine (259 mg, 1.47 mmol), tetramethyl t-butyl X-Phos (118 mg, 0.245 mmol) and Pd$_2$ dba$_3$ (112 mg, 0.123 mmol). The solution was degassed by bubbling argon, capped, and heated to 90° C. for 16 hours. The reaction mixture was cooled, filtered through celite, and purified by MPLC on silica gel (using a gradient elution of 0-100% EtOAc/hexanes) to the title compound. $^1$H NMR (600 MHz, CDCl$_3$): δ 9.35 (broad s, 1H), 7.95 (d, J=5.4 Hz, 1H), 7.70 (s, 1H), 7.29 (d, J=1.2 Hz, 1H), 7.02 (d, J=5.4 Hz, 1H), 5.50 (s, 1H), 4.02-3.98 (td, J=11.4, 4.8 Hz, 1H), 3.26-3.22 (m, 1H), 2.58-2.40 (m, 2H), 2.30-2.14 (m, 3H), 1.92-84 (m, 1H), 1.59 (m, 1H), 1.45 (s, 9H). LRMS (ESI) calc'd for C$_{21}$H$_{26}$FN$_6$O$_3$ [M+H]$^+$: 429. Found: 429.

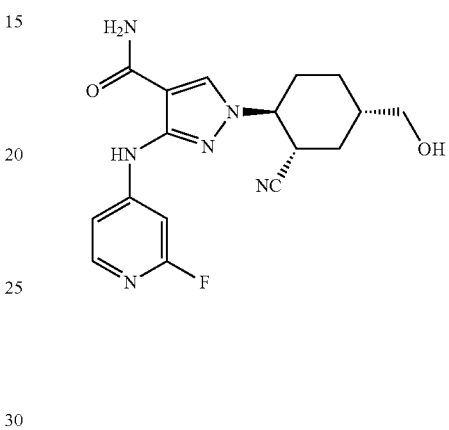

Step B: 1-((1S,2S,4S and 1R,2R,4R)-2-Cyano-4-(hydroxymethyl)cyclohexyl)-3-((2-fluoropyridin-4-yl)amino)-1H-pyrazole-4-carboxamide To a solution of 1S,3S,4S and 1R,3R,4R)-4-{4-carbamoyl-3-[(2-fluoropyridin-4-yl)amino]-1H-pyrazol-1-yl}-3-cyano-cyclohexanecarboxylate (174 mg, 0.406 mmol) in THF (4 mL) was added lithium borohydride (27 mg, 1.2 mmol) and heated to 55° C. for 3 hours. After 3 hours, another 1 eq. of lithium borohydride (27 mg, 1.2 mmol) was added and the reaction mixture was stirred for another 1 hour. The reaction mixture was cooled, filtered through celite, and purified by MPLC on silica gel (using a gradient elution of 0-20% MeOH/DCM) to afford the title compound. LRMS (ESI) calc'd for C$_{17}$H$_{20}$FN$_6$O$_2$ [M+H]$^+$: 359. Found: 359.

Step C: 1-[(1S,2S,4S and 1R,2R,4R)-2-Cyano-4-(fluoromethyl)cyclohexyl]-3-[(2-fluoropyridin-4-yl)amino]-1H-pyrazole-4-carboxamide To a solution of 1-[(1S,2S,4S and 1R,2R,4R)-2-cyano-4-(hydroxymethyl)cyclohexyl]-3-[(2-fluoropyridin-4-yl)amino]-1H-pyrazole-4-carboxamide (121 mg, 0.338 mmol) in DCM (2 mL) was added Dexo-Fluor (112 mg, 0.093 mmol). The resulting solution was stirred for 16 hours and then concentrated in vacuo. The residue was purified by MPLC on silica gel (using a gradient elution of 0-100% EtOAc/hexanes) to afford the title compound. $^1$H NMR (500 MHz, CD$_3$OD): δ 8.20 (s, 1H), 7.90 (d, J=5.5 Hz, 1H), 7.41 (s, 1H), 7.24 (d, J=5 Hz, 1H), 4.42-4.20 (m, 3H), 3.49 (m, 1H), 2.35-2.32 (m, 1H), 2.59-2.08 (m, 2H), 1.97-1.85 (m 2H), 1.69-1.64 (m, 1H), 1.47 (1.38 (m, 1H). LRMS (ESI) calc'd for $C_{17}H_{19}F_2N_6O$ [M+H]$^+$: 361. Found: 361.

Scheme #35

Example #38-1 & 38-2

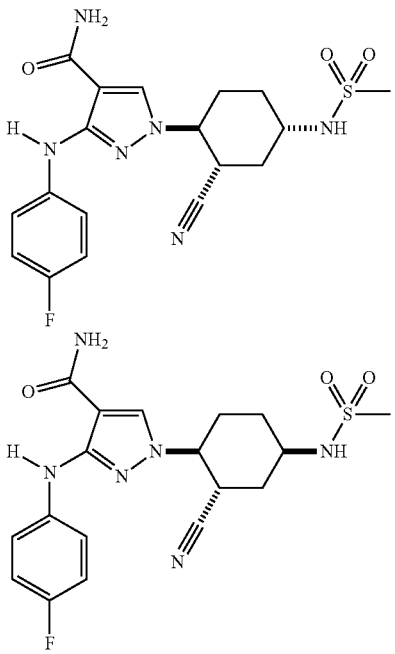

1-{(1S,2S,4S and 1R,2R,4R)-2-Cyano-4-[(methyl-sulfonyl)amino]cyclohexyl}-3-[(4-fluorophenyl)amino]-1H-pyrazole-4-carboxamide and 1-{(1S,2S,4R and 1R,2R,4S)-2-Cyano-4-[(methylsulfonyl)amino]cyclohexyl}-3-[(4-fluorophenyl)amino]-1H-pyrazole-4-carboxamide To a suspension of (3S,4S and 3R,4R)-4-(4-carbamoyl-3-((4-fluorophenyl)amino)-1H-pyrazol-1-yl)-3-cyanocyclohexanaminium trifluoroacetate (Example #27-18, 34 mg, 0.074 mmol) in DCM (0.37 mL) was added TEA (0.03 mL, 0.2 mmol), followed by methanesulfonyl chloride (0.006 mL, 0.07 mmol). The resulting mixture was allowed to stir at ambient temperature for 1 hour before saturated aqueous $NaHCO_3$ was added and the resulting mixture was extracted with EtOAc (3×). The combined organic layers were dried over anhydrous $Na_2SO_4$, filtered, and concentrated in vacuo. The residue was purified by MPLC on silica gel (using a gradient elution of 0-10%, MeOH/DCM). Desired fractions were identified, combined, and concentrated in vacuo. The major isomer was further purified by reverse-phase preparative HPLC (using a gradient elution of MeCN/water, with 0.1% v/v TFA modifier). Desired fractions were identified, combined, basified with saturated aqueous $NaHCO_3$ and extracted with EtOAc. The organic layer was dried over anhydrous $Na_2SO_4$, filtered, and concentrated in vacuo, to afford the title compounds.

Example 38-1 (Major Isomer:)

1-{(1S,2S,4S and 1R,2R,4R)-2-cyano-4-[(methylsulfonyl)amino]cyclohexyl}-3-[(4-fluorophenyl)amino]-1H-pyrazole-4-carboxamide $^1$H NMR (500 MHz, CD$_3$OD) δ 8.10 (s, 1H), 7.53 (m, 2H), 6.98 (m, 2H), 4.27 (ddd, J=11.5, 11.5, 3.5 Hz, 2H), 3.57-3.44 (m, 2H), 3.01 (s, 3H), 2.53 (m, 1H), 2.09 (m, 3H), 1.79 (ddd, J=12.5, 12.5, 12.5 Hz, 1H), 1.57, (dddd, J=13.5, 13.5, 13.5, 4 Hz, 1H). LRMS (ESI) calc'd for $C_{18}H_{21}FN_6O_3S$ [M+H]$^+$: 421. Found: 421.

Example 38-2 (Minor Isomer)

1-{(1S,2S,4R and 1R,2R,4S)-2-cyano-4-[(methylsulfonyl)amino]cyclohexyl}-3-[(4-fluorophenyl)amino]-1H-pyrazole-4-carboxamide. $^1$H NMR (500 MHz, CD$_3$OD) δ 8.13 (s, 1H), 7.54 (m, 2H), 6.99 (m, 2H), 4.32 (ddd, J=11, 11, 3.5 Hz, 1H), 3.79 (m, 1H), 3.66 (ddd, J=11.5, 11.5, 3 Hz, 1H), 3.01 (s, 3H), 2.43-2.32 (m, 2H), 2.12-1.84 (m, 4H). LRMS (ESI) calc'd for $C_{18}H_{21}FN_6O_3S$ [M+H]$^+$: 421. Found: 421.

The following compounds shown in TABLE 30 were prepared according to Scheme #35 following similar procedures described for Example #38-1 and 38-2, which can be achieved by those of ordinary skill in the art of organic synthesis.

TABLE 30

| Example | Structure | Compound Name | Exact Mass [M + H]$^+$ |
|---|---|---|---|
| 38-3 | ![structure] | 3-[(4-chlorophenyl)amino]-1-{(1S,2S,4R and 1R,2R,4S)-2-cyano-4-[(methylsulfonyl)amino]cyclohexyl}-1H-pyrazole-4-carboxamide | Calc'd 437, found 437 |

TABLE 30-continued

| Example | Structure | Compound Name | Exact Mass [M + H]+ |
|---|---|---|---|
| 38-4 | 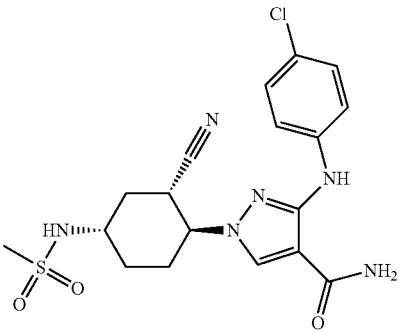 [SMILES: CS(=O)(=O)N[C@H]1CC[C@H](n2cc(C(N)=O)c(Nc3ccc(Cl)cc3)n2)[C@@H](C#N)C1] | 3-[(4-chlorophenyl)amino]-1-{(1S,2S,4R and 1R,2R,4S)-2-cyano-4-[(methylsulfonyl)amino]cyclohexyl}-1H-pyrazole-4-carboxamide | Calc'd 437, found 437 |
| 38-5 | 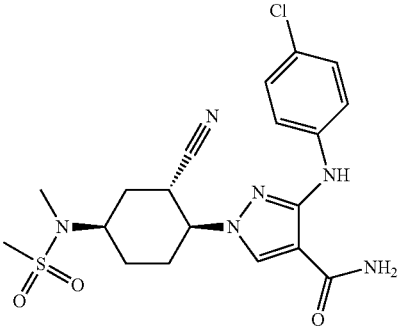 [SMILES: CN([C@@H]1CC[C@H](n2cc(C(N)=O)c(Nc3ccc(Cl)cc3)n2)[C@@H](C#N)C1)S(C)(=O)=O] | 3-[(4-chlorophenyl)amino]-1-{(1S,2S,4R and 1R,2R,4S)-2-cyano-4-[methyl(methylsulfonyl)amino]cyclohexyl}-1H-pyrazole-4-carboxamide | Calc'd 451, found 451 |
| 38-6 | 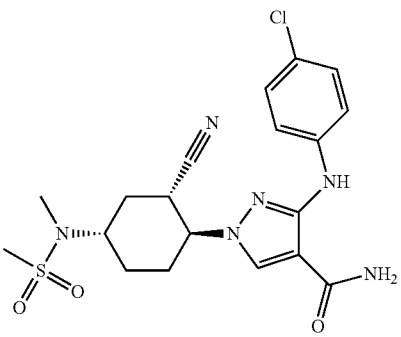 [SMILES: CN([C@H]1CC[C@H](n2cc(C(N)=O)c(Nc3ccc(Cl)cc3)n2)[C@@H](C#N)C1)S(C)(=O)=O] | 3-[(4-chlorophenyl)amino]-1-{(1S,2S,4R and 1R,2R,4S)-2-cyano-4-[methyl(methylsulfonyl)amino]cyclohexyl}-1H-pyrazole-4-carboxamide | Calc'd 451, found 451 |

Scheme #55

Example #39

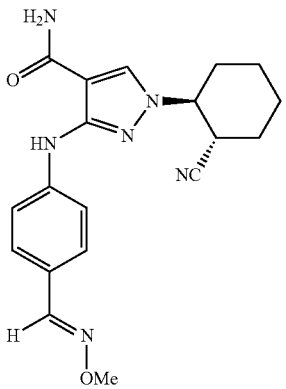

1-[(1S,2S or 1R, 2R)-2-Cyanocyclohexyl]-3-({4-[(methoxyimino)methyl]phenyl}amino)-1H-pyrazole-4-carboxamide To a solution of 1-[(1S,2S or 1R,2R)-2-cyanocyclohexyl]-3-[(4-formylphenyl)amino]-1H-pyrazole-4-carboxamide (20 mg, 0.059 mmol) in EtOH (0.5 mL) were added O-methylhydroxylamine hydrochloride (25 mg, 0.30 mmol) and triethylamine (30 mg, 0.29 mmol). The vial was sealed and heated in the microwave at 100° C. for 30 minutes. The reaction mixture was filtered and purified directly by reverse phase preparative HPLC (using a gradient elution of 10-100% MeCN water). Desired fractions were identified, combined, and concentrated in vacuo to afford the title compound. $^1$H NMR (500 MHz, CD$_3$OD): δ 8.11 (s, 1H), 8.00 (s, 1H), 7.56 (d, J=9 Hz, 2H), 7.50 (d, J=9 Hz, 2H), 4.28-4.21 (td, J=11, 4.5 Hz, 1H), 3.86 (s, 3H), 3.31-3.30 (m, 1H), 2.29-2.26 (m, 1H), 2.07-1.74 (m, 5H), 1.53-1.41 (m, 2H). LRMS (ESI) calc'd for C$_{19}$H$_{23}$N$_6$O$_2$ [M+H]$^+$: 367. Found: 367.

Scheme #55

Example #40

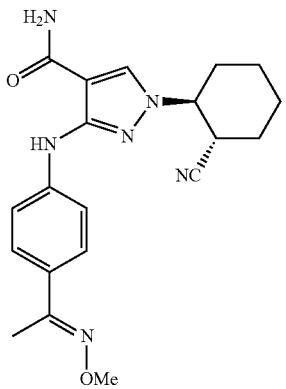 [SMILES: CO/N=C(\C)c1ccc(Nc2nn([C@H]3CCCC[C@@H]3C#N)cc2C(N)=O)cc1]

1-[(1S,2S or 1R,2R)-2-Cyanocyclohexyl]-3-{[4-(N-methoxyethanimidoyl)phenyl]amino}-1H-pyrazole-4-carboxamide 1-[(1S,2S or 1R,2R)-2-cyanocyclohexyl]-3-{[4-(N-methoxyethanimidoyl)phenyl]amino}-1H-pyrazole-4-carboxamide was prepared using the same procedure described for the preparation of as 1-[(1S,2S or 1R, 2R)-2-cyanocyclohexyl]-3-({4-[(methoxyimino)methyl]phenyl}amino)-1H-pyrazole-4-carboxamide (Example #39). $^1$H NMR (500 MHz, CD$_3$OD): δ 8.11 (s, 1H), 7.58 (d, J=9 Hz, 2H), 7.54 (d, J=9 Hz, 2H), 4.28-4.21 (td, J=11, 4 Hz, 1H), 3.92 (s, 3H), 3.31-3.30 (m, 1H), 2.31-2.26 (m, 1H), 2.18 (s, 3H), 2.1-1.70 (m, 5H) 1.58-1.40 (m, 2H). LRMS (ESI) calc'd for C$_{20}$H$_{25}$N$_6$O$_2$ [M+H]$^+$: 381. Found: 381.

Scheme #46

Example #41

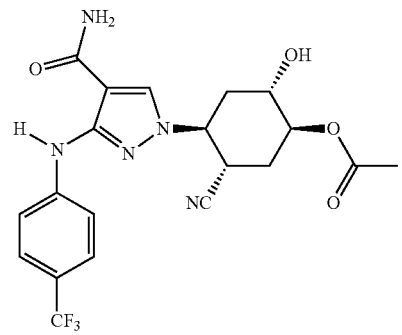 [SMILES: CC(=O)O[C@H]1C[C@H](C#N)[C@@H](n2cc(C(N)=O)c(Nc3ccc(C(F)(F)F)cc3)n2)C[C@@H]1O]

Step A-C: (1S,2S,4S,5S and 1R,2R,4R,5R)-4-(4-Carbamoyl-3-((4-(trifluoromethyl)phenyl)amino)-1H-pyrazol-1-yl)-5-cyano-2-hydroxycyclohexyl acetate BAST (0.47 mL, 2.5 mmol) was added to a mixture of 1-((1S,2S,4R)-2-cyano-4-hydroxycyclohexyl)-3-((4-(trifluoromethyl)phenyl)amino)-1H-pyrazole-4-carboxamide (Intermediate A of Example #28-1, 0.50 g, 1.3 mmol) in DCM (25.4 mL) at 23° C. 20 minutes after the addition of BAST, the reaction mixture was partitioned between EtOAc and saturated aqueous sodium bicarbonate solution. The organic layer was washed with brine, and the washed solution was dried over anhydrous sodium sulfate. The dried solution was filtered, and the filtrate was concentrated in vacuo to afford a mixture of olefin isomers and a fluorinated product. The crude reaction product was dissolved in EtOAc (12.7 mL) and m-CPBA (77% by weight, 854 mg, 3.81 mmol) was added. The reaction mixture was stirred at 23° C. for 17 hours, and then aqueous sodium bisulfite solution (40% by weight) was added. The biphasic mixture was stirred for 15 minutes, then was partitioned between EtOAc and water. The organic layer was washed sequentially with saturated aqueous sodium bicarbonate solution and brine, and the washed solution was dried over anhydrous sodium sulfate. The dried solution was filtered, and the filtrate was concentrated in vacuo. The residue was purified by MPLC on silica gel (using a gradient elution of 50-100% EtOAc/hexanes) to afford an epoxide product of undetermined stereochemistry. The epoxide product (80 mg, 0.20 mmol) was dissolved in acetic acid and heated to 70° C. After stirring for 4 hours at 70° C., the reaction mixture was cooled to 23° C. and partitioned between EtOAc and saturated aqueous sodium bicarbonate solution. The organic layer was washed with brine, dried over anhydrous sodium sulfate, filtered, and concentrated in vacuo. The residue was purified by reverse-phase preparative HPLC (using a gradient elution of MeCN/water, with 0.1% v/v TFA modifier). Desired fractions were identified, combined, neutralized with saturated aqueous NaHCO$_3$ and extracted with EtOAc. The organic layer was dried over anhydrous Na$_2$SO$_4$, filtered, and concentrated in vacuo to afford the title compound. $^1$H NMR (500 MHz, DMSO-d$_6$): δ 9.49 (s, 1H), 8.34 (s, 1H), 7.70-7.86 (m, 3H), 7.57 (d, J=8.5 Hz, 2H), 7.27 (br s, 1H), 4.79-4.77 (m, 1H), 4.59 (td, J=11.5, 4.0 Hz, 1H), 3.92-3.88 (m, 1H), 3.47 (td, J=12.0, 4.0 Hz, 1H), 2.29-2.17 (m, 3H), 2.11 (s, 3H), 1.97 (td, J=13.5, 3.4 Hz, 1H). LRMS (ESI) calc'd for C$_{20}$H$_{21}$F$_3$N$_5$O$_4$ [M+H]$^+$: 452. Found: 452.

Chiral Resolution

The following experimental procedures exemplify the chiral resolution and isolation of enantiopure Examples of the instant invention. The following Examples are for illustrative purposes only and are not intended to limit the scope of the instant invention in any way.

Examples #42-1, 42-2, 42-3, and 42-4

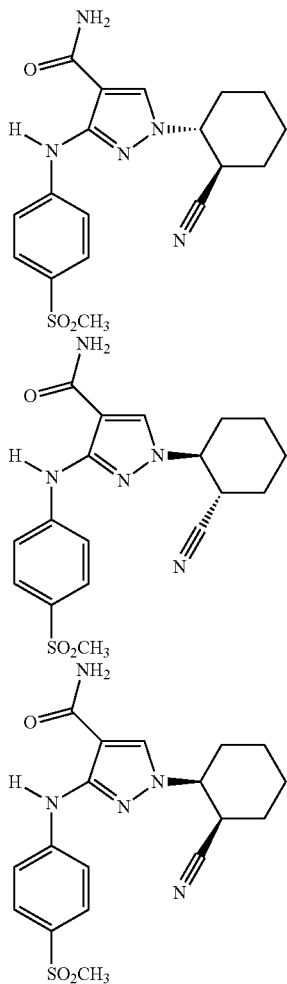

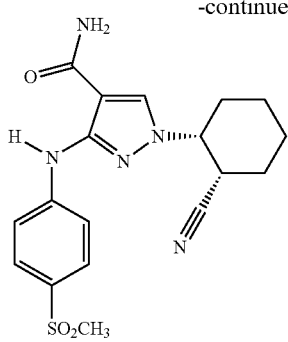

1-[(1S,2S or 1R,2R)-2-Cyanocyclohexyl]-3-{[4-(methylsulfonyl)phenyl]amino}-H-pyrazole-4-carboxamide and 1-[(1S,2R or 1R,2S)-2-cyanocyclohexyl]-3-{[4-(methylsulfonyl)phenyl]amino}-1H-pyrazole-4-carboxamide A racemic diastereomeric mixture of 1-(2-cyanocyclohexyl)-3-{[4-(methylsulfonyl)phenyl]amino}-1H-pyrazole-4-carboxamide was chirally resolved to the four constituent enantiomers by SFC chromatography (Chiral Technology AD-H 2.1×25 cm, 5 uM, 30% EtOH/CO$_2$). Desired fractions were identified, combined, and concentrated in vacuo to afford enantiomerically pure samples of the title compounds:

Example 42-1

1$^{st}$ eluting stereoisomer, 1-[(1S,2S or 1R,2R)-2-cyanocyclohexyl]-3-{[4-(methylsulfonyl)phenyl]amino}-1H-pyrazole-4-carboxamide 1HNMR (600 MHz, CDCl$_3$): δ 9.32 (s, 1H), 7.81 (d, J=9.0 Hz, 2H), 7.78 (s, 1H), 7.66 (d, J=9.0 Hz, 2H), 5.80 (s, 2H), 4.03-3.98 (m, 1H), 3.20-3.15 (m, 1H), 3.03 (s, 3H) 2.32 (br d, J=13.8 Hz, 1H), 2.12-2.06 (m, 2H), 1.96 (br d, J=12.9 Hz, 1H), 1.90-1.86 (m, 1H), 1.76-1.69 (m, 1H), 1.48-1.38 (m, 2H). LRMS (ESI) calc'd for C$_{18}$H$_{22}$N$_5$O$_3$S [M+H]$^+$: 388. Found: 388.

Example 42-2

2$^{nd}$ eluting stereoisomer, 1-[(1S,2S or 1R,2R)-2-cyanocyclohexyl]-3-{[4-(methylsulfonyl)phenyl]amino}-1H-pyrazole-4-carboxamide $^1$H NMR spectral data is consistent with the data reported for Example #42-1. LRMS (ESI) calc'd for C$_{18}$H$_{22}$N$_5$O$_3$S [M+H]+: 388. Found: 388.

Example 42-3

3$^{rd}$ eluting stereoisomer, 1-[(1S,2R or 1R,2S)-2-cyanocyclohexyl]-3-{[4-(methylsulfonyl)phenyl]amino}-1H-pyrazole-4-carboxamide 1HNMR (600 MHz, CDCl$_3$): δ 9.29 (s, 1H), 7.82-7.78 (m, 3H), 7.67 (d, J=8.4 Hz, 2H), 5.69 (s, 2H), 4.29 (dt J=12.0, 3.9 Hz, 1H), 3.71-68 (m, 1H), 3.03 (s, 3H), 2.24-2.19 (m, 2H), 2.15-2.06 (m, 2H), 1.86-1.79 (m, 2H), 1.74-1.65 (m, 1H), 1.56-1.48 (m, 1H). LRMS (ESI) calc'd for C$_{18}$H$_{22}$N$_5$O$_3$S [M+H]$^+$: 388. Found: 388.

Example 42-4

4th eluting stereoisomer, 1-[(1S,2R or 1R,2S)-2-cyanocyclohexyl]-3-{[4-(methylsulfonyl)phenyl]amino}-1H-pyrazole-4-carboxamide $^1$H NMR spectral data is consistent with the data reported for Example #42-3. LRMS (ESI) calc'd for $C_{18}H_{22}N_5O_3S$ [M+H]+: 388. Found: 388.

Examples #43-1 and 43-2

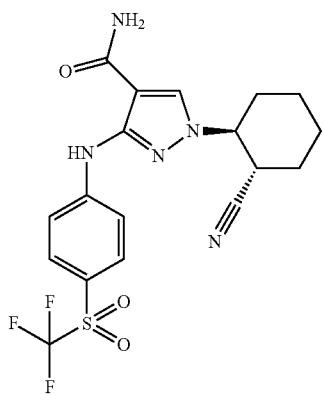

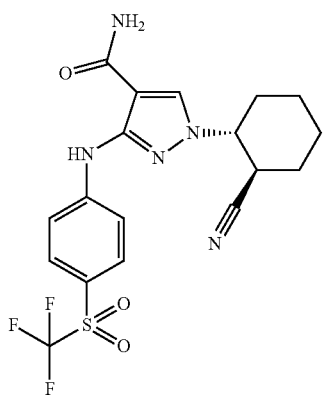

1-[(1S,2S or 1R,2R)-2-Cyanocyclohexyl]-3-({4-[(trifluoromethyl)sulfonyl]phenyl}amino)-1H-pyrazole-4-carboxamide 1-[(1S,2S and 1R,2R)-2-Cyanocyclohexyl]-3-({4-[(trifluoromethyl)sulfonyl]phenyl}amino)-1H-pyrazole-4-carboxamide was chirally resolved to the two constituent enantiomers by chiral SFC (Chiral Technology IC-H, 2.1×25 cm, 35% MeOH—$CO_2$, 100 mL/minutes, 35° C., 100 bar). Desired fractions were identified, combined, and concentrated in vacuo to afford enantiomerically pure samples of the title compounds:

Example 43-1

First-eluting enantiomer, 1-[(1S,2S or 1R,2R)-2-cyanocyclohexyl]-3-({4-[(trifluoromethyl)sulfonyl]phenyl}amino)-1H-pyrazole-4-carboxamide.

$^1$H-NMR data is consistent with spectral data reported for the racemic mixture, Example #16. LRMS (ESI) calc'd for $C_{18}H_{19}F_3N_5O_3S$ [M+H]$^+$: 442. Found: 442.

Example 43-2

Second-eluting enantiomer, 1-[(1S,2S or 1R,2R)-2-cyanocyclohexyl]-3-({4-[(trifluoromethyl)sulfonyl]phenyl}amino)-1H-pyrazole-4-carboxamide.

$^1$H-NMR data is consistent with spectral data reported for the racemic mixture, Example #16. LRMS (ESI) calc'd for $C_{18}H_{19}F_3N_5O_3S$ [M+H]$^+$: 442. Found: 442.

The following compounds shown TABLE 31 were prepared following similar procedures described for Examples #42-1 and 42-2, which can be achieved by those of ordinary skill in the art of organic synthesis.

TABLE 31

| Example | Structure | Compound Name | Exact Mass [M + H]$^+$ |
|---|---|---|---|
| 43-3 | 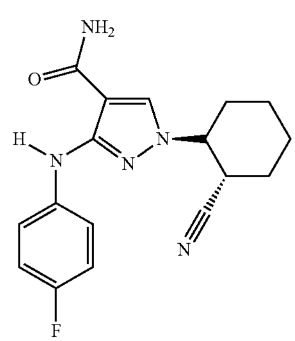 | 1-[(1S,2R or 1R,2S)-2-cyanocyclohexyl]-3-[(4-fluorophenyl)amino]-1H-pyrazole-4-carboxamide | Calc'd 328, Found 328 |

TABLE 31-continued

| Example | Structure | Compound Name | Exact Mass [M + H]+ |
|---|---|---|---|
| 43-4 | 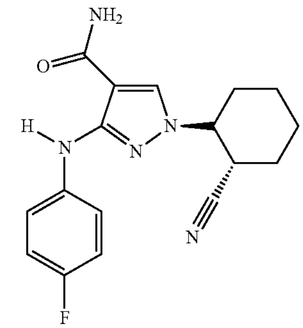 | 1-[(1R,2S or 1S,2R)-2-cyanocyclohexyl]-3-[(4-fluorophenyl)amino]-1H-pyrazole-4-carboxamide | Calc'd 328, Found 328 |
| 43-5 | 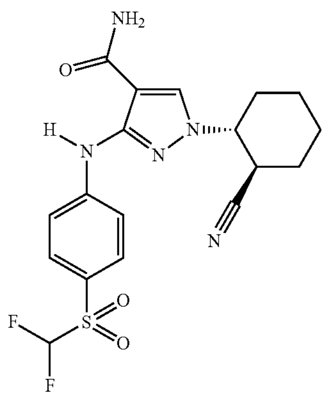 [SMILES: N#C[C@@H]1CCCC[C@H]1n1cc(C(N)=O)c(Nc2ccc(S(=O)(=O)C(F)F)cc2)n1] | 1-[(1S,2S or 1R,2R)-2-cyanocyclohexyl]-3-({4-[(difluoromethyl)sulfonyl]phenyl}amino)-1H-pyrazole-4-carboxamide | Calc'd 424, Found 424 |
| 43-6 | 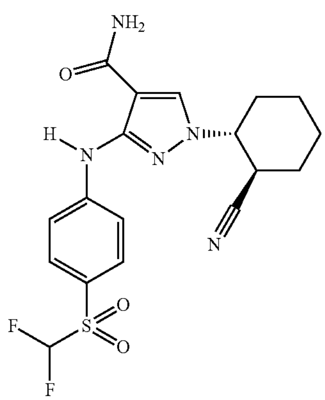 [SMILES: N#C[C@@H]1CCCC[C@H]1n1cc(C(N)=O)c(Nc2ccc(S(=O)(=O)C(F)F)cc2)n1] | 1-[(1S,2S or 1R,2R)-2-cyanocyclohexyl]-3-({4-[(difluoromethyl)sulfonyl]phenyl}amino)-1H-pyrazole-4-carboxamide | Calc'd 424, Found 424 |
| 43-7 | 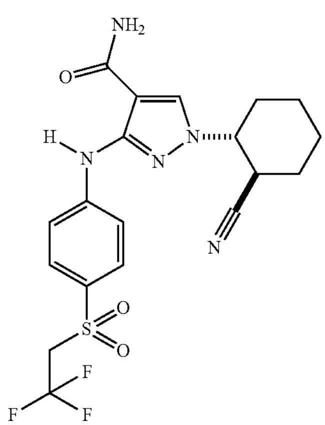 | 1-[(1S,2S or 1R,2R)-2-cyanocyclohexyl]-3-({4-[(2,2,2-trifluoroethyl)sulfonyl]phenyl}amino)-1H-pyrazole-4-carboxamide | Calc'd 456, Found 456 |

TABLE 31-continued

| Example | Structure | Compound Name | Exact Mass [M + H]+ |
|---|---|---|---|
| 43-8 | 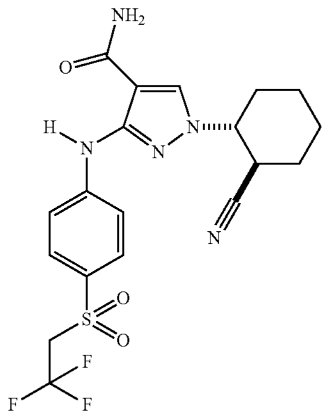 | 1-[(1S,2S or 1R,2R)-2-cyanocyclohexyl]-3-({4-[(2,2,2-trifluoroethyl)sulfonyl]phenyl}amino)-1H-pyrazole-4-carboxamide | Calc'd 456, Found 456 |
| 43-9 | 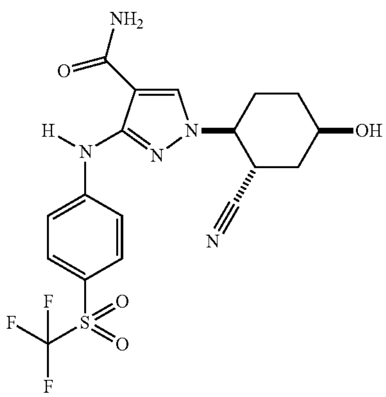 | 1-[(1S,2S,4R or 1R,2R,4S)-2-cyano-4-hydroxycyclohexyl]-3-({4-[(trifluoromethyl)sulfonyl]phenyl}amino)-1H-pyrazole-4-carboxamide | Calc'd 458, Found 458 |
| 43-10 | 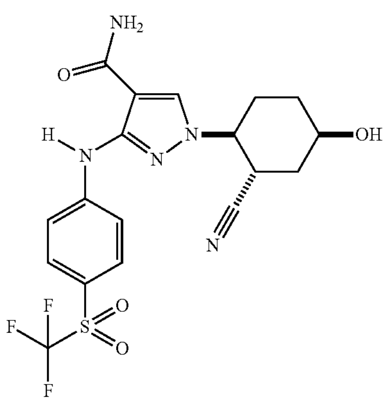 | 1-[(1S,2S,4R or 1R,2R,4S)-2-cyano-4-hydroxycyclohexyl]-3-({4-[(trifluoromethyl)sulfonyl]phenyl}amino)-1H-pyrazole-4-carboxamide | Calc'd 458, Found 458 |

Examples 44-1 and 44-2

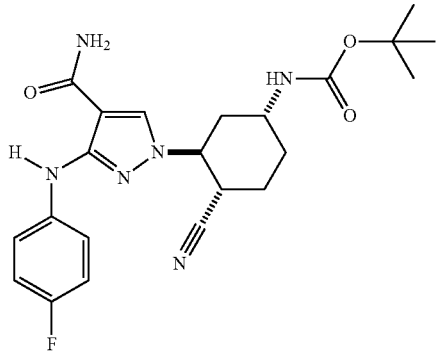

tert-Butyl[(1R,3S,4S or 1S,3R,4R)-3-{4-carbamoyl-3-[(4-fluorophenyl)amino]-1H-pyrazol-1-yl}-4-cyanocyclohexyl]carbamate tert-Butyl[(1R,3S,4S and 1S,3R,4R)-3-{4-carbamoyl-3-[(4-fluorophenyl)amino]-1H-pyrazol-1-yl}-4-cyanocyclohexyl]carbamate was chirally resolved to the constituent enantiomers by chiral SFC (Chiral Technology OD-H, 2.1× 25 cm, 25% MeOH/CO$_2$, 60 mL/minutes). Desired fractions were identified, combined, and concentrated in vacuo to afford enantiomerically pure samples of the title compounds:

Example 44-1

1 tert-Butyl[(1R,3S,4S or 1S,3R,4R)-3-{4-carbamoyl-3-[(4-fluorophenyl)amino]-1H-pyrazol-1-yl}-4-cyanocyclohexyl]carbamate, first enantiomer to elute from column. LRMS (ESI) calc'd for [M+H]$^+$: 443. Found: 443.

Example 44-2 tert-Butyl[(1R,3S,4S or 1S,3R,4R)-3-{4-carbamoyl-3-[(4-fluorophenyl)amino]-1H-pyrazol-1-yl}-4-cyanocyclohexyl]carbamate, second enantiomer to elute from column. LRMS (ESI) calc'd for [M+H]$^+$: 443. Found: 443.

Examples #45-1, 45-2, 45-3, and 45-4

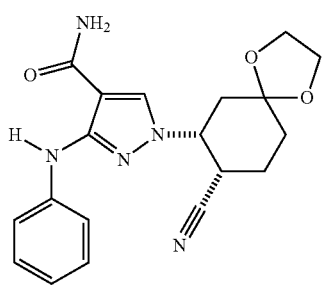

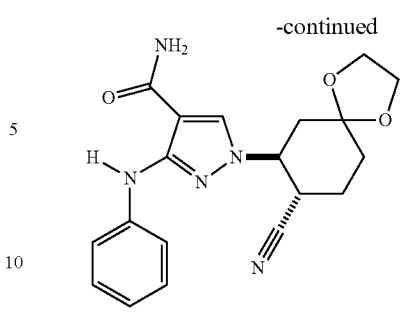

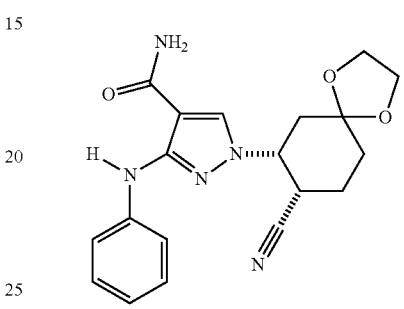

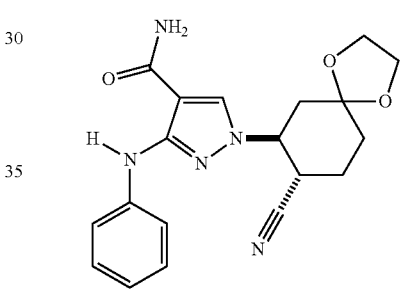

1-[(7R,8S or 7S,8R)-8-Cyano-1,4-dioxaspiro[4.5]dec-7-yl]-3-(phenylamino)-1H-pyrazole-4-carboxamide and 1-[(7S,8S or 7R,8R)-8-Cyano-1,4-dioxaspiro[4.5]dec-7-yl]-3-(phenylamino)-1H-pyrazole-4-carboxamide A racemic diastereomeric mixture of 1-(8-cyano-1,4-dioxaspiro[4.5]dec-7-yl)-3-(phenylamino)-1H-pyrazole-4-carboxamide was chirally resolved to the four constituent enantiomers by SFC chromatography (Chiral Technology AS-H 2.1×25 cm, 5 uM, 30% MeOH/CO$_2$). Desired fractions were identified, combined, and concentrated in vacuo to afford enantiomerically pure samples of the title compounds:

Example 45-1

1$^{st}$ enantiomer to elute from column; 1-[(7R,8R or 7S,8S)-8-Cyano-1,4-dioxaspiro[4.5]dec-7-yl]-3-(phenylamino)-1H-pyrazole-4-carboxamide. $^1$H NMR (600 MHz, DMSO-d$_6$): δ 9.06 (s, 1H), 8.31 (s, 1H), 7.58-7.48 (m, 3H), 7.20 (t, J=7.9 Hz, 2H), 7.12 (br s, 1H), 6.79 (t, J=7.3 Hz, 1H), 4.38 (dt, J=12.9, 3.9 Hz, 1H), 4.00-3.86 (m, 4H), 3.79-3.75 (m, 1H), 2.29-2.24 (m, 1H), 2.09 (t, J=12.8 Hz, 1H), 2.04-1.99 (m, 1H), 1.90 (tt, J=14.1, 3.8 Hz, 1H), 1.79-1.74 (m, 1H), 1.66 (td, J=13.9, 4.3 Hz, 1H). LRMS (ESI) calc'd for C$_{19}$H$_{21}$N$_5$O$_3$ [M+H]$^+$: 368. Found: 368.

Example 45-2

2$^{nd}$ enantiomer to elute from column; 1-[(7S,8R or 7R,8S)-8-Cyano-1,4-dioxaspiro[4.5]dec-7-yl]-3-(phenylamino)-1H-pyrazole-4-carboxamide. $^1$H NMR (600 MHz, DMSO-d$_6$): δ 9.11 (s, 1H), 8.24 (s, 1H), 7.60 (br s, 1H), 7.47 (d, J=7.8 Hz, 2H), 7.22 (t, J=7.9 Hz, 2H), 7.14 (br s, 1H), 6.80 (t, J=7.3 Hz, 1H), 4.34 (td, J=11.5, 4.4 Hz, 1H), 3.97-3.83 (m, 4H), 3.37 (td, J=12.0, 3.7 Hz, 1H), 2.19-2.03 (m, 3H), 1.83-1.64 (m, 3H). LRMS (ESI) calc'd for C$_{19}$H$_{21}$N$_5$O$_3$ [M+H]$^+$: 368. Found: 368.

Example 45-3

3$^{rd}$ enantiomer to elute from column; 1-[(7R,8R or 7S,8S)-8-Cyano-1,4-dioxaspiro[4.5]dec-7-yl]-3-(phenylamino)-1H-pyrazole-4-carboxamide. $^1$H NMR (600 MHz, DMSO-d$_6$): δ 9.06 (s, 1H), 8.31 (s, 1H), 7.58-7.48 (m, 3H), 7.20 (t, J=7.9 Hz, 2H), 7.12 (br s, 1H), 6.79 (t, J=7.3 Hz, 1H), 4.38 (dt, J=12.9, 3.9 Hz, 1H), 4.00-3.86 (m, 4H), 3.79-3.75 (m, 1H), 2.29-2.24 (m, 1H), 2.09 (t, J=12.8 Hz, 1H), 2.04-1.99 (m, 1H), 1.90 (tt, J=14.1, 3.8 Hz, 1H), 1.79-1.74 (m, 1H), 1.66 (td, J=13.9, 4.3 Hz, 1H). LRMS (ESI) calc'd for C$_{19}$H$_{21}$N$_5$O$_3$ [M+H]$^+$: 368. Found: 368.

Example 45-4

4$^{th}$ enantiomer to elute from column; 1-[(7S,8R or 7R,8S)-8-Cyano-1,4-dioxaspiro[4.5]dec-7-yl]-3-(phenylamino)-1H-pyrazole-4-carboxamide. $^1$H NMR (600 MHz, DMSO-d$_6$): δ 9.11 (s, 1H), 8.24 (s, 1H), 7.60 (br s, 1H), 7.47 (d, J=7.7 Hz, 2H), 7.22 (t, J=7.9 Hz, 2H), 7.14 (br s, 1H), 6.80 (t, J=7.3 Hz, 1H), 4.34 (td, J=11.5, 4.4 Hz, 1H), 3.96-3.83 (m, 4H), 3.37 (td, J=12.1, 3.8 Hz, 1H), 2.21-2.01 (m, 3H), 1.84-1.63 (m, 3H). LRMS (ESI) calc'd for C$_{19}$H$_{21}$N$_5$O$_3$ [M+H]$^+$: 368. Found: 368.

The following examples shown in TABLE 33 were prepared following similar procedures described for Examples #45-1, 45-2, 45-3, and 45-4, which can be achieved by those of ordinary skill in the art of organic synthesis.

TABLE 33

| Example | Structure | Compound Name | Exact Mass [M + H]$^+$ |
|---|---|---|---|
| 45-5 | 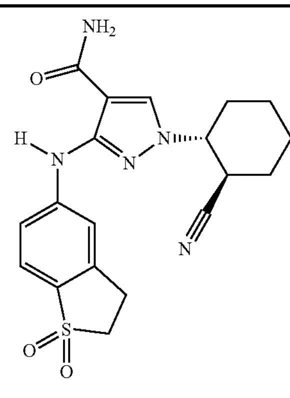 | 1-[(1S,2R or 1R,2S)-2-cyanocyclohexyl]-3-[(1,1-dioxido-2,3-dihydro-1-benzothiophen-5-yl)amino]-1H-pyrazole-4-carboxamide | Calc'd 400, Found 400 |
| 45-6 | 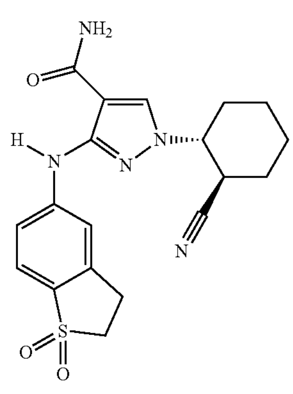 [SMILES: N#C[C@@H]1CCCC[C@H]1n1cc(C(N)=O)c(Nc2ccc3c(c2)CCS3(=O)=O)n1] | 1-[(1S,2R or 1R,2S)-2-cyanocyclohexyl]-3-[(1,1-dioxido-2,3-dihydro-1-benzothiophen-5-yl)amino]-1H-pyrazole-4-carboxamide | Calc'd 400, Found 400 |

Biological Assays

Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDE-PEGDYFEWLW-NH$_2$ (in-house). The basic assay protocol is as follows: First, 250 mL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 µL of 1.11× enzyme and 1.11× substrate in 1× assay buffer (Invitrogen kinase buffer #PV3189, 2 mM DTT, 0.05% BSA) were added to the wells and shaken and then preincubated for 30 minutes at ambient temperature to allow compound binding to equilibrate. After equilibration, 2 µL of 10×ATP in 1× assay buffer was added to initiate the kinase reaction and the plates were shaken and then incubated at ambient temperature for 120 minutes. At the end of the incubation, 20 µL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at ambient temperature and then read on a Perkin Elmer Envision ($\lambda_{ex}$=337 nm, $\lambda_{em}$=665 and 615 nm, TRF delay time=20 µs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate IC$_{50}$ values.

Final reaction conditions were:

| Enzyme | [E] (nM) | [S] (µM) | [ATP] (µM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

Biological Data

Examples of the instant invention were evaluated in JAK1 and JAK2 in vitro binding assays. The following table tabulates the biological data disclosed for the instant invention as JAK1 IC$_{50}$ and JAK2 IC$_{50}$ values.

| Example | JAK1 IC$_{50}$ | JAK2 IC$_{50}$ |
|---|---|---|
| 1-1 | 96 | 696 |
| 1-2 | 8 | 101 |
| 1-3 | 24 | 138 |
| 1-4 | 0.5 | 11 |
| 1-5 | 5 | 82 |
| 2-1 | 3 | 36 |
| 2-2 | 6 | 70 |
| 2-3 | 9 | 47 |
| 2-4 | 423 | >1500 |
| 2-5 | 700 | >1500 |
| 2-6 | 370 | 1000 |
| 2-7 | 170 | 320 |
| 2-8 | 174 | 635 |
| 2-9 | 16 | 202 |
| 2-10 | 13 | 100 |
| 2-11 | 5 | 49 |
| 2-12 | 15 | 79 |
| 2-13 | 27 | 185 |
| 2-14 | 2 | 18 |
| 2-15 | 0.6 | 9 |
| 3-1 | 6 | 109 |
| 3-2 | 2 | 49 |
| 4 | 5 | 46 |
| 5 | 2 | 13 |
| 6-1 | 410 | >1500 |
| 6-2 | 305 | >1500 |
| 6-3 | 250 | >1500 |
| 6-4 | 4 | 55 |
| 6-5 | 410 | >1500 |
| 6-6 | 11 | 170 |
| 7-1 | 17 | 464 |
| 7-2 | 14 | 101 |
| 8 | 2 | 22 |
| 9 | 12 | 247 |
| 10 | 11 | 357 |
| 11-1 | 54 | 176 |
| 11-2 | 11 | 50 |
| 11-3 | 2 | 49 |
| 11-4 | 0.8 | 20 |
| 11-5 | 0.8 | 22 |
| 11-6 | 7 | 38 |
| 11-7 | 5 | 19 |
| 11-8 | 158 | >1500 |
| 11-9 | 21 | 434 |
| 11-10 | 110 | 1300 |
| 12-1 | 7 | 50 |
| 12-2 | 257 | >1500 |
| 13-1 | 0.34 | 5 |
| 13-2 | 0.62 | 9 |
| 14 | 0.32 | 3 |
| 15 | 3 | 46 |
| 16 | 2 | 17 |
| 17-1 | 2 | 21 |
| 17-2 | 23 | 436 |
| 17-3 | 19 | 123 |
| 17-4 | 0.58 | 7 |
| 17-5 | 1 | 9 |
| 17-6 | 4 | 25 |
| 17-7 | 4 | 31 |
| 17-8 | 2 | 10 |
| 17-9 | 0.5 | 5 |
| 17-10 | 0.35 | 4 |
| 17-11 | 2 | 8 |
| 17-12 | 0.49 | 5 |
| 17-13 | 10 | 36 |
| 17-14 | 83 | 226 |
| 17-15 | 20 | 76 |
| 17-16 | 11 | 36 |
| 17-17 | 1 | 5 |
| 17-18 | 3 | 22 |
| 17-19 | 3 | 18 |
| 17-20 | 0.17 | 0.79 |
| 17-21 | 1 | 4 |
| 17-22 | 3 | 60 |
| 17-23 | 11 | 55 |
| 17-24 | 33 | 75 |
| 17-25 | 0.53 | 3 |
| 17-26 | 1 | 11 |
| 17-27 | 0.30 | 2 |
| 17-28 | 3 | 30 |
| 17-29 | 0.36 | 3 |
| 17-30 | 0.10 | 1 |
| 17-31 | 0.60 | 10 |
| 17-32 | 2 | 11 |
| 17-33 | 2 | 4 |
| 17-34 | 2 | 11 |

| Example | JAK1 IC$_{50}$ | JAK2 IC$_{50}$ | Example | JAK1 IC$_{50}$ | JAK2 IC$_{50}$ |
|---|---|---|---|---|---|
| 17-35 | 3 | 15 | 19-1 | 3 | 8 |
| 17-36 | 0.19 | 2 | 19-2 | 4 | 11 |
| 17-37 | 0.67 | 3 | 20 | 0.40 | 6 |
| 17-38 | 1 | 4 | 21-1 | 6 | 73 |
| 17-39 | 1 | 3 | 21-2 | 2 | 15 |
| 17-40 | 0.24 | 5 | 21-3 | 2 | 16 |
| 17-41 | 2 | 16 | 22-1 | 4 | 28 |
| 17-42 | 18 | 178 | 22-2 | 4 | 30 |
| 17-43 | 0.12 | 7 | 23-1 | 5 | 60 |
| 17-44 | 3 | 18 | 23-2 | 67 | 212 |
| 17-45 | 3 | 10 | 24 | 6 | 61 |
| 17-46 | 0.35 | 3 | 25-1 | 8 | 84 |
| 17-47 | 7 | 39 | 25-2 | 2 | 17 |
| 17-48 | 2 | 14 | 25-3 | 1 | 26 |
| 17-49 | 17 | 93 | 25-4 | 0.55 | 3 |
| 17-50 | 0.20 | 2 | 25-5 | 1 | 10 |
| 17-51 | 7 | 42 | 25-6 | 3 | 20 |
| 17-52 | 2 | 26 | 25-8 | 0.60 | 4 |
| 17-52 | 1 | 72 | 25-9 | 1 | 6 |
| 17-53 | 3 | 28 | 25-10 | 4 | 17 |
| 17-54 | 18 | 119 | 25-11 | 0.45 | 2 |
| 17-55 | 41 | 255 | 25-12 | 3 | 20 |
| 17-56 | 4 | 37 | 25-13 | 0.25 | 3 |
| 17-57 | 0.20 | 0.66 | 25-14 | 6 | 25 |
| 17-58 | 6 | 42 | 25-15 | 0.30 | 3 |
| 17-59 | 2 | 13 | 25-16 | 3 | 10 |
| 17-60 | 6 | 23 | 25-17 | 0.35 | 2 |
| 17-61 | 4 | 21 | 25-20 | 1 | 4 |
| 17-62 | 0.28 | 2 | 25-21 | 1 | 11 |
| 17-63 | 0.45 | 11 | 25-22 | 3 | 49 |
| 17-64 | 2 | 14 | 25-23 | 2 | 28 |
| 17-65 | 0.16 | 2 | 25-24 | 1 | 8 |
| 17-66 | 0.33 | 1 | 25-25 | 15 | 210 |
| 17-67 | 3 | 9 | 25-26 | 0.60 | 8 |
| 17-68 | 0.40 | 1 | 25-27 | 0.55 | 11 |
| 17-69 | 30 | 67 | 25-28 | 0.10 | 3 |
| 17-70 | 3 | 13 | 25-29 | 2 | 26 |
| 17-71 | 60 | 285 | 26-1 | 2 | 9 |
| 17-72 | 12 | 89 | 26-2 | 6 | 76 |
| 17-73 | 16 | 37 | 26-3 | 69 | 150 |
| 17-74 | 12 | 49 | 26-4 | 21 | 74 |
| 17-75 | 6 | 22 | 26-5 | 2 | 14 |
| 17-76 | 0.55 | 7 | 26-6 | 1 | 32 |
| 17-77 | 4 | 18 | 26-7 | 0.90 | 9 |
| 17-78 | 6 | 17 | 26-8 | 1 | 19 |
| 17-79 | 7 | 40 | 26-9 | 4 | 33 |
| 17-80 | 12 | 26 | 26-10 | 21 | 102 |
| 17-81 | 0.35 | 2 | 26-11 | 350 | >1500 |
| 17-82 | 0.50 | 1 | 27-1 | 0.20 | 5 |
| 17-83 | 0.20 | 0.90 | 27-2 | 0.5 | 12 |
| 17-84 | 0.30 | 1 | 27-3 | 0.80 | 25 |
| 17-85 | 0.90 | 4 | 27-4 | 1 | 56 |
| 17-86 | 0.25 | 0.95 | 27-5 | 0.20 | 11 |
| 17-87 | 0.50 | 2 | 27-6 | 0.08 | 5 |
| 17-88 | 1 | 9 | 27-7 | 0.40 | 9 |
| 17-89 | 0.50 | 1 | 27-8 | 0.30 | 9 |
| 17-90 | 1 | 4 | 27-9 | 3 | 51 |
| 17-91 | 0.50 | 2 | 27-10 | 0.70 | 7 |
| 17-92 | 0.90 | 3 | 27-11 | 0.55 | 6 |
| 17-93 | 0.30 | 1 | 27-12 | 0.30 | 10 |
| 17-94 | 5 | 33 | 27-13 | 0.30 | 6 |
| 17-95 | 6 | 31 | 27-14 | 0.25 | 11 |
| 17-96 | 2 | 7 | 27-15 | 0.35 | 11 |
| 17-97 | 9 | 24 | 27-16 | 1 | 35 |
| 17-98 | 0.25 | 1 | 28-1 | 0.40 | 23 |
| 17-99 | 0.40 | 1 | 28-2 | 4 | 67 |
| 17-100 | 4 | 34 | 28-3 | 5 | 87 |
| 17-101 | 2 | 9 | 28-4 | 0.75 | 39 |
| 17-102 | 6 | 39 | 28-5 | 1 | 18 |
| 17-103 | 0.70 | 5 | 28-6 | 0.55 | 16 |
| 17-104 | 2 | 25 | 28-7 | 0.40 | 49 |
| 17-105 | 2 | 19 | 28-8 | 5 | 200 |
| 17-106 | 1 | 10 | 28-9 | 2 | 84 |
| 17-107 | 0.95 | 11 | 28-10 | 3 | 64 |
| 17-108 | 8 | 120 | 28-11 | 6 | 75 |
| 17-109 | 50 | 260 | 28-12 | 380 | >1500 |
| 18 | 10 | 22 | 28-13 | 11 | 175 |

| Example | JAK1 IC$_{50}$ | JAK2 IC$_{50}$ |
|---|---|---|
| 28-14 | 7 | 100 |
| 28-15 | 0.90 | 22 |
| 28-16 | 1 | 21 |
| 28-17 | 2 | 121 |
| 28-18 | 30 | 400 |
| 28-19 | 31 | 675 |
| 28-20 | 5 | 355 |
| 28-21 | 3 | 335 |
| 28-22 | 8 | 145 |
| 28-23 | 0.45 | 23 |
| 28-24 | 0.60 | 240 |
| 28-25 | 8 | 155 |
| 28-26 | 0.40 | 35 |
| 28-27 | 50 | 800 |
| 28-28 | 3 | 77 |
| 28-30 | 15 | 575 |
| 28-31 | 105 | 1100 |
| 28-32 | 5 | 144 |
| 28-33 | 8 | 180 |
| 28-34 | 0.60 | 20 |
| 28-35 | 1 | 48 |
| 28-36 | 2 | 84 |
| 28-37 | 2 | 120 |
| 28-38 | 7 | 173 |
| 28-39 | 2 | 35 |
| 28-40 | 0.70 | 16 |
| 28-41 | 2 | 58 |
| 28-42 | 2 | 36 |
| 28-43 | 2 | 26 |
| 28-44 | 0.06 | 11 |
| 28-45 | 0.20 | 24 |
| 28-47 | 0.30 | 11 |
| 28-48 | 8 | 215 |
| 28-49 | 0.15 | 5 |
| 28-50 | 2 | 47 |
| 28-51 | 0/20 | 37 |
| 28-52 | 0.40 | 23 |
| 28-53 | 0.40 | 8 |
| 28-54 | 5 | 92 |
| 28-55 | 4 | 200 |
| 28-57 | 0.15 | 8 |
| 28-58 | 0.70 | 23 |
| 28-60 | 0.20 | 9 |
| 28-61 | 0.06 | 4 |
| 28-62 | 0.15 | 12 |
| 28-63 | 4 | 41 |
| 28-65 | 0.30 | 12 |
| 28-66 | 0.45 | 16 |
| 28-68 | 0.06 | 1 |
| 28-69 | 0.60 | 16 |
| 28-70 | 2 | 40 |
| 28-71 | 2 | 97 |
| 28-72 | 0.45 | 98 |
| 28-75 | 0.25 | 80 |
| 28-76 | 0.04 | 2 |
| 28-77 | 0.70 | 4 |
| 28-78 | 0.20 | 7 |
| 28-79 | 0.30 | 3 |
| 28-80 | 0.30 | 130 |
| 28-81 | 0.20 | 24 |
| 28-83 | 0.40 | 18 |
| 28-84 | 0.30 | 9 |
| 28-85 | 0.65 | 17 |
| 28-86 | 0.75 | 18 |
| 28-87 | 0.55 | 13 |
| 28-88 | 0.10 | 7 |
| 28-89 | 0.30 | 6 |
| 28-90 | 4 | 35 |
| 28-91 | 1 | 65 |
| 28-92 | 0.10 | 27 |
| 28-93 | 0.06 | 5 |
| 28-94 | 2 | 44 |
| 28-95 | 1 | 32 |
| 28-96 | 2 | 85 |
| 28-97 | 0.30 | 9 |
| 28-98 | 4 | 216 |
| 28-99 | 3 | 32 |
| 28-100 | 0.70 | 41 |
| 28-101 | 4 | 69 |
| 28-102 | 1 | 27 |
| 28-103 | 6 | 147 |
| 28-104 | 0.40 | 13 |
| 28-105 | 3 | 30 |
| 28-106 | 9 | 53 |
| 28-107 | 2 | 31 |
| 28-108 | 2 | 31 |
| 28-109 | 2 | 110 |
| 28-110 | 2 | 37 |
| 28-111 | 1 | 16 |
| 28-112 | 0.45 | 6 |
| 28-113 | 1 | 13 |
| 28-114 | 3 | 29 |
| 28-115 | 3 | 33 |
| 28-116 | 1 | 9 |
| 28-117 | 0.55 | 23 |
| 28-118 | 0.50 | 17 |
| 28-119 | 1 | 85 |
| 28-120 | 0.95 | 20 |
| 28-121 | 1 | 61 |
| 28-122 | 0.90 | 6 |
| 28-123 | 2 | 56 |
| 28-124 | 1 | 23 |
| 28-125 | 2 | 72 |
| 28-126 | 0.50 | 5 |
| 28-127 | 12 | 254 |
| 28-128 | 3 | 110 |
| 28-129 | 20 | 620 |
| 28-130 | 0.25 | 5 |
| 28-131 | 0.90 | 51 |
| 28-133 | 0.50 | 36 |
| 28-134 | 1 | 50 |
| 28-135 | 0.65 | 32 |
| 28-136 | 1 | 61 |
| 28-137 | 0.90 | 22 |
| 28-138 | 0.90 | 40 |
| 28-139 | 5 | 113 |
| 28-141 | 1 | 44 |
| 28-142 | 2 | 141 |
| 28-143 | 1 | 122 |
| 28-144 | 1 | 21 |
| 28-145 | 0.25 | 15 |
| 28-146 | 1 | 4 |
| 28-147 | 0.45 | 5 |
| 28-148 | 0.35 | 4 |
| 28-149 | 0.60 | 17 |
| 28-150 | 0.30 | 2 |
| 28-151 | 0.13 | 1 |
| 28-152 | 0.40 | 10 |
| 28-153 | 0.40 | 7 |
| 28-154 | 1 | 13 |
| 28-155 | 0.22 | 3 |
| 28-156 | 1 | 14 |
| 28-157 | 1 | 28 |
| 28-158 | 1 | 17 |
| 28-159 | 2 | 18 |
| 28-160 | 0.20 | 1 |
| 28-164 | 4 | 225 |
| 28-165 | 0.45 | 4 |
| 28-166 | 2 | 55 |
| 28-167 | 3 | 82 |
| 28-168 | 0.15 | 4 |
| 28-169 | 0.29 | 5 |
| 28-170 | 11 | 180 |
| 28-171 | 2 | 31 |
| 28-172 | 0.20 | 8 |
| 28-173 | 0.15 | 24 |
| 28-174 | 0.15 | 8 |
| 28-175 | 0.35 | 19 |
| 28-176 | 0.20 | 11 |
| 28-177 | 1 | 43 |
| 28-178 | 0.15 | 2 |
| 28-179 | 7 | 170 |
| 28-180 | 0.60 | 39 |
| 28-181 | 1 | 16 |

| Example | JAK1 IC$_{50}$ | JAK2 IC$_{50}$ | | Example | JAK1 IC$_{50}$ | JAK2 IC$_{50}$ |
|---|---|---|---|---|---|---|
| 28-182 | 0.15 | 12 | | 31-1 | 0.30 | 33 |
| 28-183 | 0.80 | 61 | | 31-2 | 1 | 35 |
| 28-184 | 0.20 | 23 | | 31-3 | 1 | 28 |
| 28-185 | 0.80 | 83 | | 31-4 | 1 | 34 |
| 28-186 | 0.15 | 9 | | 31-5 | 0.85 | 28 |
| 28-187 | 0.20 | 25 | | 32-1 | 13 | 59 |
| 28-188 | 0.30 | 14 | | 32-2 | 1 | 4 |
| 28-189 | 0.35 | 21 | | 32-3 | 0.70 | 3 |
| 28-190 | 2 | 270 | | 32-4 | 0.35 | 2 |
| 28-191 | 0.90 | 104 | | 32-5 | 3 | 25 |
| 28-192 | 2 | 67 | | 32-6 | 2 | 5 |
| 28-193 | 165 | 1000 | | 32-7 | 5 | 28 |
| 28-194 | 4 | 152 | | 32-8 | 0.75 | 4 |
| 28-195 | 177 | 375 | | 32-9 | 1 | 4 |
| 28-196 | 1 | 34 | | 32-10 | 1 | 9 |
| 28-197 | 7 | 430 | | 32-11 | 1 | 4 |
| 28-198 | 0.15 | 3 | | 32-12 | 1 | 10 |
| 28-199 | 0.30 | 9 | | 32-13 | 3 | 17 |
| 28-200 | 1 | 23 | | 32-14 | 15 | 73 |
| 28-201 | 2 | 62 | | 32-15 | 0.25 | 1 |
| 28-202 | 0.75 | 39 | | 32-16 | 0.85 | 6 |
| 28-203 | 2 | 285 | | 32-17 | 2 | 11 |
| 28-204 | 0.20 | 26 | | 33-1 | 0.50 | 5 |
| 28-205 | 0.90 | 21 | | 33-2 | 0.25 | 6 |
| 28-206 | 12 | 195 | | 33-3 | 2 | 12 |
| 28-207 | 1 | 22 | | 33-4 | 5 | 90 |
| 28-208 | 0.15 | 17 | | 33-5 | 0.25 | 2 |
| 28-209 | 3 | 208 | | 33-6 | 0.50 | 3 |
| 28-210 | 1 | 41 | | 33-7 | 11 | 75 |
| 28-211 | 4 | 71 | | 33-8 | 8 | 33 |
| 28-212 | 0.60 | 36 | | 33-9 | 21 | 65 |
| 28-213 | 1 | 12 | | 33-10 | 0.30 | 2 |
| 28-214 | 1 | 38 | | 33-11 | 0.45 | 3 |
| 28-215 | 0.80 | 28 | | 33-12 | 0.45 | 2 |
| 28-216 | 2 | 24 | | 33-13 | 0.20 | 0.95 |
| 28-217 | 2 | 47 | | 33-14 | 4 | 14 |
| 28-218 | 4 | 102 | | 33-15 | 0.50 | 2 |
| 28-219 | 1 | 11 | | 33-16 | 0.70 | 3 |
| 28-220 | 2 | 30 | | 33-18 | 3 | 10 |
| 28-221 | 2 | 42 | | 33-19 | 1 | 4 |
| 28-222 | 0.80 | 43 | | 33-20 | 2 | 20 |
| 28-223 | 2 | 14 | | 33-21 | 1 | 6 |
| 28-224 | 3 | 34 | | 33-22 | 2 | 17 |
| 28-225 | 12 | 51 | | 34-1 | 7 | 107 |
| 28-226 | 5 | 36 | | 34-2 | 5 | 164 |
| 28-227 | 27 | 186 | | 34-3 | 0.95 | 13 |
| 28-228 | 2 | 48 | | 34-4 | 2 | 19 |
| 28-229 | 1 | 38 | | 34-5 | 7 | 88 |
| 28-230 | 4 | 24 | | 34-6 | 1 | 12 |
| 28-231 | 16 | 170 | | 34-7 | 0.85 | 9 |
| 28-232 | 0.65 | 7 | | 34-8 | 6 | 94 |
| 28-233 | 1 | 6 | | 34-9 | 3 | 51 |
| 28-234 | 2 | 63 | | 35-1 | 6 | 45 |
| 28-235 | 0.85 | 25 | | 35-2 | 9 | 290 |
| 28-236 | 0.90 | 23 | | 35-3 | 9 | 59 |
| 28-237 | 1 | 33 | | 35-4 | 16 | 133 |
| 28-238 | 2 | 38 | | 35-5 | 13 | 169 |
| 28-239 | 2 | 20 | | 35-6 | 62 | >500 |
| 28-240 | 2 | 27 | | 35-7 | 33 | 243 |
| 28-241 | 2 | 28 | | 35-8 | 3 | 19 |
| 29 | 1 | 35 | | 35-9 | 30 | 315 |
| 30-1 | 9 | 106 | | 35-10 | 3 | 38 |
| 30-2 | 4 | 135 | | 35-11 | 10 | 78 |
| 30-4 | 1 | 265 | | 35-12 | 20 | 103 |
| 30-5 | 21 | 665 | | 35-13 | 5 | 38 |
| 30-6 | 125 | 1500 | | 35-14 | 9 | >500 |
| 30-7 | 6 | 420 | | 35-15 | 3 | 28 |
| 30-8 | 6 | 240 | | 35-16 | 9 | 58 |
| 30-9 | 16 | 910 | | 35-17 | 66 | 480 |
| 30-10 | 10 | 610 | | 35-18 | 13 | 136 |
| 30-12 | 40 | 1200 | | 35-19 | 5 | 23 |
| 30-13 | 11 | 500 | | 35-20 | 21 | 172 |
| 30-14 | 51 | 1050 | | 35-21 | 25 | 500 |
| 30-15 | 260 | >1500 | | 35-22 | 7 | 218 |
| 30-16 | 2 | 242 | | 35-23 | 37 | 295 |
| 30-17 | 0.85 | 17 | | 35-24 | 180 | >500 |
| 30-18 | 2 | 136 | | 35-25 | 21 | 306 |

-continued

| Example | JAK1 IC$_{50}$ | JAK2 IC$_{50}$ |
|---|---|---|
| 35-26 | 2 | 49 |
| 35-27 | 5 | 35 |
| 35-28 | 3 | 115 |
| 35-29 | 38 | >500 |
| 35-30 | 10 | 180 |
| 35-31 | 9 | 59 |
| 35-32 | 5 | 60 |
| 35-33 | 9 | 200 |
| 35-34 | 3 | 23 |
| 35-35 | 47 | 425 |
| 35-36 | 10 | 111 |
| 35-37 | 43 | >500 |
| 36-1 | 0.65 | 4 |
| 36-2 | 3 | 20 |
| 37 | 0.80 | 13 |
| 38-1 | 2 | 14 |
| 38-2 | 0.90 | 12 |
| 38-3 | 0.90 | 8 |
| 38-4 | 0.50 | 5 |
| 38-5 | 12 | 46 |
| 38-6 | 1 | 6 |
| 39 | 0.45 | 2 |
| 40 | 0.35 | 2 |
| 41 | 20 | 184 |
| 42-1 | 0.25 | 3 |
| 42-2 | 3 | 27 |
| 42-3 | 32 | 85 |
| 42-4 | 2 | 7 |
| 43-1 | 16 | 119 |
| 43-2 | 1 | 9 |
| 43-3 | 16 | 150 |
| 43-4 | 2 | 15 |
| 43-5 | 3 | 28 |
| 43-6 | 0.30 | 2 |
| 43-7 | 2 | 18 |
| 43-8 | 0.15 | 1 |
| 43-9 | 2 | 31 |
| 43-10 | 0.20 | 3 |
| 44-1 | 2 | 43 |
| 44-2 | 30 | 990 |
| 44-3 | 5 | 72 |
| 44-4 | 30 | 1000 |
| 44-5 | 3 | 46 |
| 44-6 | 11 | 200 |
| 44-7 | 1 | 29 |
| 45-1 | 44 | 235 |
| 45-2 | 0.85 | 4 |
| 45-3 | 147 | 308 |
| 45-4 | 13 | 59 |
| 45-6 | 2 | 32 |
| 45-7 | 0.25 | 4 |

What is claimed is:

1. A compound of formula I or a pharmaceutically acceptable salt or stereoisomer thereof:

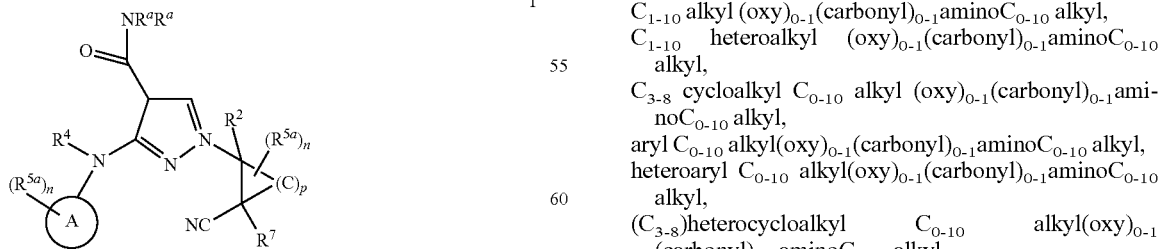

I $R^a$ and $R^4$ are each independently selected from hydrogen and $C_{1-4}$alkyl;
A is selected from aryl, and heteroaryl;
n is 0, 1, 2, 3, or 4;
p is 2, 3, or 4;
$R^2$ and $R^7$ are each independently selected from
 hydrogen,
 halogen,
 $C_{1-10}$ alkyl,
 $C_{2-10}$ alkenyl,
 $C_{2-10}$ heteroalkyl,
 aryl $C_{0-10}$ alkyl$C_{0-10}$ alkyl,
 $C_{3-8}$ cycloalkyl$C_{0-10}$ alkyl,
 heteroaryl $C_{0-10}$ alkyl,
 $(C_{3-8})$heterocycloalkyl $C_{0-10}$ alkyl,
 and wherein each of $R^2$ and $R^7$ are independently substituted with 0, 1, 2, 3, or 4 $R^{5a}$ substituents;
$R^{5a}$ is selected from:
 halogen,
 $C_{1-10}$ alkyl(oxy)$_{0-1}$(carbonyl)$_{0-1}$C$_{0-10}$ alkyl,
 $C_{1-10}$ heteroalkyl(oxy)$_{0-1}$(carbonyl)$_{0-1}$C$_{0-10}$ alkyl,
 $C_{2-10}$ alkenyl(oxy)$_{0-1}$(carbonyl)$_{0-1}$C$_{0-10}$ alkyl,
 aryl $C_{0-10}$ alkyl(oxy)$_{0-1}$(carbonyl)$_{0-1}$C$_{0-10}$ alkyl,
 aryl $C_{2-10}$ alkenyl(oxy)$_{0-1}$(carbonyl)$_{0-1}$C$_{0-10}$ alkyl,
 aryl $C_{2-10}$ alkynyl(oxy)$_{0-1}$(carbonyl)$_{0-1}$C$_{0-10}$ alkyl,
 $C_{3-8}$ cycloalkyl $C_{0-10}$ alkyl(oxy)$_{0-1}$(carbonyl)$_{0-1}$C$_{0-10}$ alkyl,
 heteroaryl $C_{0-10}$ alkyl(oxy)$_{0-1}$(carbonyl)$_{0-1}$C$_{0-10}$ alkyl,
 $(C_{3-8})$heterocycloalkyl $C_{0-10}$ alkyl(oxy)$_{0-1}$(carbonyl)$_{0-1}$C$_{0-10}$ alkyl,
 $C_{1-10}$ alkyl(carbonyl)$_{0-1}$oxyC$_{0-10}$ alkyl,
 $C_{1-10}$ heteroalkyl(carbonyl)$_{0-1}$oxyC$_{0-10}$ alkyl,
 $C_{2-10}$ alkenyl(carbonyl)$_{0-1}$oxyC$_{0-10}$ alkyl,
 $C_{1-10}$ heteroalkyl(carbonyl)$_{0-1}$oxyC$_{0-10}$ alkyl,
 aryl $C_{0-10}$ alkyl (carbonyl)$_{0-1}$oxyC$_{0-10}$ alkyl,
 $(C_{3-8})$cycloalkyl $C_{0-10}$ alkyl(carbonyl)$_{0-1}$oxyC$_{0-10}$ alkyl,
 heteroaryl$C_{0-10}$ alkyl(carbonyl)$_{0-1}$oxyC$_{0-10}$ alkyl,
 $(C_{3-8})$heterocycloalkyl $C_{0-10}$ alkyl(carbonyl)$_{0-1}$oxyC$_{0-10}$ alkyl,
 $((C_{0-10})$alkyl$)_{1-2}$aminocarbonyloxy,
 $(C_{0-10})$heteroalkylaminocarbonyloxy,
 aryl $(C_{0-10})$alkylaminocarbonyloxy,
 $(C_{3-8})$cycloalkyl$(C_{0-10})$alkylaminocarbonyloxy,
 heteroaryl$(C_{0-10})$alkylaminocarbonyloxy,
 $(C_{3-8})$heterocycloalkyl$(C_{0-10})$alkylaminocarbonyloxy,
 $C_{1-10}$ alkylamino(oxy)$_{0-1}$(carbonyl)$_{0-1}$C$_{2-10}$ alkenyl,
 $C_{1-10}$ alkylamino(oxy)$_{0-1}$(carbonyl)$_{0-1}$C$_{0-10}$ alkyl,
 $(C_{0-10})$heteroalkylamin(oxy)$_{0-1}$(carbonyl)$_{0-1}$C$_{0-10}$ alkyl,
 $C_{3-8}$ cycloalkyl $C_{0-10}$ alkylamino(oxy)$_{0-1}$carbonylC$_{0-10}$ alkyl,
 aryl $C_{0-10}$ alkylamino(oxy)$_{0-1}$carbonylC$_{0-10}$ alkyl,
 heteroaryl $C_{0-10}$ alkylamino((oxy)$_{0-1}$(carbonyl)$_{0-1}$C$_{0-10}$ alkyl,
 $(C_{3-8})$heterocycloalkyl $C_{0-10}$ alkylamino(oxy)$_{0-1}$(carbonyl)$_{0-10}$C$_{0-10}$ alkyl,
 $C_{1-10}$ alkyl (oxy)$_{0-1}$(carbonyl)$_{0-1}$aminoC$_{0-10}$ alkyl,
 $C_{1-10}$ heteroalkyl (oxy)$_{0-1}$(carbonyl)$_{0-1}$aminoC$_{0-10}$ alkyl,
 $C_{3-8}$ cycloalkyl $C_{0-10}$ alkyl (oxy)$_{0-1}$(carbonyl)$_{0-1}$aminoC$_{0-10}$ alkyl,
 aryl $C_{0-10}$ alkyl(oxy)$_{0-1}$(carbonyl)$_{0-1}$aminoC$_{0-10}$ alkyl,
 heteroaryl $C_{0-10}$ alkyl(oxy)$_{0-1}$(carbonyl)$_{0-1}$aminoC$_{0-10}$ alkyl,
 $(C_{3-8})$heterocycloalkyl $C_{0-10}$ alkyl(oxy)$_{0-1}$(carbonyl)$_{0-1}$aminoC$_{0-10}$ alkyl,
 —CO$_2$(C$_{0-10}$ alkyl),
 —(C$_{0-10}$ alkyl)CO$_2$H,
 Oxo (=O),
 formyl,
 sulfonyl, $C_{1-10}$ alkylsulfonyl,
$C_{1-10}$ heteroalkylsulfonyl,
$(C_{3-8})$ cycloalkylsulfonyl,
$(C_{3-8})$ cycloheteroalkylsulfonyl,
heteroarylsulfonyl,
arylsulfonyl,
aminosulfonyl,
—$SO_2N(C_{0-6}alkyl)_{1-2}$,
—$SO_2C_{1-6}alkyl$,
—$SO_2CF_3$,
—$SO_2CF_2H$,
—$Si(CH_3)_3$
$C_{1-10}$ alkylsulfinyl,
amino,
$(C_{0-10}$ alkyl$)_{1-2}$ amino,
$C_{1-4}$acylamino $C_{0-10}$ alkyl,
hydroxyl,
$(C_{1-10}$ alkyl)OH,
$C_{0-10}$ alkylalkoxyl,
imino($C_{0-10}$alkyl),
$(C_{0-10}$alkyl)imino,
cyano,
$C_{1-6}$alkylcyano, and
$C_{1-6}$haloalkyl;
wherein two $R^{5a}$ and the atom to which they are attached may optionally form a 3-, 4-, 5-, or 6-membered saturated ring system;
wherein $R^{5a}$ is each optionally substituted with 1, 2, 3, or 4 $R^6$ substituents and $R^6$ independently selected from:
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkenyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-8}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-8})$heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{2-10}$ alkenyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl (carbonyl)$_{0-1}$oxy$C_{0-10}$ alkyl,
$(C_{3-8})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-8})$heterocycloalkyl $C_{0-10}$ alkyl (carbonyl)$_{0-1}$oxy$C_{0-10}$ alkyl,
$((C_{0-10})$alkyl$)_{1-2}$aminocarbonyloxy,
aryl $(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{1-10}$ alkylamino(oxy)$_{0-1}$carbonyl$C_{0-10}$ alkyl,
$C_{3-8}$ cycloalkyl $C_{0-10}$ alkylamino(oxy)$_{0-1}$carbonyl $C_{0-10}$ alkyl,
aryl $C_{0-10}$ alkylamino(oxy)$_{0-1}$carbonyl$C_{0-10}$ alkyl,
heteroaryl $C_{0-10}$ alkylamino(oxy)$_{0-1}$carbonyl$C_{0-10}$ alkyl,
$(C_{3-8})$heterocycloalkyl $C_{0-10}$ alkylamino(oxy)$_{0-1}$carbonyl$C_{0-10}$ alkyl,
$C_{1-10}$ alkyl (oxy)$_{0-1}$(carbonyl)$_{0-1}$amino$C_{0-10}$ alkyl,
$C_{3-8}$ cycloalkyl $C_{0-10}$ alkyl (oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino $C_{0-10}$ alkyl,
$(C_{3-8})$heterocycloalkyl $C_{0-10}$ alkyl(oxy)$_{0-1}$(carbonyl)$_{0-1}$amino$C_{0-10}$ alkyl,
—$CO_2(C_{0-10}$ alkyl),
—$(C_{0-10}$ alkyl)$CO_2H$,
Oxo (=O),
Sulfonyl,
$C_{1-10}$ alkylsulfonyl,
$C_{1-10}$ heteroalkylsulfonyl,
$(C_{3-8})$cycloalkylsulfonyl,
$(C_{3-8})$cycloheteroalkylsulfonyl,
heteroarylsulfonyl,
arylsulfonyl,
aminosulfonyl,
—$SO_2N(C_{1-6}alkyl)_{1-2}$,
—$SO_2C_{1-6}alkyl$,
—$SO_2CF_3$,
—$SO_2CF_2H$,
$C_{1-10}$ alkylsulfinyl,
—$OSi(C_{1-10}$ alkyl)$_3$,
amino,
$(C_{0-10}$alkyl$)_{1-2}$ amino,
-(oxy)$_{0-1}$(carbonyl)$_{0-1}N(C_{0-10}$alkyl)$_{1-2}$,
$C_{1-4}$acylamino$C_{0-10}$alkyl,
imino($C_{0-10}$alkyl),
$(C_{0-10}$alkyl)imino,
hydroxy,
$(C_{1-10}$alkyl)OH,
$C_{1-10}$ alkoxy,
cyano, and
$C_{1-6}$haloalkyl;
wherein two $R^6$ and the atoms to which they are attached may optionally form a 3-, 4-, 5-, or 6-membered saturated ring system; and
$R^6$ is optionally substituted with 1, 2, or 3 substituents selected from hydrogen, hydroxy, $(C_{1-6})$alkyl, $(C_{1-6})$ alkoxy, $(C_{1-10}$ alkyl)OH, halogen, $CO_2H$, —$(C_{0-6})$ alkylCN, —$O(C=O)C_1$-$C_6$ alkyl, $NO_2$, trifluoromethoxy, trifluoroethoxy, trifluoromethyl, trifluoroethyl, —N—$C(O)O(C_{0-6})$alkyl, $C_{1-10}$ alkylsulfonyl, $C_{1-10}$ heteroalkylsulfonyl, oxo (O=), $(C_{3-8})$ cycloalkylsulfonyl, $(C_{3-8})$ cycloheteroalkylsulfonyl, heteroarylsulfonyl, arylsulfonyl, aminosulfonyl, —$SO_2N(C_{1-6}alkyl)_{1-2}$, —$SO_2C_{1-6}alkyl$, —$SO_2CF_3$, —$SO_2CF_2H$, —$C_{1-10}$ alkylsulfinyl, —$OSi(C_{1-10}$ alkyl)$_3$, —$O_{(0-1)}(C_{1-10})$haloalkyl, amino $(C_{1-6}alkyl)_{0-2}$ and $NH_2$; with the proviso that the compound of formula I is other than:

1-[(1R,2S,6S and 1S,2R,6R)-2-cyano-6-hydroxycyclohexyl]-3-(phenylamino)-1H-pyrazole-4-carboxamide;

1-[(1S,2R and 1R,2S)-2-cyanocyclohexyl]-3-{[2-(trifluoromethyl)pyridin-4-yl]amino}-1H-pyrazole-4-carboxamide; and 3-[(2-chloropyridin-4-yl)amino]-1-[(1S,2R and 1R,2S)-2-cyanocyclohexyl]-1H-pyrazole-4-carboxamide.

2. A compound of claim 1, or a pharmaceutically acceptable salt or a stereoisomer thereof, where in the compound of Group A is selected from:

1-[2-cyanocyclopentyl]-3-(phenylamino)-1H-pyrazole-4-carboxamide;

1-{2-cyanocyclopentyl}-3-(phenylamino)-1H-pyrazole-4-carboxamide;

1-[2-cyanocyclohexyl]-3-(phenylamino)-1H-pyrazole-4-carboxamide;
1-{[2-cyanocyclopentyl]}-3-{[4-(methylsulfonyl)phenyl]amino}-1H-pyrazole-4-carboxamide;
1-{[2-cyanocyclopentyl]}-3-{[4-(methylsulfonyl)phenyl]amino}-1H-pyrazole-4-carboxamide;
1-((2-cyanocyclohexyl)-3-(phenylamino)-1H-pyrazole-4-carboxamide;
1-[2-cyano-4-hydroxycyclohexyl]-3-(phenylamino)-1H-pyrazole-4-carboxamide;
1-(8-cyano-1,4-dioxaspiro[4.5]dec-7-yl)-3-(phenylamino)-1H-pyrazole-4-carboxamide;
methyl-3-[4-carbamoyl-3-(phenylamino)-1H-pyrazol-1-yl]-4-cyanocyclohexanecarboxylate;
1-[2-cyano-6-hydroxycyclohexyl]-3-(phenylamino)-1H-pyrazole-4-carboxamide;
1-[2-cyano-3-hydroxycyclohexyl]-3-(phenylamino)-1H-pyrazole-4-carboxamide;
1-[2-cyano-5-hydroxycyclohexyl]-3-(phenylamino)-1H-pyrazole-4-carboxamide;
1-[2-cyanocyclohexyl]-3-{[4-(methylsulfonyl)phenyl]amino}-1H-pyrazole-4-carboxamide;
[4-({4-Carbamoyl-1-[2-cyanocyclohexyl]-1H-pyrazol-3-yl}amino)phenyl]acetic acid;
[4-({4-carbamoyl-1-[2-cyanocyclohexyl]-1H-pyrazol-3-yl}amino)phenyl]acetic acid;
1-[2-Cyano-4-hydroxycyclohexyl]-3-[(4-fluorophenyl)amino]-1H-pyrazole-4-carboxamide;
1-[2-Cyano-4-hydroxycyclohexyl]-3-[(4-fluorophenyl)amino]-1H-pyrazole-4-carboxamide;
1-[2-cyano-5-(dimethylamino)cyclohexyl]-3-[(4-fluorophenyl)amino]-1H-pyrazole-4-carboxamide;
1-[2-cyano-5-(dimethylamino)cyclohexyl]-3-[(4-fluorophenyl)amino]-1H-pyrazole-4-carboxamide;
1-{[2-cyano-5-(methylamino)cyclohexyl]-3-[(4-fluorophenyl)amino]-1H-pyrazole-4-carboxamide;
1-{[5-(benzylamino)-2-cyanocyclohexyl]-3-[(4-fluorophenyl)amino]-1H-pyrazole-4-carboxamide;
tert-Butyl-4-{4-carbamoyl-3-[(4-fluorophenyl)amino]-1H-pyrazol-1-yl}-3-cyanocyclohexanecarboxylate;
methyl-4-{4-carbamoyl-3-[(4-fluorophenyl)amino]-1H-pyrazol-1-yl}-3-cyanocyclohexanecarboxylate;
1-2-Cyano-4-(hydroxymethyl)cyclohexyl]-3-((4-fluorophenyl)amino)-1H-pyrazole-4-carboxamide;
1-((4-(Aminomethyl)-2-cyanocyclohexyl)-3-((4-fluorophenyl)amino)-1H-pyrazole-4-carboxamide;
1-((2-Cyano-4-formylcyclohexyl)-3-((4-fluorophenyl)amino)-1H-pyrazole-4-carboxamide;
1-{2-Cyano-5,5-dimethylcyclohexyl}-3-(phenylamino)-1H-pyrazole-4-carboxamide;
tert-butyl [3-{4-carbamoyl-3-[(4-fluorophenyl)amino]-1H-pyrazol-1-yl}-4-cyanocyclohexyl]carbamate;
1-(2-cyano-5-methylcyclohexyl)-3-(phenylamino)-1H-pyrazole-4-carboxamide;
1-(5-cyanospiro[2.5]octan-6-yl)-3-[2-fluoropyridin-4-yl)amino)-1H-pyrazole-4-carboxamide;
tert-butyl {[3-{4-carbamoyl-3-[(4-fluorophenyl)amino]-1H-pyrazol-1-yl}-4-cyanocyclohexyl]methyl}carbamate;
tert-butyl {[3-{4-carbamoyl-3-[(4-fluorophenyl)amino]-1H-pyrazol-1-yl}-4-cyanocyclohexyl]methyl}carbamate;
tert-butyl 3-(4-carbamoyl-3-(phenylamino)-1H-pyrazol-1-yl)-4-cyanocyclohexanecarboxylate;
1-[2-Cyano-4-hydroxycyclohexyl]-3-({4-[(trifluoromethyl)sulfonyl]phenyl}amino)-1H-pyrazole-4-carboxamide;
1-[2-Cyano-4-hydroxycyclohexyl]-3-({4-[(difluoromethyl)sulfonyl]phenyl}amino)-1H-pyrazole-4-carboxamide;
1-[2-Cyano-4-hydroxycyclohexyl]-3-[(2-fluoropyridin-4-yl)amino]-1H-pyrazole-4-carboxamide;
1-[2-cyanocyclohexyl]-3-({4-[(trifluoromethyl)sulfonyl]phenyl}amino)-1H-pyrazole-4-carboxamide;
1-[(2-cyanocyclohexyl]-3-[(2-fluoropyridin-4-yl)amino]-1H-pyrazole-4-carboxamide;
tert-butyl 4-[4-carbamoyl-3-({4-[(trifluoromethyl)sulfonyl]phenyl}amino)-1H-pyrazol-1-yl]-3-cyanocyclohexanecarboxylate;
1-[2-Cyanocyclohexyl]-3-{[2-(trifluoromethyl)pyridin-4-yl]amino}-1H-pyrazole-4-carboxamide;
1-[2-Cyanocyclohexyl]-3-{[2-(trifluoromethyl)pyridin-4-yl]amino}-1H-pyrazole-4-carboxamide;
1-[2-cyanocyclohexyl]-3-{[4-(methylcarbamoyl)phenyl]amino}-1H-pyrazole-4-carboxamide;
1-[2-cyanocyclohexyl]-3-[(4-cyanophenyl)amino]-1H-pyrazole-4-carboxamide;
1-[2-cyanocyclohexyl]-3-{[4-(3-methyl-1,2,4-oxadiazol-5-yl)phenyl]amino}-1H-pyrazole-4-carboxamide;
3-[(2-chloropyridin-4-yl)amino]-1-[2-cyanocyclohexyl]-1H-pyrazole-4-carboxamide;
1-[2-cyanocyclohexyl]-3-{[3-fluoro-4-(methylsulfonyl)phenyl]amino}-1H-pyrazole-4-carboxamide;
1-[2-cyanocyclohexyl]-3-({4-[(difluoromethyl)sulfonyl]phenyl}amino)-1H-pyrazole-4-carboxamide;
1-[(2-cyanocyclohexyl]-3-{[4-(ethylsulfonyl)phenyl]amino}-1H-pyrazole-4-carboxamide;
1-[2-cyanocyclohexyl]-3-[(2-oxo-1,2,3,4-tetrahydroquinolin-6-yl)amino]-1H-pyrazole-4-carboxamide;
1-[2-cyanocyclohexyl]-3-({4-[(2,2,2-trifluoroethyl)sulfonyl]phenyl}amino)-1H-pyrazole-4-carboxamide;
1-[2-cyanocyclohexyl]-3-{[4-(methylcarbamoyl)phenyl]amino}-1H-pyrazole-4-carboxamide;
1-[2-cyanocyclohexyl]-3-[(4-fluorophenyl)amino]-1H-pyrazole-4-carboxamide;
1-[2-cyanocyclohexyl]-3-[(4-cyanophenyl)amino]-1H-pyrazole-4-carboxamide;
1-[2-cyanocyclohexyl]-3-({3-(hydroxymethyl)-4-[(trifluoromethyl)sulfonyl]phenyl}amino)-1H-pyrazole-4-carboxamide;
1-[2-cyanocyclohexyl]-3-[(4-fluorophenyl)amino]-1H-pyrazole-4-carboxamide;
1-[2-cyanocyclohexyl]-3-[(6-fluoropyridin-3-yl)amino]-1H-pyrazole-4-carboxamide;
1-[2-cyanocyclohexyl]-3-{[1-oxo-2-(2,2,2-trifluoroethyl)-2,3-dihydro-1H-isoindol-5-yl]amino}-1H-pyrazole-4-carboxamide;
1-[2-cyanocyclohexyl]-3-{[1-oxo-2-(2,2,2-trifluoroethyl)-2,3-dihydro-1H-isoindol-5-yl]amino}-1H-pyrazole-4-carboxamide;
1-[2-cyanocyclohexyl]-3-{[2-(1-methyl-1H-pyrazol-4-yl)pyridin-4-yl]amino}-1H-pyrazole-4-carboxamide;
1-[2-cyanocyclohexyl]-3-[(6-fluoropyridin-3-yl)amino]-1H-pyrazole-4-carboxamide;
1-[2-cyanocyclohexyl]-3-[(4-formylphenyl)amino]-1H-pyrazole-4-carboxamide;
3-[(4-bromophenyl)amino]-1-[2-cyanocyclohexyl]-1H-pyrazole-4-carboxamide;
3-[(4-acetylphenyl)amino]-1-[2-cyanocyclohexyl]-1H-pyrazole-4-carboxamide;
1-[2-cyanocyclohexyl]-3-({4-[3,3,3-trifluoro-2-hydroxy-1,1-dimethylpropyl]phenyl}amino)-1H-pyrazole-4-carboxamide;

1-[2-cyanocyclohexyl]-3-({4-[3,3,3-trifluoro-2-hydroxy-1,1-dimethylpropyl]phenyl}amino)-1H-pyrazole-4-carboxamide;
1-[2-cyanocyclohexyl]-3-({3-fluoro-4-[3,3,3-trifluoro-2-hydroxy-1,1-dimethylpropyl]phenyl}amino)-1H-pyrazole-4-carboxamide;
1-[2-cyanocyclohexyl]-3-({6-[2,2,2-trifluoro-1-hydroxy-1-methylethyl]pyridin-3-yl}amino)-1H-pyrazole-4-carboxamide;
1-[2-cyanocyclohexyl]-3-({4-[2,2,2-trifluoro-1-hydroxyethyl]phenyl}amino)-1H-pyrazole-4-carboxamide;
1-[2-cyanocyclohexyl]-3-({6-[2,2-difluoro-1-hydroxyethyl]pyridin-3-yl}amino)-1H-pyrazole-4-carboxamide;
1-[2-cyanocyclohexyl]-3-({6-[2,2-difluoro-1-hydroxy-1-methylethyl]pyridin-3-yl}amino)-1H-pyrazole-4-carboxamide;
1-[2-cyanocyclohexyl]-3-[(7-fluoroquinolin-3-yl)amino]-1H-pyrazole-4-carboxamide;
3-[(6-chloropyridin-3-yl)amino]-1-[2-cyanocyclohexyl]-1H-pyrazole-4-carboxamide;
2-[4-({4-carbamoyl-1-[2-cyanocyclohexyl]-1H-pyrazol-3-yl}amino)phenyl]-2-methylpropanoic acid;
3-[(6-chloropyridin-3-yl)amino]-1-[2-cyanocyclohexyl]-1H-pyrazole-4-carboxamide;
3-[(6-chloropyridin-3-yl)amino]-1-[(1R,2R)-2-cyanocyclohexyl]-1H-pyrazole-4-carboxamide;
3-[(6-chloropyridin-3-yl)amino]-1-[(1S,2S)-2-cyanocyclohexyl]-1H-pyrazole-4-carboxamide;
3-{[4-(aminomethyl)phenyl]amino}-1-[2-cyanocyclohexyl]-1H-pyrazole-4-carboxamide;
1-[2-cyanocyclohexyl]-3-({6-[2,2,2-trifluoro-1-hydroxyethyl]pyridin-3-yl}amino)-1H-pyrazole-4-carboxamide;
3-[(5-chloropyridin-3-yl)amino]-1-[(2-cyanocyclohexyl)-1H-pyrazole-4-carboxamide;
1-[2-cyanocyclohexyl]-3-[(6-fluoroquinolin-3-yl)amino]-1H-pyrazole-4-carboxamide;
1-[(2-cyanocyclohexyl)-3-[(3,4-dichlorophenyl)amino]-1H-pyrazole-4-carboxamide;
1-[2-cyanocyclohexyl]-3-({6-[2,2,2-trifluoro-1-hydroxyethyl]pyridin-3-yl}amino)-1H-pyrazole-4-carboxamide;
3-[(3-chloro-5-fluorophenyl)amino]-1-[2-cyanocyclohexyl]-1H-pyrazole-4-carboxamide;
2-[4-({4-carbamoyl-1-[2-cyanocyclohexyl]-1H-pyrazol-3-yl}amino)phenyl]-2-methylpropanoic acid;
1-[2-cyanocyclohexyl]-3-(pyridazin-4-ylamino)-1H-pyrazole-4-carboxamide;
1-[2-cyanocyclohexyl]-3-[(3,5-dichlorophenyl)amino]-1H-pyrazole-4-carboxamide;
1-[2-cyanocyclohexyl]-3-{[6-(difluoromethyl)pyridin-3-yl]amino}-1H-pyrazole-4-carboxamide;
3-[(4-chloro-3-fluorophenyl)amino]-1-[2-cyanocyclohexyl]-1H-pyrazole-4-carboxamide;
1-[2-cyanocyclohexyl]-3-[(4-{1,1-dimethyl-2-oxo-2-[(2,2,2-trifluoroethyl)amino]ethyl}phenyl)amino]-1H-pyrazole-4-carboxamide;
3-[(3-chloro-4-fluorophenyl)amino]-1-[2-cyanocyclohexyl]-1H-pyrazole-4-carboxamide;
1-[2-cyanocyclohexyl]-3-{[6-(difluoromethyl)pyridin-3-yl]amino}-1H-pyrazole-4-carboxamide;
3-[(6-chloroquinolin-3-yl)amino]-1-[2-cyanocyclohexyl]-1H-pyrazole-4-carboxamide;
3-[(7-chloroquinolin-3-yl)amino]-1-[2-cyanocyclohexyl]-1H-pyrazole-4-carboxamide;
1-[2-cyanocyclohexyl]-3-[(3-hydroxy-1,1-dioxido-2,3-dihydro-1-benzothiophen-5-yl)amino]-1H-pyrazole-4-carboxamide;
1-[2-cyanocyclohexyl]-3-[(1,1-dioxido-1-benzothiophen-5-yl)amino]-1H-pyrazole-4-carboxamide;
1-[(2-cyanocyclohexyl)-3-({4-[(difluoromethyl)sulfonyl]-3-(hydroxymethyl)phenyl}amino)-1H-pyrazole-4-carboxamide;
1-[2-cyanocyclohexyl]-3-({4-[(fluoromethyl)sulfonyl]phenyl}amino)-1H-pyrazole-4-carboxamide;
1-[2-cyanocyclohexyl]-3-({4-[(cyclopropylmethyl)sulfamoyl]phenyl}amino)-1H-pyrazole-4-carboxamide;
1-[2-cyanocyclohexyl]-3-{[4-(pyridin-2-ylsulfamoyl)phenyl]amino}-1H-pyrazole-4-carboxamide;
1-[2-cyanocyclohexyl]-3-({4-[(2-morpholin-4-ylethyl)sulfamoyl]phenyl}amino)-1H-pyrazole-4-carboxamide;
3-({4-[(4-benzylpiperidin-1-yl)sulfonyl]phenyl}amino)-1-[2-cyanocyclohexyl]-1H-pyrazole-4-carboxamide;
methyl 5-({4-carbamoyl-1-[2-cyanocyclohexyl]-1H-pyrazol-3-yl}amino)pyridine-2-carboxylate;
N-tert-butyl-5-({4-carbamoyl-1-[2-cyanocyclohexyl]-1H-pyrazol-3-yl}amino)pyridine-3-carboxamide;
methyl 5-({4-carbamoyl-1-[2-cyanocyclohexyl]-1H-pyrazol-3-yl}amino)pyridine-3-carboxylate;
1-[2-cyanocyclohexyl]-3-[(5-methylpyridin-3-yl)amino]-1H-pyrazole-4-carboxamide;
1-[2-cyanocyclohexyl]-3-[(5-cyanopyridin-3-yl)amino]-1H-pyrazole-4-carboxamide;
1-[2-cyanocyclohexyl]-3-[(6-cyanopyridin-3-yl)amino]-1H-pyrazole-4-carboxamide;
1-[2-cyanocyclohexyl]-3-[(7-oxo-6,7-dihydro-5H-pyrrolo[3,4-b]pyridin-3-yl)amino]-1H-pyrazole-4-carboxamide;
1-[2-cyanocyclohexyl]-3-[(6-cyano-5-methylpyridin-3-yl)amino]-1H-pyrazole-4-carboxamide;
methyl 5-({4-carbamoyl-1-[2-cyanocyclohexyl]-1H-pyrazol-3-yl}amino)-3-methylpyridine-2-carboxylate;
1-[2-cyanocyclohexyl]-3-[(6-cyano-5-fluoropyridin-3-yl)amino]-1H-pyrazole-4-carboxamide;
1-[2-cyanocyclohexyl]-3-[(6-cyclopropylpyridin-3-yl)amino]-1H-pyrazole-4-carboxamide;
1-[2-cyanocyclohexyl]-3-{[4-(pyridin-4-ylsulfamoyl)phenyl]amino}-1H-pyrazole-4-carboxamide;
1-[2-cyanocyclohexyl]-3-{[4-(cyclohexylsulfamoyl)phenyl]amino}-1H-pyrazole-4-carboxamide;
3-{[4-(benzylsulfamoyl)phenyl]amino}-1-[2-cyanocyclohexyl]-1H-pyrazole-4-carboxamide;
1-[2-cyanocyclohexyl]-3-({4-[(pyridin-3-ylmethyl)sulfamoyl]phenyl}amino)-1H-pyrazole-4-carboxamide;
1-[2-cyanocyclohexyl]-3-({4-[(pyridin-2-ylmethyl)sulfamoyl]phenyl}amino)-1H-pyrazole-4-carboxamide;
1-[2-cyanocyclohexyl]-3-({4-[(pyridin-4-ylmethyl)sulfamoyl]phenyl}amino)-1H-pyrazole-4-carboxamide;
1-[2-cyanocyclohexyl]-3-({4-[(2-pyrrolidin-1-ylethyl)sulfamoyl]phenyl}amino)-1H-pyrazole-4-carboxamide;
1-[2-cyanocyclohexyl]-3-({4-[(2,6-dimethylphenyl)sulfamoyl]phenyl}amino)-1H-pyrazole-4-carboxamide;
3-({4-[(4-acetylpiperazin-1-yl)sulfonyl]phenyl}amino)-1-[2-cyanocyclohexyl]-1H-pyrazole-4-carboxamide;
3-({4-[(4-chlorobenzyl)sulfamoyl]phenyl}amino)-1-[2-cyanocyclohexyl]-1H-pyrazole-4-carboxamide;
1-[2-cyanocyclohexyl]-3-{[4-(1,4-dioxa-8-azaspiro[4.5]dec-8-ylsulfonyl)phenyl]amino}-1H-pyrazole-4-carboxamide;

1-[2-cyanocyclohexyl]-3-({4-[(1-methylethyl)sulfamoyl]phenyl}amino)-1H-pyrazole-4-carboxamide;
1-[2-cyanocyclohexyl]-3-{[4-(quinolin-7-ylsulfamoyl)phenyl]amino}-1H-pyrazole-4-carboxamide;
1-[2-cyanocyclohexyl]-3-[(4-{[4-(trifluoromethyl)phenyl]sulfamoyl}phenyl)amino)-1H-pyrazole-4-carboxamide;
1-[2-cyanocyclohexyl]-3-[(4-{[4-(trifluoromethyl)benzyl]sulfamoyl}phenyl)amino)-1H-pyrazole-4-carboxamide;
1-[2-cyanocyclohexyl]-3-[(4-{[4-(3-methoxyphenyl)piperazin-1-yl]sulfonyl}phenyl)amino]-1H-pyrazole-4-carboxamide;
1-[2-cyanocyclohexyl]-3-({4-[(2-methoxyethyl)sulfamoyl]phenyl}amino)-1H-pyrazole-4-carboxamide;
1-[2-cyanocyclohexyl]-3-{[4-(morpholin-4-ylsulfonyl)phenyl]amino}-1H-pyrazole-4-carboxamide;
1-[2-cyanocyclohexyl]-3-[(3,4-difluorophenyl)amino]-1H-pyrazole-4-carboxamide;
1-[2-cyanocyclohexyl]-3-{[6-(trifluoromethyl)pyridin-3-yl]amino}-1H-pyrazole-4-carboxamide;
1-[2-cyanocyclohexyl]-3-{[4-(difluoromethoxy)phenyl]amino}-1H-pyrazole-4-carboxamide;
3-[(4-chlorophenyl)amino]-1-[2-cyanocyclohexyl]-1H-pyrazole-4-carboxamide;
1-[2-cyanocyclohexyl]-3-{[4-(trifluoromethyl)phenyl]amino}-1H-pyrazole-4-carboxamide;
3-[(4-chlorophenyl)amino]-1-[2-cyanocyclohexyl]-1H-pyrazole-4-carboxamide;
1-[2-cyanocyclohexyl]-3-{[6-(trifluoromethyl)pyridin-3-yl]amino}-1H-pyrazole-4-carboxamide;
1-(2-Cyano-5-hydroxy-2-methylcyclohexyl)-3-((4-fluorophenyl)amino)-1H-pyrazole-4-carboxamide;
1-(2-cyano-5-fluoro-2-methylcyclohexyl)-3-[4-fluorophenyl)amino)-1H-pyrazole-4-carboxamide;
1-2-cyano-2-methylcyclohexyl)-3-((4-fluorophenyl)amino)-1H-pyrazole-4-carboxamide;
1-[2-Cyanocyclohexyl]-3-[(1,1-dioxido-2,3-dihydro-1-benzothiophen-5-yl)amino]-1H-pyrazole-4-carboxamide;
1-[(2-Cyanocyclohexyl]-3-{[5-(1-methyl-1H-pyrazol-4-yl)pyridin-3-yl]amino}-1H-pyrazole-4-carboxamide;
1-[(2-cyanocyclohexyl]-3-{[6-(1-methyl-1H-pyrazol-4-yl)pyridin-3-yl]amino}-1H-pyrazole-4-carboxamide;
1-[2-cyanocyclohexyl]-3-{[6-(1H-pyrazol-4-yl)pyridin-3-yl]amino}-1H-pyrazole-4-carboxamide;
1-[2-Cyano-4-fluorocyclohexyl]-3-(phenylamino)-1H-pyrazole-4-carboxamide;
1-[6-cyanocyclohex-3-en-1-yl]-3-(phenylamino)-1H-pyrazole-4-carboxamide;
1-[2-Cyano-6-fluorocyclohexyl]-3-(phenylamino)-1H-pyrazole-4-carboxamide;
1-(2-cyano-4(R)-hydroxycyclohexyl)-3-((4-(trifluoromethoxy)phenyl)amino)-1H-pyrazole-4-carboxamide;
1-[2-cyano-4-hydroxycyclohexyl]-3-{[6-(difluoromethoxy)pyridin-3-yl]amino}-1H-pyrazole-4-carboxamide;
3-[(4-chloro-3-fluorophenyl)amino]-1-[2-cyano-4-hydroxycyclohexyl]-1H-pyrazole-4-carboxamide;
1-[2-cyano-4-hydroxycyclohexyl]-3-[(4-cyanophenyl)amino]-1H-pyrazole-4-carboxamide;
1-[2-cyano-4-hydroxycyclohexyl]-3-{[4-(trifluoromethyl)phenyl]amino}-1H-pyrazole-4-carboxamide;
1-[2-cyano-4-hydroxycyclohexyl]-3-[(3,4-dichlorophenyl)amino]-1H-pyrazole-4-carboxamide;
1-[2-cyano-4-hydroxycyclohexyl]-3-({4-[(1S or 1R)-2,2,2-trifluoro-1-hydroxy-1-methylethyl]phenyl}amino)-1H-pyrazole-4-carboxamide;
1-[2-cyano-4-hydroxycyclohexyl]-3-{[4-(2-fluoro-1,1-dimethylethyl)phenyl]amino}-1H-pyrazole-4-carboxamide;
1-[2-cyano-4-hydroxycyclohexyl]-3-{[6-(trifluoromethyl)pyridin-3-yl]amino}-1H-pyrazole-4-carboxamide;
1-[2-cyano-4-hydroxycyclohexyl]-3-{[4-(1-methoxy-1-methylethyl)phenyl]amino}-1H-pyrazole-4-carboxamide;
3-[(6-chloropyridin-3-yl)amino]-1-[2-cyano-4-hydroxycyclohexyl]-1H-pyrazole-4-carboxamide;
1-[2-cyano-4-hydroxycyclohexyl]-3-({4-[2,2,2-trifluoro-1-hydroxyethyl]phenyl}amino)-1H-pyrazole-4-carboxamide;
1-[2-cyano-4-hydroxycyclohexyl]-3-[(4-cyclopropylphenyl)amino]-1H-pyrazole-4-carboxamide;
1-[2-cyano-4-hydroxycyclohexyl]-3-{[6-(difluoromethyl)pyridin-3-yl]amino}-1H-pyrazole-4-carboxamide;
1-[2-cyano-4-hydroxycyclohexyl]-3-({4-[(1R)-2,2,2-trifluoro-1-hydroxy-1-methylethyl]phenyl}amino)-1H-pyrazole-4-carboxamide;
1-[2-cyano-4-hydroxycyclohexyl]-3-{[4-(3-methyloxetan-3-yl)phenyl]amino}-1H-pyrazole-4-carboxamide;
1-[2-cyano-4-hydroxycyclohexyl]-3-[(2-fluoropyridin-4-yl)amino]-1H-pyrazole-4-carboxamide;
3-[(4-chlorophenyl)amino]-1-[2-cyano-4-hydroxycyclohexyl]-1H-pyrazole-4-carboxamide;
1-[2-cyano-4-hydroxycyclohexyl]-3-{[3-fluoro-4-(trifluoromethyl)phenyl]amino}-1H-pyrazole-4-carboxamide;
1-[2-cyano-4-hydroxycyclohexyl]-3-{[4-(trifluoromethyl)phenyl]amino}-1H-pyrazole-4-carboxamide;
1-[2-cyano-4-hydroxycyclohexyl]-3-[(2-fluoropyridin-4-yl)amino]-1H-pyrazole-4-carboxamide;
1-[2-cyano-4-hydroxycyclohexyl]-3-{[4-(difluoromethoxy)phenyl]amino}-1H-pyrazole-4-carboxamide;
3-[(4-chlorophenyl)amino]-1-[2-cyano-4-hydroxycyclohexyl]-1H-pyrazole-4-carboxamide;
1-[2-cyano-4-hydroxycyclohexyl]-3-{[4-(methylsulfonyl)phenyl]amino}-1H-pyrazole-4-carboxamide;
1-[2-cyano-4-hydroxycyclohexyl]-3-(phenylamino)-1H-pyrazole-4-carboxamide;
1-[2-Cyano-4-(cyclopropylmethoxy)cyclohexyl]-3-[(2-fluoropyridin-4-yl)amino]-1H-pyrazole-4-carboxamide;
1-[2-cyano-4-(cyclopropylmethoxy)cyclohexyl]-3-({4-[(1R or 1S)-2,2,2-trifluoro-1-hydroxyethyl]phenyl}amino)-1H-pyrazole-4-carboxamide;
1-[2-cyano-4-(cyclopropylmethoxy)cyclohexyl]-3-[(4-fluorophenyl)amino]-1H-pyrazole-4-carboxamide;
1-[(4-[4-carbamoyl-3-({4-[(trifluoromethyl)sulfonyl]phenyl}amino)-1H-pyrazol-1-yl]-3-cyano-N,N-dimethylcyclohexanaminium trifluoroacetate;
1-[2-cyano-4-(methylamino)cyclohexyl]-3-[(4-fluorophenyl)amino]-1H-pyrazole-4-carboxamide;
1-[2-cyano-4-(ethylamino)cyclohexyl]-3-({4-[(trifluoromethyl)sulfonyl]phenyl}amino)-1H-pyrazole-4-carboxamide;
1-[2-cyano-4-(methylamino)cyclohexyl]-3-({4-[(trifluoromethyl)sulfonyl]phenyl}amino)-1H-pyrazole-4-carboxamide, 1-[2-cyano-4-(dimethylamino)cyclohexyl]-3-({4-[(trifluoromethyl)sulfonyl]phenyl}amino)-1H-pyrazole-4-carboxamide;
1-[2-cyano-4-(cyclopropylamino)cyclohexyl]-3-({4-[(trifluoromethyl)sulfonyl]phenyl}amino)-1H-pyrazole-4-carboxamide;
1-{2-cyano-4-[(2,2,2-trifluoroethyl)amino]cyclohexyl}-3-({4-[(trifluoromethyl)sulfonyl]phenyl}amino)-1H-pyrazole-4-carboxamide;
1-{2-cyano-4-[(2,2,2-trifluoroethyl)amino]cyclohexyl}-3-({4-[(difluoromethyl)sulfonyl]phenyl}amino)-1H-pyrazole-4-carboxamide;
1-[2-cyano-4-(morpholin-4-yl)cyclohexyl]-3-({4-[(trifluoromethyl)sulfonyl]phenyl)amino)-1H-pyrazole-4-carboxamide;
1-{(2-cyano-4-[(2,2-difluoroethyl)amino]cyclohexyl}-3-({4-[(trifluoromethyl)sulfonyl]phenyl)amino)-1H-pyrazole-4-carboxamide;
1-{2-cyano-4-[(2-hydroxyethyl)amino]cyclohexyl}-3-({4-[(trifluoromethyl)sulfonyl]phenyl)amino)-1H-pyrazole-4-carboxamide;
1-{2-cyano-4-[(2-methoxyethyl)amino]cyclohexyl}-3-({4-[(trifluoromethyl)sulfonyl]phenyl)amino)-1H-pyrazole-4-carboxamide;
1-{2-cyano-4-[(2-fluoroethyl)amino]cyclohexyl}-3-({4-[(trifluoromethyl)sulfonyl]phenyl)amino)-1H-pyrazole-4-carboxamide;
1-{2-cyano-4-[(2-fluoroethyl)amino]cyclohexyl}-3-({4-[(trifluoromethyl)sulfonyl]phenyl)amino)-1H-pyrazole-4-carboxamide;
1-[4-(Azetidin-1-yl)-2-cyanocyclohexyl]-3-{[6-(difluoromethoxy)pyridin-3-yl]amino}-1H-pyrazole-4-carboxamide;
1-((4-(Azetidin-1-yl)-2-cyanocyclohexyl)-3-(phenylamino)-1H-pyrazole-4-carboxamide;
1-(4-(tert-butyl(methyl)amino)-2-cyanocyclohexyl)-3-((4-chlorophenyl)amino)-1H-pyrazole-4-carboxamide;
1-{2-cyano-4-[3-(1-hydroxy-1-methylethyl)azetidin-1-yl]cyclohexyl}-3-{[4-(trifluoromethyl)phenyl]amino}-1H-pyrazole-4-carboxamide;
1-[2-cyano-4-{[1-cyclopropylethyl]amino}cyclohexyl]-3-{[6-(trifluoromethyl)pyridin-3-yl]amino}-1H-pyrazole-4-carboxamide;
1-{2-cyano-4-[(2,4-dimethylazetidin-1-yl]cyclohexyl}-3-{[4-(trifluoromethyl)phenyl]amino}-1H-pyrazole-4-carboxamide;
1-{2-cyano-4-[(cyclopropylmethyl)amino]cyclohexyl}-3-{[4-(trifluoromethyl)phenyl]amino}-1H-pyrazole-4-carboxamide;
1-[4-azetidin-1-yl-2-cyanocyclohexyl]-3-{[6-(trifluoromethyl)pyridin-3-yl]amino}-1H-pyrazole-4-carboxamide;
1-[2-cyano-4-(dimethylamino)cyclohexyl]-3-{[6-(difluoromethoxy)pyridin-3-yl]amino}-1H-pyrazole-4-carboxamide;
1-[2-cyano-4-{[(1S)-1-cyclopropylethyl]amino}cyclohexyl]-3-{[6-(difluoromethoxy)pyridin-3-yl]amino}-1H-pyrazole-4-carboxamide;
1-[2-cyano-4-(dimethylamino)cyclohexyl]-3-{[6-(difluoromethoxy)pyridin-3-yl]amino}-1H-pyrazole-4-carboxamide;
1-{2-cyano-4-[6-(hydroxymethyl)-3-azabicyclo [3.1.0] hex-3-yl]cyclohexyl}-3-{[4-(trifluoromethyl)phenyl]amino}-1H-pyrazole-4-carboxamide;
1-[2-cyano-4-{[(3-methyloxetan-3-yl)methyl]amino}cyclohexyl]-3-{[4-(trifluoromethyl)phenyl]amino}-1H-pyrazole-4-carboxamide;
1-[4-(2-azaspiro[3.3]hept-2-yl)-2-cyanocyclohexyl]-3-{[4-(trifluoromethyl)phenyl]amino}-1H-pyrazole-4-carboxamide;
1-[2-cyano-4-(dimethylamino)cyclohexyl]-3-{[6-(trifluoromethyl)pyridin-3-yl]amino}-1H-pyrazole-4-carboxamide;
1-[2-cyano-4-{[(1-hydroxycyclopropyl)methyl]amino}cyclohexyl]-3-{[4-(trifluoromethyl)phenyl]amino}-1H-pyrazole-4-carboxamide;
1-[4-azetidin-1-yl-2-cyanocyclohexyl]-3-[(4-chloro-3-fluorophenyl)amino]-1H-pyrazole-4-carboxamide;
3-[(4-chloro-3-fluorophenyl)amino]-1-[2-cyano-4-(dimethylamino)cyclohexyl]-1H-pyrazole-4-carboxamide;
3-[(4-chloro-3-fluorophenyl)amino]-1-[(2-cyano-4-(methylamino)cyclohexyl]-1H-pyrazole-4-carboxamide;
3-[(4-chlorophenyl)amino]-1-[2-cyano-4-(methylamino)cyclohexyl]-1H-pyrazole-4-carboxamide;
1-[2-cyano-4-(3,3-dimethylazetidin-1-yl)cyclohexyl]-3-({4-[2,2,2-trifluoro-1-hydroxyethyl]phenyl}amino)-1H-pyrazole-4-carboxamide;
1-[4-azetidin-1-yl-2-cyanocyclohexyl]-3-({4-[2,2,2-trifluoro-1-hydroxyethyl]phenyl}amino)-1H-pyrazole-4-carboxamide;
3-[(4-chloro-3-fluorophenyl)amino]-1-[2-cyano-4-{[1-cyclopropylethyl]amino}cyclohexyl]-1H-pyrazole-4-carboxamide;
1-[4-azetidin-1-yl-2-cyanocyclohexyl]-3-({4-[(1R)-2,2,2-trifluoro-1-hydroxy-1-methylethyl]phenyl}amino)-1H-pyrazole-4-carboxamide;
1-[4-azetidin-1-yl-2-cyanocyclohexyl]-3-{[6-(difluoromethyl)pyridin-3-yl]amino}-1H-pyrazole-4-carboxamide;
1-[4-(2-azaspiro[3.3]hept-2-yl)-2-cyanocyclohexyl]-3-({4-[2,2,2-trifluoro-1-hydroxyethyl]phenyl}amino)-1H-pyrazole-4-carboxamide;
1-[4-(tert-butylamino)-2-cyanocyclohexyl]-3-({4-[2,2,2-trifluoro-1-hydroxyethyl]phenyl}amino)-1H-pyrazole-4-carboxamide;
1-[4-azetidin-1-yl-2-cyanocyclohexyl]-3-{[4-(2,2,2-trifluoro ethyl)phenyl]amino}-1H-pyrazole-4-carboxamide;
1-[2-cyano-4-(dimethylamino)cyclohexyl]-3-{[4-(trifluoromethoxy)phenyl]amino}-1H-pyrazole-4-carboxamide;
1-[2-cyano-4-{[1-cyclopropylethyl]amino}cyclohexyl]-3-{[4-(trifluoromethoxy)phenyl]amino}-1H-pyrazole-4-carboxamide;
1-[4-azetidin-1-yl-2-cyanocyclohexyl]-3-{[4-(trifluoromethoxy)phenyl]amino}-1H-pyrazole-4-carboxamide;
1-[4-(2-azaspiro[3.3]hept-2-yl)-2-cyanocyclohexyl]-3-({4-[2,2,2-trifluoro-1-hydroxyethyl]phenyl}amino)-1H-pyrazole-4-carboxamide;
1-[2-cyano-4-(3,3-dimethylazetidin-1-yl)cyclohexyl]-3-({4-[2,2,2-trifluoro-1-hydroxy-1-methylethyl]phenyl}amino)-1H-pyrazole-4-carboxamide;
3-[(3-chloro-4-fluorophenyl)amino]-1-{2-cyano-4-[(2,2-difluoroethyl)amino]cyclohexyl}-1H-pyrazole-4-carboxamide;
1-[(4-azetidin-1-yl-2-cyanocyclohexyl]-3-[(4-formylphenyl)amino]-1H-pyrazole-4-carboxamide;
3-[(4-chloro-3-fluorophenyl)amino]-1-[2-cyano-4-{[1-cyclopropylethyl]amino}cyclohexyl]-1H-pyrazole-4-carboxamide;
2-[4-({1-[(4-azetidin-1-yl-2-cyanocyclohexyl]-4-carbamoyl-1H-pyrazol-3-yl}amino)phenyl]-2-methylpropanoic acid;

2-[4-({1-[4-(2-azaspiro[3.3]hept-2-yl)-2-cyanocyclohexyl]-4-carbamoyl-1H-pyrazol-3-yl}amino)phenyl]-2-methylpropanoic acid;

1-[2-cyano-4-(oxetan-3-ylamino)cyclohexyl]-3-{[4-(2,2,2-trifluoroethyl)phenyl]amino}-1H-pyrazole-4-carboxamide;

3-[(4-acetylphenyl)amino]-1-[4-azetidin-1-yl-2-cyanocyclohexyl]-1H-pyrazole-4-carboxamide;

1-[2-cyano-4-(3,3-dimethylazetidin-1-yl)cyclohexyl]-3-({4-[2,2,2-trifluoro-1-hydroxy-1-methylethyl]phenyl}amino)-1H-pyrazole-4-carboxamide;

1-[2-cyano-4-(dimethylamino)cyclohexyl]-3-[(4-fluorophenyl)amino]-1H-pyrazole-4-carboxamide;

3-[(4-chlorophenyl)amino]-1-[2-cyano-4-(3-methylazetidin-1-yl)cyclohexyl]-1H-pyrazole-4-carboxamide;

1-[4-(benzylamino)-2-cyanocyclohexyl]-3-[(2-fluoropyridin-4-yl)amino]-1H-pyrazole-4-carboxamide;

3-[(4-chlorophenyl)amino]-1-[2-cyano-4-{[(1S)-1-cyclopropylethyl]amino}cyclohexyl]-1H-pyrazole-4-carboxamide;

1-[2-cyano-4-(3-methoxyazetidin-1-yl)cyclohexyl]-3-{[4-(trifluoromethyl)phenyl]amino}-1H-pyrazole-4-carboxamide;

1-[4-azetidin-1-yl-2-cyanocyclohexyl]-3-[(4-chlorophenyl)amino]-1H-pyrazole-4-carboxamide;

1-[4-azetidin-1-yl-2-cyanocyclohexyl]-3-[(2-fluoropyridin-4-yl)amino]-1H-pyrazole-4-carboxamide;

1-[4-azetidin-1-yl-2-cyanocyclohexyl]-3-{[4-(difluoromethoxy)phenyl]amino}-1H-pyrazole-4-carboxamide;

1-[2-cyano-4-(3-fluoroazetidin-1-yl)cyclohexyl]-3-{[4-(trifluoromethyl)phenyl]amino}-1H-pyrazole-4-carboxamide;

1-{2-cyano-4-[(2,2-difluoroethyl)amino]cyclohexyl}-3-[(2-fluoropyridin-4-yl)amino]-1H-pyrazole-4-carboxamide;

1-{2-cyano-4-[(2,2,2-trifluoroethyl)amino]cyclohexyl}-3-({4-[(trifluoromethyl)sulfonyl]phenyl}amino)-1H-pyrazole-4-carboxamide;

1-[4-azetidin-1-yl-2-cyanocyclohexyl]-3-{[4-(difluoromethoxy)phenyl]amino}-1H-pyrazole-4-carboxamide;

1-[4-azetidin-1-yl-2-cyanocyclohexyl]-3-[(4-chlorophenyl)amino]-1H-pyrazole-4-carboxamide;

1-[4-azetidin-1-yl-2-cyanocyclohexyl]-3-[(2-fluoropyridin-4-yl)amino]-1H-pyrazole-4-carboxamide;

1-{2-cyano-4-[(2,2,2-trifluoroethyl)amino]cyclohexyl}-3-[(2-fluoropyridin-4-yl)amino]-1H-pyrazole-4-carboxamide;

1-[2-cyano-4-(3-fluoroazetidin-1-yl)cyclohexyl]-3-({4-[(trifluoromethyl)sulfonyl]phenyl}amino)-1H-pyrazole-4-carboxamide;

1-{2-cyano-4-[(2,2-difluoroethyl)(methyl)amino]cyclohexyl}-3-({4-[(trifluoromethyl)sulfonyl]phenyl}amino)-1H-pyrazole-4-carboxamide;

1-{2-cyano-4-[(2,2-difluoroethyl)amino]cyclohexyl}-3-[(4-cyanophenyl)amino]-1H-pyrazole-4-carboxamide;

3-[(4-chlorophenyl)amino]-1-[2-cyano-4-(dimethylamino)cyclohexyl]-1H-pyrazole-4-carboxamide;

1-[2-cyano-4-(2-oxa-6-azaspiro[3.3]hept-6-yl)cyclohexyl]-3-{[4-(trifluoromethyl)phenyl]amino}-1H-pyrazole-4-carboxamide;

1-[2-cyano-4-(3-methylazetidin-1-yl)cyclohexyl]-3-{[4-(trifluoromethyl)phenyl]amino}-1H-pyrazole-4-carboxamide;

1-{2-cyano-4-[(2,2-difluoroethyl)amino]cyclohexyl}-3-({4-[(difluoromethyl)sulfonyl]phenyl}amino)-1H-pyrazole-4-carboxamide;

3-[(4-chlorophenyl)amino]-1-[2-cyano-4-(dimethylamino)cyclohexyl]-1H-pyrazole-4-carboxamide;

1-[2-cyano-4-(dimethylamino)cyclohexyl]-3-[(2-fluoropyridin-4-yl)amino]-1H-pyrazole-4-carboxamide;

1-[4-(2-azaspiro[3.3]hept-2-yl)-2-cyanocyclohexyl]-3-{[4-(methylsulfonyl)phenyl]amino}-1H-pyrazole-4-carboxamide;

1-[4-azetidin-1-yl-2-cyanocyclohexyl]-3-{[4-(trifluoromethyl)phenyl]amino}-1H-pyrazole-4-carboxamide;

1-[4-(2-azaspiro[3.3]hept-2-yl)-2-cyanocyclohexyl]-3-[(2-fluoropyridin-4-yl)amino]-1H-pyrazole-4-carboxamide;

1-[2-cyano-4-(3,3-dimethylazetidin-1-yl)cyclohexyl]-3-[(2-fluoropyridin-4-yl)amino]-1H-pyrazole-4-carboxamide;

1-[2-cyano-4-(dimethylamino)cyclohexyl]-3-(phenylamino)-1H-pyrazole-4-carboxamide;

1-[4-(2-azaspiro[3.3]hept-2-yl)-2-cyanocyclohexyl]-3-(phenylamino)-1H-pyrazole-4-carboxamide;

1-[2-cyano-4-(cyclopropylamino)cyclohexyl]-3-{[4-(trifluoromethyl)phenyl]amino}-1H-pyrazole-4-carboxamide;

1-[2-cyano-4-(3,3-dimethylazetidin-1-yl)cyclohexyl]-3-(phenylamino)-1H-pyrazole-4-carboxamide;

1-[2-cyano-4-(cyclopropylamino)cyclohexyl]-3-{[4-(trifluoromethyl)phenyl]amino}-1H-pyrazole-4-carboxamide;

1-[2-cyano-4-(3-methylazetidin-1-yl)cyclohexyl]-3-(phenylamino)-1H-pyrazole-4-carboxamide;

1-[2-cyano-4-(3,3-dimethylazetidin-1-yl)cyclohexyl]-3-[(2-fluoropyridin-4-yl)amino]-1H-pyrazole-4-carboxamide;

1-[4-(2-azaspiro[3.3]hept-2-yl)-2-cyanocyclohexyl]-3-[(2-fluoropyridin-4-yl)amino]-1H-pyrazole-4-carboxamide, 3-[(4-chlorophenyl)amino]-1-[2-cyano-4-(3,3-dimethylazetidin-1-yl)cyclohexyl]-1H-pyrazole-4-carboxamide;

1-[4-(2-azaspiro[3.3]hept-2-yl)-2-cyanocyclohexyl]-3-{[4-(methylsulfonyl)phenyl]amino}-1H-pyrazole-4-carboxamide;

3-[(4-chlorophenyl)amino]-1-[2-cyano-4-(6-oxa-1-azaspiro[3.3]hept-1-yl)cyclohexyl]-1H-pyrazole-4-carboxamide;

1-[2-cyano-4-(3-methoxyazetidin-1-yl)cyclohexyl]-3-({4-[(trifluoromethyl)sulfonyl]phenyl}amino)-1H-pyrazole-4-carboxamide;

1-[2-cyano-4-{[2-(methylsulfonyl)ethyl]amino}cyclohexyl]-3-({4-[(trifluoromethyl)sulfonyl]phenyl}amino)-1H-pyrazole-4-carboxamide;

1-{2-cyano-4-[(2-methoxyethyl)(methyl)amino]cyclohexyl}-3-({4-[(trifluoromethyl)sulfonyl]phenyl}amino)-1H-pyrazole-4-carboxamide;

1-[2-cyano-4-(3-hydroxyazetidin-1-yl)cyclohexyl]-3-({4-[(trifluoromethyl)sulfonyl]phenyl}amino)-1H-pyrazole-4-carboxamide;

1-[2-cyano-4-{[(1,1-dioxidotetrahydrothiophen-3-yl)methyl]amino}cyclohexyl]-3-({4-[(trifluoromethyl)sulfonyl]phenyl}amino)-1H-pyrazole-4-carboxamide;

1-{2-cyano-4-[(1,1-dioxidotetrahydrothiophen-3-yl)amino]cyclohexyl}-3-({4-[(trifluoromethyl)sulfonyl]phenyl}amino)-1H-pyrazole-4-carboxamide;

1-[2-cyano-4-{[2-(dimethylsulfamoyl)ethyl] amino}cyclohexyl]-3-({4-[(trifluoromethyl)sulfonyl]phenyl}amino)-1H-pyrazole-4-carboxamide;
1-[2-cyano-4-(oxetan-3-ylamino)cyclohexyl]-3-({4-[(trifluoromethyl)sulfonyl]phenyl}amino)-1H-pyrazole-4-carboxamide;
1-{2-cyano-4-[(2R)-2-(fluoromethyl)pyrrolidin-1-yl]cyclohexyl}-3-({4-[(trifluoromethyl)sulfonyl]phenyl}amino)-1H-pyrazole-4-carboxamide;
1-{2-cyano-4-[(3S)-3-fluoropyrrolidin-1-yl]cyclohexyl}-3-({4-[(trifluoromethyl)sulfonyl]phenyl}amino)-1H-pyrazole-4-carboxamide;
N-{4-[4-carbamoyl-3-({4-[(trifluoromethyl)sulfonyl]phenyl}amino)-1H-pyrazol-1-yl]-3-cyanocyclohexyl}glycine;
1-{2-cyano-4-[(dicyclopropylmethyl)amino]cyclohexyl}-3-({4-[(trifluoromethyl)sulfonyl]phenyl}amino)-1H-pyrazole-4-carboxamide;
1-{2-cyano-4-[(2,2-difluoroethyl)amino]cyclohexyl}-3-({4-[(trifluoromethyl)sulfonyl]phenyl}amino)-1H-pyrazole-4-carboxamide;
1-{2-cyano-4-[(3,3,3-trifluoropropyl)amino]cyclohexyl}-3-({4-[(trifluoromethyl)sulfonyl]phenyl}amino)-1H-pyrazole-4-carboxamide;
1-[4-azetidin-1-yl-2-cyanocyclohexyl]-3-({4-[(trifluoromethyl)sulfonyl]phenyl}amino)-1H-pyrazole-4-carboxamide;
1-{2-cyano-4-[methyl(3,3,3-trifluoropropyl)amino]cyclohexyl}-3-({4-[(trifluoromethyl)sulfonyl]phenyl}amino)-1H-pyrazole-4-carboxamide;
1-{2-cyano-4-[(cyclopropylmethyl)amino]cyclohexyl}-3-({4-[(trifluoromethyl)sulfonyl]phenyl}amino)-1H-pyrazole-4-carboxamide;
1-{2-cyano-4-[(1-methylethyl)amino]cyclohexyl}-3-({4-[(trifluoromethyl)sulfonyl]phenyl}amino)-1H-pyrazole-4-carboxamide;
1-[2-cyano-4-{[1-cyclopropylethyl]amino}cyclohexyl]-3-({4-[(trifluoromethyl)sulfonyl]phenyl}amino)-1H-pyrazole-4-carboxamide;
1-{2-cyano-4-[(dicyclopropylmethyl)(methyl)amino]cyclohexyl}-3-({4-[(trifluoromethyl)sulfonyl]phenyl}amino)-1H-pyrazole-4-carboxamide;
1-[2-cyano-4-(dicyclopropylamino)cyclohexyl]-3-({4-[(trifluoromethyl)sulfonyl]phenyl}amino)-1H-pyrazole-4-carboxamide;
1-[2-cyano-4-{[(1R)-1-cyclopropylethyl]amino}cyclohexyl]-3-({4-[(trifluoromethyl)sulfonyl]phenyl}amino)-1H-pyrazole-4-carboxamide;
1-[2-cyano-4-(3-methylazetidin-1-yl)cyclohexyl]-3-({4-[(trifluoromethyl)sulfonyl]phenyl}amino)-1H-pyrazole-4-carboxamide;
1-[2-cyano-4-(dimethylamino)cyclohexyl]-3-{[4-(trifluoromethyl)phenyl]amino}-1H-pyrazole-4-carboxamide;
1-[2-cyano-4-{[1-cyclopropylethyl]amino}cyclohexyl]-3-{[4-(trifluoromethyl)phenyl]amino}-1H-pyrazole-4-carboxamide;
1-[2-cyano-4-{[1-cyclopropyl-2,2,2-trifluoroethyl]amino}cyclohexyl]-3-{[4-(trifluoromethyl)phenyl]amino}-1H-pyrazole-4-carboxamide;
1-[2-cyano-4-(2,2-dimethylazetidin-1-yl)cyclohexyl]-3-{[4-(trifluoromethyl)phenyl]amino}-1H-pyrazole-4-carboxamide;
1-[(2-cyano-4-(3-hydroxy-3-methylazetidin-1-yl)cyclohexyl]-3-{[4-(trifluoromethyl)phenyl]amino}-1H-pyrazole-4-carboxamide;
1-{2-cyano-4-[3-hydroxy-3-(trifluoromethyl)azetidin-1-yl]cyclohexyl}-3-{[4-(trifluoromethyl)phenyl]amino}-1H-pyrazole-4-carboxamide;
1-[4-(tert-butylamino)-2-cyanocyclohexyl]-3-{[4-(trifluoromethyl)phenyl]amino}-1H-pyrazole-4-carboxamide;
3-[(4-chlorophenyl)amino]-1-{2-cyano-4-[(1-methylcyclopropyl)amino]cyclohexyl}-1H-pyrazole-4-carboxamide;
3-[(4-chlorophenyl)amino]-1-{2-cyano-4-[(3-methyloxetan-3-yl)amino]cyclohexyl}-1H-pyrazole-4-carboxamide;
3-[(4-chlorophenyl)amino]-1-{2-cyano-4-[(1-cyclopropyl-1-methylethyl)amino]cyclohexyl}-1H-pyrazole-4-carboxamide;
3-[(4-chlorophenyl)amino]-1-{2-cyano-4-[(2-hydroxy-1,1-dimethylethyl)amino]cyclohexyl}-1H-pyrazole-4-carboxamide;
3-[(4-chlorophenyl)amino]-1-{(2-cyano-4-[3-(1-hydroxy-1-methylethyl)azetidin-1-yl]cyclohexyl}-1H-pyrazole-4-carboxamide;
3-[(4-chlorophenyl)amino]-1-{2-cyano-4-[3-hydroxy-3-(trifluoromethyl)azetidin-1-yl]cyclohexyl}-1H-pyrazole-4-carboxamide;
1-{2-cyano-4-[(1-cyclopropyl-1-methylethyl)amino]cyclohexyl}-3-(phenylamino)-1H-pyrazole-4-carboxamide;
1-[4-(tert-butylamino)-2-cyanocyclohexyl]-3-(phenylamino)-1H-pyrazole-4-carboxamide;
1-{2-cyano-4-[(1-methylcyclopropyl)amino]cyclohexyl}-3-(phenylamino)-1H-pyrazole-4-carboxamide;
3-[(4-chlorophenyl)amino]-1-[(2-cyano-4-{[(3-methyloxetan-3-yl)methyl]amino}cyclohexyl]-1H-pyrazole-4-carboxamide;
3-[(4-chlorophenyl)amino]-1-[2-cyano-4-(tetrahydro-2H-pyran-4-ylamino)cyclohexyl]-1H-pyrazole-4-carboxamide;
3-[(4-chlorophenyl)amino]-1-[2-cyano-4-{methyl [(3-methyloxetan-3-yl)methyl]amino}cyclohexyl]-1H-pyrazole-4-carboxamide;
3-[(4-chlorophenyl)amino]-1-[2-cyano-4-{[(1-hydroxycyclopropyl)methyl]amino}cyclohexyl]-1H-pyrazole-4-carboxamide;
3-[(4-chlorophenyl)amino]-1-{2-cyano-4-[(2-hydroxy-2-methylpropyl)amino]cyclohexyl}-1H-pyrazole-4-carboxamide;
3-[(4-chlorophenyl)amino]-1-[2-cyano-4-{[1-(hydroxymethyl)cyclopropyl]amino}cyclohexyl]-1H-pyrazole-4-carboxamide;
3-[(4-chlorophenyl)amino]-1-2-cyano-4-[(2,2,2-trifluoroethyl)amino]cyclohexyl}-1H-pyrazole-4-carboxamide;
3-[(4-chlorophenyl)amino]-1-[(2-cyano-4-{[1-(trifluoromethyl)cyclopropyl]amino}cyclohexyl]-1H-pyrazole-4-carboxamide;
3-[(4-chlorophenyl)amino]-1-{2-cyano-4-[(2-methoxy-2-methylpropyl)amino]cyclohexyl}-1H-pyrazole-4-carboxamide;
3-[(4-chlorophenyl)amino]-1-{2-cyano-4-[(1-cyclopropyl-1-methylethyl)(methyl)amino]cyclohexyl}-1H-pyrazole-4-carboxamide;
1-{2-cyano-4-[(3-methyloxetan-3-yl)amino]cyclohexyl}-3-(phenylamino)-1H-pyrazole-4-carboxamide;
1-{(2-cyano-4-[(2-methoxy-1,1-dimethylethyl)amino]cyclohexyl}-3-(phenylamino)-1H-pyrazole-4-carboxamide;

3-[(4-chlorophenyl)amino]-1-{(2-cyano-4-[methyl(3-methyloxetan-3-yl)amino]cyclohexyl}-1H-pyrazole-4-carboxamide;
1-{2-cyano-4-[methyl(2,2,2-trifluoroethyl)amino]cyclohexyl}-3-[(2-fluoropyridin-4-yl)amino]-1H-pyrazole-4-carboxamide;
1-{2-cyano-4-[methyl(2,2,2-trifluoroethyl)amino]cyclohexyl}-3-[(2-fluoropyridin-4-yl)amino]-1H-pyrazole-4-carboxamide;
3-[(4-chlorophenyl)amino]-1-{2-cyano-4-[(2-methoxy-1,1-dimethylethyl)(methyl)amino]cyclohexyl}-1H-pyrazole-4-carboxamide;
3-[(4-chlorophenyl)amino]-1-{2-cyano-4-[(4-methyltetrahydro-2H-pyran-4-yl)amino]cyclohexyl}-1H-pyrazole-4-carboxamide;
3-[(4-chlorophenyl)amino]-1-{2-cyano-4-[(2-methoxyethyl)amino]cyclohexyl}-1H-pyrazole-4-carboxamide;
3-[(4-chlorophenyl)amino]-1-[(2-cyano-4-{[(1S)-2-methoxy-1-methylethyl]amino}cyclohexyl]-1H-pyrazole-4-carboxamide;
3-[(4-chlorophenyl)amino]-1-{2-cyano-4-[(2-methoxyethyl)(methyl)amino]cyclohexyl}-1H-pyrazole-4-carboxamide;
3-[(4-chlorophenyl)amino]-1-[2-cyano-4-{[2-methoxy-1-methylethyl](methyl)amino}cyclohexyl]-1H-pyrazole-4-carboxamide;
3-[(4-chlorophenyl)amino]-1-[2-cyano-4-{[(1S or 1R)-2-methoxy-1-methylethyl](methyl)amino}cyclohexyl]-1H-pyrazole-4-carb oxamide;
4-{4-carbamoyl-3-[(4-fluorophenyl)amino]-1H-pyrazol-1-yl}-3-cyanocyclohexanaminium trifluoroacetate;
1-{2-Cyano-4-[methyhoxetan-3-yl)amino]cyclohexyl}-3-{[4-(trifluoromethyl)phenyl]amino}-1H-pyrazole-4-carboxamide;
1-{2-cyano-4-[(cyclopropylmethyl)(methyl)amino]cyclohexyl}-3-{[4-(trifluoromethyl)phenyl]amino}-1H-pyrazole-4-carboxamide;
1-[2-cyano-4-({[3-(1-hydroxy-1-methylethyl)cyclobutyl]methyl}amino)cyclohexyl]-3-{[4-(trifluoromethyl)phenyl]amino}-1H-pyrazole-4-carboxamide;
1-[(2-cyano-4-(spiro[3.4]oct-2-ylamino)cyclohexyl]-3-{[4-(trifluoromethyl)phenyl]amino}-1H-pyrazole-4-carboxamide;
1-{2-cyano-4-[cyclobutyl(cyclopropylmethyl)amino]cyclohexyl}-3-{[4-(trifluoromethyl)phenyl]amino}-1H-pyrazole-4-carboxamide;
1-{2-cyano-4-[(2-methylpropyl)amino]cyclohexyl}-3-{[4-(trifluoromethyl)phenyl]amino}-1H-pyrazole-4-carboxamide;
1-{2-cyano-4-[cyclobutyl(methyl)amino]cyclohexyl}-3-{[4-(trifluoromethyl)phenyl]amino}-1H-pyrazole-4-carboxamide;
1-{2-cyano-4-[(cyclopropylmethyl)(2-methylpropyl)amino]cyclohexyl}-3-{[4-(trifluoromethyl)phenyl]amino}-1H-pyrazole-4-carboxamide;
1-{2-cyano-4-[(cyclopropylmethyl)(oxetan-3-yl)amino]cyclohexyl}-3-{[4-(trifluoromethyl)phenyl]amino}-1H-pyrazole-4-carboxamide;
1-{(2-cyano-4-[(2,6-difluorobenzyl)amino]cyclohexyl}-3-{[4-(trifluoromethyl)phenyl]amino}-1H-pyrazole-4-carboxamide;
1-[(2-cyano-4-(cyclobutylamino)cyclohexyl]-3-{[4-(trifluoromethyl)phenyl]amino}-1H-pyrazole-4-carboxamide;
1-{4-[bis(cyclopropylmethyl)amino]-2-cyanocyclohexyl}-3-{[4-(trifluoromethyl)phenyl]amino}-1H-pyrazole-4-carboxamide;
1-{2-cyano-4-[(cyclobutylmethyl)amino]cyclohexyl}-3-{[4-(trifluoromethyl)phenyl]amino}-1H-pyrazole-4-carboxamide;
1-[2-cyano-4-(oxetan-3-ylamino)cyclohexyl]-3-{[4-(trifluoromethyl)phenyl]amino}-1H-pyrazole-4-carboxamide;
1-(4-(4-carbamoyl-3-((4-(trifluoromethyl)phenyl)amino)-1H-pyrazol-1-yl)-3-cyanocyclohexyl)-1-methylazetidin-1-ium 2,2,2-trifluoroacetate;
1-[4-{4-carbamoyl-3-[(4-chlorophenyl)amino]-1H-pyrazol-1-yl}-3-cyanocyclohexyl]-1-methylazetidinium;
1-[4-{4-carbamoyl-3-[(4-chlorophenyl)amino]-1H-pyrazol-1-yl}-3-cyanocyclohexyl]-1-ethylazetidinium;
1-[4-{4-carbamoyl-3-[(4-chlorophenyl)amino]-1H-pyrazol-1-yl}-3-cyanocyclohexyl]-1,3,3-trimethylazetidinium;
1-[4-{4-carbamoyl-3-[(4-chlorophenyl)amino]-1H-pyrazol-1-yl}-3-cyanocyclohexyl]-1-(cyclopropylmethyl)azetidinium;
3-[(4-Chloro-3-fluorophenyl)amino]-1-[2-cyano-4-cyclopropyl-4-hydroxycyclohexyl]-1H-pyrazole-4-carboxamide;
1-[2-cyano-4-hydroxy-4-methylcyclohexyl]-3-{[4-(3,3,3-trifluoro-hydroxy-1,1-dimethylpropyl)phenyl]amino}-1H-pyrazole-4-carboxamide;
1-[2-cyano-4-hydroxy-4-methylcyclohexyl]-3-{[4-(3,3,3-trifluoro-hydroxy-1,1-dimethylpropyl)phenyl]amino}-1H-pyrazole-4-carboxamide;
3-[(4-chlorophenyl)amino]-1-[2-cyano-4-ethenyl-4-hydroxycyclohexyl]-1H-pyrazole-4-carboxamide;
3-[(4-chloro-3-fluorophenyl)amino]-1-[2-cyano-4-hydroxy-4-methylcyclohexyl]-1H-pyrazole-4-carboxamide;
1-[2-cyano-4-hydroxy-4-methylcyclohexyl]-3-({4-[2,2,2-trifluoro-1-hydroxy-1-methylethyl]phenyl}amino)-1H-pyrazole-4-carboxamide;
3-[(4-chlorophenyl)amino]-1-[2-cyano-4-hydroxy-4-methylcyclohexyl]-1H-pyrazole-4-carboxamide;
3-[(4-chlorophenyl)amino]-1-[2-cyano-4-cyclopropyl-4-hydroxycyclohexyl]-1H-pyrazole-4-carboxamide;
1-(2-Cyano-4-hydroxycyclohexyl)-3-((4-(trifluoromethoxy)phenyl)amino)-1H-pyrazole-4-carboxamide;
3-[(4-chlorophenyl)amino]-1-[2-cyano-4-hydroxycyclohexyl]-1H-pyrazole-4-carboxamide;
3-[(4-chloro-3-fluorophenyl)amino]-1-[2-cyano-4-hydroxycyclohexyl]-1H-pyrazole-4-carboxamide;
1-[2-cyano-4-hydroxycyclohexyl]-3-{[4-(trifluoromethyl)phenyl]amino}-1H-pyrazole-4-carboxamide;
1-[2-cyano-4-hydroxycyclohexyl]-3-({4-[(trifluoromethyl)sulfonyl]phenyl}amino)-1H-pyrazole-4-carboxamide;
1-[2-cyano-4-hydroxycyclohexyl]-3-[(4-cyanophenyl)amino]-1H-pyrazole-4-carboxamide;
1-[2-cyano-4-hydroxycyclohexyl]-3-{[6-(difluoromethyl)pyridin-3-yl]amino}-1H-pyrazole-4-carboxamide;
1-[2-cyano-4-hydroxycyclohexyl]-3-{[6-(trifluoromethyl)pyridin-3-yl]amino}-1H-pyrazole-4-carboxamide;
1-[2-cyano-4-hydroxycyclohexyl]-3-({4-[2,2,2-trifluoro-1-hydroxyethyl]phenyl}amino)-1H-pyrazole-4-carboxamide;
1-[2-cyano-4-hydroxycyclohexyl]-3-({4-[2,2,2-trifluoro-1-hydroxy-1-methylethyl]phenyl}amino)-1H-pyrazole-4-carboxamide;

1-[(2-cyano-4-hydroxycyclohexyl]-3-{[4-(3,3,3-trifluoro-hydroxy-1,1-dimethylpropyl)phenyl]amino}-1H-pyrazole-4-carboxamide;
1-[2-cyano-4-hydroxycyclohexyl]-3-[(4-cyclopropylphenyl)amino]-1H-pyrazole-4-carboxamide;
1-[2-cyano-4-hydroxycyclohexyl]-3-{[4-(3-methyloxetan-3-yl)phenyl]amino}-1H-pyrazole-4-carboxamide;
1-[2-cyano-4-hydroxycyclohexyl]-3-[(3,4-dichlorophenyl)amino]-1H-pyrazole-4-carboxamide;
1-[2-cyano-4-hydroxycyclohexyl]-3-{[4-(2-fluoro-1,1-dimethylethyl)phenyl]amino}-1H-pyrazole-4-carboxamide;
1-[2-cyano-4-hydroxycyclohexyl]-3-{[6-(difluoromethoxy)pyridin-3-yl]amino}-1H-pyrazole-4-carboxamide;
4-{4-Carbamoyl-3-[(4-fluorophenyl)amino]-1H-pyrazol-1-yl}-3-cyanocyclohexyl phenylcarbamate;
4-{4-carbamoyl-3-[(4-fluorophenyl)amino]-1H-pyrazol-1-yl}-3-cyanocyclohexyl cyclohexylcarbamate;
4-{4-carbamoyl-3-[(4-fluorophenyl)amino]-1H-pyrazol-1-yl}-3-cyanocyclohexyl phenylcarbamate;
4-{4-carbamoyl-3-[(4-fluorophenyl)amino]-1H-pyrazol-1-yl}-3-cyanocyclohexyl propan-2-ylcarbamate;
4-{4-carbamoyl-3-[(4-fluorophenyl)amino]-1H-pyrazol-1-yl}-3-cyanocyclohexyl methylcarbamate;
4-{4-carbamoyl-3-[(4-fluorophenyl)amino]-1H-pyrazol-1-yl}-3-cyanocyclohexyl ethylcarbamate;
3-((4-chlorophenyl)amino)-1-(2-cyano-4-(3,3-dimethylazetidine-1-carbonyl)cyclohexyl)-1H-pyrazole-4-carboxamide;
3-[(4-chlorophenyl)amino]-1-[2-cyano-4-{[3-(1-hydroxy-1-methylethyl)azetidin-1-yl]carbonyl}cyclohexyl]-1H-pyrazole-4-carboxamide;
1-[4-(2-azaspiro[3.3]hept-2-ylcarbonyl)-2-cyanocyclohexyl]-3-[(4-chlorophenyl)amino]-1H-pyrazole-4-carboxamide;
3-[(4-chlorophenyl)amino]-1-{2-cyano-4-[(dicyclopropylmethyl)carbamoyl]cyclohexyl}-1H-pyrazole-4-carboxamide;
3-[(4-chlorophenyl)amino]-1-{2-cyano-4-[(3,3-difluoroazetidin-1-yl)carbonyl]cyclohexyl}-1H-pyrazole-4-carboxamide;
3-[(4-chlorophenyl)amino]-1-[2-cyano-4-(oxetan-3-ylcarbamoyl)cyclohexyl]-1H-pyrazole-4-carboxamide;
3-[(4-chlorophenyl)amino]-1-[2-cyano-4-{[3-(methylsulfonyl)azetidin-1-yl]carbonyl}cyclohexyl]-1H-pyrazole-4-carboxamide;
3-[(4-chlorophenyl)amino]-1-{2-cyano-4-[(2,2,2-trifluoroethyl)carbamoyl]cyclohexyl}-1H-pyrazole-4-carboxamide;
3-[(4-chlorophenyl)amino]-1-[2-cyano-4-(cyclobutylcarbamoyl)cyclohexyl]-1H-pyrazole-4-carboxamide;
3-[(4-chlorophenyl)amino]-1-[2-cyano-4-{[1-cyclopropyl-2,2,2-trifluoro ethyl]carbamoyl}cyclohexyl]-1H-pyrazole-4-carboxamide;
3-[(4-chlorophenyl)amino]-1-{2-cyano-4-[(3,3-difluorocyclobutyl)carbamoyl]cyclohexyl}-1H-pyrazole-4-carboxamide;
3-[(4-chlorophenyl)amino]-1-[2-cyano-4-(cyclopropylcarbamoyl)cyclohexyl]-1H-pyrazole-4-carboxamide;
3-[(4-chlorophenyl)amino]-1-{2-cyano-4-[(3-hydroxy-3-methylazetidin-1-yl)carbonyl]cyclohexyl}-1H-pyrazole-4-carboxamide;
3-[(4-chlorophenyl)amino]-1-{2-cyano-4-[(3,3-difluoropyrrolidin-1-yl)carbonyl]cyclohexyl}-1H-pyrazole-4-carboxamide;
3-[(4-chlorophenyl)amino]-1-[2-cyano-4-{[(3-methyloxetan-3-yl)methyl]carbamoyl}cyclohexyl]-1H-pyrazole-4-carboxamide;
3-[(4-chlorophenyl)amino]-1-{2-cyano-4-[(3-fluoroazetidin-1-yl)carbonyl]cyclohexyl}-1H-pyrazole-4-carboxamide;
1-[4-(tert-butylcarbamoyl)-2-cyanocyclohexyl]-3-[(4-chlorophenyl)amino]-1H-pyrazole-4-carboxamide;
3-[(4-chlorophenyl)amino]-1-[2-cyano-4-(2-oxa-6-azaspiro[3.3]hept-6-ylcarbonyl)cyclohexyl]-1H-pyrazole-4-carboxamide;
3-(4-Chlorophenylamino)-1-(2-cyano-4-(2-hydroxypropan-2-yl)cyclohexyl)-1H-pyrazole-4-carboxamide;
1-[2-Cyano-4-(fluoromethyl)cyclohexyl]-3-[(2-fluoropyridin-4-yl)amino]-1H-pyrazole-4-carboxamide;
1-{2-Cyano-4-[(methylsulfonyl)amino]cyclohexyl}-3-[(4-fluorophenyl)amino]-1H-pyrazole-4-carboxamide;
3-[(4-chlorophenyl)amino]-1-{2-cyano-4-[(methylsulfonyl)amino]cyclohexyl}-1H-pyrazole-4-carboxamide;
3-[(4-chlorophenyl)amino]-1-{2-cyano-4-[methyl(methylsulfonyl)amino]cyclohexyl}-1H-pyrazole-4-carboxamide;
1-[2-Cyanocyclohexyl]-3-({4-[(methoxyimino)methyl]phenyl}amino)-1H-pyrazole-4-carboxamide;
1-[2-Cyanocyclohexyl]-3-{[4-(N-methoxyethanimidoyl)phenyl]amino}-1H-pyrazole-4-carboxamide;
4-(4-Carbamoyl-3-((4-(trifluoromethyl)phenyl)amino)-1H-pyrazol-1-yl)-5-cyano-2-hydroxycyclohexyl acetate;
1-[2-Cyanocyclohexyl]-3-{[4-(methylsulfonyl)phenyl]amino}-1H-pyrazole-4-carboxamide;
1-[2-Cyanocyclohexyl]-3-({4-[(trifluoromethyl)sulfonyl]phenyl}amino)-1H-pyrazole-4-carboxamide;
1-[2-cyanocyclohexyl]-3-[(4-fluorophenyl)amino]-1H-pyrazole-4-carboxamide;
1-[2-cyanocyclohexyl]-3-({4-[(difluoromethyl)sulfonyl]phenyl}amino)-1H-pyrazole-4-carboxamide;
1-[2-cyanocyclohexyl]-3-({4-[(2,2,2-trifluoroethyl)sulfonyl]phenyl}amino)-1H-pyrazole-4-carboxamide;
1-[2-cyano-4-hydroxycyclohexyl]-3-({4-[(trifluoromethyl)sulfonyl]phenyl}amino)-1H-pyrazole-4-carboxamide;
tert-Butyl [3-{4-carbamoyl-3-[(4-fluorophenyl)amino]-1H-pyrazol-1-yl}-4-cyanocyclohexyl]carbamate;
1-[8-Cyano-1,4-dioxaspiro[4.5]dec-7-yl]-3-(phenylamino)-1H-pyrazole-4-carboxamide; and
1-[2-cyanocyclohexyl]-3-[(1,1-dioxido-2,3-dihydro-1-benzothiophen-5-yl)amino]-1H-pyrazole-4-carboxamide.

3. A pharmaceutical composition comprising a compound of claim 1 or a pharmaceutically acceptable salt or a stereoisomer thereof and a pharmaceutically acceptable carrier.

4. A method for the treatment of a JAK-mediated disease comprising administering to a patient in need thereof a therapeutically effective amount of a compound of claim 1 or a pharmaceutically acceptable salt or stereoisomer thereof.

5. A method of treating a condition in a mammal that can be ameliorated by the selective inhibition of a Janus kinase JAK1 relative to JAK 2 which condition is selected from, arthritis, asthma and obstructive airways diseases, autoimmune diseases or disorders, and cancer comprising administering to the mammal in need of such treatment, a therapeutically effective amount of a compound according to claim 1 for a pharmaceutically acceptable salt or a stereoisomer thereof.

6. A method according to claim 5, wherein said condition is arthritis.

7. A method according to claim 6, wherein said condition is selected from rheumatoid arthritis, juvenile arthritis, and psoriatic arthritis.

8. A method according to claim 5, wherein said condition is asthma or obstructive airways diseases.

9. A method according to claim 8, wherein said condition is selected from: chronic asthma, late asthma, airway hyper-responsiveness, bronchitis, bronchial asthma, allergic asthma, intrinsic asthma, extrinsic asthma, dust asthma, recurrent airway obstruction, chronic obstruction pulmonary disease (COPD), and emphysema.

10. A method according to claim 5, wherein said condition is autoimmune diseases or disorders.

11. A method of treating asthma in a mammal in need thereof, comprising administering a therapeutically effective amount of a compound according to claim 1 or a pharmaceutically acceptable salt or stereoisomer thereof.

12. A method of treating arthritis in a mammal in need thereof, comprising administering a therapeutically effective amount of a compound according to claim 1 or a pharmaceutically acceptable salt or a stereoisomer thereof.

13. A compound according to claim 1 or a pharmaceutically acceptable salt or stereoisomer thereof, wherein A is selected from: furanyl, thienyl, pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, quinoxalinyl, quinazolinyl, benzoxazolyl, benzisoxazolyl, 5,6,7,8-tetrahydroquinolinyl, imidazo[1,2-c]pyridinyl, imidazo[1,2-c]pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridinyl, thienopyridinyl, benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 1,2,3,4-tetrahydroquinolinyl, 2,3-dihydro-1H-isoindolyl, quinolinyl, pyridazinyl, 2,3-dihydro-1-benzothiophenyl, 6,7-dihydro-5H-pyrrolo[3,4-b]pyridinyl and 2,3-dihydrobenzo[b]thiophenyl. 2,3-dihydrobenzofuranyl, 2,3-dihydrobenzo-1,4-dioxinyl, imidazo(2,1-b)(1,3)thiazole, and benzo-1,3-dioxolyl, phenyl, indenyl, and naphthyl.

14. A compound according to claim 13 or a pharmaceutically acceptable salt or stereoisomer thereof, wherein A is selected from phenyl, pyridinyl, 1,2,3,4-tetrahydroquinolinyl, isoindolyl, indolyl, 2,3-dihydro-1H-isoindolyl, quinolinyl, pyridazinyl, 2,3-dihydro-1-benzothiophenyl, benzothiophenyl, 6,7-dihydro-5H-pyrrolo[3,4-b]pyridinyl, pyrrolo[3,4-b]pyridinyl, benzo[b]thiophenyl, and 2,3-dihydrobenzo[b]thiophenyl.

15. A compound according to claim 14 or a pharmaceutically acceptable salt or stereoisomer thereof, wherein $R^{5a}$ is selected from:
halogen,
C1-10 alkyl$(oxy)_{0-1}$(carbonyl)0-1C0-10 alkyl,
C1-10 heteroalkyl$(oxy)_{0-1}$(carbonyl)0-1C0-10 alkyl,
C2-10 alkenyl$(oxy)_{0-1}$(carbonyl)0-1C0-10 alkyl,
aryl C0-10 alkyl$(oxy)_{0-1}$(carbonyl)0-1C0-10 alkyl,
C3-8 cycloalkyl C0-10 alkyl$(oxy)_{0-1}$(carbonyl)0-1C0-10 alkyl,
heteroaryl C0-10 alkyl$(oxy)_{0-1}$(carbonyl)0-1 C0-10 alkyl,
aryl C0-10 alkyl (carbonyl)0-1oxyC0-10 alkyl,
aryl (C0-10)alkylaminocarbonyloxy,
C1-10 alkylamino$(oxy)_{0-1}$(carbonyl)$_{0-1}$C0-10 alkyl,
heteroarylC0-10alkylamino$((oxy)_{0-1}$(carbonyl)$_{0-1}$C0-10 alkyl,
C0-10 alkyl$(oxy)_{0-1}$(carbonyl)$_{0-1}$-aminoC0-10 alkyl,
C3-8 cycloalkyl C0-10 alkyl $(oxy)_{0-1}$(carbonyl)$_{0-1}$-aminoC0-10 alkyl,
aryl C0-10 alkyl$(oxy)_{0-1}$(carbonyl)$_{0-1}$-aminoC0-10 alkyl,
heteroaryl C0-10 alkyl$(oxy)_{0-1}$(carbonyl)$_{0-1}$aminoC0-10 alkyl,
(C3-8)heterocycloalkyl C0-10 alkyl$(oxy)_{0-1}$(carbonyl)0-1aminoC0-10 alkyl,
—CO2(C0-10 alkyl),
—(C0-10 alkyl)CO2H,
Oxo (=O),
formyl,
sulfonyl,
C1-10 alkylsulfonyl,
C1-10 heteroalkylsulfonyl,
(C3-8) cycloalkylsulfonyl,
(C3-8) cycloheteroalkylsulfonyl,
heteroarylsulfonyl,
arylsulfonyl,
aminosulfonyl,
—SO2N(C0-6alkyl)$_{1-2}$,
—SO2C1-6alkyl,
—SO2CF3,
—SO2CF2H,
—Si(CH3)$_3$,
(C0-10 alkyl)$_{1-2}$ amino,
hydroxy,
(C1-10 alkyl)OH,
C0-10 alkylalkoxyl,
imino(C0-10alkyl),
(C0-10alkyl)imino,
cyano, C1-6alkylcyano, and
C1-6haloalkyl;
wherein two $R^{5a}$ and the atom to which they are attached may optionally form a 3-, 4-, 5-, or 6-membered saturated ring system and wherein $R^{5a}$ is each optionally substituted with 1, 2, 3, or 4 $R^6$ substituents.

16. A compound according to claim 15 or a pharmaceutically acceptable salt or stereoisomer thereof, wherein $R^{5a}$ is selected from: methylsulfonyl, hydroxyl, trimethylsilyl, ethoxy, methoxy, methyloxycarbonyl, methylCOOH, hydroxycarbonylmethyl, methyloxycarbonyl, dimethylamino, fluoro, phenylcarbonyloxy, methylamino, oxo, ethylamino, benzylamino, tert-butyloxycarbonyl, methoxycarbonyl, hydroxymethyl, aminomethyl, oxymethyl, methyl, methylaminomethyl, methylaminocarbonyl, oxycarbonylamino, methyloxycarbonyl, ethyloxycarbonylamino, tert-butyloxycarbonylamino, ethyl, methyl, tert-butyloxycarbonylaminomethyl, carbonylamino, trifluoromethylsulfonyl, trifluoromethyl, trifluoroethyl, chloro, pyridinylaminocarbonyl, methylcarbonylamino, cyano, 1,2,4-oxadiazolyl, ethylsulfonyl, oxo, pyrazolyl, formyl (C=O), bromo, carbamoyl, acetyl, 3,3,3-trifluoro-1,1-dimethylpropyl, trifluoropentyl, 2,2,2-trifluoromethylethyl, difluoromethyl, 2,2-difluoromethylethyl, isopropyl, aminomethyl, methylethylcarbonylamino, tert-butylaminocarbonyl, cyclopropyl, sulfamoyl, (methylethyl)sulfamoyl, methylsulfamoyl, ethylsulfamoyl, piperazinylsulfonyl, piperidinylsulfonyl, pyridinylsulfonyl, morpholinylsulfonyl, difluoromethoxy, pyrazolyl, oxetanyl, cyclopropylmethoxy, dimethylamino, cyclopropylamino, morpholinyl, sulfonyl, azetidinyl, tert-butylamino, hydroxymethylethyl, (cyclopropylethyl)amino, (cyclopropylmethyl)amino, trifluoroethylamino, pyrrolidinyl, (oxetanylmethyl)amino, hydroxycarbonylisopropyl, oxetanylamino, hydroxymethyl, methylcarbonyl, (ethyl)(methyl)amino, methoxyethylamino, (tetrahydrothiophenylmethyl)amino, propyl(methyl)amino, cyclopropylamino, (dimethylethyl)amino, methylamino, oxetanylmethylamino, tetrahydro-2H-pyranylamino, tert-butyloxycarbonylamino, cyclobutylamino, butylamino, cyclobutylmethylamino, dimethylpropyl, ethenyl, phenylaminocarbonyloxy, cyclohexylaminocarbonyloxy, propylaminocarbonyloxy, methylaminocarbonyloxy, ethylaminocarbonyloxy, cyclopropylmethlcarbamoyl, tert-butyloxycarbonyl, hydroxycarbonyl, cyclopropylmethylaminocarbonyl, azetidinylcarbonyl, oxetanycarbamoyl, ethylcarbamoyl, cyclobutylcarbamoyl, cyclopropylmethylcarbamoyl, methylcarbamoyl, oxetanylmethycarbamoyl, pyrrolidinylcarbonyl, tert-butylcarbamoyl, hydroxypropanyl, methyloxycarbonyl, imino$C_{1-10}$ alkyl, and $C_{1-10}$ alkylimino, wherein two $R^{5a}$ and the atom to which they are attached may optionally form a 3-, 4-, 5-, or 6-membered saturated ring system and wherein $R^{5a}$ is each optionally substituted with 1, 2, 3, or 4 substituents, $R^6$.

17. compound according to claim 16 or a pharmaceutically acceptable salt or stereoisomer thereof, wherein $R^a$ is hydrogen or methyl; $R^4$ is hydrogen or methyl and $R^2$ and $R^7$ are each independently selected from hydrogen, halogen, C1-10 alkyl, and C3-8 cycloalkylC0-10 alkyl.

\* \* \* \* \*